(12) United States Patent
Doherty et al.

(10) Patent No.: US 6,809,199 B2
(45) Date of Patent: Oct. 26, 2004

(54) (HALO-BENZO CARBONYL) HETEROCYCLO FUSED PHENYL P38 KINASE INHIBITING AGENTS

(75) Inventors: James B. Doherty, Montvale, NJ (US); John E. Stelmach, Westfield, NJ (US); Meng-Hsin Chen, Westfield, NJ (US); Luping Liu, Lawrenceville, NJ (US); Julianne A. Hunt, Scotch Plains, NJ (US); Rowena D. Ruzck, Old Bridge, NJ (US); Joung L. Goulet, Westfield, NJ (US); David D. Wisnoski, Somerset, NJ (US); Swaminathan Ravi Natarajan, Edison, NJ (US); Kathleen M. Rupprecht, Cranford, NJ (US); Jianming Bao, Scotch Plains, NJ (US); Shouwu Miao, Edison, NJ (US); Xingfang Hong, Westfield, NJ (US); Peter J. Sinclair, Scotch Plains, NJ (US); Florida Kallashi, Yonkers, NY (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/023,231

(22) Filed: Dec. 17, 2001

(65) Prior Publication Data

US 2003/0092712 A1 May 15, 2003

Related U.S. Application Data

(60) Provisional application No. 60/256,822, filed on Dec. 20, 2000.

(51) Int. Cl.[7] .................. C07D 239/72; C07D 401/00; C07D 403/00; C07D 413/00; A61K 31/395
(52) U.S. Cl. ....................................... 544/256; 546/122
(58) Field of Search .......................... 544/256; 546/122

(56) References Cited

U.S. PATENT DOCUMENTS

| 5,736,381 A | 4/1998 | Davis et al. ............. 435/252.3 |
| 5,804,427 A | 9/1998 | Davis et al. ................ 435/194 |
| 6,528,508 B2 | 3/2003 | Salituro et al. | |

FOREIGN PATENT DOCUMENTS

| WO | WO 95/31451 | 11/1995 |
| WO | WO 97/22704 | 6/1997 |
| WO | WO 98/00539 | 1/1998 |
| WO | WO 98/27098 | 6/1998 |
| WO | WO 99/00357 | 1/1999 |
| WO | WO 01/37837 | 5/2001 |
| WO | WO 01/64679 | 9/2001 |
| WO | WO 02/059083 | 8/2002 |

OTHER PUBLICATIONS

Abstract of WO 2001/064679 (Sep. 7, 2001).*
M. J. Cook et al., J.C.S. Perkin II, 1295–1301(1972).
J. Chenault et al., Synthesis, 5:498–499(1987).
K.E. Brighty et al., SynLett, 1097–1099(1996).
Z. Xia et al., Science, 270: 1326–1331(1995).
W.D. Wulff et al., J. Org. Chem., 51:277–279(1986).
L.J. Street et al., J. Med. Chem., 33:2690–2697(1990).
A.R. Katritzky et al., J. Heterocyclic Chem., 32:979–984(1995).
V.R. Gaertner, Tetrahedron Lett., 39:4691–4694(1996).
M.L. Gillaspy et al., Tetrahedron Lett., 36:7399–7402(1995).
T. Okutani et al., Chem. Pharm. Bull., 22:1490–1497(1974).

* cited by examiner

*Primary Examiner*—Bruck Kifle
(74) *Attorney, Agent, or Firm*—Mitul Desai; David L. Rose

(57) ABSTRACT

Compounds described by the chemical formula (I) or a pharmaceutically acceptable salt thereof:

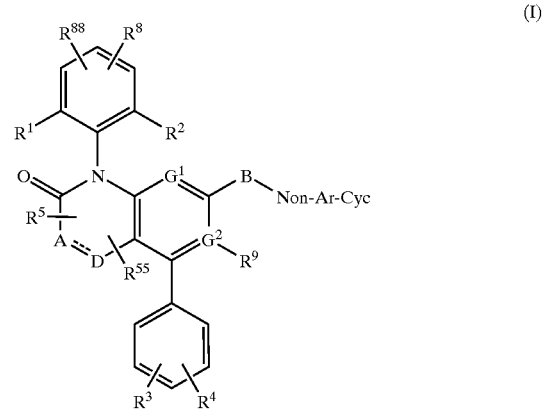

(I)

are inhibitors of p38 useful in the treatment of inflammatory diseases such as arthritis.

40 Claims, No Drawings

(HALO-BENZO CARBONYL) HETEROCYCLO FUSED PHENYL P38 KINASE INHIBITING AGENTS

This application claims priority from Provisional Application No.: 60/256,822, filed Dec. 20, 2000.

BACKGROUND OF THE INVENTION

The present invention relates to compounds that inhibit the action of the p38 mitogen-activated protein kinase, a mammalian protein kinase that is involved in cell proliferation, cell response to stimuli, and cell death. In particular, this invention relates to heterocyclic compounds that are selective and potent inhibitors of the p38 mitogen-activated protein kinase. This invention also relates to pharmaceutical compositions containing such heterocyclic compounds that inhibit the p38 mitogen-activated protein kinase.

RELATED BACKGROUND

Mitogen-activated protein ("MAP") kinases mediate the surface-to-nucleus signal transduction in a cell. Protein kinases that activate and phosphorylate MAP are known as mitogen-activated protein kinase kinases ("MKK"). One such MKK specifically phosphorylates and activates the p38 MAP kinase ("p38") and is called MKK3. U.S. Pat. Nos. 5,736,381 and 5,804,427 describe human mitogen-activated kinase kinase isoforms. International Publication No. 98/00539 describes a human gene encoding an MKK3-Interacting Protein.

Xia et al., *Science*, 270, 1326–1331 (1995) describes the p38 signal transduction pathway as being activated by proinflammatory cytokines and environmental stress. MKK3 is described as being involved in transducing stress signals such as nerve growth factor mediated apaptosis in PC12 cells. It is believed that inhibition of p38 activity can provide relief from acute and chronic inflammation by blocking production of cytokines such as IL-1 and TNF, thereby inhibiting the production of proinflammatory cytokines such as IL-6 and IL-8. In particular, it is believed that p38 inhibitors block the synthesis of TNFα and IL-1β cytokines, thereby providing relief from inflammatory diseases such as arthritis. Accordingly, it would be desirable to provide novel compounds that are selective and potent inhibitors of the action of p38.

International Publication No. 97/22704 describes the mitogen-activated protein kinase kinase MEK6, which can stimulate phosphorylation and activation of p38 substrates. International Publication Nos. 95/31451, 99/00357 and 98/27098 describe various inhibitors of p38. Nonetheless, there remains a great need to develop inhibitors of the action of p38 for various pharmaceutical and therapeutic applications.

SUMMARY OF THE INVENTION

Compounds described by the chemical formula (I) or pharmaceutically acceptable salts thereof:

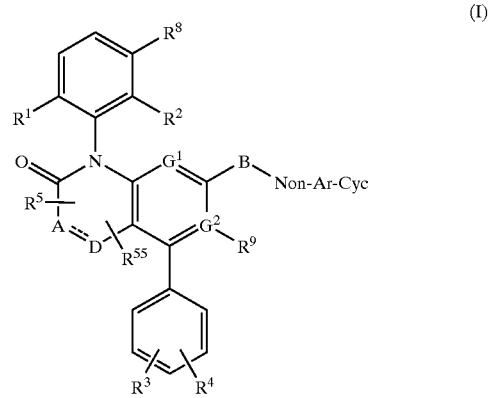

are inhibitors of p38.

DETAILED DESCRIPTION OF THE INVENTION

The present invention provides a compound that is an inhibitor of the action of p38, wherein the compound is described by the chemical formula (I):

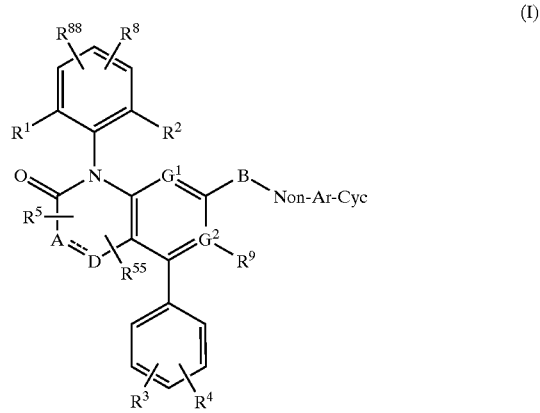

or a pharmaceutically acceptable salt thereof, wherein

Non-Ar-Cyc is

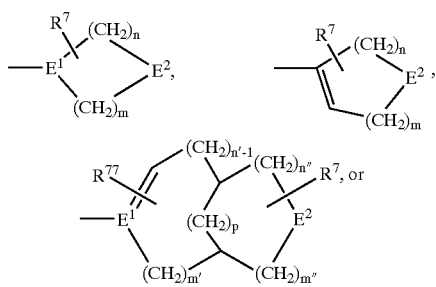

-continued

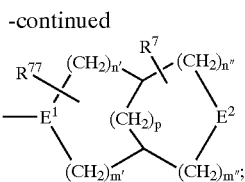

A is N, O, NH, CH$_2$, or CH;

B is —C$_{1-6}$alkyl-, —C$_{0-3}$alkyl-O—C$_{0-3}$alkyl-, —C$_{0-3}$alkyl-NH—C$_{0-3}$alkyl-, —C$_{0-3}$alkyl-NH—C$_{3-7}$cycloalkyl-, —C$_{0-3}$alkyl-N(C$_{0-3}$alkyl)—C(O)—C$_{0-3}$alkyl -, —C$_{0-3}$alkyl-NH—SO$_2$—C$_{0-3}$alkyl-, —C$_{0-3}$alkyl-, —C$_{0-3}$alkyl-S—C$_{0-3}$alkyl-, C$_{0-3}$alkyl-SO$_2$—C$_{0-3}$alkyl-, —C$_{0-3}$alkyl-PH—C$_{0-3}$alkyl-, —C$_{0-3}$alkyl-C(O)—C$_{0-3}$alkyl, or a direct bond;

D is CH, CH$_2$, N, or NH; optionally A and D are bridged by —C$_{1-4}$alkyl- to form a fused bicyclo ring with A and D at the bicyclo cusps;

E$^1$ is CH, N, or CR$^6$; or B and E$^1$ form —CH=C<;

E$^2$ is CH$_2$, CHR, C(OH)R NH, NR, O, S, —S(O)—, or —S(O)$_2$—;

G$^1$ is N, CH, or C(C$_{1-3}$alkyl);

G$^2$ is N, CH, or C(C$_{1-3}$alkyl);

R, R$^7$ and R$^{77}$ each independently is hydrogen, C$_{1-6}$alkyl-group, C$_{2-6}$alkenyl-group, C$_{4-6}$cycloalkyl-C$_{0-6}$alkyl-group, N(C$_{0-4}$alkyl)(C$_{0-4}$alkyl)-C$_{1-4}$alkyl-N(C$_{0-4}$alkyl)-group, —N(C$_{0-4}$alkyl)(C$_{0-4}$alkyl) group, C$_{1-3}$alkyl-CO—C$_{0-4}$alkyl-group, C$_{0-6}$alkyl-O—C(O)—C$_{0-4}$alkyl-group, C$_{0-6}$alkyl-C(O)—O—C$_{0-4}$alkyl-group, N(C$_{0-4}$alkyl)(C$_{0-4}$alkyl)-(C$_{0-4}$alkyl)C(O)(C$_{0-4}$alkyl)-group, phenyl-C$_{0-4}$alkyl-group, pyridyl-C$_{0-4}$alkyl-group, pyrimidinyl-C$_{0-4}$alkyl-group, pyrazinyl-C$_{0-4}$alkyl-group, thiophenyl-C$_{0-4}$alkyl-group, pyrazolyl-C$_{0-4}$alkyl-group, imidazolyl-C$_{0-4}$alkyl-group, triazolyl-C$_{0-4}$alkyl-group, azetidinyl-C$_{0-4}$alkyl-group, pyrrolidinyl-C$_{0-4}$alkyl-group, isoquinolinyl-C$_{0-4}$alkyl-group, indanyl-C$_{0-4}$alkyl-group, benzothiazolyl-C$_{0-4}$alkyl-group, any of the groups optionally substituted with 1–6 substituents, each substituent independently being —OH, —N(C$_{0-4}$alkyl)(C$_{0-4}$alkyl), C$_{1-4}$alkyl, C$_{1-6}$alkoxyl, C$_{1-6}$alkyl-CO—C$_{0-4}$alkyl-, pyrrolidinyl-C$_{0-4}$alkyl-, or halogen;

or R$^7$ together with a bond from an absent ring hydrogen is =O;

n'+n"=n;

m'+m"=m;

n is 1, 2, 3, or 4;

m is 0, 1, 2, 3, or 4;

n+m is 2, 3, 4, 5, or 6;

p is 0, 1, 2, or 3;

R$^1$, R$^2$, R$^3$, R$^4$, and R$^6$ are each independently halogen, C$_{0-4}$alkyl, —C(O)—O(C$_{0-4}$alkyl), or —C(O)—N(C$_{0-4}$alkyl)(C$_{0-4}$alkyl);

R$^5$ and R$^{55}$ independently is H, CH$_3$, CH$_2$CH$_3$, or absent;

R$^{88}$ and R$^8$ each is independently —CN, —C$_{0-4}$alkyl, —C(O)—N(C$_{0-4}$alkyl)(C$_{0-4}$alkyl), —C(O)—O—C$_{0-4}$alkyl or 1,3-dioxolan-2-yl-C$_{0-4}$alkyl-;

R$^9$ is —C$_{0-4}$alkyl, or absent; and any alkyl optionally substituted with 1–6 independent halogen or —OH.

In one aspect, the present invention provides a compound described by the chemical formula (I), or a pharmaceutically acceptable salt thereof, wherein Non-Ar-Cyc is

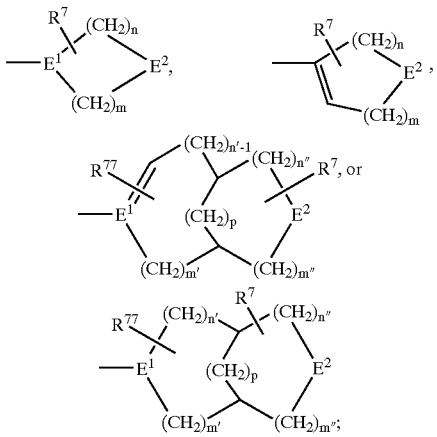

A is NH;

B is —C$_{1-6}$alkyl-, —C$_{0-3}$alkyl-O—C$_{0-3}$alkyl-, —C$_{0-3}$alkyl-NH—C$_{0-3}$alkyl-, —C$_{0-3}$alkyl-NH—C3-7cycloalkyl-, —C$_{0-3}$alkyl-N(C$_{0-3}$alkyl)-C(O)—C$_{0-3}$alkyl-, —C$_{0-3}$alkyl-NH—SO$_2$-C$_{0-3}$alkyl-, —C$_{0-3}$alkyl-, —C$_{0-3}$alkyl-S—C$_{0-3}$alkyl-, —C$_{0-3}$alkyl-SO$_2$—C$_{0-3}$alkyl-, —C$_{0-3}$alkyl-PH—C$_{0-3}$alkyl-, C$_{0-3}$alkyl-C(O)—C$_{0-3}$alkyl, or a direct bond;

D is CH$_2$;

E$^1$ is CH, N, or CR$^6$; or B and E$^1$ form —CH=C<;

E$^2$ is CH$_2$, CHR, C(OH)R NH, NR, O, S, —S(O)—, or —S(O)$_2$—;

G$^1$ is N, CH, or C(C$_{1-3}$alkyl);

G$^2$ is N, CH, or C(C$_{1-3}$alkyl);

R, R$^7$ and R$^{77}$ each independently is hydrogen, C$_{1-6}$alkyl-group, C$_{2-6}$alkenyl-group, C$_{4-6}$cycloalkyl-C$_{0-6}$alkyl-group, N(C$_{0-4}$alkyl)(C$_{0-4}$alkyl)-C$_{1-4}$alkyl-N(C$_{0-4}$alkyl)-group, —N(C$_{0-4}$alkyl)(C$_{0-4}$alkyl) group, C$_{1-3}$alkyl-CO—C$_{0-4}$alkyl-group, C$_{0-6}$alkyl-O—C(O)—C$_{0-4}$alkyl-group, C$_{0-6}$alkyl-C(O)—O—C$_{0-4}$alkyl-group, N(C$_{0-4}$alkyl)(C$_{0-4}$alkyl)-(C$_{0-4}$alkyl)C(O)(C$_{0-4}$alkyl)-group, phenyl-C$_{0-4}$alkyl-group, pyridyl-C$_{0-4}$alkyl-group, pyrimidinyl-C$_{0-4}$alkyl-group, pyrazinyl-C$_{0-4}$alkyl-group, thiophenyl-C$_{0-4}$alkyl-group, pyrazolyl-C$_{0-4}$alkyl-group, imidazolyl-C$_{0-4}$alkyl-group, triazolyl-C$_{0-4}$alkyl-group, azetidinyl-C$_{0-4}$alkyl-group, pyrrolidinyl-C$_{0-4}$alkyl-group, isoquinolinyl-C$_{0-4}$alkyl-group, indanyl-C$_{0-4}$alkyl-group, benzothiazolyl-C$_{0-4}$alkyl-group, any of the groups optionally substituted with 1–6 substituents, each substituent independently being —OH, —N(C$_{0-4}$alkyl)(C$_{0-4}$alkyl), C$_{1-4}$alkyl, C$_{1-6}$alkoxyl, C$_{1-6}$alkyl-CO—C$_{0-4}$alkyl-, pyrrolidinyl-C$_{0-4}$alkyl-, or halogen;

or R$^7$ together with a bond from an absent ring hydrogen is =O;

n'+n"=n;

m'+m"=m;

n is 1, 2, 3, or 4;

m is 0, 1, 2, 3, or 4;

n+m is 2, 3, 4, 5, or 6;

p is 0, 1, 2, or 3;

R$^1$, R$^2$, R$^3$, R$^4$, and R$^6$ are each independently halogen, C$_{0-4}$alkyl, —C(O)—O(C$_{0-4}$alkyl), or —C(O)—N(C$_{0-4}$alkyl)(C$_{0-4}$alkyl);

R$^5$ and R$^{55}$ independently is H, CH$_3$, CH$_2$CH$_3$, or absent;

R$^{88}$ and R$^8$ each is independently —CN, —C$_{0-4}$alkyl, —C(O)—N(C$_{0-4}$alkyl)(C$_{0-4}$alkyl), —C(O)—O—C$_{0-4}$alkyl or 1,3-dioxolan-2-yl-C$_{0-4}$alkyl-;

R$^9$ is —C$_{0-4}$alkyl, or absent; and any alkyl optionally substituted with 1–6 independent halogen or —OH.

In one embodiment of this aspect, the present invention provides a compound described by the chemical formula (I), or a pharmaceutically acceptable salt thereof, wherein Non-Ar-Cyc is

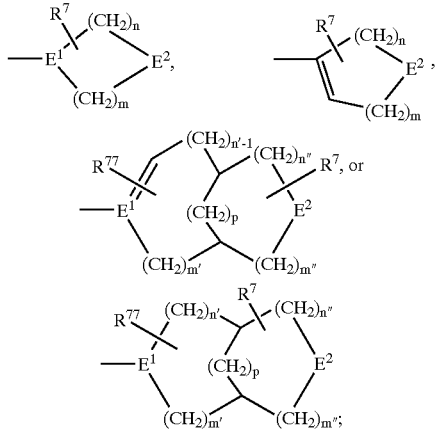

A is NH;
B is a direct bond;
D is $CH_2$;
$E^1$ is CH, N, or $CR^6$; or B and $E^1$ form —CH=C<;
$E^2$ is $CH_2$, CHR, C(OH)R NH, NR, O, S, —S(O)—, or —S(O)$_2$—;
$G^1$ is N, CH, or C($C_{1-3}$alkyl);
$G^2$ is N, CH, or C($C_{1-3}$alkyl);
R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;
or $R^7$ together with a bond from an absent ring hydrogen is =O;
n'+n"=n;
m'+m"=m;
n is 1, 2, 3, or 4;
m is 0, 1, 2, 3, or 4;
n+m is 2, 3, 4, 5, or 6;
p is 0, 1, 2, or 3;
$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);
$R^5$ and $R^{55}$ independently is H, $CH_3$, $CH_2CH_3$, or absent;
$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;
$R^9$ is —$C_{0-4}$alkyl, or absent; and
any alkyl optionally substituted with 1–6 independent halogen or —OH.

In another embodiment of this aspect, the present invention the present invention provides a compound described by the chemical formula (I), or a pharmaceutically acceptable salt thereof, wherein
Non-Ar-Cyc is

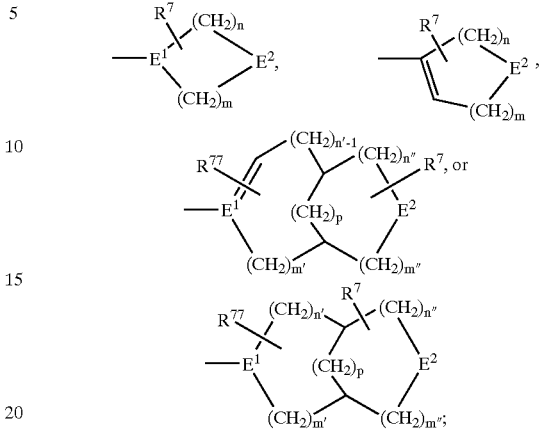

A is NH;
B is —$C_{0-3}$alkyl-O—$C_{0-3}$alkyl-;
D is $CH_2$;
$E^1$ is CH, N, or $CR^6$; or B and $E^1$ form —CH=C<;
$E^2$ is $CH_2$, CHR, C(OH)R NH, NR, O, S, —S(O)—, or —S(O)$_2$—;
$G^1$ is N, CH, or C($C_{1-3}$alkyl);
$G^2$ is N, CH, or C($C_{1-3}$alkyl);
R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl—O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;
or $R^7$ together with a bond from an absent ring hydrogen is =O;
n'n"=n;
m'+m"=m;
n is 1, 2, 3, or 4;
m is 0, 1, 2, 3, or 4;
n+m is 2, 3, 4, 5, or 6;
p is 0, 1, 2, or 3;
$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);
$R^5$ and $R^{55}$ independently is H, $CH_3$, $CH_2CH_3$, or absent;
$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;
$R^9$ is —$C_{0-4}$alkyl, or absent; and
any alkyl optionally substituted with 1–6 independent halogen or —OH.

In yet another embodiment of this aspect, the present invention provides the present invention provides a compound described by the chemical formula (I), or a pharmaceutically acceptable salt thereof, wherein Non-Ar-Cyc is

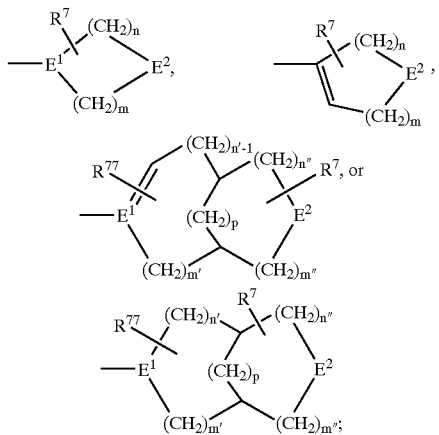

A is NH;
B is —$C_{0-3}$alkyl-C(O)—$C_{0-3}$alkyl;
D is $CH_2$;
$E^1$ is CH, N, or $CR^6$; or B and $E^1$ form —CH=C<;
$E^2$ is $CH_2$, CHR, C(OH)R NH, NR, O, S, —S(O)—, or —S(O)$_2$—;
$G^1$ is N, CH, or C($C_{1-3}$alkyl);
$G^2$ is N, CH, or C($C_{1-3}$alkyl);
R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;
or $R^7$ together with a bond from an absent ring hydrogen is =O;
n'+n"=n;
m'+m"=m;
n is 1, 2, 3, or 4;
m is 0, 1, 2, 3, or 4;
n+m is 2, 3, 4, 5, or 6;
p is 0, 1, 2, or 3;
$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);
$R^5$ and $R^{55}$ independently is H, $CH_3$, $CH_2CH_3$, or absent;
$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;
$R^9$ is —$C_{0-4}$alkyl, or absent; and
any alkyl optionally substituted with 1–6 independent halogen or —OH.

In still another embodiment of this aspect, the present invention provides a compound described by the chemical formula (I), or a pharmaceutically acceptable salt thereof, wherein Non-Ar-Cyc is

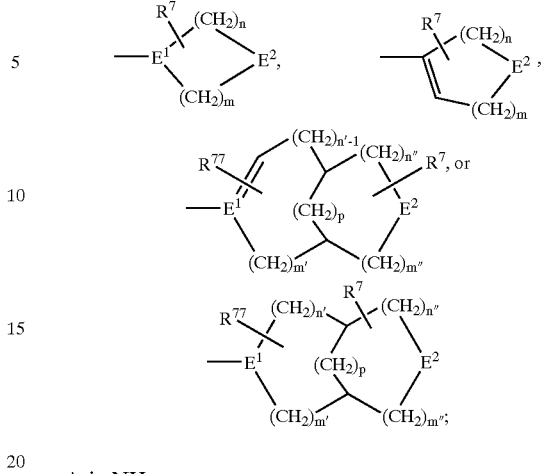

A is NH;
B is —$C_{1-6}$alkyl-;
D is $CH_2$;
$E^1$ is CH, N, or $CR^6$; or B and $E^1$ form —CH=C<;
$E^2$ is $CH_2$, CHR, C(OH)R NH, NR, O, S, —S(O)—, or —S(O)$_2$—;
$G^1$ is N, CH, or C($C_{1-3}$alkyl);
$G^2$ is N, CH, or C($C_{1-3}$alkyl);
R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;
or $R^7$ together with a bond from an absent ring hydrogen is =O;
n'+n"=n;
m'+m"=m;
n is 1, 2, 3, or 4;
m is 0, 1, 2, 3, or 4;
n+m is 2, 3, 4, 5, or 6;
p is 0, 1, 2, or 3;
$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);
$R^5$ and $R^{55}$ independently is H, $CH_3$, $CH_2CH_3$, or absent;
$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;
$R^9$ is —$C_{0-4}$alkyl, or absent; and
any alkyl optionally substituted with 1–6 independent halogen or —OH.

In still another embodiment of this aspect, the present invention provides a compound described by the chemical formula (I), or a pharmaceutically acceptable salt thereof, wherein Non-Ar-Cyc is

[structures shown]

A is NH;
B is —$C_{0-3}$alkyl-NH—$C_{0-3}$alkyl-;
D is $CH_2$;
$E^1$ is CH, N, or $CR^6$; or B and $E^1$ form —CH=C<;
$E^2$ is $CH_2$, CHR, C(OH)R NH, NR, O, S, —S(O)—, or —S(O)$_2$—;
$G^1$ is N, CH, or C($C_{1-3}$alkyl);
$G^2$ is N, CH, or C($C_{1-3}$alkyl);
R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;
or $R^7$ together with a bond from an absent ring hydrogen is =O;
n'+n"=n;
m'+m"=m;
n is 1, 2, 3, or 4;
m is 0, 1, 2, 3, or 4;
n+m is 2, 3, 4, 5, or 6;
p is 0, 1, 2, or 3;
$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);
$R^5$ and $R^{55}$ independently is H, $CH_3$, $CH_2CH_3$, or absent;
$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;
$R^9$ is —$C_{0-4}$alkyl, or absent; and
any alkyl optionally substituted with 1–6 independent halogen or —OH.

In yet another embodiment of this aspect, the present invention provides a compound described by the chemical formula (I), or a pharmaceutically acceptable salt thereof, wherein Non-Ar-Cyc is

[structures shown]

A is NH;
B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, —$C_{0-3}$alkyl-N($C_{0-3}$alkyl)-C(O)-$C_{0-3}$alkyl-, —$C_{0-3}$alkyl-NH—SO$_2$—$C_{0-3}$alkyl-, —$C_{0-3}$alkyl-, —$C_{0-3}$alkyl-S—$C_{0-3}$alkyl-, —$C_{0-3}$alkyl-SO$_2$—$C_{0-3}$alkyl-, —$C_{0-3}$alkyl-PH—$C_{0-3}$alkyl-, —$C_{0-3}$alkyl-C(O)—$C_{0-3}$alkyl, or a direct bond;
D is $CH_2$;
$E^1$ is CH, N, or $CR^6$; or B and $E^1$ form —CH=C<;
$E^2$ is $CH_2$, CHR, C(OH)R NH, NR, O, S, —S(O)—, or —S(O)$_2$—;
$G^1$ is N, CH, or C($C_{1-3}$alkyl);
$G^2$ is N;
R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;
or $R^7$ together with a bond from an absent ring hydrogen is =O;
n'+n"=n;
m'+m"=m;
n is 1, 2, 3, or 4;
m is 0, 1, 2, 3, or 4;
n+m is 2, 3, 4, 5, or 6;
p is 0, 1, 2, or 3;
$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);
$R^5$ and $R^{55}$ independently is H, $CH_3$, $CH_2CH_3$, or absent;
$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;
$R^9$ is —$C_{0-4}$alkyl, or absent; and
any alkyl optionally substituted with 1–6 independent halogen or —OH.

In yet still another embodiment of this one aspect, the present invention provides a compound described by the chemical formula (I) or a pharmaceutically acceptable salt thereof wherein Non-Ar-Cyc is

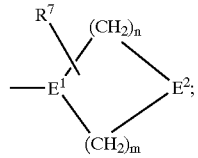

A is NH;
B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, $C_{0-3}$alkyl-N($C_{0-3}$alkyl)-C(O)—$C_{0-3}$alkyl-, —$C_{0-3}$alkyl-NH—SO$_2$—$C_{0-3}$alkyl-, —$C_{0-3}$alkyl-, —$C_{0-3}$alkyl-S—$C_{0-3}$alkyl-, —$C_{0-3}$alkyl-SO$_2$—$C_{0-3}$alkyl-, —$C_{0-3}$alkyl-PH—$C_{0-3}$alkyl-, —$C_{0-3}$alkyl-C(O)—$C_{0-3}$alkyl, or a direct bond;
D is CH$_2$;
$E^1$ is CH, N, or CR$^6$; or B and $E^1$ form —CH═C<;
$E^2$ is CH$_2$, CHR, C(OH)R NH, NR O, S, —S(O)—, or —S(O)$_2$—;
$G^1$ is N, CH, or C($C_{1-3}$alkyl);
$G^2$ is N, CH, or C($C_{1-3}$alkyl);
R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;
or $R^7$ together with a bond from an absent ring hydrogen is ═O;
n'+n"=n;
m'+m"=m;
n is 1, 2, 3, or 4;
m'is 0, 1, 2, 3, or 4;
n+m is 2, 3, 4, 5, or 6;
p is 0, 1, 2, or 3;
$R^1$, $R^2$, $R^3$, $R^4$, and $R^6$ are each independently halogen, $C_{0-4}$alkyl, —C(O)—O($C_{0-4}$alkyl), or C(O)—N($C_{0-4}$alkyl)($C_{0-4}$alkyl);
$R^5$ and $R^{55}$ independently is H, CH$_3$, CH$_2$CH$_3$, or absent;
$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;
$R^9$ is —$C_{0-4}$alkyl, or absent; and
any alkyl optionally substituted with 1–6 independent halogen or —OH.

In still another embodiment of this one aspect, the present invention provides a compound described by the chemical formula (I) or a pharmaceutically acceptable salt thereof, wherein Non-Ar-Cyc is

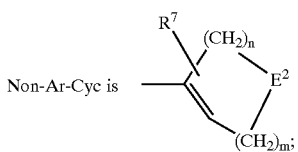

A is NH;
B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, —$C_{0-3}$alkyl-N($C_{0-3}$alkyl)-C(O)—$C_{0-3}$alkyl-, —$C_{0-3}$alkyl-NH—SO$_2$—$C_{0-3}$alkyl-, —$C_{0-3}$alkyl-, —$C_{0-3}$alkyl-S—$C_{0-3}$alkyl-, —$C_{0-3}$alkyl-SO$_2$—$C_{0-3}$alkyl-, —$C_{0-3}$alkyl-PH—$C_{0-3}$alkyl-, —$C_{0-3}$alkyl-C(O)—$C_{0-3}$alkyl, or a direct bond;
D is CH$_2$;
$E^1$ is CH, N, or CR$^6$; or B and $E^1$ form —CH═C<;
$E^2$ is CH$_2$, CHR, C(OH)R NH, NR O, S, —S(O)—, or —S(O)$_2$—;
$G^1$ is N, CH, or C($C_{1-3}$alkyl);
$G^2$ is N, CH, or C($C_{1-3}$alkyl);
R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-$C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;
or $R^7$ together with a bond from an absent ring hydrogen is ═O;
n'+n"=n;
m'+m"=m;
n is 1, 2, 3, or 4;
m is 0, 1, 2, 3, or 4;
n+m is 2, 3, 4, 5, or 6;
p is 0, 1, 2, or 3;
$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);
$R^5$ and $R^{55}$ independently is H, CH$_3$, CH$_2$CH$_3$, or absent;
$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3dioxolan-2-yl-$C_{0-4}$alkyl-;
$R^9$ is —$C_{0-4}$alkyl, or absent; and
any alkyl optionally substituted with 1–6 independent halogen or —OH.

In still another embodiment of this one aspect, the present invention provides a compound described by the chemical formula (I) or a pharmaceutically acceptable salt thereof, wherein Non-Ar-Cyc is

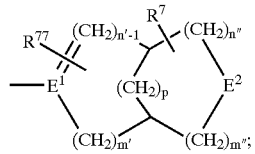

A is NH;
B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, —$C_{0-3}$alkyl-N($C_{0-3}$alkyl)-C(O)—$C_{0-3}$alkyl-, —$C_{0-3}$alkyl-NH—$SO_2$—$C_{0-3}$alkyl-, —$C_{0-3}$alkyl-, —$C_{0-3}$alkyl-S—$C_{0-3}$alkyl-, —$C_{0-3}$alkyl-$SO_2$—$C_{0-3}$alkyl-, —$C_{0-3}$alkyl-PH—$C_{0-3}$alkyl-, —$C_{0-3}$alkyl-C(O)—$C_{0-3}$alkyl, or a direct bond;
D is $CH_2$;
$E^1$ is CH, N, or $CR^6$; or B and $E^1$ form —CH=C<;
$E^2$ is $CH_2$, CHR, C(OH)R NH, NR, O, S, —S(O)—, or —$S(O)_2$—;
$G^1$ is N, CH, or C($C_{1-3}$alkyl);
$G^2$ is N, CH, or C($C_{1-3}$alkyl);
R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—($C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;
or $R^7$ together with a bond from an absent ring hydrogen is =O;
n'+n''=n;
m'+m''=m;
n is 1, 2, 3, or 4;
m is 0, 1, 2, 3, or 4;
n+m is 2, 3, 4, 5, or 6;
p is 0, 1, 2, or 3;
$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);
$R^5$ and $R^{55}$ independently is H, $CH_3$, $CH_2CH_3$, or absent;
$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;
$R^9$ is —$C_{0-4}$alkyl, or absent; and
any alkyl optionally substituted with 1–6 independent halogen or —OH.

In still another embodiment of the first aspect, the present invention provides a compound described by the chemical formula (I) or a pharmaceutically acceptable salt thereof, wherein Non-Ar-Cyc is

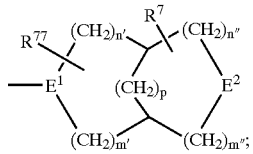

A is NH;
B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, —$C_{0-3}$alkyl-N($C_{0-3}$alkyl-C(O)—$C_{0-3}$alkyl-, —$C_{0-3}$alkyl-NH—$SO_2$—$C_{0-3}$alkyl-, —$C_{0-3}$alkyl-, —$C_{0-3}$alkyl-S—$C_{0-3}$alkyl-, —$C_{0-3}$alkyl-$SO_2$—$C_{0-3}$alkyl-, —$C_{0-3}$alkyl-PH—$C_{0-3}$alkyl-, —$C_{0-3}$alkyl-C(O)—$C_{0-3}$alkyl, or a direct bond;
D is $CH_2$;
$E^1$ is CH, N, or $CR^6$; or B and $E^1$ form —CH=C<;
$E^2$ is $CH_2$, CHR, C(OH)R NH, NR, O, S, —S(O)—, or —$S(O)_2$—;
$G^1$ is N, CH, or C($C_{1-3}$alkyl);
$G^2$ is N, CH, or C($C_{1-3}$alkyl);
R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl) group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl $C_{0-4}$alkyl-, or halogen;
or $R^7$ together with a bond from an absent ring hydrogen is =O;
n'+n''=n;
m'+m''=m;
n is 1, 2, 3, or 4;
m is 0, 1, 2, 3, or 4;
n+m is 2, 3, 4, 5, or 6;
p is 0, 1, 2, or 3;
$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);
$R^5$ and $R^{55}$ independently is H, $CH_3$, $CH_2CH_3$, or absent;
$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;
$R^9$ is —$C_{0-4}$alkyl, or absent; and
any alkyl optionally substituted with 1–6 independent halogen or —OH.

In a second aspect, the present invention provides a compound described by the chemical formula (I) or a pharmaceutically acceptable salt thereof wherein Non-Ar-Cyc is

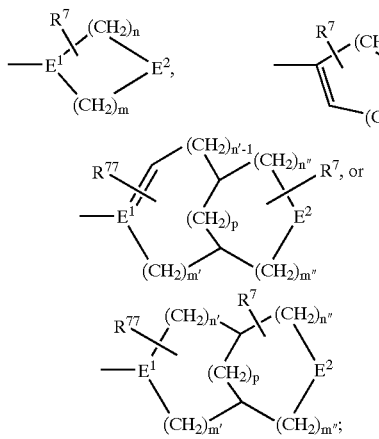

A is N;
B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, —$C_{0-3}$alkyl-N($C_{0-3}$alkyl)C(O)—$C_{0-3}$alkyl-, —$C_{0-3}$alkyl-NH—$SO_2$—$C_{0-3}$alkyl-, —$C_{0-3}$alkyl-, —$C_{0-3}$alkyl-S—$C_{0-3}$alkyl-, —$CO_3$alkyl-$SO_2$—$C_{0-3}$alkyl-, —$C_{0-3}$alkyl-PH—$C_{0-3}$alkyl-, —$C_{0-3}$alkyl-C(O)—$C_{0-3}$alkyl, or a direct bond;
D is CH;
$E^1$ is CH, N, or $CR^6$; or B and $E^1$ form —CH=C<;
$E^2$ is $CH_2$, CHR, C(OH)R NH, NR, O, S, —S(O)—, or —S(O)$_2$—;
$G^1$ is N, CH, or C($C_{1-3}$alkyl);
$G^2$ is N, CH, or C($C_{1-3}$alkyl);
R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N(CO$_4$alkyl)($C_{0-4}$alkyl)-($C_{0-4}$alkyl)C(O)($C_{0-4}$alkyl) group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;
or $R^7$ together with a bond from an absent ring hydrogen is =O;
n'+n"=n;
m'+m"=m;
n is 1, 2, 3, or 4;
m is 0, 1, 2, 3, or 4;
n+m is 2, 3, 4, 5, or 6;
p is 0, 1, 2, or 3;
$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);
$R^5$ and $R^{55}$ independently is H, $CH_3$, $CH_2CH_3$, or absent;
$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;
$R^9$ is —$C_{0-4}$alkyl, or absent; and
any alkyl optionally substituted with 1–6 independent halogen or —OH.

In an embodiment of this second aspect, the present invention provides a compound described by the chemical formula (I) or a pharmaceutically acceptable salt thereof, wherein
Non-Ar-Cyc is

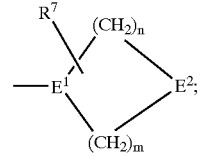

A is N;
B is $C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, —$C_{0-3}$alkyl-N($C_{0-3}$alkyl)-C(O)—$C_{0-3}$alkyl-, —$C_{0-3}$alkyl-NH—$SO_2$—$C_{0-3}$alkyl-, —$C_{0-3}$alkyl-, —$C_{0-3}$alkyl-S—$C_{0-3}$alkyl-, —$C_{0-3}$alkyl-$SO_2$—$C_{0-3}$alkyl-, —$C_{0-3}$alkyl-PH—$C_{0-3}$alkyl-, —$C_{0-3}$alkyl-C(O)—$C_{0-3}$alkyl, or a direct bond;
D is CH;
$E^3$ is CH, N, or $CR^6$; or B and $E^1$ form CH=C<;
$E^2$ is $CH_2$, CHR, C(OH)R NH, NR, O, S, —S(O)—, or —S(O)$_2$—;
$G^1$ is N, CH, or C($C_{1-3}$alkyl);
$G^2$ is N, CH, or C($C_{1-3}$alkyl);
R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl-group, —N($C_{0-4}$alkyl)($C_{0-4}$alkyl) group, $C_{1-3}$alkyl-CO—$C_{0-4}$alkyl-group, $C_{0-6}$-alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;
or $R^7$ together with a bond from an absent ring hydrogen is =O;
n'+n"=n;
m'+m"=m;
n is 1, 2, 3, or 4;
m is 0, 1, 2, 3, or 4;
n+m is 2, 3, 4, 5, or 6;
p is 0, 1, 2, or 3;
$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);
$R^5$ and $R^{55}$ independently is H, $CH_3$, $CH_2CH_3$, or absent;
$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;
$R^9$ is —$C_{0-4}$alkyl, or absent; and
any alkyl optionally substituted with 1–6 independent halogen or —OH.

In another embodiment of this second aspect, the present invention provides a compound described by the chemical formula (I) or a pharmaceutically acceptable salt thereof, wherein Non-Ar-Cyc is

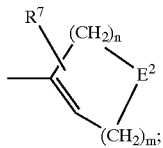

A is N;

B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, —$C_{0-3}$alkyl-N($C_{0-3}$alkyl)—C(O)—$C_{0-3}$alkyl-, —$C_{0-3}$alkyl-NH—$SO_2$—$C_{0-3}$alkyl-, —$C_{0-3}$alkyl-, —$C_{0-3}$alkyl-S—$C_{0-3}$alkyl-, —$C_{0-3}$alkyl-$SO_2$—$C_{0-3}$alkyl-, —$C_{0-3}$alkyl-PH—$C_{0-3}$alkyl-, —$C_{0-3}$alkyl-C(O)—$C_{0-3}$alkyl, or a direct bond;

D is CH;

$E^1$ is CH, N, or $CR^6$; or B and $E^1$ form —CH=C<;

$E^2$ is $CH_2$, CHR, C(OH)R NH, NR, O, S, —S(O)—, or —$S(O)_2$—;

$G^1$ is N, CH, or C($C_{1-3}$alkyl);

$G^2$ is N, CH, or C($C_{1-3}$alkyl);

R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;

or $R^7$ together with a bond from an absent ring hydrogen is =O;

n'+n"=n;
m'+m"=m;
n is 1, 2, 3, or 4;
m is 0, 1, 2, 3, or 4;
n+m is 2, 3, 4, 5, or 6;
p is 0, 1, 2, or 3;

$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);

$R^5$ and $R^{55}$ independently is H, $CH_3$, $CH_2CH_3$, or absent;

$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;

$R^9$ is —$C_{0-4}$alkyl, or absent; and any alkyl optionally substituted with 1–6 independent halogen or —OH.

In still another embodiment of this second aspect, the present invention provides a compound described by the chemical formula (I) or a pharmaceutically acceptable salt thereof, wherein Non-Ar-Cyc is

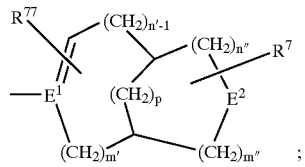

A is N;

B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, —$C_{0-3}$alkyl-N($C_{0-3}$alkyl)-C(O)—$C_{0-3}$alkyl-, —$C_{0-3}$alkyl-NH—$SO_2$—$C_{0-3}$alkyl-, —$C_{0-3}$alkyl-, —$C_{0-3}$alkyl-S—$C_{0-3}$alkyl-, —$C_{0-3}$alkyl-$SO_2$—$C_{0-3}$alkyl-, —$C_{0-3}$alkyl-PH—$C_{0-3}$alkyl-, —$C_{0-3}$alkyl-C(O)—$C_{0-3}$alkyl, or a direct bond;

D is CH;

$E^1$ is CH, N, or $CR^6$; or B and $E^1$ form —CH=C<;

$E^2$ is $CH_2$, CHR, C(OH)R NH, NR, O, S, —S(O)—, or —$S(O)_2$—;

$G^1$ is N, CH, or C($C_{1-3}$alkyl);

$G^2$ is N, CH, or C($C_{1-3}$alkyl),

R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;

or $R^7$ together with a bond from an absent ring hydrogen is =O;

n'+n"=n;
m'+m"=m;
n is 1, 2, 3, or 4;
m is 0, 1, 2, 3, or 4;
n+m is 2, 3, 4, 5, or 6;
p is 0, 1, 2, or 3;

$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);

$R^5$ and $R^{55}$ independently is H, $CH_3$, $CH_2CH_3$, or absent;

$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;

$R^9$ is —$C_{0-4}$alkyl, or absent; and any alkyl optionally substituted with 1–6 independent halogen or —OH.

In another embodiment of this second aspect, the present invention provides a compound described by the chemical formula (I) or a pharmaceutically acceptable salt thereof, wherein Non-Ar-Cyc is

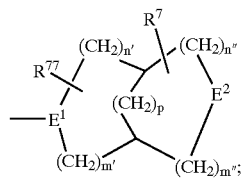

A is N;

B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, —$C_{0-3}$alkyl-N($C_{0-3}$alkyl)-C(O)—$C_{0-3}$alkyl-, —$C_{0-3}$alkyl-NH—$SO_2$—$C_{0-3}$alkyl-, —$C_{0-3}$alkyl-, —$C_{0-3}$alkyl-S—$C_{0-3}$alkyl-, —$C_{0-3}$alkyl-$SO_2$—$C_{0-3}$alkyl-, —$C_{0-3}$alkyl-PH—$C_{0-3}$alkyl-, —$C_{0-3}$alkyl-C(O)—$C_{0-3}$alkyl, or a direct bond;

D is CH;

$E^1$ is CH, N, or $CR^6$; or B and $E^1$ form CH=C<;

$E^2$ is $CH_2$, CHR, C(OH)R NH, NR, O, S, —S(O)—, or —$S(O)_2$—;

$G^1$ is N, CH, or C($C_{1-3}$alkyl);

$G^2$ is N, CH, or C($C_{1-3}$alkyl);

R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;

or $R^7$ together with a bond from an absent ring hydrogen is =O;

n'+n"=n;

m'+m"=m;

n is 1, 2, 3, or 4;

m is 0, 1, 2, 3, or 4;

n+m is 2, 3, 4, 5, or 6;

p is 0, 1, 2, or 3;

$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);

$R^5$ and $R^{55}$ independently is H, $CH_3$, $CH_2CH_3$, or absent;

$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;

$R^9$ is —$C_{0-4}$alkyl, or absent; and any alkyl optionally substituted with 1–6 independent halogen or —OH.

In one embodiment of this second aspect, the present invention provides a compound described by the chemical formula (IIIA) or a pharmaceutically acceptable salt thereof:

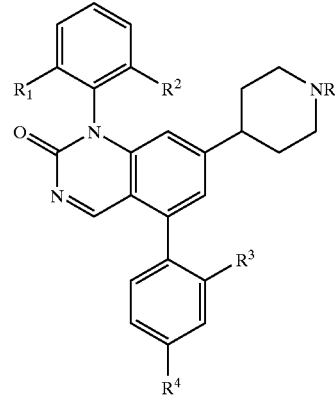

(IIIA)

In a third aspect, the present invention provides a compound described by the chemical formula (I), or a pharmaceutically acceptable salt thereof, wherein Non-Ar-Cyc is

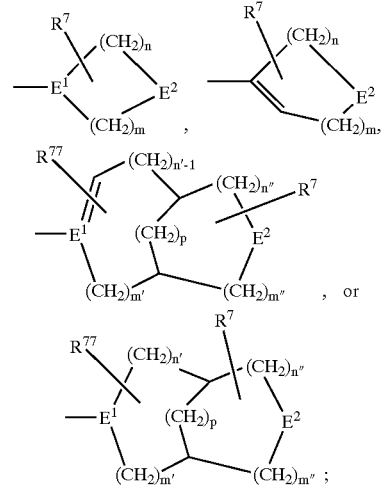

A is O;

B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, —$C_{0-3}$alkyl-N($C_{0-3}$alkyl)-C(O)—$C_{0-3}$alkyl-, —$C_{0-3}$alkyl-NH—$SO_2$—$C_{0-3}$alkyl-, —$C_{0-3}$alkyl-, —$C_{0-3}$alkyl-S—$C_{0-3}$alkyl-, —$C_{0-3}$alkyl-$SO_2$—$C_{0-3}$alkyl-, —$C_{0-3}$alkyl-PH—$C_{0-3}$alkyl-, —$C_{0-3}$alkyl-C(O)—$C_{0-3}$alkyl, or a direct bond;

D is $CH_2$;

$E^1$ is CH, N, or $CR^6$; or B and $E^1$ form —CH=C<;

$E^2$ is $CH_2$, CHR, C(OH)R NH, NR, O, S, —S(O)—, or —$S(O)_2$—;

$G^1$ is N, CH, or C($C_{1-3}$alkyl);

$G^2$ is N, CH, or C($C_{1-3}$alkyl);

R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;

or $R^7$ together with a bond from an absent ring hydrogen is =O;
n'+n"=n;
m'+m"=m;
n is 1, 2, 3, or 4;
m is 0, 1, 2, 3, or 4;
n+m is 2, 3, 4, 5, or 6;
p is 0, 1, 2, or 3;
$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);
$R^5$ and $R^{55}$ independently is H, $CH_3$, $CH_2CH_3$, or absent;
$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;
$R^9$ is —$C_{0-4}$alkyl, or absent; and
any alkyl optionally substituted with 1–6 independent halogen or —OH.

In an embodiment of the third aspect, the present invention provides a compound described by the chemical formula (I) or a pharmaceutically acceptable salt thereof wherein
Non-Ar-Cyc is

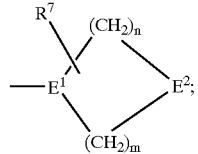

A is O;
B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, —$C_{0-3}$alkyl-N($C_{0-3}$alkyl)-C(O)—$C_{0-3}$alkyl-, —$C_{0-3}$alkyl-NH—$SO_2$—$C_{0-3}$alkyl-, —$C_{0-3}$alkyl-, —$C_{0-3}$alkyl-S—$C_{0-3}$alkyl-, —$C_{0-3}$alkyl-$SO_2$—$C_{0-3}$alkyl-, —$C_{0-3}$alkyl-PH—$C_{0-3}$alkyl-, —$C_{0-3}$alkyl-C(O)—$C_{0-3}$alkyl, or a direct bond;
D is $CH_2$;
$E^1$ is CH, N, or $CR^6$; or B and $E^1$ form —CH=C<;
$E^2$ is $CH_2$, CHR, C(OH)R NH, NR, O, S, —(O)—, or —S(O)$_2$—;
$G^1$ is N, CH, or C($C_{1-3}$alkyl);
$G^2$ is N, CH, or C($C_{1-3}$alkyl);
R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl-group, —N($C_{0-4}$alkyl)($C_{0-4}$alkyl) group, $C_{1-3}$alkyl-CO—$C_{0-4}$alkyl-group, $CO_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;

or $R^7$ together with a bond from an absent ring hydrogen is =O;
n'+n"=n;
m'+m"=m;
n is 1, 2, 3, or 4;
m is 0, 1, 2, 3, or 4;
n+m is 2, 3, 4, 5, or 6;
p is 0, 1, 2, or 3;
$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);
$R^5$ and $R^{55}$ independently is H, $CH_3$, $CH_2CH_3$, or absent;
$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;
$R^9$ is —$C_{0-4}$alkyl, or absent; and
any alkyl optionally substituted with 1–6 independent halogen or —OH.

In another embodiment of the third aspect, the present invention provides a compound described by the chemical formula (I) or a pharmaceutically acceptable salt thereof wherein
Non-Ar-Cyc is

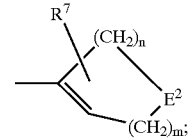

A is O;
B is-$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, —$C_{0-3}$alkyl-N($C_{0-3}$alkyl)-C(O)—$C_{0-3}$alkyl-, —$C_{0-3}$alkyl-NH—$SO_2$—$C_{0-3}$alkyl-, —$C_{0-3}$alkyl-, —$C_{0-3}$alkyl-S—$C_{0-3}$alkyl-, —$C_{0-3}$alkyl-$SO_2$—$C_{0-3}$alkyl-, —$C_{0-3}$alkyl-PH—$C_{0-3}$alkyl-, —$C_{0-3}$alkyl-C(O)—$C_{0-3}$alkyl, or a direct bond;
D is $CH_2$;
$E^1$ is CH, N, or $CR^6$; or B and $E^1$ form —CH=C<;
$E^2$ is $CH_2$, CHR, C(OH)R NH, NR, O, S, —S(O)—, or —S(O)$_2$—;
$G^1$ is N, CH, or C($C_{1-3}$alkyl);
$G^2$ is N, CH, or C($C_{1-3}$alkyl);
R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;

or $R^7$ together with a bond from an absent ring hydrogen is =O;
n'+n"=n;
m'+m"=m;
n is 1, 2, 3, or 4;
m is 0, 1, 2, 3, or 4;

n+m is 2, 3, 4, 5, or 6;

p is 0, 1, 2, or 3;

$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);

$R^5$ and $R^{55}$ independently is H, $CH_3$, $CH_2CH_3$, or absent;

$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;

$R^9$ is —$C_{0-4}$alkyl, or absent; and any alkyl optionally substituted with 1–6 independent halogen or —OH.

In an embodiment of the third aspect, the present invention provides a compound described by the chemical formula (I) or a pharmaceutically acceptable salt thereof wherein Non-Ar-Cyc is

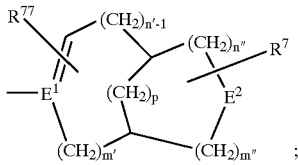

A is O;

B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, —$C_{0-3}$alkyl-N($C_{0-3}$alkyl)-C(O)—$C_{0-3}$alkyl-, —$C_{0-3}$alkyl-NH—$SO_2$—$C_{0-3}$alkyl-, —$C_{0-3}$alkyl-, —$C_{0-3}$alkyl-S—$C_{0-3}$alkyl-, —$C_{0-3}$alkyl-$SO_2$—$C_{0-3}$alkyl-, —$C_{0-3}$alkyl-PH—$C_{0-3}$alkyl-, —$C_{0-3}$alkyl-C(O)—$C_{0-3}$alkyl, or a direct bond;

D is $CH_2$;

$E^1$ is CH, N, or $CR^6$; or B and $E^1$ form —CH=C<;

$E^2$ is $CH_2$, CHR, C(OH)R NH, NR, O, S, —S(O)—, or —S(O)$_2$—;

$G^1$ is N, CH, or C($C_{1-3}$alkyl);

$G^2$ is N, CH, or C($C_{1-3}$alkyl);

R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)(C$_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;

or $R^7$ together with a bond from an absent ring hydrogen is =O;

n'+n"=n;

m'+m"=m;

n is 1, 2, 3, or 4;

m is 0, 1, 2, 3, or 4;

n+m is 2, 3, 4, 5, or 6;

p is 0, 1, 2, or 3;

$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);

$R^5$ and $R^{55}$ independently is H, $CH_3$, $CH_2CH_3$, or absent;

$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;

$R^9$ is —$C_{0-4}$alkyl, or absent; and any alkyl optionally substituted with 1–6 independent halogen or —OH.

In an embodiment of the third aspect, the present invention provides a compound described by the chemical formula (I) or a pharmaceutically acceptable salt thereof wherein Non-Ar-Cyc is

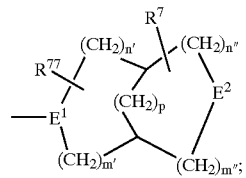

A is O;

B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, —$C_{0-3}$alkyl-N($C_{0-3}$alkyl)—C(O)—$C_{0-3}$alkyl-, —$C_{0-3}$alkyl-NH—$SO_2$—$C_{0-3}$alkyl-, —$C_{0-3}$alkyl, —$C_{0-3}$alkyl-S—$C_{0-3}$alkyl-, —$C_{0-3}$alkyl-$SO_2$—$C_{0-3}$alkyl-, —$C_{0-3}$alkyl-PH—$C_{0-3}$alkyl-, —$_{0-3}$alkyl-C(O)—$C_{0-3}$alkyl, or a direct bond;

D is $CH_2$;

$E^1$ is CH, N, or $CR^6$; or B and $E^1$ form —CH=C<;

$E^2$ is $CH_2$, CHR, C(OH)R NH, NR, O, S, —S(O)—, or —S(O)$_2$—;

$G^1$ is N, CH, or C($C_{1-3}$alkyl);

$G^2$ is N, CH, or C($C_{1-3}$alkyl);

R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;

or $R^7$ together with a bond from an absent ring hydrogen is =O;

n'+n"=n;

m'+m"=m;

n is 1, 2, 3, or 4;

m is 0, 1, 2, 3, or 4;

n+m is 2, 3, 4, 5, or 6;

p is 0, 1, 2, or 3;

$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);

$R^5$ and $R^{55}$ independently is H, $CH_3$, $CH_2CH_3$, or absent;

$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;

$R^9$ is —$C_{0-4}$alkyl, or absent; and any alkyl optionally substituted with 1–6 independent halogen or —OH.

In one embodiment of this third aspect, the present invention provides a compound described by the chemical formula (IVA) or a pharmaceutically acceptable salt thereof:

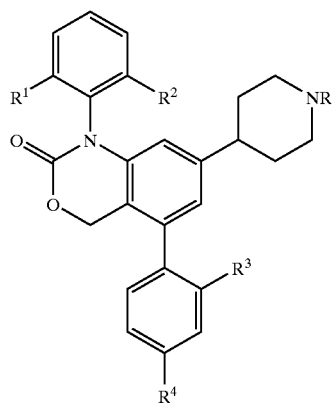

(IVA)

In a fourth aspect, the present invention provides a compound described by the chemical formula (I), or a pharmaceutically acceptable salt thereof, wherein Non-Ar-Cyc is

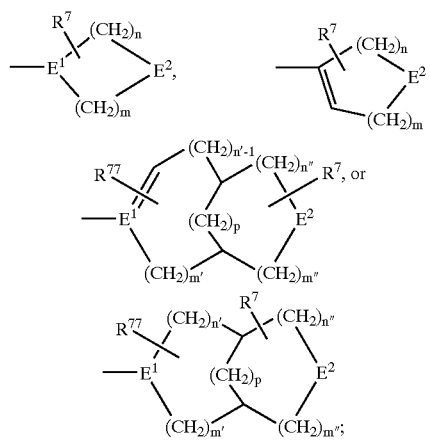

A is $CH_2$;

B is —$C_{1-6}$alkyl, —$C_{0-3}$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, —$C_{0-3}$alkyl-N($C_{0-3}$alkyl)-C(O)—$C_{0-3}$alkyl-, —$C_{0-3}$alkyl-NH—$SO_2$—$C_{0-3}$alkyl-, —$C_{0-3}$alkyl-, —$C_{0-3}$alkyl-S—$C_{0-3}$alkyl-, —$C_{0-3}$alkyl-$SO_2$—$C_{0-3}$alkyl-, —$C_{0-3}$alkyl-PH—$C_{0-3}$alkyl-, —$C_{0-3}$alkyl-C(O)—$C_{0-3}$alkyl, or a direct bond;

D is $CH_2$;

$E^1$ is CH, N, or $CR^6$; or B and $E^1$ form —CH=C<;

$E^2$ is $CH_2$, CHR, C(OH)R NH, NR, O, S, —S(O)—, or —$S(O)_2$—;

$G^1$ is N, CH, or C($C_{1-3}$alkyl);

$G^2$ is N, CH, or C($C_{1-3}$alkyl);

R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;

or $R^7$ together with a bond from an absent ring hydrogen is =O;

n'+n"=n;

m'+m"=m;

n is 1, 2, 3, or 4;

m is 0, 1, 2, 3, or 4;

n+m is 2, 3, 4, 5, or 6;

p is 0, 1, 2, or 3;

$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);

$R^5$ and $R^{55}$ independently is H, $CH_3$, $CH_2CH_3$, or absent;

$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;

$R^9$ is —$C_{0-4}$alkyl, or absent; and any alkyl optionally substituted with 1–6 independent halogen or —OH.

In one embodiment of this fourth aspect, the present invention provides a compound described by the chemical formula (I), or a pharmaceutically acceptable salt thereof, wherein Non-Ar-Cyc is

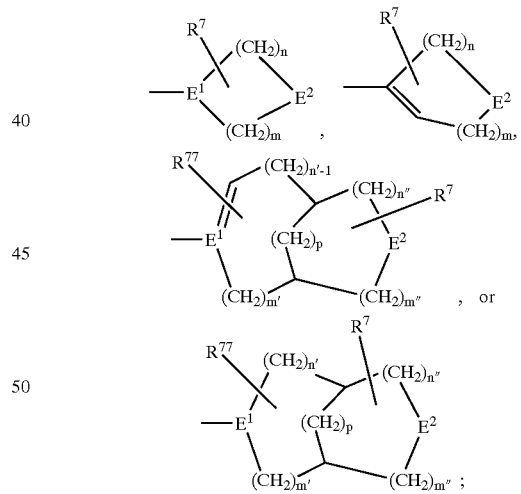

A is $CH_2$;

B is a direct bond;

D is $CH_2$;

$E^1$ is CH, N, or $CR^6$; or B and $E^1$ form —CH=C<;

$E^2$ is $CH_2$, CHR, C(OH)R NH, NR, O, S, —S(O)—, or —$S(O)_2$—;

$G^1$ is N, CH, or C($C_{1-3}$alkyl);

$G^2$ is N, CH, or C($C_{1-3}$alkyl);

R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;

or $R^7$ together with a bond from an absent ring hydrogen is =O;

n'+n"=n;
m'+m"=m;
n is 1, 2, 3, or 4;
m is 0, 1, 2, 3, or 4;
n+m is 2, 3, 4, 5, or 6;
p is 0, 1, 2, or 3;
$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);
$R^5$ and $R^{55}$ independently is H, $CH_3$, $CH_2CH_3$, or absent;
$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;
$R^9$ is —$C_{0-4}$alkyl, or absent; and
any alkyl optionally substituted with 1–6 independent halogen or —OH.

In another embodiment of the fourth aspect, the present invention provides a compound described by the chemical formula (I), or a pharmaceutically acceptable salt thereof, wherein Non-Ar-Cyc is

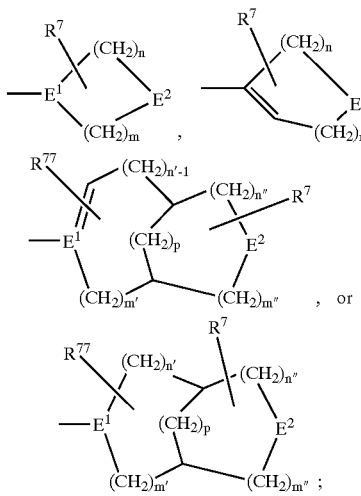

A is $CH_2$;
B is —$C_{0-3}$alkyl-O—$C_{0-3}$alkyl-;
D is $CH_2$;
$E^1$ is CH, N, or $CR^6$; or B and $E^1$ form —CH=C<;
$E^2$ is $CH_2$, CHR, C(OH)R NH, NR, O, S, —S(O)—, or —S(O)$_2$—;
$G^1$ is N, CH, or C($C_{1-3}$alkyl);
$G^2$ is N, CH, or C($C_{1-3}$alkyl);
R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;

or $R^7$ together with a bond from an absent ring hydrogen is =O;

n'+n"=n;
m'+m"=m;
n is 1, 2, 3, or 4;
m is 0, 1, 2, 3, or 4;
n+m is 2, 3, 4, 5, or 6;
p is 0, 1, 2, or 3;
$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);
$R^5$ and $R^{55}$ independently is H, $CH_3$, $CH_2CH_3$, or absent;
$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;
$R^9$ is —$C_{0-4}$alkyl, or absent; and
any alkyl optionally substituted with 1–6 independent halogen or —OH.

In another embodiment of the fourth aspect, the present invention provides a compound described by the chemical formula (I), or a pharmaceutically acceptable salt thereof, wherein Non-Ar-Cyc is A is $CH_2$;
B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, —$C_{0-3}$alkyl-N($C_{0-3}$alkyl)-C(O)—$C_{0-3}$alkyl-, —$C_{0-3}$alkyl-NH—$SO_2$—$C_{0-3}$alkyl-, —$_{0-3}$alkyl-, —$C_{0-3}$alkyl-S—$C_{0-3}$alkyl-, —$C_{0-3}$alkyl-$SO_2$—$C_{0-3}$alkyl-, —$C_{0-3}$alkyl-PH—$C_{0-3}$alkyl-, —$C_{0-3}$alkyl-C(O)—$C_{0-3}$alkyl, or a direct bond;
D is $CH_2$;
$E^1$ is CH, N, or $CR^6$; or B and $E^1$ form —CH=C<;
$E^2$ is $CH_2$, CHR, C(OH)R NH, NR, O, S, —S(O)—, or —S(O)$_2$—;
$G^1$ is N, CH, or C($C_{1-3}$alkyl);
$G^2$ is N, CH, or C($C_{1-3}$alkyl);
R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;

or $R^7$ together with a bond from an absent ring hydrogen is =O;

n'+n''=n;
m'+m''=m;
n is 1, 2, 3, or 4;
m is 0, 1, 2, 3, or 4;
n+m is 2, 3, 4, 5, or 6;
p is 0, 1, 2, or 3;
$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);
$R^5$ and $R^{55}$ independently is H, $CH_3$, $CH_2CH_3$, or absent;
$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;
$R^9$ is —$C_{0-4}$alkyl, or absent; and any alkyl optionally substituted with 1–6 independent halogen or —OH.

In still another embodiment of the fourth aspect, the present invention provides a compound described by the chemical formula (I), or a pharmaceutically acceptable salt thereof, wherein Non-Ar-Cyc is

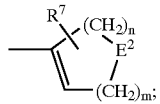

A is $CH_2$;
B is —$C_{1-6}$alkyl-, —$C_{0-3}$alkyl-O—$C_{0-3}$alkyl-, —$C_{0-3}$alkyl-NH—$C_{0-3}$alkyl-, $C_{0-3}$alkyl-NH—$C_{3-7}$cycloalkyl-, —$C_{0-3}$alkyl-N($C_{0-3}$alkyl)-C(O)—$C_{0-3}$alkyl-, —$C_{0-3}$alkyl-NH—SO$_2$—$C_{0-3}$alkyl-, —$C_{0-3}$alkyl-, —$C_{0-3}$alkyl-S—$C_{0-3}$alkyl-, —$C_{0-3}$alkyl-SO$_2$—$C_{0-3}$alkyl-, —$C_{0-3}$alkyl-PH—$C_{0-3}$alkyl-, —$C_{0-3}$alkyl-C(O)—$C_{0-3}$alkyl, or a direct bond;
D is $CH_2$;
$E^1$ is CH, N, or $CR^6$; or B and $E^1$ form —CH=C<;
$E^2$ is $CH_2$, CHR, C(OH)R NH, NR, O, S, —S(O)—, or —S(O)$_2$—;
$G^1$ is N, CH, or C($C_{1-3}$alkyl);
$G^2$ is N, CH, or C($C_{1-3}$alkyl);
R, $R^7$ and $R^{77}$ each independently is hydrogen, $C_{1-6}$alkyl-group, $C_{2-6}$alkenyl-group, —$C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;

or $R^7$ together with a bond from an absent ring hydrogen is =O;

n'+n''=n;
m'+m''=m;
n is 1, 2, 3, or 4;
m is 0, 1, 2, 3, or 4:
n+m is 2, 3, 4, 5, or 6;
p is 0, 1, 2, or 3;
$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);
$R^5$ and $R^{55}$ independently is H, $CH_3$, $CH_2CH_3$, or absent;
$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;
$R^9$ is —$C_{0-4}$alkyl, or absent; and any alkyl optionally substituted with 1–6 independent halogen or —OH.

In yet another embodiment of the fourth aspect, the present invention provides a compound described by the chemical formula (I), or a pharmaceutically acceptable salt thereof, wherein Non-Ar-Cyc is

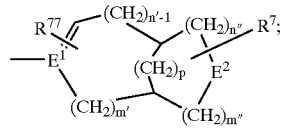

A is $CH_2$;
B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, —$C_{0-3}$alkyl-N($C_{0-3}$alkyl)-C(O)—$C_{0-3}$alkyl-, —$C_{0-3}$alkyl-NH—SO$_2$—$C_{0-3}$alkyl-, —$C_{0-3}$alkyl-, —$C_{0-3}$alkyl-S—$C_{0-3}$alkyl-, —$C_{0-3}$alkyl-SO$_2$—$C_{0-3}$alkyl-, —$C_{0-3}$alkyl-PH—$C_{0-3}$alkyl-, —$C_{0-3}$alkyl-C(O)—$C_{0-3}$alkyl, or a direct bond;
D is $CH_2$;
$E^1$ is CH, N, or $CR^6$; or B and $E^1$ form —CH=C<;
$E^2$ is $CH_2$, CHR, C(OH)R NH, NR, O, S, —S(O)—, or —S(O)$_2$—;
$G^1$ is N, CH, or C($C_{1-3}$alkyl);
$G^2$ is N, CH, or C($C_{1-3}$alkyl);
R, $R^7$ and $R^{77}$ each independently is hydrogen, $C_{1-6}$alkyl-group, $C_{2-6}$alkenyl-group, —$C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$ alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$ alkyl-group, pyridyl-$C_{0-4}$alkyl-group, pyrimidinyl-$C_{0-4}$ alkyl-group, pyrazinyl-$C_{0-4}$alkyl-group, thiophenyl-$C_{0-4}$ alkyl-group, pyrazolyl-$C_{0-4}$alkyl-group, imidazolyl-$C_{0-4}$ alkyl-group, triazolyl-$C_{0-4}$alkyl-group, azetidinyl-$C_{0-4}$ alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;

or $R^7$ together with a bond from an absent ring hydrogen is =O;

n'+n"=n;
m'+m"=m;
n is 1, 2, 3, or 4;
m is 0, 1, 2, 3, or 4;
n+m is 2, 3, 4, 5, or 6;
p is 0, 1, 2, or 3;
$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);
$R^5$ and $R^{55}$ independently is H, $CH_3$, $CH_2CH_3$, or absent;
$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;
$R^9$ is —$C_{0-4}$alkyl, or absent; and
any alkyl optionally substituted with 1–6 independent halogen or —OH.

In another embodiment of the fourth aspect, the present invention provides a compound described by the chemical formula (I), or a pharmaceutically acceptable salt thereof, wherein
Non-Ar-Cyc is

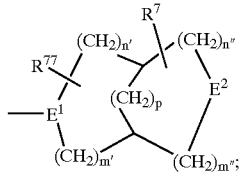

A is $CH_2$;
B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, —$C_{0-3}$alkyl-N($C_{0-3}$alkyl)-C(O)—$C_{0-3}$alkyl-, —$C_{0-3}$alkyl-NH—$SO_2$—$C_{0-3}$alkyl-, —$C_{0-3}$alkyl-, —$C_{0-3}$alkyl-S—$C_{0-3}$alkyl-, —$C_{0-3}$alkyl-$SO_2$—$C_{0-3}$alkyl-, —$C_{0-3}$alkyl-PH—$C_{0-3}$alkyl-, —$C_{0-3}$alkyl-C(O)-$C_{0-3}$alkyl, or a direct bond;
D is $CH_2$;
$E^1$ is CH, N, or $CR^6$; or B and $E^1$ form —CH=C<;
$E^2$ is $CH_2$, CHR, C(OH)R NH, NR, O, S, —S(O)—, or —S(O)$_2$—;
$G^1$ is N, CH, or C($C_{1-3}$alkyl);
$G^2$ is N, CH, or C($C_{1-3}$alkyl);
R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;
or $R^7$ together with a bond from an absent ring hydrogen is =O;
n'+n"=n;
m'+m"=m;
n is 1, 2, 3, or 4;
m is 0, 1, 2, 3, or 4;
n+m is 2, 3, 4, 5, or 6;
p is 0, 1, 2, or 3;
$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);
$R^5$ and $R^{55}$ independently is H, $CH_3$, $CH_2CH_3$, or absent;
$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;
$R^9$ is —$C_{0-4}$alkyl, or absent; and
any alkyl optionally substituted with 1–6 independent halogen or —OH.

In a fifth aspect, the present invention provides a compound described by the chemical formula (I), or a pharmaceutically acceptable salt thereof, wherein
Non-Ar-Cyc is

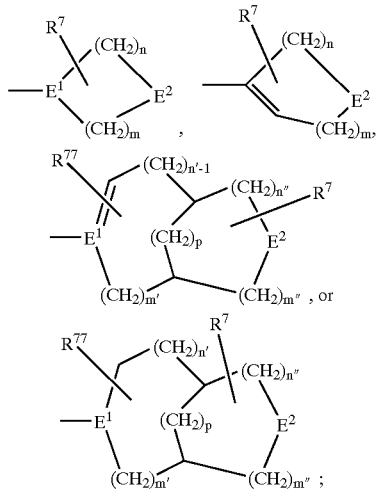

A is CH;
B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, —$C_{0-3}$alkyl-N($C_{0-3}$alkyl)-C(O)—$C_{0-3}$alkyl-, —$C_{0-3}$alkyl-NH—$SO_2$—$C_{0-3}$alkyl-, —$C_{0-3}$alkyl-, —$C_{0-3}$alkyl-S—$C_{0-3}$alkyl-, —$C_{0-3}$alkyl-$SO_2$—$C_{0-3}$alkyl-, —$C_{0-3}$alkyl-PH—$C_{0-3}$alkyl-, —$C_{0-3}$alkyl-C(O)—$C_{0-3}$alkyl, or a direct bond;
D is CH;
$E^1$ is CH, N, or $CR^6$; or B and $E^1$ form —CH=C<;
$E^2$ is $CH_2$, CHR, C(OH)R NH, NR, O, S, —S(O)—, or —S(O)$_2$—;
$G^1$ is N, CH, or C($C_{1-3}$alkyl);
$G^2$ is N, CH, or C($C_{1-3}$alkyl);
R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;

or $R^7$ together with a bond from an absent ring hydrogen is =O;

$n'+n''=n$;
$m'+m''=m$;
n is 1, 2, 3, or 4;
m is 0, 1, 2, 3, or 4;
n+m is 2, 3, 4, 5, or 6;
p is 0, 1, 2, or 3;
$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);
$R^5$ and $R^{55}$ independently is H, $CH_3$, $CH_2CH_3$, or absent;
$R^{88}$ and $R^8$ each is independently —CN, $C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;
$R^9$ is —$C_{0-4}$alkyl, or absent; and
any alkyl optionally substituted with 1–6 independent halogen or —OH.

In an embodiment of the fifth aspect, the present invention provides a compound described by the chemical formula (I), or a pharmaceutically acceptable salt thereof, wherein Non-Ar-Cyc is

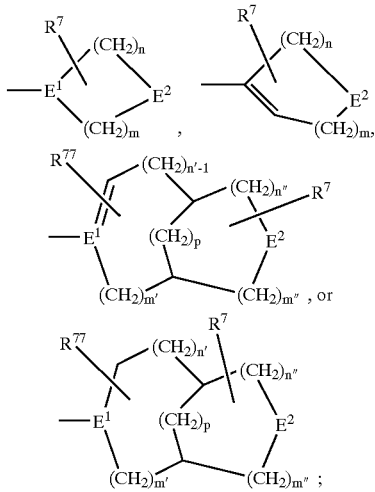

A is CH;
B is a direct bond;
D is CH;
$E^1$ is CH, N, or $CR^6$; or B and $E^1$ form —CH=C<;
$E^2$ is $CH_2$, CHR, C(OH)R NH, NR, O, S, —S(O)—, or —S(O)$_2$—,
$G^1$ is N, CH, or C($C_{1-3}$alkyl);
$G^2$ is N, CH, or C($C_{1-3}$alkyl);
R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;

or $R^7$ together with a bond from an absent ring hydrogen is =O;

$n'+n''=n$;
$m'+m''=m$;
n is 1, 2, 3, or 4;
m is 0, 1, 2, 3, or 4;
n+m is 2, 3, 4, 5, or 6;
p is 0, 1, 2, or 3;
$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);
$R^5$ and $R^{55}$ independently is H, $CH_3$, $CH_2CH_3$, or absent;
$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;
$R^9$ is —$C_{0-4}$alkyl, or absent; and
any alkyl optionally substituted with 1–6 independent halogen or —OH.

In another embodiment of the fifth aspect, the present invention provides a compound described by the chemical formula (I), or a pharmaceutically acceptable salt thereof, wherein Non-Ar-Cyc is

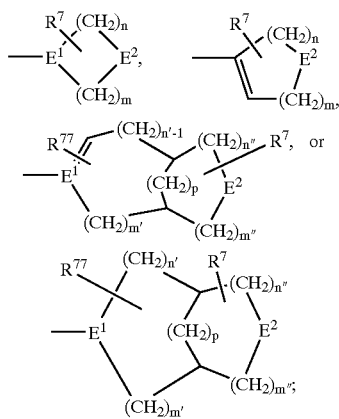

A is CH;
B is —$C_{0-3}$alkyl-O—$C_{0-3}$alkyl-;
D is CH;
$E^1$ is CH, N, or $CR^6$; or B and $E^1$ form —CH=C<;
$E^2$ is $CH_2$, CHR, C(OH)R NH, NR, O, S, —S(O)—, or —S(O)$_2$—;
$G^1$ is N, CH, or C($C_{1-3}$alkyl);
$G^2$ is N, CH, or C($C_{1-3}$alkyl);
R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;

or $R^7$ together with a bond from an absent ring hydrogen is =O;

n'+n"=n;
m'+m"=m;
n is 1, 2, 3, or 4;
m is 0, 1, 2, 3, or 4;
n+m is 2, 3, 4, 5, or 6;
p is 0, 1, 2, or 3;
$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);
$R^5$ and $R^{55}$ independently is H, $CH_3$, $CH_2CH_3$, or absent; $R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;
$R^9$ is —$C_{0-4}$alkyl, or absent; and
any alkyl optionally substituted with 1–6 independent halogen or —OH.

In an embodiment of the fifth aspect, the present invention provides a compound described by the chemical formula (I), or a pharmaceutically acceptable salt thereof, wherein
Non-Ar-Cyc is

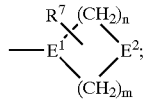

A is CH;
B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, —$C_{0-3}$alkyl-N($C_{0-3}$alkyl)-C(O)—$C_{0-3}$alkyl-, —$C_{0-3}$alkyl-NH—$SO_2$—$C_{0-3}$alkyl-, —$C_{0-3}$alkyl-, —$C_{0-3}$alkyl-S—$C_{0-3}$alkyl-, —$C_{0-3}$alkyl-$SO_2$—$C_{0-3}$alkyl-, —$C_{0-3}$alkyl-PH—$C_{0-3}$alkyl-, —$C_{0-3}$alkyl-C(O)—$C_{0-3}$alkyl, or a direct bond;
D is CH;
$E^1$ is CH, N, or $CR^6$; or B and $E^1$ form —CH=C<;
$E^2$ is $CH_2$, CHR, C(OH)R NH, NR, O, S, —S(O)—, or —S(O)$_2$—;
$G^1$ is N, CH, or C($C_{1-3}$alkyl);
$G^2$ is N, CH, or C($C_{1-3}$alkyl);
R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;
or $R^7$ together with a bond from an absent ring hydrogen is =O;
n'+n"=n;
m'+m"=m;
n is 1, 2, 3, or 4;
m is 0, 1, 2, 3, or 4;
n+m is 2, 3, 4, 5, or 6;
p is 0, 1, 2, or 3;
$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);
$R^5$ and $R^{55}$ independently is H, $CH_3$, $CH_2CH_3$, or absent; $R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;
$R^9$ is —$C_{0-4}$alkyl, or absent; and
any alkyl optionally substituted with 1–6 independent halogen or —OH.

In another embodiment of the fifth aspect, the present invention provides a compound described by the chemical formula (I), or a pharmaceutically acceptable salt thereof, wherein
Non-Ar-Cyc is

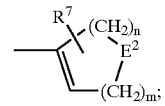

A is CH;
B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, —$C_{0-3}$alkyl-N($C_{0-3}$alkyl)-C(O)—$C_{0-3}$alkyl-, —$C_{0-3}$alkyl-NH—$SO_2$—$C_{0-3}$alkyl-, —$C_{0-3}$alkyl-, —$C_{0-3}$alkyl-S—$C_{0-3}$alkyl-, —$C_{0-3}$alkyl-, —$C_{0-3}$alkyl-$SO_2$—$C_{0-3}$alkyl-, —$C_{0-3}$alkyl-PH—$C_{0-3}$alkyl-, —$C_{0-3}$alkyl-C(O)—$C_{0-3}$alkyl, or a direct bond;
D is CH;
$E^1$ is CH, N, or $CR^6$; or B and $E^1$ form —CH=C<;
$E^2$ is $CH_2$, CHR, C(OH)R NH, NR, O, S, —S(O)—, or —S(O)$_2$—;
$G^1$ is N, CH, or C($C_{1-3}$alkyl);
$G^2$ is N, CH, or C($C_{1-3}$alkyl);
R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;
or $R^7$ together with a bond from an absent ring hydrogen is =O;
n'+n"=n;
m'+m"=m;
n is 1, 2, 3, or 4;
m is 0, 1, 2, 3, or 4;
n+m is 2, 3, 4, 5, or 6;
p is 0, 1, 2, or 3;
$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);
$R^5$ and $R^{55}$ independently is H, $CH_3$, $CH_2CH_3$, or absent; $R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;
$R^9$ is —$C_{0-4}$alkyl, or absent; and
any alkyl optionally substituted with 1–6 independent halogen or —OH.

In an embodiment of the fifth aspect, the present invention provides a compound described by the chemical formula (I), or a pharmaceutically acceptable salt thereof, wherein Non-Ar-Cyc is

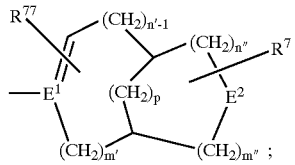

A is CH;

B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, —$C_{0-3}$alkyl-N($C_{0-3}$alkyl)-C(O)—$C_{0-3}$alkyl-, —$C_{0-3}$alkyl-NH—$SO_2$—$C_{0-3}$alkyl-, —$C_{0-3}$alkyl-, —$C_{0-3}$alkyl-S—$C_{0-3}$alkyl-, —$C_{0-3}$alkyl-$SO_2$—$C_{0-3}$alkyl-, —$C_{0-3}$alkyl-PH—$C_{0-3}$alkyl-, —$C_{0-3}$alkyl-C(O)—$C_{0-3}$alkyl, or a direct bond;

D is CH;

$E^1$ is CH, N, or $CR^6$; or B and $E^1$ form —CH=C<;

$E^2$ is $CH_2$, CHR, C(OH)R NH, NR, O, S, —S(O)—, or —$S(O)_2$—;

$G^1$ is N, CH, or C($C_{1-3}$alkyl);

$G^2$ is N, CH, or C($C_{1-3}$alkyl);

R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;

or $R^7$ together with a bond from an absent ring hydrogen is =O;

n'+n"=n;

m'+m"=m;

n is 1, 2, 3, or 4;

m is 0, 1, 2, 3, or 4;

n+m is 2, 3, 4, 5, or 6;

p is 0, 1, 2, or 3;

$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);

$R^5$ and $R^{55}$ independently is H, $CH_3$, $CH_2CH_3$, or absent;

$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;

$R^9$ is —$C_{0-4}$alkyl, or absent; and any alkyl optionally substituted with 1–6 independent halogen or —OH.

In an embodiment of the fifth aspect, the present invention provides a compound described by the chemical formula (I), or a pharmaceutically acceptable salt thereof, wherein Non-Ar-Cyc is

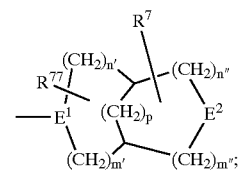

A is CH;

B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, —$C_{0-3}$alkyl-N($C_{0-3}$alkyl)C(O)—$C_{0-3}$alkyl-, —$C_{0-3}$alkyl-NH—$SO_2$—$C_{0-3}$alkyl-, —$C_{0-3}$alkyl-, —$C_{0-3}$alkyl-S—$C_{0-3}$alkyl-, —$C_{0-3}$alkyl-$SO_2$—$C_{0-3}$alkyl-, —$C_{0-3}$alkyl-PH—$C_{0-3}$alkyl-, —$C_{0-3}$alkyl-C(O)—$C_{0-3}$alkyl, or a direct bond;

D is CH;

$E^1$ is CH, N, or $CR^6$; or B and $E^1$ form —CH=C<;

$E^2$ is $CH_2$, CHR, C(OH)R NH, NR, O, S, —S(O)—, or —$S(O)_2$—;

$G^1$ is N, CH, or C($C_{1-3}$alkyl);

$G^2$ is N, CH, or C($C_{1-3}$alkyl);

R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;

or $R^7$ together with a bond from an absent ring hydrogen is =O;

n'+n"=n;

m'+m"=m;

n is 1, 2, 3, or 4;

m is 0, 1, 2, 3, or 4;.

n+m is 2, 3, 4, 5, or 6;

p is 0, 1, 2, or 3;

$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);

$R^5$ and $R^{55}$ independently is H, $CH_3$, $CH_2CH_3$, or absent;

$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;

$R^9$ is —$C_{0-4}$alkyl, or absent; and any alkyl optionally substituted with 1–6 independent halogen or —OH.

In a sixth aspect, the present invention provides a compound described by the chemical formula (I), or a pharmaceutically acceptable salt thereof, wherein Non-Ar-Cyc is

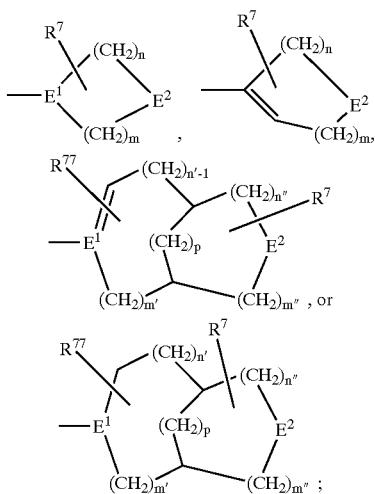

A is CH;
B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, —$C_{0-3}$alkyl-N($C_{0-3}$alkyl)-C(O)—$C_{0-3}$alkyl-, —$C_{0-3}$alkyl-NH—SO$_2$—$C_{0-3}$alkyl-, —$C_{0-3}$alkyl-, —$C_{0-3}$alkyl-S—$C_{0-3}$alkyl-, —$C_{0-3}$alkyl-SO$_2$—$C_{0-3}$alkyl-, —$C_{0-3}$alkyl-PH—$C_{0-3}$alkyl-, —$C_{0-3}$alkyl-C(O)—$C_{0-3}$alkyl, or a direct bond;
D is CH;
$E^1$ is CH, N, or $CR^6$; or B and $E^1$ form —CH=C<;
$E^2$ is CH$_2$, CHR, C(OH)R NH, NR, O, S, —S(O)—, or —S(O)$_2$—;
$G^1$ is N;
$G^2$ is N, CH, or C($C_{1-3}$alkyl);
R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;
or $R^7$ together with a bond from an absent ring hydrogen is =O;
n'+n"=n;
m'+m"=m;
n is 1, 2, 3, or 4;
m is 0, 1, 2, 3, or 4;
n+m is 2, 3, 4, 5, or 6;
p is 0, 1, 2, or 3;
$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);
$R^5$ and $R^{55}$ independently is H, CH$_3$, CH$_2$CH$_3$, or absent;
$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;
$R^9$ is —$C_{0-4}$alkyl, or absent; and
any alkyl optionally substituted with 1–6 independent halogen or —OH.

In an embodiment of the sixth aspect, the present invention provides a compound described by the chemical formula (I), or a pharmaceutically acceptable salt thereof, wherein
Non-Ar-Cyc is

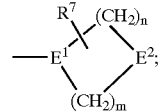

A is CH;
B is —$C_{1-6}$alkyl-, —CO$_3$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, —$C_{0-3}$alkyl-N($C_{0-3}$alkyl)-C(O)—$C_{0-3}$alkyl-, —$C_{0-3}$alkyl-NH-SO$_2$—$C_{0-3}$alkyl-, —$C_{0-3}$alkyl-, —$C_{0-3}$alkyl-S—$C_{0-3}$alkyl-, —$C_{0-3}$alkyl-SO$_2$—$C_{0-3}$alkyl-, —$C_{0-3}$alkyl-PH—$C_{0-3}$alkyl-, —$C_{0-3}$alkyl-C(O)—$C_{0-3}$alkyl, or a direct bond;
D is CH;
$E^1$ is CH, N, or $CR^6$; or B and $E^1$ form —CH=C<;
$E^2$ is CH$_2$, CHR, C(OH)R NH, NR, O, S, —S(O)—, or —S(O)$_2$—;
$G^1$ is N;
$G^2$ is N, CH, or C($C_{1-3}$alkyl);
R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;
or $R^7$ together with a bond from an absent ring hydrogen is =O;
n'+n"=n;
m'+m"=m;
n is 1, 2, 3, or 4;
m is 0, 1, 2, 3, or 4;
n+m is 2, 3, 4, 5, or 6;
p is 0, 1, 2, or 3;
$R^1$, $R^2$, $R^3$, $R^4$, and $R^6$ are each independently halogen, $C_{0-4}$alkyl, —C(O)—O($C_{0-4}$alkyl), or —C(O)—($C_{0-4}$alkyl)($C_{0-4}$alkyl);
$R^5$ and $R^{55}$ independently is H, CH$_3$, CH$_2$CH$_3$, or absent;
$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;
$R^9$ is —$C_{0-4}$alkyl, or absent; and
any alkyl optionally substituted with 1–6 independent halogen or —OH.

In still another embodiment of the fifth aspect, the present invention provides a compound described by the chemical formula (I), or a pharmaceutically acceptable salt thereof, wherein Non-Ar-Cyc is

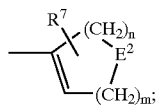

A is CH;

B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, —$C_{0-3}$alkyl-N($C_{0-3}$alkyl)-C(O)—$C_{0-3}$alkyl-, —$C_{0-3}$alkyl-NH—$SO_2$—$C_{0-3}$alkyl-, —$C_{0-3}$alkyl-, —$C_{0-3}$alkyl-S—$C_{0-3}$alkyl-, —$C_{0-3}$alkyl-$SO_2$—$C_{0-3}$alkyl-, —$C_{0-3}$alkyl-PH—$C_{0-3}$alkyl-, —$C_{0-3}$alkyl-C(O)—$C_{0-3}$alkyl, or a direct bond;

D is CH;

$E^1$ is CH, N, or $CR^6$; or B and $E^1$ form —CH═C<;

$E^2$ is $CH_2$, CHR, C(OH)R NH, NR, O, S, —S(O)—, or —$S(O)_2$—;

$G^1$ is N;

$G^2$ is N, CH, or C($C_{1-3}$alkyl);

R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;

or $R^7$ together with a bond from an absent ring hydrogen is ═O;

n'+n"=n;

m'+m"=m;

n is 1, 2, 3, or 4;

m is 0, 1, 2, 3, or 4;

n+m is 2, 3, 4, 5, or 6;

p is 0, 1, 2, or 3;

$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);

$R^5$ and $R^{55}$ independently is H, $CH_3$, $CH_2CH_3$, or absent;

$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;

$R^9$ is —$C_{0-4}$alkyl, or absent; and any alkyl optionally substituted with 1–6 independent halogen or —OH.

In another embodiment of the fifth aspect, the present invention provides a compound described by the chemical formula (I), or a pharmaceutically acceptable salt thereof, wherein Non-Ar-Cyc is

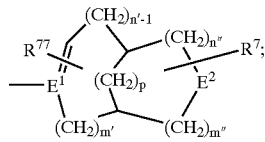

A is CH;

B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, —$C_{0-3}$alkyl-N($C_{0-3}$alkyl)-C(O)—$C_{0-3}$alkyl-, —$C_{0-3}$alkyl-NH—$SO_2$—$C_{0-3}$alkyl-, —$C_{0-3}$alkyl-, —$C_{0-3}$alkyl-S—$C_{0-3}$alkyl-, —$C_{0-3}$alkyl-$SO_2$—$C_{0-3}$alkyl-, —$C_{0-3}$alkyl-PH—$C_{0-3}$alkyl-, —$C_{0-3}$alkyl-C(O)—$C_{0-3}$alkyl-, or a direct bond;

D is CH;

$E^1$ is CH, N, or $CR^6$; or B and $E^1$ form —CH═C<;

$E^2$ is $CH_2$, CHR, C(OH)R NH, NR, O, S, —S(O)—, or —$S(O)_2$—;

$G^1$ is N;

$G^2$ is N, CH, or C($C_{1-3}$alkyl);

R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)—($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;

or $R^7$ together with a bond from an absent ring hydrogen is ═O;

n'+n"=n;

m'+m"=m;

n is 1, 2, 3, or 4;

m is 0, 1, 2, 3, or 4;

n+m is 2, 3, 4, 5, or 6;

p is 0, 1, 2, or 3;

$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);

$R^5$ and $R^{55}$ independently is H, $CH_3$, $CH_2CH_3$, or absent;

$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;

$R^9$ is —$C_{0-4}$alkyl, or absent; and any alkyl optionally substituted with 1–6 independent halogen or —OH.

In yet another embodiment of the fifth aspect, the present invention provides a compound described by the chemical formula (I), or a pharmaceutically acceptable salt thereof, wherein Non-Ar-Cyc is

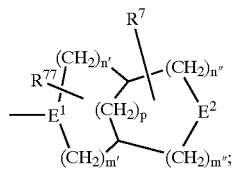

A is CH;

B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, —$C_{0-3}$alkyl-N($C_{0-3}$alkyl)-C(O)—$C_{0-3}$alkyl, —$C_{0-3}$alkyl-NH—$SO_2$—$C_{0-3}$alkyl-, —$C_{0-3}$alkyl-, —$C_{0-3}$alkyl-S—$C_{0-3}$alkyl-, —$C_{0-3}$alkyl-$SO_2$—$C_{0-3}$alkyl-, —$C_{0-3}$alkyl-PH—$C_{0-3}$alkyl-, —$C_{0-3}$alkyl-C(O)—$C_{0-3}$alkyl, or a direct bond;

D is CH;

$E^1$ is CH, N, or $CR^6$; or B and $E^1$ form —CH=C<;

$E^2$ is $CH_2$, CHR, C(OH)R NH, NR, O, S, —S(O)—, or —$S(O)_2$—;

$G^1$ is N;

$G^2$ is N, CH, or C($C_{1-3}$alkyl);

R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;

or $R^7$ together with a bond from an absent ring hydrogen is =O;

n'+n"=n;
m'+m"=m;
n is 1, 2, 3, or 4;
m is 0, 1, 2, 3, or 4;
n+m is 2, 3, 4, 5, or 6;
p is 0, 1, 2, or 3;

$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);

$R^5$ and $R^{55}$ independently is H, $CH_3$, $CH_2CH_3$, or absent;

$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;

$R^9$ is —$C_{0-4}$alkyl, or absent; and any alkyl optionally substituted with 1–6 independent halogen or —OH.

In a seventh aspect, the present invention provides a compound described by the chemical formula (I), or a pharmaceutically acceptable salt thereof, wherein Non-Ar-Cyc is

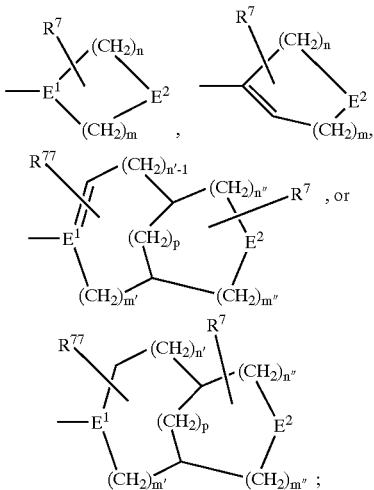

A is CH;

B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, —$C_{0-3}$alkyl-N($C_{0-3}$alkyl)-C(O)—$C_{0-3}$alkyl-, —$C_{0-3}$alkyl-NH—$SO_2$—$C_{0-3}$alkyl-, —$C_{0-3}$alkyl-, —$C_{0-3}$alkyl-S—$C_{0-3}$alkyl-, —$C_{0-3}$alkyl-$SO_2$—$C_{0-3}$alkyl-, —$C_{0-3}$alkyl-PH—$C_{0-3}$alkyl-, —$C_{0-3}$alkyl-C(O)—$C_{0-3}$alkyl, or a direct bond;

D is CH;

$E^1$ is CH, N, or $CR^6$; or B and $E^1$ form —CH=C<;

$E^2$ is $CH_2$, CHR, C(OH)R NH, NR, O, S, —S(O)—, or —$S(O)_2$—;

$G^1$ is N, CH, or C($C_{1-3}$alkyl);

$G^2$ is N;

R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;

or $R^7$ together with a bond from an absent ring hydrogen is =O;

n'+n"=n;
m'+m"=m;
n is 1, 2, 3, or 4;
m is 0, 1, 2, 3, or 4;
n+m is 2, 3, 4, 5, or 6;
p is 0, 1, 2, or 3;

$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);

$R^5$ and $R^{55}$ independently is H, $CH_3$, $CH_2CH_3$, or absent;

$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$CO_{0-4}$alkyl-;

$R^9$ is —$C_{0-4}$alkyl, or absent; and any alkyl optionally substituted with 1–6 independent halogen or —OH.

In an embodiment of the seventh aspect, the present invention provides a compound described by the chemical formula (I), or a pharmaceutically acceptable salt thereof, wherein Non-Ar-Cyc is

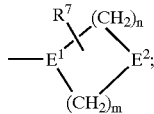

A is CH;

B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, —$C_{0-3}$alkyl-N($C_{0-3}$alkyl)-C(O)—$C_{0-3}$alkyl-, —$C_{0-3}$alkyl-NH—SO$_2$—$C_{0-3}$alkyl-, —$C_{0-3}$alkyl-, —$C_{0-3}$alkyl-S—$C_{0-3}$alkyl-, —$C_{0-3}$alkyl-SO$_2$—$C_{0-3}$alkyl-, —$C_{0-3}$alkyl-PH—$C_{0-3}$alkyl-, —$C_{0-3}$alkyl-C(O)—$C_{0-3}$alkyl, or a direct bond;

D is CH;

$E^1$ is CH, N, or $CR^6$; or B and $E^1$ form —CH═C<;

$E^2$ is CH$_2$, CHR, C(OH)R NH, NR, O, S, —S(O)—, or —S(O)$_2$—;

$G^1$ is N, CH, or C($C_{1-3}$alkyl);

$G^2$ is N;

R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;

or $R^7$ together with a bond from an absent ring hydrogen is ═O;

n'+n"=n;

m'+m"=m;

n is 1, 2, 3, or 4;

m is 0, 1, 2, 3, or 4;

n+m is 2, 3, 4, 5, or 6;

p is 0, 1, 2, or 3;

$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);

$R^5$ and $R^{55}$ independently is H, CH$_3$, CH$_2$CH$_3$, or absent;

$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;

$R^9$ is —$C_{0-4}$alkyl, or absent; and any alkyl optionally substituted with 1–6 independent halogen or —OH.

In an embodiment of the seventh aspect, the present invention provides a compound described by the chemical formula (I), or a pharmaceutically acceptable salt thereof, wherein Non-Ar-Cyc is

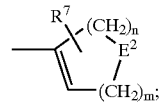

A is CH;

B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, —$C_{0-3}$alkyl-N($C_{0-3}$alkyl)-C(O)—$C_{0-3}$alkyl-, —$C_{0-3}$alkyl-NH—SO$_2$—$C_{0-3}$alkyl-, —$C_{0-3}$alkyl-, —$C_{0-3}$alkyl-S—$C_{0-3}$alkyl-, —$C_{0-3}$alkyl-SO$_2$—$C_{0-3}$alkyl-, —$C_{0-3}$alkyl-PH—$C_{0-3}$alkyl-, —$C_{0-3}$alkyl-C(O)—$C_{0-3}$alkyl, or a direct bond;

D is CH;

$E^1$ is CH, N, or $CR^6$; or B and $E^1$ form —CH═C<;

$E^2$ is CH$_2$, CHR, C(OH)R NH, NR, O, S, —S(O)—, or —S(O)$_2$—;

$G^1$ is N, CH, or C($C_{1-3}$alkyl);

$G^2$ is N;

R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;

or $R^7$ together with a bond from an absent ring hydrogen is ═O;

n'+n"=n;

m'+n"=m;

n is 1, 2, 3, or 4;

m is 0, 1, 2, 3, or 4;

n+m is 2, 3, 4, 5, or 6;

p is 0, 1, 2, or 3;

$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);

$R^5$ and $R^{55}$ independently is H, CH$_3$, CH$_2$CH$_3$, or absent;

$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;

$R^9$ is —$C_{0-4}$alkyl, or absent; and any alkyl optionally substituted with 1–6 independent halogen or —OH.

In another embodiment of the seventh aspect, the present invention provides a compound described by the chemical formula (I), or a pharmaceutically acceptable salt thereof, wherein Non-Ar-Cyc is

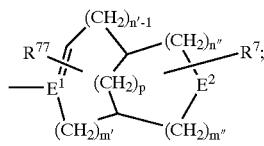

A is CH;
B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, —$C_{0-3}$alkyl-N($C_{0-3}$alkyl)-C(O)—$C_{0-3}$alkyl-, —$C_{0-3}$alkyl-NH—$SO_2$—$C_3$alkyl-, —$C_{0-3}$alkyl-, —$C_{0-3}$alkyl-S—$C_{0-3}$alkyl-, —$C_{0-3}$alkyl-$SO_2$—$C_{0-3}$alkyl-, —$C_{0-3}$alkyl-PH—$C_{0-3}$alkyl-, —$C_{0-3}$alkyl-C(O)—$C_{0-3}$alkyl, or a direct bond;
D is CH;
$E^1$ is CH, N, or $CR^6$; or B and $E^1$ form —CH=C<;
$E^2$ is $CH_2$, CHR, C(OH)R NH, NR, O, S, —S(O)—, or —$S(O)_2$—;
$G^1$ is N, CH, or C($C_{1-3}$alkyl);
$G^2$ is N;
R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;
or $R^7$ together with a bond from an absent ring hydrogen is =O;
n'+n"=n;
m'+m"=m;
n is 1, 2, 3, or 4;
m is 0, 1, 2, 3, or 4;
n+m is 2, 3, 4, 5, or 6;
p is 0, 1, 2, or 3;
$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);
$R^5$ and $R^{55}$ independently is H, $CH_3$, $CH_2CH_3$, or absent;
$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;
$R^9$ is —$C_{0-4}$alkyl, or absent; and
any alkyl optionally substituted with 1–6 independent halogen or —OH.

In still another embodiment of the seventh aspect, the present invention provides a compound described by the chemical formula (I), or a pharmaceutically acceptable salt thereof, wherein Non-Ar-Cyc is

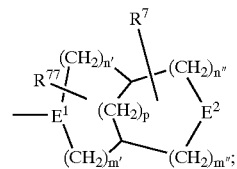

A is CH;
B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, —$C_{0-3}$alkyl-N($C_{0-3}$alkyl)-C(O)—$C_{0-3}$alkyl-, —$C_{0-3}$alkyl-NH—$SO_2$—$C_{0-3}$alkyl-, —$C_{0-3}$alkyl-, —$C_{0-3}$alkyl-S—$C_{0-3}$alkyl-, —$C_{0-3}$alkyl-$SO_2$—$C_{0-3}$alkyl-, —$C_{0-3}$alkyl-PH—$C_{0-3}$alkyl-, —$C_{0-3}$alkyl-C(O)—$C_{0-3}$alkyl, or a direct bond;
D is CH;
$E^1$ is CH, N, or $CR^6$; or B and $E^1$ form —CH=C<;
$E^2$ is $CH_2$, CHR, C(OH)R NH, NR, O, S, —S(O)—, or —$S(O)_2$—;
$G^1$ is N, CH, or C($C_{1-3}$alkyl);
$G^2$ is N;
R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;
or $R^7$ together with a bond from an absent ring hydrogen is =O;
n'+n"=n;
m'+m"=m;
n is 1, 2, 3, or 4;
m is 0, 1, 2, 3, or 4;
n+m is 2, 3, 4, 5, or 6;
p is 0, 1, 2, or 3;
$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);
$R^5$ and $R^{55}$ independently is H, $CH_3$, $CH_2CH_3$, or absent;
$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;
$R^9$ is —$C_{0-4}$alkyl, or absent; and
any alkyl optionally substituted with 1–6 independent halogen or —OH.

In an eighth aspect, the present invention provides a compound described by the chemical formula (I), or a pharmaceutically acceptable salt thereof, wherein Non-Ar-Cyc is

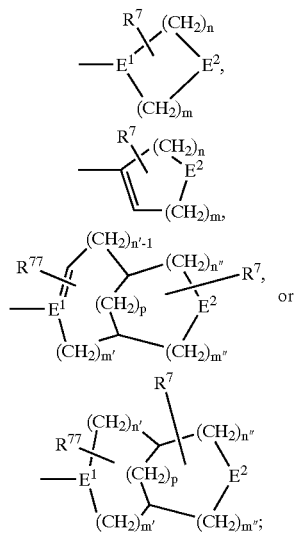

A is CH;
B is —$C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, —$C_{0-3}$alkyl-N($C_{0-3}$alkyl)-C(O)—$C_{0-3}$alkyl-, —$C_{0-3}$alkyl-NH—$SO_2$—$C_{0-3}$alkyl-, —$C_{0-3}$alkyl-, —$C_{0-3}$alkyl-S—$C_{0-3}$alkyl-, —$C_{0-3}$alkyl-$SO_2$—$C_{0-3}$alkyl-, —$C_{0-3}$alkyl-PH—$C_{0-3}$alkyl-, —$C_{0-3}$alkyl-C(O)—$C_{0-3}$alkyl, or a direct bond;

D is CH, and A and D are bridged by —$C_{1-4}$alkyl- to form a fused bicyclo ring with A and D at the bicyclo cusps;

$E^1$ is CH, N, or $CR^6$; or B and $E^1$ form —CH=C<;
$E^2$ is $CH_2$, CHR, C(OH)R NH, NR, O, S, —S(O)—, or —S(O)$_2$—;
$G^1$ is N, CH, or C($C_{1-3}$alkyl);
$G^2$ is N, CH, or C($C_{1-3}$alkyl);

R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;

or $R^7$ together with a bond from an absent ring hydrogen is =O;
n'+n"=n;
m'+m"=m;
n is 1, 2, 3, or 4;
m is 0, 1, 2, 3, or 4;
n+m is 2, 3, 4, 5, or 6;
p is 0, 1, 2, or 3;
$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);

$R^5$ and $R^{55}$ independently is H, $CH_3$, $CH_2CH_3$, or absent;
$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;
$R^9$ is —$C_{0-4}$alkyl, or absent; and
any alkyl optionally substituted with 1–6 independent halogen or —OH.

In a ninth aspect, the present invention provides a compound described by the chemical formula (I), or a pharmaceutically acceptable salt thereof, wherein Non-Ar-Cyc is

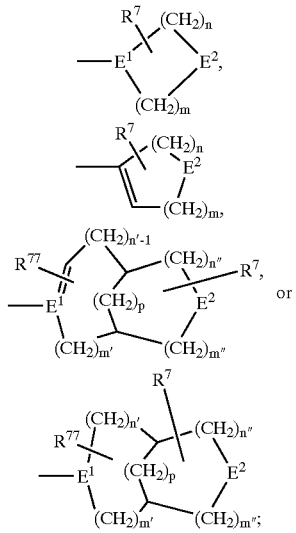

A is $CH_2$;
B is $C_{1-6}$alkyl-, —$C_{0-3}$alkyl-O—$C_{0-3}$alkyl-, —$C_{0-3}$alkyl-NH—$C_{0-3}$alkyl-, —$C_{0-3}$alkyl-NH—$C_{3-7}$cycloalkyl-, —$C_{0-3}$alkyl-N($C_{0-3}$alkyl)-C(O)—$C_{0-3}$alkyl-, —$C_{0-3}$alkyl-NH—$SO_2$—$C_{0-3}$alkyl-, —$C_{0-3}$alkyl-, —$C_{0-3}$alkyl-S—$C_{0-3}$alkyl-, —$C_{0-3}$alkyl-$SO_2$—$C_{0-3}$alkyl-, —$C_{0-3}$alkyl-PH—$C_{0-3}$alkyl-, —$C_{0-3}$alkyl-C(O)—$C_{0-3}$alkyl, or a direct bond;
D is $CH_2$;
$E^1$ is CH, N, or $CR^6$; or B and $E^1$ form —CH=C<;
$E^2$ is $CH_2$, CHR, C(OH)R NH, NR, O, S, —S(O)—, or —S(O)$_2$—;
$G^1$ is N, CH, or C($C_{1-3}$alkyl);
$G^2$ is N;

R, $R^7$ and $R^{77}$ each independently is hydrogen, $C_{1-6}$alkyl-group, $C_{2-6}$alkenyl-group, $C_{4-6}$cycloalkyl-$C_{0-6}$alkyl-group, N($C_{0-4}$alkyl)($C_{0-4}$alkyl)-$C_{1-4}$alkyl-N($C_{0-4}$alkyl)-group, —N($C_{0-4}$alkyl)($C_{0-4}$alkyl) group, $C_{1-3}$alkyl-CO—$C_{0-4}$alkyl-group, $C_{0-6}$alkyl-O—C(O)—$C_{0-4}$alkyl-group, $C_{0-6}$alkyl-C(O)—O—$C_{0-4}$alkyl-group, N($C_{0-4}$alkyl)($C_{0-4}$alkyl)-($C_{0-4}$alkyl)C(O)($C_{0-4}$alkyl)-group, phenyl-$C_{0-4}$alkyl-group, pyridyl-$C_{0-4}$alkyl-group, pyrimidinyl-$C_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;

or $R^7$ together with a bond from an absent ring hydrogen is =O;
n'+n"=n;
m'+m"=m;

n is 1, 2, 3, or 4;
m is 0, 1, 2, 3, or 4;
n+m is 2, 3, 4, 5, or 6;
p is 0, 1, 2, or 3;
$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl);
$R^5$ and $R^{55}$ independently is H, $CH_3$, $CH_2CH_3$, or absent;
$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3-dioxolan-2-yl-$C_{0-4}$alkyl-;
$R^9$ is —$C_{0-4}$alkyl, or absent; and
any alkyl optionally substituted with 1–6 independent halogen or —OH.

As used herein, "alkyl" as well as other groups having the prefix "alk" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains containing at least one unsaturated C—C bond.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantane, indanyl, indenyl, fluorenyl, 1,2,3,4-tetrahydronaphthalene and the like. Similarly, "cycloalkenyl" means carbocycles containing no heteroatoms and at least one non-aromatic C—C double bond, and include mono-, bi- and tricyclic partially saturated carbocycles, as well as benzofused cycloalkenes. Examples of cycloalkenyl include cyclohexenyl, indenyl, and the like.

The term "aryl" means an aromatic substituent which is a single ring or multiple rings fused together. When formed of multiple rings, at least one of the constituent rings is aromatic. The preferred aryl substituents are phenyl and naphthyl groups.

The term "cycloalkyloxy" unless specifically stated otherwise includes a cycloalkyl group connected by a short $C_{1-2}$alkyl length to the oxy connecting atom.

The term "$C_{0-6}$alkyl" includes alkyls containing 6, 5, 4, 3, 2, 1, or no carbon atoms. An alkyl with no carbon atoms is a hydrogen atom substituent when the alkyl is a terminal group and is a direct bond when the alkyl is a bridging group.

The term "hetero" unless specifically stated otherwise includes one or more O, S, or N atoms. For example, heterocycloalkyl and heteroaryl include ring systems that contain one or more O, S, or N atoms in the ring, including mixtures of such atoms. The hetero atoms replace ring carbon atoms. Thus, for example, a heterocyclo$C_5$alkyl is a five-member ring containing from 4 to no carbon atoms. Examples of heteroaryls include pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, benzoxazolyl, isoxazolyl, thiazolyl, benzothiazolyl, isothiazolyl, imidazolyl, benzimidazolyl, oxadiazolyl, thiadiazolyl, triazolyl, and tetrazolyl. Examples of heterocycloalkyls include azetidinyl, pyrrolidinyl, piperidinyl, piperazinyl, morpholinyl, tetrahydrofuranyl, imidazolinyl, pyrolidin-2-one, piperidin-2-one, and thiomorpholinyl.

The term "hetero$C_{0-4}$alkyl" means a heteroalkyl containing 3, 2, 1, or no carbon atoms. However, at least one heteroatom must be present. Thus, as an example, a hetero$C_{0-4}$alkyl having no carbon atoms but one N atom would be a —NH— if a bridging group and a —$NH_2$ if a terminal group. Analogous bridging or terminal groups are clear for an O or S heteroatom.

The term "amine" unless specifically stated otherwise includes primary, secondary and tertiary amines substituted with $C_{0-6}$alkyl.

The term "carbonyl" unless specifically stated otherwise includes a $C_{0-6}$alkyl substituent group when the carbonyl is terminal. That is, "carbonyl" means —C(O)—$C_{0-6}$alkyl unless otherwise stated.

The term "halogen" includes fluorine, chlorine, bromine and iodine atoms.

The term "optionally substituted" is intended to include both substituted and unsubstituted. Thus, for example, optionally substituted aryl could represent a pentafluorophenyl or a phenyl ring. When a group has an optional substituent, that optional substituent can be on any of the sites readily determined and understood by chemists. That is, for example, a substituent on a cyclopropyl-$C_{1-4}$alkyl group can be on the cyclopropyl or on the $C_{1-4}$alkyl. Further, optionally substituted multiple moieties such as, for example, alkylaryl are intended to mean that the aryl and the aryl groups are optionally substituted. If only one of the multiple moieties is optionally substituted then it will be specifically recited such as "an alkylaryl, the aryl optionally substituted with halogen or hydroxyl."

Compounds described herein contain one or more double bonds and may thus give rise to cis/trans isomers as well as other conformational isomers. The present invention includes all such possible isomers as well as mixtures of such isomers unless specifically stated otherwise.

Compounds described herein can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

Unless specifically stated otherwise or indicated by a bond symbol (dash or double dash), the connecting point to a recited group will be on the right-most stated group. That is, for example, a phenylalkyl group is connected to the main structure through the alkyl and the phenyl is a substituent on the alkyl.

The compounds of the present invention are useful in various pharmaceutically acceptable salt forms. The term "pharmaceutically acceptable salt" refers to those salt forms which would be apparent to the pharmaceutical chemist. i.e., those which are substantially non-toxic and which provide the desired pharmacokinetic properties, palatability, absorption, distribution, metabolism or an excretion. Other factors, more practical in nature, which are also important in the selection, are cost of the raw materials, ease of crystallization, yield, stability, hygroscopicity and flowability of the resulting bulk drug. Conveniently, pharmaceutical compositions may be prepared from the active ingredients in combination with pharmaceutically acceptable carriers.

The pharmaceutically acceptable salts of the compounds of formula I include conventional non-toxic salts or quarternary ammonium salts of the compounds of formula I formed e.g. from non-toxic inorganic or organic acids. For example, non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, sulfanilic, 2-acetoxybenzoic, fumaric, toluenesulfonic, methanesulfonic, ethane disulfonic, oxalic, isethionic, trifluoroacetic and the like.

The pharmaceutically acceptable salts of the present invention can be synthesized by conventional chemical methods. Generally, the salts are prepared by reacting the free base or acid with stoichiometric amounts or with an excess of the desired salt-forming inorganic or organic acid or base, in a suitable solvent or solvent combination.

The compounds of the present invention may have asymmetric centers and occur as racemates, racemic mixtures, and as individual diastereomers. All such isomers, including optical isomers, being included in the present invention.

The invention described herein also includes a pharmaceutical composition which is comprised of a compound described by Formula (I), or a pharmaceutically acceptable salt thereof, in combination with a pharmaceutically acceptable carrier. The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. Such additional therapeutic ingredients include, for example, i) leukotriene receptor antagonists, ii) leukotriene biosynthesis inhibitors, iii) corticosteroids, iv) H1 receptor antagonists, v) beta 2 adrenoceptor agonists, vi) COX-2 selective inhibitors, vii) statins, viii) non-steroidal anti-inflammatory drugs ("NSAID"), and ix) M2/M3 antagonists.

The invention described herein also includes a method of treating arthritis which is comprised of administering to a mammalian patient in need of such treatment a compound described by Formula (I), or a pharmaceutically acceptable salt thereof, in an amount which is effective to treat arthritis. The invention includes methods of treating arthritis by administering to a mamalian patient in need of such treatment a compound described by Formula (I), or a pharmaceutically acceptable salt thereof, in combination or in coadministration with a COX-2 inhibitor.

The invention described herein also includes a method of treating a cytokine mediated disease in a mammal, comprising administering to a mammalian patient in need of such treatment an amount of a compound described by Formula (I), or a pharmaceutically acceptable salt thereof, in an amount which is effective to treat said cytokine mediated disease.

Of particular interest is a method of treating inflammation in a mammalian patient in need of such treatment, which is comprised of administering to said patient an anti-inflammatory effective amount of a compound described by Formula (I), or a pharmaceutically acceptable salt thereof.

Another method which is of particular interest is a method of treating a cytokine mediated disease as described herein wherein the disease is osteoporosis.

Another method which is of particular interest is a method of treating a cytokine mediated disease as described herein wherein the disease is non-osteoporotic bone resorption.

Yet another method which is of particular interest is a method of treating a cytokine mediated disease as described herein wherein the disease is Crohn's disease.

This invention also relates to a method of treating arthritis in a mammal in need such treatment, which comprises administering to said mammal an amount of a compound of formula I which is effective for treating arthritis. Such method includes the treatment of rheumatoid and osteoarthritis.

When administered to a patient for the treatment of athritis, the dosage used can be varied depending upon the type of arthritis, the age and general condition of the patient, the particular compound administered, the presence or level of toxicity or adverse effects experienced with the drug, and other factors. A representative example of a suitable dosage range is from as low as about 0.01 mg/kg to as high as about 100 mg/kg. However, the dosage administered is generally left to the discretion of the physician.

This invention also relates to a method of inhibiting the action of p38 in a mammal in need thereof, which comprises administering to said mammal an effective amount of a compound described by Formula (I), or a pharmaceutically acceptable salt thereof, to inhibit said action of p38, down to normal levels, or in some cases to subnormal levels, so as to ameliorate, prevent or treat the disease state.

The compounds of formula I can be used in the prophylactic or therapeutic treatment of disease states in mammals which are exacerbated or caused by excessive or unregulated cytokines, more specifically IL-1, IL-6, IL-8 or TNF.

The compounds of this invention demonstrates efficacy in the assays described below. Efficacy is shown in the assays by results of less than 10 $\mu$M. Advantageously, compounds have results less than 1 $\mu$M. Even more advantageously, compounds have results less than 0.1 $\mu$M. Still more advantageously, compounds have results in the assays of less than 0.01 $\mu$M. Because the compounds of formula I inhibit cytokines, such as IL-1, IL6, IL-8 and TNF, by inhibiting the action of p38 the compounds are useful for treating diseases in which cytokine presence or activity is implicated, such as rheumatoid arthritis, rheumatoid spondylitis, osteoarthritis, gouty arthritis and other arthritic conditions.

The compounds described by Formula (I), or a pharmaceutically acceptable salt thereof, are also useful to treat other disease states mediated by excessive or unregulated TNF production or activity. Such diseases include, but are not limited to sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, such as osteoporosis, reperfusion injury, graft v. host rejection, allograft rejection, fever, myalgia due to infection, cachexia secondary to infection or malignancy, cachexia secondary to acquired immune deficiency syndrome (AIDS), AIDS, ARC (AIDs related complex), keloid formation, scar tissue formation, Crohn's disease, ulcerative colitis, pyresis, AIDS and other viral infections, such as cytomegalovirus (CMV), influenza virus, and the herpes family of viruses such as Herpes Zoster or Simplex I and II.

The compounds described by Formula (I), or a pharmaceutically acceptable salt thereof, are also useful topically in the treatment of inflammation such as in the treatment of rheumatoid arthritis, rheumatoid spondylitis, osteoarthritis, gouty arthritis and other arthritic conditions; inflamed joints, eczema, psoriasis or other inflammatory skin conditions such as sunburn; inflammatory eye conditions including conjunctivitis; pyresis, pain and other conditions associated with inflammation.

The compounds described by Formula (I), or a pharmaceutically acceptable salt thereof, are also useful in treating diseases characterized by excessive IL-8 activity. These disease states include psoriasis, inflammatory bowel disease, asthma, cardiac and renal reperfusion injury, adult respiratory distress syndrome, thrombosis and glomerulonephritis.

The invention thus includes a method of treating psoriasis, inflammatory bowel disease, asthma, cardiac and renal reperfusion injury, adult respiratory distress syndrome, thrombosis and glomerulonephritis, in a mammal in need of such treatment, which comprises administering to said mammal a compound described by Formula (I), or a pharmaceutically acceptable salt thereof, in an amount which is effective for treating said disease or condition.

When administered to a patient for the treatment of a disease in which a cytokine or cytokines are implicated, the dosage used can be varied depending upon the type of disease, the age and general condition of the patient, the particular compound administered, the presence or level of toxicity or adverse effects experienced with the drug, and other factors. A representative example of a suitable dosage range is from as low as about 0.01 mg/kg to as high as about 100 mg/kg. However, the dosage administered is generally left to the discretion of the physician.

The methods of treatment are preferably carried out by delivering the compound of formula I parenterally. The term 'parenteral' as used herein includes intravenous, intramuscular, or intraperitoneal administration. The subcutaneous and intramuscular forms of parenteral administration are generally preferred. The instant invention can also be carried out by delivering the compound of Formula I subcutaneously, intranasally, intrarectally, transdermally or intravaginally.

The compounds of Formula I may also be administered by inhalation. By 'inhalation' is meant intranasal and oral inhalation administration. Appropriate dosage forms for such administration, such as an aerosol formulation or a metered dose inhaler, may be prepared by convention techniques.

The invention also relates to a pharmaceutical composition comprising a compound of formula I and a pharmaceutically acceptable carrier. The compounds of formula I may also be included in pharmaceutical compositions in combination with a second therapeutically active compound.

The pharmaceutical carrier employed may be, for example, either a solid, liquid or gas. Examples of solid carriers include lactose, terra alba, sucrose, talc, gelatin, agar, pectin, acacia, magnesium stearate, stearic acid and the like. Examples of liquid carriers are syrup, peanut oil, olive oil, water and the like. Examples of gaseous carriers include carbon dioxide and nitrogen.

Similarly, the carrier or diluent may include time delay material well known in the art, such as glyceryl monostearate or glyceryl distearate, alone or with a wax.

A wide variety of pharmaceutical dosage forms can be employed. If a solid dosage is used for oral administration, the preparation can be in the form of a tablet, hard gelatin capsule, troche or lozenge. The amount of solid carrier will vary widely, but generally will be from about 0.025 mg to about 1 g. When a liquid dosage form is desired for oral administration, the preparation is typically in the form of a syrup, emulsion, soft gelatin capsule, suspension or solution. When a parenteral dosage form is to be employed, the drug may be in solid or liquid form, and may be formulated for administration directly or may be suitable for reconstitution.

Topical dosage forms are also included. Examples of topical dosage forms are solids, liquids and semi-solids. Solids would include dusting powders, poultices and the like. Liquids include solutions, suspensions and emulsions. Semi-solids include creams, ointments, gels and the like.

The amount of a compound of formula I used topically will, of course, vary with the compound chosen, the nature and severity of the condition, and can be varied in accordance with the discretion of the physician. A representative, topical, dose of a compound of formula I is from as low as about 0.01 mg to as high as about 2.0 g, administered one to four, preferably one to two times daily.

The active ingredient may comprise, for topical administration, from about 0.001% to about 10% w/w.

Drops according to the present invention may comprise sterile or non-sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container aseptically. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous liquid, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surfactant such as sorbitan esters or polyoxyethylene derivatives thereof. Suspending agents such as natural gums, cellulose derivatives or inorganic materials such as silicas, and other ingredients such as lanolin may also be included.

Assays

Protein Expression and Purification.

Murine p38 containing the FLAG epitope tag was expressed in Drosophila S2 cells under transcriptional control of a copper-inducible metallothionein promoter. Expression of recombinant p38 was induced by treating transfected cells with 1 mM $CuSO_4$ for 4 hours. To generate active recombinant murine p38, $CuSO_4$-treated S2 cells were stimulated 10 minutes prior to harvest with 400 mM NaCl, 2 mM $Na_3VO_4$, and 100 μg/L okadaic acid. Cell pellets were washed with phosphate-buffered saline, 2 mM $Na_3VO_4$, and lysed in 20 mM Tris HCl, pH 7.5, 120 mM NaCl, 1% Triton X-100, 2 mM EDTA, 20 mM NaF, 4 mM $Na_3VO_4$, 2 mM Prefabloc SC (Boehringer Mannheim). Cell lysates were centrifuged for 10 min at 13,000×g, and activated, recombinant murine p38 was immunoaffinity purified from the lysate by column chromatography through anti-FLAG M2 resin (Kodak) that had been equilibrated with lysis buffer. After loading the extract the resin was washed with 10 column volumes of lysis buffer, 10 column volumes buffer A (10 mM Tris HCl, pH 7.5, 500 mM NaCl, 20% glycerol) and 10 column volumes of buffer B (10 mM Tris HCl pH 7.5, 150 mM NaCl, 20% glycerol). The fusion protein was eluted in buffer B containing 100 μg/mL FLAG peptide (Kodak).

The N-terminal 115 amino acids of ATF-2 was expressed in E. coli as a fusion protein with glutathione-S-transferase. The fusion protein was purified over glutathione agarose according to standard procedures (Pharmacia).

p38 Kinase Assay.

p38 kinase assays were performed in a reaction volume of 100 μL in a 96-well plate, at 30° for 45–1200 min under the following conditions: 25 mM Hepes, pH 7.4, 10 mM $mgCl_2$, 20 mM β-glycerolphosphate, 2 mM DTT, 5 μM ATP, 10 μCi [γ-$^{33}$P]-ATP and ~2 μM GST-ATF2. Serial dilutions of compounds were added to each reaction in 2 μL DMSO. 2 μL of DMSO was added to the last row of each reaction plate as the no inhibitor control for each inhibitor titration. The reaction was terminated with an equal volume of a stop solution containing 100 mM EDTA and 15 mM sodium pyrophosphate. PVDF filter plates (MAEPNOB50, Millipore) were pre-wet with methanol and washed with the stop solution. 50 μL aliquots from a single reaction were applied to the filter under vacuum, and the filler was washed twice with 75 mM phosphoric acid. The filter plates were counted in a scintillation counter (Top Count, Packard) and the percent inhibition at each compound concentration is determined.

TNF-α Release Assay.

Blood was obtained from healthy volunteers by venipuncture using sodium heparin as an anti-coagulant. Peripheral blood mononuclear cells (PBMCs) were isolated using Lymphocyte Separation Medium (ICN) according to manufacturers specifications. Isolated PBMCs were washed 3 times with HBSS and diluted to a density of 2×10$^6$ cells/mL in RPMI +5% autologous human serum. 50 μL of the serial dilutions of inhibitor were added to wells of a 96-well tissue culture plate followed by addition of 100 μL of PBMCs and then 50 μL of RPMI complete medium containing 400 ng/mL LPS. A control well of cells without compound but with LPS (maximal stimulation control) and one without compound and without LPS (background control) were included in each titration. The cells were incubated for 16 hours in a humidified incubator at 37° C., 5% $CO_2$. Supernatants were then harvested and TNF-α levels were quantified by immunoassay using commercial reagents (R&D, Inc).

The compounds of this invention demonstrated efficacy in the above assays by results of less than 10 μM. Advantageous compounds had results less than 1 μM. Even more advantageous compounds had results less than 0.1 μM. Still more advantageous compounds had results in the assays of less than 0.01 μM.

Compounds described by Formula (IIIA) are less advantageous because such compounds tend to be less stable. Accordingly, such compounds need to be tested for stability and stabilized if appropriate before use.

EXAMPLES

The compounds of the present invention are prepared by the following illustrative schemes:

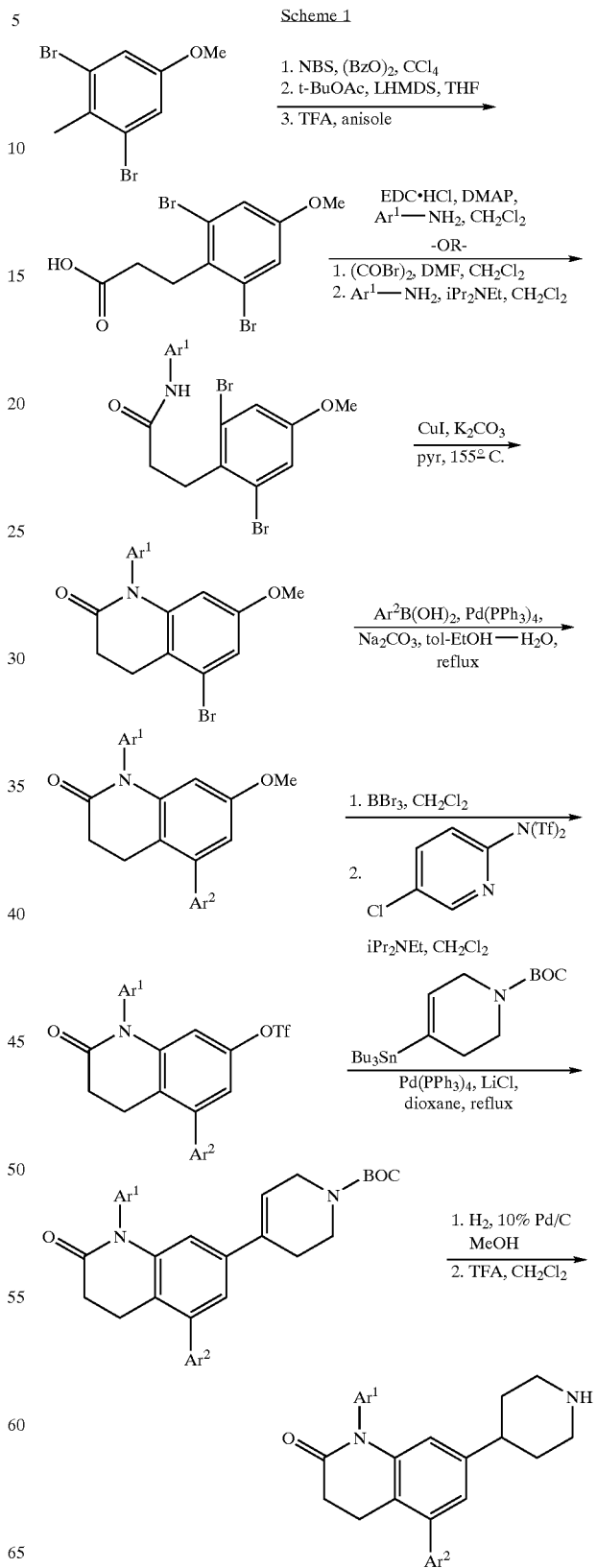

Scheme 1

Scheme 2:
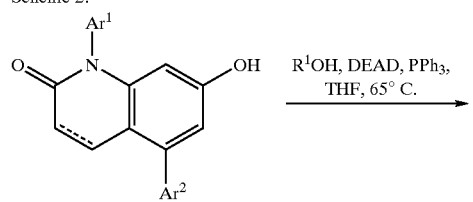
Scheme 3:
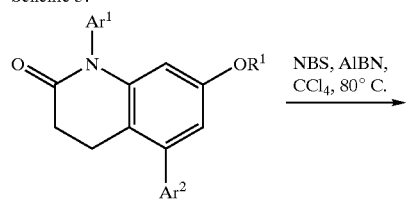
Scheme 4:
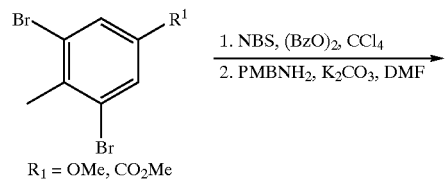
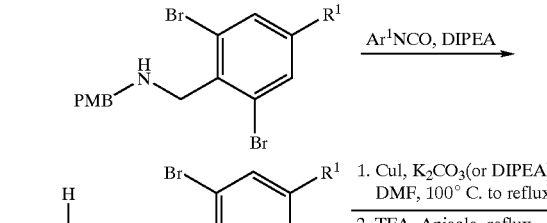
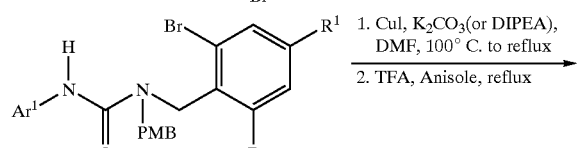
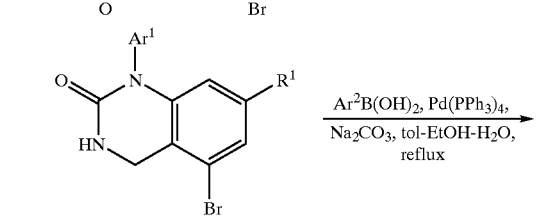
Scheme 5:
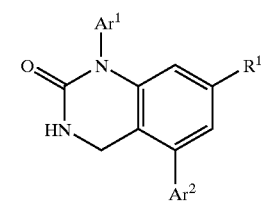
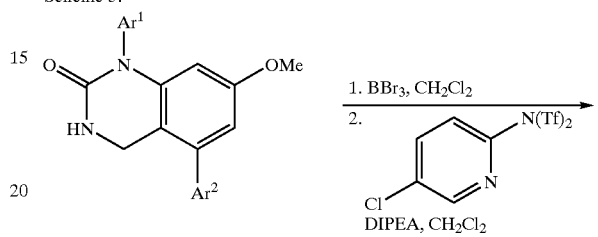
Scheme 6:
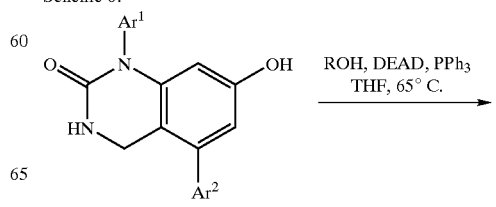

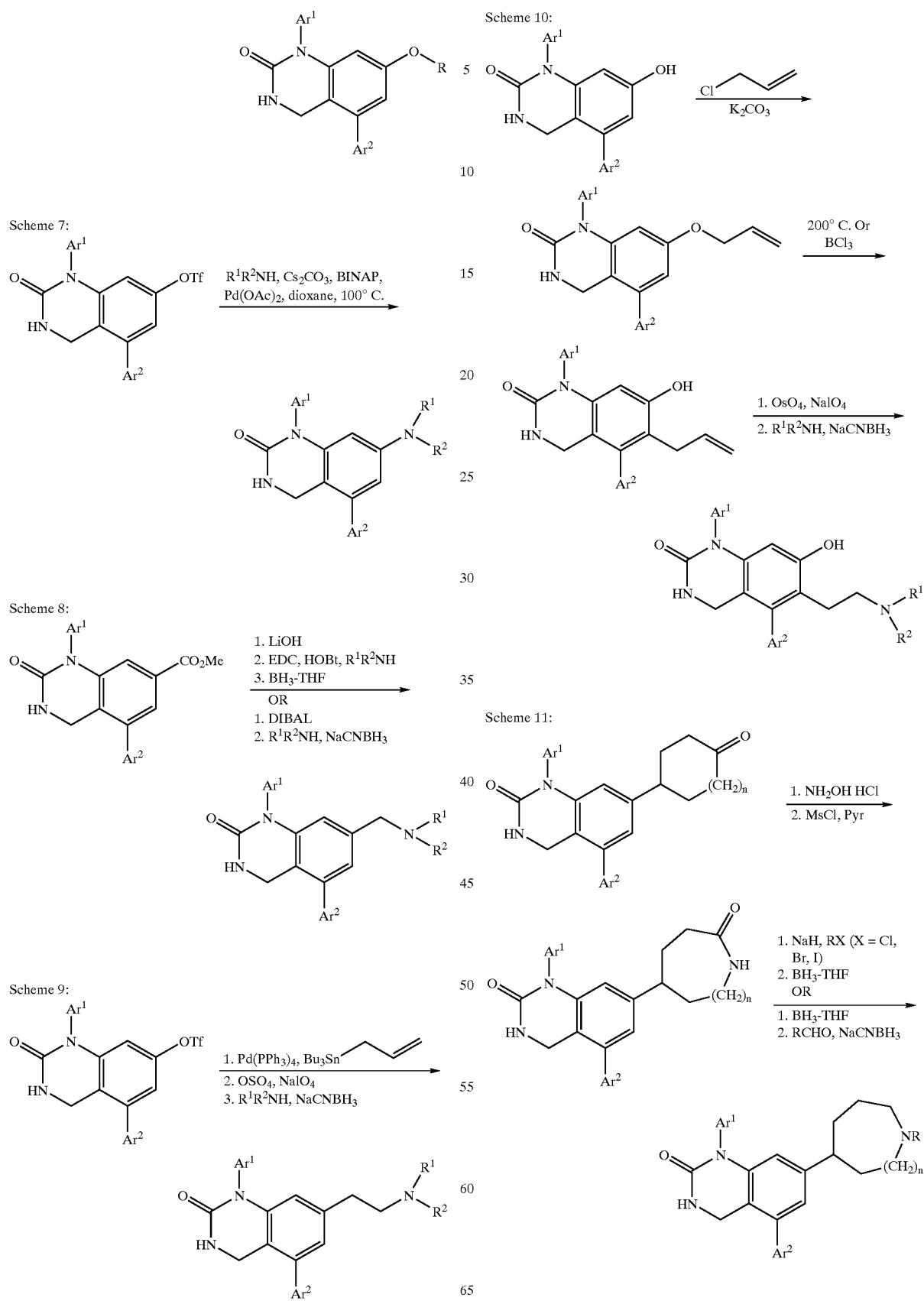

Scheme 12:
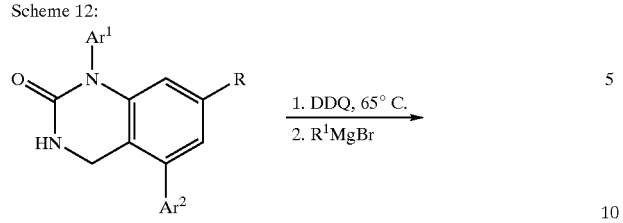
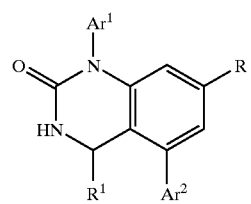
Scheme 13:
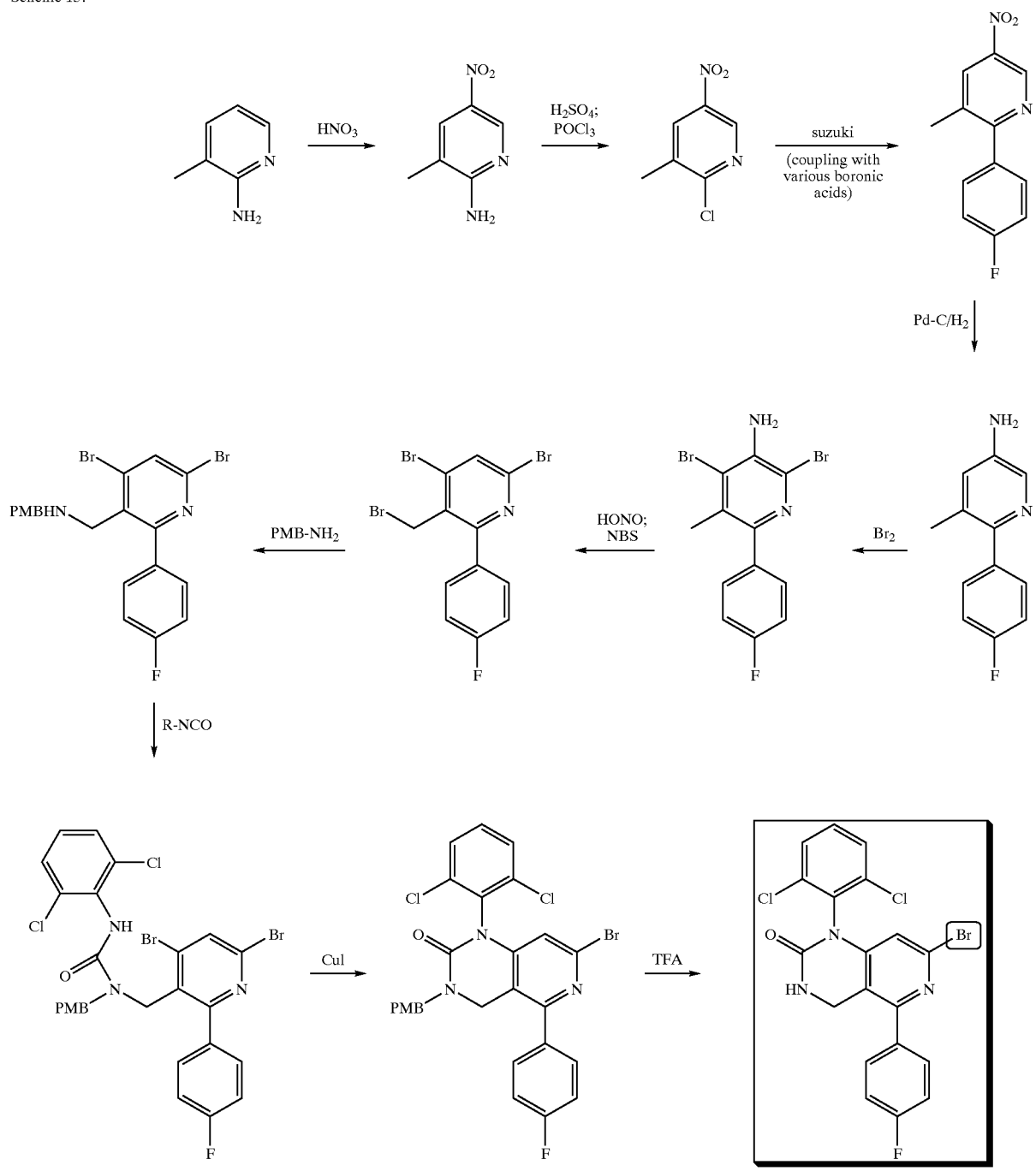

Scheme 14:

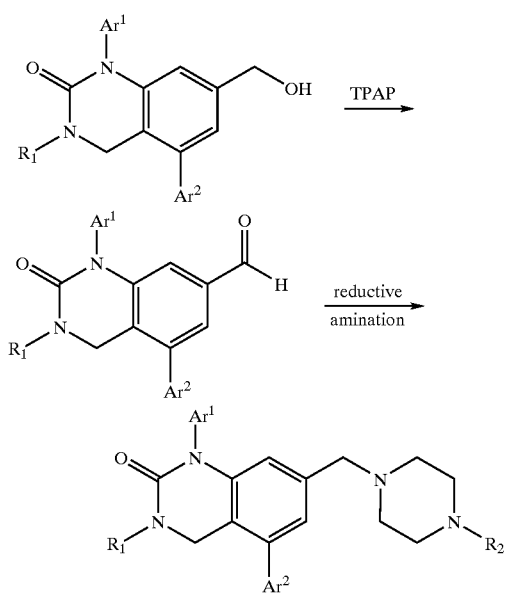

Scheme 15:

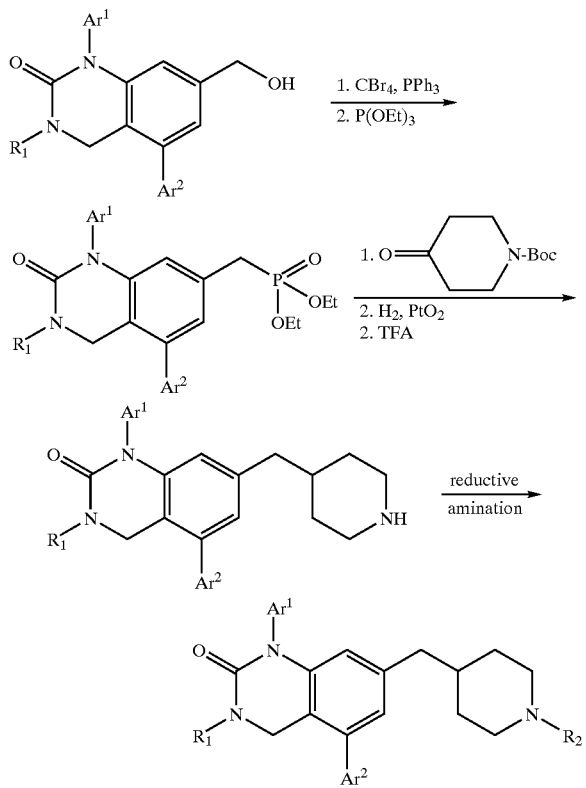

HPLC Conditions
LC 1. Retention time using the following conditions:
Column: YMC ODS A, 5 m, 4.6×50 mm;
Gradient Eluent: 10:90 to 95:5 v/v acetonitrile/water+ 0.05% TFA over 4.5 min;
Detection: PDA, 200–600 nm; Flow Rate: 2.5 mL/min.
LC 2. Retention time using the following conditions:
Column: YMC Pro-$C_{18, 5}$ m, 4.6×50 mm;
Gradient Eluent: 10:90 to 95:5 v/v acetonitrile/water+ 0.05% TFA over 3.0 min;
Detection: PDA, 200–600 nm; Flow Rate: 2.5 mL/min.

INTERMEDIATE 1

5-Bromo-1-(2,6-dichlorophenyl)-3,4-dihydro-7-methoxy-2(1H)-quinolinone

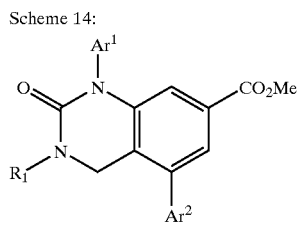

Step A: 2,6-Dibromo-4-methoxy-benzyl bromide

To a suspension of 5.0 g of 2,6-dibromo-4-methoxytoluene in 90 mL of $CCl_4$ was added N-bromosuccinimide and benzoyl peroxide. The resulting mixture was heated to reflux and stirred at the refluxing temperature while irradiating with a sunlamp for 2 h, then cooled and concentrated. The resulting residue was dissolved in 1:1 hexanes-$Et_2O$ and filtered through a pad of silica gel, then purified by flash chromatography on a Biotage 40M column, eluting with 98:2 hexanes-$Et_2O$, to yield 2,6-Dibromo-4-methoxy-benzyl bromide as a pale yellow solid. $^1$H NMR (500 MHz, $CDCl_3$): δ 7.11 (s, 2H); 4.82 (s, 2H); 3.80 (s, 3H).

Step B: t-Butyl 3-(2,6-dibromo-4-methoxyphenyl)-propionate

To 5 mL of THF at −78° C. was added 6.5 mL of a 1.0M solution of lithium hexamethyldisilazane in THF. t-Butyl acetate (0.9 mL) was added dropwise to the resulting cold solution, and the resulting mixture was stirred for 10 min at −78° C. 2,6-Dibromo-4-methoxy-benzyl bromide (1.2 g) in 5 mL of $CCl_4$ was added dropwise over 5 min. The mixture was stirred 20 min at −78° C., then quenched by addition of 1 mL of saturated aqueous $NaHCO_3$. The mixture was warmed to room temperature, diluted with 50 mL of saturated aqueous $NaHCO_3$, and extracted with 3×20 mL of EtOAc. The combined organics were washed with 25 mL of brine, dried over $MgSO_4$, and concentrated to yield t-Butyl 3-(2,6-dibromo-4-methoxyphenyl)-propionate as an oily yellow solid. Mass spectrum (ESI) 320.9 (M-OtBu). $^1$H NMR (500 MHz, $CDCl_3$): δ 7.08 (s, 2H); 3.76 (s, 3H); 3.20 (m, 2H); 2.45 (m, 2H); 1.47 (s, 9H).

Step C: 3-(2.6-dibromo-4-methoxyphenyl)-propionic acid

To a solution of t-butyl 3-(2,6-dibromo-4-methoxyphenyl)-propionate (1.32 g) in 3.6 mL of an isole was added 20 mL of trifluoroacetic acid dropwise. The resulting mixture was stirred for 20 min at room temperature, then concentrated. The resulting residue was redissolved in 20 mL of EtOAc and extracted with 40 mL of pH 4 buffer solution. The aqueous phase was extracted with 2×20 mL of EtOAc and the combined resulting organics were washed with 20 mL of brine, dried over $MgSO_4$, and concentrated to yield 3-(2,6-dibromo-4-methoxyphenyl)-propionic acid as a pale yellow solid. ¹H NMR (500 MHz, CDCl₃): δ 7.09 (s, 2H); 3.77 (s, 3H); 3.27 (m, 2H); 2.62 (m, 2H).

Step D: N-(2,6-Dichlorophenyl)-3-(2,6-dibromo-4-methoxyphenyl)-propionamide

To a −78° C. solution of 11.56 g of 3-(2,6-dibromo-4-methoxyphenyl)-propionic acid in 300 mL of CH₂Cl₂ was added dropwise 17.1 mL of a 1.0M solution of oxalyl bromide, then 1.7 mL of DMF. The mixture was allowed to warm to room temperature. When gas evolution ceased, the mixture was recooled to −78° C. Diisopropyl ethylamine (7.14 mL) was added dropwise, then a solution of 5.54 g of 2,6-dichloroaniline in 10 mL of CH₂Cl₂ was added dropwise. The mixture was allowed to warm to room temperature, then stirred overnight at this temperature. The white precipitate was collected to yield the N-(2,6-Dichlorophenyl)-3-(2,6-dibromo-4-methoxyphenyl)-propionamide as a white solid. The filtrate was concentrated and recrystallized from EtOH to yield an additional amount of N-(2,6-Dichlorophenyl)-3-(2,6-dibromo-4-methoxyphenyl)-propionamide as a white solid. Mass spectrum (ESI) 481.9 (M+1). ¹H NMR (500 MHz, DMSO-d6): δ 9.89 (s, 1H); 7.53 (d, J=8.2 Hz, 2H); 7.34 (t, J=8.0 Hz, 1H); 7.27 (s, 2H); 3.77 (s, 3H); 3.16 (m, 2H); 2.53 (m, 2H).

Step E: 5-Bromo-1-(2,6-dichlorophenyl)-3,4-dihydro-7-methoxy-2(1H)-quinolinone

To a suspension of 340 mg of N-(2,6-dichlorophenyl)-3-(2,6-dibromo-4-methoxyphenyl)-propionamide in 20 mL of pyridine was added CuI (137 mg) and powdered, dried K₂CO₃ (99 mg). The resulting mixture was heated to 160° C. in a sealed tube overnight (20 h), then concentrated. The reside was purified by flash chromatography on a Biotage 40S column, eluting with 100% CH₂Cl₂, to yield 5-Bromo-1-(2,6-dichlorophenyl)-3,4-dihydro-7-methoxy-2(1H)-quinolinone as a white solid. Mass spectrum (ESI) 402.0 (M+1). ¹H NMR (500 MHz, CDCl₃): δ 7.48 (d, J=8.0 Hz, 2H); 7.34 (t, J=8.0 Hz, 1H); 6.83 (d, J=2.5 Hz, 1H); 5.77 (d, J=2.5 Hz, 1H); 3.67 (s, 3H); 3.18 (m, 2H); 2.84 (m, 2H).

INTERMEDIATE 2
1-(2,6-Dichlorophenyl)-5-(2,4-difluorophenyl)-3,4-dihydro-7-methoxy-2(1H)-quinolinone

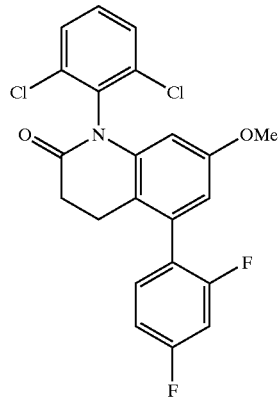

A A mixture of 24 mg of 5-bromo-1-(2,6-dichlorophenyl)-3,4-dihydro-7-methoxy-2(1H)-quinolinone (INTERMEDIATE 1), 28 mg of 2,4-difluorophenylboronic acid, 3 mg of Pd(Ph₃P)₄, and 0.15 mL of a 1M aqueous Na₂CO₃ solution in 2 mL of toluene and 0.2 mL of EtOH in a 10 mL flask equipped with a reflux condenser was evacuated and purged three times with Ar. The mixture was heated to reflux and stirred at this temperature for 3.5 h, then cooled and diluted with 15 mL EtOAc and 10 mL of saturated aqueous NaHCO₃. The phases were separated and the organic phase was dried over MgSO₄ and concentrated. The resulting residue was purified by preparative thin-layer chromatography, eluting with 3:1 hexanes-EtOAc, to yield 1-(2,6-Dichlorophenyl)-5-(2,4-difluorophenyl)-3,4-dihydro-7-methoxy-2(1H)-quinolinone. Mass spectrum (ESI) 434.0 (M+1). ¹H NMR (500 MHz, CDCl₃): δ 7.50 (d, J=8.0 Hz, 2H); 7.35 (t, J=8.0 Hz, 1H); 7.32 (m, 1H); 6.96, (m, 2H); 6.52 (d, J=2.5 Hz, 1H); 5.89 (d, J=2.5 Hz, 1H); 3.69 (s, 3H); 2.64–3.00 (m, 4H).

INTERMEDIATE 3
1-(2,6-Dichlorophenyl)-5-(2,4-difluorophenyl)-3,4-dihydro-7-hydroxy-2(1H)-quinolinone

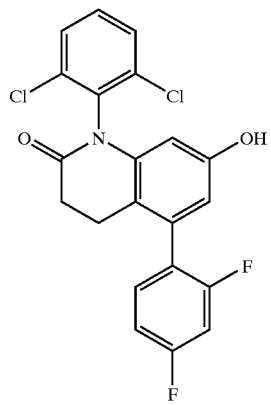

To a solution of 18 mg of 1-(2,6-dichlorophenyl)-5-(2,4-difluorophenyl)-3,4-dihydro-7-methoxy-2(1H)-quinolinone (INTERMEDIATE 2) in 1 mL of CH₂Cl₂ was added 0.1 mL of BBr₃. The resulting mixture was stirred 30 min at 0° C., then warmed to room temperature and stirred at this temperature for 1 h. The mixture was concentrated and the resulting residue was purified preparative thin layer chromatography, eluting with 98:2 CH₂Cl₂-MeOH, to yield 1-(2,6-Dichlorophenyl)-5-(2,4-difluorophenyl)-3,4-dihydro-7-hydroxy-2(1H)-quinolinone. Mass spectrum (ESI) 421.0 (M+1). ¹H NMR (500 MHz, CDCl₃): δ 7.47 (d, J=8.0 Hz, 2H); 7.33 (t, J=8.0 Hz, 1H); 7.27 (m, 1H); 6.95, (m, 2H); 5.82 (s, 1H); 5.23 (s, 1H); 2.56–3.00 (m, 5H).

INTERMEDIATE XI
2-chloro-4-fluoro-phenylboronic acid

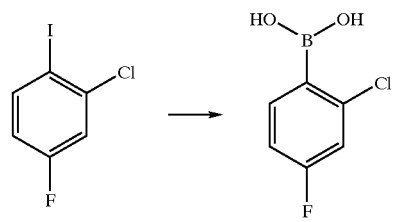

A solution of isopropyl magnesium chloride (100 mL, 2.0M in Ethyl Ether) was added to a solution of 2-chloro-4-fluoro-1-iodobenzene (25 g, 97.5 mmol) in 300 mL THF chilled in an ice bath. The solution was then stirred at RT overnight. The solution was chilled in a CO₂/acetone bath and trimethyl borate was added (23 mL, 200 mmol). The solution was warmed to RT and stirred for 6 h. The suspension was partitioned between water and ethyl ether (emulsion). The phases were separated and the organic phase concentrated. The residue was treated with 200 mL 2N HCl and stirred overnight. The suspension was then extracted with ethyl ether (2×) and the combined organics washed with brine, dried over MgSO₄, filtered and concentrated to give 13.3 g solid. The crude solid was suspended in hexanes, filtered and washed 2× (hexanes) to give 2-chloro-4-fluoro-phenylboronic acid. LC 1: 1.65 min.

INTERMEDIATE XII 2-methyl-4-fluoro-phenylboronic acid

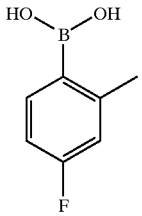

To dry magnesium (113g, 46.4 mmol) in 25 mL THF was added a small amount of 1,2-dibromoethane (2 drops) and iodine (2crystals). 1-Bromo-4-fluoro-2-methylbenzene (4.95 mL, 39.15 mmol) was added the resulting solution was refluxed for 4 h. The solution was cooled to RT and transferred by syringe to a solution of trimethylborate (4.5 mL, 40 mmol) in 20 mL THF at −78° C. The solution was warmed to RT and stirred for 2 days. Water (200 mL) was added and the mixture was concentrated (to remove most of the organics). The mixture was then treated with 2N HCl (200 mL) and stirred 2 hrs. The suspension was extracted with ethyl ether, dried over MgSO₄, filtered and concentrated to give 2-methyl-4-fluoro-phenylboronic acid. LC₁: 1.72 min.

INTERMEDIATE 1

1-(2,6-Dichlorophenyl)-5-(2,4-difluorophenyl)-3,4-dihydro-7-(piperidinyl)-2(1H)-quinolinone

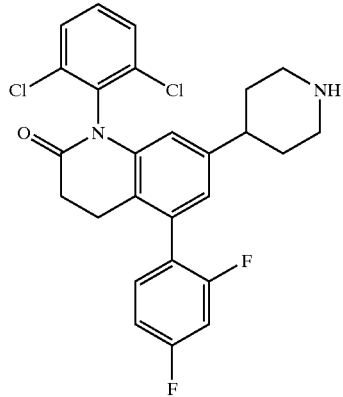

Step A: 1-(2,6-Dichlorophenyl)-5-(2,4-difluorophenyl)-3,4-dihydro-7-(trifluoromethylsulfonato)-2(1H)-quinolinone To a −78° C. solution of 24 mg of 1-(2,6-dichlorophenyl)-5-(2,4-difluorophenyl)-3,4-dihydro-7-hydroxy-2(1H)-quinolinone (INTERMEDIATE 3) in 1 mL of CH₂Cl₂ was added 27 mg of 2-[N,N-bis(trifluoromethylsulfonyl)amino]-5-chloropyridine, and 6 μL of diisopropylethylamine. The resulting mixture was stirred 30 min at −78° C., then warmed to room temperature and stirred at this temperature for 2 h. The mixture was concentrated and the resulting residue was purified by preparative thin layer chromatography, eluting with 1:1 hexanes-EtOAc, to yield 1-(2,6-Dichlorophenyl)5-(2,4-difluorophenyl)-3,4-dihydro-7-(trifluoromethylsulfonato)-2(1H)-quinolinone. Mass spectrum (ESI) 552.1 (M+1).

Step B: 7-(1-tert-Butoxycarbonyl-1,2,3,6-tetrahydro-4-pyridinyl)-1-(2,6-dichlorophenyl)-5-(2,4-difluorophenyl)-3,4-dihydro-2(1H)-quinolinone A mixture of 22 mg of 1-(2,6-dichlorophenyl)-5-(2,4-difluorophenyl)-3,4-dihydro-7-(trifluoromethylsulfonato)-2(1H)-quinolinone, 28 mg of 1-tert-butoxycarbonyl-4-trimethylstannyl-1,2,3,6-tetrahydropyridine (See EXAMPLE 41), 7 mg of Pd(Ph₃P)₄, and 10 mg of crushed, dried LiCl in 1 mL of dioxane in a 5 mL flask equipped with a reflux condenser was evacuated and purged three times with Ar. The mixture was heated to reflux and stirred at this temperature for 4.5 h, filtered through Celite, washing with EtOAc and 10 mL of saturated aqueous NaHCO₃, then concentrated. The residue was purified by preparative thin-layer chromatography, eluting with 3:1 hexanes-EtOAc, to yield 7-(1-tert-Butoxycarbonyl-1,2,3,6-tetrahydro-4-pyridinyl)-1-(2,6-dichlorophenyl)-5-(2,4-difluorophenyl)-3,4-dihydro-2(1H)-quinolinone. Mass spectrum (ESI) 585.2 (M+1).

Step C: 1-(2,6-Dichlorophenyl)-5-(2,4-difluorophenyl)-3,4-dihydro-7-(4-piperidinyl)-2(1H)-qinolinone A solution of 55 mg of 7-(1-tert-butoxycarbonyl-1,2,3,6-tetrahydro-4-pyridinyl)-1-(2,6-dichlorophenyl)-5-(2,4-difluorophenyl)-3,4-dihydro-2(1H)-quinolinone and 27 mg of 10% palladium on carbon in 12 mL of MeOH was hydrogenated in a Parr shaker at 22 psi for 45 min. The resulting compound was purified by preparative thin-layer chromatography, eluting with 2:1 hexanes-EtOAc, to yield 1-(2,6-dichlorophenyl)-5-(2,5-difluorophenyl)-3,4-dihydro-7-(1-tert-butoxycarbonyl-4-piperidinyl)-2(1H)-quinolinone.

To a solution of this quinolinone compound (32 mg) in 2 mL of methylene chloride was added 1 mL of trifluoroacetic acid. The resulting mixture was stirred at room temperature for 1 h, then diluted with EtOAc, extracted with 2N NaOH saturated with sodium chloride, dried over Na₂SO₄, and purified by preparative thin-layer chromatography, eluting with 95:5 CH₂Cl₂-MeOH, to yield 1-(2,6-Dichlorophenyl)-5-(2,4-difluorophenyl)-3,4-dihydro-7-(4-piperidinyl)-2(1H)-quinolinone. Mass spectrum (ESI) 488.0 (M+1). ¹H NMR (500 MHz, CDCl₃): δ 7.52 (d, J=8.5 Hz, 2H); 7.38 (t, J=8.5 Hz, 1H); 7.29 (br q, J=8.5 Hz, 1H); 6.99 (dt, J=2, 5, 8.0 Hz, 1H); 6.94 (dt, J=2,5, 9.0 Hz, 1H); 6.85 (br s, 1H); 6.13 (br s, 1H); 2.19 (br d, J=12 Hz, 2H); 2.90–3.02 (m, 1H); 2.66–3.02 (m, 4H); 2.51 (m, 1H); 1.79 (br d, J=13 Hz, 2H); 1.59 (m, 3H).

EXAMPLE 2

1-(2,6-Dichlorophenyl)-5-(2,4-difluorophenyl)-3,4-dihydro-7-[2-(1-piperidinyl)ethoxy]-2(1H)-quinolinone

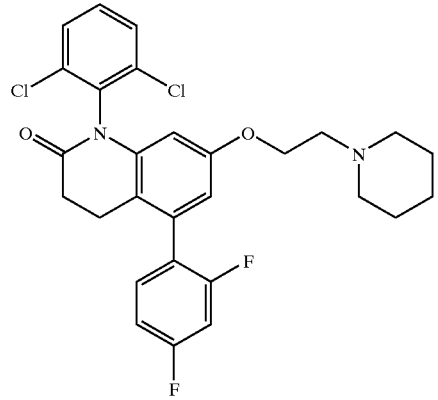

To a solution of 10 mg of 1-(2,6-dichlorophenyl)-5-(2,4-difluorophenyl)-3,4-dihydro-7-hydroxy-2(1H)-quinolinone (INTERMEDIATE 3) dissolved in 2 mL of anhydrous THF was added 87 mg of Ph₃P and 43 mg of 1-piperidine ethanol. The resulting mixture was heated to 65° C. for 10 min. Then 72 mg of diisopropyl azodicarboxylate was added dropwise over 2 min and the mixture was stirred for 1 h at 65° C. The resulting reaction mixture was concentrated and purified by preparative thin-layer chromatography, eluting with 100% EtOAc, to yield 1-(2,6-Dichlorophenyl)-5-(2,4-difluorophenyl)-3,4-dihydro-7-[2-(1-piperidinyl)ethoxy]-2(1H)-quinolinone. Mass spectrum (ESI) 531.3 (M+1). ¹H NMR (500 MHz, CDCl₃): δ ¹H NMR (500 MHz, CDCl₃) δ 7.51 (d, J=8 Hz, 2H); 7.38 (t, J=8 Hz, 1H); 7.31 (q, J=6.5 Hz, 1H); 6.98 (m, 2H); 6.54 (s, 1H); 5.90 (s, 1H); 4.08 (s, 2H); 2.83 (m, 6H); 2.61 (s, 4H); 1.68 (s, 4H); 1.48 (s, 2H).

EXAMPLE 3
1-(2,6-Dichlorophenyl)-5-(2,4-difluorophenyl)-3,4-dihydro-7-[2-(1-piperazinyl)ethoxy]-2(1H)-quinolinone

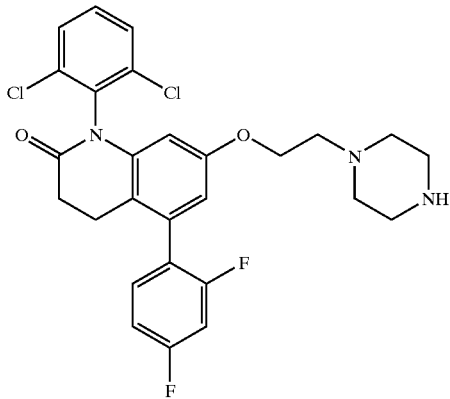

1-(2,6-Dichlorophenyl)-5-(2,4-difluorophenyl)-3,4-dihydro-7-[2-(1-piperazinyl)ethoxy]-2(1H)-quinolinone was prepared from 1-(2,6-dichlorophenyl)-5-(2,4-difluorophenyl)-3,4-dihydro-7-hydroxy-2(1H)-quinolinone (INTERMEDIATE 3) and 1-piperazine ethanol by a procedure analogous to that described in EXAMPLE 2. Mass spectrum (ESI) 532.3 (M+1). ¹H NMR (500 MHz, CDCl₃): δ 7.51 (d, J=8.5 Hz, 2H); 7.36 (t, J=8 Hz, 1H); 7.29 (q, J=6 Hz, 1H); 6.96 (m, 2H); 6.52 (s, 1H); 5.90 (s, 1H); 3.96 (t, J=5.5 Hz, 2H); 2.88 (m, 4H); 2.70 (m, 4H); 2.47 (br, 4H); 2.10 (br, 2H).

INTERMEDIATE 4
1-(2,6-Dichlorophenyl)-5-(2,4-difluorophenyl)-7-methoxy-2(1H)-quinolinone

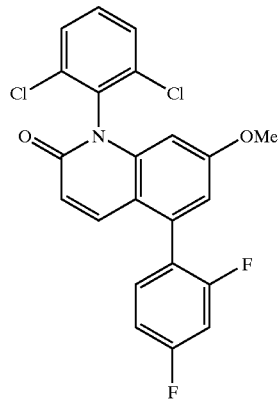

To a solution of 11 mg of 1-(2,6-dichlorophenyl)-5-(2,4-difluorophenyl)-3,4-dihydro-7-methoxy-2(1H)-quinolinone in 2.5 mL of CCl₄ was added 12 mg of N-bromosuccinimide and 6 mg of 2,2'azobis(2-methylpropionitrile). The mixture was heated to 80° C. for 1.5 h, then concentrated and purified by preparative thin-layer chromatography, eluting with 1:1 hexanes-EtOAc, to yield 1-(2,6-Dichlorophenyl)-5-(2,4-difluorophenyl)-7-methoxy-2(1H)-quinolinone. Mass spectrum (ESI) 432.1 (M+1). ¹H NMR (500 MHz, CDCl₃): δ 7.56 (m, 3H); 7.44 (m, 1H); 7.37 (m, 1H); 7.02 (m, 2H); 6.76 (s, 1H); 6.58 (d, J=10 Hz, 1H); 6.01 (s, 1H); 3.73 (s, 3H).

INTERMEDIATE 5
1-(2,6-Dichlorophenyl)-5-(2,4-difluorophenyl)-7-hydroxy-2(1H)-quinolinone

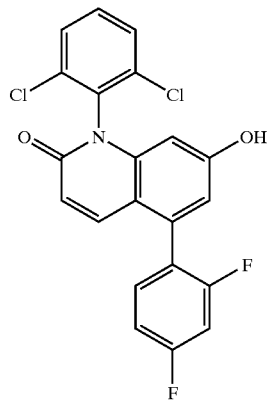

1-(2,6-Dichlorophenyl)-5-(2,4-difluorophenyl)-7-hydroxy-2(1H)-quinolinone was prepared from 1-(2,6-dichlorophenyl)-5-(2,4-difluorophenyl)-7-methoxy-2(1H)-quinolinone (INTERMEDIATE 4) by a procedure analogous to that described in INTERMEDIATE 3. Mass spectrum (ESI) 418.0 (M+1). ¹H NMR (500 MHz, CDCl₃): δ 7.57 (d, J=8 Hz, 1H); 7.47 (d, J=7.5 Hz, 2H); 7.33 (m, 2H); 7.02 (m, 2H); 6.96 (s, 1H); 6.52 (d, J=9.5, 1H); 6.01 (s, 1H).

INTERMEDIATE 6
5-(2-Chlorophenyl)-1-(2,6-dichlorophenyl)-3,4-dihydro-7-methoxy-2(1H)-quinolinone

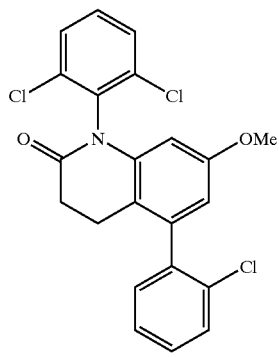

5-(2-Chlorophenyl)-1-(2,6-dichlorophenyl)-3,4-dihydro-7-hydroxy-7-methoxy-2(1H)-quinolinone was prepared from 5-bromo-1-(2,6-dichlorophenyl)-3,4-dihydro-7-methoxy-2(1H)-quinolinone (INTERMEDIATE 1) and 2-chlorophenylboronic acid by a procedure analogous to that described in INTERMEDIATE 2. Mass spectrum (ESI) 434.0 (M+1). ¹H NMR (500 MHz, CDCl₃): δ 7.43–7.54 (m, 2H); 7.30–7.42 (m, 4H) 6.48 (d, J=2.5 Hz, 1H); 5.82 (d, J=2.5 Hz, 1H); 5.89 (d, J=2.5 Hz, 1H); 3.69 (s, 3H); 2.63–2.88 (m, 4H).

INTERMEDIATE 7
5-(2-Chlorophenyl)-1-(2,6-dichlorophenyl)-3,4-dihydro-7-hydroxy-2(1H)-quinolinone

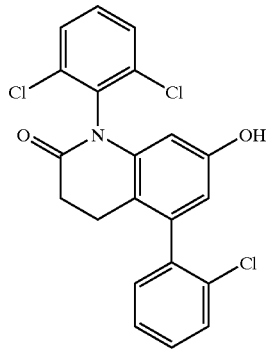

5-(2-Chlorophenyl)-1-(2,6-dichlorophenyl)-3,4-dihydro-7-hydroxy-2(1H)-quinolinone was prepared from 5-(2-chlorophenyl)-1-(2,6-dichlorophenyl)-3,4-dihydro-7-methoxy-2(1H)-quinolinone (INTERMEDIATE 6) by a procedure analogous to that described in INTERMEDIATE 3 Mass spectrum (ESI) 418.1 (M+1). $^1$H NMR (500 MHz, CDCl$_3$): δ 7.43–7.52 (m, 2H); 7.22–7.40 (m, 4H); 6.38 (d, J=2.5 Hz, 1H); 5.82 (d, J=2.5 Hz, 1H); 2.58–2.85 (m, 4H).

EXAMPLE 4
5-(2-Chlorophenyl)-1-(2,6-dichlorophenyl)-3,4-dihydro-7-(piperidinyl)-2(1H)-quinolinone

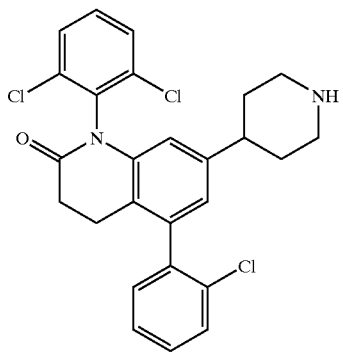

Step A: 5-(2-Chlorophenyl)-1-(2.6-dichlorophenyl-3,4-dihydro-7-(trifluoromethylsulfonato)-2(1H)-quinolinone 5(2-Chlorophenyl)-1-(2,6dichlorophenyl)-3,4-dihydro-7-(trifluoromethylsulfonato)-2(1H)-quinolinone was prepared from 5-(2-chlorophenyl)-1-(2,6-dichlorophenyl)-3,4-dihydro-7-hydroxy-2(1H)-quinolinone (INTERMEDIATE 7) by a procedure analogous to that described in EXAMPLE 1, Step A. Mass spectrum (ESI) 550.0 (M+1).

Step B: 7-(1-tert-Butoxycarbonyl-1,2,3,6-tetrahydro-4-pridinyl)-5-(2-chlorophenyl)-1-(2,6-dichlorophenyl)-3,4-dihydro-2(1H)-quinolinone 7-(1-tert-Butoxycarbonyl-1,2,3,6-tetrahydro-4pyridinyl)-5-(2-chlorophenyl-1-(2,6-dichlorophenyl)-3,4-dihydro-2(1H)-quinolinone was prepared from 5-(2-chlorophenyl)-1-(2,6-dichlorophenyl)-3,4-dihydro-7-(trifluoromethylsulfonato)-2(1H)-quinolinone by a procedure analogous to that described in EXAMPLE 1, Step B. Mass spectrum (ESI) 583.2 (M+1).

Step C: 5-(2-Chlorophenyl)-1-(2,6-dichlorophenyl)-3,4-dihydro-7-(4-pireridinyl)-2(1H)-quinolinone 5-(2-Chlorophenyl)-1-(2,6-dichlorophenyl)-3,4-dihydro-7-(4-piperidinyl)-2(1H)-quinolinone was prepared from 7-(1-tert-butoxycarbonyl-1,2,3,6-tetrahydro-4-pyridinyl)-5-(2-chlorophenyl)-1-(2,6-dichlorophenyl)-3,4-dihydro-2(1H)-quinolinone by a procedure analogous to that described in EXAMPLE 1, Step C.

Mass spectrum (ESI) 485.2 (M+1). $^1$H NMR (500 MHz, CDCl$_3$): δ 7.52 (m, 3H); 7.36 (m, 4H); 6.82 (s, 1H); 6.15 (s, 1H); 3.12 (d, J=12 Hz, 2H); 2.79 (m, 4H); 2.66 (t, J=12 Hz, 2H); 2.49 (m, 1H); 1.88 (s, 1H); 1.75 (d, J=12.5 Hz, 2H); 1.49 (m, 2H).

INTERMEDIATE 8
5-(2-Chlorophenyl)-1-(2,6-dichlorophenyl)-7-methoxy-2(1H)-quinolinone

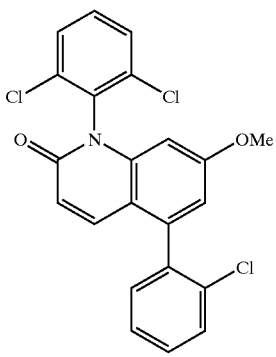

5-(2-Chlorophenyl)-1-(2,6-dichlorophenyl)-7-methoxy-2(1H)-quinolinone was prepared from 5-(2-chlorophenyl)-1-(2,6-dichlorophenyl)-3,4-dihydro-7-methoxy-2(1H)-quinolinone (INTERMEDIATE 6), N-bromosuccinimide, and 2,2'-azobis(2-methylpropionitrile) by a procedure analogous to that described in INTERMEDIATE 4. Mass spectrum (ESI) 430.0 (M+1). $^1$H NMR (500 MHz, CDCl$_3$): δ 7.53–7.62 (m, 3H); 7.30–7.49 (m, 5H); 6.77 (d, J=2.0 Hz, 1H); 6.61 (d, J=9.5 Hz, 1H); 6.03 (d, J=2.5 Hz, 1H); 3.74 (s, 3H).

INTERMEDIATE 9
5-(2-Chlorophenyl)-1-(2,6-dichlorophenyl)-7-hydroxy-2(1H)-quinolinone

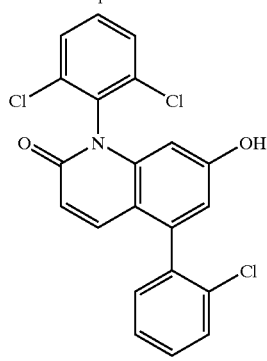

5-(2-Chlorophenyl)-1-(2,6-dichlorophenyl)-7-hydroxy-2(1H)-quinolinone was prepared from 5-(2chlorophenyl)-1-(2,6-dichlorophenyl)-7-methoxy-2(1H)-quinolinone (INTERMEDIATE 8) by a procedure analogous to that described in INTERMEDIATE 3. Mass spectrum (ESI)

416.05 (M+1). $^1$H NMR (500 MHz, CDCl$_3$): δ 7.49–7.56 (m, 3H); 7.31–7.41 (m, 5H); 6.63 (d, J=2.0 Hz, 1H); 6.46 (d, J=9.5 Hz, 1H); 5.97 (d, J=2.0 Hz, 1H).

EXAMPLE 5
1-(2,6-Dichlorophenyl)-5-(2,5-difluorophenyl)-7-[2-(1-piperidinyl)ethoxyl-2(1H)-quinolinone

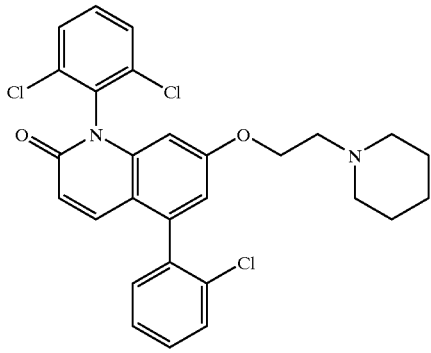

1-(2,6-Dichlorophenyl)-5-(2,5-difluorophenyl)-7-[2-(1-piperidinyl)ethoxyl]-2(1H)-quinolinone was prepared from 5-(2-chlorophenyl)-1-(2,6-dichlorophenyl)-7-hydroxy-2(1H)-quinolinone (INTERMEDIATE 9), Ph$_3$P, 1-piperidine ethanol, and diethyl azodicarboxylate by a procedure analogous to that described in EXAMPLE 2. Mass spectrum (ESI) 527.1 (M+1). $^1$H NMR (500 MHz, CDCl3): δ 7.50–7.61 (m, 3H); 7.36–7.47 (m, 5H); 6.75 (d, J=2.5 Hz, 1H); 6.53 (d, J=9.5 Hz, 1H); 6.02 (d, J=2.0 Hz, 1H); 4.00 (t, J=6.0 Hz 2H); 2.69 (t, J=6.0 Hz 2H); 2.42 (br s, 4H); 1.45–1.65 (m, 6H).

INTERMEDIATE 10
5-(2-Chloro-5-fluorophenyl)-1-(2,6-dichlorophenyl)-3,4-dihydro-7-methoxy-2(1H)-quinolinone

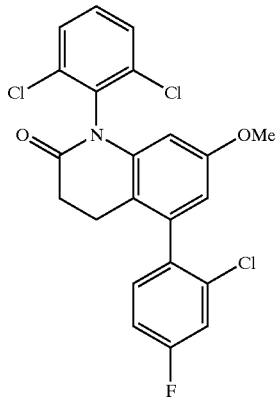

5-(2-Chloro-5-fluorophenyl)-1-(2,6-dichlorophenyl)-3,4-dihydro-7-methoxy-2(1H)-quinolinone was prepared from 5-bromo-1-(2,6-dichlorophenyl)-3,4-dihydro-7-methoxy-2(1H)-quinolinone (INTERMEDIATE 1) and 2chloro-5-fluorophenylboronic acid by a procedure analogous to that described in INTERMEDIATE 2. Mass spectrum (ESI) 450.0 (M+1). $^1$H NMR (500 MHz, CDCl$_3$): δ 7.52 (dd, J=3.0 Hz, 8.0 Hz, 2H); 7.25–7.42 (m, 3H); 7.10 (dt, J=2.5 Hz, 1H); 6.47 (d. J=2.0 Hz, 1H); 5.91 (d, J=2.5 Hz, 1H); 3.70 (s, 3H), 2.62–2.89 (m 4H).

INTERMEDIATE 11
5-(2-Chloro-5-fluorophenyl)-1-(2,6-dichlorophenyl)-3,4-dihydro-7-hydroxy-2(1H)-quinolinone

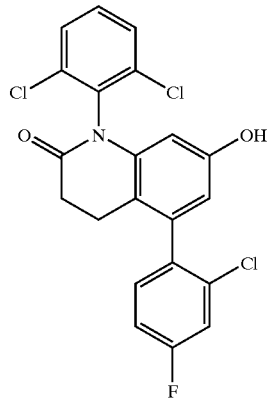

5-(2-Chloro-5-fluorophenyl)-1-(2,6-dichlorophenyl)-3,4-dihydro-7-hydroxy-2(1H)-quinolinone was prepared from 5-(2-chloro-5-fluorophenyl)-1-(2,6-dichlorophenyl)-3,4dihydro-7-methoxy-2(1H)-quinolinone (INTERMEDIATE 10) by a procedure analogous to that described in INTERMEDIATE 3. Mass spectrum (ESI) 438.1 (M+1). $^1$H NMR (500 MHz, CDCl$_3$): δ 7.49 (d, J=7.5 Hz, 2H); 7.36 (t, J=8 Hz, 1H); 7.27 (m, 2H); 7.07 (m, 1H); 6.38 (s, 1H); 5.83 (s, 1H); 2.73 (m, 4H).

EXAMPLE 6
1-(2,6-Dichlorophenyl)-5-(2-chloro-4-fluorophenyl)-3,4-dihydro-7-(piperidinyl)-2(1H)-quinolinone

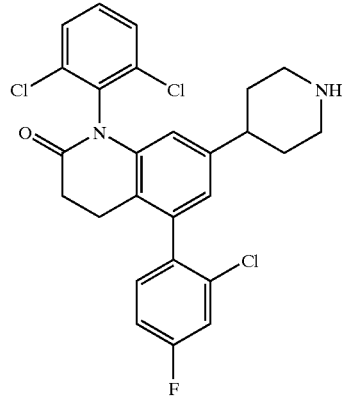

Step A: 5-(2-Chloro-4-fluorophenyl)-1-(2,6-dichlorophenyl)-3,4-dihydro-7-(trifluoromethylsulfonato)-2(1H)-quinolinone 5-(2-Chloro-4-fluorophenyl)-1-(2,6-dichlorophenyl)-3,4-dihydro-7-(trifluoromethylsulfonato)-2(1H)-quinolinone was prepared from 5-(2-chloro4-fluorophenyl)-1-(2,6-dichlorophenyl)-3,4-dihydro-7-hydroxy-2(1H)-quinolinone (INTERMEDIATE 9) by a procedure analogous to that described in EXAMPLE 1, Step A. Mass spectrum (ESI) 568.0 (M+1).

Step B: 7-(1-tert-Butoxycarbonyl-1,2,3,6-tetrahydro-4-pyridinyl)-5-(2-chloro-4-fluorophenyl)-1-(2,6-dichlorophenyl)-3,4-dihydro-2(1H)-quinolinone 7-(1-tert-Butoxycarbonyl-1,2,3,6-tetrahydro-4-pyridinyl)-5-(2chloro-4-fluorophenyl)-1-(2,6-dichlorophenyl)-3,4-dihydro-2(1H)-quinolinone was prepared from 5-(2-chloro-4-fluorophenyl)-1-(2,6-dichlorophenyl)-3,4-dihydro-7-(trifluoromethylsulfonato)-2

(1H)-quinolinone by a procedure analogous to that described in EXAMPLE 1, Step B. Mass spectrum (ESI) 603.1 (M+1).
Step C: 5-(2-Chloro-4-fluorophenyl)-1-(2,6-dichlorophenyl)-3,4-dihydro-7-(4-piperidinyl)-2(1H)-quinolinone 5-(2-Chloro-4-fluorophenyl)-1-(2,6-dichlorophenyl)-3,4-dihydro-7-(4-piperidinyl)-2(1H)-quinolinone was prepared from 7-(1-tert-butoxycarbonyl-1,2,3,6-tetrahydro-4-pyridinyl)-5-(2-chloro-4-fluorophenyl)-1-(2,6-dichlorophenyl)-3,4-dihydro-2(1H)-quinolinone by a procedure analogous to that described in EXAMPLE 1, Step C. Mass spectrum (ESI) 505.2 (M+1). $^1$H NMR (500 MHz, CDCl$_3$): δ 7.52 (d, J=7.5 Hz, 2H); 7.36 (t, J=8 Hz, 1H); 7.28 (m, 2H); 7.08 (m, 1H); 6.78 (s, 1H); 6.14 (s, 1H); 3.12 (d, J=12 Hz, 2H); 2.71 (m, 6H); 2.49 (m, 2H); 1.74 (d, J=12.5 Hz, 2H); 1.50 (m, 2H).

INTERMEDIATE 12
1-(2,6-Dichlorophenyl)-3,4-dihydro-5-(4-fluoro-2-methylphenyl)-7-methoxy-2(1H)-quinolinone

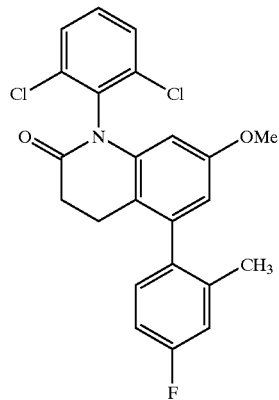

1-2,6-Dichlorophenyl)-3,4-dihydro-5-(4-fluoro-2-methylphenyl)-7-methoxy-2(1H)-quinolinone was prepared from 5-bromo-1-(2,6-dichlorophenyl)-3,4-dihydro-7-methoxy-2(1H)-quinolinone (INTERMEDIATE 1) and 4-fluoro-2-methylphenylboronic acid by a procedure analogous to that described in INTERMEDIATE 2. Mass spectrum (ESI) 430.1 (M+1). $^1$H NMR (500 MHz, CDCl$_3$): δ 7.50 (m, 2H); 7.36 (m, 1H); 7.17 (m, 1H); 6.98 (m, 2H); 6.45 (s, 1H); 5.89 (s, 1H); 3.69 (s, 3H); 2.72 (m, 4H); 2.15 (s, 3H).

INTERMEDIATE 13
1-(2,6-Dichlorophenyl)-3,4-dihydro-5-(4-fluoro-2-methylphenyl)-7-hydroxy-2(1H)-quinolinone

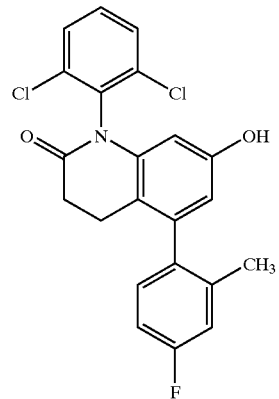

1-(2,6-Dichlorophenyl)-3,4-dihydro-5-(4-fluoro-2-methylphenyl)-7-hydroxy-2(1H)-quinolinone was prepared from 1-(2,6-dichlorophenyl)-3,4-dihydro-5-(4-fluoro-2-methylphenyl)-7-methoxy-2(1H)-quinolinone (INTERMEDIATE 12) by a procedure analogous to that described in INTERMEDIATE 3. Mass spectrum (ESI) 416.0 (M+1). $^1$H NMR (500 MHz, CDCl$_3$): δ 7.56 (m, 3H); 7.44 (m, 1H); 7.37 (m, 1H); 7.02 (m, 2H); 6.76 (s, 1H); 6.58 (d, J=10 Hz, 1H); 6.01 (s, 1H); 3.73 (s, 3H).

EXAMPLE 7
1-(2,6-Dichlorophenyl)-3,4-dihydro-5-(4-flouro-2-methylphenyl)-7-(piperidinyl)-2(1H)-quinolinone

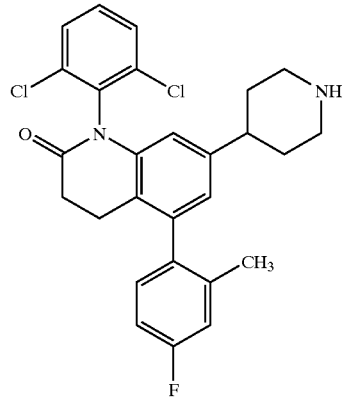

Step A: 1-(2,6-Dichlorophenyl)-3,4-dihydro-5-(4-fluoro-2-methylphenyl)-7-(trifluoromethylsulfonato)-2(1H)-quinolinone 1-(2,6-Dichlorophenyl)-3,4-dihydro-5-(4-fluoro-2-methylphenyl)-7-(trifluoromethylsulfonato)-2(1H)-quinolinone was prepared from 1-(2,6-dichlorophenyl)-3,4-dihydro-5-(4-fluoro-2-methylphenyl)-7-hydroxy-2(1H)-quinolinone (INTERMEDIATE 13) by a procedure analogous to that described in EXAMPLE 1, Step A. Mass spectrum (ESI) 548.1 (M+1).

Step B: 7-(1-tert-Butoxycarbonyl-1,2,3,6-tetrahydro-4-pyridinyl)-1-(2,6-dichlorophenyl)-3,4-dihydro-5-(4-fluoro-2-methylphenyl)-2(1H)-quinolinone 7-(1-tert-Butoxycarbonyl-1,2,3,6-tetrahydro-4-pyridinyl)-1-(2,6-dichlorophenyl)-3,4-dihydro-5-(4-fluoro-2-methylphenyl)-2(1H)-quinolinone was prepared from 1-(2,6-dichlorophenyl)-3,4-dihydro-5-(4-fluoro-2-methylphenyl)-7-(trifluoromethylsulfonato)-2(1H)-quinolinone by a procedure analogous to that described in EXAMPLE 1, Step B. Mass spectrum (ESI) 581.2 (M+1).

Step C: 1-(2,6-Dichlorophenyl)-3,4-dihydro-5-(4-fluoro-2-methylphenyl)-7-(4-piperidinyl)-2(1H)-quinolinone 1-(2,6-Dichlorophenyl)-3,4-dihydro-5-(4-fluoro-2-methylphenyl)-7-(4-piperidinyl)-2(1H)-quinolinone was prepared from 7-(1-tert-butoxycarbonyl-1,2,3,6-tetrahydro-4-pyridinyl)-1-(2,6-dichlorophenyl)-3,4-dihydro-5-(5-fluoro-2-methylphenyl)-2(1H)-quinolinone by a procedure analogous to that described in EXAMPLE 1, Step C. Mass spectrum (ESI) 483.2 (M+1). $^1$H NMR (500 MHz, CDCl$_3$): δ 7.41 (d, J=8.5 Hz, 2H); 7.28 (t, J=8 Hz, 1H); 7.03 (m, 1H); 6.85 (m, 2H); 6.65 (s, 1H); 6.00 (s, 1H); 3.02 (d, J=12 Hz, 2H); 2.61 (m, 6H); 2.36 (m, 1H); 2.00 (s, 3H); 1.64 (m, 2H); 1.39 (m, 2H).

INTERMEDIATE 14

5-Bromo-3,4-dihydro-7-methoxy-1-(3-methoxycarbonyl-6-methylphenyl)-2(1H)-quinolinone

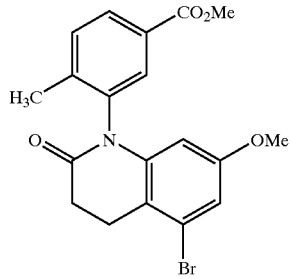

Step A: N-(3-Methoxycarbonyl-6-methylphenyl)-3-(2,6-dibromo-4-methoxyphenyl)-propionamide To a solution of 2.00 g of 3-(2,6-dibromo-4-methoxyphenyl)-propionic acid (INTERMEDIATE 1, Step C), 1.25 g of 1(3-dimethylaminopropyl)-3-ethylcarbodiimide hydrochloride, and 361 mg of DMAP in 100 mL of $CH_2Cl_2$ was added 1.95 g of methyl 3-amino-4-methylbenzoate. The resulting mixture was stirred at room temperature overnight, then concentrated and recrystallized from EtOH to yield 1.85 g (64%) of N-(3-Methoxycarbonyl-6-methylphenyt)-3-(2,6-dibromo-4-methoxyphenyl)-propionamide as a white solid. Mass spectrum (ESI) 486.0 (M+1).

$^1$H NMR (500 MHz, DMSO-d6): δ 9.46 (s, 1H); 8.10 (br s, 1H); 7.65 (br d, J=2.1 Hz, 1H); 7.35 (d, J=3.2 Hz, 1H); 7.27 (s, 2H); 3.83 (s, 3H); 3.77 (s, 3H); 3.17 (m, 2H); 2.76 (m, 2H); 2.63 (s, 3H).

Step B: 5-Bromo-3,4dihydro-7-methoxy-1-(3-methoxycarbonyl-6-methylphenyl)-2(1H)-quinolinone 5-Bromo-3,4-dihydro-7-methoxy-1-(3-methoxycarbonyl-6-methylphenyl)-2(1H)-quinolinone was prepared from N-(3-methoxycarbonyl-6-methylphenyl)-3-(2,6-dibromo-4-methoxyphenyl)-propionamide by a procedure analogous to that described in INTERMEDIATE 1, Step E. Mass spectrum (ESI) 374.0 (M-OMe). $^1$H NMR (500 MHz, CDCl$_3$): δ 8.02 (dd, J=2.0, 8.0 Hz, 1H); 7.80 (d, J=8.5 Hz, 1H); 6.80 (d, J=2.5 Hz, 1H); 5.73 (d, J=2.5 Hz, 1H); 3.89 (s, 3H); 3.63 (s, 3H); 3.16 (m, 2H); 2.80 (m, 2H); 2.13 (s, 3H).

INTERMEDIATE 15

5-(2.4-Diflourophenyl)-3,4-dihydro-7-methoxy-1-(3-methoxycarbonyl-6-methylphenyl)-2(1H)-quinolinone

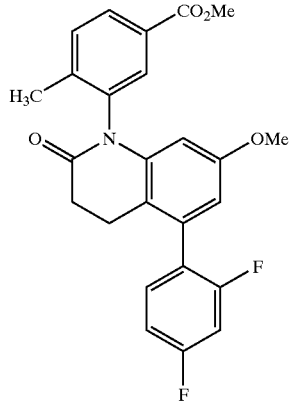

5-(2,4-Difluorophenyl)-3,4-dihydro-7-methoxy-1-(3-methoxycarbonyl-6-methylphenyl)-2(1H)-quinolinone was prepared from 5-bromo-3,4-dihydro-7-methoxy-1-(3-methoxycarbonyl-6-methylphenyl)-2(1H)-quinolinone (INTERMEDIATE 14) and 2,5-difluorophenylboronic acid by a procedure analogous to that described in INTERMEDIATE 2. Mass spectrum (ESI) 438.1 (M+1). 1H NMR (500 MHz, CDCl$_3$): δ 8.06 (d, J=5.0 Hz, 1H); 7.89 (s, 1H); 7.42 (d, J=5.0 Hz, 2H); 7.01 (m, 2H); 6.49 (s, 1H); 5.86 (s, 1H); 3.95 (s, 3H); 3.68 (s, 3H); 2.81 (m, 4H); 2.21 (s, 3H).

INTERMEDIATE 16

5-(2.4-Difluorophenyl)-3,4-dihydro-7-hydroxy-1-(3-methoxycarbonyl-6-methylphenyl)-2(1H)-quinolinone

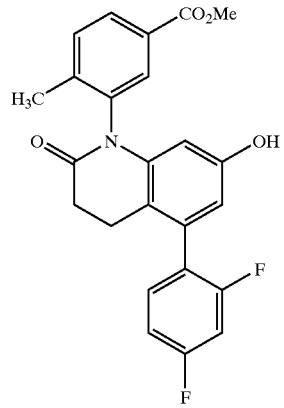

5-(2,4-Difluorophenyl)-3,4-dihydro-7-hydroxy-1-(3-methoxycarbonyl-6-methylphenyl)-2(1H)-quinolinone was prepared from 5-bromo-3,4-dihydro-7-methoxy-1-(3-methoxycarbonyl-6-methylphenyl)-2(1H)-quinolinone (INTERMEDIATE 15) by a procedure analogous to that described in INTERMEDIATE 3. Mass spectrum (ESI) 424.1 (M+1). $^1$H NMR (500 MHz, DMSO-d6): δ 9.44 (s, 1H); 7.96 (d, J=8.0 Hz, 1H); 7.75 (s, 1H); 7.59 (d, J=8.0 Hz, 1H); 7.41 (m, 2H); 7.18 (t, J=6.0 Hz, 2H); 6.33 (s, 1H); 5.63 (s, 1H); 3.84 (s, 3H); 2.61 (m, 4H); 2.09 (s, 3H).

INTERMEDIATE 17

5-(2-Chlorophenyl)-3,4-dihydro-7-methoxy-1-(3-methoxycarbonyl-6-methylphenyl)-2(1H)-quinolinone

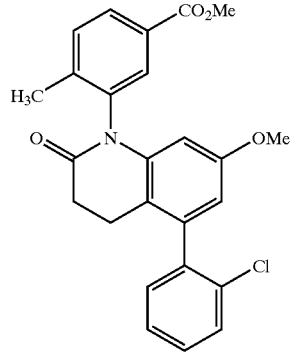

5-(2-Chlorophenyl)-3,4-dihydro-7-methoxy-1-(3-methoxycarbonyl-6-methylphenyl)-2(1H)-quinolinone was prepared from 5-bromo-3,4-dihydro-7-methoxy-1-(3-methoxycarbonyl-6-methylphenyl)-2(1H)-quinolinone (INTERMEDIATE 16) and 2-chlorophenylboronic acid by a procedure analogous to that described in INTERMEDIATE 2. Mass spectrum (ESI) 436.3 (M+1). $^1$H NMR (500 MHz, CDCl$_3$): 7.95 (m, 1H); 7.81 (d, J=19.0 Hz, 1H); 7.41 (m, 1H); 7.37 (d, J=8.0 Hz, 1H); 7.27 (m, 2H); 7.21 (m, 1H); 6.35 (s, 1H); 5.76 (s, 1H); 3.81 (s, 3H); 3.55 (s, 3H); 2.65 (m, 4H); 2.11 (d, J=11.5 Hz, 3H).

INTERMEDIATE 18

5-(2-chlorophenyl)-3,4-dihydro-7-hydroxy-1-(3-methoxycarbonyl-6-methylphenyl)-2(1H)-quinolinone

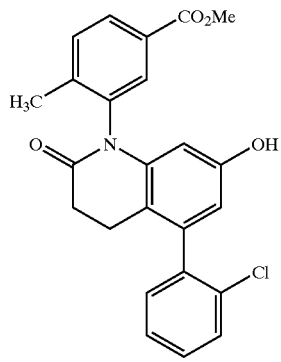

5-(2-Chlorophenyl)-3,4-dihydro-7-hydroxy-1-(3-methoxycarbonyl-6-methylphenyl)-2(1H)-quinolinone was prepared from 5-(2-chlorophenyl)-3,4-dihydro-7-methoxy-1-(3-methoxycarbonyl-6-methylphenyl)-2(1H)-quinolinone (INTERMEDIATE 17) by a procedure analogous to that described in INTERMEDIATE 3. Mass spectrum (ESI) 422.2 (M+1). $^1$H NMR (500 MHz, CDCl$_3$): δ 7.93 (d, J=7.5 Hz, 1H); 7.85 (d, J=17.5 Hz, 1H); 7.49 (m, 3H); 7.7.26 (m, 1H); 6.34 (s, 1H); 5.78 (s, 1H); 3.85 (s, 3H); 2.62 (m, 4H); 2.14 (d, J=10.5 Hz, 3H).

EXAMPLE 8

5-(2-Chlorophenyl)-3,4-dihydro-1-(3-methoxycarbonyl-6-methylphenyl)-7-(4-piperidinyl)-2(1H)-quinolinone

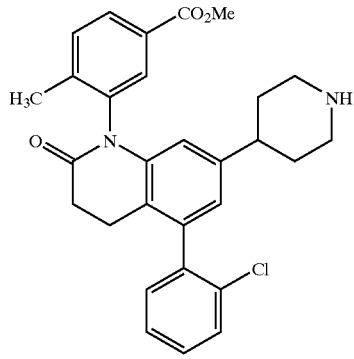

Step A: 5-(2-Chlorophenyl)-3,4-dihydro-1-(3-methoxycarbonyl-6-methylphenyl)-7-(trifluoromethylsulfonato)-2(1H)-quinolinone 5-(2-Chlorophenyl)-3,4-dihydro-1-(3-methoxycarbonyl-6-methylphenyl)-7-(trifluoromethylsulfonato)-2(1H)-quinolinone was prepared from 5-(2-chlorophenyl)-3,4-dihydro-7-hydroxy-1-(3-methoxycarbonyl-6-methylphenyl)-2(1H)-quinolinone (INTERMEDIATE 18) by a procedure analogous to that described in EXAMPLE 1, Step A. Mass spectrum (ESI) 554.2 (M+1).

Step B: 7-(1-tert-Butoxycarbonyl-1,2,3,6-tetrahydro-4-pyridinyl)-5-(2-chlorophenyl)-3,4-dihydro-1-(3-methoxycarbonyl-6-methylphenyl)-2(1H)-quinolinone 7-(1-tert-Butoxycarbonyl-1,2,3,6-tetrahydro-4-pyridinyl)-5-(2-chlorophenyl)-3,4dihydro-1-(3-methoxycarbonyl-6-methylphenyl)-2(1H)-quinolinone was prepared from 5-(2-chlorophenyl)-3,4-dihydro-1-(3-methoxycarbonyl-6-methylphenyl)-7-(trifluoromethylsulfonato)-2(1H)-quinolinone by a procedure analogous to that described in EXAMPLE 1, Step B. Mass spectrum (ESI) 531.2 (M−tBu).

Step C: 5-(2-Chlorophenyl)-3,4-dihydro-1-(3-methoxycarbonyl-6-methylphenyl)-7-(4-piperidinyl)-2(1H)-quinolinone 5-(2-Chlorophenyl)-3,4-dihydro-1-(3-methoxycarbonyl-6-methylphenyl)-7-(4-piperidinyl)-2(1H)-quinolinone was prepared from 7-(1-tert-butoxycarbonyl-1,2,3,6-tetrahydro-4-pyridinyl)-5-(2-chlorophenyl)-3,4-dihydro-1-(3-methoxycarbonyl-6-methylphenyl)-2(1H)-quinolinone by a procedure analogous to that described in EXAMPLE 1, Step C. Mass spectrum (ESI) 489.2 (M+1).

$^1$H NMR (500 MHz, CDCl$_3$): δ 7.84 (d, J=23 Hz, 1H); 7.45 (m, 2H); 7.31 (m, 2H); 7.25 (m, 1H); 6.74 (s, 1H); 6.05 (s, 1H); 3.87 (s, 3H); 3.08 (m, 2H); 2.67 (m, 6H); 2.37 (m, 1H); 2.16 (d, J=14 Hz, 3H); 1.67 (m, 2H); 1.44 (m, 2H).

INTERMEDIATE 19

2-bromomethyl-1,3-dibromo-5-methoxy-benzene

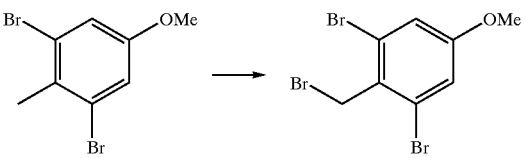

To a solution of 1,3-dibromo-5-methoxy-2-methyl-benzene (16.50 g, 58.9 mmol) in 300 mL of anhydrous CCl$_4$ under a nitrogen atmosphere was added N-bromosuccininide (12.59 g, 70.7 mmol) and benzoyl peroxide (1.57 g, 6.5 mmol). The solution was then heated to reflux. Once the solution reached reflux it was irradiated with a 250 W sun lamp. After 3.5 h the solution was cooled to RT and concentrated. To the residue was added ca. 50 mL DCM and the resulting suspension filtered. The filtrate was purified by silica gel chromatography (450 g SiO$_2$) using 5% DCM in hexanes as the eluent to give 2-bromomethyl-1,3-dibromo-5-methoxy-benzene. $^1$H NMR(CDCl$_3$, 500 MHz): δ 3.81 (s, 3H), 4.83 (s, 2H), 7.13 (s, 2H). MS(ES) 277 (M−Br); LC 1: 3.93 min.

INTERMEDIATE 20

N, N-[(2,6-dibromo-4-methoxyphenyl)methyl]-[4-methoxyphenyl)methyl]

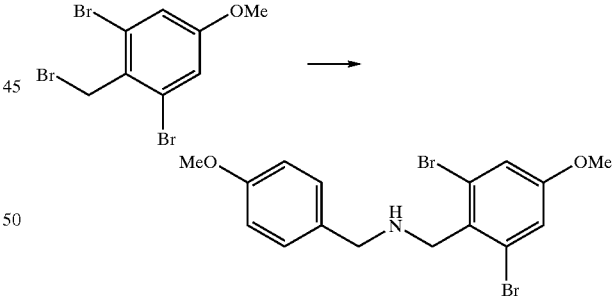

A solution of 2-bromomethyl-1,3-dibromo-5-methoxy-benzene (20.30 g, 56.6 mmol) (INTERMEDIATE 19) in 100 mL of DMF was added to a solution of 4-methoxybenzylamine (19.40 g, 141 mmol) and potassium carbonate (11.73 g, 85.9 mmol) in 100 mL DMF chilled in an ice bath. The rate of addition was controlled to maintain the internal temperature at 5° C. or less. After the completion of the addition the solution was allowed to warm to RT and stirred overnight. The solution was poured into 2 L of water and extracted with ethyl ether (3×700 ml). The combined organics were washed with 1 L NaHCO$_3$, 500 mL water (3×) and 1 L of brine. The solution was dried over Na$_2$SO$_4$, filtered and concentrated. The residue (ca. 25 g) was purified by silica gel chromatography (550 g SiO$_2$) using 10 to 35% ethyl ether in hexanes as the eluent to give N,N-[(2,6-dibromo-4-methoxyphenyl)methyl]-[(4-methoxyphenyl)methyl]. $^1$H NMR(CDCl$_3$, 500 MHz): δ 3.79 (s, 3H), 3.807 (s, 2H), 3.813 (s, 3H), 4.10 (s, 2H), 6.88 (d, 2H, J=8.5 Hz), 7.11 (s, 2H), 7.32 (d, 2H, J=8.5 Hz). MS(ES) 414 (M+1); LC 1: 2.32 min.

INTERMEDIATE 21

N-[(2,6-dibromo-4-methoxyphenyl)methyl]-N'-(2,6-dichlorophenyl)-N-[(4-methoxyphenyl)methyl]urea

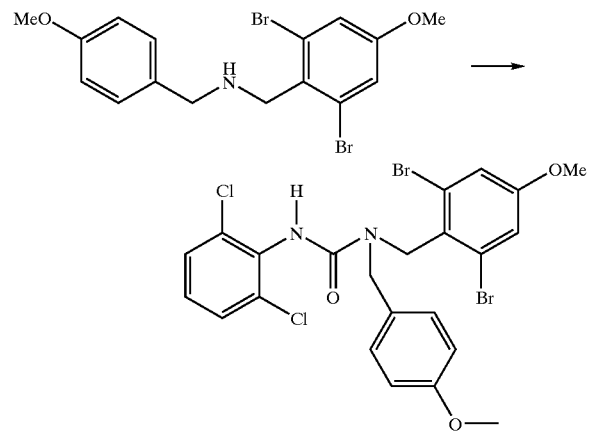

To a solution of N,N-[(2,6-dibromo-4-methoxyphenyl)methyl]-[(4-methoxyphenyl)methyl] (22.10 g, 0.053 mol) (INTERMEDIATE 20) and N,N-diisopropylethyl amine (12.0 ml, 0.064 mol) in 200 mL of DCM under a nitrogen atmosphere was added solid 2,6-dichlorophenyl isocyanate (10.0 g, 0.053 mol). An additional 300 mL DCM was added to assist in stirring. After ca. 30 min. an additional 0.5 g of 2,6-dichlorophenyl isocyanate was added and the solution was stirred overnight. The solution was then concentrated to give a white solid which was suspended in 500 mL of 1/1 ethyl ether/hexanes. The solution was concentrated again and the resulting solid suspended in 200 mL 1/1 ethyl ether/hexanes. The suspension was filtered and the recovered solid washed with ethyl ether/hexanes (1/1) and air dried to give N-[(2,6-dibromo-4-methoxyphenyl)methyl]-N'-(2,6dichlorophenyl)-N-[(4-methoxyphenyl)methyl]urea. $^1$H NMR(CDCl$_3$, 500 MHz): δ 3.80 (s, 6H), 4.46 (s, 2H), 5.13 (s, 2H), 6.22 (s, 1H), 6.86 (d, 2H, J=8.6 Hz), 7.06 (t, 1H, J=8.6 Hz), 7.28 (s, 2H), 7.30 (d, 2H, J=8.0 Hz). MS(ES) 601 (M+1); LC 1: 3.96 min.

INTERMEDIATE 22

1-(2,6-dichlorophenyl)-3-(4-methoxyphenyl)methyl-5-bromo-7-methoxy-3,4-dihydro-2(1H)-quinazolinone

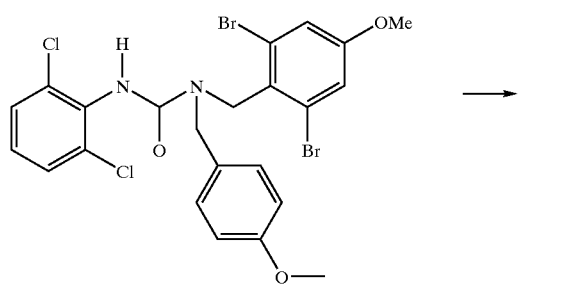

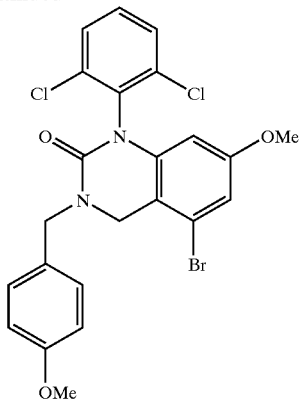

To a flask containing dry, finely ground potassium carbonate (22.17 g, 0.160 mol) under a nitrogen atmosphere was added anhydrous DMF (800 ml), N-[(2,6-dibromo-4-methoxyphenyl)methyl]-N'-(2,6 dichlorophenyl)-N-[(4-methoxyphenyl)methyl]urea (32.25 g, 0.0535 mol) (INTERMEDIATE 21) and copper iodide (6.80 g, 0.0353 mol). After refluxing one hour the solution was cooled to RT and poured into a solution containing 700 mL NH$_4$OH (28%) and water (8 L). The precipitated product was filtered, washed with water (5×500 mL), hexanes (4×500 mL) and air dried to give 1-(2,6-dichlorophenyl)-3-(4-methoxyphenyl)methyl]-5-bromo-7-methoxy-3,4-dihydro-2(1H)-quinazolinone. $^1$H NMR(CDCl$_3$, 500 MHz): δ 3.67 (s, 3H), 3.83 (s, 3H), 4.44 (s, 2H), 4.68 (s, 2H), 5.59 (d, 1H, J=2.3 Hz), 674 (d, 1H, J=2.3 Hz), 6.91 (d, 2H, J=8.7 Hz), 7.34–7.37 (m, 3H), 7.50 (d, 2H, J=8.0 Hz), MS(ES) 521 (M+1); LC 1:4.15 min.

INTERMEDIATE 23

1-(2,6-dichlorophenyl)-5-bromo-7-methoxy-3,4-dihydro-2(1H)-quinazolinone

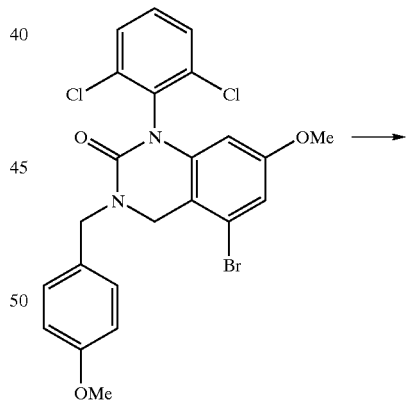

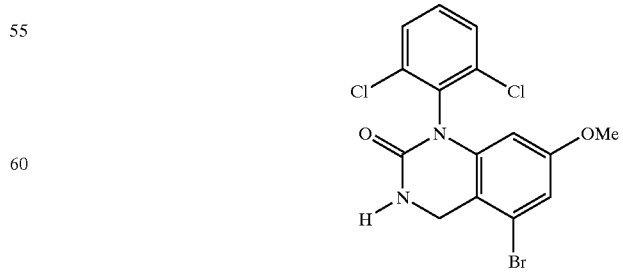

A solution of 1-(2,6-dichlorophenyl)-3-(4-methoxyphenyl)methyl-5-bromo-7-methoxy-3,4-dihydro-2

(1H)-quinazolinone (30.91 g, 0.0592 mol) (INTERMEDIATE 22) and anisole (28 ml, 0.258 mol) in 350 mL trifluoroacetic acid under a nitrogen atmosphere was refluxed for 2 h. The solution was cooled to RT and concentrated. The residue was partitioned between 500 mL NaHCO$_3$ and 500 mL EtOAc. The organic phase was washed with water (500 mL) and brine (500 mL) and concentrated. The NaHCO$_3$ and brine phases contained a suspension of precipitated product. This material was collected by filtration and combined with the crude. The combined crude was suspended in ethyl ether, filtered and washed with ethyl ether and hexanes to give 1-(2,6-dichlorophenyl)-5-bromo-7-methoxy-3,4-dihydro-2(1H)-quinazolinone. $^1$H NMR(CDCl$_3$, 500 MHz): δ 3.68 (s, 3H), 4.64 (s, 2H), 5.46 (s, 1H), 5.62 (d, 1H, J=2.3 Hz), 6.79 (d, 1H, J=2.5 Hz), 7.36 (t, 1H, J=8.1 Hz), 7.50 (d, 2H, J=8.2 Hz). MS(ES) 401 (M+1); LC 1: 3.18 min.

INTERMEDIATE 24

Methyl-4-bromomethyl-3,5-dibromo-benzoate

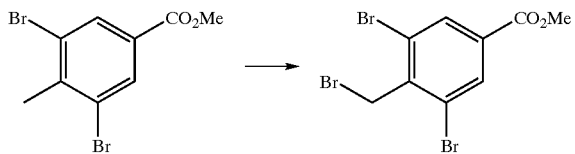

To a solution of methyl 3,5-dibromo-4-methylbenzoate (150.0 g, 0.487 mol) in 2 L anhydrous CCl$_4$ under a nitrogen atmosphere was added N-bromosuccinimide (125.7 g, 0.706 mol) and benzoyl peroxide (12.98 g, 0.054 mol). The solution was then heated to reflux. Once the solution reached reflux it was irradiated with a 250 W sun lamp. After 6 h the solution was cooled to RT and filtered. The precipitate (succinimde) was washed with DCM and the filtrate concentrated. The residue (ca. 246 g) was purified by silica gel chromatography (3 Kg SiO$_2$) using 5 to 25% DCM/hexanes as the eluent to give methyl-4-bromomethyl-3,5-dibromo-benzoate. $^1$H NMR(CDCl$_3$, 500 MHz): δ 3.93 (s, 3H), 4.84 (s, 2H), 8.21 (s, 2H). MS(ES) 385 (M+1); LC 1: 3.93 min.

INTERMEDIATE 25

N,N-[(2,6-dibromo-4-methylcarboxylate)methyl]-[4-methoxyphenyl)methyl]

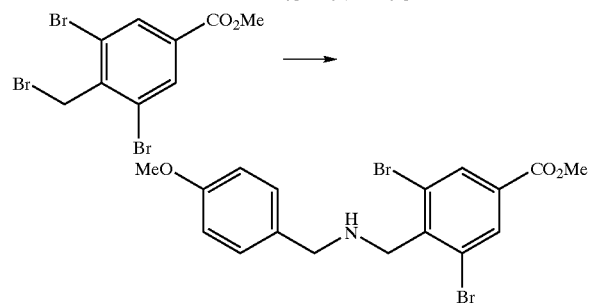

A solution of methyl 4bromomethyl-3,5-dibromo-benzoate (188.44 g, 0.425 mmol) (INTERMEDIATE 24) in 1.6 L DMF was added to a solution of 4-methoxybenzylamine (127 mL, 0.972 mol) and potassium carbonate (67.32 g, 0.487 mol) in 900 mL DMF chilled in an ice bath. The rate of addition was controlled to maintain the internal temperature at 5° C. or less. After the addition was complete the solution was warmed to RT and stirred 2 days. The solution was partitioned between 24 L water and 6 L ethyl ether. Solid sodium chloride was added to assist in the separation of phases. The phases were separated and the aqueous extracted with 4 L ethyl ether. The combined organics were washed with 2 L NaHCO$_3$, 2 L water, 2 L brine and dried over Na$_2$SO$_4$. The solution was filtered and concentrated to give N,N-[(2,6-dibromo-4-methylcarboxylate)methyl]-[(4-methoxyphenyl)methyl]. $^1$H NMR(CDCl$_3$, 500 MHz): δ 3.80 (s, 2H), 3.81 (s, 3H), 3.94 (s, 3H), 4.17 (s, 2H), 6,87 (d, 2H, J=8.7 Hz), 7.29 (d, 2H, J=9.0 Hz), 8.19 (s, 2H). MS(ES) 442 (M+1); LC 1: 2.22 min.

INTERMEDIATE 26

N-[(2,6-dibromo-4-methylcarboxyl)methyl]-N'-(2,6-dichlorophenyl)-N-[(4-methoxyphenyl)methyl]urea

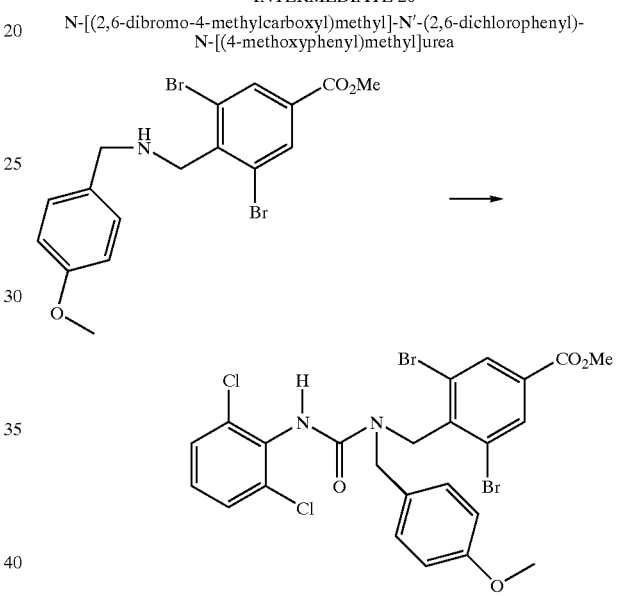

To a solution of N,N-[(2,6-dibromo-4-m)methyl]-[(4-methoxyphenyl)methyl] (215.86 g, 0.487 mol) (INTERMEDIATE 25) and N,N-diisopropylethyl amine (96.7 mL, 0.556 mol) in 3 L of DCM under a nitrogen atmosphere was added solid 2,6-dichlorophenyl isocyanate (99.8 g, 0.531 mol). After ca. 2 h the solution was concentrated and the residue suspended in 1 L 1/1 ethyl ether/ hexanes. The solution was filtered and the solid washed with ethyl ether/hexanes (1/1) and air dried to give N-[(2,6-dibromo-4-methylcarboxyl)methyl]-N'-(2,6-dichlorophenyl)-N-[(4-methoxyphenyl)methyl]urea. The filtrate was concentrated and the residue treated with 500 mL ethyl ether/hexanes (1/1). The suspension was filtered and the solid washed with ether/hexanes (1/1) to give additional N-[(2,6-dibromo-4-methylcarboxyl)methyl]-N'-(2,6-dichlorophenyl)-N-[(4-methoxyphenyl)methyl]urea. $^1$H NMR(CDCl$_3$, 500 MHz): δ 3.79 (s, 3H), 3.94 (s, 3H), 4.46 (s, 2H), 5.22 (s, 2H), 6.26 (s, 1H), 6.84 (d, 2H, J=8.6 Hz), 7.07 (t, 1H, J=8.1 Hz), 7.18 (d, 2H, J=8.6 Hz), 7.29 (d, 2H, J=7.2 Hz), 8.20 (s, 2H). MS(ES) 629 (M+H); LC 1: 3.94 min.

INTERMEDIATE 27
1-(2,6-dichlorophenyl)-3-(4-methylcarboxylate)methyl-5-bromo-7-methoxy-3,4-dihydro-2(1H)-quinazolinone

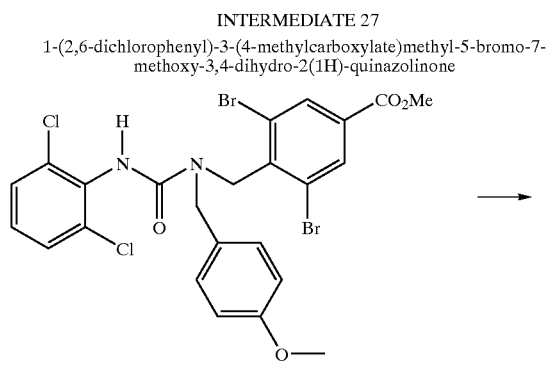

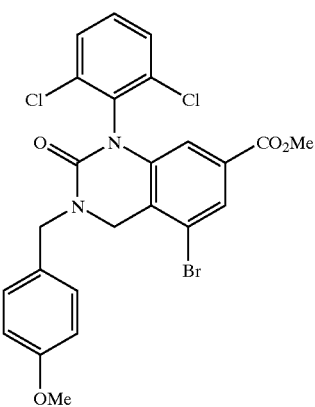

INTERMEDIATE 28
1-(2,6-dichlorophenyl)-5-bromo-7-methylcarboxylate-3,4-dihydro-2(1H)-quinazolinone

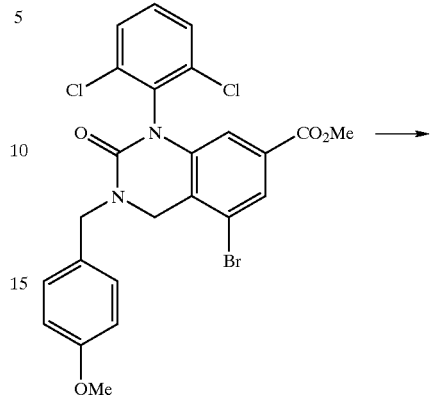

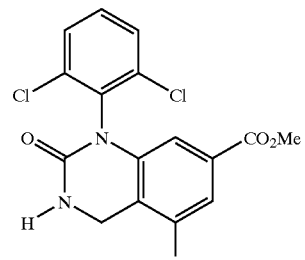

N-[(2,6-dibromo-4-methylcarboxyl)methyl]-N'-(2,6-dichlorophenyl)-N-[(4methoxyphenyl)methyl]urea (10.0 g, 15.8 mmol) (INTERMEDIATE 26), copper iodide (3.32 g, 17.4 mmol) and N,N-diisopropylethyl amine (4.14 mL, 23.8 mmol) in 150 mL anhydrous DMF under a nitrogen atmosphere was heated at 100° C. After 13 h the solution was cooled to RT and partitioned between 800 mL water and 500 mL ether. The mixture was filtered and the residue washed with ethyl ether. The two layers of the filtrate were separated and the organic phase washed with 500 mL water (3x), 500 mL brine and dried over $MgSO_4$. The solution was treated with charcoal, filtered through solka flock, and concentrated. The residue (white solid) was suspended in hexanes, filtered and air dried to give 1-(2,6-dichlorophenyl)-3-(4-methylcarboxylate)methyl-5-bromo-7-methoxy-3,4-dihydro-2(1H)-quinazolinone. The filtrate was concentrated and the solid residue suspended in hexanes, filtered and air dried to give additional 1-(2,6-dichlorophenyl)-3-(4-methylcarboxylate)methyl-5-bromo-7-methoxy-3,4-dihydro-2(1H)-quinazolinone. $^1$H NMR(CDCl$_3$, 500 MHz): δ 3.83 (s, 6H), 4.53 (s, 2H), 4.69 (s, 2H), 5.32 (s, 1H), 6.65 (s, 1H), 6.92 (d, 2H, J=8.5 Hz), 7.36 (d, 2H, J=8.5 Hz), 7.40 (t, 1H, J=8.2 Hz), 7.54 (d, 2H, J=8.2 Hz), 7.86 (s, 1H). MS(ES) 549 (M+H); LC 1: 4.05 min.

A solution of 1-(2,6-dichlorophenyl)-5-bromo-7-methylcarboxyl-3,4-dihydro-2(1H)-quinazolinone (100 g, 0.182 mol) (INTERMEDIATE 27) and anisole (85.9 mL. 0.790 mol) in 1132 mL triflubroacetic acid under a nitrogen atmosphere was refluxed for 2 h. The solution was cooled to RT and concentrated. The residue was partitioned between 2.5 L NaHCO$_3$ and 3 L of EtOAc. The phases were separated and he aqueous extracted with 1.5 L EtOAc. The combined organics were washed with 1 L water, 1 L brine, dried over MgSO$_4$, filtered and concentrated. The residue was suspended in hexanes and filtered. The recovered solid was washed with hexanes and air dried to give 1-(2,6-dichlorophenyl)-5-bromo-7-methylcarboxylate-3,4-dihydro-2(1H)-quinazolinone.

The aqueous phases, which contained a suspension of the product, were filtered. The recovered solid was washed with water (2x) and hexanes (2x). The recovered solid was then dissolved in a solution of 2 L EtOAc and 6 L DCM. This solution was then treated with 2 L water and enough NaHCO$_3$ to bring the aqueous to ca. pH 8. The layers were separated and the organic phase dried over MgSO$_4$, filtered and concentrated. The solid residue was suspended in hexanes, filtered, washed (hexanes) and air dried to give additional 1-(2,6-dichlorophenyl)-5-bromo-7-methylcarboxylate-3,4-dihydro-2(1H)-quinazolinone. $^1$H NMR(CDCl$_3$, 500 MHz): 3.84 (s, 3H), 4.74 (d, 2H, J=1.6 Hz), 5.80(s, 1H), 6.68 (d, 1H, J=1.3 Hz), 7.41 (t, 1H, J=7.6 Hz), 7.53 (d, 2H, J=7.7 Hz), 7.91 (d, 1H, J=1.4 Hz). MS(ES) 429 (M+H); LC 1: 3.01 min.

INTERMEDIATE 29

1-(2,6-dichlorophenyl)-5-(2-chlorophenyl)-7-methoxy-3,4-dihydro-2(1H)-quinazolinone

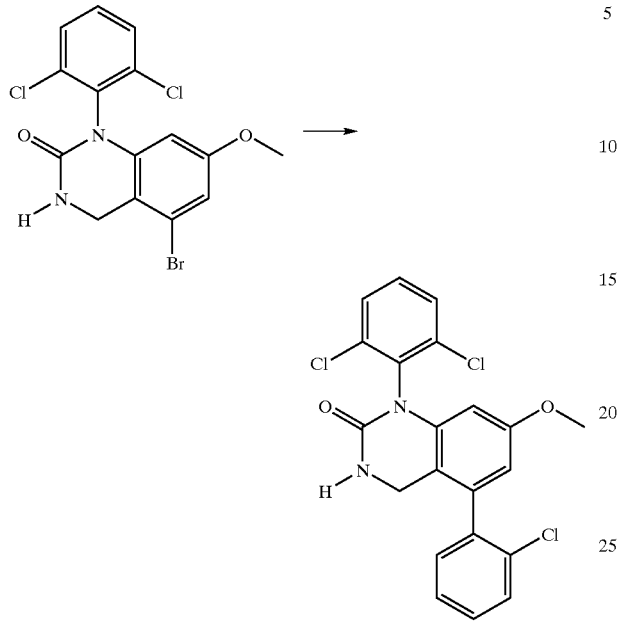

Palladium tetrakis triphenylphosine (140 mg, 0.12 mmol) was added to 1-(2,6-dichlorophenyl)-5-bromo-7-methoxy-3,4-dihydro-2(1H)-quinazolinone (1.02 g, 2.54 mmol) (INTERMEDIATE 23), 2-chlorophenyl boronic acid (642 mg, 4.11 mmol) and sodium carbonate (436 mg, 4.11 mmol) in 150 mL toluene, 40 mL EtOH and 40 mL water under an argon atmosphere. After refluxing 3 h the solution was cooled to RT and partition between water and EtOAc. The organic phase was washed with water'(1×) and brine (1×) and dried over MgSO$_4$. The solution was filtered and concentrated. The residue was absorbed on SiO2 and purified by silica gel bromatography using 3 to 5% acetone in DCM to give 1-(2,6-dichlorophenyl)-5-(2-chlorophenyl)-7-methoxy-3,4-dihydro-2(1H)-quinazolinone as a white solid. $^1$H NMR (CDCl$_3$, 500 MHz): δ 3.68 (s, 3H), 4.17 (d, 1H, J=14.0 Hz), 4.36 (d, 1H, J=14.0 Hz), 5.28 (s, 1H), 5.74 (d, 1H, J=2.3 Hz), 6.43 (d, 1H, J=2.5 Hz), 7.29–7.37 (m, 4H), 7.47–7.51 (m, 3H). MS(ES) 433 (M+H); LC 1: 3.12 min.

INTERMEDIATE 30

1-(2,6-dichlorophenyl)-5-(2-chloro-4-fluorophenyl)-7-methoxy-3,4-dihydro-2(1H)-quinazolinone The title compound was prepared from 1-(2,6-dichlorophenyl)-5-bromo-7-methoxy-3,4-dihydro-2(1H)-quinazolinone (INTERMEDIATE 23) as described in INTERMEDIATE 29 (replacing 2-chlorophenyl boronic acid with 2-chloro-4-fluorophenyl boronic). $^1$H NMR (CDCl$_3$, 500 MHz): δ 3.67 (s, 3H), 4.19 (app dd, 1H, J=13.9 Hz, 1.6 Hz), 4.36 (app dd, 1H, J=13.9 Hz, 1.4 Hz), 5.08 (s, 1H), 5.76 (d, 1H, J=2.3 Hz), 6.42 (d, 1H, J=2.3 Hz), 7.09 (dt, 1H, J=8.2, 2.5 Hz), 7.25–7.33 (m, 2H), 7.37 (t, 1H, J=8.1 Hz), 7.52 (d, 2H, J=7.8 Hz). MS(ES) 451 (M+H); LC 1: 3.17 min.

INTERMEDIATE 31

1-(2,6-dichlorophenyl)-5-(2,4-difluorophenyl)-7-methoxy-3,4-dihydro-2(1H)-quinazolinone The title compound was prepared from 1-(2,6-dichlorophenyl)-5-bromo-7-methoxy-3,4-dihydro-2(1H)-quinazolinone (INTERMEDIATE 23) as described in INTERMEDIATE 29 (replacing 2-chlorophenyl boronic acid with 2,4-difluorophenyl boronic). $^1$H NMR(CDCl$_3$, 500 MHz): δ 3.70 (s, 3H), 4.20–4.49 (br m, 2H), 5.23 (s, 1H), 5.76 (d, 1H, J=2.3 Hz), 6.48 (d, 1H, J=2.3 Hz), 6.92–7.02 (m, 2H), 729–32 (m, 1H), 7.37 (t, 1H, J=8.1 Hz), 7.52 (d, 2H, J=8.1 Hz). MS(ES) 435 (M+H); LC 1: 3.68 min.

INTERMEDIATE 32

1-(2,6-dichlorophenyl)-5-(2-chlorophenyl)-7-methylcarboxylate-3,4-dihydro-2(1H)-quinazolinone

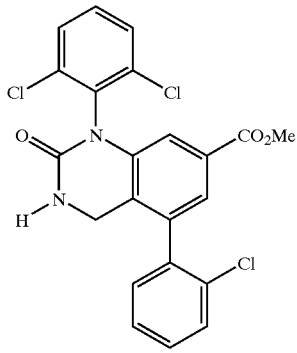

The title compound was prepared from 1-(2,6-dichlorophenyl)-5-bromo-7-methylcarboxylate-3,4-dihydro-2(1H)-quinazolinone (INTERMEDIATE 28) as described in INTERMEDIATE 29 (replacing ethanol with methanol). $^1$H NMR(CDCl$_3$, 500 MHz): δ 3.83 (s, 3H), 4.30 (app dd, 1H, J=15.0, 1.8 Hz), 4.49 (app dd, 1H, J=15.3, 1.6 Hz), 5.4 (s, 1H), 6.83 (d, 1H, J=1.4 Hz), 7.29–7.32 (m, 1H), 7.37–7.43 (m, 3H), 7.51–7.57 (m, 3H), 7.60 (d, 1H, J=1.3 Hz). MS(ES) 461 (M+H); LC 1: 3.63 min.

INTERMEDIATE 33

1-(2,6-dichlorophenyl)-5-(3chlorophenyl)-7-methylcarboxylate-3,4-dihydro-2(1H)-quinazolinone The title compound was prepared from 1-(2,6-dichlorophenyl)-5-bromo-7-methylcarboxyl-3,4-dihydro-2(1H)-quinazolinone (INTERMEDIATE 28) as described in INTERMEDIATE 29 (replacing ethanol with methanol and 2-chlorophenyl boronic acid with 3-chlorophenyl boronic acid). $^1$H NM(CDCl$_3$, 500 MHz): δ 3.84 (s, 3H), 4.56 (d, 2H, J=1.6 Hz), 5.28 (s, 1H), 6.82 (d, 1H, J=1.6 Hz), 7.23–7.26 (m, 1H), 7.36–38 (m, 1H), 7.40 (m, 3H), 7.55 (d, 2H, J=8.5 Hz), 7.66 (d, 1H, J=1.3 Hz). MS(ES) 461 (M+H); LC 1: 3.84 min.

INTERMEDIATE 34

1-(2,6-dichlorophenyl)-5-(4-chlorophenyl)-7-methylcarboxylate-3,4-dihydro-2(1H)-quinazolinone The title compound was prepared from 1-(2,6-dichlorophenyl)-5-bromo-7-methylcarboxyl-3,4-dihydro-2(1H)-quinazolinone (INTERMEDIATE 28) as described in INTERMEDIATE 29 (replacing ethanol with methanol and 2-chlorophenyl boronic acid with 4-chlorophenyl boronic acid). $^1$H NMR(CDCl$_3$, 500 MHz): δ 3.84 (s, 3H), 4.55 (d, 2H, J=1.8 Hz), 5.26 (s, 1H), 6.81 (d, 1H, J=1.6 Hz), 7.29 (d, 2H, J=8.5 Hz), 7.42 (app t, 1H, J=7.7 Hz), 7.47 (d, 2H, J=8.3 Hz), 7.55 (d, 2H, J=8.0 Hz), 7.66 (d, 1H, J=1.6 Hz). MS(ES) 461 (M+H); LC 1: 3.84 min.

INTERMEDIATE 35

1-(2,6-dichlorophenyl)-7-methylcarboxylate-3,4-dihydro-2(1H)-quinazolinone

The title compound was prepared from 1-(2,6-dichlorophenyl)-5-bromo-7-methylcarboxyl-3,4-dihydro-2

(1H)-quinazolinone (INTERMEDIATE 28) and was isolated as a minor product in the preparation of INTERMEDIATE 36. $^1$H NMR(CDCl$_3$, 500 MHz): δ 3.84 (s, 3H), 4.73 (s, 2H), 5.34 (s, 1H), 6.77 (d, 1H, J=1.4 Hz), 7.23 (d, 1H, J=7.7 Hz), 7.40 (t, 1H, J=7.7 Hz), 7.53 (d, 2H, J=8.2 Hz), 7.72 (app dd, 1H, J=7.7, 1.4 Hz). MS(ES) 351 (M+H); LC 2: 1.99 min.

INTERMEDIATE 36

1-(2,6-dichlorophenyl)-5-(2,6-difluorophenyl)-7-methylcarboxylate-3,4-dihydro-2(1H)-quinazolinone The title compound was prepared from 1-(2,6-dichlorophenyl)-5-bromo-7-methylcarboxyl-3,4-dihydro-2 (1H)-quinazolinone (INTERMEDIATE 28) as described in INTERMEDIATE 29 (replacing ethanol with methanol and 2-chlorophenyl boronic acid with 2,6-difluorophenyl boronic acid). $^1$H NMR(CDCl$_3$, 500 MHz): δ 3.84 (s, 3H), 4.46 (d, 2H, J=1.6 Hz), 5.21 (s, 1H), 6.86 (d, 1H, J=1.4 Hz), 7.04–7.09 (m, 2H), 7.38–7.46 (m, 2H), 7.55 (d, 2H, J=8.0 Hz), 7.70 (d, 1H, J=0.9 Hz). MS(ES) 463 (M+H); LC 1: 3.41 min.

INTERMEDIATE 37

1-(2,6-dichlorophenyl)-5-(2,4-difluorophenyl)-7-methylcarboxylate-3,4-dihydro-2(1H)-quinazolinone The title compound was prepared from 1-(2,6-dichlorophenyl)-5-bromo-7-methylcarboxyl-3,4-dihydro-2 (1H)-quinazolinone (INTERMEDIATE 28) as described in INTERMEDIATE 29 (replacing ethanol with methanol and 2-chlorophenyl boronic acid with 2,4-difluorophenyl boronic acid). $^1$H NMR(CDCl$_3$, 500 MHz): δ 3.84 (s, 3H), 4.30–4.61 (br m, 2H), 5.50 (s, 1H), 6.83.(d, 1H, J=1.4 Hz), 6.95–7.05 (m, 2H), 7.28–7.43 (m, 1H), 7.42 (app t, 1H, J=7.8 Hz), 7.55 (d, 2H, J=8.0 Hz), 7.65 (d, 1H, J=1.4 Hz). MS(ES) 463 (M+H), LC 1: 3.55 min.

INTERMEDIATE 38

1-(2,6-dichlorophenyl)-5-(2-fluorophenyl)-7-methylcarboxylate-3,4-dihydro -2(1H)-quinazolinone The title compound was prepared from 1-(2, 6dichlorophenyl)-5-bromo-7-methylcarboxyl-3,4-dihydro-2 (1H)-quinazolinone (INTERMEDIATE 28) as described in INTERMEDIATE 29 (replacing ethanol with methanol and 2-chlorophenyl boronic acid with 2-fluorophenyl boronic acid). $^1$H NMR(CDCl$_3$, 500 MHz): δ 3.83 (s, 3H), 4.30–4.62 (br m, 2H), 5.45 (s, 1H), 6.83 (d, 1H, J=1.6 Hz), 7.21 (app t, 1H, J=8.7 Hz), 7.26–7.30 (m, 1H), 7.41 (app t, 1H, J=7.8 Hz), 7.43–7.47 (m, 1H), 7.55 (d, 2H, J=8.0 Hz), 7.68 (d, 1H, J=1.4 Hz). MS(ES) 445 (M+H); LC 1: 3.47 min.

INTERMEDIATE 39

1-(2,6-dichlorophenyl)-5-(4-fluorophenyl)-7-methylcarboxylate-3,4-dihydro-2(1H)-quinazolinone The title compound was prepared from 1-(2,6-dichlorophenyl)-5-bromo-7-methylcarboxyl-3,4-dihydro-2 (1H)-quinazolinone (INTERMEDIATE 28) as described in INTERMEDIATE 29 (replacing ethanol with methanol and 2-chlorophenyl boronic acid with 4-fluorophenyl boronic acid). $^1$H NMR(CDCl$_3$, 500 MHz): δ 3.84 (s, 3H), 4.54 (d, 2H, J=1.4 Hz), 7.14–7.20 (m, 2H), 7.30–7.34 (m, 2H), 7.41 (app t, 1H, J=7.7 Hz), 7.55 (d, 2H, J=8.0 Hz), 7.66 (d, 1H, J=1.6 Hz). MS(ES) 445 (M+H); LC 1: 3.57 min.

INTERMEDIATE 40

1-(2,6-dichlorophenyl)-5-(2-methylphenyl)-7-methylcarboxylate-3,4-dihydro-2(1H)-quinazolinone The title compound was prepared from 1-(2,6-dichlorophenyl)-5-bromo-7-methylcarboxyl-3,4-dihydro-2 (1H)-quinazolinone (INTERMEDIATE 28) as described in INTERMEDIATE 29 (replacing ethanol with methanol and 2-chlorophenyl boronic acid with 2-methylphenyl boronic acid). $^1$H NMR(CDCl$_3$, 500 MHz): δ 3.83 (s, 3H), 4.21 (app dd, 1H, J=15.3, 1.8 Hz), 4.39 (app dd, 1H, J=15.3, 1.6 Hz), 5.17 (s, 1H), 6.79 (d, 1H, J=1.4 Hz), 7.17 (d, 1H, J=7.3 Hz), 7.28–7.37 (m, 3H), 7.42 (app t, 1H, J=7.8 Hz), 7.56 (d, 2H, J=8.3 Hz), 7.58 (d, 1H, J=1.4 Hz). MS(ES) 441 (M+H); LC 1: 3.65 min.

INTERMEDIATE 41

1-(2,6-dichlorophenyl)-5-phenyl-7-methylcarboxylate-3,4-dihydro-2(1H)-quinazolinone The title compound was prepared from 1-(2,6-dichlorophenyl)-5-bromo-7-methylcarboxyl-3,4-dihydro-2 (1H)-quinazolinone (INTERMEDIATE 28) as described in INTERMEDIATE 29 (replacing ethanol with methanol and 2-chlorophenyl boronic acid with phenyl boronic acid). $^1$H NMR(CDCl$_3$, 500 MHz): δ 3.83 (s, 3H), 4.56 (s, 2H), 5.41 (s, 1H), 6.80 (d, 1H, J=1.6 Hz), 7.34–7.37 (m, 2H), 7.39–7.50 (m, 4H), 7.55 (d, 2H, J=8.0 Hz), 7.69 (d, 1H, J=1.6 Hz). MS(ES) 427 (M+H); LC 1: 3.52 min.

INTERMEDIATE 42

1-(2,6-dichlorophenyl)-5-(3-fluorophenyl)-7-methylcarboxylate-3,4-dihydro-2(1H)-quinazolinone The title compound was prepared from 1-(2,6-dichlorophenyl)-5-bromo-7-methylcarboxyl-3,4-dihydro-2 (1H)-quinazolinone (INTERMEDIATE 28) as described in INTERMEDIATE 29 (replacing ethanol with methanol and 2-chlorophenyl boronic acid with 3-fluorophenyl boronic acid). $^1$H NMR(CDCl$_3$, 500 MHz): δ 3.84 (s, 3H), 4.56 (d, 2H, J=1.2 Hz), 5.55 (s, 1H), 6.81 (d, 1H, J=1.4 Hz), 7.04–7.09 (m, 1H), 7.11–7.17 (m, 2H), 7.41 (app t, 1H, J=7.5 Hz), 7.44–7.48 (m, 1H), 7.56 (d, 2H, J=8.0 Hz), 7.67 (d, 1H, J=1.6 Hz). MS(ES) 459 (M+H); LC 1: 3.57 min.

INTERMEDIATE 43

1-(2,6-dichlorophenyl)-5-(2-trifluoromethylphenyl)-7-methylcarboxylate-3,4-dihydro-2(1H)-quinazolinone The title compound was prepared from 1-(2,6-dichlorophenyl)-5-bromo-7-methylcarboxyl-3,4-dihydro-2 (1H)-quinazolinone (INTERMEDIATE 28) as described in INTERMEDIATE 29 (replacing ethanol with methanol and 2-chlorophenyl boronic acid with 2-trifluoromethylphenyl boronic acid). $^1$H NMR(CDCl$_3$, 500 MHz): δ 3.83 (s, 3H), 4.20–4.27 (m, 2H), 5.14 (s, 1H), 6.83 (d, 1H, J=1.6 Hz), 7.35 (d, 1H, J=7.3 Hz), 7.41 (app t, 1H, J=7.8 Hz), 7.55 (m, 1H), 7.56 (m, 1H), 7.58–7.62 (m, 2H), 7.65 (app t, 1H, J=7.6 Hz), 7.83 (d, 1H, J=7.8 Hz). MS(ES) 495 (M+H); LC 1: 3.76 min.

INTERMEDIATE 44

1-(2,6-dichlorophenyl)-5-(3-methylphenyl)-7-methylcarboxylate-3,4dihydro-2(1H)-quinazolinone The title compound was prepared from 1-(2,6-dichlorophenyl)-5-bromo-7-methylcarboxyl-3,4-dihydro-2

(1H)-quinazolinone (INTERMEDIATE 28) as described in INTERMEDIATE 29 (replacing ethanol with methanol and 2-chlorophenyl boronic acid with 3-methylphenyl boronic acid). $^1$H NMR(CDCl$_3$, 500MHz): δ 2.44 (s, 3H), 3.84 (s, 3H), 4.57 (d, 2H, J=1.6 Hz), 5.21 (s, 1H), 6.79 (d, 1H, J=1.6 Hz), 7.12–7.18 (m, 2H), 7.24–7.27 (m, 1H), 7.36 (t, 1H, J=7.5 Hz), 741 (app t, 1H, J=7.8 Hz), 7.56 (d, 2H, J=8.0 Hz), 7.68 (d, 1H, J=1.6 Hz). MS(ES) 441 (M+H), LC 1: 3.76 min.

INTERMEDIATE 45

1-(2,6-dichlorophenyl)-5-(4-methylphenyl)-7-methylcarboxylate-3,4-dihydro-2(1H)-quinazolinone The title compound was prepared from 1-(2,6-dichlorophenyl)-5-bromo-7-methylcarboxyl-3,4-dihydro-2(1H)-quinazolinone (INTERMEDIATE 28) as described in INTERMEDIATE 29 (replacing ethanol with methanol and 2-chlorophenyl boronic acid with 4-methylphenyl boronic acid). $^1$H NMR(CDCl$_3$, 500 MHz): δ 2.44 (s, 3H), 3.83 (s, 3H), 4.57 (d, 2H, J=1.6 Hz), 5.24 (s, 1H), 6.78 (d, 1H, J=1.6 Hz), 7.24 (d, 2H, J=8.0 Hz), 7.29 (d, 2H, J=7.8 Hz), 7.41 (app tl, 1H, J=7.8 Hz), 7.55 (d, 2H, J=8.2 Hz), 7.68 (d, 1H, J=1.4 Hz). MS(ES) 441 (M+H); LC 1: 3.71 min.

INTERMEDIATE 46

1-(2,6-dichlorophenyl)-5-(4-trifluoromethylphenyl)-7-methylcarboxylate-3,4-dihydro-2(1H)-quinazolinone The title compound was prepared from 1-(2,6-dichlorophenyl)-5-bromo-7-methylcarboxyl-3,4-dihydro-2(1H)-quinazolinone (INTERMEDIATE 28) as described in INTERMEDIATE 29 (replacing ethanol with methanol and 2-chlorophenyl boronic acid with 4-trifluoromethylphenyl boronic acid). $^1$H NMR(CDCl$_3$, 500 MHz): δ 3.85 (s, 3H), 4.55 (d, 2H, J=1.9 Hz), 5.26 (s, 1H), 6.84 (d, 1H, J=1.6 Hz), 7.43 (app 1, 1H, J=7.6 Hz), 7.50 (d, 2H, J=8.1 Hz), 7.68 (d, 2H, J=8.0 Hz), 7.68 (d, 1H, J=1.4 Hz), 7.76 (d, 2H, J=8.3 Hz). MS(ES) 495 (M+H); LC 1: 3.89 min.

INTERMEDIATE 47

1-(2,6-dichlorophenyl)-5-(3-trifluoromethylphenyl)-7-methylcarboxylate-3,4-dihydro-2(1H)-quinazolinone The title compound was prepared from 1-(2,6-dichlorophenyl)-5-bromo-7-methylcarboxyl-3,4-dihydro-2(1H)-quinazolinone (INTERMEDIATE 28) as described in INTERMEDIATE 29 (replacing ethanol with methanol and 2-chlorophenyl boronic acid with 3-trifluoromethylphenyl boronic acid). $^1$H NMR(CDCl$_3$, 500 MHz): δ 3.85 (s, 3H), 4.55 (d, 2H, J=1.8 Hz), 5.17 (s, 1H), 6.84 (d, 1H, J=1.4 Hz), 7.43 (app t, 1H, J=7.6 Hz), 7.54–7.58 (m, 3H), 7.61–7.65 (m, 2H), 7.68 (d, 1H, J=1.6 Hz), 7.71–7.74 (m, 1H). MS(ES) 495 (M+H); LC 1: 3.87 min.

INTERMEDIATE 48

1-(2,6-dichlorophenyl)-5-(2,4-difluorophenyl)-7-hydroxy-3,4-dihydro-2(1H)-quinazolinone

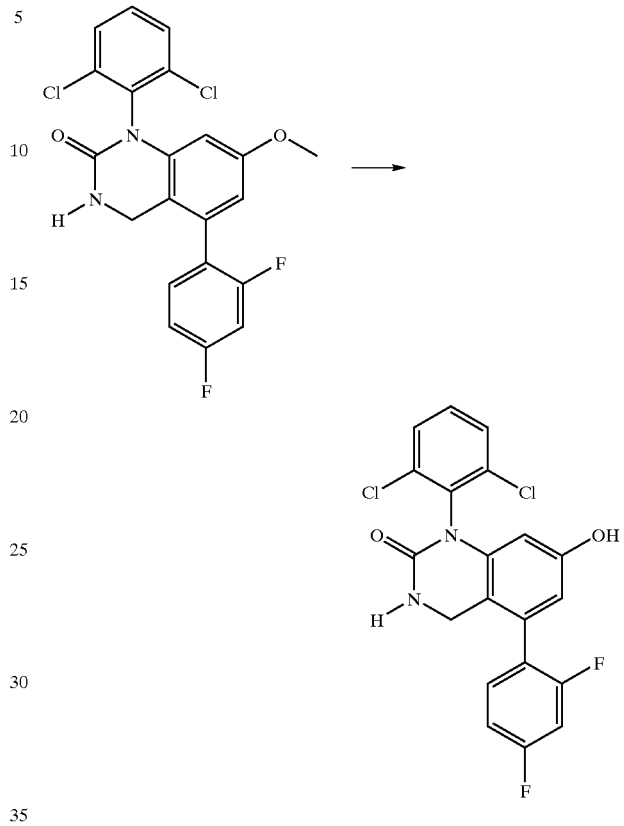

Boron tribromide (1.0M DCM, 0.15 mL) was added to 1-(2,6-dichlorophenyl)-5-(2,4-difluorophenyl)-7-methoxy-3,4-dihydro-2(1H)-quinazolinone (18 mg, 0.041 mmol) (INTERMEDIATE 31) in 1 mL DCM. After 1.2 h the solution was partitioned between EtOAc (15 ml) and pH 4 buffer (5 mL). The phases were separated and the organic phase washed with brine, dried over Na$_2$SO$_4$, filtered and concentrated. The residue was purified by silica gel chromatography using EtOAc/Hexanes as the eluent to give 1-(2,6-dichlorophenyl)-5-(2,4-diflutorophenyl)-7-hydroxy-3,4-dihydro-2(1H)-quinazolinone. $^1$H NMR(CD$_3$OD, 500 MHz): δ 4.23 (brm, 2H), 5.62 (d, 1H, J=2.1 Hz), 6.38 (d, 1H, 2.3 Hz), 7.04–7.10 (m, 2H), 7.31–7.38 (m, 1H), 7.48 (t, 1H, J=8.5 Hz), 7.61 (d, 2H, J=8.0 Hz). MS(ES) 421 (M+H); LC 1: 2.88 min.

INTERMEDIATE 49

1-(2,6-dichlorophenyl)-5-(2-chlorophenyl)-7-hydroxy-3,4-dihydro-2(1H)-quinazolinone The title compound was prepared from 1-(2,6-dichlorophenyl)-5-(2-chlorophenyl)-7-methoxy-3,4-dihydro-2(1H)-quinazolinone (INTERMEDIATE 29) as described in INTERMEDIATE 48. $^1$H NMR(CD$_3$OD, 500 MHz): δ 4.11 (d, 1H, J=14.5 Hz), 4.21 (d, 1H, J=14.5 Hz), 5.59 (d, 1H, J=2.1 Hz), 6.31 (d, 1H, J=2.3 Hz), 7.29–7.32 (m, 1H), 7.37–7.42 (m, 2H), 7.46–7.52 (m, 2H), 7.60–7.63 (m, 2H) MS(ES) 419 (M+H); LC 1: 2.96 min.

INTERMEDIATE 50

1-(2,6-dichlorophenyl)-5-(2-chloro-4-fluorophenyl)-7-hydroxy-3,4-dihydro-2(1H)-quinazolinone The title compound was prepared from 1-(2,6-dichlorophenyl)-5-(2-chloro-4-fluorophenyl)-7-methoxy-3, 4-dihydro-2(1H)-quinazolinone (INTERMEDIATE 30) as described in INTERMEDIATE 48. ¹H NMR(DMSO, 500 MHz): δ 5.50 (s, 1H); 6.21 (s, 1H); 7.23–7.34 (m, 2H); 7.42 (t, 1H, J=6.5 Hz); 7.51–7.60 (m, 2H); 7.69 (d, 2H, J=8.0 Hz). MS(ES) 437 (M+H); LC 1: 2.73 min.

INTERMEDIATE 51

1-(2,6-dichlorophenyl)-5-(2-chlorophenyl)-7-nitro-benzoxazin-2-one

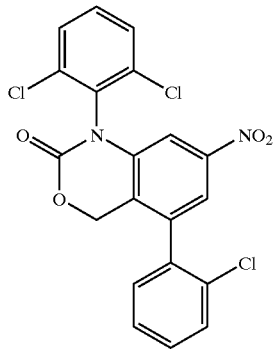

Step A: 1-Bromomethyl-2,6-dibromo-4-nitrobenzene.

A mixture of 2,6-dibromo-4-nitrotoluene (3.83 g, 1 eq.), N-bromosuccinimide (3.23 g, 1.4 eq.) and dibenzoylperoxide (315 mg, 0.1 eq.) in CCl₄ was degassed with argon. The mixture was brought to reflux and azobisisobutyronitrile (213 mg, 0.1 eq.) was added. The mixture was maintained at reflux for 6 hours. The reaction was cooled to room temperature, concentrated and purified to give 1-Bromomethyl-2,6-dibromo-4nitrobenzene. ¹H NMR (500 MHz, CDCl₃) δ CHCl₃: 4.81 (2H, s), 8.41(2H, s).

Step B: 1-Hydroxymethyl-2,6-dibromo-4-nitrobenzene

A mixture of 1-bromomethyl-2,6-dibromo-4-nitrobenzene (4.45 g, 1 eq.) and CaCO₃ (5.7 g, 5 eq.) in 1,4-dioxane (20 mL) and water (20 mL) was heated to and maintained at reflux overnight. The mixture was cooled, poured into water and extracted with ethyl acetate. The organic layer was washed with brine, dried over anhydrousmgSO₄, filtered and concentrated. The product was purified by silica gel chromatography (eluted with 4:1 hexanes:ethyl acetate) to give 1-Hydroxymethyl-2,6-dibromo-4-nitrobenzene. ¹H NMR (500 MHz, CDCl₃) δ CHCl₃: 2.28 (1H, broad t), 5.05(2H, m), 8.397(2H, s).

Step C: 1-N-(2,6-dichlorophenyl)carbamoyloxymethyl-2,6-dibromo-4-nitrobenzene.

To a solution of 1-hydroxymethyl-2,6-dibromo-4-nitrobenzene (1.73 g) in CH₂Cl₂ (30 mL) was added 2,6-ichlorophenylisocyanate (1.15 g, 1.1 eq.). A few crystals of N,N-dimethylaminopyridine were added and the mixture was allowed to stir overnight. The CH₂Cl₂ was removed and the residue dissolved in hot ethyl acetate. The solution was filtered, diluted with hexanes and allowed to crystallize. The crystals were collected and washed with cold 1:1 hexanes:ethyl acetate to yield 1-(N-(2,6-dichlorophenyl) carbamoyloxymethyl-2,6-dibromo-4-nitrobenzene. Mass spectrum (ESI) 496.9 (M+1). ¹H NMR (500 MHz, CDCl₃) δ CHCl₃: 5.569 (2H, s), 6.342 (1H boad s), 7.162(1H, t, J=8 Hz), 7.350 (2H, d, J=8 Hz), 8.411 (2H, s).

Step D: 1-(2,6-dichlorophenyl)-5-bromo-7-nitro-benzoxazin-2-one

A mixture of 1-(N-(2,6-dichlorophenyl) carbamoyloxymethyl-2,6-dibromo-4-nitrobenzene (25 mg, 1 eq.) and CuI (20 mg, 2 eq.) in N,N-dimethylformamide (1 mL) was degassed with argon. To the mixture was added N,N-diisopropylethylamine (0.02 mL) and the mixture was lowered into a 130° C. heating bath. The mixture was heated for 1 hour under argon. The mixture was cooled, filtered and concentrated under reduced pressure. The residue was taken up in CH₂Cl₂, filtered, concentrated and purified by preparative thin layer chromatography (eluted with 4:1 hexanes:ethyl acetate) to yield 1-(2,6-dichlorophenyl)-5-bromo-7-nitro-benzoxazin-2-one. Mass spectrum (ESI) 417.0 (M+1). ¹H NMR (500 MHz, CDCl₃) δ CHCl₃: 5.569 (2H, s), 6.964 (1H, d, J=2 Hz). 7.44–7.48 (1H, m), 7.558 (2H, d, J=8 Hz), 8.169 (1H, d, J=2 Hz).

Step E: 1-(2,6-dichloropheny)-5-(2-chlorophenyl)-7-nitro-benzoxazin-2-one

A mixture of 1-(2,6-dichlorophenyl)-5-bromo-7-nitro-benzoxazin-2-one (96 mg, 1 eq.) and 2-chlorophenylboronic acid (44 mg, 1.2 eq.) in n-butanol (2 mL) was degassed with argon. To the mixture was added 1M Na₂CO₃ (1 mL) and Pd(dppf)Cl₂.CH₂Cl₂ (10 mg, 0.05 eq.) and the mixture was lowered into a 90° C. heating bath. After 75 minutes the mixture was cooled to room temperature. The mixture was diluted with water and brine and extracted 3× with ethyl acetate. The organic extracts were combined, dried over anhydrous Na₂SO₄, filtered and concentrated. The product was purified by silica gel chromatography (eluted with 8:1 hexanes:ethyl acetate) to yield 1-(2,6-dichlorophenyl)-5-(2-chlorophenyl)-7-nitro-benzoxazin-2-one. Mass spectrum (ESI) 449.1 (M+1). ¹H NMR (500 MHz, CDCl₃) δ CHCl₃: 5.130 (1H, ½ ABq, J=14.5 Hz), 5.367 (1H, ½ ABq, J=14.5 Hz), 7.100 (1H, d, J=2 Hz), 7.322 (1H, m), 7.40–7.48 (3H, m), 7.54–7.59 (3H, m), 7.905 (1H, d, J=2 Hz).

INTERMEDIATE 52

1-(2,6-dichlorophenyl)-5-(2-chlorophenyl)-7-amino-benzoxazin-2-one

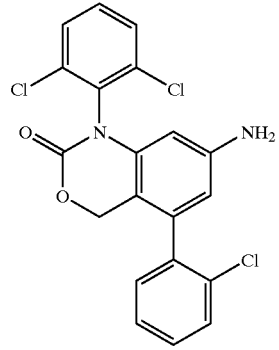

To a stirred solution of 1-(2,6-dichlorophenyl)-5-(2-chlorophenyl)-7-nitro-benzoxazin-2-one (55 mg) in ethyl acetate (5 mL) was added 10% palladium on carbon (dry weight, approx 50% water) (40 mg). Hydrogen gas was bubbled through the mixture for 5 minutes and the mixture was then allowed to stir under a balloon of hydrogen. After 50 minutes the reaction flask was purged with argon. The catalyst was filtered off and washed with methanol. The filtrate was concentrated and purified by preparative thin layer chromatography (eluted 2× with 2:1 hexanes:acetone) to yield 1-(2,6-dichlorophenyl)-5-(2-chlorophenyl)-7-amino-benzoxazin-2-one. Mass spectrum (ESI) 419.0 (M+1). ¹H NMR (500 MHz, CDCl₃) δ CHCl₃: 4.941 (1H, ½ ABq, J=13 Hz), 5.195 (1H, ½ ABq, J=13 Hz), 5.561 (1H, d, J=2 Hz), 6.288 (1H d, J=2 Hz), 7.26–7.39 (4H, m), 7.45–7.51 (3H, m).

EXAMPLE 9
1-(2,6-dichlorophenyl)-5-(2-chlorophenyl)-7-[2-(1-piperidinyl)ethoxyl-3,4-dihydro-2(1H)-quinazolinone

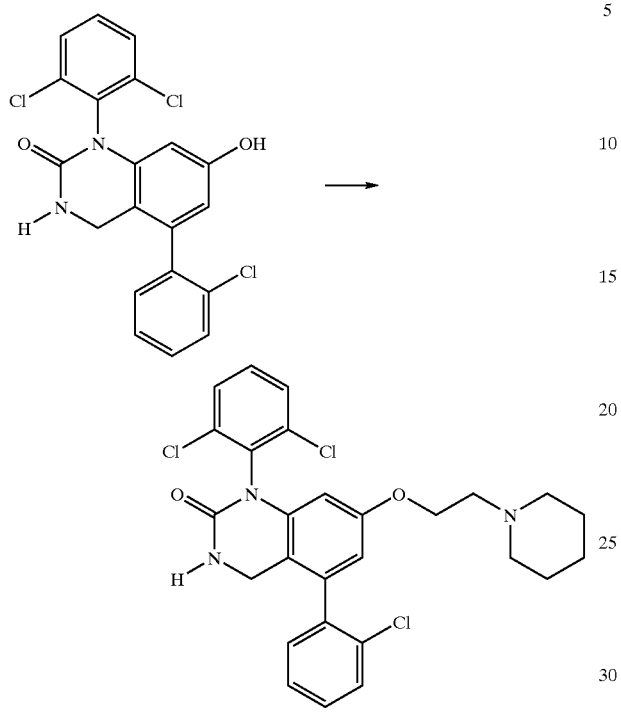

Diethyl azodicarboxylate (50 μL, 0.32 mmol) was added dropwise to a solution of 1-(2,6dichlorophenyl)-5-(2-chlorophenyl)-7-hydroxy-3,4-dihydro-2(1H)-quinazolinone (30 mg, 0.07 mmol) INTERMEDIATE 49), triphenylphosphine (95 mg, 0.36 mmol) and 1-(2-hydroxyethyl)piperidine (55 mg, 0.43 mmol) in 1 mL tetrahydrofuran at 65° C. under an argon atmosphere. After 1 h the solution was cooled to RT and partitioned between saturated NaHCO$_3$ (5 mL) and EtOAc (15 mL). The organic phase was separated, dried over Na$_2$SO$_4$, filtered and concentrated. The residue was purified by thin layer chromatography using EtOAc followed by CHCl$_3$/MeOH/NH$_4$OH (87/12/1) as the eluent to give 1-(2,6-dichlorophenyl)-5-(2-chlorophenyl)-7-[2-(1-piperidinyl)ethoxy]-3,4-dihydro-2(1H)-quinazolinone. $^1$H NMR(CDCl$_3$, 500 MHz): δ 1.44 (m, 2H), 1.62 (m, 4H), 2.48 (m, 4H), 2.72 (m, 2H), 4.00 (t, 2H, J=6.0 Hz), 4.18 (d, 1H, J=14.0 Hz), 4.36 (d, 1H, J-14.0 Hz), 5.22 (s, 1H), 5.76 (d, 1H, J=1.8 Hz), 6.45 (d, 1H, J=2.0 Hz), 7.28–7.39 (m, 4H), 7.45–7.53 (m, 3H). MS(ES) 530 (M+H); LC 1: 2.28 min.

EXAMPLE 10
1-(2,6-dichlorophenyl)-5-(2-chlorophenyl)-7-[2-(1-morpholinyl)ethoxy]-3,4-dihydro-2(1H)-quinazolinone

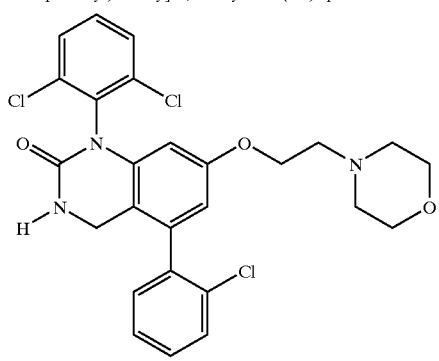

The title compound was prepared similarly to EXAMPLE 9 (replacing 1-(2-hydroxyethyl)piperidine with 1-(2-hydroxyethyl)morpholine. $^1$H NMR(CDCl$_3$, 500 MHz): 2.52 (m, 4H), 2.73 (m, 2H), 3.72 (m, 4H), 3.99 (m, 2H), 4.19 (d, 1H, J=14.2 Hz), 4.36 (d, 1H, J=14.0 Hz), 5.15 (s, 1H), 5.78 (d, 1H, J=2.3 Hz), 6.45 (d, 1H, J=2.2 Hz), 7.29–7.40(m, 4H), 7.48–7.54 (m, 3H). MS(ES) 532 (M+H); LC 1: 2.07 min.

EXAMPLE 11
1-(2,6-dichlorophenyl)-5-(2-chlorophenyl)-7-[2-(1-pyrrolidinyl)ethoxy]-3,4-dihydro-2(1H)-quinazolinone

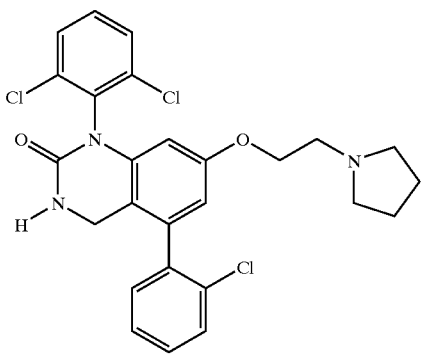

The title compound was prepared as described in EXAMPLE 9 (replacing 1-(2-hydroxyethyl)piperidine with 1-(2-hydroxyethyl)pyrrolidine). $^1$H NMR(CDCl$_3$, 500 MHz): δ 1.85 (brm, 4H), 2.72 brm, 4H), 2.93 (t, 2H, J=5.4 Hz), 4.05 (t, 2H, J=5.2 Hz), 4.19 (d, 1H, 14.2 Hz), 4.36 (d, 1H, J=13.9 Hz), 5.26 (s, 1H), 5.78 (d, 1H, J=2.3 Hz), 6.45 (d, 1H, J=2.3 Hz), 7.29–7.38 (m, 4H), 7.48–7.52 (m, 3H). MS(ES) 516.1 (M+H); LC 1: 2.19 min.

EXAMPLE 12
1-(2,6-dichlorophenyl)-5-(2-chlorophenyl)-7-[oxy-(4-piperidinyl)]-3,4-dihydro-2(1H)-quinazolinone

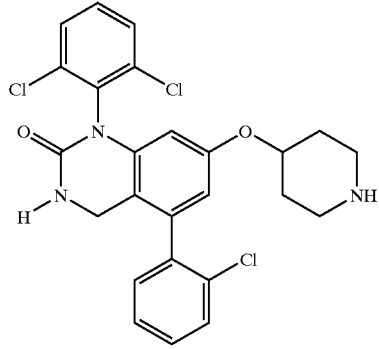

The title compound was prepared as described in EXAMPLE 9 (replacing 1-(2-hydroxyethyl)piperidine with 4-hydoxy-1-Boc-piperidine). The tert-butoxycarbonyl carbonyl group was subsequently removed by treatment with 1/1 TFA/DCM as described in EXAMPLE 34 Step B. $^1$H NMR(CD$_3$OD, 500 MHz): δ 1.55–1.65 (m, 2H), 1.88–1.96 (m, 2H), 2.64–2.70 (m, 2H), 2.97–3.06 (m, 2H), 4.19 (ABq, 2H, 14.7 Hz), 4.25–4.31 (m, 1H), 5.61 (d, 1H, J=2.0 Hz), 6.49 (d, 1H, J=2.3 Hz), 7.30–7.35 (m, 1H, 7.36–7.43 (m, 2H), 7.46–7.56 (m, 2H), 7.60–7.63 (m, 2H). MS(ES) 543 (M+CH3CN+H), 502 (M+H); LC 1: 2.21 min.

EXAMPLE 13
1-(2,6-dichlorophenyl)-5-(2-chlorophenyl)-7-[oxy-(3-(S)-pyrrolidinyl)]-3,4-dihydro-2(1H)-quinazolinone

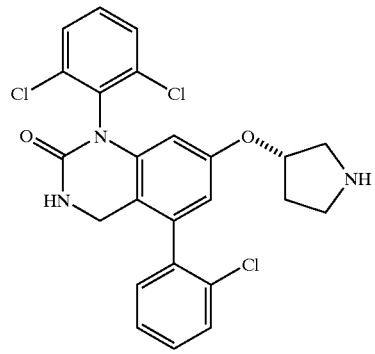

The title compound was prepared as described in EXAMPLE 9 (replacing 1-(2-hydroxyethyl)piperidine with (R)-3-hydroxy-N-Boc-pyrrolidine). The tert-butoxycarbonyl carbonyl group was subsequently removed by treatment with 1/1 TFA/DCM as described in EXAMPLE 34 Step B. $^1$H NMR(CDCl$_3$, 500 MHz): δ 1.86–2.00 (m, 2H); 2.84–2.98 (m, 2H), 3.08–3.18 (m, 2H), 4.19 (d, 1H, J=14.2 Hz), 4.34 (d, 1H, J=14.0 Hz), 4.65 (m, 1H), 5.51 (s, 1H), 5.67 (d, 1H, J=2.1 Hz), 6.38 (d, 1H, J=2.0 Hz), 7.26–7.31 (m, 1H), 7.32–7.39 (m, 3H), 7.43–7.53 (m, 3H). MS(ES) 488 (M+H); LC 1: 2.01 min.

EXAMPLE 14
1-(2,6-dichlorophenyl)-5-(2-chlorophenyl)-7-[oxy-(1-hydroxyacetyl-3-(S)-pyrrolidinyl)]-3,4-dihydro-2(1H)-quinazolinone

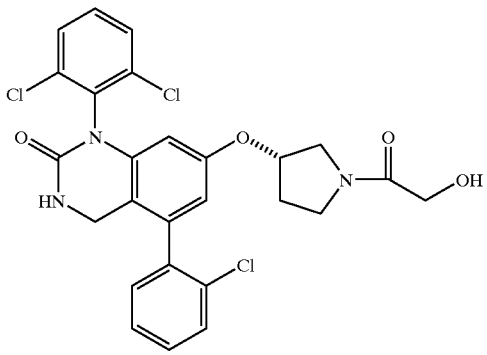

1-[3-(dimethylamino)propyl]-3-ethylcarbodiimide hydrochloride (50 mg, 0.26 mmol) was added to a solution of 1-(2,6-dichlorophenyl)-5-(2-chlorophenyl)-7-[oxy-(3-(S)-pyrrolidinyl)]-3,4dihydro-2(1H)-quinazolinone (40 mg, 0.08 mmol) (EXAMPLE 13), 1-hydroxybenzotriazole hydrate (35 mg, 0.26 mmol), N,N-diisopropylethylamine (0.1 ml, 0.57 mmol) and glycolic acid (20 mg, 0.26 mmol) in DCM (1.5 ml). After stirring overnight the solution was partitioned between EtOAc and water. The phases were separated and the organic phase washed with brine, dried over MgSO$_4$, filtered and concentrated. The residue was purified by preparative thin layer chromatography using EtOAc as the eluent to give 15 mg of the title compound.

$^1$H NMR(CDCl$_3$, 500 MHz): selected data, rotamers δ 1.94–2.15 (m, 1H), 2.19–2.35 (m, 2H), 3.39–3.50 (m, 2H), 3.57–3.65 (m, 1H), 3.72–3.89 (m, 1H), 4.00–4.25 (m, 2H), 4.30–4.38 (m, 1H), 4.78–4.88 (m, 1H). MS(ES) 516 (M+H); LC 1: 2.47 min.

EXAMPLE 15
1-(2,6-dichlorophenyl)-5-(2-chlorophenyl)-7-[oxy-(1-methyl-3-(S)-pyrrolidinyl)]-3,4-dihydro-2(1H)-quinazolinone

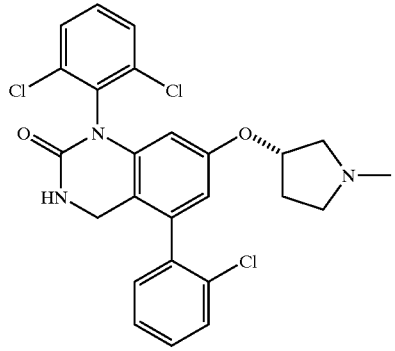

To 1-(2,6dichlorophenyl)-5-(2-chlorophenyl)-7-[oxy-(3-(S)-pyrrolidinyl)]-3,4-dihydro-2(1H)-quinazolinone (40 mg, 0.082 mmol) (EXAMPLE 13) in 1.5 mL MeOH was added formaldehyde (37%, 100 mg, 1.2 mmol) followed by sodium cyanoborohydride (80 mg, 1.27 mmol). After stirring overnight the solution was concentrated and the residue partitioned between EtOAc and 1N NaOH. The phases were separated and the organic phase washed with brine, dried over Na$_2$SO$_4$, filtered and concentrated. The residue was purified by preparative thin layer chromatography using CHCl$_3$/MeOH/NH$_4$OH (87/12/1). The isolated material contained the title compound along with the corresponding 3-hydroxymethyl product. This material was treated with MeOH and K$_2$CO$_3$ (spatula tip) and stirred overnight. The solution was concentrated and the residue partitioned between EtOAc and water. The phases were separated and the organic phase washed with brine, dried over Na$_2$SO$_4$, filtered and concentrated. The residue was purified by preparative thin layer chromatography using CHCl$_3$/MeOH/NH$_4$OH (91/9/1) to give 1-(2,6-dichlorophenyl)-5-(2chlorophenyl)-7-[oxy-(1-methyl-3-(S)-pyrrolidinyl)]-3,4-dihydro-2(1H)-quinazolinone. $^1$H NMR(CDCl$_3$, 500 MHz): δ 1.90–1.98 (m, 1H), 2.13–2.22 (m, 1H), 2.38–2.46 (m, 1H), 2.39 (s, 3H), 2.64–2.74 (m, 1H), 2.78–2.88 (m, 2H), 4.18) d, 1H, J=13.9 Hz), 4.34 (d, 1H, J=14.2 Hz), 4.67 (brm, 1H), 5.40 (s, 1H), 5.71 (s, 1H), 6.35 (m, 1H), 7.26–7.31 (m, 1H), 7.32–7.39 (m, 3H), 7.48–7.53 (m, 3H). MS(ES) 502 (M+H); LC 1: 2.13 min.

EXAMPLE 16

1-(2,6-dichlorophenyl)-3-methyl-5-(2-chlorophenyl)-7-[oxy-(1-methyl-3-(S)-pyrrolidinyl)]-3,4-dihydro-2(1H)-quinazolinone

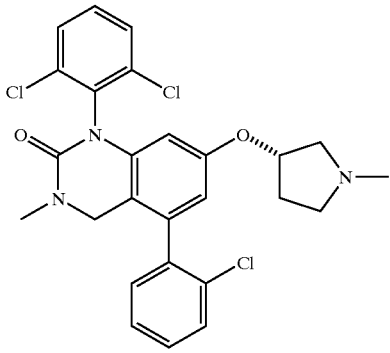

Sodium hydride (60%, spatula tip, excess) was added to 1-(2,6-dichlorophenyl)-5-(2-chlorophenyl)-7-[oxy-(1-methyl-3-(S)-pyrrolidinyl)]-3,4-dihydro-2(1H)-quinazolinone (11.9 mg, 0.0237 mmol) (EXAMPLE 15) in 1 mL DMF at 0° C. After stirring 10 min methyl iodide (0.67M in DMF, 40 μL, 0.027 mmol) was added. The solution was then stirred at RT for 1.5 h. The solution was partitioned between EtOAc and 1N NaOH. The phases were separated and the organic phase washed with brine, dried over Na$_2$SO$_4$, filtered and concentrated. The residue was purified by preparative thin layer chromatography using CHCl$_3$/MeOH/NH$_4$OH (94/6/1) as the eluent to give 1-(2,6-dichlorophenyl)-3-methyl-5-(2chlorophenyl)-7-[oxy-(1-methyl-3-(S)-pyrrolidinyl)]-3,4-dihydro-2(1H)-quinazolinone. $^1$H NMR(CDCl$_3$, 500 MHz): δ 1.90–1.98 (m, 1H), 2.12–2.21 (m, 1H), 2.35–2.41 (m, 1H), 2.38 (s, 3H), 2.61–2.70 (m, 1H), 2.78–2.86 (m, 2H), 2.99 (s, 3H), 4.11 (dd, 1H, J=14.4, 2.0 Hz), 4.26 (d, 1H, J=14.4 Hz), 4.67 (brm, 1H), 5.67 (d, 1H, J=1.9 Hz), 6.33 (m, 1H), 7.30–7.40 (m, 4H), 7.49–7.57 (m, 3H). MS(ES) 516 (M+H); LC 1: 2.44 min.

INTERMEDIATE 53

1-(2,6-dichlorophenyl)-5-(2-chlorophenyl)-7-allyloxy-3,4-dihydro-2(1H)-quinazolinone

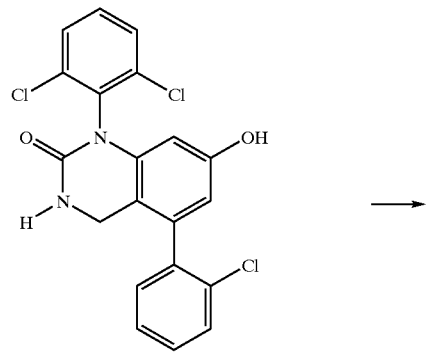

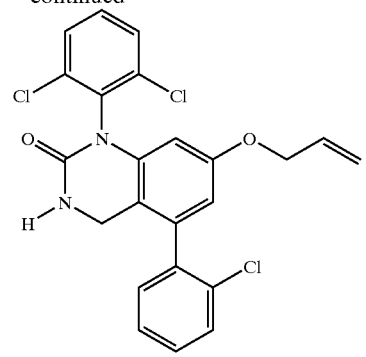

A solution containing 1-(2,6 dichlorophenyl)-5-(2-chlorophenyl)-7-hydroxy-3,4-dihydro-2(1H)-quinazolinone (259 mg, 0.617 mmol) (INTERMEDIATE 49), potassium carbonate (300 mg, 2.2 mmol), allyl chloride (0.45 mL, 5.53 mmol) and sodium iodide (87 mg, 0.58 mmol) in 15 mL acetone was refluxed for seven hours. The solution was concentrated and the residue partitioned between EtOAc and water. The organic phase was washed with brine, dried over Na$_2$SO$_4$, filtered and concentrated. The residue was purified by silica gel chromatography using 2% acetone in DCM to give 1-(2,6-dichlorophenyl)-5-(2chlorophenyl)-7-allyloxy-3,4-dihydro-2(1H)-quinazolinone. $^1$H NMR(CDCl$_3$, 500 MHz): δ 4.18 (d, 1H, 14.2 Hz), 4.34 (d, 1H, J=14.2 Hz), 4.40 (app d, 2H, J=5.5 Hz), 5.20–5.32(m, 2H), 5.77 (d, 1H, J=2.3 Hz), 5.82 (s, 1H), 5.90–6.00 (m, 1H), 6.44 (d, 1H, J=2.3 Hz), 7.27–7.31 (m, 1H), 7.32–7.38 (m, 3H), 7.48–7.52 (m, 3H). MS(ES) 459 (M+H); LC 1: 3.30 min.

INTERMEDIATE 54

1-(2,6-dichlorophenyl)-5-(2-chlorophenyl)-6-allyl-7-oxy-3,4-dihydro-2(1H)-quinazolinone

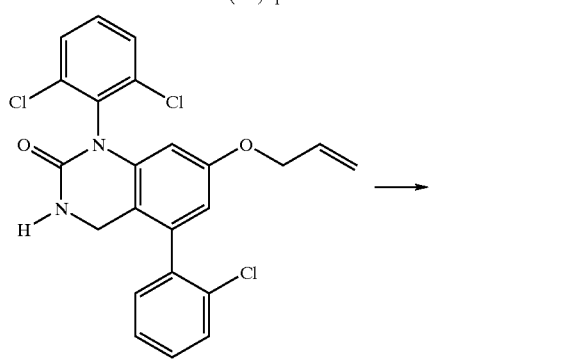

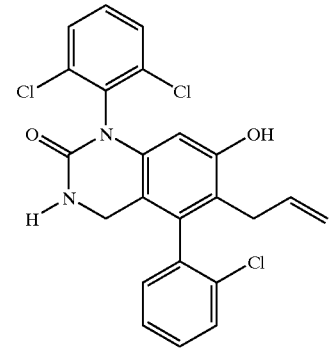

A solution containing 1-(2,6-dichlorophenyl)-5-(2-chlorophenyl)-7-allyloxy-3,4-dihydro-2(1H)-quinazolinone (200 mg, 0.435 mmol) (INTERMEDIATE 53) and 2,6-di-tert-butyl-4-methylphenol (20 mg) in 200 mL 1,2,4-trichlorobenzene under an argon atmosphere was refluxed for 10 hrs. The solution was cooled to RT and partitioned between acetonitrile and hexanes. The phases were separated and the lower phase (CH3CN) washed with hexanes (2×). The solution was concentrated and the residue purified by silica gel chromatography using 70% ethyl ether in hexanes as the eluent to give 1-(2,6-dichlorophenyl)-5-(2-chlorophenyl)-6-allyl-7-oxy-3,4-dihydro2(1H)-quinazolinone. $^1$H NMR(CDCl$_3$, 500 MHz): δ 2.95 (dd, 1H, J=16.2, 6.4 Hz), 3.13 (dd, 1H, J=16.3, 5.9 Hz), 4.08 (dd, 1H, J=14.0, 1.5 Hz), 4.18 (dd, 1H, J=13.9, 1.0 Hz), 5.00–5.09 (m, 2H), 5.74 (s, 1H), 5.80–5.87 (m, 1H), 7.21–7.25 (m, 1H), 7.35–7.40 (m, 3H), 7.51–7.55 (m, 3H). MS(ES) 459 (M+H); LC 1: 3.03 min.

INTERMEDIATE 55

1-(2,6-dichlorophenyl)-5-(2-chlorophenyl)-6-propyl-7-oxy-3,4-dihydro-2(1H)-quinazolinone

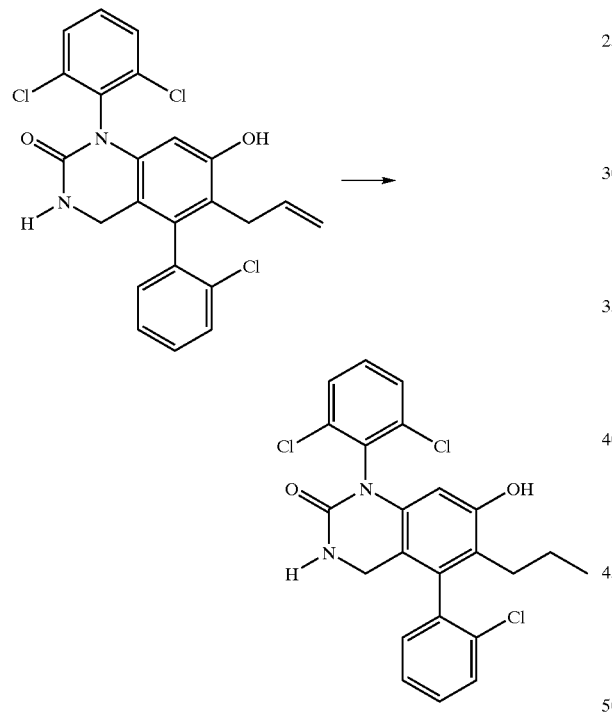

Platinum(IV) oxide (4 mg) was added to a solution of 1-(2,6-dichlorophenyl)-5-(2-chlorophenyl)-6-allyl-7-oxy-3,4-dihydro-2(1H)-quinazolinone (20 mg, 0.044 mmol) (INTERMEDIATE 54) in 4 mL EtOAc. The solution was stirred under a hydrogen atmosphere (ballon) for 2 h. The solution was filtered through Celite and concentrated. The residue was purified by preparative thin layer chromatography using 8% acetone in DCM as the eluent to give 1-(2,6-dichlorophenyl)-5-(2-chlorophenyl)-4-propyl-7-oxy-3,4-dihydro-2(1H)-quinazolinone. $^1$H NMR(CD$_3$OD, 500 MHz): δ 0.70 (t, 3H, J=7.3 Hz), 1.28–1.44 (m, 2H), 2.01–2.09 (m, 1H), 2.26–2.32 (m, 1H), 4.01 (app d, 2H, J=4.3 Hz), 5.67 (s, 1H), 7.24–7.28 (m, 1H), 7.39–7.43 (m, 3H), 7.47 (t, 1H, J=8.0 Hz), 7.52–7.56 (m, 1H), 7.59 (d, 2H, J=8.7 Hz). MS(ES) 461 (M+H); LC 1:3.37 min.

EXAMPLE 17

1-(2,6-dichlorophenyl)-5-(2-chlorophenyl)-6-propyl-7-[2-(1-piperidinyl)ethoxy]-3,4-dihydro-2(1H)-quinazolinone

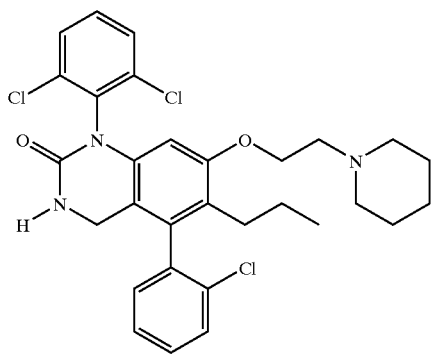

The title compound was prepared from 1-(2,6-dichlorophenyl)-5-(2-chlorophenyl)-6-propyl-7-hydroxy-3,4-dihydro-2(1H)-quinazolinone (INTERMEDIATE 55) as described in EXAMPLE 9. $^1$H NMR(CDCl$_3$, 500 MHz): 0.74 (t, 3H, J=7.4 Hz), 1.25–1.32 (m, 2H), 1.44 (brm, 2H), 1.59(brm, 4H), 2.02–2.11 (m, 1H), 2.88–2.35 (m, 1H), 2.48 (brm, 4H), 2.70 (t, 2H, 5.6 Hz), 3.83 (t, 2H, J=5.7 Hz), 4.03 (d, 1H, 14.2 Hz), 4.16 (d, 1H, J=14.0 Hz), 5.16 (s, 1H), 5.66 (s, 1H), 7.21–7.25 (m, 1H), 7.33–7.39 (m, 3H), 7.49–7.53 (m, 3H). MS(ES) 572.2 (M+H); LC 1: 2.64 min.

INTERMEDIATE 56

1-(2,6-dichlorophenyl)-5-(2-chloro-4-fluorophenyl)-7-(methoxy)-2(1H)-quinazolinone

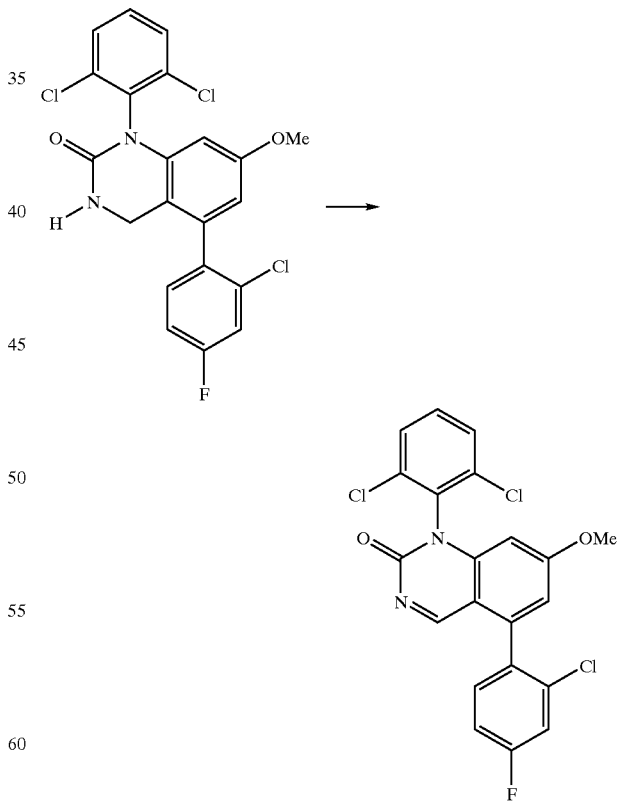

To a solution of 1-(2,6-dichlorophenyl)-5-(2-chlorofluorophenyl)-7-methoxy-3,4-dihydro-2(1H)-quinazolinone (112 mg, 0.248 mmol) (INTERMEDIATE 30) in 1,4-dioxane (5 mL) at 65° C. under an argon atmosphere was added a solution of 2,3-dichloro-5,6-dicyano-1,4-benzoquinone (115 mg, 0.51 mmol) in 1,4-dioxane (2.5 mL). After 2 h the solution was cooled to RT and partitioned between NaHCO₃ and EtOAc. The phases were separated and the organic phase washed with brine, dried over MgSO₄, filtered and concentrated. The residue was purified by silica gel chromatography using 3 to 5% acetone in DCM as the eluent to give 1-(2,6-dichlorophenyl)-5-(2-chloro-4-fluorophenyl)-7-(methoxy)-2(1H)-quinazolinone. ¹H NMR (CDCl₃, 500 MHz): δ 3.70 (s, 3H), 5.94 (d, 1H, J=2.1 Hz), 6.74 (d, 1H, J=2.1 Hz), 7.18 (app dt, 1H, J=8.1, 2.5 Hz), 7.35 (m, 1H), 7.42 (m, 1H), 7.47 (t, 1H, J=8.2 Hz), 7.56–7.60 (m, 2H). MS(ES) 449 (M+H); LC 1: 3.40 min.

INTERMEDIATE 57

1-(2,6-dichlorophenyl)-5-(2-chlorophenyl)-7-(methoxy)-2(1H)-quinazolinone

The title compound was prepared from 1-(2,6-dichlorophenyl)-5-(2-chlorophenyl)-7-methoxy-3,4-dihydro-2(1H)-quinazolinone (INTERMEDIATE 29) as described in INTERMEDIATE 56. ¹H NMR(CDCl₃, 500 MHz): 63.81 (s, 3H), 5.95 (d, 1H, J=2.3 Hz0), 6.79 (d, 1H, J=2.1 Hz), 7.40–7.51 (m, 4H), 7.55–7.63 (m, 3H), 8.78 (s, 1H). MS(ES) 431 (M+H); LC 1: 3.47 min.

INTERMEDIATE 58

1-(2,6-dichlorophenyl)-3-methyl-5-(2-chloro-4-fluorophenyl)-7-methoxy-3,4-dihydro-2(1H)-quinazolinone

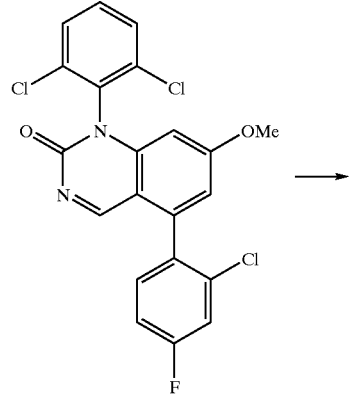

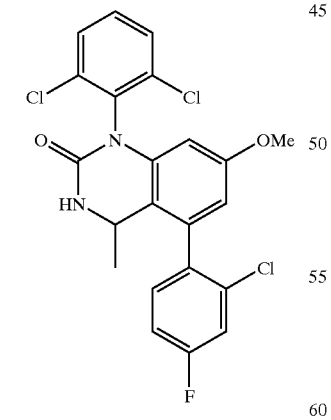

A solution of methylmagnesium bromide (3.0M ethyl ether, 0.5 mL) was added dropwise to 1-(2,6-dichlorophenyl)-5-(2-chloro-4-fluorophenyl)-7-(methoxy)-2(1H)-quinazolinone (230 mg, 0.511 mmol) (INTERMEDIATE 56) in THF (10 mL) at −78C. After 20 min the solution was warmed to 0° C. After 40 min at 0° C. the solution was partitioned between NaHCO₃ and EtOAc. The phases were separated and the organic phase washed with brine, dried over MgSO₄, filtered and concentrated. The crude was absorbed on SiO₂ and purified by silica gel chromatography using 2% acetone in DCM as the eluent to give 1-(2,6-dichlorophenyl)-3-methyl-5-(2-chloro-4-fluorophenyl)-7-methoxy-3,4-dihydro-2(1H)-quinazolinone. ¹H NMR(CDCl₃, 500 MHz): diastereomeric atropisomers δ 1.29 (m, 3H), 3.69 (s, 3H), 4.31 (m, 0.5H), 4.41 (m, 0.5H), 5.32 (m, 0.5H), 5.35 (m, 0.5H), 5.76 (m, 1H), 6.37 (d, 0.5H, J=2.5 Hz), 6.44 (d, 0.5H, J=2.2 Hz), 7.08–7.14 (m, 1H), 7.28–7.40 (m, 3H), 7.50–7.56 (m, 2H). MS(ES) 465 (M+H); LC 1: 3.63 min. and MS(ES) 465 (M+H); LC 1: 3.71 min.

EXAMPLE 18

1-(2,6-dichlorophenyl)-4-methyl-5-(2-chloro-4-fluorophenyl)-7-[2-(1-piperidinyl)ethoxy]-3,4-dihydro-2(1H)-quinazolinone

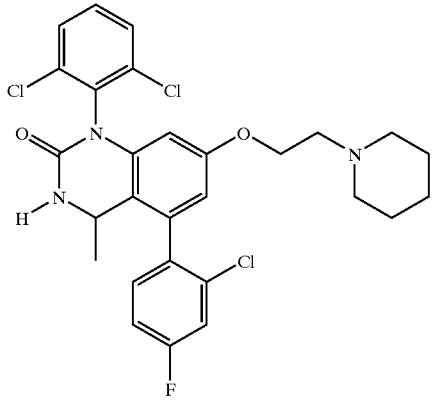

The title compound was prepared from 1-(2,6-dichlorophenyl)-3-methyl-5-(2-chloro-4-fluorophenyl)-7-methoxy-3,4-dihydro-2(1H)-quinazolinone (INTERMEDIATE 58) as described in EXAMPLE 30 and EXAMPLE 34. ¹H NMR(CDCl₃, 500 MHz): diastereomeric atropisomers δ 1.27 (m, 3H), 1.42 (m, 2H), 1.58 (m, 4H), 2.43 (brm, 4H), 2.67 (brm, 2H), 3.96 (m, 2H), 4.29 (m, 0.5H), 4.39 (m, 0.5H), 5.63 (d, 0.5H, J=3.0 Hz), 5.77 (m, 1.5H), 6.37 (d, 0.5H, J=2.3 Hz), 6.43 (d, 0.5H, J=2.3 Hz), 7.06–7.11 (m, 1H), 7.25–7.31 (m, 1H), 7.32–7.40 (m, 2H), 7.48–7.55 (m, 2H). MS(ES) 562 (M+H); LC 1: 2.41 min.

INTERMEDIATE 59

1-(2,6-dichlorophenyl)-5-(2-chlorophenyl)-7-carboxylate-3,4-dihydro-2(1H)-quinazolinone

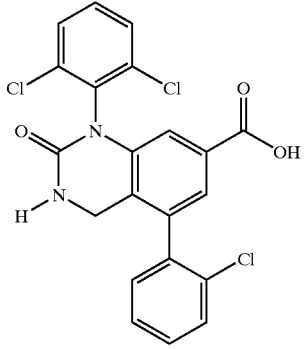

To 1-(2,6dichlorophenyl)-5-(2-chlorophenyl)-7-methylcarboxylate-3,4-dihydro-2(1H)-quinazolinone (9.6 mg, 0.021 mmol) (INTERMEDIATE 32) in 1.5 mL MeOH and 0.5 mL THF was added a solution of lithium hydroxide monohydrate (129 mg in 1.5 mL water). After stirring overnight, 2N HCl (2 mL) was added. The reaction mixture was partitioned between water and ethyl acetate. The phases were separated and the organic phase washed with brine and concentrated. The residue was purified by preparative thin layer chromatography using 20% acetone in DCM with 1% HOAc as the eluent to give 1-(2,6-dichlorophenyl)-5-(2-chlorophenyl)-7-carboxylate-3,4-dihydro-2(1H)-quinazolinone. $^1$H NMR (CD$_3$OD): δ 4.33 (ABq, 2H, J=33.0 Hz), 6.77 (d, 1H, J=1.4 Hz), 7.32–7.34 (m, 1H), 7.40–7.44 (m, 2H), 7.49 (t, 1H, J=8.3 Hz), 7.53 (s, 2H), 7.59 (d, 1H, J=1.6 Hz), 7.60–7.62 (m, 1H). MS(ES) 447 (M+H); LC 1: 2.80 min.

EXAMPLE 19
1-(2,6-dichlorophenyl)-5-(2-chlorophenyl)-7-[N-(2-chlorophenyl)-piperazinylcarbonyl]-3,4-dihydro-2(1H)-quinazolinone

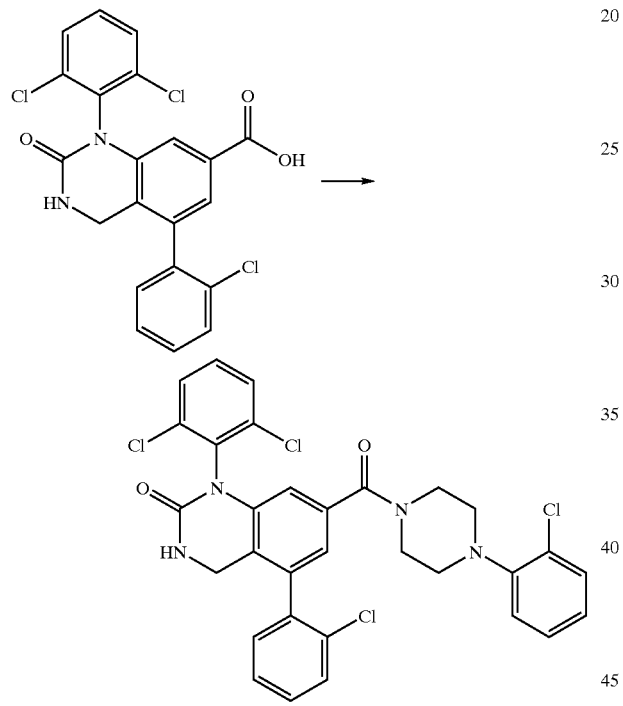

To a mixture of 1-[3-(dimethylamino)propyl]-3-ethylcarbodiimide hydrochloride (33 mg, 0.17 mmol) and 1-hydroxybenzotriazole hydrate (30 mg, 0.22 mmol) in DMF (1.3 mL) was added 1-(2,6-dichlorophenyl)-5-(2-chlorophenyl)-7-carboxyl-3,4-dihydro-2(1H)-quinazolinone (50 mg, 0.11 mmol) (INTERMEDIATE 59). The mixture was stirred at room temperature for 15 minutes. To this was added N-(2-chlorophenyl)piperazine (33 mg, 0.17 mmol). The reaction mixture was then stirred at room temperature for 20 hours. Removal of the solvent and subsequent purification by preparative thin layer chromatography using 45% acetone in hexane provided 1-(2,6-dichlorophenyl)-5-(2-chlorophenyl)-7-[N-(2-chlorophenyl)-piperazinylcarbonyl]-3,4-dihydro-2(1H)-quinazolinone (yellow solid). $^1$H NMR(CDCl$_3$, 500 MHz): δ 2.90 (brs, 2H), 3.08 (brs, 2H), 3.59 (brs, 2H), 3.89 (brm, 2H), 4.34 (d, 1H, J=14.9 Hz), 4.43 (d, 1H, J=14.9 Hz), 5.20 (s, 1H), 6.24 (s, 1H), 6.98–7.08 (m, 3H), 7.22–7.44 (m, 6H), 7.50–7.57 (m, 3H). MS(ES) 627 (M+H); LC 1: 3.75 min.

EXAMPLE 20
1-(2,6-dichlorophenyl)-5-(2-chloro-4-fluorophenyl)-7-[N-(1-piperazinylcarbonyl]-3,4-dihydro-2(1H)-quinazolinone

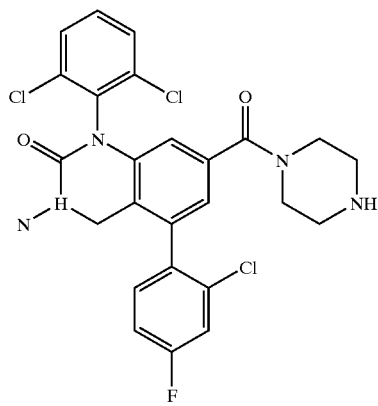

The title compound was prepared as described in EXAMPLE 19 (replacing N-(2-chlorophenyl)piperazine with 1-tert-butoxycarbonyl-piperazine). The tert-butoxycarbonyl group was subsequently removed as described in EXAMPLE 34 Step B. $^1$H NMR(CDCl$_3$, 500 MHz): selected data δ 1.58–2.10 (brs, 1H), 2.63–2.87 (brm, 4H); 3.28–3.43 (brm, 2H); 3.60–3.76 (brm, 2H); 4.39 (ABq, 2H, J=13.0 Hz). MS(ES) 533 (M+H); LC 1: 1.80 min.

EXAMPLE 21
1-(2,6-dichlorophenyl)-5-(2-chlorophenyl)-7-[N-(5-chloropyridin-2-yl)piperazinylcarbonyl]-3,4-dihydro-2(1H)-quinazolinone

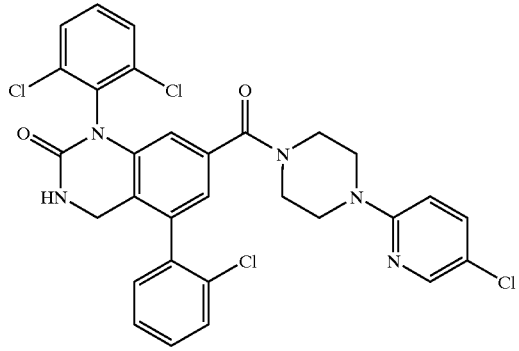

The title compound was prepared from 1-(2,6-dichlorophenyl)-5-(2-chlorophenyl)-7-carboxyl-3,4-dihydro-2(1H)-quinazolinone (INTERMEDIATE 59) as described in EXAMPLE 19 (replacing N-(2-chlorophenyl) piperazine with N-(5-chloropyridin-2-yl)piperazine). $^1$H NMR(CDCl$_3$, 500 MHz): δ 3.53(brs, 6H), 3.80 (brs, 2H), 4.35 (d, 1H, J=14.6 Hz), 4.43 (d, 1H, J=14.8 Hz), 5.11 (s, 1H), 6.24 (s, 1H), 6.63 (d, 1H, J=9.1 Hz), 7.00 (s, 1H), 7.30–7.43 (m, 4H), 7.48–7.57 (m, 4H), 8.16 (d, 1H, J=2.3 Hz). MS(ES) 628 (M+H); LC 1: 3.36 min.

EXAMPLE 22

1-(2,6-dichlorophenyl)-5-(2-chlorophenyl)-7-[N-((pyridin-4-yl)methyl)piperazinylcarbonyl]-3,4-dihydro-2(1H)-quinazolinone

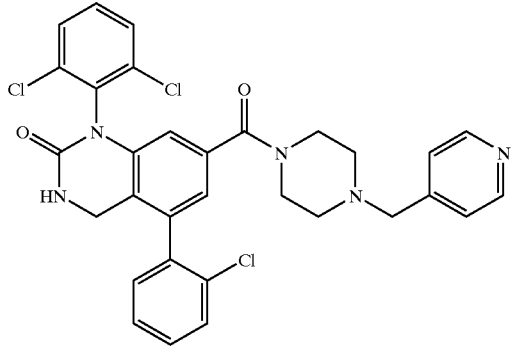

The title compound was prepared from 1-(2,6-dichlorophenyl)-5-(2-chlorophenyl)-7-carboxyl-3,4-dihydro-2(1H)-quinazolinone (INTERMEDIATE 59) as described in EXAMPLE 19 (replacing N-(2-chlorophenyl)piperazine with N-(pyridin-4-yl)methylpiperazine). $^1$H NMR(CDCl$_3$, 500 MHz): δ 2.38 (brs, 2H), 2.52 (brs, 2H), 3.45 (brs, 2H), 3.58 (s, 2H), 3.74 (brs, 2H), 4.33 (d, 1H, J=14.7 Hz), 4.41 (d, 1H, J=14.7 Hz), 5.11 (s, 1H), 6.20 (s, 1H), 6.97 (s, 1H), 7.25–7.45 (m, 6H), 1.50–756 (m, 3H), 8.60 (d, 2H, J=5.0 Hz). MS(ES) 608 (M+H); LC 1: 1.95 min.

EXAMPLE 23

1-(2,6-dichlorophenyl)-5-(2-chlorophenyl)-7-[N-(isoquinolin-1-yl)piperazinylcarbonyl]-3,4-dihydro-2(1H)-quinazolinone

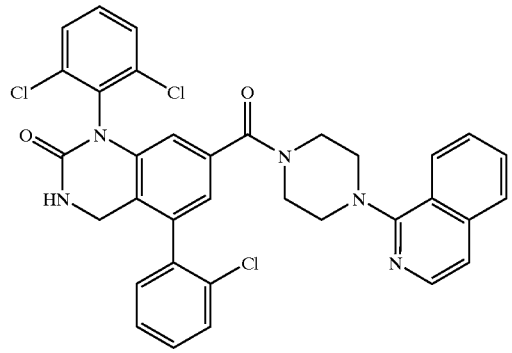

The title compound was prepared from 1-(2,6-dichlorophenyl)-5-(2-chlorophenyl)-7-carboxyl-3,4-dihydro-2(1H)-quinazolinone (INTERMEDIATE 59) as described in EXAMPLE 19 (replacing N-(2-chlorophenyl)piperazine with N-(isoquinolin-1-yl)piperazine). $^1$H NMR (CDCl$_3$, 500 MHz): δ 3.40(brs, 4H), 3.68 (brs, 2H), 3.95 (brs, 2H), 4.35 (d, 1H, J=14.9 Hz), 4.44 (d, 1H, J=14.6 Hz), 5.10 (s, 1H), 6.28 (s, 1H), 7.02 (s, 1H), 7.30–7.58 (m, 9H), 7.64 (m, 11H), 7.80 (m, 1H), 8.09 (m, 1H), 8.16 (d, 1H, J=5.9 Hz). MS(ES) 643 (M+H); LC 1: 2.51 min.

EXAMPLE 24

1-(2,6-dichlorophenyl)-5-(2-chlorophenyl)-7-[N-(indan-2-yl)piperazinylcarbonyl]-3,4-dihydro-2(1H)-quinazolinone

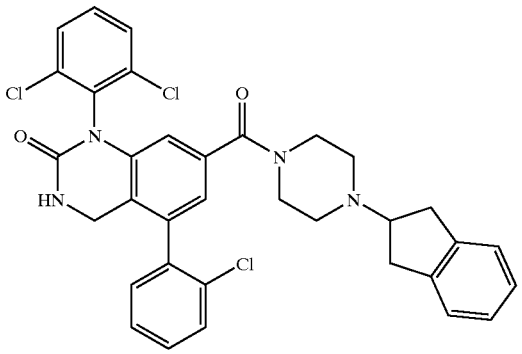

The title compound was prepared from 1-(2,6-dichlorophenyl)-5-(2-chlorophenyl)-7-carboxyl-3,4-dihydro-2(1H)-quinazolinone (INTERMEDIATE 59) as described in EXAMPLE 19 (replacing N-(2-chlorophenyl)piperazine with N-(indan-2-yl)piperazine). $^1$H NMR (CDCl$_3$, 500 MHz): selected data δ 3.17(brs, 4H), 3.60 (brs, 1H), 3.80 (brm, 4H), 4.20 (brm, 4H). MS(ES) 633 (M+H); LC 1: 2.42 min.

EXAMPLE 25

1-(2,6-dichlorophenyl)-5-(2-chlorophenyl)-7-[N-(benzoisothiazol-3-yl)piperazinylcarbonyl]-3,4-dihydro-2(1H)-quinazolinone

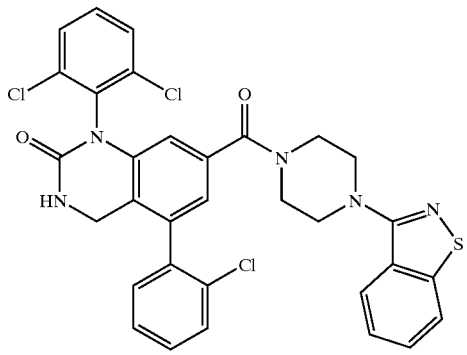

The title compound was prepared from 1-(2,6-dichlorophenyl)-5-(2-chlorophenyl)-7-carboxyl-3,4-dihydro-2(1H)-quinazolinone (INTERMEDIATE 59) as described in EXAMPLE 19 but replacing N-(2-chlorophenyl)piperazine with N-(benzoisothiazol-3-yl)piperazine. $^1$H NMR(CDCl$_3$, 500 MHz): δ 3.46(brs, 2H), 3.58 (brs, 2H), 3.66 (brs, 2H), 3.93 (brs, 2H), 4.35 (d, 1H, J=14.7 Hz), 4.44 (d, 1H, J=14.9 Hz), 5.16 (s, 1H), 6.26 (s, 1H), 7.02 (s, 1H), 7.30–7.44 (m, 5H), 7.50–7.58 (m, 3H), 7.86 (d, 1H, J=8.0 Hz), 7.92 (d, 1H, J=8.3 Hz), 8.04 (s, 1H). MS(ES) 650 (M+H); LC 1: 3.73 min.

EXAMPLE 26

1-(2,6-dichlorophenyl)-5-(2-chlorophenyl)-7-[N-(4-methoxypyridin-2-yl)piperazinylcarbonyl]-3,4-dihydro-2(1H)-quinazolinone

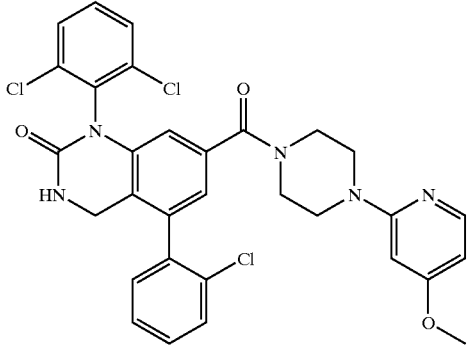

The title compound was prepared from 1-(2,6-dichlorophenyl)-5-(2-chlorophenyl)-7-carboxyl-3,4-dihydro-2(1H)-quinazolinone (INTERMEDIATE 59) as described in EXAMPLE 19 but replacing N-(2-chlorophenyl)piperazine with N-(4-methoxypyridin-2-yl) piperazine. $^1$H NMR(CDCl$_3$, 500 MHz): δ 3.52(brs, 6H), 3.80 (brs, 2H), 3.85 (s, 3H), 4.34 (d, 1H, J=14.9 Hz), 4.44 (d, 1H, J=14.8 Hz), 5.28 (s, 1H), 6.11 (s, 1H), 6.23 (s, 1H), 6.33 (d, 1H, J=4.8 Hz), 7.00 (s, 1H), 7.30–7.42 (m, 4H), 7.50–7.56 (m, 3H), 8.06 (d, 1H, J=5.7 Hz). MS(ES) 624 (M+H); LC 1: 2.31 min.

EXAMPLE 27

1-(2,6-dichlorophenyl)-5-(2-chlorophenyl)-7-[N-(2-chlorophenyl)piperazinylmethyl]-3,4-dihydro-2(1H)-quinazolinone

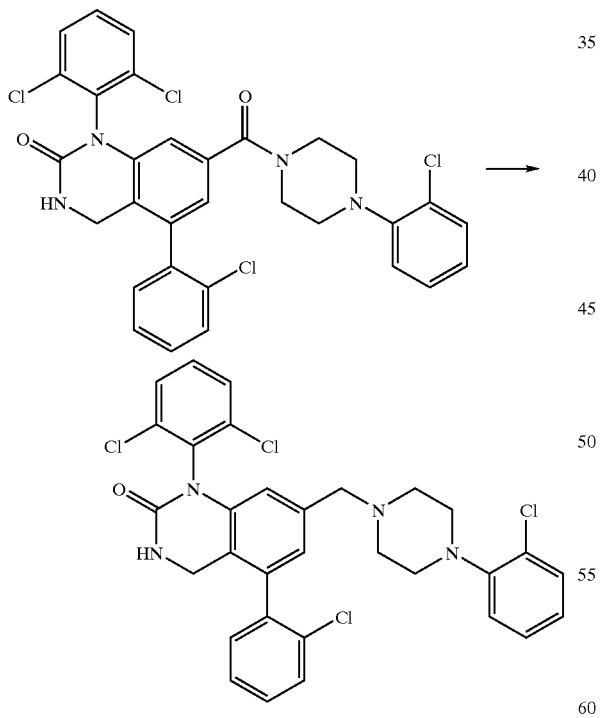

A solution of 1-(2,6-dichlorophenyl)-5-(2-chlorophenyl)-7-[N-(2-chlorophenyl)piperazinylcarbonyl]-3,4-dihydro-2(1H)-quinazolinone (EXAMPLE 19) (36 mg, 0.0575 mmol) and borane-THF complex (0.5 mL of 1.0M solution, 0.5 mmol) was stirred at room temperature for two hours. Methanol (1 mL) was added and the mixture was stirred for 15 minutes. The solution was concentrated and the residue treated with 4.0M HCl solution in dioxane (1 mL). The mixture was stirred at room temperature for two hours. The solvent was removed and neutralized with a minimum amount of 2N ammonia solution in methanol. Removal of the solvent and subsequent purification by preparative thin layer chromatography using 50% acetone in hexanes provided 1-(2,6-dichlorophenyl)-5-(2-chlorophenyl)-7-[N-(2-chlorophenyl)piperazinylmethyl]-3,4-dihydro-2(1H)-quinazolinone. $^1$H NMR(CDCl$_3$, 500 MHz): δ 2.59 (brs, 4H), 3.02 (brs, 4H), 3.49 (brs, 2H), 4.28 (d, 1H, J=14.6 Hz), 4.44 (d, 1H, J=14.2 Hz), 5.09 (s, 1H), 6.22 (s, 1H), 6.92(s, 1H), 6.98 (t, 1H), 7.03 (d, 1H, J=7.1 Hz), 7.23 (t, 1H, J=7.5 Hz), 7.32–7.43 (m, 5H), 7.48–7.58 (m, 3H). MS(ES) 613 (M+H); LC 1: 2.73 min.

EXAMPLE 28

1-(2,6-dichlorophenyl)-5-(2-chlorophenyl)-7-[N-(isoquinolin-1-yl)piperazinylmethyl]-3,4-dihydro-2(1H)-quinazolinone

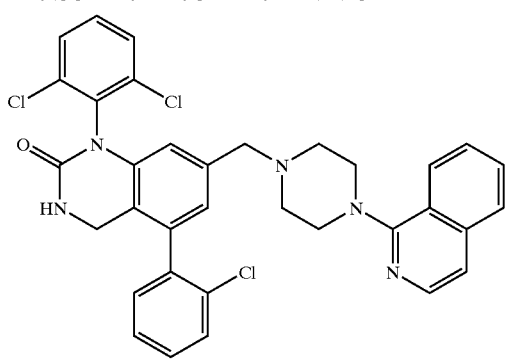

The title compound was prepared from 1-(2,6-dichlorophenyl)-5-(2-chlorophenyl)-7-[N-(isoquinolin-1-yl)piperazinylcarbonyl]-3,4-dihydro-2(1H)-quinazolinone (EXAMPLE 23) similarly to that procedure described in EXAMPLE 27. $^1$H NMR(CDCl$_3$, 500 MHz): δ 2.68 (brs, 4H), 3.39 (brs, 4H), 3.55 (brs, 2H), 4.28 (d, 1H, J=14.5 Hz), 4.44 (d, 1H, J=14.4 Hz), 5.16 (s, 1H), 6.25 (s, 1H), 6.94 (s, 1H), 7.25 (d, 1H, J=6.0 Hz), 7.30–7.42 (m, 4H), 7.47–7.57 (m, 4H), 7.62 (t, 1H, J=7.5 Hz), 7.76 (d, 1H, J=8.0 Hz), 8.07 (d, 1H, J=8.5 Hz), 8.15 (d, 1H, J=5.8 Hz). MS(ES) 630 (M+H); LC 1: 2.35 min.

EXAMPLE 29

1-(2,6-dichlorophenyl)-5-(2-chlorophenyl)-7-[N-(5-chloropyridin-2-yl)piperazinylmethyl]-3,4-dihydro-2(1H)-quinazolinone

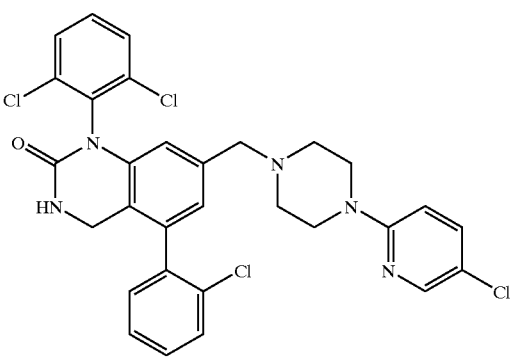

The title compound was prepared from 1-(2,6-dichlorophenyl)-5-(2-chlorophenyl)-7-[N-(5-chloropyridin-2-yl)piperazinylcarbonyl]-3,4-dihydro-2(1H)-quinazolinone (EXAMPLE 21) as described in EXAMPLE 27. MS(ES) 614 (M+H); LC 1: 2.68 min.

EXAMPLE 30
1-(2,6-dichlorophenyl)-5-(2-chlorophenyl)-7-[N-((pyridin-4-y1)methyl)piperazinylmethyl]-3,4-dihydro-2(1H)-quinazolinone

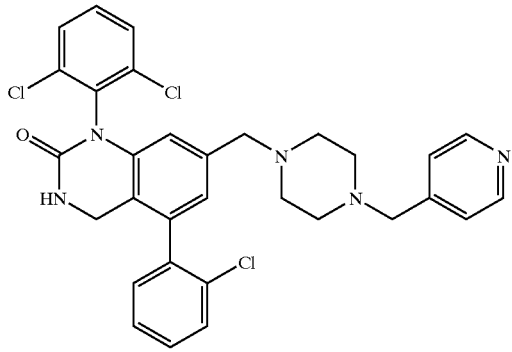

The title compound was prepared from 1-(2,6-dichlorophenyl)-5-(2-chlorophenyl)-7-[N(pyridin4-yl)methyl)piperazinylcarbonyl]-3,4-dihydro-2(1H)-quinazolinone (EXAMPLE 22) as described in EXAMPLE 27. $^1$H NMR(CDCl$_3$, 500 MHz): δ 2.44 (brs, 8H), 3.43 (brs, 2H), 3.51 (s, 2H), 4.26 (d, 1H, J=14.6 Hz), 4.42 (d, 1H, J=14.2 Hz), 5.12 (s, 1H), 6.16 (s, 1H), 6.88 (s, 1H), 7.22–7.57 (m, 9H), 8.55 (d, 2H, J=5.3 Hz). MS MS(ES) 594 (M+H); LC 1: 1.84 min.

EXAMPLE 31
1-(2,6-dichlorophenyl)-5-(2-chlorophenyl)-7-[N-(indan-2-yl)piperazinylmeythl]-3,4-dihydro-2(1H)-quinazolinone

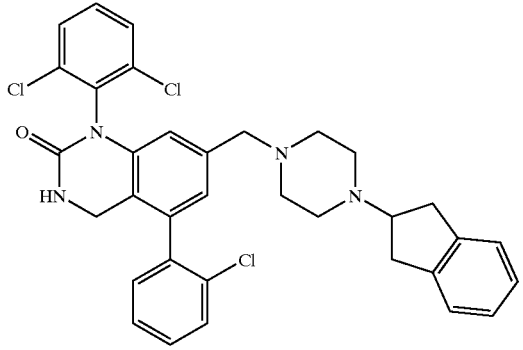

The title compound was prepared from 1-(2,6-dichlorophenyl)-5-(2-chlorophenyl)-7-[N-(indan-2-yl)piperazinylcarbonyl]-3,4-dihydro-2(1H)-quinazolinone (EXAMPLE 24) as described in EXAMPLE 27. $^1$H NMR (CDCl$_3$, 500 MHz): δ 2.55 (brs, 8H), 2.96 (brs, 2H), 3.10 (brs, 2H), 3.22 (brs, 2H), 3.45 (s, 2H), 4.26 (d, 1H, J=14.4 Hz), 4.43 (d, 1H, J=14.4 Hz), 5.09 (s, 1H), 6.16 (s, 1H), 6.88 (s, 1H), 7.13–7.22 (m, 4H), 7.30–7.43 (m, 4H), 7.48–7.57 (m, 3H).

MS(ES) 619 (M+H); LC 1: 2.61 min.

EXAMPLE 32
1-(2,6-dichlorophenyl)-5-(2-chlorophenyl)-7-[N-(4-methoxypyridin-2-y1)piperazinylmethyl]-3,4-dihydro-2(1H)-quinazolinone

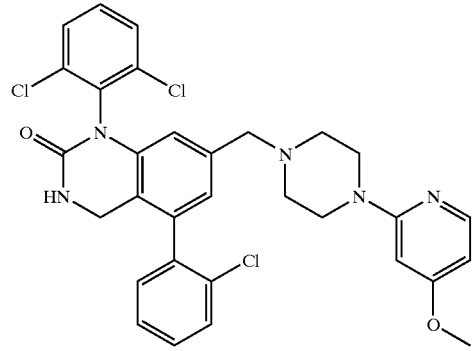

The title compound was prepared from 1-(2,6-dichlorophenyl)-5-(2-chlorophenyl)-7-[N-(4-methoxypyridin-2-yl)piperazinylcarbonyl]-3,4-dihydro-2(1H)-quinazolinone. (EXAMPLE 26) as described in EXAMPLE 27. $^1$H NMR(CDCl$_3$, 500 MHz): δ 2.51 (brs, 4H), 3.48 (brs, 6H), 3.83 (s, 3H), 4.27 (d, 1H, J=14.1 Hz), 4.44 (d, 1H, J=14.5 Hz), 5.13 (s, 1H), 6.09 (s, 1H), 6.22 (s, 1H), 6.28 (d, 1H, J=5.3 Hz), 6.90 (s, 1H), 7.30–7.42 (m, 4H), 7.48–7.57(m, 3H), 8.05 (d, 1H, J=5.9 Hz). MS(ES) 610 (M+H); LC 1: 1.9 min.

INTERMEDIATE 60
1-(2,6-dichlorophenyl)-5-(2,4-difluorophenyl)-7-trifluoromethylsulfonato-3,4-dihydro-2(1H)-quinazolinone

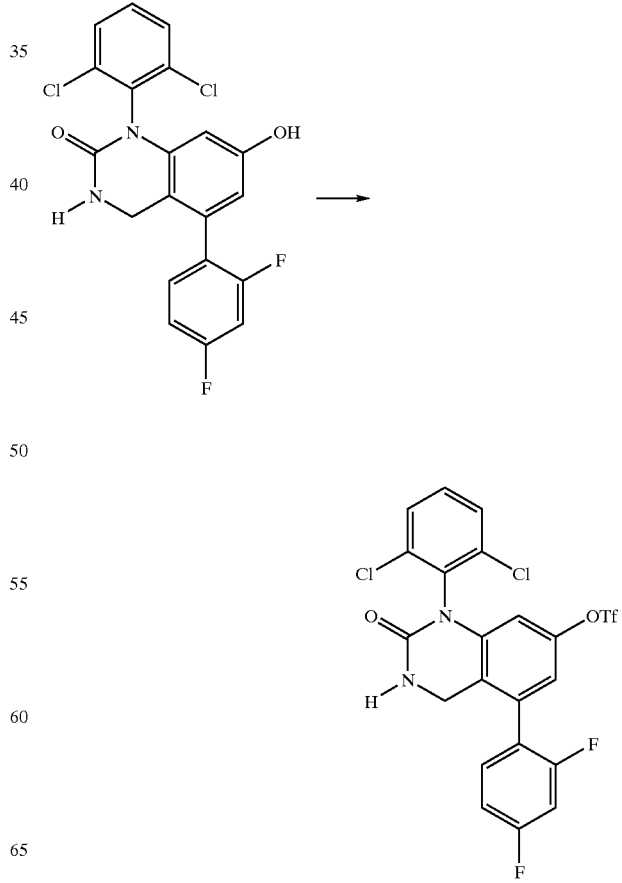

Solid 2-[N,N-Bis(trifluoromethylsulfonyl)amino]-5-chloropyridine (60 mg, 0.20 mmol) was added to 1-(2,6-dichlorophenyl)-5-(2,4-difluorophenyl)-7-hydroxy-3,4-dihydro-2(1H)-quinazolinone (64 mg, 0.152 mmol) (INTERMEDIATE 48) in 2 mL THF. After 1 h the solution was partitioned between EtOAc and NaHCO$_3$. The phases were separated and the organic phase washed with brine, dried over Na$_2$SO$_4$, filtered and concentrated. The residue was purified by silica gel chromatography using 3% acetone in DCM to give 1-(2,6-dichlorophenyl)-5-(2,4-difluorophenyl)-7-trifluoromethylsulfonato-3,4-dihydro-2(1H)-quinazolinone. $^1$H NMR(CDCl$_3$, 500MHz): δ 4.25–4.54 (brm, 2H), 5.75 (s, 1H), 6.05 (d, 1H, J=2.3 Hz), 6.89 (d, 1H, J=2.3 Hz), 6.95–7.07 (m, 2H), 7.22–7.37 (m, 1H), 7.43 (t, 1H, J=7.7 Hz), 7.56 (d, 2H, J=8.0 Hz). MS(ES) 553 (M+H); LC 1: 4.03 min.

INTERMEDIATE 61

1-(2,6-dichlorophenyl)-5-(2-chlorophenyl)-7-trifluoromethylsulfonato-3,4-dihydro-2(1H)-quinazolinone The title compound was prepared from 1-(2,6-dichlorophenyl)-5-(2-chlorophenyl)-7-hydroxy-3,4-dihydro-2(1H)-quinazolinone (INTERMEDIATE 49) as described in INTERMEDIATE 60. $^1$H NMR(CDCl$_3$, 500 MHz): δ 4.27 (dd, 1H, J=14.9, 1.6 Hz), 4.41 (dd, 1H, J=14.8, 1.3 Hz), 5.38 (s, 1H), 6.03 (d, 1H, J=2.3 Hz), 6.84 (d, 1H, J=2.3 Hz), 7.28–7.31 (m, 3H), 7.35–7.44 (m, 3H), 7.51–7.57 (m, 3H). MS(ES) 551 (M+H); LC 1: 3.47min.

INTERMEDIATE 62

1-(2,6-dichlorophenyl)-5-(2chloro-4-fluorophenyl)-7-trifluoromethylsulfonato-3,4-dihydro-2(1H)-quinazolinone The title compound was prepared from 1-(2,6-dichlorophenyl)-5-(2-chloro-4-fluorophenyl)-7-hydroxy-3,4-dihydro-2(1H)-quinazolinone (INTERMEDIATE 50) as described in INTERMEDIATE 60. MS(ES) 569 (M+H); LC 1: 3.51 min.

EXAMPLE 33

1-(2,6-dichlorophenyl)-5-(2,4-difluorophenyl)-7-(1-morpholinyl)-3,4-dihydro-2(1H)-quinazolinone

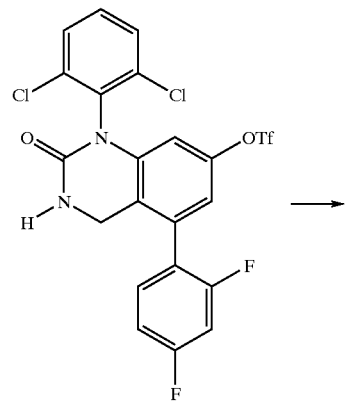

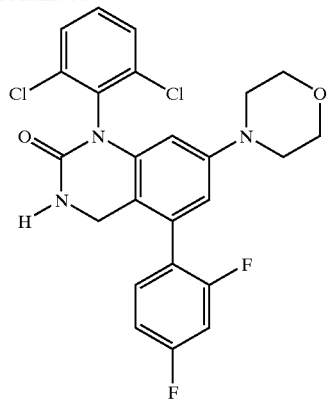

To dry Cs$_2$CO$_3$ (46 mg, 0.141 mmol) under argon was added Pd(OAc)$_2$ (6 mg, 0.027 mmol), racemic BINAP (25 mg, 0.04 mmol) and 1.2 mL anhydrous 1,4-dioxane. To the orange suspension was added morpholine (0.09 mL, 1.02 mmol) and 1-(2,6-dichlorophenyl)-5-(2,4-difluorophenyl)-7-oxytrifluormethylsulfonyl-3,4-dihydro-2(1H)-quinazolinone (19 mg, 0.034 mmol) (INTERMEDIATE 60). The solution was then heated at 96° C. for 2 hours under an argon atmosphere. The solution was cooled to RT and partitioned between saturated NaHCO$_3$ (5 mL) and EtOAc (15 mL). The organic phase was washed with brine and dried over MgSO$_4$. The solution was filtered through a small plug of silica gel and concentrated. The residue was purified by thin layer chromatography using ethyl ether as the eluent to give 1-(2,6-dichlorophenyl)-5-(2,4-difluorophenyl)-7-(1-morpholinyl)-3,4-dihydro-2(1H)-quinazolinone. $^1$H NMR (CDCl$_3$, 500 MHz): δ 2.98 (t, 4H, J=4.8 Hz), 3.77 (t, 4H, J=4.8 Hz), 4.20–4.50 (br m, 2H), 5.31 (s, 1H), 5.69 (d, 1H, J=2.2 Hz), 6.47 (d, 1H, J=2.5 Hz), 6.90–7.00 (m, 2H), 7.23–7.31 (m, 1H), 7.38 (t, 1H, J=8.1 Hz), 7.54 (d, 2H, J=8.0 Hz). MS(ES) 490 (M+H); LC 1: 3.12 min.

EXAMPLE 34

1-(2,6-dichlorophenyl)-5-(2,4-difluorophenyl)-7-(1-piperazinyl)-3,4-dihydro-2(1H)-quinazolinone

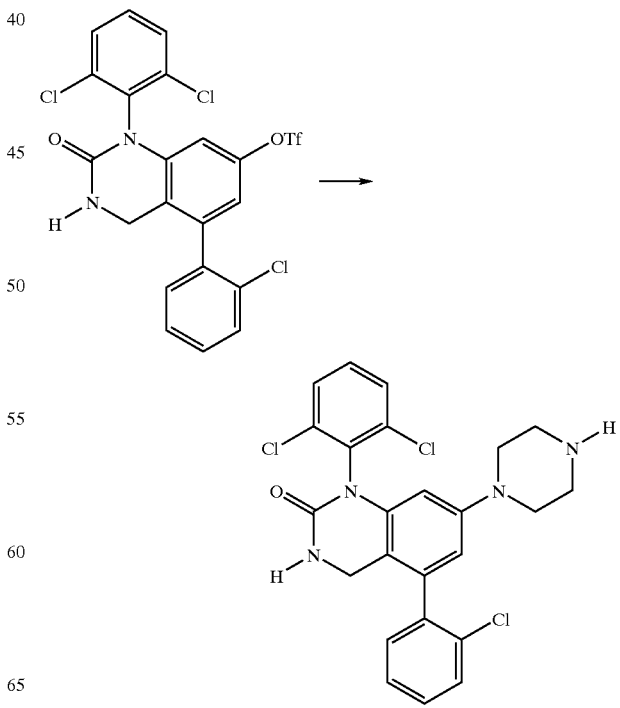

Step A: 1-(2,6-dichlorophenyl-5-(2,4-difluorophenyl)-7-(N-Boc-piperazinyl)-3,4-dihydro-2(1H)-quinazolinone To dry Cs$_2$CO$_3$ (130 mg, 0.399 mmol) under argon was added Pd(OAc)$_2$ (6.5 mg, 0.029 mmol), racemic BINAP (35 mg, 0.056 mmol), 1-tert-butoxycarbonyl-piperazine (60 mg, 0.32 mmol) and 1-(2,6-dichlorophenyl)-5-(2-chlorophenyl)-7-trifluoromethylsulfonato-3,4dihydro-2(1H)-quinazolinone (54 mg, 0.098 mmol) (INTERMEDIATE 61) in 2 mL 1,4-dioxane. The solution was then heated at 100° C. for 8 hrs under an argon atmosphere. The solution was cooled to RT and partition between NaHCO$_3$ and ethyl ether. The phases were separated and the organic phase washed with brine, dried over MgSO$_4$, filtered and concentrated. The residue was absorbed on SiO$_2$ and purified by silica gel chromatography using 1 to 5% acetone in DCM as the eluent to give 1-(2,6-dichlorophenyl)-5-(2,4-difluorophenyl)-7-(N-Boc-piperazinyl)-3,4-dihydro-2(1H)-quinazolinone. MS(ES) 587 (M+H), 531 (M-tBu+2H); LC 1: 4.04 min.

Step B:

To 1-(2,6dichlorophenyl)-5-(2,4-difluorophenyl)-7-(N-Boc-piperazinyl)-3,4-dihydro-2(1H)-quinazolinone (34 mg, 0.058 mmol) was added anisole (0.4 mL) and 1/1 TFA/DCM (5 mL). After 2 h the solution was concentrated and the residue partition between EtOAc and 1N NaOH (saturated with NaCl). The phases were separated and the organic phase dried over Na$_2$SO$_4$, filtered and concentrated. The residue was purified by thin layer chromatography using EtOAC followed by CHCl$_3$/MeOH/NH$_4$OH (87/12/1) as the eluent to give 1-(2,6-dichlorophenyl)-5-(2,4-difluorophenyl)-7-(1-piperazinyl)-3,4-dihydro-2(1H)-quinazolinone. $^1$H NMR(CDCl$_3$, 500M): δ 1.80 (brs, 1H, NH), 2.89–3.00 (m, 8H), 4.17 (d, 1H, J=13.9 Hz), 4.36 (d, 1H, 13.8 Hz), 5.28 (s, 1H), 5.69 (d, 1H, J=2.0 Hz), 6.45 (d, 1H, J=2.2 Hz), 7.30–7.40 (m, 4H), 7.47–7.51 (m, 1H), 7.53 (d, 2H, J=8.2 Hz). MS(ES) 487 (M+H); LC 1: 2.04 min.

EXAMPLE 35

1-(2,6-dichlorophenyl)-5-(2,4-difluorophenyl)-7-piperazinyl-3,4-dihydro-2(1H)-quinazolinone

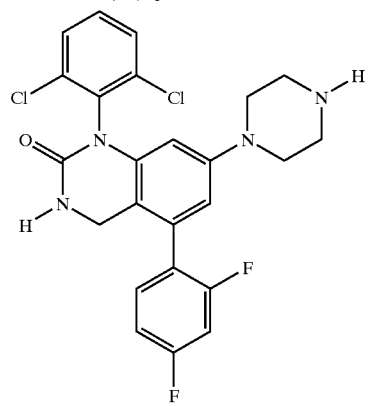

The title compound was prepared from 1-(2,6-dichlorophenyl)-5-(2,4-difluorophenyl)-7-trifluoromethylsulfonato-3,4-dihydro-2(1H)-quinazolinone (INTERMEDIATE 60) as described in EXAMPLE 34. $^1$H NM(CDCl$_3$, 500 MHz): δ 2.89–3.0 (m, 8H), 4.20–4.50 (br m, 2H), 5.16 (s, 1H), 5.72 (d, 1H, J=2.3 Hz), 6.48 (d, 1H, J=2.3 Hz), 6.90–7.01 (m, 1H), 7.25–7.32 (m, 1H), 7.38 (app t, 1H, J=8 Hz), 7.53 (d, 2H, J=8.2 Hz). MS(ES) 489 (M+H); LC 1: 2.00 min.

EXAMPLE 36

1-(2,6-Dichlorophenyl)-5-(2,4-difluorophenyl)-7-(4-methyl)piperazinyl-3,4-dihydro-2(1H)-quinazolinone

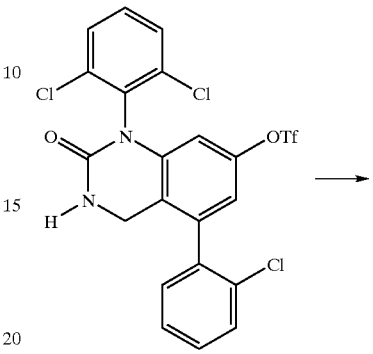

The title compound was prepared from 1-(2,6-dichlorophenyl)-5-(2-chlorophenyl)-7-trifluoromethylsulfonato-3,4-dihydro-2(1H)-quinazolinone (INTERMEDIATE 61) and 4-methylpiperazine as described in EXAMPLE 33. $^1$H NMR (CDCl$_3$, 500 MHz): selected data δ 2.41 (s, 3H), 2.64 (brs, 4H), 3.11 (m, 4H). MS(ES) 501 (M+H); LC 1: 1.98 min.

EXAMPLE 37

1-(2,6-Dichlorophenyl)-5-(2,4-difluorophenyl)-7-[4-(2-propyl)piperazinyl]-3,4-dihydro-2(1H)-quinazolinone

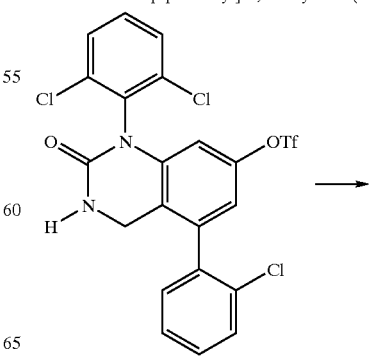

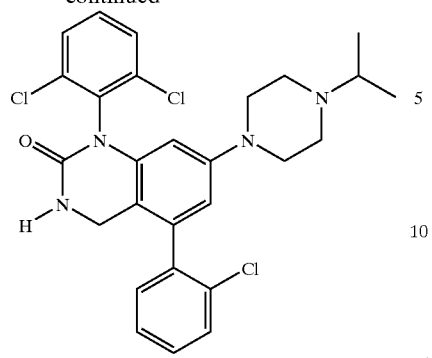

1-(2,6-Dichlorophenyl)-5-(2,4-difluorophenyl)-7-[4-(2-propyl)piperazinyl]-3,4-dihydro-2(1H)-quinazolinone was prepared from 1-(2,6-dichlorophenyl)-5-(2-chlorophenyl)-7-trifluoromethylsulfonato-3,4-dihydro-2(1H)-quinazolinone (INTERMEDIATE 61) and 4-isopropylpiperazine as described in EXAMPLE 33. $^1$H NMR (CDCl$_3$, 500 MHz): selected data δ 1.03 (d, J=6.6 Hz, 6H), 2.58 (m, 4H), 2.65 (m, 1H), 3.0 (m, 4H). MS(ES) 529 (M+H); LC 1: 2.24 min.

EXAMPLE 38
1-(2,6-dichlorophenyl)-5-(2,4-difluorophenyl)-7-(4-amino-1-piperidinyl-3,4-dihydro-2(1H)-quinazolinone

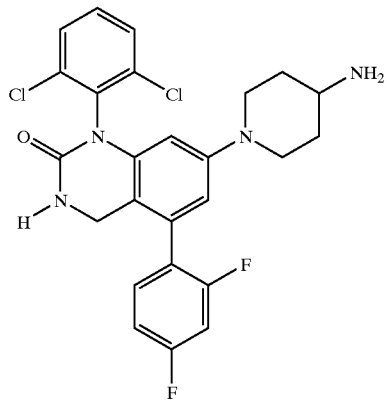

The title compound was prepared from 1-(2,6-dichlorophenyl)-5-(2,4-difluorophenyl)-7-trifluoromethylsulfonato-3,4-dihydro-2(1H)-quinazolinone (INTERMEDIATE 60) as described in EXAMPLE 34 (replacing 1-Boc-piperazine with 4-Boc-amino-1-piperidine). $^1$H NMR(CDCl$_3$, 500 MHz): δ 1.34–1.46 (brm, 2H), 1.80–1.86 (brm, 2H), 2.67 (app t, 2H, J=11.9 Hz), 2.79 (brm, 1H), 3.36–3.43 (m, 2H), 4.20–4.45 (brm, 2H), 5.18 (s, 1H), 5.72 (s, 1H), 6.50 (s, 1H), 6.89–7.00 (m, 2H), 7.29–7.31 (m, 1H), 7.38(t, 1H, J=7.9 Hz), 7.53 (d, 2H, J=8.0 Hz). MS(ES) 503 (M+H); LC 1: 2.03 min.

EXAMPLE 39
1-(2,6-dichlorophenyl)-5-(2,4-difluorophenyl)-7-(amino(N-4-piperidinyl))-3,4-dihydro-2(1H)-quinazolinone

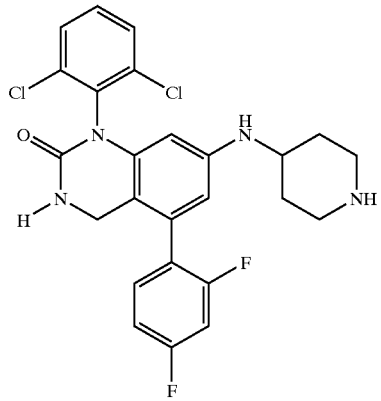

The title compound was prepared from 1-(2,6-dichlorophenyl)-5-(2,4-difluorophenyl)-7-trifluoromethylsulfonato-3,4-dihydro-2(1H)-quinazolinone (INTERMEDIATE 60) as described in EXAMPLE 34 (replacing 1-Boc-piperazine with 4-amino-1-Boc-piperidine). $^1$H NMR(CDCl$_3$, 500 MHz): δ 1.30–1.41 (brm, 2H), 2.02 (brm, 2H), 2.67 (brm, 2H), 3.17 (brm, 2H), 3.52 (brm, 1H), 4.15–4.42 (brm, 2H), 5.22 (s, 1H), 5.36 (d, 1H, J=2.3 Hz), 6.16 (d, 1H, J=2.3 Hz), 6.90–7.00 (m, 2H), 7.25–7.31 (m, 1H), 7.38 (t, 1H, J=8.1 Hz), 7.53 (d, 2H, J=8.0 Hz). MS(ES) 503 (M+H), 420 (M-piperidine+2H); LC 1: 2.31 min.

INTERMEDIATE 63
1-(2,6-dichlorophenyl)-5-(2-chloro-4-fluorophenyl)-3,4-dihydro-2(1H)-quinazolinone

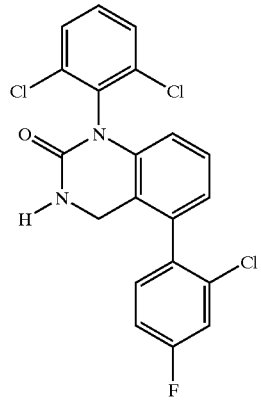

The title compound was prepared from 1-(2,6-dichlorophenyl)-5-(2-chloro-4-fluorophenyl)-7-trifluoromethylsulfonato-3,4-dihydro-2(1H)-quinazolinone (INTERMEDIATE 62) and was isolated as a minor component in the preparation of EXAMPLE 43. $^1$H NMR(CDCl$_3$, 500 MHz): δ 4.27 (dd, 1H, J=14.4, 1.7 Hz), 4.43 (dd, 1H, J=14.5, 1.2 Hz), 5.30 (s, 1H), 6.19 (d, 1H, J=8.2 Hz), 6.88 (d, 1H, J=7.6 Hz), 7.09 (app dt, 1H, J=8.2, 2.5 Hz), 7.17 (t, 1H, J=8.0 Hz), 7.25–7.31 (m, 2H), 7.38 (t, 1H, J=8.0 Hz), 7.53 (d, 2H, J=8.2 Hz). MS(ES) 421 (M+H); LC 1: 4.37 min.

INTERMEDIATE 64
1-(2,6-dichlorophenyl)-5-(2-chlorophenyl-4-fluoro)-7-allyl-3,4-dihydro-2(1H)-quinazolinone

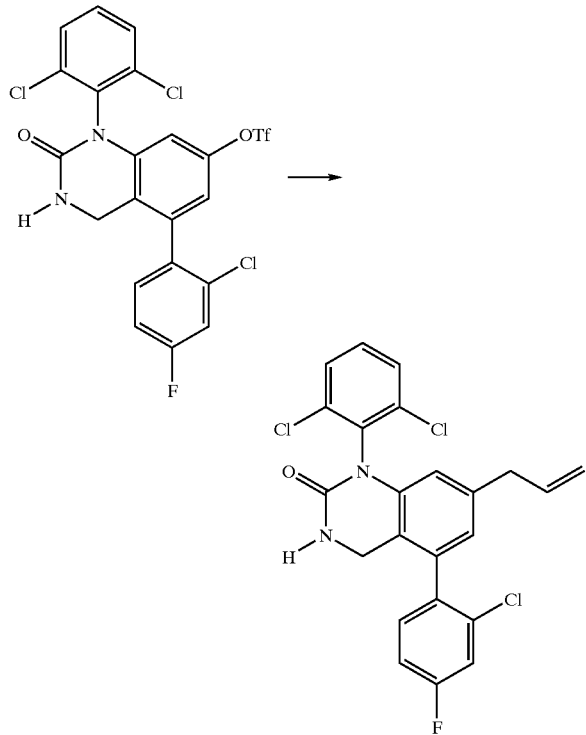

To dry lithium chloride (23.1 mg, 0.546 mmol) was added 1-(2,6-dichlorophenyl)-5-(2chloro-4-fluorophenyl)-7-trifluoromethylsulfonato-3,4-dihydro-2(1H)-quinazolinone (29.6 mg, 0.052 mmol) (INTERMEDIATE 62), 2 mL anhydrous 1,4-dioxane, allyltri-n-butyl tin (52.1 mg, 0.157 mmol) and palladium tetrakis triphenyl phosphine (8.3 mg, 0.0072 mmol). The solution was then reflux under an argon atmosphere. After 4 hours the solution was cooled to RT, diluted with ethyl acetate, filtered through Celite and concentrated. The residue was purified by preparative thin layer chromatography using 5% acetone in methylene chloride as the eluent to give 1-(2,6-dichlorophenyl)-5-(2-chlorophenyl-4-fluoro)-7-allyl-3,4-dihydro-2(1H)-quinazolinone. $^1$H NMR(CDCl$_3$, 500 MHz): selected data δ 3.26 (d, 2H, J=6.4 Hz), 5.00 (dd, 1H, J=27.7 and 1.5 Hz); 5.01 (s, 1H); 5.86–5.98 (m, 1H). MS(ES) 461 (M+H); LC 1: 3.84 min.

INTERMEDIATE 65
1-(2,6-dichlorophenyl)-5-(2-chlorophenyl-4-fluoro)-7-acetylaldehyde-3,4-dihydro-2(1H)-quinazolinone

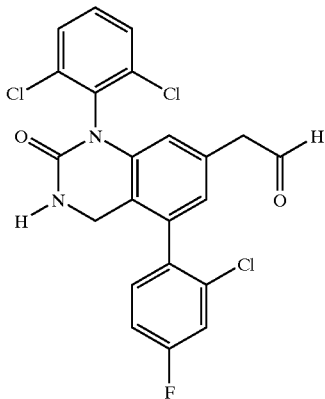

1-(2,6-dichlorophenyl)-5-(2-chlorophenyl-4-fluoro)-7-allyl-3,4-dihydro-2(1H)-quinazolinone (15 mg, 0.032 mmol) (INTERMEDIATE 64) in 0.5 mL THF was added NaIO$_4$ (26.3 mg, 0.123 mmol) in 0.3 mL water followed by catalytic amount of OsO4. After stirring at room temperature overnight the solution was partitioned between EtOAc and water. The phases were separated and the organic phase washed with brine, dried over Na$_2$SO$_4$, filtered and concentrated. The residue was purified by preparative thin layer chromatography using 5% acetone in DCM as the eluent to give 1-(2,6-dichlorophenyl)-5-(2-chlorophenyl-4-fluoro)-7-acetylaldehyde-3,4-dihydro-2(1H)-quinazolinone. $^1$H NMR (CDCl$_3$, 500 MHz): selected data δ 3.49 (s, 2H); 9.57 (s, 1H). MS(ES) 463 (M+H); LC 1: 2.98 min.

EXAMPLE 40
1-(2,6-dichlorophenyl)-5-(2-chloro-4-difluorophenyl)-7-[ethyl-2-(1-piperazinyl)]-3,4-dihydro-2(1H)-quinazolinone

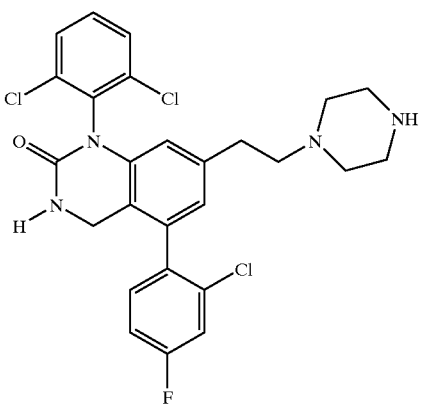

Step A: 1-(2,6-dichlorophenyl)-5-(2-chloro-4-fluorophenyl)-7-(N-Boc-piperazinylethyl)-3,4-dihydro-2(1H)-quinazolinone To 1-(2,6-dichlorophenyl)-5-(2-chlorophenyl-4-fluoro)-7-acetylaldehyde-3,4-dihydro-2(1H)-quinazolinone (4.3 mg, 0.0093 mmol) (INTERMEDIATE 65) in 1.0 mL methanol was added 1-Boc-piperazine (7.5 mg, 0.040 mmol) and sodium cyanoborohydide (95 mg, 0.15 mmol). The reaction mixture was stirred at room temperature overnight. The reaction mixture was partition between water and ethyl acetate. The phases were separated and the organic phase washed with brine, dried over MgSO$_4$, filtered and concentrated. The residue was purified by preparative thin layer chromatography using 6% acetone in DCM as the eluent to give 1-(2,6-dichlorophenyl)-5-(2-chloro-4-fluorophenyl)-7-(N-Boc-piperazinylethyl)-3,4-dihydro-2(1H)-quinazolinone. MS(ES) 633 (M+H); LC 1: 2.64 min.

Step B: 1-(2,6-dichlorophenyl)-5-(2-chloro-4-difluorophenyl)-7-[ethyl-2-(1-piperazinyl)]-3,4-dihydro-2(1H)-quinazolinone To 1-(2,6-dichlorophenyl)-5-(2-chloro-4-fluorophenyl)-7-(N-Boc-piperazinylethyl)-3,4-dihydro-2(1H)- quinazolinone (1.7 mg, 0.0027 mmol) was added 1/1 TFA/DCM (0.5 mL). After 2 hours the solution was concentrated and the residue partition between EtOAc and water. The phases were separated and the organic phase was concentrated. The residue was purified by thin layer chromatography using CHCl$_3$/MeOH/NH$_4$OH (87/12/1) as the eluent to give 1-(2,6-dichlorophenyl)-5-(2-chloro-4-difluorophenyl)-7-[ethyl-2-(1-piperazinyl)]-3,4-dihydro-2(1H)-quinazolinone. $^1$H NMR(CDCl$_3$, 500 MHz): selected data δ 2.41 (brs, 4H); 2.49 (t, 2H, J=7.8 Hz); 2.67 (t, 2H, J=7.4 Hz); 2.86 (t, 4H, J=4.8 Hz). MS(ES) 533 (M+H); LC 1: 1.89 min.

INTERMEDIATE 66

1-(2,6-dichlorophenyl)-5-(2-chloro-4-fluorophenyl)-7-acetylaldehyde-3,4-dihydro-2(1H)-quinazolinone

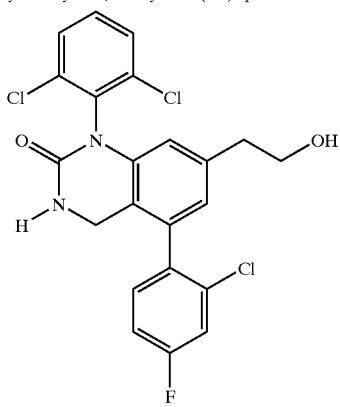

The title compound was prepared from 1-(2,6-dichlorophenyl)-5-(2-chloro-4-fluorophenyl)-7-acetylaldehyde-3,4-dihydro-2(1H)-quinazolinone (4.3 mg, 0.0093 mmol) (INTERMEDIATE 65) was isolated as a minor component in EXAMPLE 40. $^1$H NMR(CDCl$_3$, 500 MHz): selected data δ 2.74 (t, 2H, J=6.5 HZ), 3.77 (m, 2H). MS(ES) 465 (M+H); LC 1: 2.79 min.

INTERMEDIATE 67

(1,4-Dioxaspiro(4.5)dec-7-ene-8-yl)trifluoromethylsulfurate

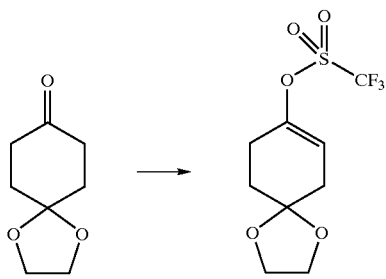

To a solution of 1,4-cyclohexanedione mono-ethylene ketal (1.35 g, 8.64 mmol) in THF (15 mL) at 78° C. was added lithium bis(trimethylsilyl)amide (12.1 mL, 1.0M in THF) dropwise. The mixture was stirred for 30 minutes at −78° C. then warmed to 0° C. for 30 minutes. It was cooled down to −78° C. again then added 2-[N,N-bis(trifluoromethylsulfonyl)amino]-5-chloropyridine (4.75 g, 12.1 mmol) dissolved in THF (10 mL) rapidly. The reaction mixture was stirred while the bath temperature was warming to −40° C. over 4 h. The reaction was quenched with saturated NaHCO$_3$ solution and removed the solvent in vacuo. It was extracted three times with EtOAc, the combined extracts were washed with brine, and it was dried over Na$_2$SO$_4$. After removal of solvent, the crude material was purified by flash chromatography eluting with 1:10 EtOAc:hexanes to obtain (1,4-Dioxaspiro(4.5)dec-7-ene-8-yl)trifluoromethylsulfurate. $^1$H NMR (CDCl$_3$, 500 MHz): δ 1.9 (t, 2H, J=6.6 Hz), 2.4 (m, 2H), 2.53 (m, 4H), 3.98 (m, 4H), 5.65 (m, 1H).

INTERMEDIATE 68

4-trifluoromethylsulfonato-1-Boc-1,2,3,6-tetrahydro-pyridine

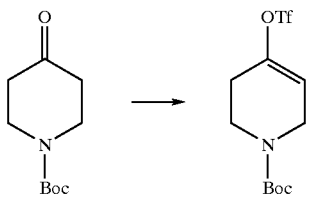

The title compound was prepared from 1-Boc-4-piperidone as described in INTERMEDIATE 67. $^1$H NMR (CDCl$_3$, 500 MHz): δ 1.49 (s, 1H), 2.46 (brs, 2H), 3.65 (brs, 2H), 4.06 (brs, 2H), 5.78 (s, 1H).

INTERMEDIATE 69

4-trimethyltin-1-Boc-1,2,3,6-tetrahydro-pyridine

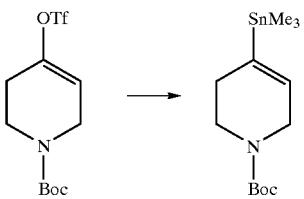

To 4-trifluoromethylsulfonate-1-Boc 1,2,3,6-tetrahydro-pyridine (189 mg, 0.57 mmol) (INTERMEDIATE 68) and hexamethyldilin (220 mg, 0.67 mmol) in THF (2 mL) under an argon atmosphere was added LiCl (95 mg, 2.24 mmol) and palladium tetrakis triphenyl phosphine (15 mg, 0.013 mmol). After refluxing overnight the solution was concentrated and the residue partitioned between water and ethyl ether. The phases were separated and the organic washed with brine, dried over Na$_2$SO$_4$, filtered and concentrated. The residue was purified by silica gel chromatography using 5 to 10% ethyl ether in hexanes (with 1% triethylamine) as the eluent to give 4-trimethyltin-1-Boc-1,2,3,6-tetrahydro-pyridine, $^1$H NMR(CDCl$_3$, 590 MHz): δ 0.11 (s, 6H), 1.46 (s, 9H), 2.26 (brs, 2H), 3.46 (m, 2H), 3.90 (brs, 2), 5.75 (brs, 1H). LC 1: 4.37 min.

INTERMEDIATE 70

(1,4-Dioxaspiro(4.5)dec-7-ene-8-yl)trimethyl tin

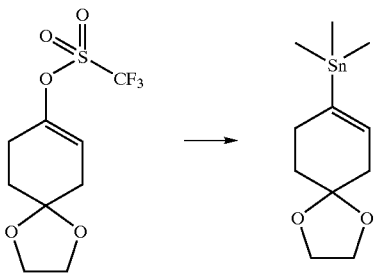

The title compound was prepared according to the procedure found in Wulff, W. D.; et. al., *J. Org. Chem.*, 1986, 51, 277. $^1$H NMR (CDCl$_3$, 500 MHz): δ 0.1 (s, 9H), 1.75 (t, 2H, J=6.4 Hz), 2.34 (m, 2H), 2.41 (m, 4H), 3.98 (m, 4H), 5.74 (m, 1H).

EXAMPLE 41

1-(2,6-dichlorophenyl)-5-(2,4-difluorophenyl)-7-(1,2,3,6-tetrahydro-4-pyridinyl)-3,4-dihydro-2(1H)-quinazolinone

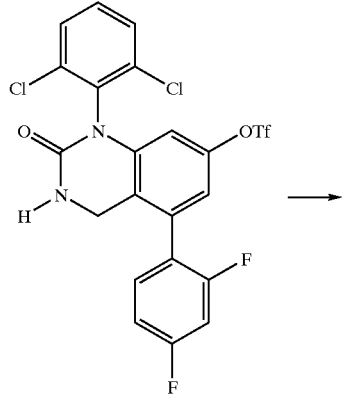

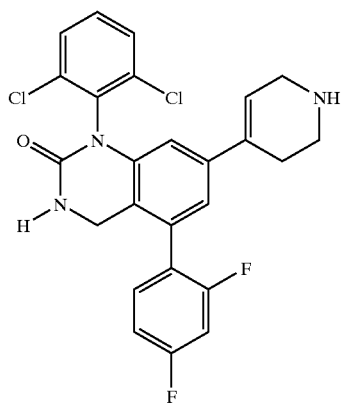

Step A: To dry lithium chloride (43 mg, 1.01 mmol) was added 1-(2,6-dichlorophenyl)-5-(2,4-difluorophenyl)-7-trifluoromethylsulfonato-3,4-dihydro-2(1H)-quinazolinone (167 mg, 0.302 mmol) (INTERMEDIATE 60), 6 mL anhydrous 1,4-dioxane, 4-trimethyltin-1-Boc-1,2,3,6-tetrahydropyridine (250 mg, 0.724 mmol) (INTERMEDIATE 69) and palladium tetrakis triphenyl phosphine (58 mg, 0.05 mmol). The solution was then heated at 100° C. under an argon atmosphere. After 24 hours the solution was cooled to RT, diluted with ethyl ether, filtered through Celite and concentrated. The residue was purified by silica gel chromatography using 3% to 8% acetone in DCM as the eluent to give 160 mg of product (90% yield). ¹H NMR(CDCl₃, 500 MHz): δ 1.47 (s, 9H), 2.34 (brs, 2H), 3.56 (brs, 2H), 4.00 (brs, 2H), 4.28–4.57 (brm, 2H), 5.14 (s, 1H), 5.85 (brs, 1H), 6.15 (s, 1H), 6.95 (s, 1H), 6.96–7.00 (m, 2H), 7.29–7.32 (m, 1H), 7.41 (t, 1H, 8.0 Hz), 7.55 (d, 2H, J=8.3 Hz). MS(ES) 586 (M+H); LC 1: 3.97 min.

Step B: The tert-butoxycarbonyl substituent was removed as described in EXAMPLE 34, Step B. ¹H NMR(CDCl₃, 500 MHz): δ 2.30 (brm, 2H), 3.05 (t, 2H, J=5.8 Hz), 3.48 (d, 2H, J=3.0 Hz), 4.24–4.58(brm, 4H), 5.18 (s, 1H), 5.92 (brs, 1H), 6.16 (t, 1H, J=7.8 Hz), 7.55 (d, 2H, J=8.0 Hz). MS(ES) 486 (M+H); LC 1: 1.99 min.

EXAMPLE 42

1-(2,6-dichlorophenyl)-5-(2-chlorophenyl)-7-(1,2,3,6-tetrahydro-4-pyridinyl)-3,4-dihydro-2(1H)-quinazolinone

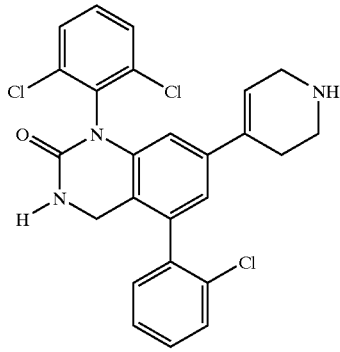

The title compound was prepared from 1-(2,6-dichlorophenyl)-5-(2-chlorophenyl)-7-trifluoromethylsulfonato-3,4-dihydro-2(1H)-quinazolinone (INTERMEDIATE 61) as described in EXAMPLE 41. ¹H NMR(CDCl₃, 500 MHz): δ 2.15 (brm, 1H, NH), 2.28 (brm, 2H), 3.03 (t, 2H, J=5.7 Hz), 4.24 (d, 1H, 14.7 Hz), 4.42 (d, 1H, J=14.7 Hz), 5.56 (s, 1H), 5.93 (s, 1H), 6.13 (d, 1H, J=1.4 Hz), 6.91 (d, 1H), J=1.4 Hz), 7.28–7.40 (m, 4H), 7.48–7.56 (m, 3H). MS(ES) 484 (M+H); LC 1: 2.10 min.

EXAMPLE 43

1-(2,6-dichlorophenyl)-5-(2-chloro-4-fluorophenyl)-7-(1,2,3,6-tetrahydro-4-pyridinyl)-3,4-dihydro-2(1H)-quinazolinone

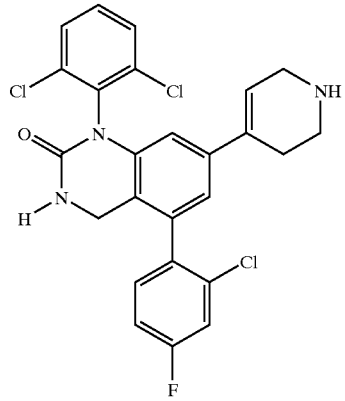

The title compound was prepared from 1-(2,6-dichlorophenyl)-5-(2-chloro-4-fluorophenyl)-7-trifluoromethylsulfonato-3,4-dihydro-2(1H)-quinazolinone (INTERMEDIATE 62) as described in EXAMPLE 41. ¹H NMR(CDCl₃, 500 MHz): 2.42 (brs, 2H), 3.14 (t, 2h, J=5.7 Hz), 3.57 (m, 2H), 4.25 (app dd, 1H, J=1.6, 14.7 Hz), 4.42 (app dd, 1H, J=1.7, 14.6 Hz), 5.14 (s, 1H), 5.90 (s, 1H), 6.14 (d, 1H, J=1.4 Hz), 6.88 (d, 1H, J=1.6 Hz), 7.08–7.12 (m, 1H), 7.26–7.32 (m, 2H), 7.40 (t, 1H, J=8.0 Hz), 7.55 (d, 2H, J=8.2 Hz). MS(ES) 502 (M+H); LC 1: 2.06 min.

EXAMPLE 44
1-(2,6-dichlorophenyl)-3-methyl-5-(2-chloro-4-fluorophenyl)-7-(1,2,3,6-tetrahydro-4-pyridinyl)-3,4-dihydro-2(1H)-quinazolinone

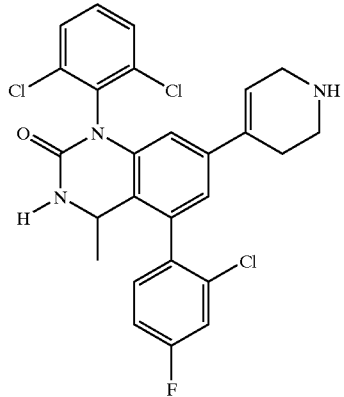

The title compound was prepared from 1-(2,6-dichlorophenyl)-3-methyl-5-(2-chloro-4-fluorophenyl)-7-trifluoromethylsulfonato-3,4-dihydro-2(1H)-quinazolinone as described in EXAMPLE 41. 1-(2,6-dichlorophenyl)-3-methyl-5-(2-chloro-4-fluorophenyl)-7-trifluoromethylsulfonato-3,4-dihydro-2(1H)-quinazolinone was prepared from 1-(2,6-dichlorophenyl)-3-methyl-5-(2-chloro-4-fluorophenyl)-7-methoxy-3,4-dihydro-2(1H)-quinazolinone (INTERMEDIATE 58) as described in INTERMEDIATE 48 and INTERMEDIATE 60. $^1$H NMR (CDCl$_3$, 500 MHz): diastereomeric atropisomers δ 1.32 (m, 3H), 2.37 (brs, 2H), 2.51 (brm, 1H), 3.10 (t, 2H, J=5.7 Hz), 3.53 (brs, 2H), 4.36 (m, 0.5H), 4.47 (m, 0.5H), 5.51 (d, 0.5H, 2.9 Hz), 5.58 (d, 0.5H, J=2.7 Hz), 5.90 (brs, 1H), 6.13 (s, 0.5H), 6.15 (s, 0.5H), 6.83 (s, 0.5H), 6.90 (s, 0.5H), 7.09–7.13 (m, 1H), 7.28–7.42 (m, 3H), 7.51–7.58 (m, 2H). MS(ES) 516 (M+H); LC 1: 2.22 min.

EXAMPLE 45
1-(2,6-dichlorophenyl)-5-(2-chlorophenyl)-7-(1,2,3,6-tetrahydro-5-pyridinyl)-3,4-dihydro-2(1H)-quinazolinone

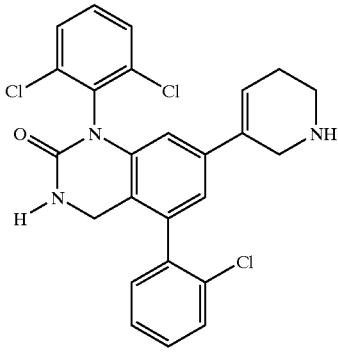

The title compound was prepared from 1-(2,6-dichlorophenyl)-5-(2-chlorophenyl)-7-trifluoromethylsulfonato-3,4-dihydro-2(1H)-quinazolinone (INTERMEDIATE 61) and 5-trimethyltin-1-Boc-1,2,3,6-tetrahydro-pyridine as described in EXAMPLE 41. 5-Trimethyltin-1-Boc-1,2,3,6-tetrahydro-pyridine was prepared as described in INTERMEDIATE 68 and INTERMEDIATE 69 replacing 1-Boc-4-piperidone with 1-Boc-3-piperidone. $^1$H NMR(CD$_3$OD, 500 MHz): δ 2.15–2.22 (m, 2H), 2.87 (t, 2H, J=5.9 Hz), 3.44 (m, 2H), 4.21 (d, 1H, J=15.1 Hz), 4.29 (d, 1H, J=15.1 Hz), 5.97 (m, 1H), 6.05 (d, 1H, 1.6 Hz), 6.86 (d, 1H, J=1.4 Hz), 7.31–7.35 (m, 1H), 7.40–7.44 (m, 2H), 7.47–7.56 (m, 2H), 7.61–7.64 (m, 2H). MS(ES) 525 (M+CH$_3$CN+H), 484 (M+H); LC 1: 2.15 min.

EXAMPLE 46
1-(2,6-dichlorophenyl)-5-(2-chloro-4-fluorophenyl)-7-(1,2,3,6-tetrahydro-1-methyl-4-pyridinyl)-3,4-dihydro-2(1H)-quinazolinone

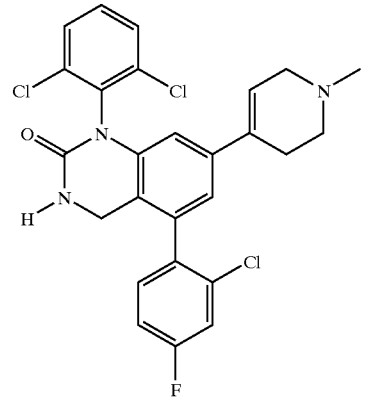

The title compound was prepared from 1-(2,6-dichlorophenyl)-5-(2-chloro-4-fluorophenyl)-7-(1,2,3,6-tetrahydro-4-pyridinyl)-3,4-dihydro-2(1H)-quinazolinone (EXAMPLE 43) as described in EXAMPLE 15. $^1$H NMR (CDCl$_3$, 500 MHz): δ 2.37 (s, 3H), 2.39 (brm, 2H) 2.59 (t, 2H, J=5.8 Hz), 3.00 (m, 2H), 4.23 (app dd, 1H, J=1.7, 14.5 Hz), 4.39 (app dd, 1H, J=1.4, 14.6 Hz), 5.34 (s, 1H), 5.85 (m, 1H), 6.14 (d, 1H, J=1.4 Hz), 6.87 (d, 1H, J=1.6 Hz), 7.06–7.10 (m, 1H), 7.24–7.31 (m, 2H), 7.38 (t, 1H, J=8.0 Hz), 7.53 (d, 2H, J=7.8 Hz). MS(ES) 516 (M+H); LC 1: 2.13 min.

EXAMPLE 47
1-(2,6-dichlorophenyl)-5-(2-chloro-4-fluorophenyl)-7-(1,2,3,6-tetrahydro-1-(2,2,2-trifluoroethyl)-4-pyridinyl)-3,4-dihydro-2(1H)-quinazolinone

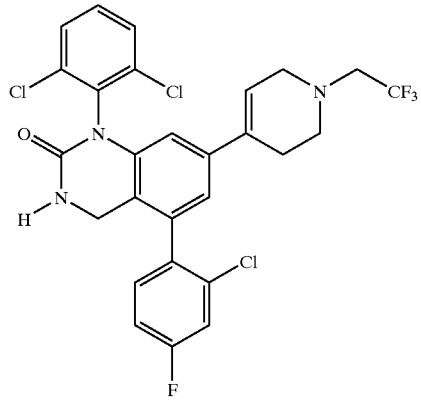

To 1-(2,6-dichlorophenyl)-5-(2-chlorophenyl-4-fluoro)-7-(1,2,3,6-tetrahydro-5-pyridinyl-1-3,4-dihydro-2(1H)-quinazolinone (13.1 mg, 0.026 mmol) (EXAMPLE 43) in 0.5 mL dichloromethane was added 2,2,2-trifluoroethyl trifluoromethanesulfonate (33.9 mg, 0.146 mmol) followed by N,N-diisopropylethylamine (37.1 mg, 0.288 mmol). The reaction mixture was stirred at room temperature overnight. The reaction mixture was partitioned between water and ethyl acetate. The phases were separated and the organic phase washed with brine and concentrated. The residue was purified by preparative thin layer chromatography using 5% acetone in DCM as the eluent to give 1-(2,6-dichlorophenyl)-5-(2-chloro-4-fluorophenyl)-7-(1,2,3,6-tetrahydro-1-(2,2,2-trifluoroethyl)-4-pyridinyl)-3,4- dihydro-2(1H)-quinazolinone. ¹H NMR(CDCl₃, 500 MHz): selected data δ: 2.40 (d, 2H, J=1.8 Hz); 2.87 (t, 2H, J=5.7 Hz); 3.07 (q, 2H, J=9.6 Hz); 3.33 (d, 2H, J=3.0 Hz). MS(ES) 584 (M+H); LC 1: 3.25 min.

EXAMPLE 48

1-(2,6-dichlorophenyl)-5-(2-chloro-4-fluorophenyl)-7-(1,2,3,6-tetrahydro-1-trifluoracetyl)-4-pyridinyl)-3,4-dihydro-2(1H)-quinazolinone

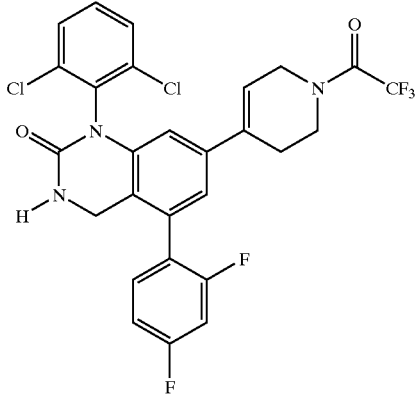

To 1-(2,6-dichlorophenyl)-5-(2-chlorophenyl-4-fluoro)-7-(1,2,3,6-tetrahydro-5-pyridinyl-1-3,4-dihydro-2(1H)-quinazolinone (4.6 mg, 0.0091 mmol) (EXAMPLE 43) in 0.25 mL dichloromethane was added trifluoroacetic anhydride (15 mg, 0.71 mmol) followed by N,N-diisopropylethylamine (37.1 mg, 0.288 mmol). The reaction mixture was stirred at room temperature for 30 min. The reaction mixture was partitioned between water and ethyl acetate. The phases were separated and the organic phase washed with brine and concentrated. The residue was purified by preparative thin layer chromatography using 5% acetone in DCM as the eluent to give 1-(2,6-dichlorophenyl)-5-(2-chloro-4-fluorophenyl)-7-(1,2,3,6-tetrahydro-1-(trifluoracetyl)-4-pyridinyl)-3,4-dihydro-2(1H)-quinazolinone. ¹H NMR(CDCl₃, 500 MHz): selected data δ 2.48 (brm, 2H); 3.75 (t, 1H, J=5.8 Hz); 3.79–3.87 (m, 1H); 4.19–4.25 (m, 2H); 5.89 (m, 1H). MS(ES) 598 (M+H), LC 1: 3.65 min.

EXAMPLE 49

1-(2,6-dichlorophenyl)-5-(2-chloro-4-fluorophenyl)-7-(1,2,3,6-tetrahydro-1-(methylcyclopropyl)-4-pyridinyl)-3,4-dihydro-2(1H)-quinazolinone

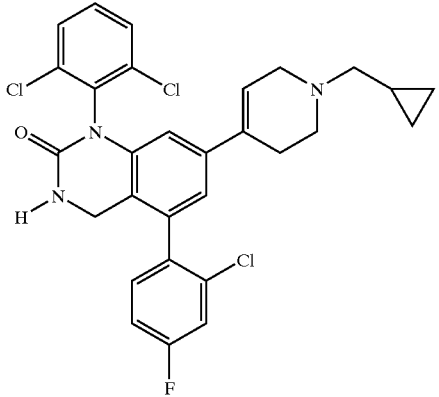

To 1-(2,6-dichlorophenyl)-5-(2-chlorophenyl-4-fluoro)-7-(1,2,3,6-tetrahydro-5-pyridinyl-1-3,4-dihydro-2(1H)-quinazolinone (14.8 mg, 0.0294 mmol) (EXAMPLE 43) in 1 mL ethanol was added (bromomethyl)-cyclopropane (20.6 mg, 0.153 mmol) followed by triethylamine (25 mg, 0.24 mmol). The reaction mixture was stirred at room temperature for 2 days. The reaction mixture was partitioned between water and ethyl acetate. The phases were separated and the organic phase washed with brine and concentrated. The residue was purified by preparative thin layer chromatography using 4% methanol in ethyl acetate to give 1-(2,6-dichlorophenyl)-5-(2-chloro-4-fluorophenyl)-7-(1,2,3,6-tetrahydro-1-(methylcyclopropyl)-4-pyridinyl)-3,4-dihydro-2(1H)-quinazolinone. ¹H NMR(CDCl₃, 500 MHz): selected data δ 0.17 (d, 2H, J=4.1 Hz); 0.81–0.86 (m, 1H); 0.56 (d, 2H, J=7.6 Hz); 2.40 (s, 2H); 2.45 (s, 2H); 2.77 (s, 2H); 3.23 (s, 2H); 5.88 (s, 1H). MS(ES) 556 (M+H), LC 1: 2.53 min.

EXAMPLE 50

1-(2,6-dichlorophenyl)-5-(2-chloro-4-fluorophenyl)-7-(1,2,3,6-tetrahydro-1-(acetyl)-4-pyridinyl)-3,4-dihydro-2(1H)-quinazolinone

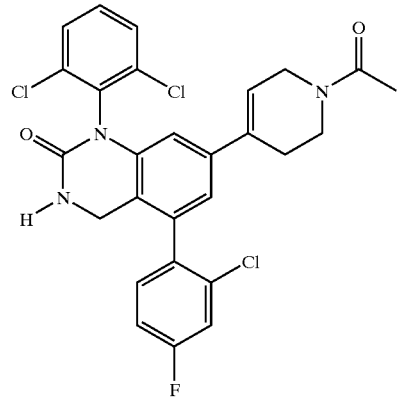

The title compound was prepared as described in EXAMPLE 48 (replacing trifluoroacetic anhydride with acetic anhydride). ¹H NMR(CDCl₃, 500 MHz): selected data δ: 2.38 (d, 2H, J=31.1 Hz); 3.59 (t, 1H, J=5.7 Hz); 3.68–3.79 (m, 1H); 4.06 (d, 1H, J=2.8 Hz); 4.16 (d, 1H, J=2.8 Hz); 5.88 (d, 1H, J=20.4 Hz). MS(ES) 544 (M+H), LC 1: 3.06 min.

INTERMEDIATE 71

1-(2,6-Dichlorophenyl)-5-(2-chlorophenyl)-7-(1,4-dioxaspiro(4.5)dec-7-ene-8-yl)-3,4-dihydro-2(1H)-quinazolinone

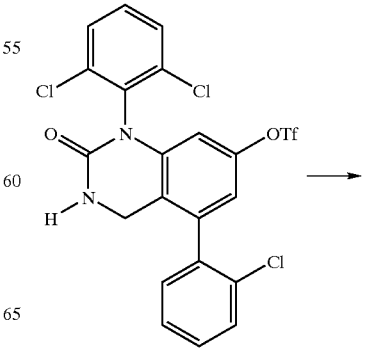

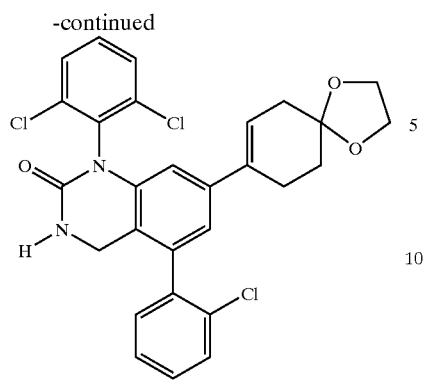

The title compound was prepared from 1-(2,6-dichlorophenyl)-5-(2-chlorophenyl)-7-trifluoromethylsulfonato-3,4-dihydro-2(1H)-quinazolinone (INTERMEDIATE 61) and (1,4-Dioxaspiro(4.5)dec-7-ene-8-yl)trimethyl tin (INTERMEDIATE 70) as described in EXAMPLE 41. $^1$H NMR (CDCl$_3$, 500 MHz): selected data δ 1.82 (t, 2H, J=6.4 Hz), 2.38 (brs, 2H), 2.47 (m, 2H), 3.97 (s, 4H), 5.83 (t, 1H, J=3.9 Hz). MS(ES) 541 (M+H); LC 1: 3.64 min.

INTERMEDIATE 72
1-(2,6-Dichlorophenyl)-5-(2-chlorophenyl)-7-(1,4-dioxaspiro(4.5)dec-8-yl)-3,4-dihydro-2(1H)-quinazolinone

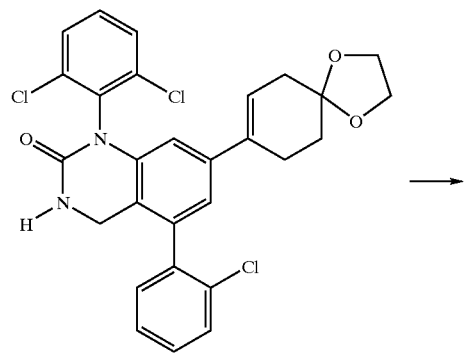

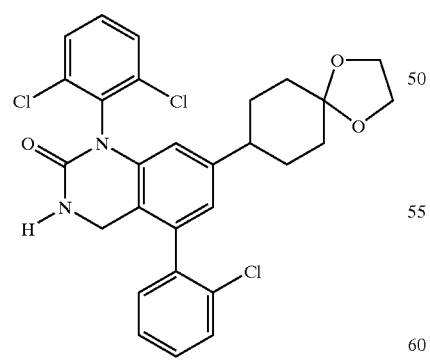

To 1-(2,6-dichlorophenyl)-5-(2-chlorophenyl)-7-(1,4-dioxaspiro(4.5)dec-7-ene-8-yl)-3,4-dihydro-2(1H)-quinazolinone (818.8 mg, 1.51 mmol) (INTERMEDIATE 71) in ethyl acetate (25 mL) under a nitrogen atmosphere was added platinum oxide (Adam's catalyst, 164 mg). The reaction mixture was purged with H$_2$ (via balloon) and stirred for 2 hours. Proton NMR analysis of an aliquot showed incomplete reduction. An additional 82 mg of PtO$_2$ was added and the solution stirred under a H$_2$ atmosphere for another hour. The reaction mixture was filtered over Celite, rinsed with 10% MeOH in DCM and concentrated. The crude material purified by silica gel chromatography eluting with 1% MeOH in DCM to give 1-(2,6-Dichlorophenyl)-5-(2-chlorophenyl)-7-(1,4-dioxaspiro(4.5)dec-8-yl)-3,4-dihydro-2(1H)-quinazolinone. $^1$H NMR (CDCl$_3$, 500 MHz): selected data δ 1.61 (m, 4H), 1.78 (m, 4H), 2.38 (m, 1H), 3.92 (m, 4H).

INTERMEDIATE 73
1-(2,6-Dichlorophenyl)-5-(2-chlorophenyl)-7-(1-cyclohexanon-4-yl)-3,4-dihydro-2(1H)-quinazolinone

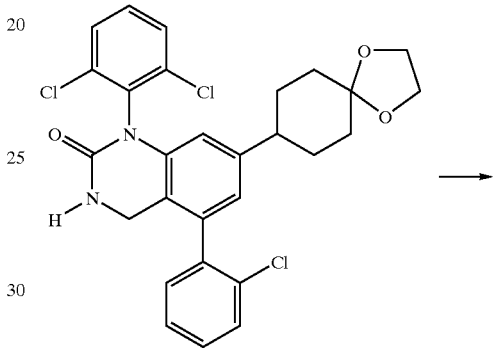

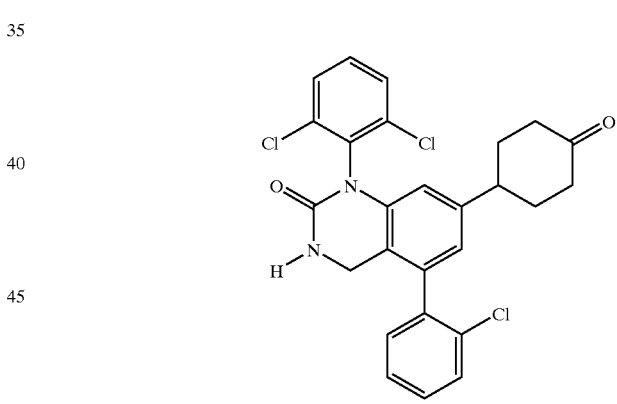

To a suspension of 1-(2,6-Dichlorophenyl)-5-(2-chlorophenyl)-7-(1,4-dioxaspiro(4.5)dec-8-yl)-3,4-dihydro-2(1H)-quinazolinone (248 mg, 0.456 mmol) (INTERMEDIATE 72) in acetone (12 mL) was added Amberlyst-15 (130 mg). The mixture was stirred at RT for 6 hours at which time the reaction mixture became homogeneous. The solution was filtered and the solvent concentrated. The crude material was purified by silica gel chromatography eluting with 1:4 acetone:hexanes followed by 1:3 acetone:hexanes to give 1-(2,6-Dichlorophenyl)-5-(2-chlorophenyl)-7-(1-cyclohexanon-4-yl)-3,4-dihydro-2(1H)-quinazolinone. $^1$H NMR (CDCl$_3$, 500 MHz): selected data δ 1.78 (m, 2H), 2.14 (m, 2H), 2.4 (m, 4H) 2.86 (m, 1H). MS(ES) 499 (M+H); LC 1: 3.19 min.

EXAMPLE 51
1-(2,6-Dichlorophenyl)-5-(2-chlorophenyl)-7-(1-dimethylaminocyclohexan-4-yl)-3,4-dihydro-2(1H)-quinazolinone

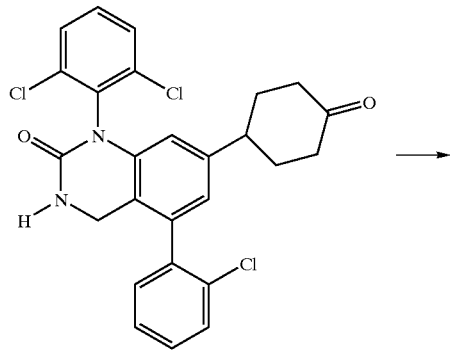

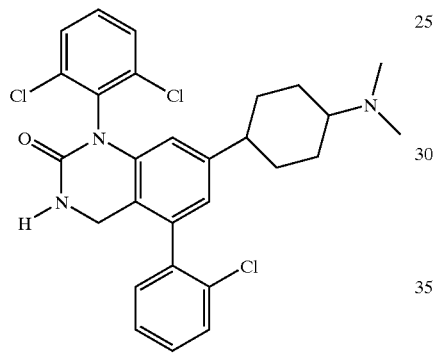

2.41 (m, 1H), 2.71 (s, 6H), 3.01 (m, 1H). MS(ES) 528 (M+H); LC 1: 2.313 min.

INTERMEDIATE 74
1-(2,6-Dichlorophenyl)-5-(2-chlorophenyl)-7-(1-hydroxyiminocyclohexan-4-yl)-3,4-dihyrdo-2(1H)-quinazolinone

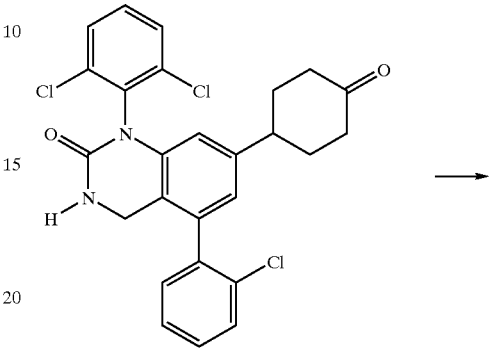

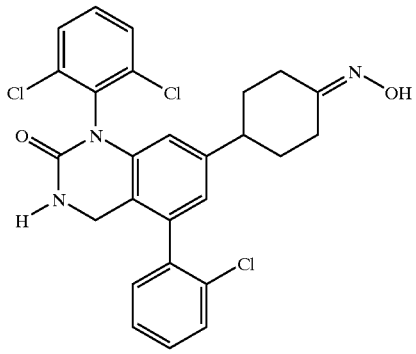

To a solution of 1-(2,6-Dichlorophenyl)-5-(2-chlorophenyl)-7-(1-cyclohexanon-4-yl)-3,4-dihydro-2(1H)-quinazolinone (33 mg, 0.066 mmol) (INTERMEDIATE 73) in 1,2-dichloroethane (1.0 mL) at RT (under a nitrogen atmosphere) was added dimethylamine hydrochloride (11 mg, 0.132 mmol) followed by triethylamine (18 μL, 0.132 mmol). The reaction-mixture was stirred for 10 min then NaBH(OAc)$_3$ (21 mg, 0.099 mmol) was added to the reaction. After 1.5 h the reaction mixture was diluted with EtOAc, washed with saturated NaHCO$_3$ solution followed by brine, and dried over Na$_2$SO$_4$. The crude residue was purified by preparative thin layer chromatography using 5% MeOH in DCM as the eluent to give 1-(2,6-Dichlorophenyl)-5-(2-chlorophenyl)-7-(1-dimethylaminocyclohexan-4-yl)-3,4-dihydro-2(1H)-quinazolinone (diastereomer A and diastereomer B).

Diastereomer A $^1$H NMR (CDCl$_3$, 500 MHz): selected data δ 1.60 (brm, 4H), 1.72 (brm, 2H), 1.91 (brm, 2H), 2.34 (s, 6H), 2.42 (brm, 1H), 2.66 (brs, 1H). MS(ES) 528 (M+H); LC 1: 2.296 min.

Diastereomer B $^1$H NMR (CDCl$_3$, 500 MHz): selected data δ 1.40 (m, 2H), 1.62 (brm, 2H), 2.02 (m, 2H), 2.29 (m, 2H), To a solution of hydroxylamine hydrochloride (29 mg, 0.416 mmol) in methanol (1.0 mL) was added solid NaHCO$_3$ (37 mg, 0.437 mmol). After stirring 15 minutes at RT 1-(2,6-Dichlorophenyl)-5-(2-chlorophenyl)-7-(1-cyclohexanon-4-yl)-3,4-dihydro-2(1H)-quinazolinone (52 mg, 0.104 mmol) (INTERMEDIATE 73) was added. After stirring 18 hours the solution was concentrated. The residue was suspended in DCM and the solid filtered. The filtrate solution was concentrated and the residue purified by preparative thin layer chromatography using 5% MeOH in DCM as the eluent to give 1-(2,6-Dichlorophenyl)-5-(2-chlorophenyl)-7-(1-hydroxyiminocyclohexan-4-yl)-3,4-dihydro-2(1H)-quinazolinone. $^1$H NMR (CDCl$_3$, 500 MHz):

selected data 1.53 (m, 2H), 1.87 (dt, 1H, J=5.4, 14.2 Hz), 1.98 (m, 2H), 2.19 (m, 1H), 2.57 (brd, 1H, J=14.4 Hz), 2.64 (m, 1H), 3.38 (brd, 1H, J=15.2 Hz).

MS(ES) 514 (M+H); LC 1: 3.027 min.

EXAMPLE 52
1-(2,6-dichlorophenyl)-5-(2,4-difluorophenyl)-7-(4-piperidinyl)-3,4-dihydro-2(1H)-quinazolinone

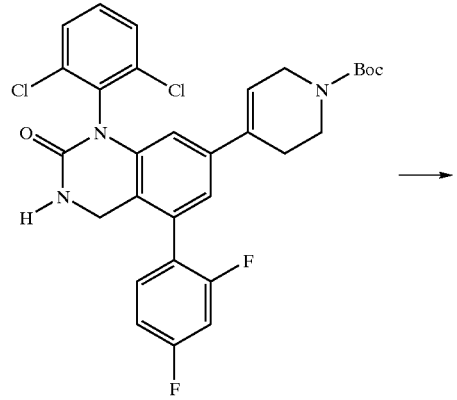

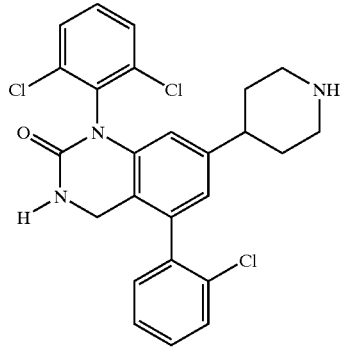

The title compound was prepared from 1-(2,6-dichlorophenyl)-5-(2,4difluorophenyl)-7-(1-Boc-1,2,3,6-tetrahydro-4-pyridinyl)-3,4-dihydro-2(1H)-quinazolinone (EXAMPLE 41 Step A) as described in INTERMEDIATE 72 (replacing Pt₂O with 10% Pd on carbon and EtOAc with MeOH). The tert-butoxycarbonyl substituent was removed as described in EXAMPLE 34 Step B. ¹H NMR(CDCl₃, 500 MHz): δ 1.41–1.52 (m, 2H), 1.64(1H, NH), 1.70–1.79 (m, 2H), 2.48(m, 1H), 2.66(app t, 2H, J=12.1 Hz), 3.12 (app d, 2H, J=11.9 Hz), 4.21–4.58 (br m, 2H), 5.19 (s, 1H), 6.03 (s, 1H), 6.82 (s, 1H), 6.91–7.01 (m, 2H), 7.28–7.33 (m, 1H), 7.40 (app t, 1H, J=8.0 Hz), 7.54 (d, 2H, J=8.3 Hz). MS(ES) 488 (M+H); LC 1: 2.14 min.

EXAMPLE 53
1-(2,6-dichlorophenyl)-5-(2-chlorophenyl)-7-(4-piperidinyl)-3,4-dihydro-2(1H)-quinazoline The title compound was prepared from 1-(2,6-dichlorophenyl)-5-(2-chlorophenyl)-7-(1-Boc-1,2,3,6-tetrahydro-4-pyridinyl)-3,4-dihydro-2(1H)-quinazolinone (EXAMPLE 42 Step A) as described in INTERMEDIATE 72 (replacing Pt₂O with 10% Pd on carbon and EtOAc with MeOH). The tert-butoxycarbonyl substituent was removed as described in EXAMPLE 34 Step B. ¹H NMR(CD₃OD, 500 MHz): δ 1.40–1.51 (m, 2H), 1.67–1.73 (m, 2H), 2.48–2.56 (m, 1H), 2.57–2.67 (m, 2H), 3.01–3.07 (m, 2H), 4.20 (d, 1H, J=14.8 Hz), 4.27 (d, 1H, J=14.9 Hz), 5.99 (d, 1H, J=1.1 Hz), 6.78 (d, 1H, J=1.1 Hz), 7.30 (m, 1H), 7.38–7.42 (m, 2H), 7.43–7.56 (m, 2H), 7.58–7.63 (m, 2H). MS(ES) 486 (M+H); LC 1: 2.14 min.

EXAMPLE 54
1-(2,6-dichlorophenyl)-5-(2-chloro-4-fluorophenyl)-7-(4-piperidinyl)-3,4-dihydro-2(1H)-quinazoline

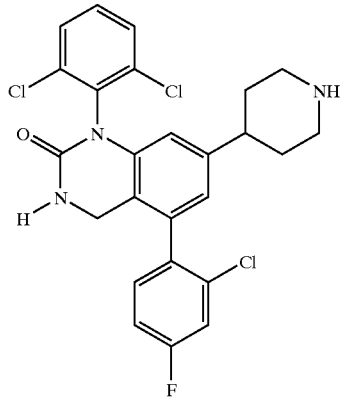

The title compound was prepared from 1-(2,6-dichlorophenyl)-5-(2-chloro-4-fluorophenyl)-7-(1-Bo3,6-tetrahydro-4-pyridinyl)-3,4-dihydro-2(1H)-quinazolinone (EXAMPLE 43 Step A) as described in INTERMEDIATE 72 (replacing Pt₂O with 10% Pd on carbon and EtOAc with MeOH). The tert-butoxycarbonyl substituent was removed as described in EXAMPLE 34 Step B. ¹H NMR(CDCl₃, 500 MHz): δ 1.6 (m, 4H), 2.51 (m, 1H), 2.73 (min 2H), 3.24 (m, 2H), 4.22 (d, 1H, J=14.4 Hz), 4.39 (d, 1H, J=14.4 Hz), 5.13 (s, 1H), 6.00 (d, 1H, J=0.9 Hz), 6.74 (d, 1H, J=0.9 Hz), 7.03–7.11 (m, 1H), 7.25–7.31 (m, 2H), 7.39 (t, 1H, J=8.1 Hz), 7.54 (d, 2H, J=8.2 Hz). MS(ES) 504 (M+H); LC 1: 2.04 min. c-1,2,

EXAMPLE 55
1-(2-chlorophenyl-6-methyl)-5-(2-chloro-4-fluoro-phenyl)-7-(4-piperidinyl)-3,4-dihydro-2(1H)-quinazolinone

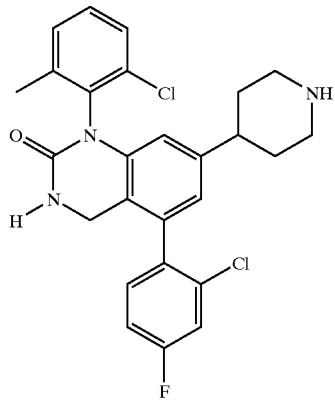

The title compound was prepared as described in EXAMPLE 54 (replacing 2,6-dichlorophenyl isocyanate with 2-chloro-6-methyl isocyanate in INTERMEDIATE 21). $^1$H NMR(CDCl$_3$, 500 MHz): δ 1.52–1.61 (m, 2H), 1.72–1.81 (m, 2H), 2.27,(d, 3H, J=2.3 Hz), 2.42–2.52 (m, 1H), 2.69 (t, 2H, J=12.3 Hz), 3.22 (d, 2H, J=12.1 Hz), 4.17–4.45 (m, 2H), 5.11–5.13 (m, 1H), 5.98 (s, 1H), 6.71 (s, 1H), 7.08 (td, 1H, J=11.0, 2.8 Hz), 7.25–7.30 (m, 2H), 7.31 (t, 2H, J=7.6 Hz), 7.44 (dd, 1H, J=7.3, 2.0 Hz). MS(ES) 484 (M+H); LC 1: 2.03 min

EXAMPLE 56
1-(2,6-dichlorophenyl)-5-(2-chloro-4-fluorophenyl)-7-(1-methyl-4-piperidinyl-3,4-dihydro-2(1H)-quinazolinone

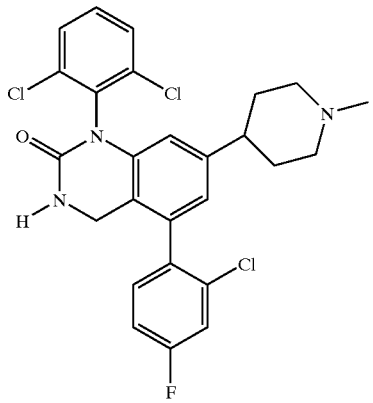

The title compound was prepared from 1-(2,6-dichlorophenyl)-5-(2-chloro-4-fluorophenyl)-7-(4-piperidinyl)-3,4-dihydro-2(1H)-quinazolinone (EXAMPLE 54) as described in EXAMPLE 15. $^1$H NMR(CDCl$_3$, 500 MHz): δ 1.61 (m, 2H), 1.73 (m, 2H), 1.96 (m, 2H), 2.27 (s, 3H), 2.35 (m, 1H), 2.89 (m, 2H), 4.22 (app dd, 1H, J=1.8, 14.2 Hz), 4.39 (app dd, 1H, J=1.4, 14.2 Hz), 5.19 (s, 1H), 6.03 (d, 1H, J=0.9 Hz), 6.74 (d, 1H, J=0.9 Hz), 7.05–7.10 (m, 1H), 7.24–7.31 (m, 2H), 7.39(t, 1H, J=8.1 Hz), 7.53 (d, 2H, 8.2 Hz). MS(ES) 518 (M+H); LC 1: 2.04 min.

EXAMPLE 57
1-(2,6-dichlorophenyl)-5-(2-chloro-4-fluorophenyl)-7-(1-cyclopropyl-4-piperidinyl)-3,4-dihydro-2(1H)-quinazolinone

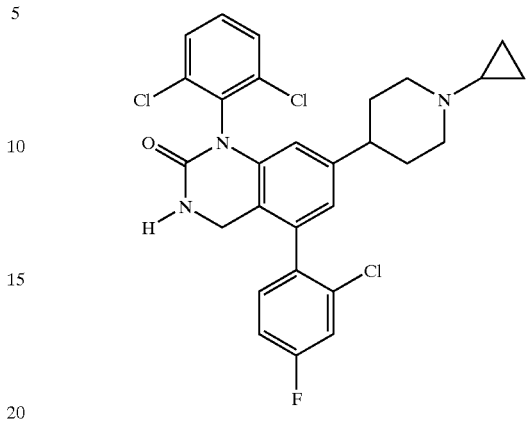

The title compound was prepared from 1-(2,6-dichlorophenyl)-5-(2-chloro-4-fluorophenyl)-7-(4-piperidinyl)-3,4-dihydo-2(1H)-quinazolinone (EXAMPLE 54) as described by M. L. Gillaspy, B. A. Lefker, et al Tetrahedron Letters 1995, V36 (41), 7399–7402. $^1$H NMR (CDCl$_3$, 500 MHz): δ 0.39–0.48 (brm, 4H), 1.52–1.68 (brm, 3H), 1.75(d, 2H, J=10.9 Hz), 2.22 (brs, 2H), 2.41 (t, 1H), J=1.8 Hz), 3.11 (brs, 2H), 4.24 (app dd, 1H, J=1.7, 14.3 Hz), 4.38 (app dd, 1H, J=1.5, 14.3 Hz), 5.10 (s, 1H), 6.02 (d, 1H, J=1.2 Hz), 6.75 (s, 1H), 7.05–7.1 (m, 1H), 7.24–7.30 (m, 2H), 7.39 (t, 1H, J=8.1 Hz), 7.53 (d, 2H, J=8.0 Hz). MS(ES) 544 (M+H); LC 1: 2.25 min.

EXAMPLE 58
1-(2,6-dichlorophenyl)-5-(2-chloro-4-fluorophenyl)-7-(4-(N-ethyl)piperidinyl)-3,4-dihydro-2(1H)-quinazolinone

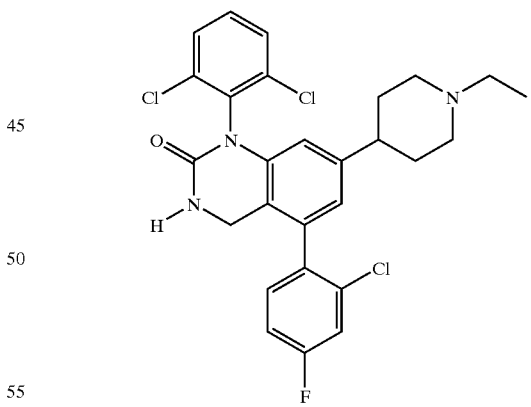

To 1-(2,6-chlorophenyl)-5-(2-chloro-4-fluorophenyl)-7-(4-piperidinyl)-3,4-dihydro-2(1H)-quinazolinone (15.3 mg, 0.030 mmol) (EXAMPLE 54) in 1 mL ethanol was added bromoethane (20.1 mg, 0.184 mmol) and potassium carbonate (30 mg, 0.217 mmol). After stirring at room temperature for 12 hours the reaction mixture was partition between water and ethyl acetate. The phases were separated and the organic phase washed with brine and concentrated. The-residue was purified by preparative thin layer chromatography using $CHCl_3/MeOH/NH_4OH$ (87/12/1) as the eluent to give 1-(2,6-dichlorophenyl)-5-(2-chloro-4-fluorophenyl)-7-(4-(N-ethyl)piperidinyl)-3,4-dihydro-2(1H)-quinazolinone. $^1H$ NMR($CDCl_3$, 500 MHz): selected data δ 1.08 (t, 3H, J=7.2 Hz); 1.63 (appt, 2H, J=11.7 Hz); 1.70–1.78 (m, 2H); 1.91–1.93 (m, 2H); 2.38–2.41 (m, 3H); 3.00–3.02 (d, 2H, J=10.7 Hz). MS(ES) 532 (M+H); LC 1: 2.23 min.

EXAMPLE 59
1-(2,6-dichlorophenyl)-5-(2-chloro-4-fluorophenyl)-7-(4-(1-isopropyl)-piperidinyl)-3,4-dihydro-2(1H)-quinazolinone

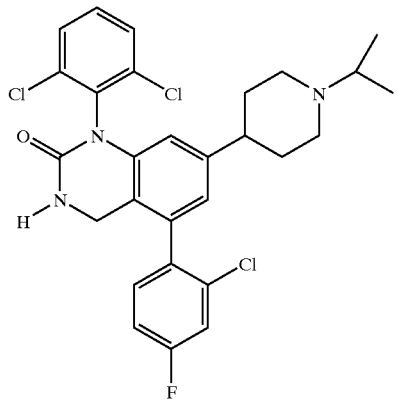

The title compound was prepared as described in EXAMPLE 58 (replacing bromoethane with 2-iodopropane). $^1H$ NMR($CDCl_3$, 500 MHz): selected data δ 1.04 (d, 6H, J=6.4 Hz); 1.59 (app t, 2H, J=11.8 Hz); 1.73–1.78 (m, 2H); 2.13–2.18 (m, 2H), 2.29–2.39 (m, 1H); 2.62–2.71 (m, 1H); 2.93–2.95 (m, 2H). MS(ES) 546 (M+H); LC 1: 2.32 min.

EXAMPLE 59B
1-(2,6-dichlorophenyl)-5-(2-chloro-4-fluorophenyl)-7-(4-(1-cyclopropylmethyl)-piperidinyl)-3,4-dihydro-2(1H)-quinazolinone

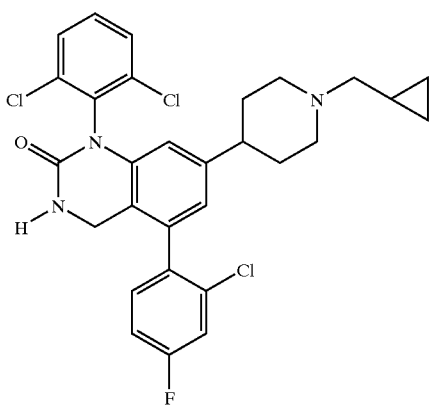

The title compound was prepared as described in EXAMPLE 58 (replacing bromoethane with cyclopropylmethyl bromide). $^1H$ NMR($CDCl_3$, 500 MHz): selected data δ 0.40 (brs, 2H); 0.76 (brs, 2H); 1.24 (brs, 1H); 1.85–2.02 (brm, 2H), 2.20–2.95 (brm, 7H); 3.58–3.81 (brm, 2H). MS(ES) 558 (M+H); LC 1: 2.48 min.

EXAMPLE 60
1-(2,6-dichlorophenyl)-5-(2-chloro-4-fluorophenyl)-7-(4-(N-2-hydroxyethyl)-piperidinyl)-3,4-dihydro-2(1H)-quinazolinone

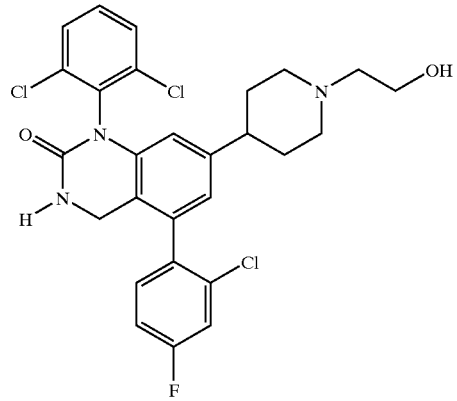

The title compound was prepared as described in EXAMPLE 58 (replacing bromoethane with 2-bromoethanol). $^1H$ NMR($CDCl_3$, 500 MHz): selected data δ 1.53–1.66 (m, 2H); 1.71–1.80 (m, 2H); 2.07–2.12 (m, 2H); 2.31–2.42 (m, 1H); 2.50–2.54 (m, 2H); 2.95–2.97 (m, 2H); 3.60–3.62 (m, 2H). MS(ES) 548 (M+H); LC 1: 2.13 min.

EXAMPLE 61
1-(2,6-dichlorophenyl)-5-(2-chloro-4-fluorophenyl)-7-(4-(N-t-butylacetate)-piperidinyl)-3,4-dihydro-2(1H)-quinazolinone

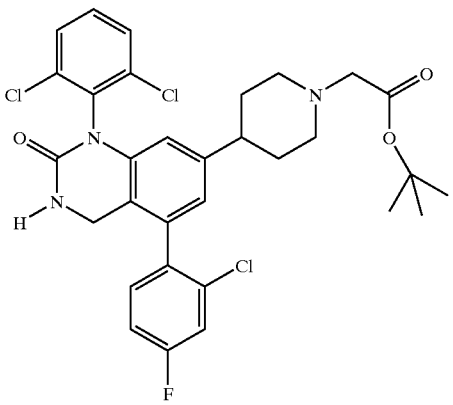

The tide compound was prepared as described in EXAMPLE 58 (replacing bromoethane with t-butyl bromoacetate). $^1H$ NMR($CDCl_3$, 500 MHz): selected data δ 1.47 (s, 9H); 1.62–1.69 (m, 4H); 2.19 (app t, 2H, J=1.8 Hz); 2.31–2.40 (m, 1H); 3.05 (d, 2H, J=11.0 Hz); 3.11 (s, 2H). MS(ES) 618 (M+H); LC 1: 2.65 min

EXAMPLE 62
1-(2,6-dichlorophenyl)-5-(2-chloro-4-fluorophenyl)-7-(4-(1-acetic acid)-piperidinyl)-3,4-dihydro-2(1H)-quinazolinone

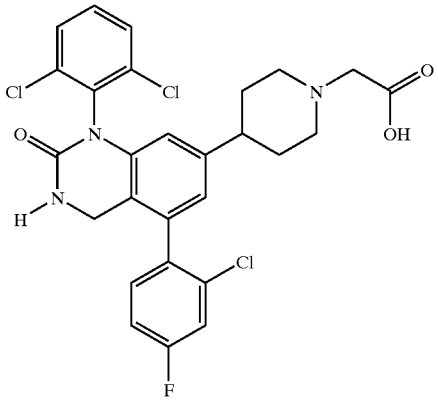

1-(2,6-dichlorophenyl)-5-(2-chloro-4-fluoro-phenyl)-7-(N-(t-butylacetate)-1,2,3,6-tetrahydro-5-pyridinyl)-3,4-dihydro-2(1H)-quinazolinone (11.7 mg, 0.0189 mmol) (EXAMPLE 61) in 1 mL 1/1 TFA/DCM was stirred at room temperature for 12 h. The solution was concentrated and the residue washed with ethyl ether to give 1-(2,6-dichlorophenyl)-5-(2-chloro-4-fluorophenyl)-7-(4-(1-acetic acid)-piperidinyl)-3,4-dihydro-2(1H)-quinazolinone. $^1$H NMR(CDCl$_3$, 500 MHz): selected data δ 1.81–1.92 (m, 2H); 2.00 (app d, 2H, J=12.3 Hz); 2.77 (t, 1H, J=1.8 Hz); 3.30 (t, 2H, J=1.8 Hz); 3.64 (d, 2H, J=10.3 Hz); 4.23 (ABq, 2H, J=15.0 Hz). MS(ES) 562 (M+H); LC 1: 2.1 min.

EXAMPLE 63
1-(2,6-dichlorophenyl)-5-(2-chloro-4-fluorophenyl)-7-(1-hydroxyacetyl-4-piperidinyl)-3,4-dihydro-2(1H)-quinazolinone

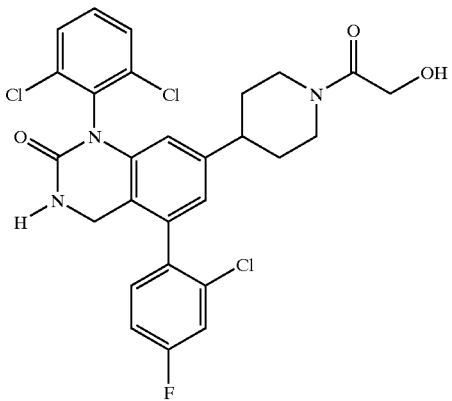

The title compound was prepared from 1-(2,6-dichlorophenyl)-5-(2-chloro-4-fluorophenyl)-7-(4-piperidinyl)-3,4-dihydro-2(1H)-quinazolinone (EXAMPLE 54) as described in EXAMPLE 14. $^1$H NMR(CDCl$_3$, 500 MHz): selected data δ 1.42–1.57 (m, 2H); 1.84–1.87 (m, 2H); 2.63 (t, 1H, 13.3 Hz); 3.03 (t, 1H, J=13.8 Hz); 3.55 (d, 1H, J=13.8 Hz); 4.15 (ABq, 2H, J=5.3 Hz); 4.68 (d, 1H, J=13.3 Hz). MS(ES) 562 (M+H); LC 1: 2.76 min.

EXAMPLE 64
1-(2,6-dichlorophenyl)-5-(2-chloro-4-fluorophenyl)-7-(1-imidine-4-piperidinyl-3,4-dihydro-2(1H)-quinazolinone

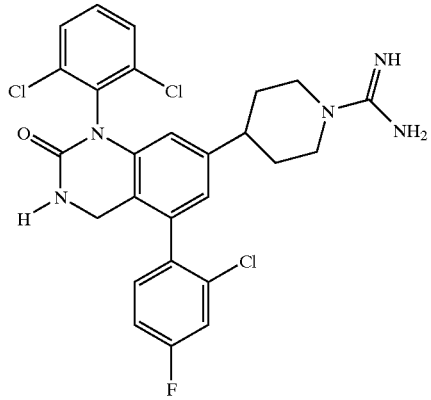

To 1-(2,6-dichlorophenyl)-5-(2-chloro-4-fluorophenyl)-7-(4-piperidinyl)-3,4-dihydro-2(1H)-quinazolinone (11.2 mg, 0.022 mmol) (EXAMPLE 54) in 0.5 mL THF was added N,N'-bis-Boc-1-guanylpyrazole (12.6 mg, 0.041 mmol). The reaction mixture was stirred at 55° C. (oil bath) for 12 hours. The solution was concentrated and the residue purified by preparative thin layer chromatography using CHCl$_3$/MeOH/NH$_4$OH (87/12/1) as the eluent. The isolated material (N-Boc) was stirred in 1 mL 1/1 TFA/DCM for 1.5 h at RT. The solution was concentrated and the residue purified by preparative thin layer chromatography using CHCl$_3$/MeOH/NH$_4$OH (87/12/1) as the eluent to give 1-(2,6-dichlorophenyl)-5-(2-chloro-4-fluorophenyl)-7-(1-imidine-4-piperidinyl)-3,4-dihydro-2(1H)-quinazolinone. $^1$H NMR(CDCl$_3$, 500 MHz): selected data δ 1.55 (m, 2H); 1.84 (d, 2H, 10.7 Hz); 2.75 (m, 1H); 3.12 (t, 2H, J=11.5 Hz); 3.90 (d, 2H, J=13.8 Hz); 4.24 (ABq, 2H, J=8.0 Hz). MS(ES) 546 (M+H); LC 1: 2.20 min.

EXAMPLE 65
1-(2,6-dichlorophenyl)-5-(2-chlorophenyl)-7-(N-bicyclo[2.2.1]piperazinylcarbonyl)-3,4-dihydro-2(1H)-quinazolinone

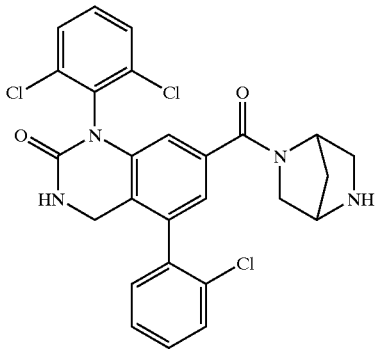

The title compound was prepared from 1-(2,6-dichlorophenyl)-5-(2-chlorophenyl)-7-carboxyl-3,4-dihydro-2(1H)-quinazolinone (INTERMEDIATE 59) as described in EXAMPLE 19 [replacing N-(2-chlorophenyl) piperazine with N-BOC-bicyclo[2.2.1]piperazine]. The tert-butoxy carbonyl substituent was subsequently removed as described in EXAMPLE 34 Step B. $^1$H NMR(CDCl$_3$, 500 MHz): selected data δ 2.66–3.24 (m, 3H), 3.27–3.33 (m, 2H), 3.41–3.49 (m, 1H), 3.62–3.68 (m, 1H), 3.8–3.9 (m, 1H). MS(ES) 527 (M+H); LC 1: 1.9 min.

EXAMPLE 66
1-(2,6-dichlorophenyl)-5-(2-chlorophenyl)-7-bicyclo[2.2.1]piperazinylmethyl-3,4-dihydro-2(1H)-quinazolinone

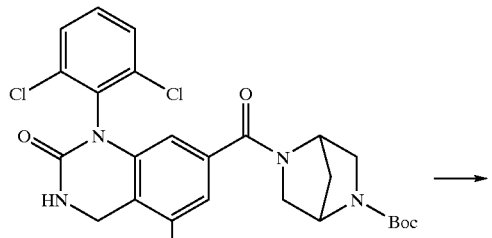

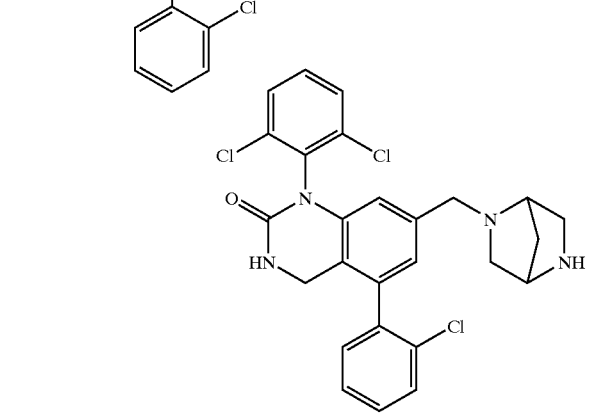

A solution of 1-(2,6-dichlorophenyl)-5-(2-chlorophenyl)-7-[N-BOC-bicyclo[2.2.1]piperazinylcarbonyl]-3,4-dihydro-2(1H)-quinazolinone (52 mg, 0.083 mmol) (EXAMPLE 65, Step A) and borane-THF complex (2 mL of 1.0M solution, 2 mmol) was stirred at room temperature for two hours. Methanol (1 mL) was added and the mixture was stirred for 10 minutes. The solution was concentrated a solution of TFA (1 mL) and methylene chloride (0.5 mL) was added. The mixture was stirred at room temperature for 16 hours. Removal of the solvent and subsequent purification by preparative thin layer chromatography using 10% 2N ammonia in methanol/methylene chloride provided 1-(2,6-dichlorophenyl)-5-(2-chlorophenyl)-7-bicyclo[2.2.1]piperazinylmethyl-3,4-dihydro-2(1H)-quinazolinone. $^1$H NMR(CDCl$_3$, 500 MHz): δ 1.72 (brd, 1H), 1.85 (d, 1H, J=10.0 Hz), 2.64 (d, 1H, J=10.7 Hz), 2.80–2.86 (m, 1H), 2.90–2.98 (m, 1H), 3.20 (t, 1H, J=11.2 Hz), 3.40 (s, 1H), 3.50 (s, 2H), 3.61 (s, 1H), 3.84 (d, 1H, J=5.3 Hz), 4.22–4.30 (m, 1H), 4.38–4.46 (m, 1H), 5.32 (s, 1H), 6.14 (s, 1H), 6.88 (s, 1H), 7.28–7.40 (m, 4H), 7.42–7.56 (m, 4H). MS(ES) 513 (M+H); LC 1: 1.78 min.

EXAMPLE 67
1-(2,6-dichlorophenyl)-5-(2-chlorophenyl)-7-amino(azabicyclo[3.1.0]hexane)-3,4-dihydro-2(1H)-quinazolinone

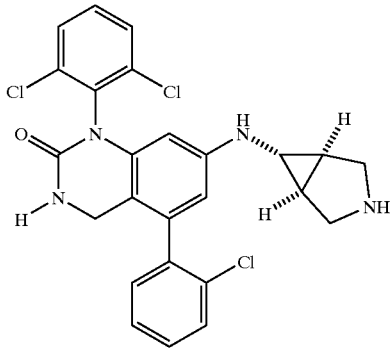

The title compound was prepared from 1-(2,6-dichlorophenyl)-5-(2-chlorophenyl)-7-trifluoromethylsulfonato-3,4-dihydro-2(1H)-quinazolinone (INTERMEDIATE 61) as described in EXAMPLE 34 (replacing 1-Boc-piperazine with (1α, 5α, 6α)-3-benzyloxycarbonyl-6-amino-3-azabicyclo[3.1.0]hexane). See K. E. Brighty and M. J. Castaldi Synlett 1996, 1097–1099. The benzyloxycarbonyl group was subsequently cleaved with HBr in AcOH. $^1$H NMR(CD$_3$OD, 500 MHz): selected data δ 1.63 (brm, 2H), 2.03 (s, 1H), 2.93–2.98 (m, 2H), 3.02–3.08 (m, 2H). MS(ES) 499 (M+H); LC 1: 2.07 min.

EXAMPLE 68
1-(2,6-dichlorophenyl)-5-(2-chlorophenyl)-7-(azabicyclo[3.1.0]hexane)-3,4-dihydro-2(1H)-quinazolinone

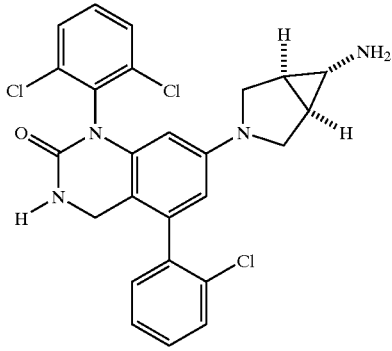

The title compound was prepared from 1-(2,6-dichlorophenyl)-5-(2-chlorophenyl)-7-trifluoromethylsulfonato-3,4-dihydro-2(1H)-quinazolinone (INTERMEDIATE 61) as described in EXAMPLE 34 (replacing 1-Boc-piperazine with (1α, 5α, 6α)-6-tert-butoxycarbonylamino-3-azabicyclo[3.1.0]hexane). See K. E. Brighty and M. J. Castaldi Synlett 1996, 1097–1099. $^1$H NMR(CD$_3$OD, 500 MHz): selected data δ 1.60 (s, 2H), 2.06 (s, 1H), 2.99–3.03 (m, 2H), 3.21 (app d, 2H, J=9.2 Hz). MS(ES) 499 (M+H); LC 1: 2.27 min.

EXAMPLE 69
1-(2,6-Dichlorophenyl)-5-(2-chlorophenyl)-7-[2-(1-piperidinyl)ethoxyl]-2(1H)-quinolinone

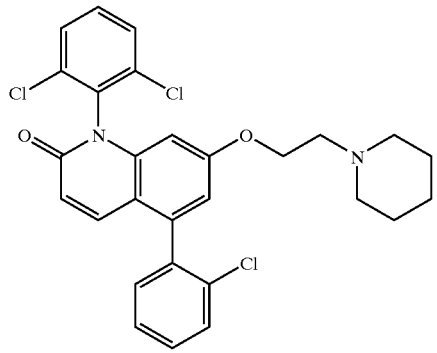

The title compound was prepared from 5-(2-chlorophenyl)-1-(2,6-dichlorophenyl)-7-hydroxy-2(1H)- quinolinone (INTERMEDIATE 9), Ph₃P, 1-piperidine ethanol, and diethyl azodicarboxylate by a procedure analogous to that described in EXAMPLE 2. Mass spectrum (ESI) 527.1 (M+1). ¹H NMR (500 MHz, CDCl₃): δ 7.50–7.61 (m, 3H); 7.36–7.47 (m, 5H); 6.75 (d, J=2.5 Hz, 1H); 6.53 (d, J=9.5 Hz, 1H); 6.02 (d, J=2.0 Hz, 1H); 4.00 (t, J=6.0 Hz 2H); 2.69 (t, J=6.0 Hz 2H); 2.42 (br s, 4H); 1.45–1.65 (m, 6H).

EXAMPLE 70

5-(2-Chlorophenyl)-1-(2,6-dichlorophenyl)-7-piperazin(1-yl)-2(1H)-quinolinone

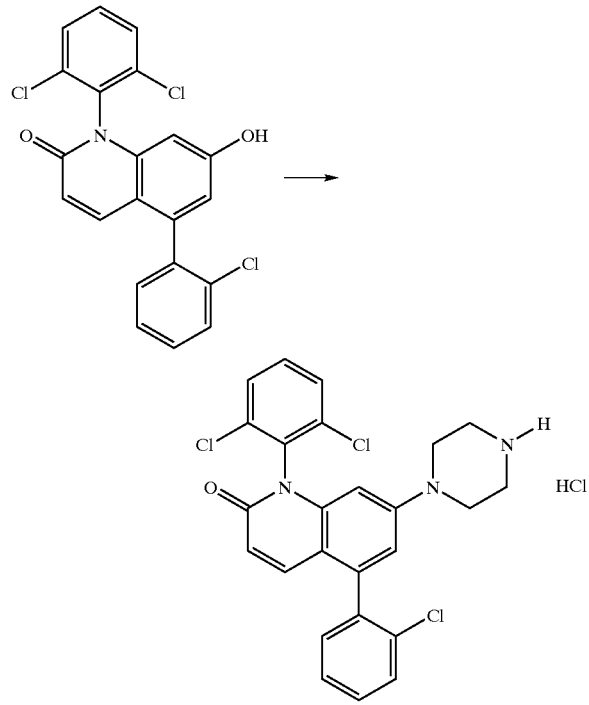

Step A: Triflate

To a suspension solution of 5-(2-Chlorophenyl)-1-(2,6-dichlorophenyl)-7-hydroxy-2(1H)-quinolinone (INTERMEDIATE 9) (100 mg) in DCM (5 mL) was added N,N-diisopropylethylamine (0.083 mL) and trifluoromethanesulfonic anhydride (0.06 mL) at −78° C. After stirring at −78° C. for 10 min., the mixture was warmed to room temperature and stirred an additional 10 min. The reaction was quenched with methanol and concentrated. The residue was purified by silica gel chromatography (hexanes/ethyl acetate=4/1) to give 82 mg of the desired triflate. ¹H NMR(CDCl₃, 500 MHz): δ 7.64 (m, 2H), 7.59 (d, 1H), 7.49 (m, 5H), 7.11 (d, 1H), 6.77 (d, 1H), 6.44 (d, 1H).

Step B: BOC Intermediate

A solution of the triflate from Step A above (80 mg) in toluene (3 mL) was added tris(dibenzylideneacetone)dipalladium (7 mg), 1,1-bis(diphenylphosphino)ferrocene (7 mg), sodium t-butoxide (19 mg) and 1-t-butoxycarbonylpiperaine (50 mg) and heated 100° C. for 16 h. The resulting reaction mixture was cooled to room temperature and diluted with ethyl acetate. The solution was filtered through celite and concentrated. The residue was purified by silica gel chromatography (hexanes/ethyl acetate=2/1) to give the BOC intermediate coupling product (62 mg). ¹H NMR(CDCl₃, 500 MHz): δ 7.56 (m, 3H), 7.40 (m, 5H), 6.73 (d, 1H), 6.50 (d, 1H), 5.84 (d, 1H), 3.52 (t, 4H), 3.13 (t, 4H), 1.47 (s, 9H).

Step C: 5-(2-Chlorophenyl)-1-(2,6-dichlorophenyl)-7-piperazin(1-yl)-2(1H)-quinolinone A solution of the BOC intermediate from Step B above (61 mg) in ethyl acetate (3 mL) was cooled to 0° C. While stirring, hydrogen chloride gas was bubbled into the mixture for 30 seconds. The mixture was stirred for 15 minutes, until TLC analysis indicated that the reaction was complete. The solution was concentrated to remove the ethyl acetate. The residue was the diluted with hexanes and followed by evaporation in vacuo to yield 5-(2-Chlorophenyl)-1-(2,6-dichlorophenyl)-7-piperazin(1-yl)-2(1H)-quinolinone as a solid.

EXAMPLE 71

5-(2-Chlorophenyl)-1-(2,6-dichlorophenyl)-7-(1-(2-amino-ethan-1-one)-piperazin(4-yl))-2(1H)-quinolinone

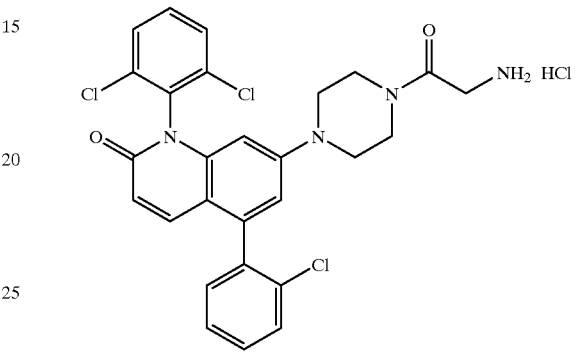

To a solution of EXAMPLE 70 (5 mg), BOP reagent (9 mg), Boc-Glycine (3.5 mg) in DCM (0.5 mL) was added triethylamine (0.003 ml). The reaction was stirred at room temperature for 24 h. Removal of the solvent and subsequent purification by preparative thin layer chromatography (hexanes/ethyl acetate=1/1) provided the desired Boc Intermediate coupling product. A solution of the Boc intermediate in ethyl acetate (1 mL) was cooled to 0° C. While stirring, hydrogen chloride gas was bubbled into the mixture for 30 seconds. The mixture was stirred for 15 minutes, until TLC analysis indicated that the reaction was complete. The solution was concentrated to remove the ethyl acetate. The residue was the diluted with hexanes and followed by evaporation in vacuo to give 5-(2-Chlorophenyl)-1-(2,6-dichlorophenyl)-7-(1-(2-amino-ethan-1-one)-piperazin(4-yl))-2(1H)-quinolinone. ¹H NMR(CD₃OD, 500 MHz): δ 7.71 (m, 2H), 7.60 (m, 2H), 7.45 (m, 4H), 6.91 (d, 1H), 6.45 (d, 1H), 5.90 (d, 1H), 3.94 (s, 2H), 3.70 (t, 2H), 3.54 (t, 2H), 3.25 (t, 2H), 3.21 (t, 2H). MS(ES) 542 (M+H).

EXAMPLE 72

5-(2-Chlorophenyl)-1-(2, 6-dichlorophenyl)-7-(1-(2-amino-2-methyl-ethan-1-one)-piperazin(4-yl))-2(1H)-quinolinone

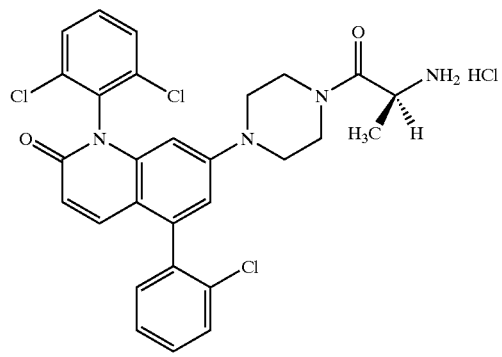

The title compound was prepared as described in EXAMPLE 71 (replacing Boc-Glycine with Boc-L-

Alanine). $^1$H NMR(CD$_3$OD, 500 MHz): δ 7.72 (m, 2H), 7.60 (m, 2H), 7.44 (m, 4H), 6.92 (d, 1H), 6.45 (d, 1H), 5.91 (d, 1H), 4.39 (q, 1H), 3.61 (m, 4H), 3.25 (m, 4H), 1.44 (d, 3H). MS(ES) 556 (M+H).

EXAMPLE 73

5-(2-Chlorophenyl)-1-(2,6-dichlorophenyl)-7-(1-(2-amino-2-methyl-ethan-1-one)-piperazin(4-yl))-2(1H)-quinolinone

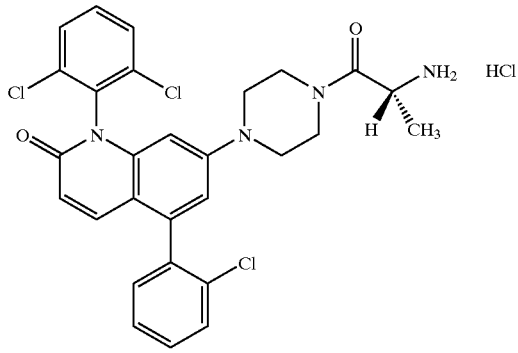

The title compound was prepared as described in EXAMPLE 71 (replacing Boc-Glycine with Boc-D-Alanine). $^1$H NMR(CD$_3$OD, 500 MHz): δ 7.72 (m, 2H), 7.60 (m, 2H), 7.44 (m, 4H), 6.92 (d, 1H), 6.45 (d, 1H), 5.91 (d, 1H), 4.39 (q, 1H), 3.61 (m, 4H), 3.25 (m, 4H), 1.44 (d, 3H). MS(ES) 556 (M+H).

EXAMPLE 74

5-(2-Chlorophenyl)-1-(2, 6-dichlorophenyl)-7-(1-(3-amino-propan-1-one)-piperazin(4-yl))-2(1H)-quinolinone

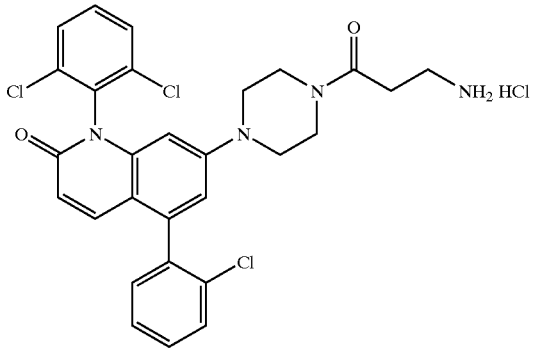

The title compound was prepared as described in EXAMPLE 71 (replacing Boc-Glycine with Boc-β-Alanine). $^1$H NMR(CD$_3$OD, 500 MHz): δ 7.71 (m, 2H), 7.60 (m, 2H), 7.45 (m, 4H), 6.91 (d, 1H), 6.44 (d, 1H), 5.90 (d, 1H), 3.68 (brs, 2H), 3.61 (brs, 2H), 3.25 (brs, 2H); 3.18 (brs, 2H), 2.79 (t, 2H), 2.71 (t, 2H). MS(ES) 556 (M+H).

EXAMPLE 75

5-(2-Chlorophenyl)-1-(2,6-dichlorophenyl)-7-(1-(2-methylamino-ethan-1-one)-piperazin(4-yl))-2(1H)-quinolinone

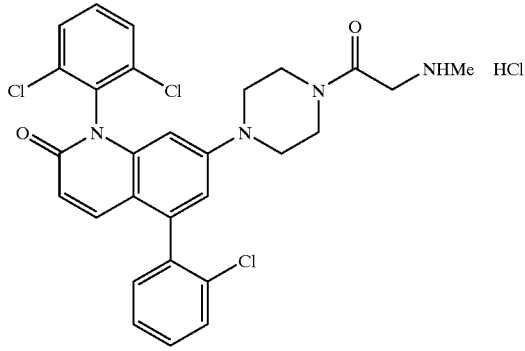

The title compound was prepared as described in EXAMPLE 71 (replacing Boc-Glycine with Boc-Sarcosine). $^1$H NMR(CD$_3$OD, 500 MHz): δ 7.71 (m, 2H), 7.60 (m, 2H), 7.45 (m, 4H), 6.91 (d, 1H), 6.44 (d, 1H), 5.91 (d, 1H), 4.07 (s, 2H), 3.69 (t, 2H), 3.55 (t, 2H), 3.25 (t, 2H), 3.22 (t, 2H), 2.73 (s, 3H). MS(ES) 556 (M+H).

EXAMPLE 76

5-(2-Chlorophenyl)-1-(2, 6-dichlorophenyl)-7-(1-(2-amino-2, 2-dimethyl-ethan-1-one)-piperazin(4-yl))-2(1H)-quinolinone

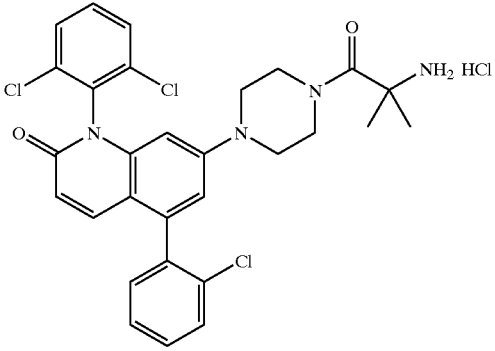

The title compound was prepared as described in EXAMPLE 71 (replacing Boc-Glycine with Boc-α-methylalanine). $^1$H NMR(CD$_3$OD, 500 MHz): δ 7.71 (m, 2H), 7.60 (m, 2H), 7.48 (m, 4H), 6.91 (d, 1H), 6.45 (d, 1H), 5.92 (d, 1H), 3.75 (brs, 4H), 3.22 (brs, 4H), 1.65 (s, 3H), 1.57 (s, 3H). MS(ES) 570 (M+H).

EXAMPLE 77

1-(2,6-Dichlorophenyl)-5-(2,4-difluorophenyl)-7-(2-oxoazepan-5-yl)-3,4-dihydro-2(1H)-quinazolinone

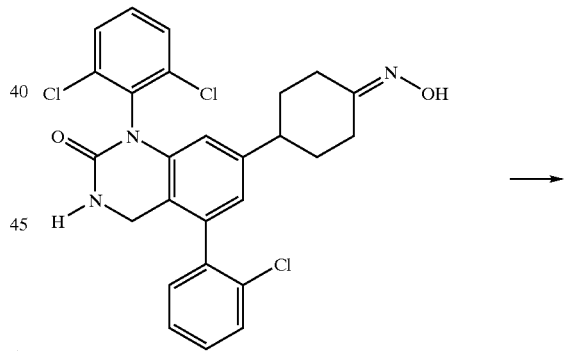

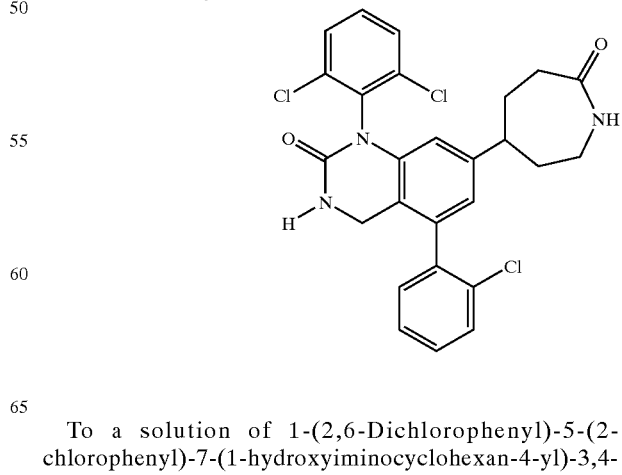

To a solution of 1-(2,6-Dichlorophenyl)-5-(2-chlorophenyl)-7-(1-hydroxyiminocyclohexan-4-yl)-3,4- dihydro-2(1H)-quinazolinone (46 mg, 0.089 mmol) in DCM (2.0 mL) at 0° C. was added methanesulfonyl chloride (35 µL, 0.445 mmol) followed by pyridine (36 µL, 0.445 mmol). The ice bath was removed after 10 minutes and the reaction mixture was stirred at RT for 20 hours. A few drops of water was added to the reaction mixture and the solution stirred for an additional 30 minutes. The solution was concentrated and the residue suspended in DCM. The solid was filtered and rinsed with EtOAc. The filtrate solution was concentrated and the crude residue purified by preparative thin layer chromatography 3% MeOH in DCM to give 1-(2,6-Dichlorophenyl)-5-(2,4-difluorophenyl)-7-(2-oxoazepane-3-yl)-3,4-dihydro-2(1H)-quinazolinone. $^1$H NMR (CDCl$_3$, 500 MHz): selected data δ 1.55 (m, 2H), 1.92 (m, 2H), 2.49 (m, 2H), 2.59 (m, 1H), 3.25 (m, 2H). MS(ES) 514 (M+H); LC 1: 2.592 min.

INTERMEDIATE 75
1-(2,6-Dichlorophenyl)-3-(4-methoxybenzyl)-5-(2-chlorophenyl)-7-(1,4-dioxaspiro(4.5) dec-8-yl)-3, 4-dihydro-2(1H)-quinazolinone

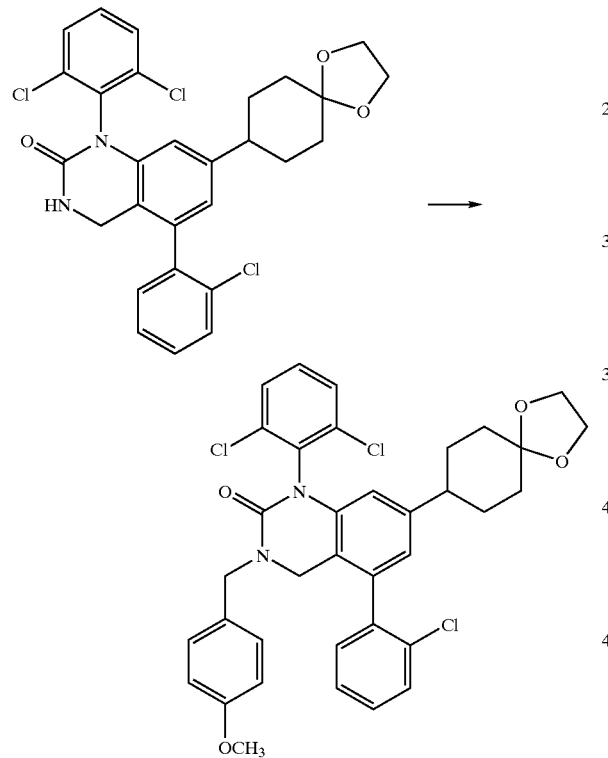

To a solution of 1-(2,6-dichlorophenyl)-5-(2-chlorophenyl)-7-(1,4-dioxaspiro(4.5)dec-8-yl)-3,4-dihydro-2(1H)-quinazolinone (INTERMEDIATE 72) (102 mg, 0.187 mmol) in DMF (2 mL) at 0° C. was added NaH (15 mg, 0.375 mmol).

The resulting reaction mixture was stirred until it became homogeneous. 4-Methoxybenzyl chloride (51 µL, 0.375 mmol) was then added and the ice bath was removed. The reaction was stirred for 2 hours at RT, cooled down with an ice bath, and quenched with H$_2$O. It was diluted with CH$_2$Cl$_2$, separated layers, and the organic layer was washed with H$_2$O three times. The combined aqueous layer was back-extracted once with CH$_2$Cl$_2$, and the combined organic layer was washed with brine and dried over Na$_2$SO$_4$. The crude material was purified by preparative TLC eluting with 1:2 acetone:hexanes to obtain 1-(2,6-Dichlorophenyl)-3-(4-methoxybenzyl)-5-(2-chlorophenyl)-7-(1,4-dioxaspiro(4.5) dec-8-yl)-3,4-dihydro-2(1H)-quinazolinone.
MS(ES) 665 (M+H); LC 1: 4.56 min.

INTERMEDIATE 76
1-(2,6-Dichlorophenyl)-3-(4-methoxybenzyl)-5-(2-chlorophenyl)-7-(1-cyclohexanon-4-yl))-3,4-dihydro-2(1H)-quinazolinone

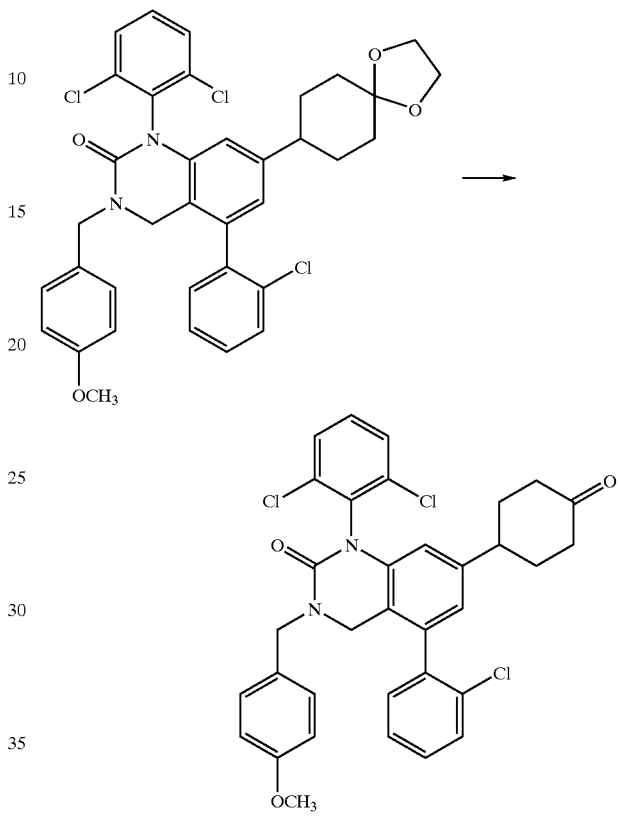

The title compound was prepared from 1-(2,6-Dichlorophenyl)-3-(4-methoxybenzyl)-5-(2-chlorophenyl)-7-(1,4-dioxaspiro(4.5)dec-8-yl)-3,4-dihydro-2(1H)-quinazolinone (INTERMEDIATE 75) according to the procedure described in INTERMEDIATE 73. $^1$H NMR (CDCl$_3$, 500 MHz): selected data δ 1.77 (m, 2H), 2.13 (m, 2H), 2.4 (m, 4H), 2.86 (m, 1H), 3.78 (s, 3H), 4.4 (d, J=4.8 Hz, 1H), 4.65 (d, J=4.8 Hz, 1H). MS(ES) 619 (M+H); LC 1: 3.92 min.

INTERMEDIATE 77
1-(2,6-Dichlorophenyl)-3-(4-methoxybenzyl)-5-(2-chlorophenyl)-7-(1-hydroxyiminocyclohexan-4-yl)-3,4-dihydro-2(1H)-quinazolinone

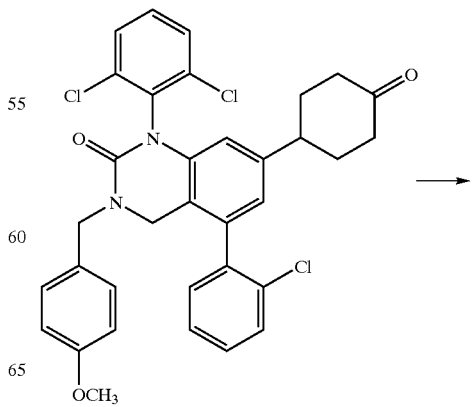

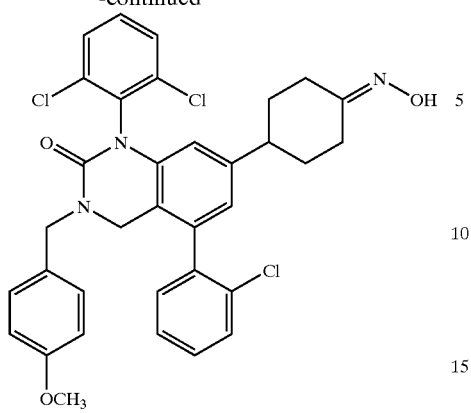

The title compound was prepared from 1-(2,6-Dichlorophenyl)-3-(4-methoxybenzyl)-5-(2-chlorophenyl)-7-(1-cyclohexanon-4-yl)-3,4-dihydro-2(1H)-quinazolinone (INTERMEDIATE 76) according to the procedure described in INTERMEDIATE 74. ¹H NMR (CDCl₃, 500 MHz): selected data δ 1.49 (m, 2H), 1.80 (dt, 1H, J=5.0, 14.2 Hz, 1H), 1.97 (m, 2H), 2.16 (m, 1H), 2.45 (brd, J=12.5 Hz, 1H), 2.62 (m, 1H), 3.37 (brd, 1H, J=14.2 Hz), 3.78 (s, 3H). MS(ES) 634 (M+H); LC 1: 3.76 min.

INTERMEDIATE 78
1-(2,6-Dichlorophenyl)-3-(4-methoxybenzyl)-5-(2-chlorophenyl)-7-(2-oxoazepan-5-yl)-3,4-dihydro-2(1H)-quinazolinone

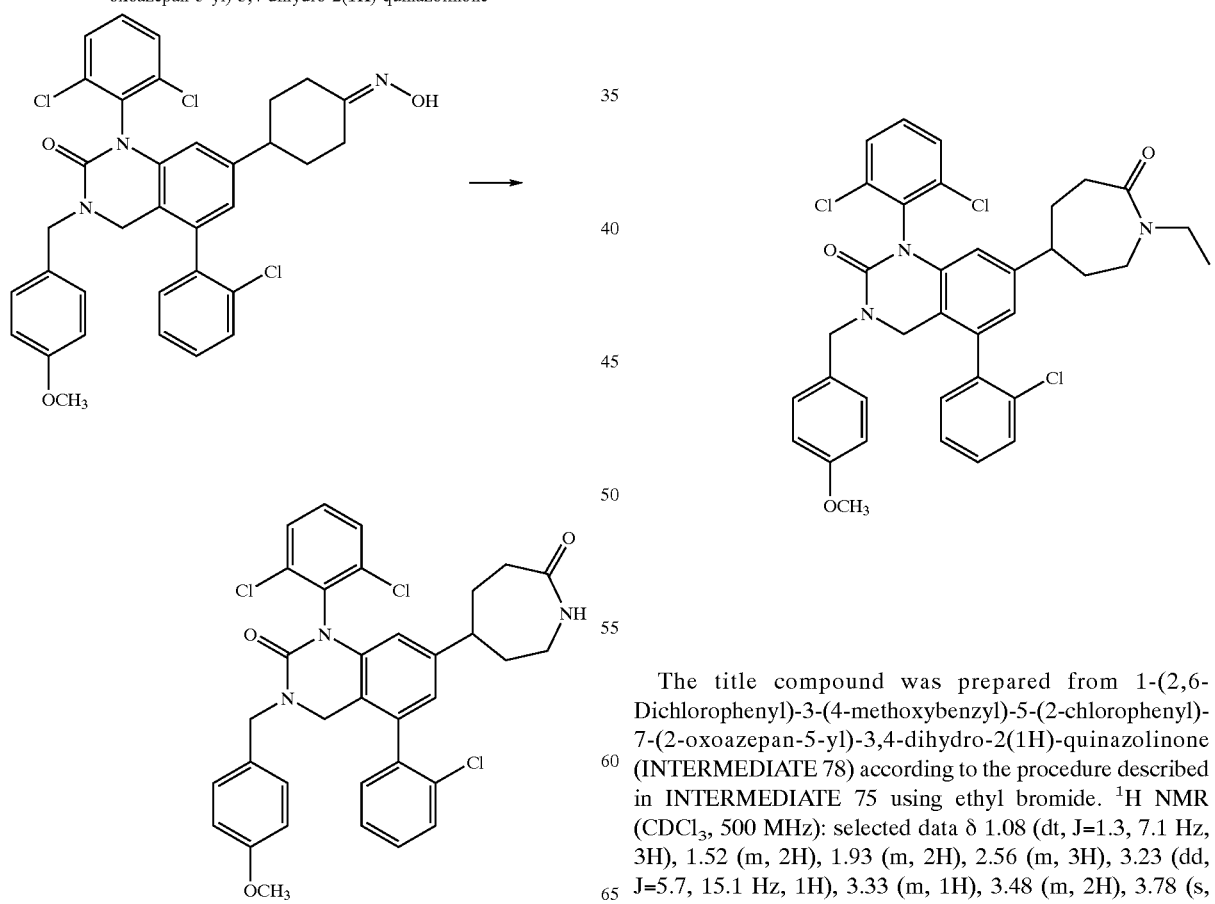

The title compound was prepared from 1-(2,6-Dichlorophenyl)-3-(4-methoxybenzyl)-5-(2-chlorophenyl)-7-(1-hydroxyiminocyclohexan-4-yl)-3,4-dihydro-2(1H)-quinazolinone (INTERMEDIATE 77) according to the procedure described in the EXAMPLE 77. ¹H NMR (CDCl₃, 500 MHz): selected data δ 1.55 (m, 2H), 1.92 (m, 2H), 2.49 (m, 2H), 2.59 (m, 1H), 3.25 (m, 2H), 3.78 (s, 3H). MS(ES) 634 (M+H); LC 1:3.48 min.

INTERMEDIATE 79
1-(2,6-Dichlorophenyl)-3-(4-methoxybenzyl)-5-(2-chlorophenyl)-7-(1-ethyl-2-oxoazepane-5-yl)-3,4-dihydro-2(1H)-quinazolinone

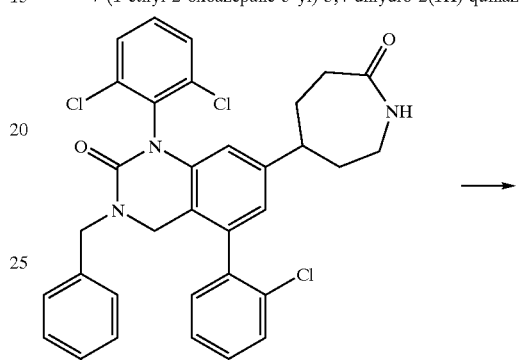

The title compound was prepared from 1-(2,6-Dichlorophenyl)-3-(4-methoxybenzyl)-5-(2-chlorophenyl)-7-(2-oxoazepan-5-yl)-3,4-dihydro-2(1H)-quinazolinone (INTERMEDIATE 78) according to the procedure described in INTERMEDIATE 75 using ethyl bromide. ¹H NMR (CDCl₃, 500 MHz): selected data δ 1.08 (dt, J=1.3, 7.1 Hz, 3H), 1.52 (m, 2H), 1.93 (m, 2H), 2.56 (m, 3H), 3.23 (dd, J=5.7, 15.1 Hz, 1H), 3.33 (m, 1H), 3.48 (m, 2H), 3.78 (s, 3H). MS(ES) 664 (M+H); LC 1: 3.71 min.

EXAMPLE 78

1-(2,6-Dichlorophenyl)-5-(2-chlorophenyl)-7-(1-ethyl-2-oxoazepan-5-yl)-3,4-dihydro-2(1H)-quinazolinone

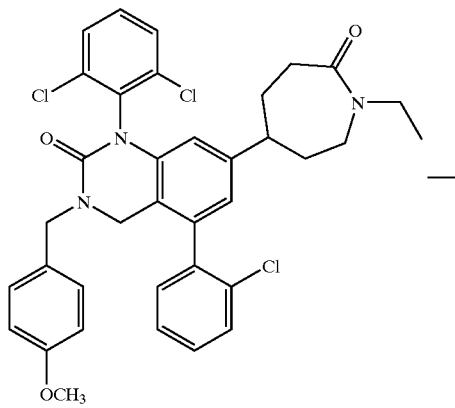

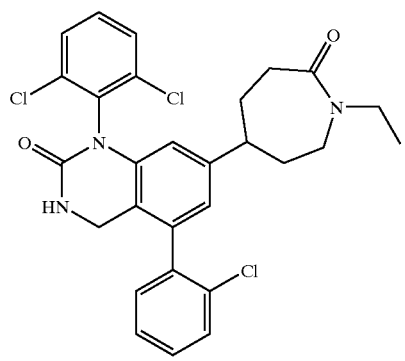

The title compound was prepared from 1-(2,6-Dichlorophenyl)-3-(4-methoxybenzyl)-5-(2-chlorophenyl)-7-(1-ethyl-2-oxoazepane-5-yl)-3,4-dihydro-2(1H)-quinazolinone (INTERMEDIATE 79) according to the procedure described in INTERMEDIATE 23. $^1$H NMR (CDCl$_3$, 500 MHz): selected data δ 1.08 (dt, J=1.8, 7.1 Hz, 3H), 1.52 (m, 2H), 1.94 (m, 2H), 2.55 (m, 3H), 3.23 (dd, J=5.9, 15.3 Hz, 1H), 3.34 (m, 1H), 3.49 (m, 2H), 4.22 (apparent m, 1H), 4.37 (apparent m, 1H). MS(ES) 544 (M+H); LC 1: 3.06 min.

EXAMPLE 79

1-(2, 6-Dichlorophenyl)-5-(2-chlorophenyl)-7-(ethylazepan-5-yl)-3, 4-dihydro-2(1H)-quinazolinone

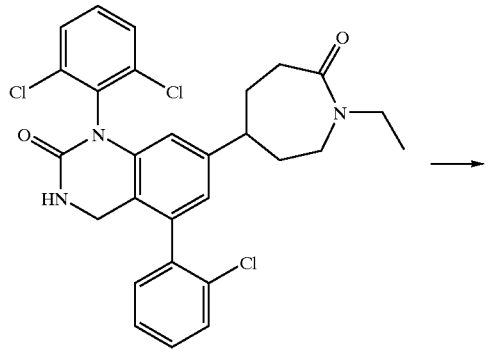

-continued

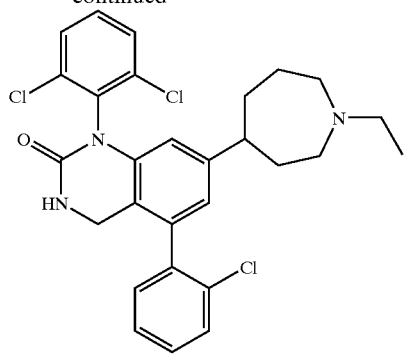

To a solution of 1-(2,6-dichlorophenyl)-5-(2-chlorophenyl)-7-(1-ethyl-2-oxoazepan-5-yl)-3,4-dihydro-2(1H)-quinazolinone (EXAMPLE 78) (9.7 mg, 0.018 mmol) in THF (0.2 mL) under N$_2$ atmosphere was added BH$_3$.THF (88 μL, 1.0M solution in THF). The reaction was stirred at RT overnight. The solvent was removed in vacuo, and the residue was dissolved in CH$_2$Cl$_2$. The resulting solution was washed with brine and dried over Na$_2$SO$_4$. After removal of the solvent in vacuo, the residue was re-dissolved in CH$_2$Cl$_2$ (0.5 mL) then cooled down to 0° C. To this was added Et$_3$SiH (3 μL, 0.036 mmol) followed by BF$_3$.Et$_2$O (2.5 μL, 0.04 mmol), and the mixture was slowly warmed to RT over 2 hours. It was quenched with saturated solution of NaHCO$_3$, then extracted with CH$_2$Cl$_2$ three times. The combined extracts were washed with brine and dried over Na$_2$SO$_4$. The crude residue was purified by preparative TLC eluting with 5% 2M NH$_3$ in MeOH(CH$_2$Cl$_2$ to obtain 1-(2,6-Dichlorophenyl)-5-(2-chlorophenyl)-7-(1-ethylazepan-5-yl)-3,4-dihydro-2(1H)-quinazolinone. $^1$H NMR (CDCl$_3$, 500 MHz): selected data δ 1.03 (t, J=7.1 Hz, 3H), 1.6–1.87 (m, 6H), 2.52 (q, J=7.1 Hz, 2H), 2.56–2.73 (m, 5H). MS(ES) 530 (M+H); LC 1: 2.36 min.

EXAMPLE 80

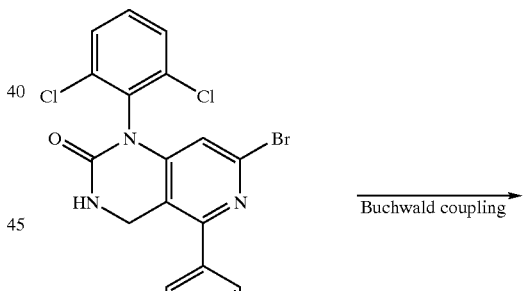

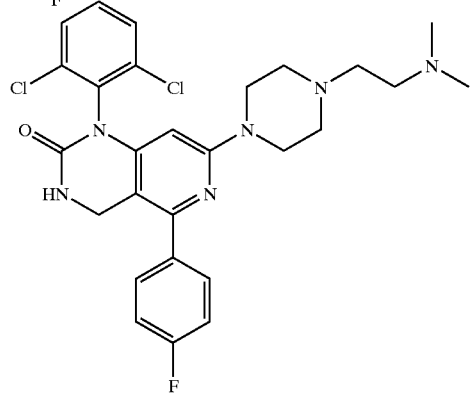

EXAMPLE 80

Referring to scheme 13, to Pd$_2$(DBA)$_3$ (0.1 mmole) and BINAP (0.2 mmole) was added 0.5 mL of deoxygenated toluene. The resulting reaction mixture was evacuated and back filled with argon. The reaction mixture was heated under an argon atmosphere, at 40° C. After 20 min heating, a clear homogenous solution resulted. The reaction mixture was brought to room temperature and charged with sodium t-butoxide (1.0 mmole) and 4-dimethyl amino ethyl-piperazine (1.2 mmole) followed by addition of the aryl bromide (1.0 mmole) as a solution in 3.0 mL of toluene. The reaction mixture was evacuated and back filled with argon a few times. The reaction mixture was heated under argon at 80° C. for 12 h. TLC analysis was used to measure the consumption of starting material. The reaction mixture was diluted with 8.0 mL of ethyl acetate and extracted with brine (5.0 mL×3). The organic phase was dried over sodium sulphate and concentrated. The residue was purified by flash column chromatography (gradient: 0–7% methanol in dichloromethane) to yield EXAMPLE 80. $^1$H NMR (CDCl$_3$, 500 MHz, ppm): 7.55–7.49 (4H, m); 7.40 (1H, t, 8 Hz); 7.15 (2H, m); 5.31 (1H, s); 5.29 (1H, bs); 4.55 (2H, bs); 3.41 (4H, bs); 2.56–2.51 (8H, m); 2.36 (6H, bs). MS: [M+H]=543.0

EXAMPLE 81

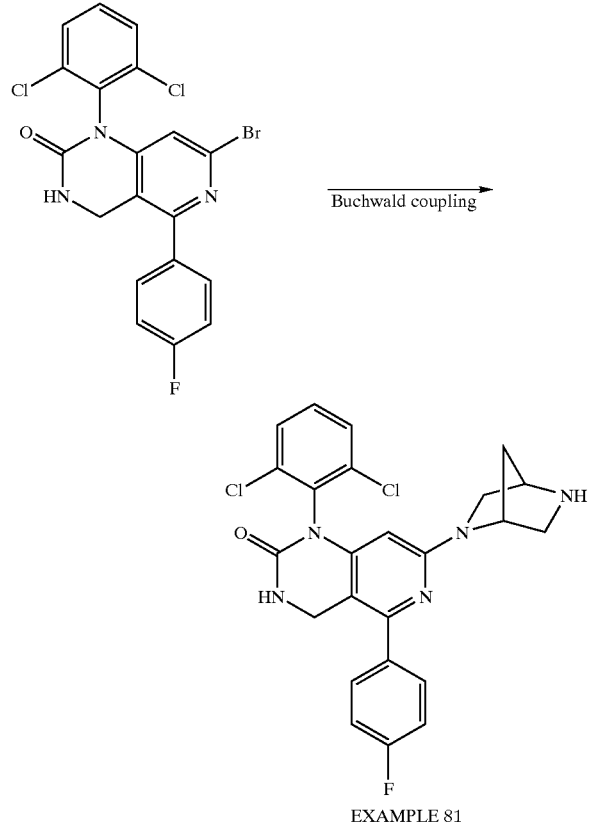

EXAMPLE 81

EXAMPLE 81 was made by following the procedure described above for EXAMPLE 80 using the corresponding N-boc-bridged piperazine. The Buchwald product obtained in the previous step was dissolved in 15 mL of TFA and stirred at room temperature. The consumption of starting material was monitored by TLC. After completion of reaction as indicated by TLC, the reaction mixture was evaporated and the resulting residue was purified by RP-HPLC. The EXAMPLE 81 was obtained either by lyophilization or evaporation of the eluants. The free base was obtained by neitralization, extraction into organic phase and evaporation.

$^1$H NMR (CDCl$_3$, 500 MHz, ppm): 7.55–7.49 (4H, m); 7.40 (1H, t, 8 Hz); 7.15 (2H, m); 5.92 (1H, bs); 4.98 (1H, s); 4.81 (1H, bs); 4.51 (2H, bs); 3.62 (3H, m); 3.22 (3H, bs); 1.95 (2H, bs). MS: [M+H]=485.0

COMPOUND VV-1

4,6-dibromo-3-(bromomethyl)-2-(2-chloro-phenyl)pyridine

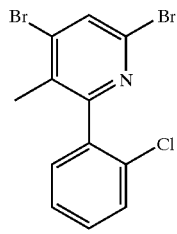

This compound was prepared in a similar fashion as COMPOUND PS below. Data: $^1$H NMR: 7.8 (1H, s); 7.2–7.5 (4H, m); 2.2 (3H, s); LCMS: [M+H]=360.

COMPOUND VV-2

3-trimethylstannyl-8-methyl-8-azabicyclo[3.2.1]oct-2-ene

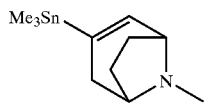

This compound was prepared in a similar fashion as INTERMEDIATE 69 starting from commercially available tropinone. Data: 1H NMR: 5.95 (1H, bs); 4.15 (1H, m); 4.09 (1H, m); 2.85 (3H, s); 2.65–1.8 (6H, m); 0.22 (9H, t, J=24 Hz); LCMS [M+H]=288.

COMPOUND VV-2

3-trimethylstannyl-8-methyl-8-azabicyclo[3.2.1]oct-2-ene

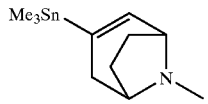

This compound was prepared in a similar fashion as INTERMEDIATE 69 starting from commercially available tropinone. Data: 1H NMR: 5.95 (1H, bs); 4.15 (1H, m); 4.09 (1H, m); 2.85 (3H, s); 2.65–1.8 (6H, m); 0.22 (9H, t, J=24 Hz); LCMS [M+H]=288.

COMPOUND VV-3

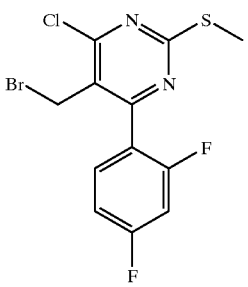

Step A: Ethyl-3-(2,4-difluorophenyl)-2-methyl-3-oxopropanoate 2,4-difluorobenzoic acid (25 g, 158.1 mmole) was dissolved 100 mL of THF followed by careful addition of carbonyl diimidazolide (27 g, 166 mmole). This reaction was allowed to stir for 6 h. In another flask 32 g of ethyl hydrogen malonate was dissolved in 100 mL THF followed by careful addition of magnesium ethoxide (9.44 g, 82.5 mmole). This reaction was allowed to stir for 2 h then evaporated to yield a fluffy white powder. This powder was added to the first reaction flask containing the acid imidazolide. The reaction was allowed to stir overnight (10 h). The reaction was quenched with 1N HCl and the resulting was extracted with ethyl acetate, combined organic extracts were dried and stripped to yield a colorless oil. LCMS [M+H]=229.

19 g of the compound obtained above was dissolved in 100 mL THF followed by careful addition of NaH (4 g, 100 mmole) at 0° C. After all the addition of NaH, methyl iodide (6.2 mL, 100 mmole) was added. The reaction was stirred at rt for 12 h. An additional amount of NaH (4 g, 100 mmole) was added followed by addition of MeI (6.2 mL, 100 mmole). The reaction was stirred another 12 h. The reaction was carefully quenched and subjected to standard work up. The resulting oil was taken into the next step without further purification. LCMS: [M+H]=243.

Step B: 6-(2,4-difluorophenyl)-5-methyl2-(methylthio)pyrimidin-4-ol

Ethyl-3-(2,4-difluorophenyl)-2-methyl-3-oxopropanoate obtained above was refluxed with thiourea (6.85 g, 90 mmole) and sodium ethoxide (12.25 g, 180 mmole) in 75 mL of ethanol for 2 h. The reaction mixture was cooled to room temperature and concentrated. The residue was dissolved in water, acidified and extrated into ethyl acetate which was concentrated and this polar solid obtained was suspended in water (50 mL) followed by addition of KOH (5.0 g, 90 mmole) and then MeI (5.6 mL, 90 mmole). The reaction was stirred for 2 h at rt. As the reaction proceeded the reaction mixture became turbid. After 2 h the reaction was cooled to 0° C., acidified, and extracted into ethyl acetate. The combined extracts were concentrated and subjected to filtration on a pad of silica gel eluting with ethyl acetate. The combined eluants were concentrated to provide a white solid. Data LCMS=[M+H]=255.

Step C: 4-Chloro-6-(2,4-difluorophenyl)-5-methyl-2-(methylthio)pyrimidine

A solution of 5.9 g of 6-(2,4-difluorophenyl)-5-methyl-2-(methylthio)pyrimidin-4-ol in 25 mL of POCl₃ was heated to reflux and stirred at this temperature for 5 h. All but ca. 5 mL of POCl₃ was removed by vacuum distillation, and the residue was quenched by pouring into 200 mL of ice-water, neutralizing with Na₂CO₃ and extracting with 3×100 mL of EtOAc. The combined organics were washed with 100 mL of brine, dried, and concentrated. The residue was purified by flash chromatography on a Biotage 40M column, eluting with 95:5 hexanes-acetone to yield the title compound as a light yellow solid. Mass spectrum (ESI) 287 (M+1).

Step D: 5-(bromomethyl)-4-chloro-6-(2,4-difluorophenyl)-2-(methylthio)pyrimidine A suspension of 5.4 g of 4-chloro-6-(2,4-difluorophenyl)-5-methyl-2-(methylthio)pyrimidine. 3.69 g of N-bromosuccinimide, and 460 mg of benzoyl peroxide in 75 mL of CCl₄ was heated to reflux and stirred at this temperature for 6 h, then cooled in the freezer for 1 h. The solids were filtered and washed liberally with cold CCl₄, and the filtrate was concentrated. The residue was purified by flash chromatography on a Biotage 40M column, eluting with a gradient system of 99:1 to 97:3 hexanes-acetone to yield the title compound. Mass spectrum (ESI) 367 (M+1).

COMPOUND PPP-1
1-(2,6-dichloro-4-carbomethoxyphenyl)-5-bromo-7-methoxy-3,4-dihydro-2(1H)-quinazolinone

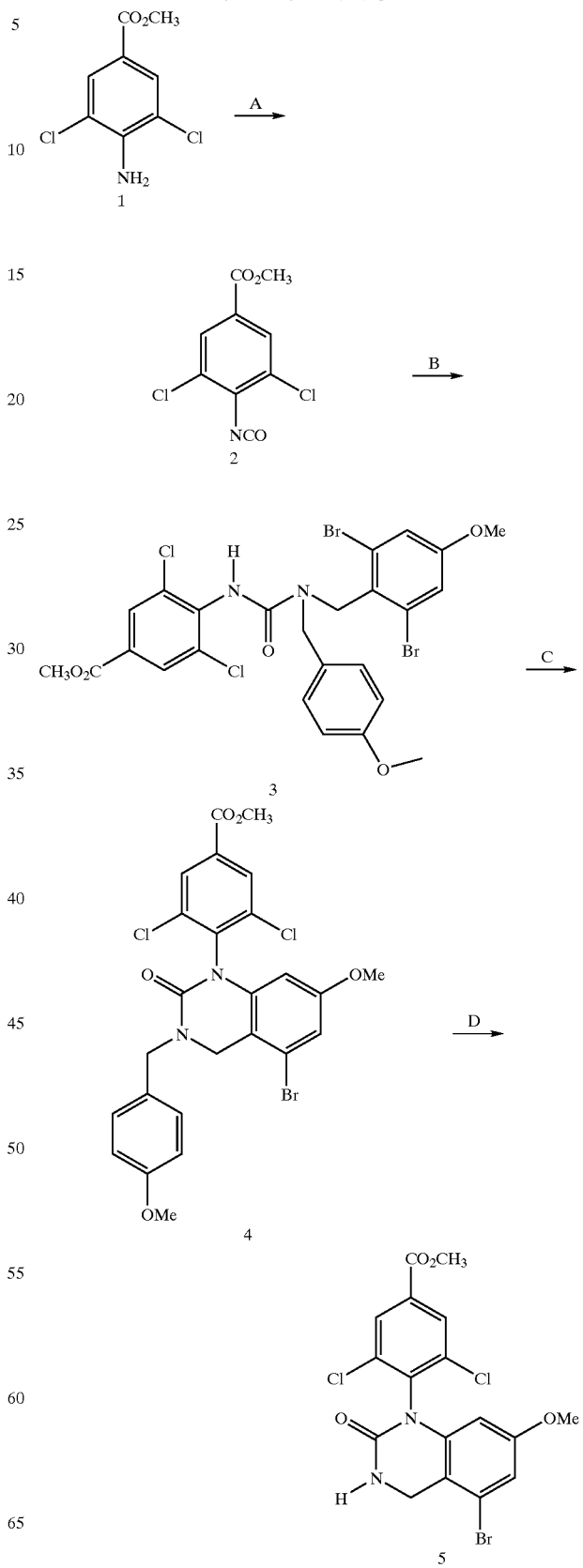

Step A: 2,6-Dichloro-4-Carbomethyoxyphenylisocyanate

A mixture of 10.95 g (50 mmol) of methyl 4-amino-3,5-dichlorobenzoate and 50 mL of a 2M solution of phosgene in toluene was sealed and heated at 110° C. for 18 h. After cooling to rt, the solution was concentrated under vacuum and solid residue was dried under high vacuum for 48 h to afford 2 as a white solid. Mass spectrum (ESI), 246 (M+1), 248 (M+3).

Step B: N-[(2,6-dibromo-4-methoxyphenyl)methyl]-N'-(2,6-dichloro-4-carbomethoxyphenyl)-N-[(4-methoxyphenyl)methyl]urea Compound 2 was converted to 3 by reaction with INTERMEDIATE 20 under the conditions described for preparation of INTERMEDIATE 21. Mass spectrum (ESI), 659 (M+1), 661 (M+3), 663 (M+5), 665 (M+7).

Step C: 1-(2,6-dichloro-4-carbomethoxyphenyl)-3-(4-methoxyphenyl)methyl-5-bromo-7-methoxy-3,4-dihydro-2(1H)-quinazolinone Compound 3 was converted to 4 using the conditions described for preparation of INTERMEDIATE 22. Mass spectrum (ESI), 521 (M+1), 523 (M+3), 525 (M+5).

Step D: 1-(2,6-dichloro-4-carbomethoxyphenyl)-5-bromo-7-methoxy-3,4-dihydro-2(1H)-quinazolinone Compound 4 was converted to 5 using the conditions described for preparation of INTERMEDIATE 23. Mass Spectrum (ESI), 401 (M+1), 403 (M+3), 405 (M+5)

EXAMPLE PPP1

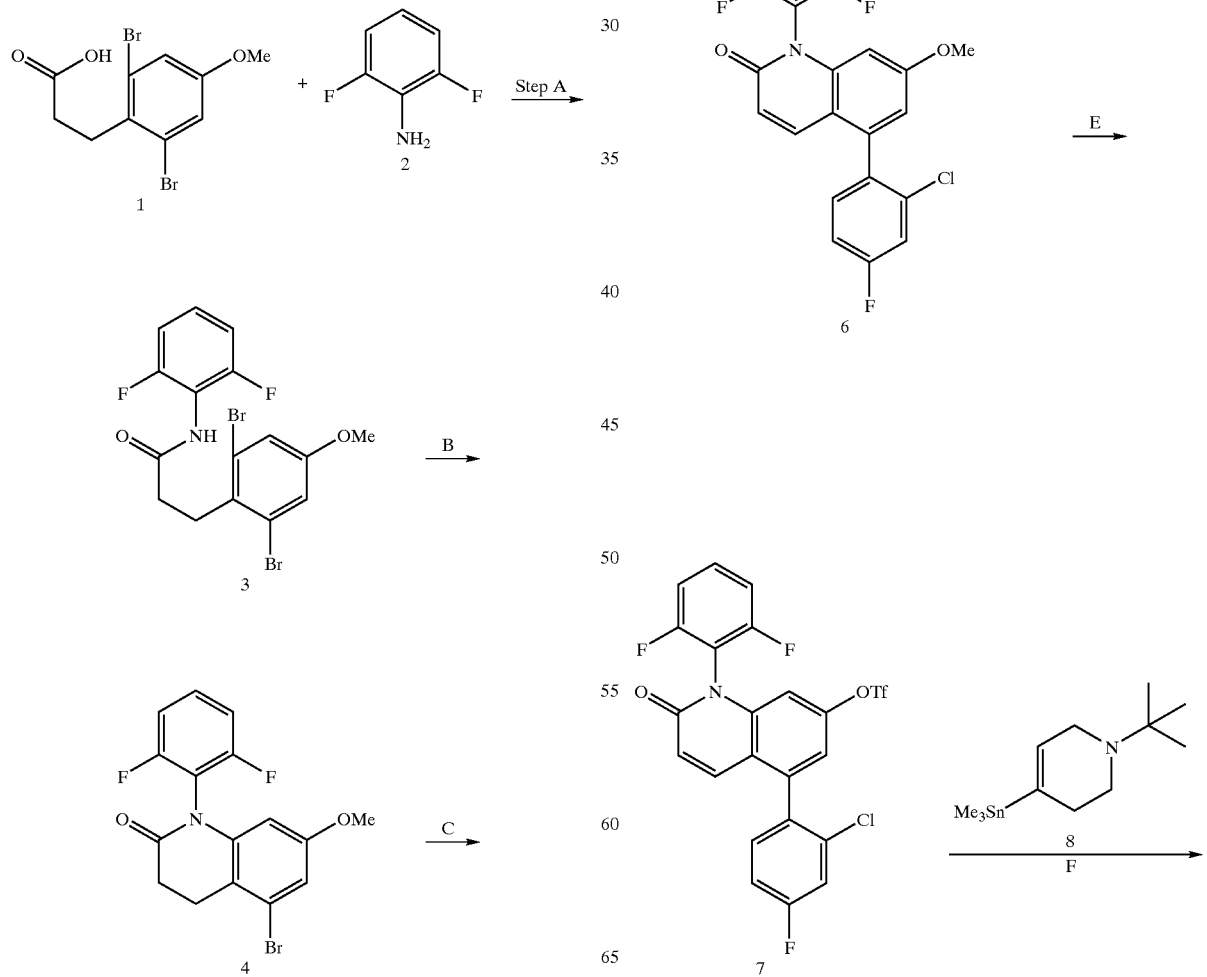

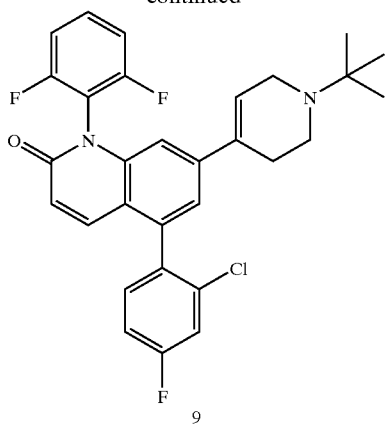

9

G | H2/PtO2

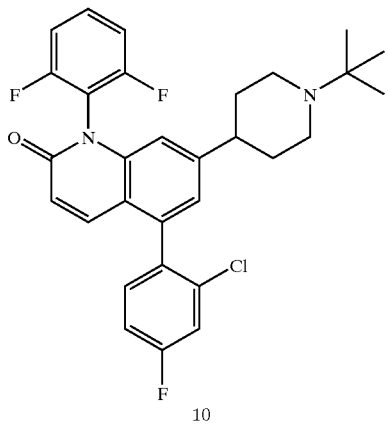

10

Step A: A solution of 1 (0.532 mg, 1.52 mmol), in 20 mL of CH$_2$Cl$_2$ was added oxalyl bromide (0.84 mL as 2M solution) at −78° C. and the DMF (0.91 mmol, 0.071 mL). The solution was allowed to warmed to rt for 1 h and ethyl diisopropyl amine (1.82 mmol, 0.318 mL) and 2,6-difluoroaniline (1.52 mmol, 0.164 mL) was added. The solution was stirred at rt for 4 h and white solid was collected by filtering as 3.

Step B: Compound 1 (5.16 g, 11.5 mmol), K$_2$CO$_3$ (4.76 g, 34.5 mmol) and CuI (1.44 mmol, 7.6 mmol) in 115 mL of DMF was heated at 140° C. for 2.2 h and DMF was removed by vacuum. The residue was dissolved in EtOAc and the solution was washed with brine, dried with Na$_2$SO$_4$ and filtered through celite. Upon removal of solvent, the residue was purified by EtOAc/Hex=1:4 to give 4 as a solid. Mass spectrum (ESI) 368 (M+1):

Step C: A solution of 4 (1.02 g, 2.76 mmol), 2-Cl-4-F boronic acid (0.77 g, 4.42 mmol), Pd(PPh$_3$)4 (0.16 g, 0.14 mmol) and Na$_2$CO$_3$ (4.42 mmol, as 2M solotion) in 5 mL of toluene was added EtOH (5 mL) and water (2 mL). The solution was purged with N$_2$ and was heated to 102° C. for 6 h. It was then poured into ether and washed with NaHCO$_3$ (1×), brine (1×), and dried with Na$_2$SO$_4$. The residue was purified by EtOAc/Hex=1:6 to 1:4 to give 5 as a solid. Mass spectrum (ESI) 418 (M+1).

Step D: A solution of 5 (1.12 g, 2.68 mmol), NBS (0.50 g, 2.81 mmol) and benzoyl peroxide (0.071 g, 0.29 mmol) in 60 mL of CCl$_4$ was heated to reflux under IR lamp for 30 min. Solvent was removed and the residue was purified by flash chromatography with EtOAc/hex=1:3 to give 6. Mass spectrum (ESI) for 6, 416 (+1).

Step E:. A solution of 6 (1.10 g, 2.68 mmol) in 16 mL of CH$_2$Cl$_2$ was added BBr$_3$ (10.7 mmol, as 1M solution) and was stirred at rt for 4 h. It was poured in EtOAc and washed with pH=7 buffer solution. The organic layer was dried with Na$_2$SO$_4$, filtered and concentrated to give a white solid. The solid was dissolved in 30 mL of CH$_2$Cl$_2$ and was added Et$_3$N (1.49 mL) and 2-[N,N-bis(trifluoromethylsulfonyl)amino]-5-chloropyridine (1.58 g, 4.02 mmol). After 40 min, volatiles were removed and the residue was purified by flash chromatography with EtOAc/hex=1:4 to give 7. Mass spectrum (EST) for 7, 534 (M+1).

Step F: A solution of 7 (0.912 g, 1.71 mmol), 8 (0.72 g, 2.39 mmol), LiCl (0.29 g, 6.84 mmol) and Pd(PPh$_3$)4 (0.20 g, 0.17 mmol) in 30 mL of 1,4-dioxane was heated at 108° C. under N$_2$ for 20 h. Upon removal of solvent, it was dissolved in EtOAc and was washed with NaHCO$_3$ (1×). The organic layer was dried with Na$_2$SO$_4$, filtered and concentrated. The residue was purified by flash chromatography with Hex/EtOAc/2N NH$_3$ in MeOH=100:10:2 give 9. Mass spectrum (ESI) for 9, 523(M+1).

Step G: A solution of 9 (0.674 g, 1.20 mmol as HCl salt) in 20 mL of EtOAc was added 2.5 mL of MeOH and PtO$_2$ (0.27 g). The solution was hydrogenated on Parr shaker at 3 psi for 20 min and was added 4 mL of 2N NH$_3$ in MeOH. The mixture was filtered through Celite and the residue was purified by flash chromatography with Hex/EtOAc/2N NH$_3$ in MeOH=100:10:2 give 10 (EXAMPLE PPP1). Mass spectrum (ESI) for 10, 525 (M+1).

EXAMPLE PPP2

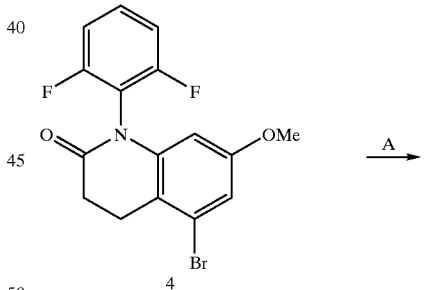

4

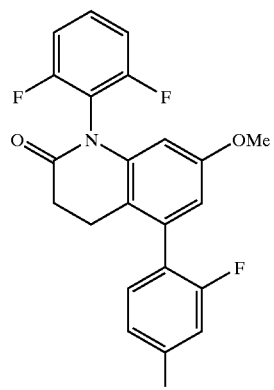

11

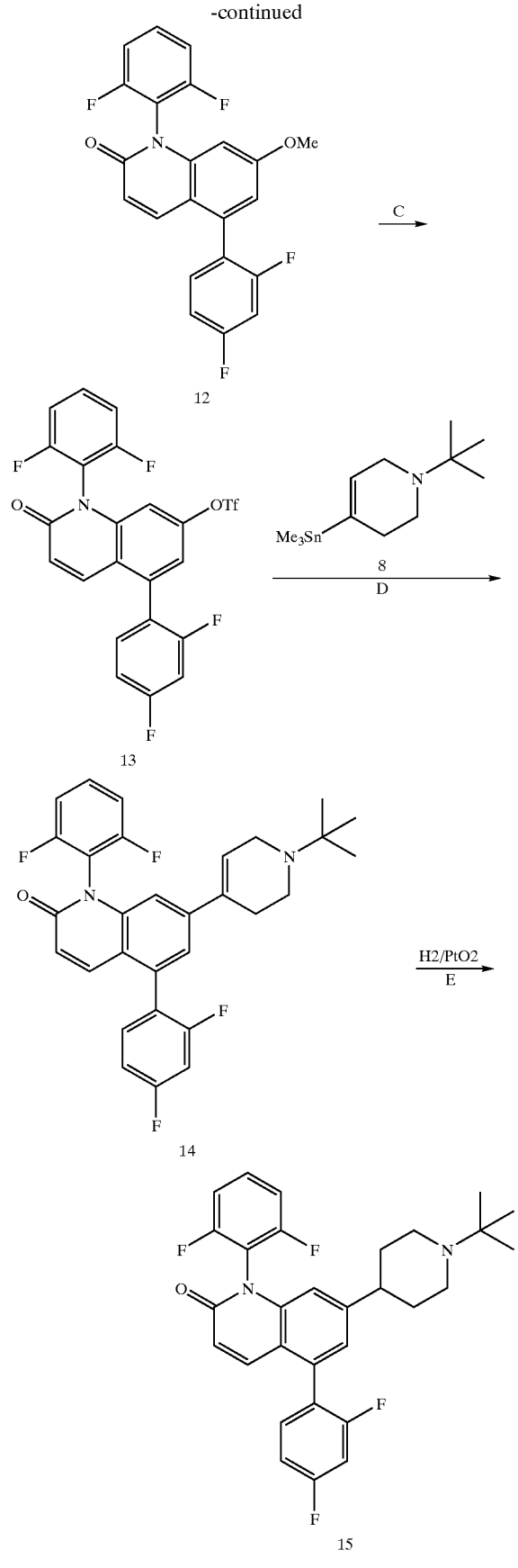

Step A: The compound 11 was prepared as described in Step C of EXAMPLE PPP1 except that 2,4-difluorophenylboronic acid was used instead of 2-chloro-4-fluorophenylboronic acid. Mass spectrum (ESI), 402 (M+1).

Step B: Compound 11 was converted to 12 using the conditions described in Step D of EXAMPLE PPP1. Mass spectrum (ESI), 400 (M+1).

Step C: Compound 12 was converted to 13 using the conditions described in Step E of EXAMPLE PPP1. Mass spectrum (ESI), 518 (M+1).

Step D: Compound 13 was converted to 14 using the conditions described in Step F of EXAMPLE PPP1. Mass Spectrum (ESI), 507 (M+1)

Step E: Compound 14 was converted to 15 (EXAMPLE PPP2) using the conditions described in Step G of EXAMPLE PPP1. Mass Spectrum (ESI), 509 (M+1)

EXAMPLE PPP3

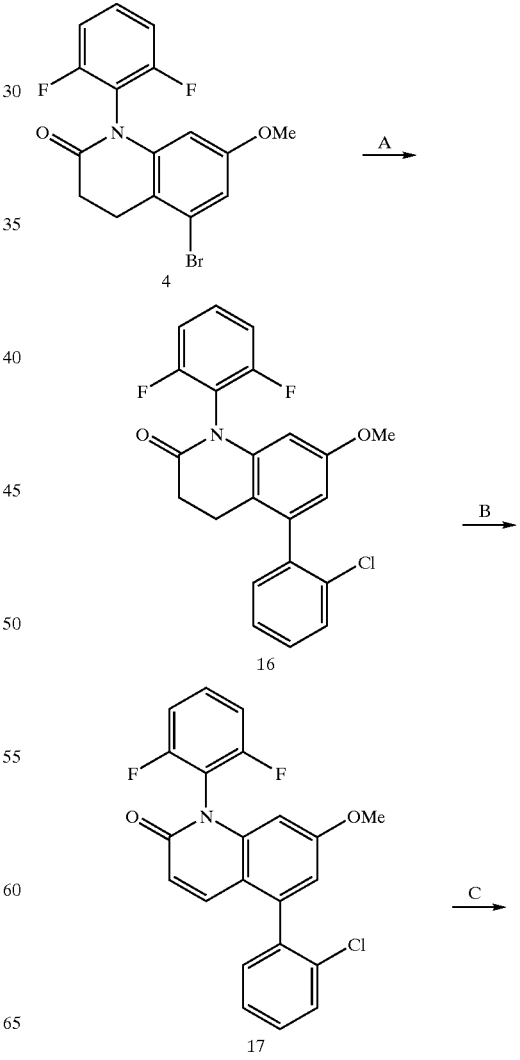

-continued

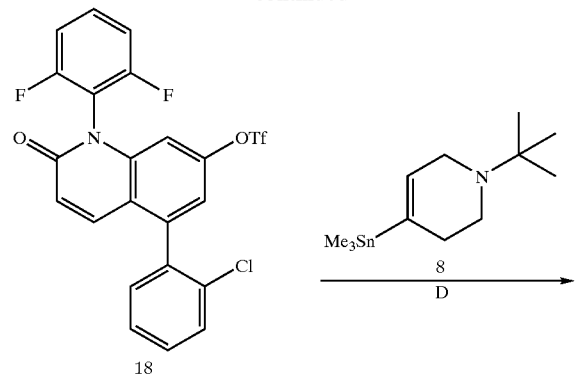

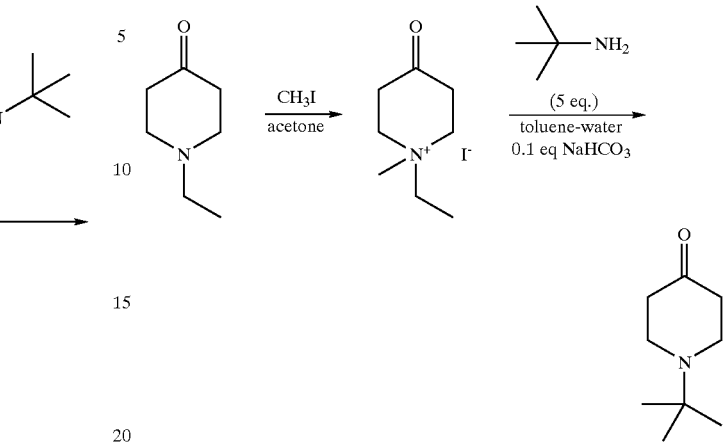

Step A: The compound 16 was prepared as described in Step C of EXAMPLE PPP1 except that 2chlorophenylboronic acid was used instead of 2-chloro-4-fluorophenylboronic acid. Mass spectrum (ESI), 400 (M+1).

Step B: Compound 16 was converted to 17 using the conditions described in Step D of EXAMPLE PPP1. Mass spectrum (ESI), 398 (M+1).

Step C: Compound 17 was converted to 18 using the conditions described in Step E of EXAMPLE PPP1. Mass spectrum (ESI), 516 (M+1).

Step D: Compound 18 was converted to 19 using the conditions described in Step F of EXAMPLE PPP1. Mass Spectrum (ESI), 505 (M+1)

Step E: Compound 19 was converted to 20 (EXAMPLE PPP3) using the conditions described in Step G of EXAMPLE PPP1. Mass Spectrum (ESI), 507 (M+1)

COMPOUND PPA-1
1-tert-Butyl-4-Oxopiperidine

Step A: 1-Ethyl-1-Methyl-4-Oxopiperidinium Iodide

A solution of 100 g (0.789 mol) of 1-ethyl-4-oxopiperidine in 1000 mL of acetone was stirred at rt in a water bath. To this was added 62.2 mL (142 g, 1 mol) of methyl iodide, dropwise at such a rate to keep the temperature below 30 degrees. A precipitate developed within minutes and the mixture was stirred at rt for 4 h. The mixture was filtered and the precipitate washed with acetone and dried to afford the title compound as a white solid. Mass spectrum (ESI) 142 (M+).

Step B 1-tert-Butyl-4-Oxopiperidine

To a solution of 137 mL (1.3 moles) of tert-butylamine in 700 mL of toluene was added solution of 70 g (0.260 moles) of 1-ethyl-1-methyl-4-oxopiperidinium iodide and 2.18 g (0.026 moles) of $NaHCO_3$ in 100 mL of water. The mixture was stirred at 78° C. for 6 h. After it had cooled to rt, the layers were separated and the aq layer was washed with three 200 mL portions of ethyl acetate. The combined organic layers were washed with brine, dried ($MgSO_4$), and concentrated to an oil that purified by distillation under reduced pressure. Fractions distilling at 72° C. at 3 mm were collected to afford the title compound as a colorless liquid. $^1$H NM($CDCl_3$, 500 MHz): δ 1.15 (s, 9H), 2.45 (t, 4H, J=6.1 Hz), 2.86 (t, 4H, J=6.1H); Mass spectrum (ESI) 156 (M+1).

COMPOUND PPA-2
1-tert-butyl-4-(trimethylstannyl)-1,2,3,6-tetrahydropyridine

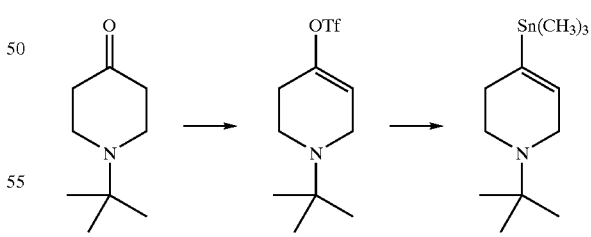

Step A: 1-tert-Butyl-4-Trifluoromethanesulfonlyoxy-1,2,3,6-tetrahydropyridine

A solution of 8.0 g (52 mmol) of 1-tert-butyl-4-oxopiperidine in 60 mL of anhydrous tetrahydrofuran was cooled to −78° C. under $N_2$. To this was added 72 mL of a 1M solution of lithium hexamethyldisilamide. The solution was stirred at −78° C. for 10 min, warmed to 0° C. for 30 min, and then re-cooled to −78° C. To this was added 28.3 g (72 mmol) of 2-[N,N-bis(trifluoromethylsulfonyl)amino]-

5-chloropyridine and the solution was stirred at −30° C. for 2 h. The reaction was quenched by addition of 10 mL saturated NaHCO$_3$ and the solution was concentrated under vacuum. The residue was dissolved in 200 mL ether, washed with 50 mL portions of saturated NaHCO$_3$ solution and brine, dried over Na$_2$SO$_4$, and concentrated. That residue was applied to a Biotage 65 silica gel column that had been pre-treated with 30 mL triethylamine before equilibration with ethyl acetate-hexane-triethylamine, 500:50:1. The column was eluted with the same mixture and homogeneous fractions were pooled and concentrated to give the title compound as a colorless liquid. $^1$H NMR(CDCl$_3$, 500 MHz): δ 1.154(s, 9H), 2.45 (m, 2H), 2.78 (t, 2H, J=5.4H), 3.28 (m, 2H), 5.76 (m, 1H).

Step B: 1-tert-butyl-4-(trimethylstannyl)-1,2,3,6-tetrahydropyridine

A solution of 10.36 g (36.1 mmol) of 1-tert-butyl-4-trifluoromethanesulfonlyoxy-1,2,3,6-tetrahydropyridine, 15.4 g (46.9 mmol) of hexamethylditin, 6.1 g (145 mmol) of LiCl, and 2.1 g (1.8 mmol) tetrakis(triphenylphosphine)palladium in 120 mL of anhydrous THF was purged with Ar. After 15 min, the mixture was heated at reflux (84° C.) for 4 h. The black solution was diluted with 300 mL ether and washed with saturated KHCO$_3$ solution, and brine, dried over Na$_2$SO$_4$, filtered, and concentrated. That residue was applied to a Biotage 65 silica gel column that had been pre-treated with 30 mL triethylamine before equilibration with ethyl acetate-hexane-triethylamine, 500:50:1. The column was eluted with the same mixture and homogeneous fractions were pooled and concentrated to give the title compound as a pale yellow liquid. $^1$H NMR(CDCl$_3$, 500 MHz): δ 0.06–0.16 (m, 9H), 1.11(s, 9H), 2.35 (m, 2H), 2.64 (t, 2H, J=5.5H), 3.20 (m, 2H), 5.85 (m, 1H).

COMPOUND PPA-3

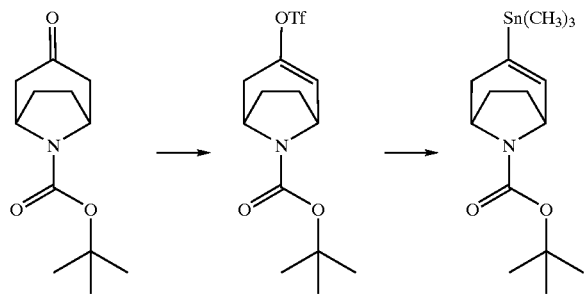

Step A: 8-t-Butoxycarbonyl-3-(trinfluoromethansulfonyloxy)-8-azabicyclo[3.2.1]oct-2-ene The N-t-butoxycarobonylnortropanone was converted to the corresponding triflate using the conditions described in Part A of COMPOUND PPA-2. $^1$H NMR(CDCl$_3$, 500 MHz): δ 1.15(s, 9H), 1.75 (m, 1H), 1.99–2.3 (m, 4H), 2.9–3.2 (m, 1H), 4.48 (m, 2H), 6.11 (s, 1H).

Step B: 8-t-Butoxycarbonyl-3-(trimethylstannyl)-8-azabicyclo[3.2.1]oct-2-ene

The 8-t-Butoxycarbonyl-3-(trifluoromethansulfonyloxy)-8-azabicyclo[3.2.1]oct-2-ene was converted to the corresponding trimethylstannyl analog using the conditions described in Part B of COMPOUND PPA-2. $^1$H NMR (CDCl$_3$, 500 MHz): δ 0.06–0.16 (m, 9H), 1.47(s, 9H), 1.68 (m, 1H), 1.87–2.0 (m, 3H), 2.18 (m, 1H), 2.8–3.0 (m, 1H), 4.19–3.32 (m, 2H), 6.14 (m, 1H).

INTERMEDIATE AAA1

5-(2-chlorophenyl)-1-(2,6-dichlorophenyl)-2-oxo-1,2,3,4-tetrahydroquinazoline-7-carbaldehyde

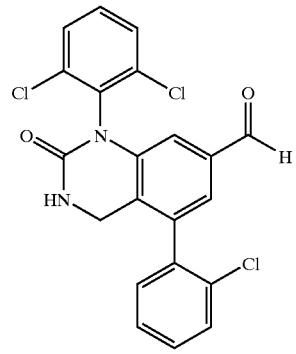

STEP A: 5-(2-chlorophenyl)-1-(2,6-dichlorophenyl)-7-(hydroxymethyl)-3,4-dihydroquinazolin-2(1H)-one To a stirred solution of methyl 5-(2-chlorophenyl)-1-(2,6-dichlorophenyl)-2-oxo-1,2,3,4-tetrahydroquinazoline-7-carboxylate (INTERMEDIATE 32) (8.23 g) in THF (140 mL) was added lithium aluminum hydride (14 mL of a 1.0M solution in THF) and the mixture was let stir 1.5 h. More lithium aluminum hydride (4.5 mL of a 1.0M solution in THF) was added and the mixture was stirred overnight. Another portion of lithium aluminum hydride (4.5 mL of a 1.0M solution in THF) was added and stirred 4 h. The reaction was carefully poured into a flask containing 1N aqueous HCl (500 mL) and stirred. To the mixture was added ethyl acetate (500 mL) and the layers were mixed, then separated. The organic layer was washed with brine (300 mL), dried over anhydrous MgSO$_4$, filtered and concentrated. The resulting solid was triturated with hexanes, then CH$_2$Cl$_2$ to give the 5-(2-chlorophenyl)-1-(2,6-dichlorophenyl)-7-(hydroxymethyl)-3,4-dihydroquinazolin-2(1H)-one compound.

STEP B: 5-(2-chlorophenyl)-1-(2,6-dichlorophenyl)-2-oxo-1,2,3,4-tetrahydroquinazoline-7-carbaldehyde To a suspension of 5-(2-chlorophenyl)-1-(2,6-dichlorophenyl)-7-(hydroxymethyl)-3,4-dihydroquinazolin-2(1H)-one (780 mg, 1.8 mmol) in methylene chloride (15 mL) was added 4-methylmorpholine N-oxide (316 mg, 2.7 mmol). To the resulting clear solution was added molecular sieves (900 mg) followed by tetrapropylammonium perruthenate (32 mg, 0.09 mmol). The resulting mixture was stirred at rt for 2 h. The mixture was then filtered through silica gel eluting with ethyl acetate. Removal of the solvent and subsequent purification by flash chromatography using 25% acetone/hexane provided 5-(2-chlorophenyl)-1-(2,6-dichlorophenyl)-2-oxo-1,2,3,4-tetrahydroquinazoline-7-carbaldehyde as a white solid. $^1$H NMR (CDCl$_3$, 500 MHz): δ 4.43 (abq, 2H, J=15.5 Hz), 5.37 (s, 1H), 6.66 (s, 1H), 7.30–7.60 (m, 8H), 9.85 (s, 1).

EXAMPLE AAA1

5-(2-chlorophenyl)-1-(2,6-dichlorophenyl)-7-[(2-methylpiperazin-1-yl)methyl]-3,4-dihydroquinazolin-2(1H)-one

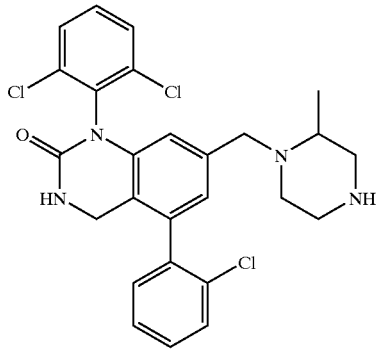

STEP A: tert-butyl 4-{[5-(2-chlorophenyl)-1-(2,6-dichlorophenyl)-2-oxo-1,2,3,4-tetrahydroquinazolin-7-yl]methyl}-3-methylpiperazine-1-carboxylate A solution of 5-(2-chlorophenyl)-1-(2,6-dichlorophenyl)-2-oxo-1,2,3,4-tetrahydroquinazoline-7-carbaldehyde (Intermediate AAA1, 208 mg, 0.48 mmol) and 1-BOC-3-methylpiperazine (96 mg, 0.48 mmol) in dichloroethane (5 mL) was stirred at rt for 30 min. To this was added sodium triacetoxyborohydride (150 mg, 0.67 mmol) followed by acetic acid (29 mg, 0.48 mmol). The resulting reaction mixture was stirred at rt for 20 h. The reaction was quenched with 2N NaOH solution (6 mL) followed by extraction with ethyl acetate (100 mL×2). The organic layer was washed with brine and dried over anhydrous sodium sulfate. Removal of the solvent and subsequent purification by flash chromatography using 25% acetone/hexane provided tert-butyl 4-{[5-(2-chlorophenyl)-1-(2,6-dichlorophenyl)-2-oxo-1,2,3,4-tetrahydroquinazolin-7-yl]methyl}-3-methylpiperazine-1-carboxylate as a white solid. $^1$H NMR (CDCl$_3$, 500 MHz): δ 0.98 (s, 3H), 1.46 (s, 9H), 2.06 (brs, 1H), 2.39 (brs, 1H), 2.60 (brs, 1H), 2.82 (brs, 1H), 3.05 (brs, 1H), 3.15 (m, 1H), 3.54 (brs, 2H), 3.82 (brs, 1H), 4.34 (abq, 2H, J=14.2 Hz), 5.15 (s, 1H), 6.16 (d, 1H, J=5.2 Hz), 6.88 (s, 1H), 7.20–7.60 (m, 7H). MS (API-ES+): 617 (M+H).

STEP B: 5-(2-chlorophenyl)-1-(2,6-dichlorophenyl)-7-[(2-methylpitprazin-1-yl)methyl]-3,4-dihydroquinazolin-2(1H)-one To a solution of tert-butyl 4-{[5-(2-chlorophenyl)-1-(2,6-dichlorophenyl)-2-oxo-1,2,3,4-tetrahydroquinazolin-7-yl]methyl}-3-methylpiperazine-1-carboxylate (186 mg, 0.30 mmol) in methylene chloride (1 mL) at 0° C. was added trifluoroacetic acid (0.92 mL) dropwise. Then the reaction was stirred at rt for 1 h. Removal of the solvent and subsequent purification by preparative thin layer chromatography using 8% of 2N ammonium in methanol/methylene chloride as eluent provided the 5-(2-chlorophenyl)-1-(2,6-dichlorophenyl)-7-[(2-methylpiperazin-1-yl)methyl]-3,4-dihydroquinazolin-2(1H)-one compound. $^1$H NMR (CDCl$_3$, 500 MHz): δ 0.98 (m, 3H), 2.06 (m, 2H), 2.32 (s, 1H), 2.48 (m, 1H), 2.63 (m, 1H), 2.72 (t, 1H, J=10.2 Hz), 2.84 (m, 2H), 3.15 (dd, 1H, J$_1$=14.0 Hz, J$_2$=6.0 Hz), 3.86 (t, 1H, J=13.2 Hz), 4.34 (abq, 2H, J=14.2 Hz), 5.23 (s, 1H), 6.15 (d, 1H, J=9.4 Hz), 6.88 (s, 1H), 7.20–7.60 (m, 7H). MS (API-ES+): 517 (M+H).

EXAMPLE AAA2

5-(2-chlorophenyl)-1-(2,6-dichlorophenyl)-7-[(4-isopropyl-2-methylpiperazin-1-yl)methyl]-3,4-dihydroquinazolin-2(1H)-one

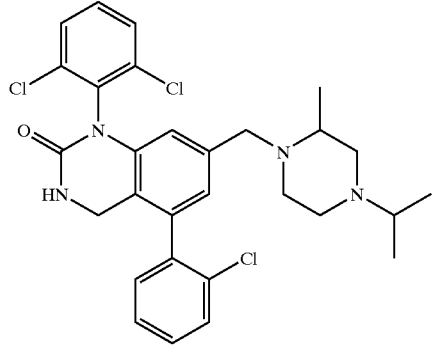

The title compound was prepared from 5-(2-chlorophenyl)-1-(2,6-dichlorophenyl)-7-[(2-methylpiperazin-1-yl)methyl]-3,4-dihydroquinazolin-2(1H)-one (EXAMPLE AAA1) and acetone as described in EXAMPLE AAA1, STEP A. $^1$H NMR (CDCl$_3$, 500 MHz): δ 1.00 (s, 9H), 1.40 (brs, 1H), 1.60 (brs, 1H), 2.20 (brs, 2H), 2.40 (brs, 1H), 2.65 (brs, 3H), 3.15 (brs, 1H), 3.90 (brs, 1H), 4.34 (abq, 2H, J=14.4 Hz), 5.00 (s, 1H), 6.13 (brs, 1H), 6.89 (s, 1H), 7.30–7.60 (m, 7H). MS (API-ES+): 559 (M+H).

EXAMPLE AAA3

5-(2-chlorophenyl)-1-(2,6-dichlorophenyl)-7-{[(1S,4S)-5-isopropyl-2,5-diazabicyclo[2.2.1]hept-2-yl]methyl}-3,4-dihydroquinazolin-2(1H)-one

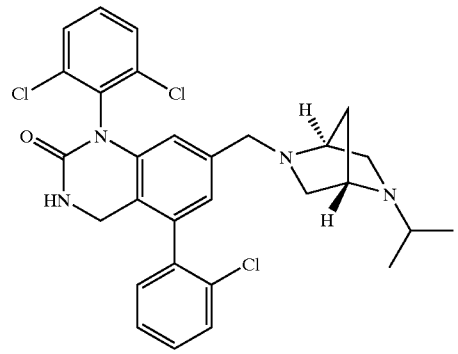

The title compound was prepared from 5-(2-chlorophenyl)-7-[(1R,4S)-2,5-diazabicyclo[2.2.1]hept-2-ylmethyl]-1-(2,6-dichlorophenyl)-3,4-dihydroquinazolin-2(1H)-one (EXAMPLE 66) and acetone as described in EXAMPLE AAA1, STEP A. $^1$H NMR (CDCl$_3$, 500 MHz): δ 1.06 (m, 6H), 2.42 (m, 2H), 2.57 (brs, 1H), 2.86 (brs, 2H), 3.17 (brs, 1H), 3.55 (t, 2H, J=13.5 Hz), 3.66 (t, 1H, J=13.5 Hz), 4.34 (abq, 2H, J=14.4 Hz), 5.04 (s, 1H), 6.24 (s, 1H), 6.87 (s, 6.87 (s, 1H), 7.30–7.60 (m, 7H). MS (API-ES+): 557 (M+H).

EXAMPLE AAA4
5-(2-chlorophenyl)-1-(2,6-dichlorophenyl)-7-[(3-methylpiperazin-1-yl)methyl]-3,4-dihydroquinazolin-2(1H)-one

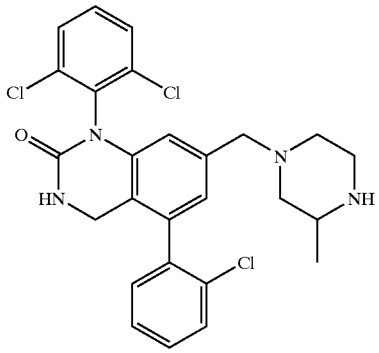

STEP A: benzyl 4-{[5-(2-chlorophenyl)-1-(2,6-dichlorophenyl)-2-oxo-1,2,3,4-tetrahydroquinazolin-7-yl]methyl}-2-methylpiperazine-1-carboxylate The benzyl 4-{[5-(2-chlorophenyl)-1-(2,6-dichlorophenyl)-2-oxo-1,2,3,4-tetrahydroquinazolin-7-yl]methyl}-2-methylpiperazine-1-carboxylate was prepared from 5-(2-chlorophenyl)-1-(2,6-dichlorophenyl)-2-oxo-1,2,3,4-tetrahydroquinazoline-7-carbaldehyde (INTERMEDIATE AAA1) and 1-CBz-2-methylpiperazine as described in EXAMPLE AAA1, STEP A. $^1$H NMR (CDCl$_3$, 500 MHz): δ 1.08 (d, 3H, J=5.9 Hz), 2.00 (m, 1H), 2.10 (m, 1H), 2.52 (d, 1H, J=11.0 Hz), 2.70 (m, 1H), 3.06 (m, 1H), 3.26 (m, 1H), 3.46 (m, 1H), 3.86 (d, 1H, J=12.5 Hz), 4.24.5 (m, 3H), 5.05 (s, 1H), 5.14 (abq, 2H, J=12.4 Hz), 6.25 (d, 1H, J=13.3 Hz), 6.82 (s, 1H), 7.30–7.60 (m, 12H). MS (API-ES+): 651 (M+H).

STEP B: 5-(2-chlorophenyl)-1-(2,6-dichlorophenyl)-7-[(3-methylpiperazin-1-yl)methyl]-3,4-dihydroquinazolin-2(1H)-one To a solution of benzyl 4-{[5-(2-chlorophenyl)-1-(2,6-dichlorophenyl)-2-oxo-1,2,3,4-tetrahydroquinazolin-7-yl]methyl}-2-methylpiperazine-1-carboxylate (105 mg, 0.16 mmol) in methylene chloride (2 mL) at 0° C. was added 30% HBr/HOAc (0.32 mL, 1.62 mmol) slowly. The resulting reaction mixture was stirred at 0° C. for 30 min, and then at rt for 30 min. The reaction was quenched with water, then added 5N NaOH solution to pH ~1, and extracted with methylene chloride (50 mL×3) and ethyl acetate (50 mL×2). The organic layer was washed with brine and dried over anhydrous sodium sulfate. Removal of the solvent and subsequent purification by preparative thin layer chromatography using 8% of 2N ammonium in methanol/methylene chloride as eluent provided 5-(2-chlorophenyl)-1-(2,6-dichlorophenyl)-7-[(3-methylpiperazin-1-yl)methyl]-3,4-dihydroquinazolin-2(1H)-one as a white solid. $^1$H NMR (CDCl$_3$, 500 MHz): δ 1.06 (d, 3H, J=4.8 Hz), 1.72 (m, 1H), 2.06 (m, 1H), 2.69 (m, 2H), 2.82 (t, 2H, J=9.3 Hz), 2.98 (d, 1H, J=11.9 Hz), 3.40 (m, 2H), 4.34 (abq, 2H, J=14.4 Hz), 5.10 (s, 1H), 6.17 (s, 1H), 6.84 (s, 1H), 7.30–7.60 (m, 7H). MS (API-ES+): 517 (M+H).

EXAMPLE AAA5
5-(2-chlorophenyl)-1-(2,6-dichlorophenyl)-7-[(4-isopropyl-3-methylpiperazin-1-yl)methyl]-3,4-dihydroquinazolin-2(1H)-one

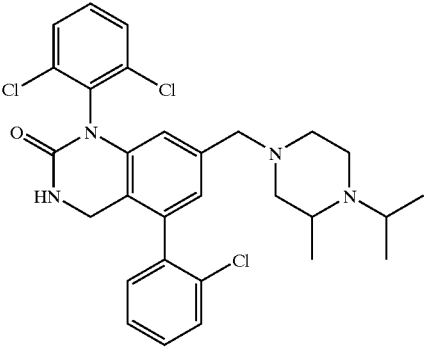

The title compound was prepared from 5-(2-chlorophenyl)-1-(2,6-dichlorophenyl)-2-oxo-1,2,3,4-tetrahydroquinazoline-7-carbaldehyde (INTERMEDIATE AAA1) and 1-isopropyl-2-methylpiperazine as described in EXAMPLE AAA1, STEP A. $^1$H NMR (CDCl$_3$, 500 MHz): δ 0.90 (brs, 3H), 0.93 (brs, 3H), 0.98 (brs, 3H), 1.92 (brs, 1H), 2.16 (brs, 1H), 2.31 (brs, 1H), 2.57 (m, 2H), 2.67 (brs, 1H), 3.21 (brs, 1H), 3.40 (s, 2H), 4.22–4.485 (m, 2H), 5.05 (s, 1H), 6.17 (s, 1H), 6.85 (d, 1H, J=3.7 Hz), 7.30–7.60 (m, 7H). MS (API-ES+): 559 (M+H).

EXAMPLE AAA6
5-(2-chlorophenyl)-1-(2,6-dichlorophenyl)-7-({4-[2-dimethylamino)piperazin-1-yl}methyl)-3,4-dihydroquinazolin-2(1H)-one

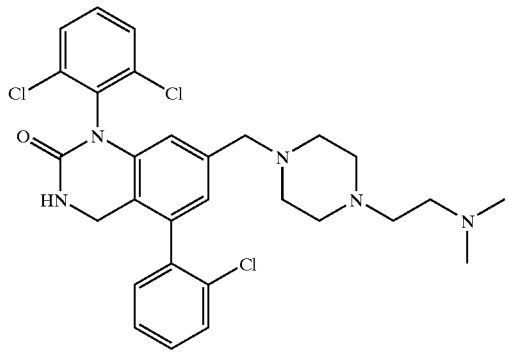

The title compound was prepared from 5-(2-chlorophenyl)-1-(2,6-dichlorophenyl)-2-oxo-1,2,3,4-tetrahydroquinazoline-7-carbaldehyde (INTERMEDIATE AAA1) and 1-(2-dimethylaminoethyl)-piperazine as described in EXAMPLE AAA1, STEP A. $^1$H NMR (CDCl$_3$, 500 MHz): δ 2.30 (s, 6H), 2.46 (m, 12H), 3.40 (abq, 2H, J=14.0 Hz), 4.34 (abq, 2H, J=14.4 Hz), 5.06 (s, 1H), 6.15 (s, 1H), 6.86 (s, 1H), 7.30–7.60 (m, 7H). MS (API-ES+): 574 (M+H).

EXAMPLE AAA7

5-(2-chlorophenyl)-1-(2,6-dichlorophenyl)-7-{[4-(2-pyrrolidin-1-ylethyl)piperidin-1-yl]methyl}-3,4-dihydroquinazolin-2(1H)-one

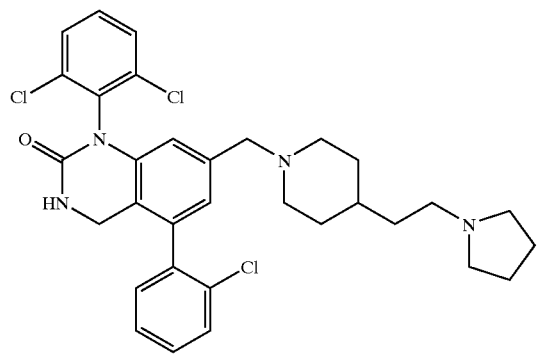

The title compound was prepared from 5-(2-chlorophenyl)-1-(2,6-dichlorophenyl)-2-oxo-1,2,3,4-tetrahydroquinazoline-7-carbaldehyde (INTERMEDIATE AAA1) and 4-(2-pyrrolidinoethyl)-piperidin as described in EXAMPLE AAA1, STEP A. $^1$H NMR (CDCl$_3$, 500 MHz): δ 1.18 (m, 2H), 1.28 (m, 1H), 1.61 (m, 6H), 1.88 (m, 6H), 2.56 (brs, 4H), 2.76 (m, 2H), 3.38 (s, 2H), 4.34 (abq, 2H, J=14.4 Hz), 4.98 (s, 1H), 6.15 (s, 1H), 6.86 (s, 1H), 7.30–7.58 (m, 7H). MS (API-ES+): 599 (M+H).

EXAMPLE AAA8

5-(2-chlorophenyl)-1-(2,6-dichlorophenyl)-7-[(4-isopropylpiperazin-1-yl)methyl]-3,4-dihydroquinazolin-2(1H)-one

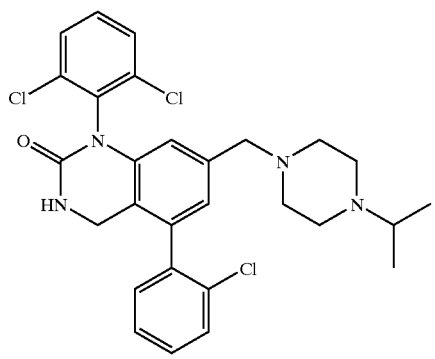

The title compound was prepared from 5-(2-chlorophenyl)-1-(2,6-dichlorophenyl)-2-oxo-1,2,3,4-tetrahydroquinazoline-7-carbaldehyde (INTERMEDIATE AAA1) and 1-isopropylpiperazine as described in EXAMPLE AAA1, STEP A. $^1$H NMR (CDCl$_3$, 500 MHz): δ 1.06 (s, 6H), 2.48 (brs, 8H), 2.65 (brs, 1H), 3.41 (abq, 2H, J=13.9 Hz), 4.34 (abq, 2H, J=14.4 Hz), 5.08 (s, 1H), 6.16 (s, 1H), 6.87 (s, 1H), 7.30–7.56 (m, 7H). MS (API-ES+): 545 (M+H).

EXAMPLE AAA9

5-(2-chlorophenyl)-1-(2,6-dichlorophenyl)-7-{[4-(2-pyrrolidin-1-ylethyl)piperazin-1-yl]methyl}-3,4-dihydroquinazolin-2(1H)-one

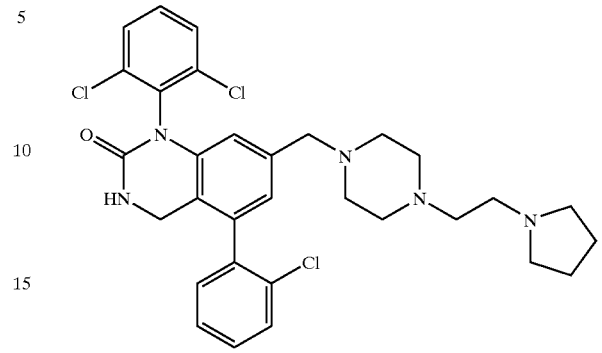

The title compound was prepared from 5-(2-chlorophenyl)-1-(2,6-dichlorophenyl)-2-oxo-1,2,3,4-tetrahydroquinazoline-7-carbaldehyde (INTERMEDIATE AAA1) and 1-(2-pyrrolidinoethyl)-piperazine as described in EXAMPLE AAA1, STEP A. $^1$H NMR (CDCl$_3$, 500 MHz): δ 1.81 (s, 4H), 2.42 (brs, 8H), 2.56 (m, 6H), 2.64 (m, 2H), 3.40 (abq, 2H, J=13.7 Hz), 4.34 (abq, 2H, J=14.4 Hz), 5.14 (s, 1H), 6.16 (s, 1H), 6.86 (s, 1H), 7.29–7.56 (m, 7H). MS (API-ES+): 598 (M+H).

EXAMPLE AAA10 and EXAMPLE AAA10A tert-butyl 4-{[5-(2-chlorophenyl)-1-(2,6-dichlorophenyl)-2-oxo-1,2,3,4-tetrahydroquinazolin-7-yl]methyl}piperazine-2-carboxylate and tert-butyl 1-allyl-4-{[5-(2-chlorophenyl)-1-(2,6-dichlorophenyl)-2-oxo-1,2,3,4-tetrahydroquinazolin-7-yl]methyl}piperazine-2-carboxylate

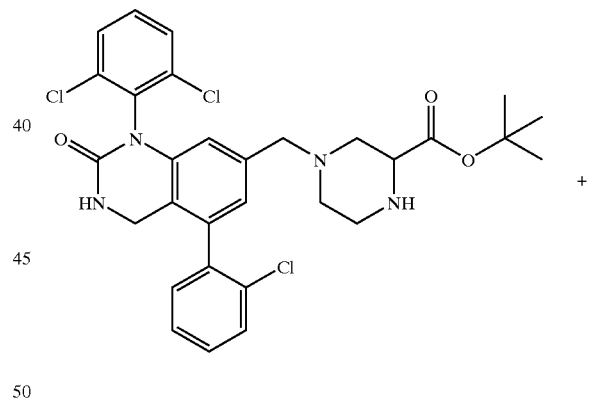

+

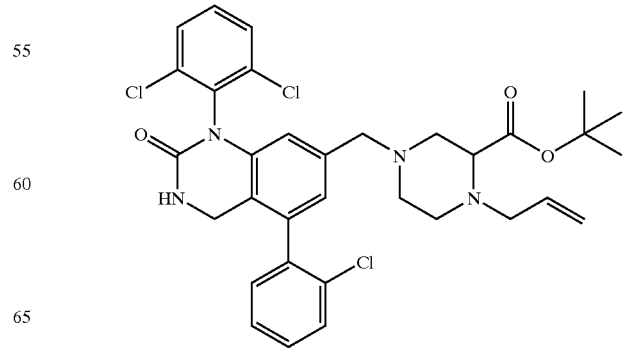

STEP A: 1-allyl 2-tert-butyl 4-{[5-(2-chlorophenyl)-1-(2,6-dichlorophenyl)-2-oxo-1,2,3,4-tetrahydroquinazolin-7-yl]methyl}piperazine-1,2-dicarboxylate The 1-allyl 2-tert-butyl 4-{[5-(2-chlorophenyl)-1-(2,6-dichlorophenyl)-2-oxo-1,2,3,4-tetrahydroquinazolin-7-yl]methyl}piperazine-1,2-dicarboxylate was prepared from 5-(2-chlorophenyl)-1-(2,6-dichlorophenyl)-2-oxo-1,2,3,4-tetrahydroquinazoline-7-carbaldehyde (INTERMEDIATE AAA1) and 1-allyloxycarbonyl-2-t-butyloxycarbonyl piperazine as described in EXAMPLE AAA1, STEP A. $^1$H NMR (CDCl$_3$, 500 MHz): 1.34 (s, 9H), 1.92 (m, 1H), 2.26 (m, 1H), 2.70 (m, 1H), 3.12 (m, 1H), 3.30 (m, 3H), 3.50 (m, 1H), 3.83 (m, 1H), 4.34 (abq, 2H, J=14.4 Hz), 4.54 (m, 1H), 4.62 (brs, 2H), 5.03 (s, 1H), 5.16–5.36 (m, 2H), 5.93 (brs, 1H), 6.11 (s, 1H), 6.85 (d, 1H, J=10.1 Hz), 7.32–7.56 (m, 7H). MS (API-ES+): 687 (M+H).

STEP B: tert-butyl 4-{[5-(2-chlorophenyl)-1-(2,6-dichlorophenyl)-2-oxo-1,2,3,4-tetrahydroquinazolin-7-yl]methyl}piperazine-2-carboxylate and tert-butyl 1-allyl-4-{[5-(2-chlorophenyl)-1-(2,6-dichlorophenyl)-2-oxo-1,2,3,4-tetrahydroquinazolin-7-yl]methyl}piperazine-2-carboxylate To a mixture of 1-allyl 2-tert-butyl 4-{[5-(2-chlorophenyl)-1-(2,6-dichlorophenyl)-2-oxo-1,2,3,4-tetrahydroquinazolin-7-yl]methyl}piperazine-1,2-dicarboxylate (EXAMPLE AAA10, STEP A, 200 mg, 0.29 mmol) and dichlorobis(triphenylphosphine)palladium(II) (10.2 mg, 0.0146 mL) in methylene chloride (3 mL) was added water (30 μL). To this mixture was added tributyltin hydride (94 μL, 0.348 mmol) rapidly. The mixture was stirred at rt for 5 h, diluted with methylene chloride, washed with water and brine, and dried over anhydrous sodium sulfate. Removal of the solvent and subsequent purification by preparative thin layer chromatography using 5% of 2N ammonium in methanol/methylene chloride as eluent provided tert-butyl 4-{[5-(2-chlorophenyl)-1-(2,6-dichlorophenyl)-2-oxo-1,2,3,4-tetrahydroquinazolin-7-yl]methyl}piperazine-2-carboxylate and tert-butyl 1-allyl-4-{[5-(2-chlorophenyl)-1-(2,6-dichlorophenyl)-2-oxo-1,2,3,4-tetrahydroquinazolin-7-yl]methyl}piperazine-2-carboxylate.

tert-butyl 4-{[5-(2-chlorophenyl)-1-(2,6-dichlorophenyl)-2-oxo-1,2,3,4-tetrahydroquinazolin-7-yl]methyl}piperazine-2-carboxylate: $^1$H NMR (CDCl$_3$, 500 MHz): δ .43 (s, 9H), 2.10 (m, 1H), 2.22 (m, 1H), 2.52 (m, 1H), 2.73 (m, 1H), 2.88 (m, 1H), 3.37 (m, 1H), 3.43 (s, 2H), 4.34 (d of abq, 2H, J$_1$=14.4 Hz, J$_2$=6.8 Hz), 5.03 (s, 1H), 6.17 (d, 1H, J=6.4 Hz), 6.85 (d, 1H, J=9.4 Hz), 7.30–7.56 (m, 7H). MS (API-ES+): 603 (M+H).

EXAMPLE AAA10A: tert-butyl 1-allyl-4-{[5-(2-chlorophenyl)-1-(2,6-dichlorophenyl)-2-oxo-1,2,3,4-tetrahydroquinazolin-7-yl]methyl}piperazine-2-carboxylate: $^1$H NMR (CDCl$_3$, 500 MHz): δ 1.40 (s, 9H), 2.27 (m, 1H), 2.40 (m, 2H), 2.54 (m, 1H), 2.64 (m, 1H), 3.02 (m, 3H), 3.37 (m, 3H), 4.25 (dd, 1H, J$_1$=14.4 Hz, J$_2$=5.7 Hz), 4.43 (dd, 1H, J$_1$=14.1 Hz, J$_2$=10.0 Hz), 5.05 (s, 1H), 5.16 (m, 2H), 5.86 (m, 1H), 6.13 (s, 1H), 6.86 (d, 1H, J=5.9 Hz), 7.28–7.58 (m, 7H). MS (API-ES+): 643 (M+H).

EXAMPLE AAA11
tert-butyl 4-{[5-(2-chlorophenyl)-1-(2,6-dichlorophenyl)-2-oxo-1,2,3,4-tetrahydroquinazolin-7-yl]methyl}-1-isopropylpiperazine-2-carboxylate

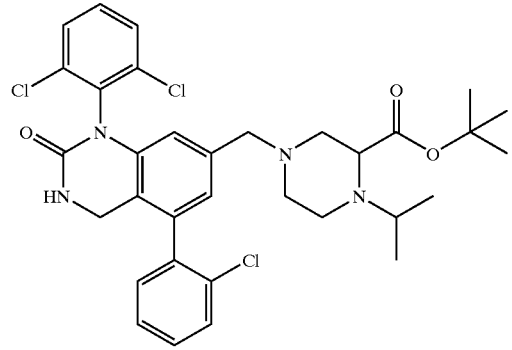

The title compound was prepared from tert-butyl 4-{[5-(2-chlorophenyl)-1-(2,6-dichlorophenyl)-2-oxo-1,2,3,4-tetrahydroquinazolin-7-yl]methyl}piperazine-2-carboxylate (EXAMPLE AAA10) and acetone as described in EXAMPLE AAA1, STEP A. $^1$H NMR (CDCl$_3$, 500 MHz): δ 0.96 (d, 3H, J=6.2 Hz), 1.11 (d, 3H, J=6.4 Hz), 1.41 (s, 9H), 2.42 (m, 3H), 2.53 (m, 1H), 2.62 (m, 1H), 2.86 (m, 1H), 3.03 (m, 1H), 3.28 (m, 1H), 3.38 (m, 2H), 4.25 (dd, 1H, J$_1$=14.4 Hz, J$_2$=5.3 Hz), 4.44 (dd, 1H, J$_1$=14.4 Hz, J$_2$=8.2 Hz), 5.00 (s, 1H), 6.15 (s, 1H), 6.85 (s, 1H) 7.30–7.60 (m, 7H). MS (API-ES+): 645 (M+H).

EXAMPLE AAA12
4-{[5-(2-chlorophenyl)-1-(2,6-dichlorophenyl)-2-oxo-1,2,3,4-tetrahydroquinazolin-7-yl]methyl}-1-isopropylpiperazine-2-carboxylic acid

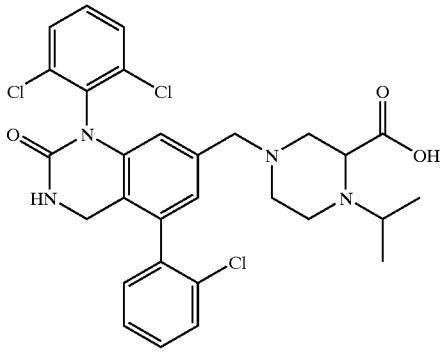

To the solution of tert-butyl 4-{[5-(2-chlorophenyl)-1-(2,6-dichlorophenyl)-2-oxo-1,2,3,4-tetrahydroquinazolin-7-yl]methyl}-1-isopropylpiperazine-2-carboxylate (EXAMPLE AAA11, 30 mg, 0.047 mmol) in trifluoroacetic acid (0.6 mL) was added water (0.03 mL). The reaction was stirred at rt for 20 h. Removal of the solvent and subsequent addition of ether resulted in a white precipitate. Filtration of the precipitate followed by washing with ether provided the title compound. $^1$H NMR (CDCl$_3$, 500 MHz): δ 1.22 (d, 3H, J=7.0 Hz), 1.24 (d, 3H, J=6.9 Hz), 3.12 (m, 2H), 3.30 (m, 1H), 3.44 (m, 1H), 3.50 (abq, 2H, J=7.1 Hz), 3.74 (m, 1H), 3.81 (m, 1H), 3.96 (m, 1H), 4.07 (m, 1H), 4.28 (dd, 1H, J$_1$=14.6 Hz, J$_2$=5.7 Hz), 4.42 (dd, 1H, J$_1$=14.9 Hz, J$_2$=10.1 Hz), 5.80 (brs, 1H), 6.13 (d, 1H, J=9.8 Hz), 6.95 (s, 1H), 7.32–7.58 (m, 7H). MS (API-ES+): 589 (M+H).

EXAMPLE AAA13
4-{[5-(2-chlorophenyl)-1-(2,6-dichlorophenyl)-2-oxo-1,2,3,4-tetrahydroquinazolin-7-yl]methyl}piperazine-2-carboxylic acid

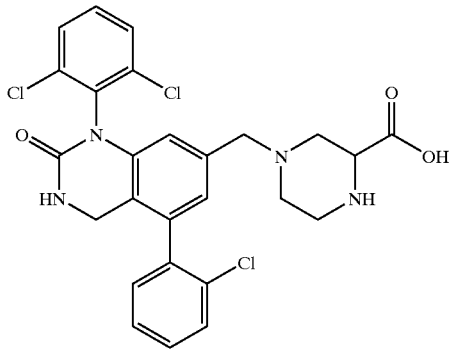

The title compound was prepared from tert-butyl 4-{[5-(2-chlorophenyl)-1-(2,6-dichlorophenyl)-2-oxo-1,2,3,4-tetrahydroquinazolin-7-yl]methyl}piperazine-2-carboxylate (EXAMPLE AAA10) as described in EXAMPLE AAA12. $^1$H NMR (DMSO, 500 MHz): δ 2.30 (m, 1H), 2.40 (m, 1H), 2.63 (m, 1H), 2.93 (m, 2H), 3.18 (m, 1H), 3.49 (s, 2H), 4.00 (m, 1H), 4.10 (m, 2H), 6.00 (s, 1H), 6.83 (d, 1H, J=6.4 Hz), 7.30–7.72 (m, 8H), 9.05 (brs, 2H). MS (API-ES+): 547 (M+H).

EXAMPLE AAA14
1-allyl-4-{[5-(2-chlorophenyl)-1-(2,6-dichlorophenyl)-2-oxo-1,2,3,4-tetrahydroquinazolin-7-yl]methyl}piperazine-2-carboxylic acid

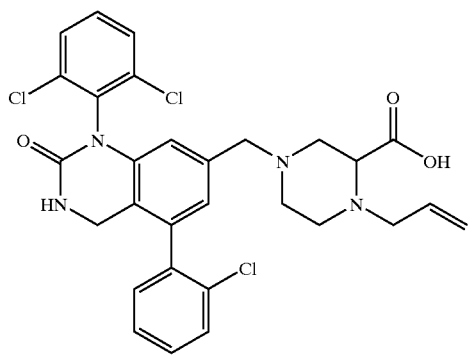

The title compound was prepared from tert-butyl 1-allyl-4-{[5-(2-chlorophenyl)-1-(2,6-dichlorophenyl)-2-oxo-1,2,3,4-tetrahydroquinazolin-7-yl]methyl}piperazine-2-carboxylate (EXAMPLE AAA10) as described in EXAMPLE AAA12. $^1$H NMR (CDCl$_3$, 500 MHz): δ 2.98 (m, 2H), 3.20 (m, 1H), 3.60 (m, 2H), 3.76 (m, 3H), 4.13 (m, 1H), 4.28 (m, 1H), 4.43 (m, 1H), 5.36 (m, 2H), 5.66 (s, 1H), 5.81 (m, 1H), 6.10 (d, 1H, J=5.5 Hz), 6.93 (d, 1H, J=6.7 Hz), 7.30–7.60 (m, 7H). MS (API-ES+): 586 (M+H).

EXAMPLE AAA15
Methyl 1-allyl-4-{[5-(2-chlorophenyl)-1-(2,6-dichlorophenyl)-2-oxo-1,2,3,4-tetrahydroquinazolin-7-yl]methyl}piperazine-2-carboxylate

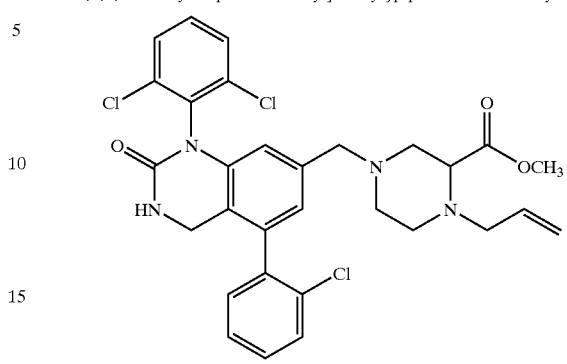

A mixture of 1-allyl-4-{[5-(2-chlorophenyl)-1-(2,6-dichlorophenyl)-2-oxo-1,2,3,4-tetrahydroquinazolin-7-yl]methyl}piperazine-2-carboxylic acid (EXAMPLE AAA14, 95 mg, 0.16 mmol), methanol (0.02 mL, 0.49 mmol), 1-[3-(dimethylamino)propyl]-3-ethylcarbodiimide hydrochloride (47 mg, 0.24 mmol) and 4-(dimethylamino)-pyridine (50 mg, 0.41 mmol) in methylene chloride (1 mL) was stirred at rt for 20 h. Removal of the solvent and subsequent purification by preparative thin layer chromatography using 5% of 2N ammonium in methanol/methylene chloride as eluent provided the title compound as a white solid. $^1$H NMR (CDCl$_3$, 500 MHz): δ 2.31 (brs, 1H), 2.42 (m, 1H), 2.47 (m, 1H), 2.56 (m, 1H), 2.64 (m, 1H), 3.02 brs, 2H), 3.20 (brs, 1H), 3.32 (m, 1H), 3.42 (m, 2H), 3.65 (s, 3H), 4.25 (dd, 1H, J$_1$=14.2 Hz, J$_2$=6.2 Hz), 4.43 (dd, 1H, J$_1$=14.4 Hz, J$_2$=8.0 Hz), 5.06 (s, 1H), 5.16 (s, 2H), 5.84 (m, 1H), 6.11 (d, 1H, J=13.3 Hz), 6.83 (d, 1H, J=3.2 Hz), 7.30–7.60 (m, 7H). MS (API-ES+): 601 (M+H).

EXAMPLE AAA16
5-(2-chloro-4-fluorophenyl)-1-(2,6-dichlorophenyl)-7-[(5-isopropyl-2,5-diazabicyclo[2.2.1]hept-2-yl)methyl]-3,4-dihydroquinazolin-2(1H)-one

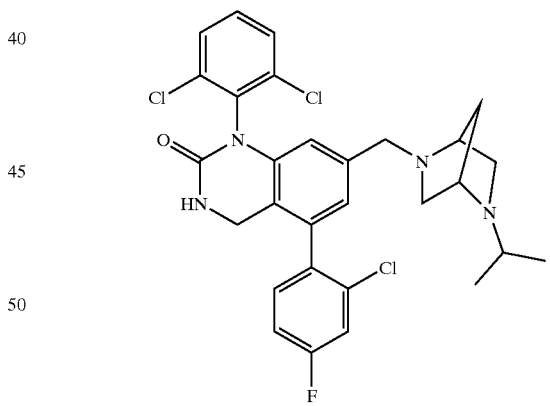

STEP A: 5-bromo-1-(2,6-dichlorophenyl)-7-(hydroxymethyl)-3-(4-methoxybenzyl)-3,4-dihydroquinazolin-2(1H)-one:

To a solution of methyl 5-bromo-1-(2,6-dichlorophenyl)-3-(4-methoxybenzyl)-2-oxo-1,2,3,4-tetrahydroquinazoline-7-carboxylate (INTERMEDIATE 27)(2 g, 3.63 mmol) in anhydrous THF at 0° C. was added lithium aluminum hydride (1.0M in THF, 4.7 mL, 4.73 mmol) slowly. The reaction was stirred at 0° C. for 40 min, quenched with water slowly and diluted with methylene chloride. The mixture was filtered through celite and rinsed with methylene chloride. Removal of the solvent and subsequent purification by flash chromatography using 20% of acetone in hexane as eluent provided the 5-bromo-1-(2,6-dichlorophenyl)-7-(hydroxymethyl)-3-(4-methoxybenzyl)-3,4-dihydroquinazolin-2(1H)-one as a white solid. $^1$H NMR (CDCl$_3$, 500 MHz): δ 3.83 (s, 3H), 4.49 (s, 2H), 4.50 (s, 2H), 4.69 (s, 2H), 5.98 (s, 1H), 6.92 (d, 2H, J=8.5 Hz), 7.23 (s, 1H), 7.36 (m, 3H), 7.52 (d, 2H, J=8.0 Hz). MS (API-ES+): 523 (M+H).

STEP B: 5-bromo-1-(2,6-dichlorophenyl)-3-(4-methoxybenzyl)-2-oxo-1,2,3,4-tetrahydroquinazoline-7-carbaldehyde:

The 5-bromo-1-(2,6-dichlorophenyl)-3-(4-methoxybenzyl)-2-oxo-1,2,3,4-tetrahydroquinazoline-7-carbaldehyde was prepared from 5-bromo-1-(2,6-dichlorophenyl)-7-(hydroxymethyl)-3-(4-methoxybenzyl)-3,4-dihydroquinazolin-2(1H)-one (EXAMPLE AAA16, STEP A) as described in INTERMEDIATE AAA1. $^1$H NMR (CDCl$_3$, 500 MHz): δ 3.84 (s, 3H), 4.56 (s, 2H), 4.70 (s, 2H), 6.47 (s, 1H), 6.93 (d, 2H, J=8.7 Hz), 7.36 (d, 2H, J=8.4 Hz), 7.42 (t, 1H, J=8.0 Hz), 7.55 (d, 2H, J=8.0 Hz), 7.69 (s, 1H), 9.75 (s, 1H).

STEP C: 5-bromo-1-(2,6-dichlorophenyl)-7-[(5-isopropyl-2,5-diazabicyclo[2.2.1]hept-2-yl)methyl]-3-(4-methoxybenzyl)-3,4-dihydroquinazolin-2(1H)-one The 5-bromo-1-(2,6-dichlorophenyl)-7-[(5-isopropyl-2,5-diazabicyclo[2.2.1]hept-2-yl)methyl]-3-(4-methoxybenzyl)-3,4-dihydroquinazolin-2(1H)-one was prepared from 5-bromo-1-(2,6-dichlorophenyl)-3-(4-methoxybenzyl)-2-oxo-1,2,3,4-tetrahydroquinazoline-7-carbaldehyde (EXAMPLE AAA16, STEP B) and 2-isopropyl-2,5-diazabicyclo[2.2.1]heptane (INTERMEDIATE ABA2) as described in EXAMPLE AAA1, STEP A. $^1$H NMR (CDCl$_3$, 500 MHz): δ 1.15 (brs, 3H), 1.22 (brs, 3H), 1.74 (brs, 1H), 1.90 (brs, 1H), 243 (brs, 2H), 2.72 (brs, 1H), 2.88 (brs, 1H), 3.07 (brs, 1H), 3.16 (s, 2H), 3.53 (abq, 2H, J=14.2 Hz), 3.72 (brs, 1H), 3.83 (s, 3H), 4.48 (s, 2H), 4.68 (s, 2H), 6.05 (s, 1H), 6.91 (d, 2H, J=8.5 Hz), 7.17 (s, 1H), 7.36 (d, 2H, J=8.4 Hz), 7.38 (t, 1H, J=8.0 Hz), 7.52 (d, 2H, J=8.0 Hz). MS (API-ES+): 645 (M+H).

STEP D: 5-(2-chloro-4-fluorophenyl)-1-(2,6-dichlorophenyl)-7-[(5-isopropyl-2,5-diazabicyclo[2.2.1]hept-2-yl)methyl]-3-(4-methoxybenzyl)-3,4-dihydroquinazolin-2(1H)-one To a solution of 5-bromo-1-(2,6-dichlorophenyl)-7-[(5-isopropyl-2,5-diazabicyclo[2.2.1]hept-2-yl)methyl]-3-(4-methoxybenzyl)-3,4-dihydroquinazolin-2(1H)-one (200 mg, 0.31 mmol) and 2-chloro-4-fluoro-benzene boronic acid (98 mg, 0.62 mmol) in toluene (3 mL) and ethanol (0.3 mL) was added sodium carbonate (2M solution, 0.39 mL) and tetrakis(triphenylphosphine)palladium (0) (18 mg, 0.0155 mmol). The flask was evacuated and purged with nitrogen a few times. The reaction mixture was heated to reflux for 2 h and diluted with methylene chloride. The organic layer was washed with water and brine, and dried over anhydrous sodium sulfate. Removal of the solvent and subsequent purification by preparative thin layer chromatography using 5% of 2N ammonium in methanol/methylene chloride as eluent provided the 5-(2-chloro-4-fluorophenyl)-1-(2,6-dichlorophenyl)-7-[(5-isopropyl-2,5-diazabicyclo[2.2.1]hept-2-yl)methyl]-3-(4-methoxybenzyl)-3,4-dihydroquinazolin-2(1H)-one as a white solid. $^1$H NMR (CDCl$_3$, 500 MHz): δ 1.03 (s, 3H), 1.08 (s, 3H), 1.64 (m, 2H), 2.40 (m, 1H), 2.57 (brs, 1H), 2.83 (t, 1H, J=7.3 Hz), 2.90 (brs, 1H), 3.14 (s, 1H), 3.53 (m, 2H), 3.63 (t, 1H, J=13.2 Hz), 3.81 (s, 3H), 4.11 (abq, 2H, J=14.9 Hz), 4.55 (abq, 2H, J=14.9 Hz), 6.22 (s, 1H), 6.78 (s, 1H), 6.84 (d, 2H, J=8.4 Hz), 6.99 (t, 1H, J=8.0 Hz), 7.12 (dd, 1H, J$_1$=8.4 Hz, J$_2$=6.0 Hz), 7.21 (d, 3H, J=8.7 Hz), 7.38 (t, 1H, J=8.0 Hz), 7.54 (m, 2H). MS (API-ES+): 695 (M+H).

STEP E: 5-(2-chloro-4-fluorophenyl)-1-(2,6-dichlorophenyl)-7-[(5-isopropyl-2,5-diazabicyclo[2.2.1]hept-2-yl)methyl]-3,4-dihydroquinazolin-2(1H)-one The solution of 5-(2-chloro-4-fluorophenyl)-1-(2,6-dichlorophenyl)-7-[(5-isopropyl-2,5-diazabicyclo[2.2.1]hept-2-yl)methyl]-3-(4-methoxybenzyl)-3,4-dihydroquinazolin-2(1H)-one (136 mg, 0.20 mmol) in trifluoroacetic acid (1.5 mL) was stirred at 60° C. for 1 h. It was cooled to rt and treated with 5N NaOH solution to pH 9~10. The resulting mixture was extracted with methylene chloride. The organic layer was washed with water and brine, and dried over anhydrous sodium sulfate. Removal of the solvent and subsequent purification by preparative thin layer chromatography using 8% of 2N ammonium in methanol/methylene chloride as eluent provided the 5-(2-chloro-4-fluorophenyl)-1-(2,6-dichlorophenyl)-7-[(5-isopropyl-2,5-diazabicyclo[2.2.1]hept-2-yl)methyl]-3,4-dihydroquinazolin-2(1H)-one as a white solid. $^1$H NMR (CDCl$_3$, 500 MHz): δ 1.03 (d, 3H, J=5.7 Hz), 1.08 (d, 3H, J=5.7 Hz), 1.66 (m, 2H), 2.37 (t, 1H, J=8.2 Hz), 2.43 (t, 1H, J=11.9 Hz), 2.56 (brs, 1H), 2.83 (t, 1H, J=9.2 Hz), 2.90 (d, 1H, J=8.7 Hz), 3.14 (s, 1H), 3.54 (m, 2H), 3.64 (t, 1H, J=13.0 Hz), 4.33 (abq, 2H, J=14.2 Hz), 5.12 (s, 1H), 6.24 (s, 1H), 6.84 (s, 1H), 7.08 (t, 1H, J=8.0 Hz), 7.28 (m, 2H), 7.39 (d, 1H, J=8.0 Hz), 7.54 (t, 1H, J=8.0 Hz). MS (API-ES+): 573 (M+H).

EXAMPLE AAA17

1-(2,6-dichlorophenyl)-5-(2,4-difluorophenyl)-7-[(5-isopropyl-2,5-diazabicyclo[2.2.1]hept-2-yl)methyl]-3,4-dihydroquinazolin-2(1H)-one

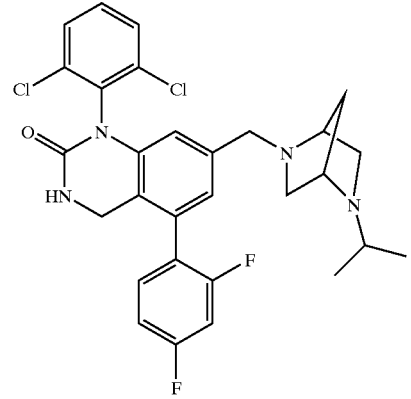

STEP A: 1-(2,6-dichlorophenyl)-5-(2,4-difluorophenyl)-7-[(5-isopropyl-2,5-diazabicyclo[2.2.1]hept-2-yl)methyl]-3-(4-methoxybenzyl)-3,4-dihydroquinazolin-2(1H)-one The 1-(2,6-dichlorophenyl)-5-(2,4-difluorophenyl)-7-[(5-isopropyl-2,5-diazabicyclo[2.2.1]hept-2-yl)methyl]-3-(4-methoxybenzyl)-3,4-dihydroquinazolin-2(1H)-one was prepared from 5-bromo-1-(2,6-dichlorophenyl)-7-[(5-isopropyl-2,5-diazabicyclo[2.2.1]hept-2-yl)methyl]-3-(4-methoxybenzyl)-3,4-dihydroquinazolin-2(1H)-one (EXAMPLE AAA16, STEP C) and 2,4-difluorobenzene boronic acid as described in EXAMPLE AAA16, STEP D. $^1$H NMR (CDCl$_3$, 500 MHz): δ 1.03 (s, 3H), 1.08 (s, 3H), 1.59 (brs, 2H), 2.40 (m, 2H), 2.56 (brs, 1H), 2.83 (m, 1H), 2.90 (brs, 1H), 3.15 (s, 1H), 3.58 (abq, 3H, J=14.5 Hz), 3.81 (s, 3H), 4.20 (brs, 2H), 4.58 (brs, 2H), 6.23 (s, 1H), 6.85 (m, 3H), 6.91 (m, 2H), 7.14 (q, 1H, J=7.1 Hz), 7.23 (d, 2H, J=8.5 Hz), 7.39 (t, 1H, J=8.0 Hz), 7.54 (d, 2H, J=8.1 Hz). MS (API-ES+): 677 (M+H).

STEP B: 1-(2,6-dichlorophenyl)-5-(2,4-difluorophenyl)-7-[(5-isopropyl-2,5-diazabicyclo[2.2.1]hept-2-yl)methyl]-3,4-dihydroquinazolin-2(1H)-one The 1-(2,6-dichlorophenyl)-5-(2,4-difluorophenyl)-7-[(5-isopropyl-2,5-diazabicyclo[2.2.1]hept-2-yl)methyl]-3,4-dihydroquinazolin-2(1H)-one was prepared from 1-(2,6-dichlorophenyl)-3-(4-methoxybenzyl)-5-(2,4-difluorophenyl)-7-(N-isopropylbicyclo[2.2.1]piperazinylmethyl)-3,4-dihydro-2(1H)-quinazolinone as described in EXAMPLE AAA16, STEP E. $^1$H NMR (CDCl$_3$, 500 MHz): δ 1.03 (d, 3H, J=5.5 Hz), 1.08 (d, 3H, J=5.8 Hz), 1.66 (m, 2H), 2.37 (d, 1H, J=9.2 Hz), 2.43 (d, 1H, J=9.1 Hz), 2.56 (brs, 1H), 2.83 (d, 1H, J=9.2 Hz), 2.91 (brs, 1H), 3.15 (s, 1H), 3.60 (abq, 3H, J=14.2 Hz), 4.31 (brs, 1H), 4.50 (brs, 1H), 5.10 (s, 1H), 6.26 (s, 1H), 6.91 (s, 1H), 6.94 (dt, 1H, J$_1$=9.4 Hz, J$_2$=2.3 Hz), 6.99 (dt, 1H, J$_1$=8.0 Hz, J$_2$=2.3 Hz), 7.31 (m, 1H), 7.39 (d, 1H, J=8.0 Hz), 7.54 (d, 1H, J=8.0 Hz). MS (API-ES+): 557 (M+H).

EXAMPLE AAA18

5-(2-chlorophenyl)-1-(2,6-dichlorophenyl)-7-(piperidin-4-ylidenemethyl)-3,4-dihydroquinazolin-2(1H)-one

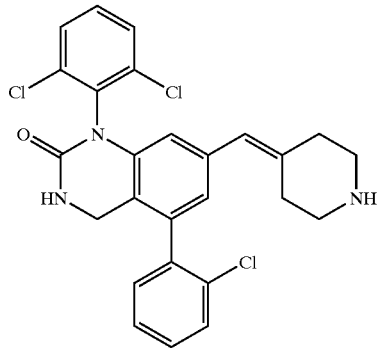

STEP A: 7-(bromomethyl)-5-(2-chlorophenyl)-1-(2,6-dichlorophenyl)-3,4-dihydroquinazolin-2(1H)-one A solution of 5-(2-chlorophenyl)-1-(2,6-dichlorophenyl)-7-(hydroxymethyl)-3,4-dihydroquinazolin-2(1H)-one (500 mg, 1.15 mmol), triphenyl phosphine (363 mg, 1.38 mmol) and carbon tetrabromide (459 mg, 1.38 mmol) in acetonitrile (34 mL) was stirred at rt for 24 h. Removal of the solvent and subsequent purification by flash chromatography using 22% acetone/hexane as eluent provided 7-(bromomethyl)-5-(2-chlorophenyl)-1-(2,6-dichlorophenyl)-3,4-dihydroquinazolin-2(1H)-one as a white solid. $^1$H NMR (CDCl$_3$, 500 MHz): δ 4.26 (d, 1H, J=14.7 Hz), 4.35 (abq, 2H, J=10.5 Hz), 4.44 (d, 1H, J=14.6 Hz), 5.01 (s, 1H), 6.18 (s, 1H), 6.96 (s, 1H), 7.30–7.60 (m, 7H). MS (API-ES+): 497 (M+H).

STEP B: diethyl [5-(2-chlorophenyl)-1-(2,6-dichlorophenyl)-2-oxo-1,2,3,4-tetrahydroquinazolin-7-yl]methylphosphonate A mixture of 7-(bromomethyl)-5-(2-chlorophenyl)-1-(2,6-dichlorophenyl)-3,4-dihydroquinazolin-2(1H)-one (55 mg, 0.11 mmol) and triethylphosphite (0.8 mL, 4.66 mmol) in DMF (0.5 mL) was stirred at 100° C. for 1.75 h. After it was cooled to rt, the resulting mixture was treated with ether and hexane to form a precipitate. Filtration of the precipitate provided diethyl [5-(2-chlorophenyl)-1-(2,6-dichlorophenyl)-2-oxo-1,2,3,4-tetrahydroquinazolin-7-yl]methylphosphonate as a white solid. $^1$H NMR (CDCl$_3$, 500 MHz): δ 1.20 (m, 6H), 3.01 (s, 1H), 3.06 (s, 1H), 3.97 (m, 4H), 4.34 (abq, 2H, J=14.1 Hz), 5.12 (s, 1H), 6.12 (s, 1H), 6.86 (s, 1H), 7.26–7.60 (m, 7H). MS (API-ES+): 553 (M+H).

STEP C: tert-butyl 4-{[5-(2-chlorophenyl)-1-(2,6-dichlorophenyl)-2-oxo-1,2,3,4-tetrahydroquinazolin-7-yl]methylene}piperidine-1-carboxylate To a solution of diethyl [5-(2-chlorophenyl)-1-(2,6-dichlorophenyl)-2-oxo-1,2,3,4-tetrahydroquinazolin-7-yl]methylphosphonate (422 mg, 0.762 mmol) in a mixture of THF (9 mL) and DMF (2 mL) at 0° C. was added sodium hydride (60%, 61 mg, 1.52 mmol). The resulting mixture was stirred at rt for 20 min and then cooled to 0° C. again. To this was added a solution of t-butyl-4-oxo-1-piperidinecarboxylate (310 mg, 1.524 mmol) in THF (2 mL). Then the reaction was stirred at rt for 22 h. The mixture was quenched with brine, and extracted with ethyl acetate. The organic layer was washed with brine and dried over anhydrous sodium sulfate. Removal of the solvent and subsequent purification by flash chromatography using 20% acetone/hexane as eluent provided tert-butyl 4-{[5-(2-chlorophenyl)-1-(2,6-dichlorophenyl)-2-oxo-1,2,3,4-tetrahydroquinazolin-7-yl]methylene}piperidine-1-carboxylate as a white solid. $^1$H NMR (CDCl$_3$, 500 MHz): δ 1.48 (s, 9H), 2.24 (brs, 2H), 2.31 (t, 2H, J=5.7 Hz), 3.31 (t, 2H, J=5.5 Hz), 3.45 (t, 2H, J=5.5 Hz), 4.35 (abq, 2H, J=14.4 Hz), 5.10 (s, 1H), 5.96 (s, 1H), 6.21 (s, 1H), 6.74 (s, 1H), 7.30–7.58 (m, 7H). MS (API-ES+): 600 (M+H).

STEP D: 5-(2-chlorophenyl)-1-(2,6-dichlorophenyl)-7-(piperidin-4-ylidenemethyl)-3,4-dihydroquinazolin-2(1H)-one The 5-(2-chlorophenyl)-1-(2,6-dichlorophenyl)-7-(piperidin-4-ylidenemethyl)-3,4-dihydroquinazolin-2(1H)-one was prepared from tert-butyl 4-{[5-(2-chlorophenyl)-1-(2,6-dichlorophenyl)-2-oxo-1,2,3,4-tetrahydroquinazolin-7-yl]methylene}piperidine-1-carboxylate as described in EXAMPLE AAA1, STEP B.

$^1$H NMR (CDCl$_3$, 500 MHz): δ 1.80 (brs, 1H), 2.26 (t, 2H, J=5.5 Hz), 2.33 (t, 2H, J=5.5 Hz), 2.77 (t, 2H, J=5.5 Hz), 2.92 (t, 2H, J=5.5 Hz), 4.35 (abq, 2H, J=14.4 Hz), 5.12 (s, 1H), 5.96 (s, 1H), 6.15 (s, 1H), 6.74 (s, 1H), 7.30–7.56 (m, 7H). MS (API-ES+): 500 (M+H).

EXAMPLE AAA19

5-(2-chlorophenyl)-1-(2,6-dichlorophenyl)-7-(piperidin-4-ylmethyl)-3,4-dihydroquinazolin-2(1H)-one

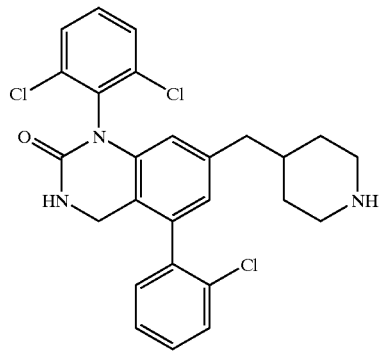

STEP A: tert-butyl 4-{[5-(2-chlorophenyl)-1-(2,6-dichlorophenyl)-2-oxo-1,2,3,4-tetrahydroquinazolin-7-yl]methyl}piperidine-1-carboxylate A solution of tert-butyl 4-{[5-(2-chlorophenyl)-1-(2,6-dichlorophenyl)-2-oxo-1,2,3,4-tetrahydroquinazolin-7-yl]

methylene}piperidine-1-carboxylate (EXAMPLE AAA18, STEP C, 150 mg, 0.25 mmol) in ethyl acetate (4 mL) was purged and filled with nitrogen. To this was added platinum (IV) oxide hydrate (30 mg, 20% weight). The mixture was evacuated and filled with hydrogen via balloon. Then the reaction was stirred at rt under hydrogen for 1 h, filtered through celite and rinsed with ethyl acetate and methanol. Removal of the solvent provided tert-butyl 4-{[5-(2-chlorophenyl)-1-(2,6-dichlorophenyl)-2-oxo-1,2,3,4-tetrahydroquinazolin-7-yl]methyl}piperidine-1-carboxylate as a white solid used directly for the next step.

$^1$H NMR (CDCl$_3$, 500 MHz): δ 1.06 (m, 2H), 1.46 (s, 9H), 1.55 (m, 3H), 2.40 (m, 2H), 2.61 (t, 2H, J=12.4 Hz), 4.04 (d, 2H, J=12.8 Hz), 4.33 (abq, 2H, J=14.2 Hz), 5.19 (s, 1H), 5.91 (s, 1H), 6.70 (s, 1H), 7.28–7.60 (m, 7H).

STEP B: 5-(2-chlorophenyl)-1-(2,6-dichlorophenyl)-7-(piperidin-4-ylmethyl)-3,4-dihydroquinazolin-2(1H)-one The 5-(2-chlorophenyl)-1-(2,6-dichlorophenyl)-7-(piperidin-4-ylmethyl)-3,4-dihydroquinazolin-2(1H)-one was prepared from tert-butyl 4-{[5-(2-chlorophenyl)-1-(2,6-dichlorophenyl)-2-oxo-1,2,3,4-tetrahydroquinazolin-7-yl]methyl}piperidine-1-carboxylate as described in EXAMPLE AAA1, STEP B. $^1$H NMR (CDCl$_3$, 500 MHz): δ 1.17 (m, 2H), 1.54 (m, 1H), 1.63 (d, 2H, J=12.3 Hz), 2.40 (m, 2H), 2.57 (m, 2H), 2.80 (brs, 1H), 3.11 (d, 2H, J=12.4 Hz), 4.35 (abq, 2H, J=14.4 Hz), 5.27 (s, 1H), 5.90 (s, 1H), 6.69 (s, 1H), 7.29–7.56 (m, 7H). MS (API-ES+): 500 (M+H).

EXAMPLE AAA20

5-(2-chlorophenyl)-1-(2,6-dichlorophenyl)-7-[1-ethylpiperidin-4-yl)methyl]-3,4-dihydroquinazolin-2(1H)-one

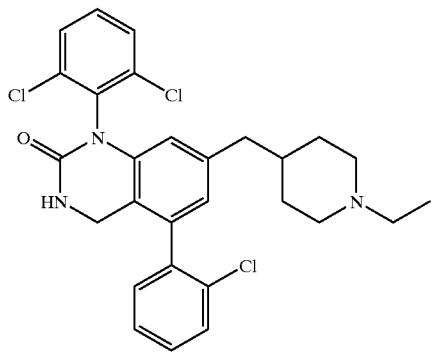

The title compound was prepared as a byproduct from 5-(2-chlorophenyl)-1-(2,6-dichlorophenyl)-7-(piperidin-4-ylmethyl)-3,4-dihydroquinazolin-2(1H)-one (EXAMPLE AAA19) and cyclopropyl methyl ketone as described in EXAMPLE AAA1, STEP A. $^1$H NMR (CDCl$_3$, 500 MHz): δ 1.08 (t, 3H, J=7.1 Hz), 1.24 (m, 2H), 1.40 (m, 1H), 1.61 (brs, 2H), 1.80 (t, 2H, J=10.5 Hz), 2.80 (brs, 1H), 2.39 (m, 4H), 2.90 (d, 2H, J=11.0 Hz), 4.33 (abq, 2H, J=14.2 Hz), 5.01 (s, 1H), 5.91 (s, 1H), 6.70 (s, 1H), 7.29–7.58 (m, 7H). MS (API-ES+): 530 (M+H).

EXAMPLE AAA21

5-(2-chlorophenyl)-1-(2,6-dichlorophenyl-7-[(1-isopropylpiperidin-4-yl)methyl]-3,4-dihydroquinazolin-2(1H)-one

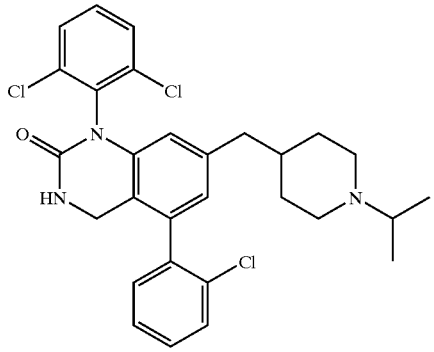

The title compound was prepared from 5-(2-chlorophenyl)-1-(2,6-dichlorophenyl)-7-(piperidin-4-ylmethyl)-3,4-dihydroquinazolin-2(1H)-one (EXAMPLE AAA19) and acetone as described in EXAMPLE AAA1, STEP A. $^1$H NMR (CDCl$_3$, 500 MHz): δ 1.04 (brs, 6H), 1.20 (brs, 1H), 1.38 (brs, 1H), 1.61 (brs, 3H), 2.04 (brs, 2H), 2.40 (d, 2H, J=6.2 Hz), 2.68 (brs, 1H), 2.84 (brs, 2H), 4.33 (d of abq, 2H, J$_1$=14.2 Hz, J$_2$=1.6 Hz), 5.05 (s, 1H), 5.32 (s, 1H), 5.90 (s, 1H), 6.69 (s, 1H), 7.29–7.56 (m, 7H). MS (API-ES+): 542 (M+H).

EXAMPLE AAA22

5-(2-chlorophenyl)-7-[(1-cyclobutylpiperidin-4-yl)methyl]-1-(2,6-dichlorophenyl)-3,4-dihydroquinazolin-2(1H)-one

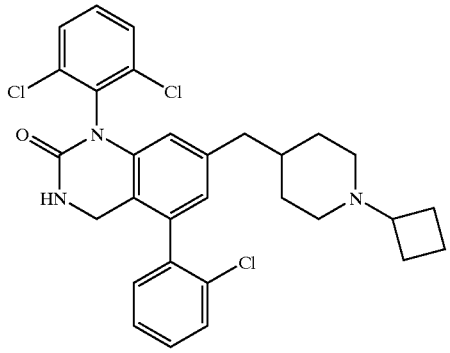

The title compound was prepared from 5-(2-chlorophenyl)-1-(2,6-dichlorophenyl)-7-(piperidin-4-ylmethyl)-3,4-dihydroquinazolin-2(1H)-one (EXAMPLE AAA19) and cyclobutanone as described in EXAMPLE AAA1, STEP A. $^1$H NMR (CDCl$_3$, 500 MHz): δ 1.20 (m, 2H), 1.38 (brs, 1H), 1.66 (m, 6H), 1.86 (t, 2H, J=8.4 Hz), 2.02 (m, 2H), 2.40 (d, 2H, J=5.7 Hz), 2.63 (m, 1H), 2.82 (d, 2H, J=9.1 Hz), 4.33 (abq, 2H, J=14.2 Hz), 5.01 (s, 1H), 5.90 (s, 1H), 6.69 (s, 1H), 7.29–7.56 (m, 7H). MS (API-ES+): 554 (M+H).

EXAMPLE AAA23

5-(2-chlorophenyl)-1-(2,6-dichlorophenyl)-7-[(E)-piperidin-3-ylidenemethyl]-3,4-dihydroquinazolin-2(1H)-one

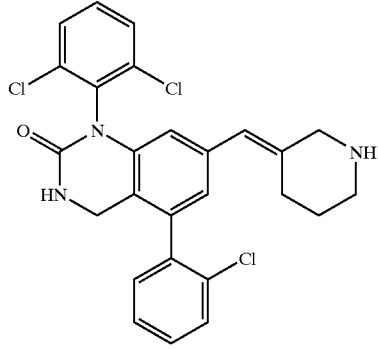

STEP A: tert-butyl (3E)-3-{[5-(2-chlorophenyl)-1-(2,6-dichlorophenyl)-2-oxo-1,2,3,4-tetrahydroquinazolin-7-yl]methylene}piperidine-1-carboxylate The tert-butyl (3E)-3-{[5-(2-chlorophenyl)-1-(2,6-dichlorophenyl)-2-oxo-1,2,3,4-tetrahydroquinazolin-7-yl]methylene}piperidine-1-carboxylate was prepared from diethyl [5-(2-chlorophenyl)-1-(2,6-dichlorophenyl)-2-oxo-1,2,3,4-tetrahydroquinazolin-7-yl]methylphosphonate (EXAMPLE AAA18, STEP B) as described in EXAMPLE AAA18, STEP C. $^1$H NMR (CDCl$_3$, 500 MHz): δ1.45 (s, 9H), 1.52 (m, 2H), 1.67 (m, 1H), 2.37 (m, 2H), 3.45 (m, 2H), 3.92 (s, 1H), 4.35 (abq, 2H, J=14.4 Hz), 5.04 (s, 1H), 5.99 (s, 1H), 6.26 (s, 1H), 6.76 (s, 1H), 7.30–7.58 (m, 7H). MS (API-ES+): 600 (M+H).

STEP B: 5-(2-chlorophenyl)-1-(2,6-dichlorophenyl)-7-[(E)-piperidin-3-ylidenemethyl]-3,4-dihydroquinazolin-2(1H)-one The 5-(2-chlorophenyl)-1-(2,6-dichlorophenyl)-7-[(E)-piperidin-3-ylidenemethyl]-3,4-dihydroquinazolin-2(1H)-one was prepared from tert-butyl (3E)-3-{[5-(2-chlorophenyl)-1-(2,6-dichlorophenyl)-2-oxo-1,2,3,4-tetrahydroquinazolin-7-yl]methylene}piperidine-1-carboxylate as described in EXAMPLE AAA1, STEP B.

$^1$H NMR (CDCl$_3$, 500 MHz): δ 1.60 (m, 3H), 2.40 (t, 2H, J=5.7 Hz), 3.01 (s, 2H), 3.45 (s, 2H), 4.35 (abq, 2H, J=14.0 Hz), 5.04 (s, 1H), 5.99 (s, 1H), 6.25 (s, 1H), 6.75 (s, 1H), 7.30–7.60 (m, 7H). MS (API-ES+): 500 (M+H).

EXAMPLE AAA24

5-(2-chlorophenyl)-1-(2,6-dichlorophenyl)-7-(piperidin-3-ylmethyl)-3,4-dihydroquinazolin-2(1H)-one

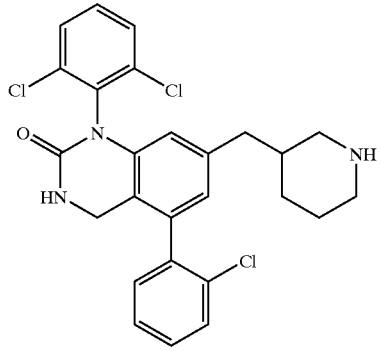

STEP A: tert-butyl 3-{[5-(2-chlorophenyl)-1-(2,6-dichlorophenyl)-2-oxo-1,2,3,4-tetrahydroquinazolin-7-yl]methyl}piperidine-1-carboxylate The tert-butyl 3-{[5-(2-chlorophenyl)-1-(2,6-dichlorophenyl)-2-oxo-1,2,3,4-tetrahydroquinazolin-7-yl]methyl}piperidine-1-carboxylate was prepared from tert-butyl (3E)-3-{[5-(2-chlorophenyl)-1-(2,6-dichlorophenyl)-2-oxo-1,2,3,4-tetrahydroquinazolin-7-yl]methylene}piperidine-1-carboxylate (EXAMPLE AAA23, STEP A) as described in EXAMPLE AAA19, STEP A. $^1$H NMR (CDCl$_3$, 500 MHz): δ 1.00 (brs, 1H), 1.40 (s, 9H), 1.60 (m, 3H), 1.70 (m, 1H), 2.30 (brs, 1H), 2.45 (brs, 2H), 2.70 (m, 1H), 3.90 (brs, 2H), 4.33 (d, 2H, J=14.4 Hz), 5.15 (s, 1H), 5.93 (s, 1H), 6.70 (s, 1H), 7.28–7.60 (m, 7H).

STEP B: 5-(2-chlorophenyl)-1-(2,6-dichlorophenyl)-7-(piperidin-3-ylmethyl)-3,4-dihydroquinazolin-2(1H)-one The 5-(2-chlorophenyl)-1-(2,6-dichlorophenyl)-7-(piperidin-3-ylmethyl)-3,4-dihydroquinazolin-2(1H)-one was prepared from tert-butyl 3-{[5-(2-chlorophenyl)-1-(2,6-dichlorophenyl)-2-oxo-1,2,3,4-tetrahydroquinazolin-7-yl]methyl}piperidine-1-carboxylate as described in EXAMPLE AAA1, STEP B. $^1$H NMR (CDCl$_3$, 500 MHz): δ 1.00 (m, 1), 1.46 (m, 1H), 1.66 (m, 2H), 1.74 (m, 1H), 2.26 (m, 2H), 2.37 (m, 2H), 2.54 (m, 1H), 3.03 (m, 2H), 4.33 (abq, 2H, J=14.4 Hz), 5.20 (s, 1H), 5.90 (s, 1H), 6.69 (s, 1H), 7.25–7.60 (m, 7H). MS (API-ES+): 500 (M+H).

EXAMPLE AAA25

5-(2-chlorophenyl)-1-(2,6-dichlorophenyl)-7-[(1-isopropylpiperidin-3-yl)methyl]-3,4-dihydroquinazolin-2(1H)-one

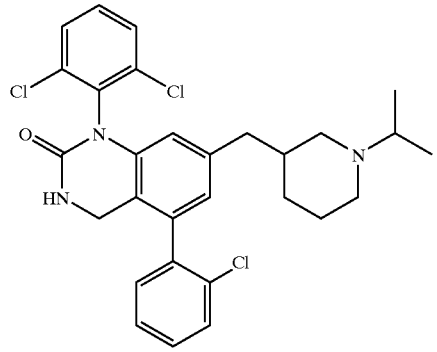

The title compound was prepared from 5-(2-chlorophenyl)-1-(2,6-dichlorophenyl)-7-(piperidin-3-ylmethyl)-3,4-dihydroquinazolin-2(1H)-one (EXAMPLE AAA24) and acetone as described in EXAMPLE AAA1, STEP A. $^1$H NMR (CDCl$_3$, 500 MHz): δ 0.83 (m, 1H), 0.99 (m, 6H), 1.46 (m, 1H), 1.66 (m, 4H), 2.05 (t, 1H, J=11.4 Hz), 2.38 (m, 2H), 2.68 (m, 2H), 2.78 (m, 1H), 4.24 (d, 1H), 4.41 (dd, 1H, J$_1$=14.2 Hz, J$_2$=6.7 Hz), 5.04 (s, 1H), 5.92 (s, 1H), 6.70 (s, 1H), 7.22–7.60 (m, 7H). MS (API-ES+): 542 (M+H)n.

EXAMPLE AAA26

5-(2-chlorophenyl)-1-(2,6-dichlorophenyl)-7-[(1-ethylpiperidin-3-yl)methyl]-3,4-dihydroquinazolin-2(1H)-one

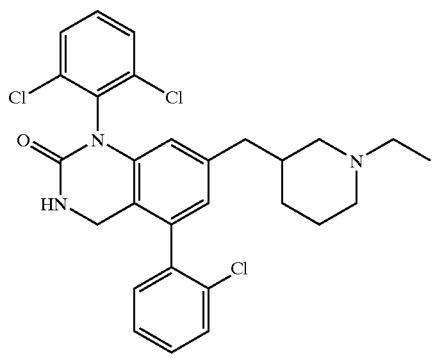

The title compound was prepared as a byproduct from 5-(2-chlorophenyl)-1-(2,6-dichlorophenyl)-7-(piperidin-3-ylmethyl)-3,4-dihydroquinazolin-2(1H)-one (EXAMPLE AAA24) and cyclopropyl methyl ketone as described in EXAMPLE AAA1, STEP A. $^1$H NMR (CDCl$_3$, 500 MHz): δ 1.85 (m, 1H), 1.04 (brs, 3H), 1.52 (m, 2H), 1.65 (m, 2H), 1.75 (m, 2H), 2.35 (m, 3H), 2.43 (m, 41H), 2.76 (m, 1H), 2.85 (m, 1H), 4.33 (abq, 2H, J=14.4 Hz), 5.00 (s, 1H), 5.92 (s, 1H), 6.70 (s, 1H), 7.24–7.60 (m, 7H). MS (API-ES+): 530 (M+H).

Compounds of this invention can be made according to the scheme shown below:

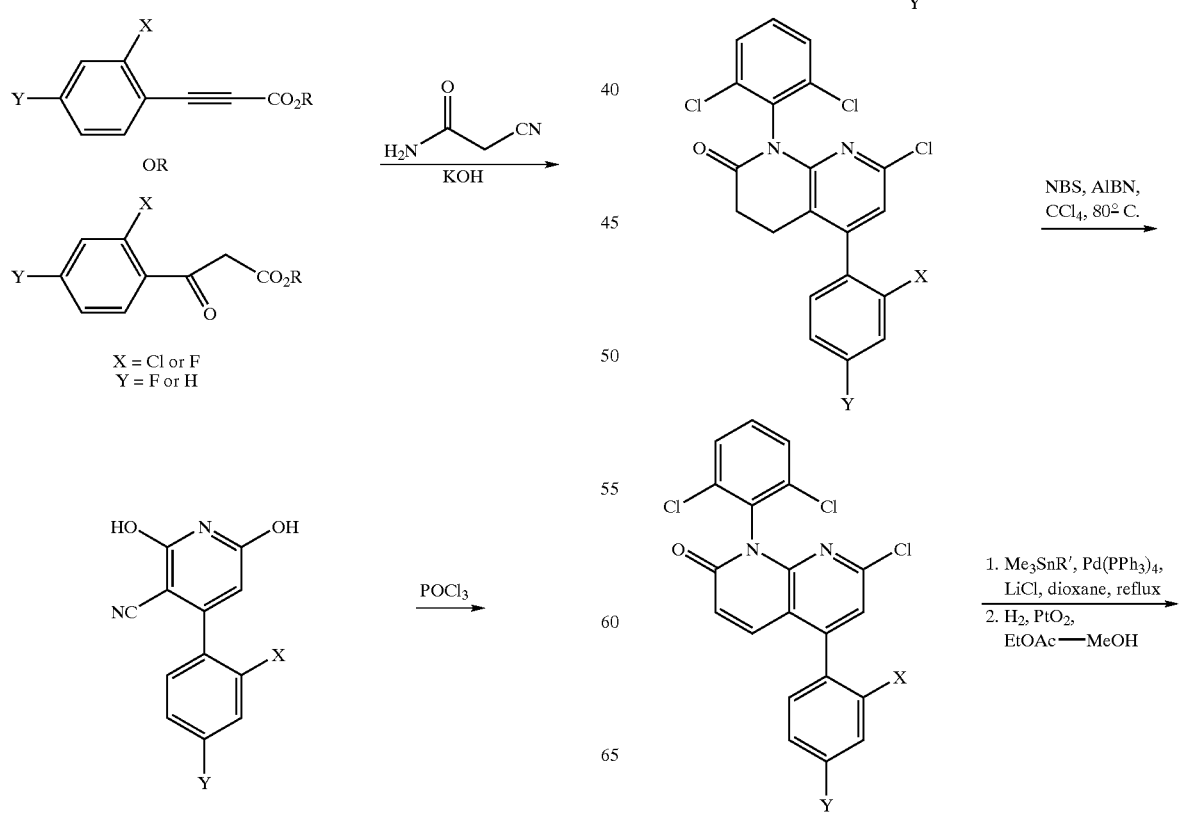

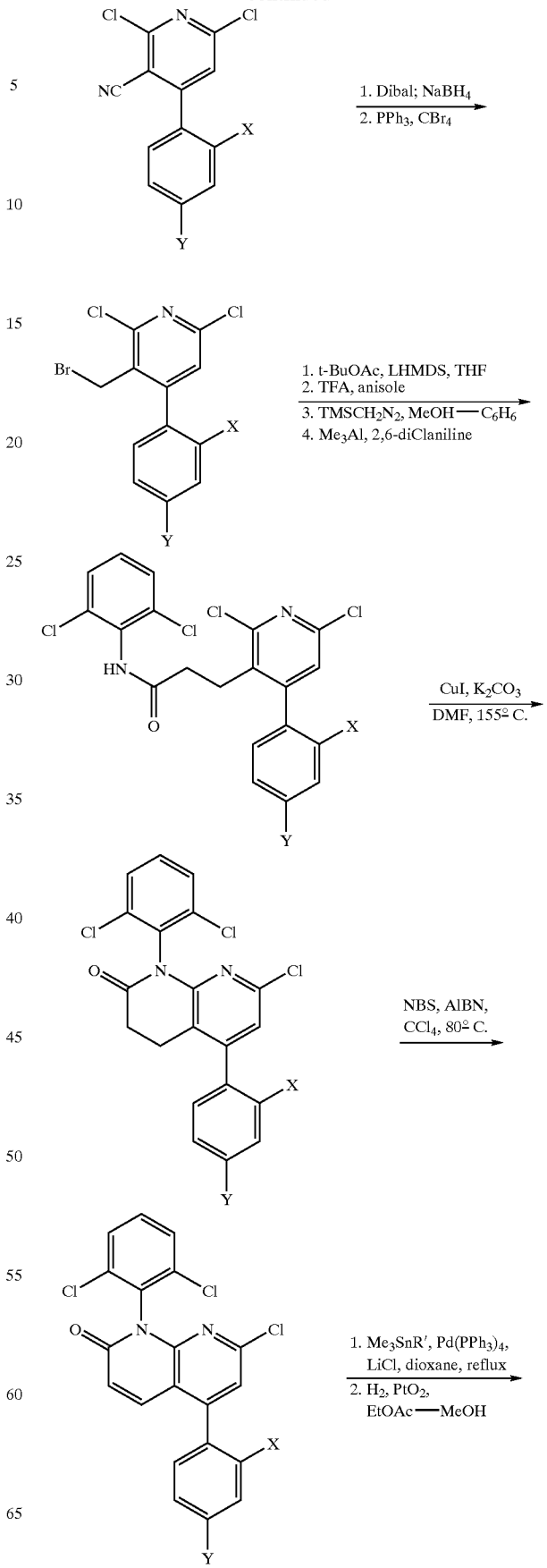

-continued

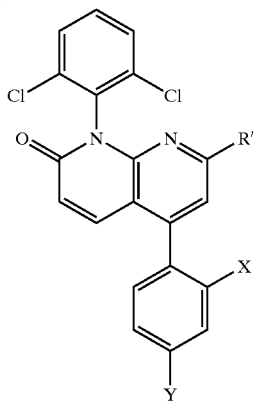

COMPOUND BBB1
3-(bromomethyl)-2,6-dichloro-4-(2-chloro-4-fluorophenyl)pyridine

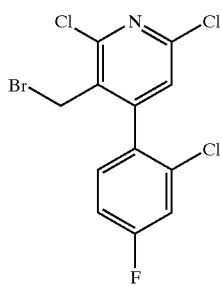

STEP A: 4-(2-chloro-4-fluorophenyl)-2,6-dihydroxynicotinonitrile

Potassium hydroxide (5.1 g, 91 mmol) was added to a solution of 2-cyanoacetamide (7.2 g, 86 mmol) in 270 mL ethanol and stirred briefly at rt. A solution of ethyl 3-(2-chloro-4-fluorophenyl)prop-2-ynoate (3.58 g, 16.9 mmol) in 30 mL ethanol was added and the solution stirred for 10 min (heavy precipitate). The resulting suspension was then refluxed for 1 h and stirred overnight at rt. The mixture was concentrated and the solid residue (4-(2-chloro-4-fluorophenyl)-2,6-dihydroxynicotinonitrile) was used without further purification. Mass spectrum (ESI) 265 (M+1). (Ethyl 3-(2-chloro-4-fluorophenyl)prop-2-ynoate was prepared from 2-chloro-4-fluorobenzaldehyde as described by Chenault, J.; Dupin, J. E. *Synthesis* 1987, 5, 498.)

STEP B: 2,6-dichloro-4-(2-chloro-4-fluorophenyl)nicotinonitrile

Crude 4-(2-chloro-4-fluorophenyl)-2,6-dihydroxynicotinonitrile (16.9 mmol theoretical) was heated in 50 mL phosphorous oxychloride at 175° C. in a sealed tube. After 15 h the solution was cooled and concentrated. Water was added to the residue and the resultant mixture extracted with ethyl acetate (3×). The combined extracts were washed with water, brine and dried over magnesium sulfate. The solvent was concentrated and the residue crystallized from ethyl ether/hexanes to give 2,6-dichloro-4-(2-chloro-4-fuorophenyl)nicotinonitrile as a light brown solid. More product was obtained after silica gel chromatography purification (1/9 ethyl acetate/hexanes eluent) of the supernatant. Mass spectrum (ESI) 301 (M+1). $^1$H NMR (500 MHz, CDCl$_3$): δ 7.18–7.22(m, 1H); 7.34–7.39(m, 2H); 7.41(s, 1H).

STEP C: [2,6-dichloro-4-(2-chloro-4-fluorophenyl)pyridin-3-yl]methanol

Diisobutylaluminum hydride (1.5M toluene, 1.56 mL, 2.34 mmol) was added dropwise to a solution of 2,6-dichloro-4-(2-chloro-4-fluorophenyl)nicotinonitrile (0.644 g, 2.14 mmol) in dichloromethane at 0° C. The solution was stirred at 0° C. until no starting material remained (TLC analysis, 1 h). The solution was concentrated and 50 mL THF/2N HCl (9/1) was added to the residue. After stirring 15 min the solution was concentrated and the residue partitioned between water and dichloromethane. The phases were separated and the organic concentrated. The residue was dissolved in 50 mL THF/pH 7 buffer (9/1) and cooled to 0° C. Sodium borohydride (200 mg, 5.4 mmol) was added and the solution stirred for 40 min. The solution was then concentrated and the residue partitioned between water and ethyl acetate. The organic phase was washed with brine, dried over magnesium sulfate, filtered and concentrated. The residue ([2,6-dichloro-4-(2-chloro-4-fluorophenyl)pyridin-3-yl]methanol) was used without further purification. Mass spectrum (ESI) 306 (M+1). $^1$H NMR (500 MHz, CDCl$_3$): δ 4.37(d, 1H, J=12.6 Hz); 4.69(d, 1H, J=12.6 Hz); 7.12–7.17 (m, 1H); 7.20(s, 1H); 7.28–7.35(m, 2H).

STEP D: 3-(bromomethyl)-2,6-dichloro-4-(2-chloro-4-fluorophenyl)pyridine.

Triphenyl phosphine (0.67 g, 2.55 mol) and carbon tetrabromide (0.85 g, 2.56 mmol) were added to a solution of [2,6-dichloro-4-(2-chloro-4-fluorophenyl)pyridin-3-yl]methanol (2.14 mmol theoretical) in 15 mL acetonitrile at rt. After stirring overnight, the solution was concentrated and the residue partitioned between water and dichloromethane. The organic phase was washed with brine, dried over magnesium sulfate and concentrated. The residue was purified by silica gel chromatography using ethyl ether/hexanes as the eluent to give 3-(bromomethyl)-2,6-dichloro-4-(2-chloro-4-fluorophenyl)pyridine. Mass spectrum (ESI) 368 (M+1). $^1$H NMR (500 MHz, CDCl$_3$): δ 4.10(d, 1H, J=10.8 Hz); 4.53(d, 1H, J=10.6 Hz); 7.17(s, 1H); 7.15–7.21(m, 1H); 7.30–7.34(m, 1H); 7.36–7.41(m, 1H).

COMPOUND BBB2
7-chloro-5-(2-chloro-4-fluorophenyl)-1-(2,6-dichlorophenyl)-1,8-naphthyridin-2(1H)-one

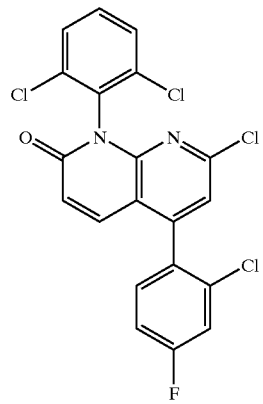

The title compound was, prepared from 3-(bromomethyl)-2,6-dichloro-4-(2-chloro-4-fluorophenyl)pyridine (COMPOUND BBB1) by a procedure analogous to that described in COMPOUND HH1 and COMPOUND HH2. Mass spectrum (ESI) 453 (M+1). $^1$H NMR (500 MHz, CDCl$_3$): δ 6.8 (d, 1H, J=9.9 Hz); 7.13 (s, 1H); 7.18–7.24 (m, 1H); 7.36–7.40(m, 2H); 7.42–7.48(m, 2H); 7.54–7.58(m, 2H).

COMPOUND BBB3
7-chloro-5-(2-fluorophenyl)-1-(2,6-dichlorophenyl)-1,8-napthyridin-2(1H)-one

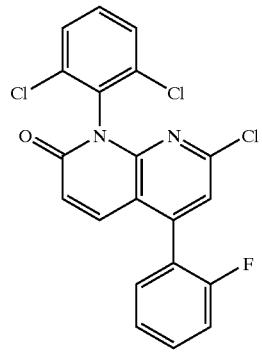

The title compound was prepared as described in COMPOUND BBB2 and COMPOUND BBB1 with the following exception: 4-(2-fluorophenyl)-2,6-dihydroxynicotinonitrile was prepared from 2-cyanoacetamide and ethyl 3-(2-fluorophenyl)-3-oxopropanoate as described by Katritzky, A. R.; et al *J. Heterocycl. Chem.* 1995, 32, 979. Mass spectrum (ESI) 419 (M+1).

COMPOUND BBB4
7-chloro-1-(2,6-dichlorophenyl)-5-phenyl-1,8-naphthyridin-2(1H)-one

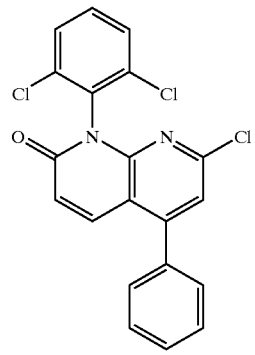

The title compound was prepared by a procedure analogous to that described in COMPOUND BBB3. Mass spectrum (ESI) 401 (M+1).

EXAMPLE BBB1
7-(1-tert-butylpiperidin-4-yl)-5-(2-chloro-4-fluorophenyl)-1-(2,6-dichlorophenyl)-1,8-naphthyridin-2(1H)-one

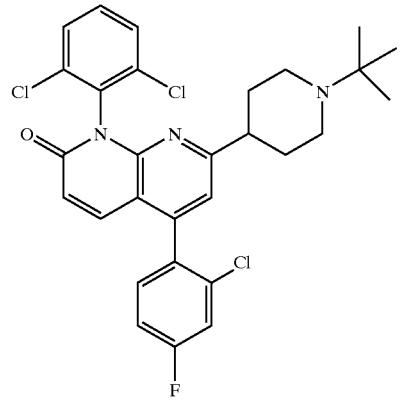

The title compound was prepared from 7-chloro-5-(2-chloro-4-fluorophenyl)-1-(2,6-dichlorophenyl)-1,8-naphthyridin-2(1H)-one (COMPOUND BBB2) by a procedure analogous to that described inn EXAMPLE HH1. Mass spectrum (ESI) 558 (M+1). $^1$H NMR (500 MHz, CD$_3$OD): δ 1.15(s, 9H); 1.61–1.77(m, 2H); 1.89–1.96(m, 2H); 2.41–2.52(m, 2H); 2.77–2.86(m, 1H); 3.08–3.18(m, 2H); 6.75(d, 1H, J=9.6 Hz); 7.29–7.34(m, 1H); 7.48–7.55(m, 3H); 7.61–7.64(m, 2H); 7.66(d, 1H, J=9.9 Hz).

EXAMPLE BBB2
7-(1-tert-butylpiperidin-4-yl)-1-(2,6-dichlorophenyl)-5-(2-fluorophenyl)-1,8-naphthyridin-2(1H)-one

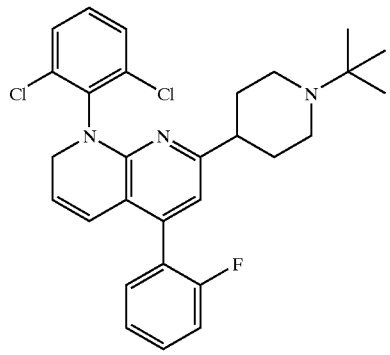

The title compound was prepared from 7-chloro-5-(2-fluorophenyl)-1-(2,6-dichlorophenyl)-1,8-naphthyridin-2(1H)-one (COMPOUND BBB3) by a procedure analogous to that described in EXAMPLE HH1. Mass spectrum (ESI) 524 (M+1). $^1$H NMR (500 MHz, CD$_3$OD): δ 1.10(s, 9H); 1.64–1.73(m 2H); 1.83–1.90(m, 2H); 2.29–2.38(m, 2H); 2.70–2.79(m, 1H); 3.01–3.09(m, 2H); 6.75(d, 1H, 9.9 Hz); 7.24(s, 1H); 7.32–7.43(m, 2H); 7.46–7.54(m, 2H); 7.57–7.63(m, 3H, 7.77–7.82(m, 1H).

EXAMPLE BBB3
7-(1-tert-butylpiperidin-4-yl)-1-(2,6-dichlorophenyl)-5-phenyl-1,8-napthyridin-2(1H)-one

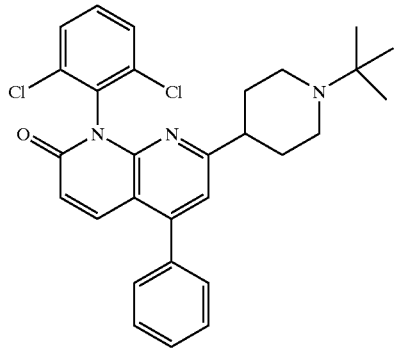

The title compound was prepared from 7-chloro-1-(2,6-dichlorophenyl)-5-phenyl-1,8-naphthyridin-2(1H)-one (COMPOUND BBB4) by a procedure analogous to that described in EXAMPLE HH1. Mass spectrum (ESI) 506 (M+1).). $^1$H NMR (500 MHz, CD$_3$OD): δ 1.09(s, 9H); 1.62–1.72(m, 2H); 1.82–1.89(m, 2H); 2.25–2.33(m, 2H); 2.68–2.76(m, 1H); 3.00–3.07(m, 2H); 6.74(d, 1H, J=9.8 Hz); 7.22(s, 1H); 7.49–7.63(m, 1H); 8.03(d, 1H, J=9.8 Hz).

EXAMPLE BBB4
7-(1-tert-butylpiperidin-4-yl)-5-(2-chloro-4-fluorophenyl)-1-(2,6-dichlorophenyl)-3,4-dihydroquinazolin-2(1H)-one

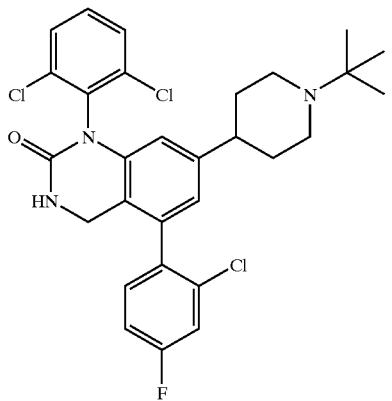

The title compound was prepared from 1-(2,6-dichlorophenyl)-5-(2-chloro-4-fluorophenyl)-7-oxytrifluormethylsulfunyl-3,4-dihydro-2(1H)-quinazolinone (INTERMEDIATE 62) by a procedure analogous to that described in EXAMPLE HH1. Mass spectrum (ESI) 560 (M+1). $^1$H NMR (500 MHz, CD$_3$OD): δ 1.10(s, 9H); 1.50–1.60(m, 2H); 1.74–1.79(m, 2H); 2.21–2.30(m, 2H); 2.37–2.45(m, 1H); 3.09–3.15(m, 2H); 4.24(m, 2H); 6.03(s, 1H); 6.78(s, 1H); 7.17–7.22(m, 1H); 7.34–7.39(m, 2H); 7.51(t, 1H, J=8.1 Hz); 7.60–7.64(m, 2H).

EXAMPLE BBB5
7-[(1-tert-butylpiperidin-4-yl)oxy]-5-(2-chloro-4-fluorophenyl)-1-(2,6-dichlorophenyl)-1,8-naphthyridin-2(1H)-one

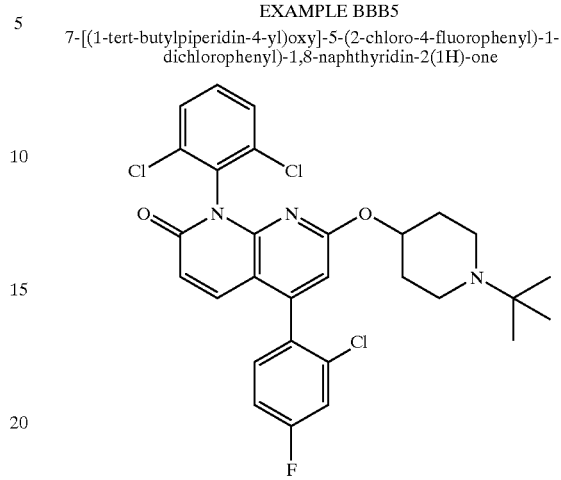

The title compound was prepared from 7-chloro-5-(2-chloro-4-fluorophenyl)-1-(2,6-dichlorophenyl)-1,8-naphthyridin-2(1H)-one (COMPOUND BBB2) by a procedure analogous to that described in EXAMPLE HH10. Mass spectrum (ESI) 574 (M+1). $^1$H NMR (500 MHz, CD$_3$OD): δ 1.12(s, 9H); 1.60–1.71(m, 2H); 1.82–1.91(m, 2H); 2.13–2.26(m, 2H); 2.88–2.96(m, 2H); 4.34–4.42(m, 1H); 6.61(s, 1H); 6.63(d, 1H, J=3.4 Hz); 7.27–7.30(m, 1H); 7.47–7.50(m, 2H); 7.54–7.58(m, 2H); 7.65–7.69(m, 2H).

EXAMPLE BBB6
7-[(1-tert-butylpiperidin-4-yl)oxy]-1-(2,6-dichlorophenyl)-5-(2-fluorophenyl)-1,8-naphthyridin-2(1H)-one

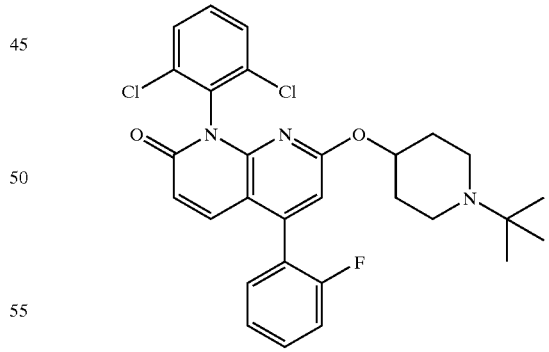

The title compound was prepared from 7-chloro-5-(2-fluorophenyl)-1-(2,6-dichlorophenyl)-1,8-naphthyridin-2(1H)-one (COMPOUND BBB3) by a procedure analogous to that described in EXAMPLE HHH10. Mass spectrum (ESI) 540 (M+1).

EXAMPLE BBB7

7-[(1-tert-butylazetidin-3-yl)oxy]-1-(2,6-dichlorophenyl)-5-(2-fluorophenyl)-1,8-naphthyridin-2(1H)-one

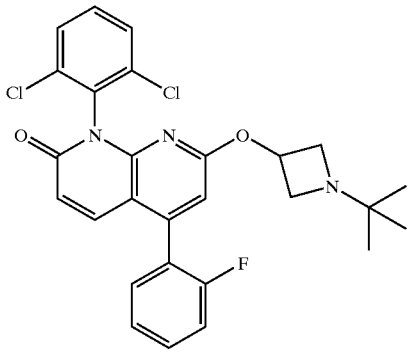

The title compound was prepared from 7-chloro-5-(2-fluorophenyl)-1-(2,6-dichlorophenyl)-1,8-naphthyridin-2(1H)-one (COMPOUND BBB3) by a procedure analogous to that described in EXAMPLE RRR-4. Mass spectrum (ESI) 512 (M+1). (1-tert-Butylazetidin-3-ol was prepared as described by Gaertner, V. *Tetrahedron Letters* 1966, 4691.)

EXAMPLE BBB8

7-{[(1R,5S)-3-tert-butyl-3-azabicyclo[3.1.0]hex-6-yl]methoxy}-5-(2-chloro-4-fluorophenyl)-1-(2,6-dichlorophenyl)-1,8-naphthyridin-2(1H)-one

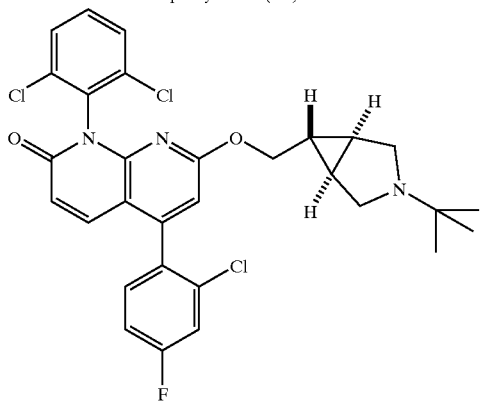

The title compound was prepared from 7-chloro-5-(2-chloro-4-fluorophenyl)-1-(2,6-dichlorophenyl)-1,8-naphthyridin-2(1H)-one (COMPOUND BBB2) by a procedure analogous to that described in EXAMPLE HHH10. Mass spectrum (ESI) 586 (M+1). (The requisite primary alcohol was prepared by a procedure analogous to that described in Brighty, K. E.; Castaldi, M. J. *SYNLETT* 1996, 1097.)

EXAMPLE BBB9

7-[(1-tert-butylazetidin-3-yl)thio]-5-(2-chloro-4-fluorophenyl)-1-(2,6-dichlorophenyl)-1,8-naphthyridin-2(1H)-one

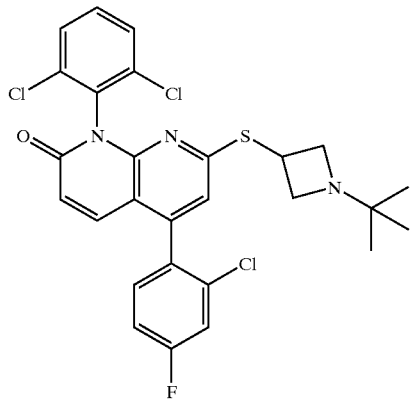

Potassium thioacetate 69 mg, 0.60 mmol) was added to a solution of 1-tert-butylazetidin-3-yl 4-methylbenzenesulfonate (103 mg, 0.36 mmol) in 1.5 mL dimethylformamide. After stirring at 50° C. overnight, the solution was cooled to rt and sodium borohydride (30 mg, 0.8 mmol) was added. After stirring for 1 hour, 7-chloro-5-(2-chloro-4-fluorophenyl)-1-(2,6-dichlorophenyl)-1,8-naphthyridin-2(1H)-one (COMPOUND BBB2) (30 mg, 0.07 mmol) was added. The solution was then stirred at 50° C. for 1.5 h. The reaction mixture was concentrated and the crude residue partitioned between ethyl acetate and $K_2CO_3$ aq. The organic phase was dried over magnesium sulfate and concentrated. The residue was purified by preparative thin layer silica gel chromatography using EtOAc/MeOH/Et$_3$N (98.5/1/0.5) as the eluent to give the title compound. Mass spectrum (ESI) 562 (M+1). $^1$H NMR (500 MHz, CD$_3$OD): δ 0.93(s, 9H); 3.01–3.07(m, 2H); 3.15–3.20(m, 2H); 3.67–3.74(m, 1H); 6.69(d, 1H, J=9.8 Hz); 7.12(s, 1H); 7.28–7.33(m, 1H); 7.47–7.51(m, 2H); 7.57–7.63(m, 2H); 7.69–7.73(m, 2H). (1-tert-Butylazetidin-3-yl 4-methylbenzenesulfonate was prepared as described by Okutani, T.; et al *Chem. Pharm. Bull.* 1974, 22, 1490.)

EXAMPLE BBB10

7-[(1-tert-butylpiperidin-4-yl)thio]-5-(2-chloro-4-fluorophenyl)-1-(2,6-dichlorophenyl)-1,8-naphthyridin-2(1H)-one

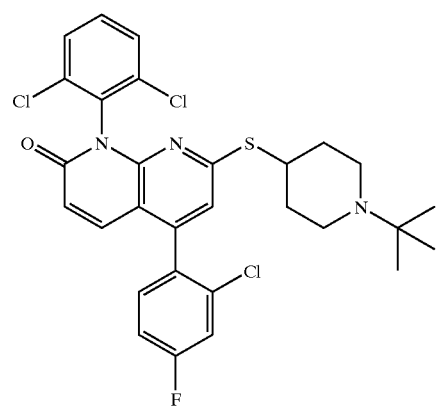

The title compound was prepared from 7-chloro-5-(2-chloro-4-fluorophenyl)-1-(2,6-dichlorophenyl)-1,8-naphthyridin-2(1H)-one (COMPOUND BBB2) by a procedure analogous to that described in EXAMPLE BBB9. Mass spectrum (ESI) 590 (M+1).

EXAMPLE BBB11

7-(4-tert-butylpiperazin-1-yl)-5-(2-chloro-4-fluorophenyl)-1-(2,6-dichlorophenyl)-1,8-naphthyridin-2(1H)-one

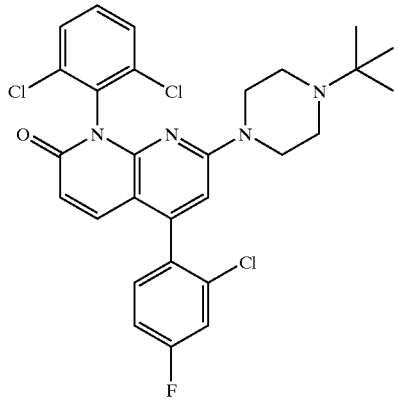

The title compound was prepared from 7-chloro-5-(2-chloro-4-fluorophenyl)-1-(2,6-dichlorophenyl)-1,8-naphthyridin-2(1H)-one (COMPOUND BBB2) and 1-tert-butylpiperazine by a procedure analogous to that described in EXAMPLE CCC6. Mass spectrum (ESI) 559 (M+1). (1-tert-Butylpiperazine was prepared as described by Cook, M. J.; et al *J.C.S. Perkin II* 1973, 325.)

EXAMPLE BBB12

7-[(1-tert-butylpiperidin-4-yl)amino]-5-(2-chloro-4-fluorophenyl)-1-(2,6-dichlorophenyl)-1,8-naphthyridin-2(1H)-one

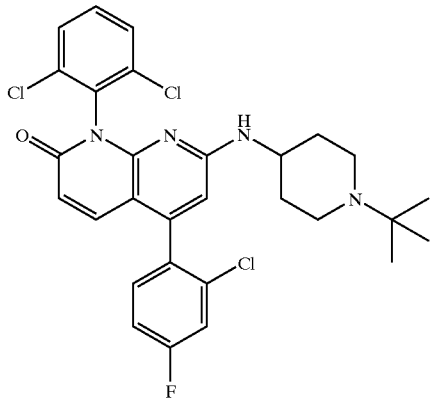

The title compound was prepared from 7-chloro-5-(2-chloro-4-fluorophenyl)-1-(2,6-dichlorophenyl)-1,8-naphthyridin-2(1H)-one (COMPOUND BBB2) and 1-tert-butylpiperidin-4-amine (COMPOUND BBB5) by a procedure analogous to that described in EXAMPLE CCC6. Mass spectrum (ESI) 573 (M+1).

$^1$H NMR (500 MHz, CDCl$_3$): δ 1.08(s, 9H); 1.27–1.42(m, 2H); 1.80–2.00(m, 4H); 2.85–2.95(m, 2H); 3.18–3.28(m, 1H); 4.67(m, 1H); 6.13(s, 1H); 6.45(d, 1H, J=9.6 Hz); 7.12–7.17(m, 1H); 7.26–7.38(m, 4H); 7.49–7.54(m, 2H).

EXAMPLE BBB13

7-[(1-tert-butylazetidin-3-yl)amino]-5-(2-chloro-4-fluorophenyl)-1-(2,6-dichlorophenyl)-1,8-naphthyridin-2(1H)-one

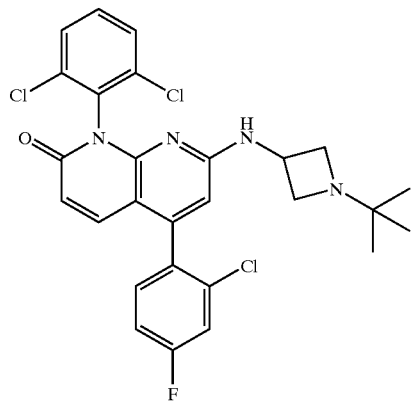

The title compound was prepared from 7-chloro-5-(2-chloro-4-fluorophenyl)-1-(2,6-dichlorophenyl)-1,8-naphthyridin-2(1H)-one (COMPOUND BBB2) and 1-tert-butylazetidin-3-amine by a procedure analogous to that described in EXAMPLE CCC6. Mass spectrum (ESI) 545 (M+1). (1-tert-Butylazetidin-3-amine was prepared as described by Okutani, T.; et al *Chem. Pharm. Bull.* 1974, 22, 1490)

COMPOUND BBB5

1-tert-butylpiperidin-4-amine

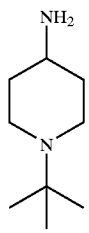

STEP A: N-benzyl-1-tert-butylpiperidin-4-amine

A dichloromethane solution (3 mL) containing 1-tert-butylpiperidin-4-one (COMPOUND PPA-1) (120 mg, 0.77 mmol), benzyl amine (0.17 mL, 1.56 mmol), acetic acid (0.05 mL) and sodium triacetoxy borohydride (246 mg, 1.16 mmol) was stirred for several days. The solution was concentrated and the residue partitioned between aqueous potassium carbonate and ethyl acetate. The organic phase was dried over sodium sulfate, filtered and concentrated. The residue was purified by silica gel chromatography using CHCl$_3$/MeOH/NH$_4$OH (87/12/1) as eluent to give N-benzyl-1-tert-butylpiperidin-4-amine. Mass spectrum (ESI) 247 (M+1). $^1$H NMR (500 MHz, CD$_3$OD): δ 1.09(s, 9H); 1.38–1.48(m, 2H); 1.91–1.97(m, 2H); 2.11–2.18(m, 2H); 2.40–2.48(m, 1H); 3.02–3.08(m, 2H); 3.76(s, 2H); 4.87(s, 1H); 7.21–7.26(m, 1H); 7.29–7.36(m, 4H).

STEP B: 1-tert-butylpiperidin-4-amine

A solution of N-benzyl-1-tert-butylpiperidin-4-amine (150 mg) and 10% palladium on carbon (200 mg) in 30 mL of MeOH was hydrogenated in a Parr shaker at 50 psi for 16 h. The solution was filtered and concentrated to give 1-tert-butylpiperidin-4-amine which was used without further purification. Mass spectrum (ESI) 157 (M+1).

EXAMPLE BBB14 methyl 1-tert-butyl-4-[4-(2-chloro-4-fluorophenyl)-8-(2,6-dichlorophenyl)-7-oxo-7,8-dihydro-1,8-naphthyridin-2-yl]piperidine-4-carboxylate

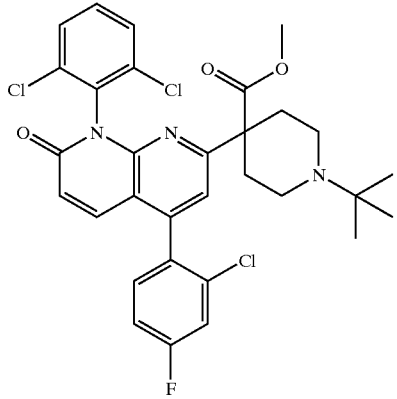

A solution of LHMDS (1.0M in THF, 0.2 mL) was added to methyl 1-tert-butylpiperidine-4-carboxylate (31 mg, 0.16 mmol) in 2 mL THF at −78° C. After 20 minutes the solution was warmed to 0° C. and stirred for an additional 10 minutes. 7-Chloro-5-(2-chloro-4-fluorophenyl)-1-(2,6-dichlorophenyl)-1,8-naphthyridin-2(1H)-one (COMPOUND BBB2) (28.5 mg, 0.063 mmol) was added and the reaction mixture stirred at 45° C. for 30 min. The solution was cooled to rt and quenched with saturated NH₄Cl. The mixture was then partitioned between water and ethyl acetate. The organic phase was washed with water, brine and dried over magnesium sulfate. The filtered solution was concentrated and the residue purified by preparative silica gel thin layer chromatography using CHCl₃/MeOH/NH₄OH (87/12/1) as eluent to give the title compound. Mass spectrum (ESI) 616 (M+1). (Methyl 1-tert-butylpiperidine-4-carboxylate was prepared from 1-tert-butylpiperidin-4-one (COMPOUND PPA-1) by a procedure analogous to that described by Street, L. J.; et al *J. Med. Chem.* 1990, 33, 2690.)

EXAMPLE BBB15

1-tert-butyl-4-[4-(2-chloro-4-fluorophenyl)-8-(2,6-dichlorophenyl)-7-oxo-7,8-dihydro-1,8-naphthyridin-2-yl]piperidine-4-carboxylic acid

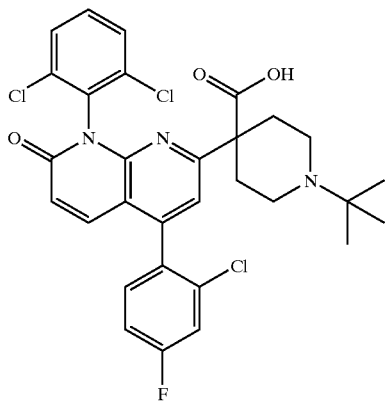

A solution of LiOH hydrate (15 mg) in 0.5 mL water was added to methyl 1-tert-butyl-4-[4-(2-chloro-4-fluorophenyl)-8-(2,6-dichlorophenyl)-7-oxo-7,8-dihydro-1,8-naphthyridin-2-yl]piperidine-4-carboxylate (EXAMPLE BBB9) (6.4 mg, 0.01 mmol) in 0.5 mL THF. After stirring 2 days, the solution was concentrated and the residue treated with 2 mL 2N HCl. The mixture was extracted with ethyl acetate(2×) and the combined organics washed with water and brine. The solvent was dried over magnesium sulfate and concentrated to give the title compound. Mass spectrum (ESI) 602 (M+1).

EXAMPLE BBB16

1-tert-butyl-4-[4-(2-chloro-4-fluorophenyl)-8-(2,6-dichlorophenyl)-7-oxo-7,8-dihydro-1,8-naphthyridin-2-yl]piperidine-4-carboxamide

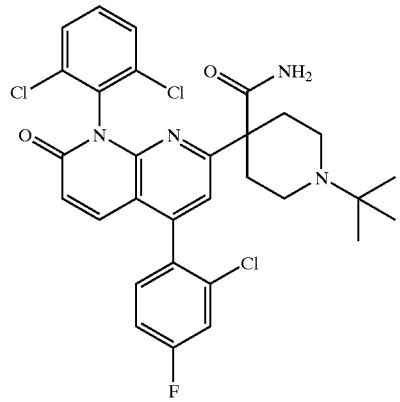

To a suspension of ammonium chloride (15.5 mg, 0.29 mmol) in 1 mL benzene at 0° C. was added trimethylaluminum(2.0M in toluene, 0.15 mL). The reaction was warmed to rt and stirred for 1 h. Methyl 1-tert-butyl-4-[4-(2-chloro-4-fluorophenyl)-8-(2,6-dichlorophenyl)-7-oxo-7,8-dihydro-1,8-naphthyridin-2-yl]piperidine-4-carboxylate (EXAMPLE BBB9) (9.7 mg, 0.016 mmol) was added and the solution was stirred overnight at 50° C. The solution was then heated at 80° C. for 10 h. The solution was then cooled to rt and concentrated. The residue was partitioned between EtOAc/NaHCO₃ sat. The organic phase was washed with water, brine, dried over magnesium sulfate and filtered. The solution was concentrated and the residue purified by preparative silica gel thin layer chromatography using CHCl₃/MeOH/NH₄OH (95/5/0.5) as the eluent to give the,title compound. Mass spectrum (ESI) 601 (M+1).

EXAMPLE BBB17

7-[1-tert-butyl-4-(hydroxymethyl)piperidin-4-yl]-5-(2-chloro-4-fluorophenyl)-1-(2,6-dichlorophenyl)-1,8-naphthyridin-2(1H)-one

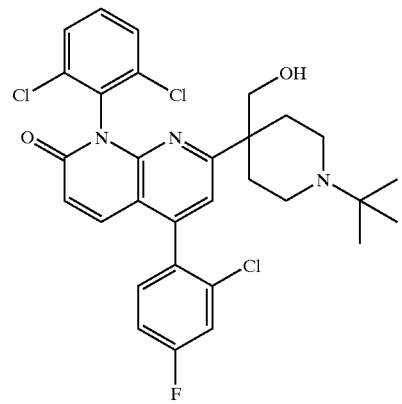

Lithium aluminum hydride (1.0M THF, 0.1 mL) was added dropwise to a solution of methyl 1-tert-butyl-4-[4-(2-chloro-4-fluorophenyl)-8-(2,6-dichlorophenyl)-7-oxo-7,8-dihydro-1,8-naphthyridin-2-yl]piperidine-4-carboxylate (EXAMPLE BBB9) (10.4 mg, 0.017 mmol) in 0.5 mL THF at 0° C. After 20 min, the reaction was quenched with 2N HCl. The reaction mixture was extracted with ethyl acetate (2×) and the combined extracts washed with water and brine. The solution was concentrated and the residue purified by preparative silica gel thin layer chromatography using CHCl$_3$/MeOH/NH$_4$OH (95/5/0.5) as the eluent to give the title compound. Mass spectrum (ESI) 588 (M+1).

SCHEME ABA-1

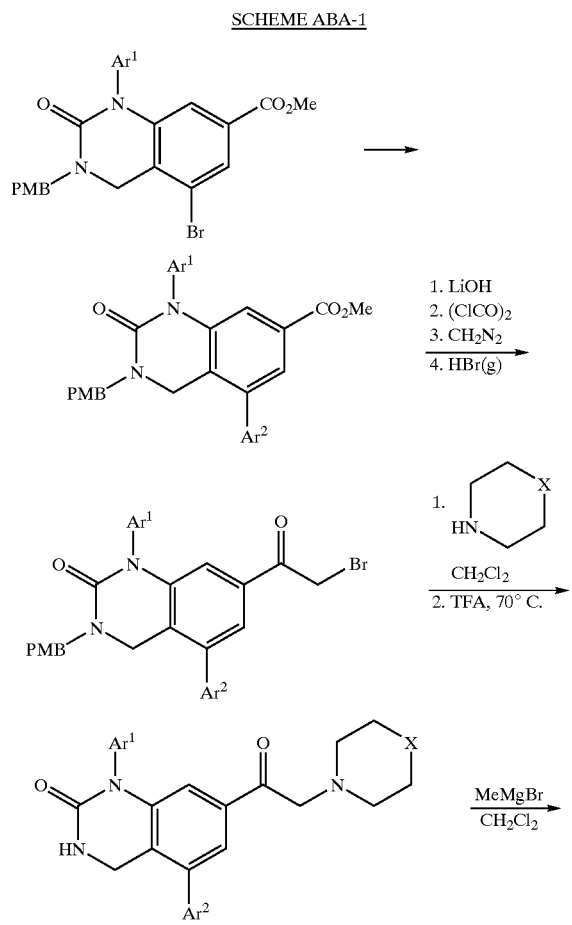

SCHEME ABA-2

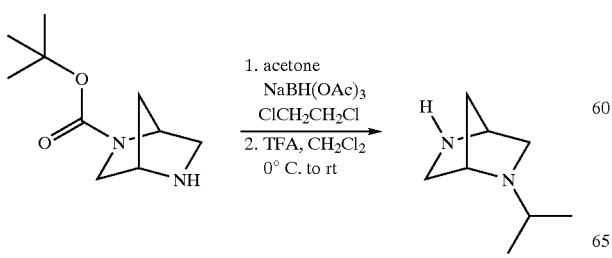

SCHEME ABA-3

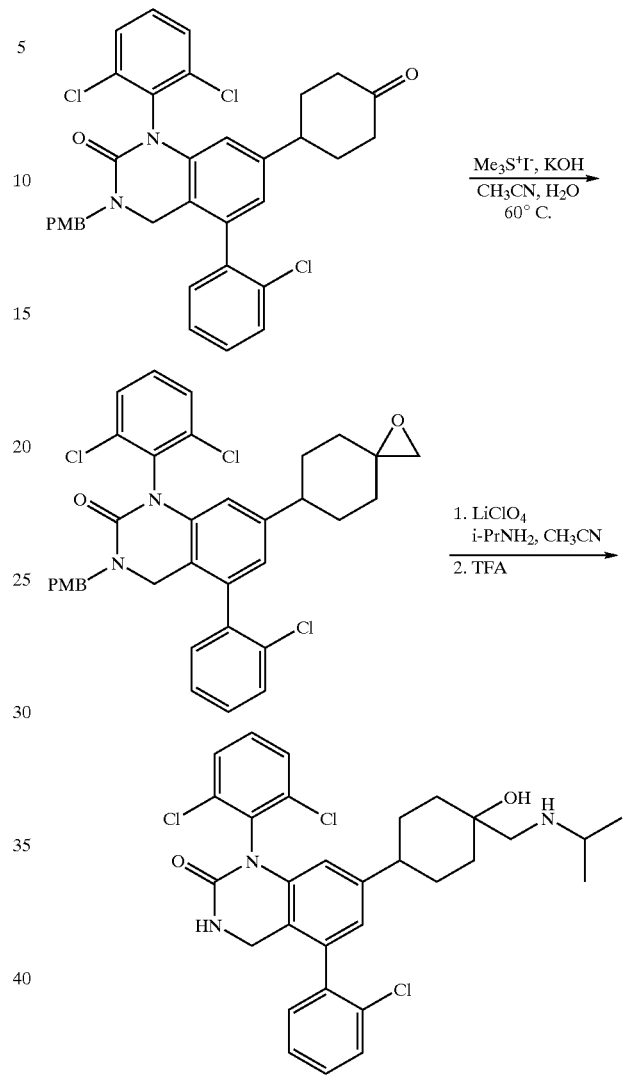

SCHEME ABA-4

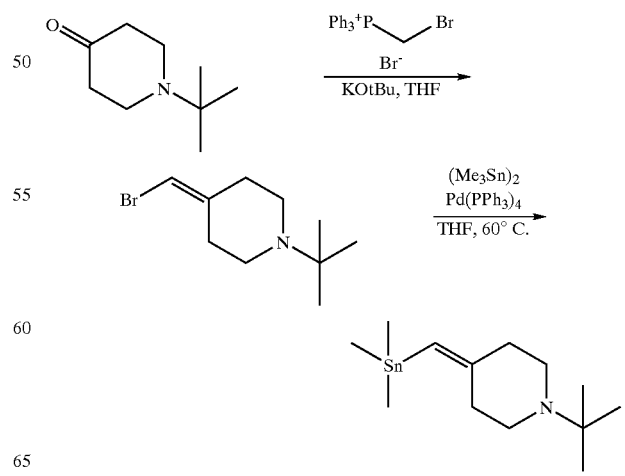

SCHEME ABA-5

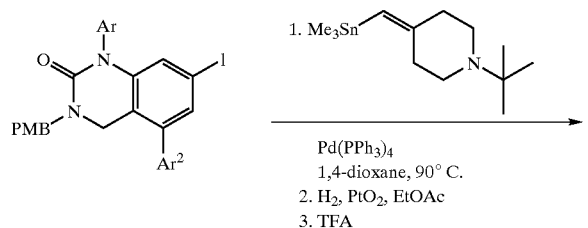

SCHEME ABA-6

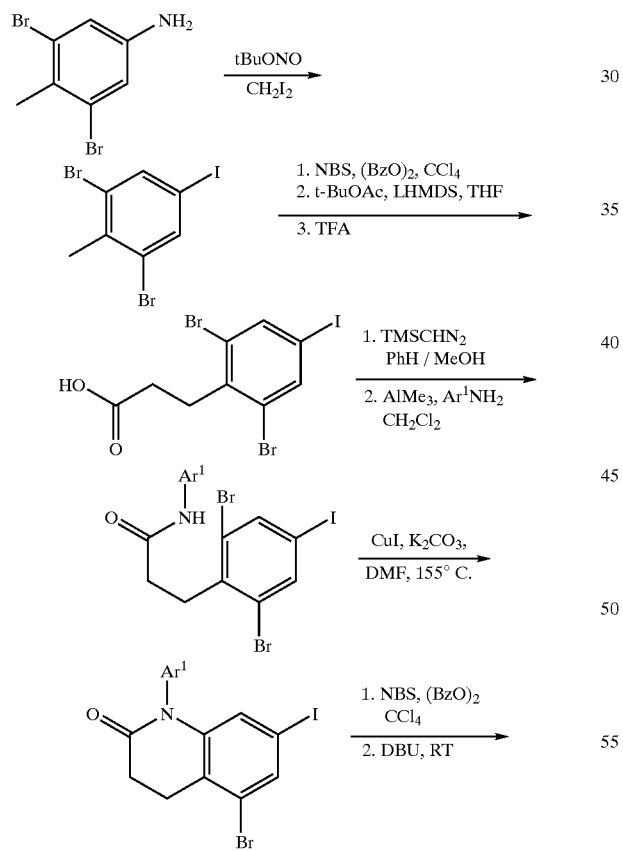

SCHEME ABA-7

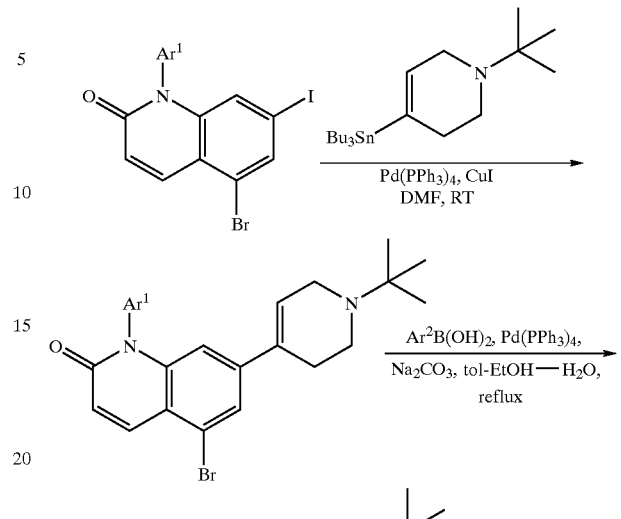

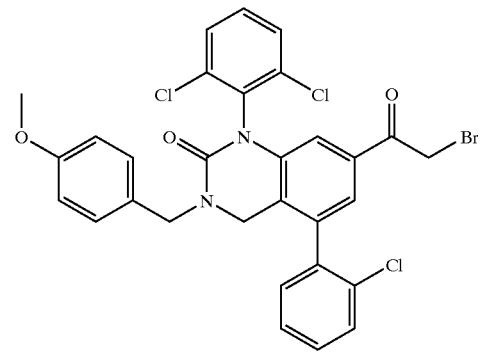

INTERMEDIATE ABA1

7-(Bromoacetyl)-5-(2-chlorophenyl)-1-(2,6-dichlorophenyl)-3-(4-methoxybenzyl)-3,4-dihydroquinazolin-2(1H)-one

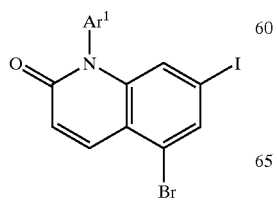

Step A: Methyl 5-(2-chlorophenyl)-1-(2,6-dichlorophenyl)-3-(4-methoxybenzyl)-2-oxo-1,2,3,4-tetrahydroquinazoline-7-carboxylate The title compound was prepared from methyl 5-bromo-1-(2,6-dichlorophenyl)-3-(4-methoxybenzyl)-2-oxo-1,2,3,4-tetrahydroquinazoline-7-carboxylate (INTERMEDIATE 28) as described in INTERMEDIATE 29.

Mass spectrum (ESI): 581.2 (M+1).

Step B: 5-(2-Chlorophenyl)-1-(2,6-dichlorophenyl)-3-(4-methoxybenzyl)-2-oxo-1,2,3,4-tetrahydroquinazoline-7-carboxylic acid The title compound was prepared from methyl 5-(2-chlorophenyl)-1-(2,6-dichlorophenyl)-3-(4-methoxybenzyl)-2-oxo-1,2,3,4-tetrahydroquinazoline-7-carboxylate (INTERMEDIATE ABA1, Step A) as described INTERMEDIATE 59.

Mass spectrum (ESI): 567 (M+1).

Step C: 7-(Bromoacetyl)-5-(2-chlorophenyl)-1-(2,6-dichlorophenyl)-3-(4-methoxybenzyl)-3,4-dihydroquinazolin-2(1H)-one To a solution of 5-(2-chlorophenyl)-1-(2,6-dichlorophenyl)-3-(4-methoxybenzyl)-2-oxo-1,2,3,4-tetrahydroquinazoline-7-carboxylic acid (770 mg, 1.34 mmol) in CH$_2$Cl$_2$ (10 mL) at 0° C. was added oxalyl chloride (175 µL, 2.01 mmol) followed by DMF (20 µL, catalytic amount). The reaction mixture was stirred at 0° C. for 10 min followed by 3 h at rt. After this time, the solvent was removed in vacuo, the residue was dissolved in THF (10 mL), then the mixture was cooled down to 0° C. Diazomethane in ether was added to this slowly until the reaction mixture turned yellow and stirred for 15 min at 0° C. followed by 30 min at rt. The excess diazomethane was quenched by addition of a few drops of acetic acid, and the solvent was removed in vacuo to give crude diazomethyl ketone. Diazomethyl ketone was dissolved in CHCl$_3$ (10 mL) and cooled down to 0° C., and HBr was bubbled into the reaction mixture briefly (evolution of N$_2$ was visible). The reaction turned dark yellow, and TLC analysis indicated the reaction was complete. The solvent was removed in vacuo, and the crude product was purified by flash chromatography eluting with 1:5 acetone:hexane to obtain the title compound. $^1$H NMR (CDCl$_3$, 500 MHz): δ 7.56–6.75 (m, 13 aromatic H's); 4.68 (d, J=14.9 Hz, 1H); 4.41 (d, J=14.9 Hz); 4.27 (m, 3H); 4.13 (d, J=15.8 Hz, 1H); 3.8 (s, 3H).

EXAMPLE ABA1

5-(2-Chlorophenyl)-1-(2,6-dichlorophenyl)-7-[(4-isopropylpiperazin-1-yl)acetyl]-3,4 dihydroquinazolin-2(1H)-one

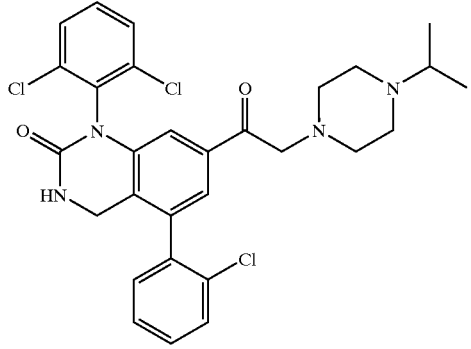

Step A: 5-(2-Chlorophenyl)-1-(2,6-dichlorophenyl)-7-[(4-isopropylpiperazin-1-yl)acetyl]-3-(4-methoxybenzyl)-3,4-dihydroquinazolin-2(1H)-one To a solution of 7-(bromoacetyl)-5-(2-chlorophenyl)-1-(2,6-dichlorophenyl)-3-(4-methoxybenzyl)-3,4-dihydroquinazolin-2(1H)-one (38 mg, 0.059 mmol) in CH$_2$Cl$_2$ (1 mL) was 1-isopropylpiperazine (15 mg, 0.118 mmol) at rt. The reaction mixture was stirred for 1.5 h, then the solvent was removed in vacuo. The resulting crude material was purified by preparative thin layer chromatography using 10% MeOH in CH$_2$Cl$_2$ as an eluent to give the title compound. Mass spectrum (ESI): 691.2 (M+1).

Step B: 5-(2-Chlorophenyl)-1-(2,6-dichlorophenyl)-7-[(4-isopropylpiperazin-1-yl)acetyl]-3,4-dihydroquinazolin-2(1H)-one 5-(2-Chlorophenyl)-1-(2,6-dichlorophenyl)-7-[(4-isopropylpiperazin-1-yl)acetyl]-3-(4-methoxybenzyl)-3,4-dihydroquinazolin-2(1H)-one (36 mg, 0.052 mmol) was dissolved in trifluoroacetic acid (0.8 mL), and this mixture was heated at 70° C. for 30 min. After cooling it down, trifluoroacetic acid was removed by co-evaporation with toluene to give crude product. This was purified by preparative thin layer chromatography using 5% 2M NH$_3$ in MeOH/CH$_2$Cl$_2$ as an eluent to give the title compound. $^1$H NMR (CDCl$_3$, 500 MHz): δ 7.54–7.29 (m, 8H); 6.94 (s, 1H); 5.44 (s, 1H); 4.47 (d, J=15.6 Hz, 1H); 4.29 (d, J=15.6 Hz, 1H); 3.54 (Abq, J=4.1, 14.9 Hz, 2H); 2.62 (m, 1H); 2.48 (brs, 8H); 1.03 (2 s, 6H). Mass spectrum (ESI): 571.2 (M+1).

EXAMPLE ABA2

5-(2-Chlorophenyl)-1-(2,6-dichlorophenyl)-7-(morpholin-4-ylacetyl)-3,4-dihydroquinazolin-2(1H)-one

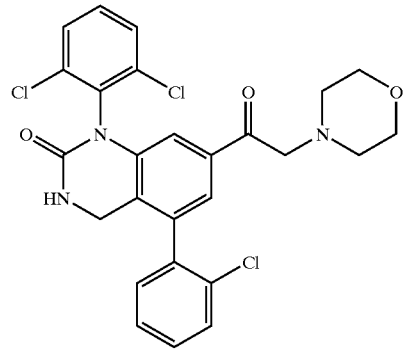

The title compound was prepared from 7-(bromoacetyl)-5-(2-chlorophenyl)-1-(2,6-dichlorophenyl)-3-(4-methoxybenzyl)-3,4-dihydroquinazolin-2(1H)-one and using morpholine as an amine as described in EXAMPLE ABA1. $^1$H NMR (CDCl$_3$, 500MHz): δ 7.53–7.27 (m, 8H); 6.92 (s, 1H); 5.91 (brs, 1H); 4.45 (d, J=15.5 Hz, 1H); 4.28 (d, J=15.5 Hz, 1H); 3.64 (m, 4H); 3.55 (Abq, J=3.7, 15.8 Hz, 2H); 2.44 (m, 4H). Mass spectrum (ESI): 530 (M+1).

EXAMPLE ABA3

5-(2-Chlorophenyl)-1-(2,6-dichlorophenyl)-7-({4-[2-(dimethylamino)ethyl]piperazin-1-yl}acetyl)-3,4-dihydroquinazolin-2(1H)-one

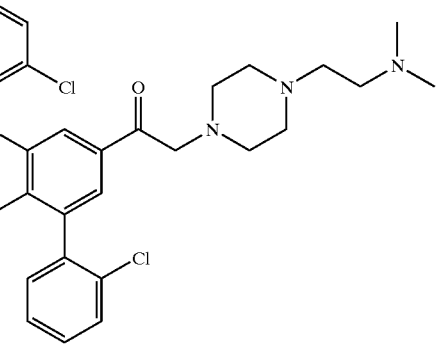

The title compound was prepared from 7-(bromoacetyl)-5-(2-chlorophenyl)-1-(2,6-dichlorophenyl)-3-(4-methoxybenzyl)-3,4-dihydroquinazolin-2(1H)-one and using N,N-dimethyl-N-(2-piperazin-1-ylethyl)amine as an amine as described in EXAMPLE ABA1. $^1$H NMR (CDCl$_3$, 500 MHz): δ 7.53–7.28 (m, 8H); 6.92 (s, 1H); 5.6 (s, 1H);

4.46 (d, J=15.4 Hz, 1H); 4.28 (d, J=15.4 Hz, 1H); 3.54 (Abq, J=2.7, 16.1 Hz, 2H); 2.42 (m, 12H); 2.24 (s, 6H). Mass spectrum (ESI): 600.2 (M+1).

EXAMPLE ABA4

5-(2-Chlorophenyl)-1-(2,6-dichlorophenyl)-7-(piperazin-1-ylacetyl)-3,4-dihydroquinazolin-2(1H)-one

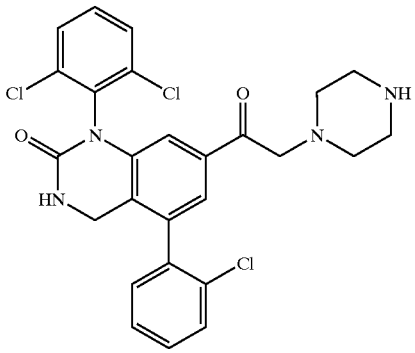

Step A: 2,6-Dibromo-4-iodotoluene

To a solution of 3,5-dibromo-4-methylaniline (4.17 g, 15.74 mmol) in CH$_2$I$_2$ (10 mL) was added tert-butylnitrite (3.0 mL, 23.61 mmol) slowly at 0° C. while stirring vigorously. The ice bath was removed and the reaction mixture was stirred at rt while the reaction was very exothermic, then placed in 80° C. oil bath and heated for 20 min. CH$_2$I$_2$ was distilled off under high vacuum, and the remaining residue was purified by flash chromatography eluting with 100% hexane to give the title compound.

Step B: 5-Bromo-1-(2,6-dichlorophenyl)-7-iodoquinolin-2(1H)-one

The title compound was prepared from 2,6-dibromo-4-iodotoluene by procedures analogous to that described in COMPOUND HHH1 and COMPOUND HHH2. $^1$H NMR (CDCl$_3$, 500 MHz): δ 8.2 (d, J=9.9 Hz, 1H); 7.84 (s, 1H); 7.59–7.45 (m, 3H); 6.87 (d, J=9.9 Hz, 1H); 6.76 (s, 1H). Mass spectrum (ESI): 496.2 (M+1).

EXAMPLE ABA5

5-(2-Chlorophenyl)-1-(2,6-dichlorophenyl)-7-(1-hydroxy-1-methyl-2-piperazin-1-ylethyl)-3,4-dihydroquinazolin-2(1H)-one

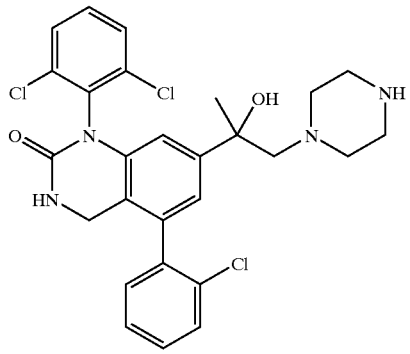

Step A: tert-Butyl 4-{2-[5-(2-chlorophenyl)-1-(2,6-dichlorophenyl)-3-(4-methoxybenzyl)-2-oxo-1,2,3,4-tetrahydroquinazolin-7-yl]-2-hydroxypropyl}piperazine-1-carboxylate To a solution of methylmagnesium bromide (68 μL, 1.4M) in CH$_2$Cl$_2$ (0.2 mL) at 0° C. was added tert-butyl 4-{2-[5-(2-chlorophenyl)-1-(2,6-dichlorophenyl)-3-(4-methoxybenzyl)-2-oxo-1,2,3,4-tetrahydroquinazolin-7-yl]-2-oxoethyl}piperazine-1-carboxylate (EXAMPLE ABA4, Step A) (35.6 mg, 0.047 mmol) dissolved in CH$_2$Cl$_2$ (0.3 mL) slowly. The reaction mixture was stirred for 2 h while warming up to rt. It was quenched with saturated aqueous solution of NH$_4$Cl, and extracted with CH$_2$Cl$_2$. The combined organic layers were washed with brine and dried over Na$_2$SO$_4$. After removal of the solvent, the crude product was purified by preparative thin layer chromatography eluting with 1:3 acetone:hexane to obtain the title compound. Mass spectrum (ESI): 765.2 (M+1).

Step B: 5-(2-Chlorophenyl)-1-(2,6-dichlorophenyl)-7-(1-hydroxy-1-methyl-2-piperazin-1-ylethyl)-3,4-dihydroquinazolin-2(1H)-one The title compound was prepared from tert-butyl 4-{2-[5-(2-chlorophenyl)-1-(2,6-dichlorophenyl)-3-(4-methoxybenzyl)-2-oxo-1,2,3,4-tetrahydroquinazolin-7-yl]-2-hydroxypropyl}piperazine-1-carboxylate as described in EXAMPLE ABA1, Step B. Partial $^1$H NMR (CDCl$_3$, 500 MHz): δ 7.53–7.26 (m, 7H); 5.48 (brs, 1H); 4.4–4.2 (m, 2H); 2.7 (m, 4H); 2.22 (m, 4H); 1.3 (2s, 3H). Mass spectrum (ESI): 545.2 (M+1).

EXAMPLE ABA6

5-(2-chlorophenyl)-1-(2,6-dichlorophenyl)-7-(4-{[2-(dimethylamino)ethyl]amino}cyclohexyl)-3,4-dihydroquinazolin-2(1H)-one

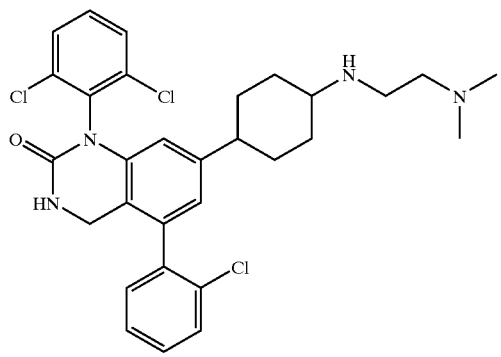

The title compound was prepared from 5-(2-chlorophenyl)-1-(2,6-dichlorophenyl)-7-(4-oxocyclohexyl)-3,4-dihydroquinazolin-2(1H)-one (INTERMEDIATE 73) and using N,N-dimethylethane-1,2-diamine as described in EXAMPLE 51. Diastereomer A $^1$H NMR (CDCl$_3$, 500 MHz): δ 7.52–7.29 (m, 7H); 6.79 (s, 1H); 5.98 (s, 1H); 5.21 (s, 1H); 4.39 (d, J=14.2 Hz, 1H); 4.21 (d, J=14.2 Hz, 1H); 2.77 (m, 1H); 2.61 (m, 2H); 2.38 (m, 3H); 2.19 (s, 6H); 1.74–1.51 (m, 8H). Diastereomer B $^1$H NMR (CDCl$_3$, 500 MHz): δ 7.53–7.27 (m, 7H); 6.74 (s, 1H); 5.95 (s, 1H); 5.27 (s, 1H); 4.37 (d, J=14.4 Hz, 1H); 4.21 (d, J=14.4 Hz, 1H); 2.68 (t, J=6.2 Hz, 2H); 2.39 (t, J=6.2 Hz, 2H); 2.33 (m, 2H); 2.2 (s, 6H); 1.99–1.14 (m, 8H).

Mass spectrum (ESI): 571.2 (M+1).

INTERMEDIATE ABA2

2-Isopropyl-2,5-diazabicyclo[2.2.1]heptane

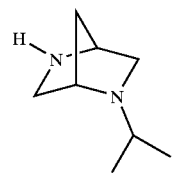

Step A: tert-Butyl 5-isopropyl-2,5-diazabicyclo[2.2.1]heptane-2-carboxylate

The title compound was prepared from tert-butyl 2,5-diazabicyclo[2.2.1]heptane-2-carboxylate and using acetone as described in EXAMPLE AAA1, Step A.

Step B: 2-Isopropyl-2,5-diazabicyclo[2.2.1]heptane

The title compound was prepared from tert-Butyl 5-isopropyl-2,5-diazabicyclo[2.2.1]heptane-2-carboxylate as described in EXAMPLE AAA1, Step B.

$^1$H NMR (CDCl$_3$, 500 MHz): δ 3.61(s, 1H); 3.51 (s, 1H); 3.19 (d, J=10.7 Hz, 1H); 3.15 (dd, J=2.4, 9.7 Hz, 1H); 2.78 (d, J=10.3 Hz, 1H); 2.62 (m, 1H); 2.27 (d, J=9.8 Hz, 2H); 1.83(d, J=9.6 Hz, 1H); 1.61 (d, J=9.8 Hz, 1H); 1.07(d, J=6.2 Hz, 3H); 1.04 (d, J=6.2 Hz, 3H).

EXAMPLE ABA7

5-(2-Chlorophenyl)-1-(2,6-dichlorophenyl)-7-(5-isopropyl-2,5-diazabicyclo-[2.2.1]hept-2-yl)-3,4-dihydroquinazolin-2(1H)-one

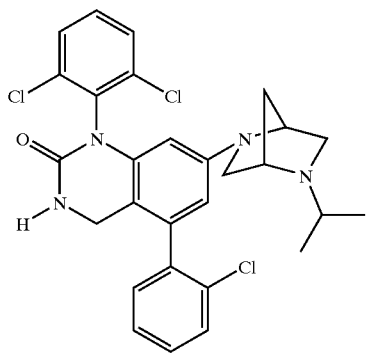

Step A: 5-(2-Chlorophenyl)-1-(2,6-dichlorophenyl)-7-(5-isopropyl-2,5-diazabicyclo[2.2.1]hept-2-yl)-3-(4-methoxybenzyl)-3,4-dihydroquinazolin-2(1H)-one The title compound was prepared from 5-(2-chlorophenyl)-1-(2,6-dichlorophenyl)-7-iodo-3-(4-methoxybenzyl)-3,4-dihydroquinazolin-2(1H)-one (EXAMPLE CCC34) and using 2-isopropyl-2,5-diazabicyclo[2.2.1]heptane (INTERMEDIATE ABA2) as described in EXAMPLE 80. Mass spectrum (ESI): 661.3 (M+1).

Step B: 5-(2-Chlorophenyl)-1-(2,6-dichlorophenyl)-7-(5-isopropyl-2,5-diazabicyclo-[2.2.1]hept-2-yl)-3,4-dihydroquinazolin-2(1H)-one The title compound was prepared from 5-(2-chlorophenyl)-1-(2,6-dichlorophenyl)-7-(5-isopropyl-2,5-diazabicyclo[2.2.1]hept-2-yl)-3-(4-methoxybenzyl)-3,4-dihydroquinazolin-2(1H)-one (EXAMPLE ABA7, Step A) as described in EXAMPLE ABA1, Step B. $^1$H NMR (CDCl3, 500 MHz): δ 7.52–7.31 (m, 7H); 6.07 (m, 1H); 5.3 (m, 1H); 5.13 (s, 1H); 4.32 (m, 1H); 4.13 (m, 1H); 3.88 (d, J=31.6 Hz, 1H); 3.7 (s, 1H); 3.16–3.0 (m, 3H); 2.45 (M, 2H); 1.85 (m, 2H); J=6.2 Hz, 6H). Mass spectrum (ESI): 541.2 (M+1).

EXAMPLE ABA8

5-(2-Chlorophenyl)-1-(2,6-dichlorophenyl)-7-{4-hydroxy-4-[(isopropylamino)methyl]cyclohexyl}-3,4-dihydroquinazolin-2(1H)-one

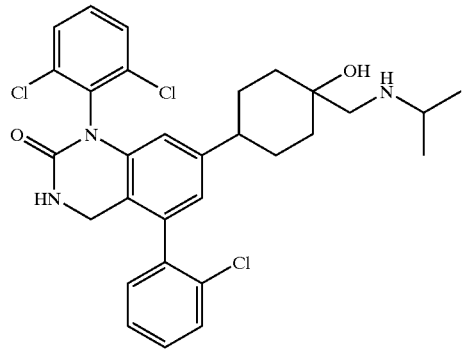

Step A: 5-(2-Chlorophenyl)-1-(2,6-dichlorophenyl)-3-(4-methoxybenzyl)-7-(1-oxaspiro[2.5]oct-6-yl)-3,4-dihydroquinazolin-2(1H)-one To a suspension of trimethylsulfonium iodide (20 mg, 0.096 mmol) in CH$_3$CN (0.3 mL) was added one drop of H$_2$O followed KOH (s) (22 mg, 0.384 mmol). This mixture was heated at 60° C. for 10 min, then added 5-(2-chlorophenyl)-1-(2,6-dichlorophenyl)-3-(4-methoxybenzyl)-7-(4-oxocyclohexyl)-3,4-dihydroquinazolin-2(1H)-one (INTERMEDIATE 76) (40 mg, 0.064 mmol) in CH$_3$CN (0.3 mL) and DMSO (0.2 mL) slowly. The reaction mixture was heated another 3.5 h, cooled to RT and diluted with CH$_2$Cl$_2$. It was washed with H$_2$O followed by brine then dried over Na$_2$SO$_4$. After removal of the solvent, the crude product was purified by preparative thin layer chromatography eluting with 1:3 acetone:hexane to give the title compound as a mixture of diastereomers. Mass spectrum (ESI): 633.2 (M+1).

Step B: 5-(2-Chlorophenyl-1-(2,6-dichlorophenyl)-7-{4-hydroxy-4-[(isopropylamino)methyl]cyclohexyl}-3-(4-methoxybenzyl)-3,4-dihydroquinazolin-2(1H)-one To a solution of 5-(2-chlorophenyl)-1-(2,6-dichlorophenyl)-3-(4 methoxybenzyl)-7-(1-oxaspiro[2.5]oct-6-yl)-3,4-dihydroquinazolin-2(1H)-one (EXAMPLE ABA8, Step A) (24.3 mg, 0.038 mmol) in CH$_3$CN (0.5 mL) was added LiClO$_4$ (24.6 mg, 0.23 mmol) and isopropylamine (10.5 mL, 0.114 mmol). The reaction mixture was heated at 55° C. for 5 days, then it was cooled. It was diluted with EtOAc, washed with H$_2$O and brine, then it was dried over Na$_2$SO$_4$. The crude material was purified by preparative TLC eluting with 5% 2M NH$_3$ in MeOH/CH$_2$Cl$_2$ to obtain diastereomer A and diastereomer B of the title compound. Mass spectrum (ESI): 692.2 (M+1).

Step C: 5-(2-Chlorophenyl)-1-(2,6-dichlorophenyl)-7-{4-hydroxy-4-[(isopropylamino)methyl]cyclohexyl}-3,4-dihydroquinazolin-2(1H)-one The title compound was obtained from 5-(2-chlorophenyl)-1-(2,6-dichlorophenyl)-7-{4-hydroxy-4-[(isopropylamino)methyl]cyclohexyl}-3-(4-methoxybenzyl)-3,4-dihydroquinazolin-2(1H)-one (each diastereomer was reacted separately) as described in EXAMPLE ABA1, Step B as diastereomer A and diastereomer B. Diastereomer A $^1$H NMR (CDCl$_3$, 500 MHz): δ 7.52–7.28 (m, 7H); 6.8 (s, 1H); 5.99 (s, 1H); 5.16 (s, 1H); 4.4 (d, J=14.2 Hz, 1H); 4.22 (d, J=14.2 Hz, 1H); 2.79 (m, 1H); 2.47 (s, 2H); 2.3 (m, 1H); 1.9–1.6 (m, 6H); 1.26 (m, 2H); 1.06 (d, J=6.2 Hz, 6H). Diastereomer B ¹H NMR (CDCl₃, 500 MHz): δ 7.53–7.28 (m, 7H); 6.74 (s, 1H); 5.96 (s, 1H); 5.2 (s, 1H); 4.39 (d, J=14.4 Hz, 1H); 4.23 (d, J=14.4 Hz, 1H); 2.77 (m, 1H); 2.63 (s, 2H); 2.41 (m, 1H); 1.79–1.36 (m, 8H); 1.06 (d, J=6.4 Hz, 6H). Mass spectrum (ESI): 572.2 (M+1).

INTERMEDIATE ABA3

1-tert-Butyl-4-[(trimethylstannyl)methylene]piperidine

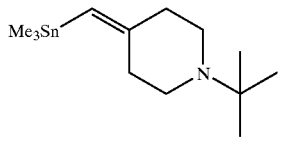

Step A: 4-(Bromomethylene)-1-tert-butylpiperidine

To a solution of (bromomethyl)triphenylphosphonium bromide (1.52 g, 3.48 mmol) in dry THF (15 mL) at −78° C. was added potassium tert-butoxide (3.5 mL, 1.0M) slowly. After stirring 20 minutes, 1-tert-butylpiperidin-4-one (COMPOUND PPA-1) (595 mg, 3.83 mmol) in THF (2 mL) was added, and the reaction mixture was warmed up to rt slowly over 2 h. The reaction mixture was quenched with brine, and it was extracted with CH₂Cl₂. The combined extracts were dried over Na₂SO₄ then concentrated in vacuo. The crude material was purified by flash chromatography eluting first with hexane then gradually increasing to 5% acetone/hexane to give the title compound. ¹H NMR (CDCl₃, 500 MHz): δ 5.85 (s, 1H); 2.56 (m, 4H); 2.43 (t, J=5.6 Hz, 2H); 2.28 (t, J=5.6 Hz, 2H); 1.08 (s, 9H).

Step B: 1-tert-Butyl-4-[(trimethylstannyl)methylene]piperidine

The title compound was prepared from 4-(bromomethylene)-1-tert-butylpiperidine (INTERMEDIATE ABA3, Step A) as described in INTERMEDIATE 69. ¹H NMR (CDCl₃, 500 MHz): δ 5.39 (s, 1H); 2.57 (m, 4H); 2.34 (t, J=5.5 Hz, 2H); 2.24 (t, J=5.5 Hz, 2H); 1.07 (s, 9H); 0.13 (s, 9H). Mass spectrum (ESI): 318.4 (M+1).

EXAMPLE ABA9

7-[(1-tert-Butylpiperidin-4-ylidene)methyl]-5-(2-chlorophenyl)-1-(2,6-dichlorophenyl)-3,4-dihydroquinazolin-2(1H)-one

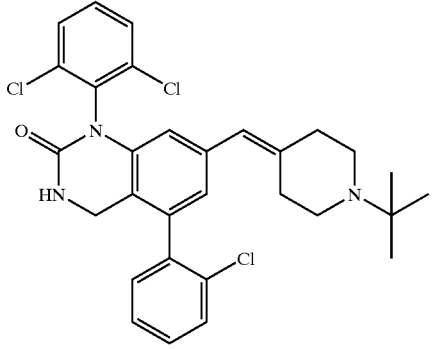

Step A: 7-[(1-tert-Butylpiperidin-4-ylidene)methyl]-5-(2-chlorophenyl)-1-(2,6-dichlorophenyl)-3-(4-methoxybenzyl)-3,4-dihydroquinazolin-2(1H)-one The title compound was prepared from 5-(2-chlorophenyl)-1-(2,6-dichlorophenyl)-7-iodo-3-(4-methoxybenzyl)-3,4-dihydroquinazolin-2(1H)-one (EXAMPLE CCC34) and using 1-tert-butyl-4-[(trimethylstannyl)methylene]piperidine (INTERMEDIATE ABA3) as described in EXAMPLE 41, Step A. Mass spectrum (ESI): 674.5 (M+1).

Step B: 7-[(1-tert-Butylpiperidin-4-ylidene)methyl]-5-(2-chlorophenyl)-1-(2,6-dichlorophenyl)-3,4-dihydroquinazolin-2(1H)-one The title compound was prepared from 7-[(1-tert-butylpiperidin-4-ylidene)methyl]-5-(2-chlorophenyl)-1-(2,6-dichlorophenyl)-3-(4-methoxybenzyl)-3,4-dihydroquinazolin-2(1H)-one (EXAMPLE ABA9, Step A) as described in EXAMPLE ABA1, Step B. ¹H NMR (CDCl₃, 500 MHz): δ 7.52–7.29 (m, 7H); 6.72 (s, 1H); 6.08 (s, 1H); 5.94 (s, 1H); 5.22 (, 1H); 4.41 (d, J=14.4 Hz, 1H); 4.23 (d, J=14.4 Hz, 1H); 2.58–2.29 (m, 8H); 1.06 (s, 9H). Mass spectrum (ESI): 554.4 (M+1).

EXAMPLE ABA10

7-[(1-tert-Butylpiperidin-4-yl)methyl]-5-(2-chlorophenyl)-1-(2,6-dichlorophenyl)-3,4-dihydroquinazolin-2(1H)-one

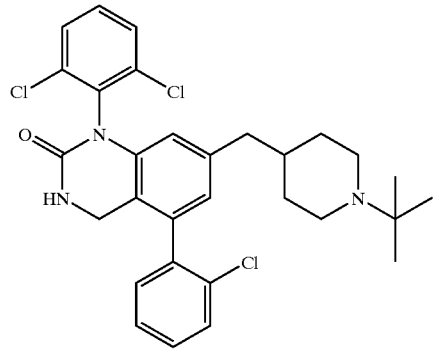

Step A: 7-[(1-tert-Butylpiperidin-4-ylidene)methyl]-5-(2-chlorophenyl)-1-(2,6-dichlorophenyl)-3-(4-methoxybenzyl)-3,4-dihydroquinazolin-2(1H)-one The title compound was prepared from 5-(2-chlorophenyl)-1-(2,6-dichlorophenyl)-7-iodo-3-(4-methoxybenzyl)-3,4-dihydroquinazolin-2(1H)-one (Kallashi) and using 1-tert-butyl-4-[(trimethylstannyl)methylene]piperidine as described in EXAMPLE 41, Step A. Mass spectrum (ESI): 674.5 (M+1).

Step B: 7-[(1-tert-Butylpiperidin-4-yl)methyl]-5-(2-chlorophenyl)-1-(2,6-dichlorophenyl)-3-(4-methoxybenzyl)-3,4-dihydroquinazolin-2(1H)-one The title compound was prepared from 7-[(1-tert-butylpiperidin-4-ylidene)methyl]-5-(2-chlorophenyl)-1-(2,6-dichlorophenyl)-3-(4-methoxybenzyl)-3,4-dihydroquinazolin-2(1H)-one as described in INTERMEDIATE 72. Mass spectrum (ESI): 676.6 (M+1).

Step C: 7-[(1-tert-Butylpiperidin-4-yl)methyl]-5-(2-chlorophenyl)-1-(2,6-dichlorophenyl)-3,4-dihydroquinazolin-2(1H)-one The title compound was prepared from 7-[(1-tert-butylpiperidin-4-yl)methyl]-5-(2-chlorophenyl)-1-(2,6-dichlorophenyl)-3-(4-methoxybenzyl)-3,4-dihydroquinazolin-2(1H)-one as described in EXAMPLE ABA1, Step B. ¹H NMR (CDCl₃, 500 MHz): δ 7.53–7.28 (m, 7H); 6.67 (s, 1H); 5.88 (s, 1H); 5.07 (s, 1H); 4.39 (d, J=14.2 Hz, 1H); 4.23 (d, J=14.2 Hz, 1H); 2.96 (brd, J=10.8 Hz, 2H); 2.37 (d, J=6.2 Hz, 2H); 1.95 (brt, J=11.1 Hz, 2H); 1.58 (brd, J=12.6 Hz, 2H); 1.34 (m, 1H); 1.15 (m, 2H); 1.04 (s, 9H). Mass spectrum (ESI): 556.6 (M+1).

INTERMEDIATE ABA4

5-Bromo-1-(2,6-dichlorophenyl)-7-iodoquinolin-2(1H)-one

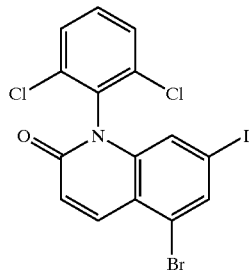

Step A: 2,6-Dibromo-4-iodotoluene

To a solution of 3,5-dibromo-4-methylaniline (4.17 g, 15.74 mmol) in CH$_2$I$_2$ (10 mL) was added tert-butylnitrite (3.0 mL, 23.61 mmol) slowly at 0° C. while stirring vigorously. The ice bath was removed and the reaction mixture was stirred at rt while the reaction was very exothermic, then placed it in a 80° C. oil bath and heated for 20 min. CH$_2$I$_2$ was distilled off under high vacuum, and the remaining residue was purified by flash chromatography eluting with 100% hexane to gave the title compound.

Step B: 5-Bromo-1-(2,6-dichlorophenyl)-7-iodoquinolin-2(1H)-one

The title compound was prepared from 2,6-dibromo-4-iodotoluene by procedures analogous to that described in COMPOUND HHH1 and COMPOUND HHH2. $^1$H NMR (CDCl$_3$, 500 MHz): δ 8.2 (d, J=9.9 Hz, 1H); 7.84 (s, 1H); 7.59–7.45 (m, 3H); 6.87 (d, J=9.9 Hz, 1H); 6.76 (s, 1H). Mass spectrum (ESI): 496.2 (M+1).

INTERMEDIATE ABA5

5-Bromo-7-(1-tert-butyl-1,2,3,6-tetrahydropyridin-4-yl)-1-(2,6-dichlorophenyl)quinolin-2(1H)-one

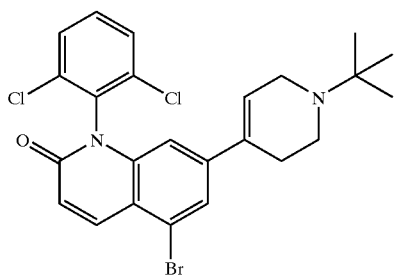

To a solution of 5-bromo-1-(2,6-dichlorophenyl)-7-iodoquinolin-2(1H)-one (INTERMEDIATE ABA4) (541 mg, 1.09 mmol) in DMF (5 mL) was added 1-tert-butyl-4-(trimethylstannyl)-1,2,3,6-tetrahydropyridine (COMPOUND PPA-2) (494 mg, 1.64 mmol) in DMF (5 mL). Tetrakis(triphenylphosphine)palladium (126 mg, 0.1 mmol) was added to this followed by CuI (156 mg, 0.82 mmol), and the reaction mixture was purged with argon and stirred at RT. After 18 h, it was filtered over Celite® and rinsed thoroughly with EtOAc. The filtrate was washed with H$_2$O followed by brine and dried over Na$_2$SO$_4$. The crude material was purified by flash chromatography eluting with 2% MeOH/CH$_2$Cl$_2$ to give 315 mg of the title compound. $^1$H NMR (CDCl$_3$, 500 MHz) of TFA salt: δ 8.24 (d, J=10 Hz, 1H); 7.56 (m, 1H); 7.46 (m, 1H); 7.25 (m, 1H); 7.17 (m, 1H); 6.87 (d, J=10 Hz, 1H); 6.32 (s, 1H); 5.88 (m, 1H); 4.20 (m, 1H); 3.76 (m, 1H); 3.53 (m, 1H); 3.11 (m, 1H); 2.87 (m, 1H); 2.44 (m, 1H); 1.47 (s, 9H). Mass spectrum (ESI): 505.3 (M+1).

EXAMPLE ABA11

7-(1-tert-Butylpiperidin-4-yl)-1-(2,6-dichlorophenyl)-5-(4-fluorophenyl)quinolin-2(1H)-one

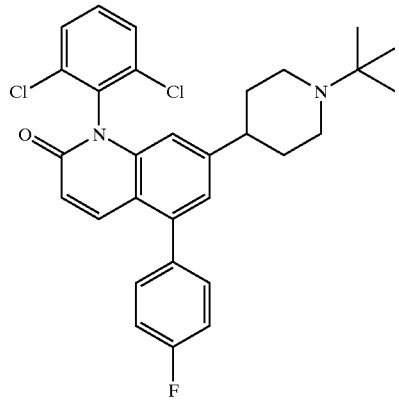

Step A: 7-(1-tert-Butyl-1,2,3,6-tetrahydropyridin-4-yl)-1-(2,6-dichlorophenyl)-5-(4-fluorophenyl)quinolin-2(1H)-one The title compound was prepared from 5-bromo-7-(1-tert-butyl-1,2,3,6-tetrahydropyridin-4-yl)-1-(2,6-dichlorophenyl)quinolin-2(1H)-one (INTERMEDIATE ABA5) and using 4-fluorophenylboronic acid by procedures analogous to that described in INTERMEDIATE 2. The title compound was converted to HCl salt by treating it with 2M HCl in Et$_2$O. Mass spectrum (ESI): 521.5 (M+1).

Step B: 7-(1-tert-Butylpiperidin-4-yl)-1-(2,6-dichlorophenyl)-5-(4-fluorophenyl)quinolin-2(1H)-one The title compound was prepared from HCl salt of 7-(1-tert-butyl-1,2,3,6-tetrahydropyridin-4-yl)-1-(2,6-dichlorophenyl)-5-(4-fluorophenyl)quinolin-2(1H)-one (EXAMPLE ABA11, Step A) by procedures analogous to that described in EXAMPLE HHH1, Step B, as a TFA salt. $^1$H NMR (CD$_3$OD, 500 MHz) of TFA salt: δ 7.97 (d, J=9.8 Hz, 1H); 7.73 (m, 2H); 7.62 (m, 1H); 7.49 (m, 1H); 7.28 (m, 3H); 6.69 (d, J=9.8 Hz, 1H); 6.47 (s, 1H); 3.67 (m, 2H); 3.08 (m, 2H); 2.96 (m, 1H); 2.1 (m, 2H); 1.99 (m, 2H); 1.42 (s, 9H). Mass spectrum (ESI): 523.3 (M+1).

EXAMPLE ABA12

7-(1-tert-Butylpiperidin-4-yl)-1-(2,6-dichlorophenyl)-5-(4-fluoro-3-methylphenyl)quinolin-2(1H)-one

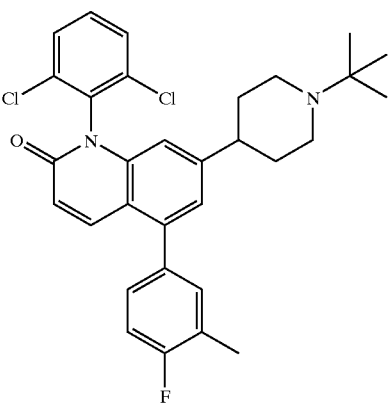

The title compound was prepared from 5-bromo-7-(1-tert-butyl-1,2,3,6-tetrahydropyridin-4-yl)-1-(2,6-dichlorophenyl)quinolin-2(1H)-one (INTERMEDIATE ABA5) and using 4-fluoro-3-methylphenylboronic acid as described in EXAMPLE ABA11. $^1$H NMR (CD$_3$OD, 500

MHz): δ 1.252 (s, 9H), 1.734 (bs, 2H), 1.955 (bs, 2H), 2.084 (s, 3H), 2.665 (bs, 4H), 3.307 (m, 1H), 3.394 (bs, 2H), 6.471 (s, 1H), 6.650 (d, J=9.9 Hz, 1H), 7.064 (t, J=5.7 Hz, 1H), 7.123 (s, 1H), 7.146 (dd, J=2.7, 9.9 Hz, 1H), 7.243 (dd, J=5.7, 8.5 Hz, 1H), 7.570 (d, J=9.9 Hz, 1H), 7.616 (t, J=8.5 Hz, 1H), 7.737 (m, 2H). Mass spectrum (ESI): 537.2 (M+1).

EXAMPLE ABA13

7-(1-tert-Butylpiperidin-4-yl)-5-(4-chloro-3-fluorophenyl)-1-(2,6-dichlorophenyl)quinolin-2(1H)-one

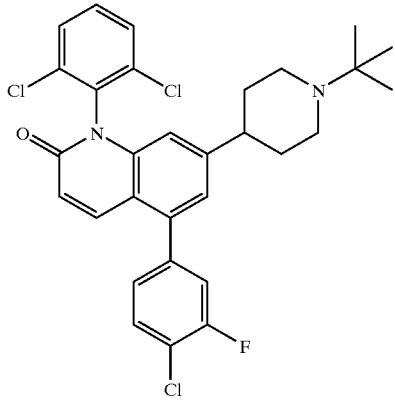

The title compound was prepared from 5-bromo-7-(1-tert-butyl-1,2,3,6-tetrahydropyridin-4-yl)-1-(2,6-dichlorophenyl)quinolin-2(1H)-one (INTERMEDIATE ABA5) and using 4-chloro-3-fluorophenylboronic acid as described in EXAMPLE ABA11. $^1$H NMR (CD$_3$OD, 500 MHz) TFA salt: δ 1.415 (s, 9H), 1.813 (dd, J=10.7, 12.8 Hz, 2H), 2.120 (m, 2H), 2.947 (tt, J=3.7, 12.4, 24.7 Hz, 1H), 3.064 (t, J=12.8 Hz, 1H), 3.674 (d, J=12.6 Hz, 2H), 6.490 (s, 1H), 6.736 (d, J=9.8 Hz, 1H), 7.245 (s, 1H), 7.289 (dd, J=1.6, 8.3 Hz, 1H), 7.411 (dd, 1.8, 9.8 Hz, 1H), 7.619 (m, 2H), 7.728 (m, 2H), 7.981 (d, J=9.8 Hz, 1H). Mass spectrum (ESI): 559.5 (M+1).

EXAMPLE ABA14

7-(1-tert-Butylpiperidin-4-yl)-1-(2,6-dichlorophenyl)-5-(3,5-difluorophenyl)quinolin-2(1H)-one

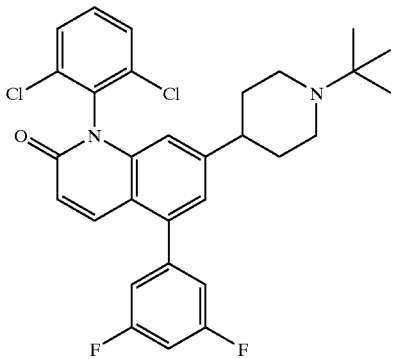

The title compound was prepared from 5-bromo-7-(1-tert-butyl-1,2,3,6-tetrahydropyridin-4-yl)-1-(2,6-dichlorophenyl)quinolin-2(1H)-one (INTERMEDIATE ABA5) and using 3,5-difluorophenylboronic acid as described in EXAMPLE ABA11. $^1$H NMR (CD$_3$OD, 500 MHz) TFA salt: δ 1.416 (s, 9H), 1.827 (m, 2H), 2.119 (d, J=14.7 Hz, 2H), 2.948 (m, 1H), 3.063 (t, J=11.0 Hz, 2H), 3.675 (d, J=12.6 Hz, 2H), 6.497 (s, 1H), 6.747 (d, J=9.9 Hz, 1H). 7.122 (m, 3H), 7.249 (s, 1H), 7.619 (t, J=7.6 Hz, 1H), 7.728 (m, 2H), 7.987 (d, J=10.1 Hz, 1H). Mass spectrum (ES): 541.5 (M+1).

EXAMPLE ABA15

7-(1-tert-Butylpiperidin-4-yl)-1-(2,6-dichlorophenyl)-5-(3-fluorophenyl)quinolin-2(1H)-one

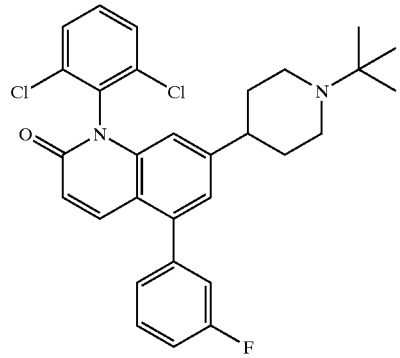

The title compound was prepared from 5-bromo-7-(1-tert-butyl-1,2,3,6-tetrahydropyridin-4-yl)-1-(2,6-dichlorophenyl)quinolin-2(1H)-one (INTERMEDIATE ABA5) and using 3-fluorophenylboronic acid as described in EXAMPLE ABA11. $^1$H NMR (CD$_3$OD, 500 MHz): δ 1.294 (s, 9H), 1.756 (bs, 2H), 2.015 (bs, 2H), 2.809 (bs, 3H), 3.447 (bs, 2H), 6.480 (s, 1H), 6.713 (d, J=10.1 Hz, 1H), 7.245 (m, 4H), 7.557 (m, 1H), 7.624 (t, J=7.6 Hz, 1H), 7.735 (m, 2H), 7.986 (d, J=10.1 Hz, 1H). Mass spectrum (ESI): 523.5 (M+1).

EXAMPLE ABA16

7-(1-tert-Butylpiperidin-4-yl)-1-(2,6-dichlorophenyl)-5-(3,4-difluorophenyl)quinolin-2(1H)-one

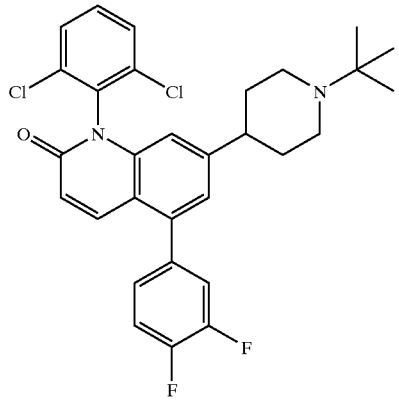

The title compound was prepared from 5-bromo-7-(1-tert-butyl-1,2,3,6-tetrahydropyridin-4-yl)-1-(2,6-dichlorophenyl)quinolin-2(1H)-one (INTERMEDIATE ABA5) and using 3-fluorophenylboronic acid as described in EXAMPLE ABA11. $^1$H NMR (CD$_3$OD, 500 MHz): δ 1.272 (s, 9H), 1.700 (bs, 2H), 1.742 (bs, 2H), 2.520–2.818 (bs, 3H), 3.379 (bs, 2H), 6.478 (s, 1H), 6.710 (d, J=10.0 Hz, 1H), 7.228 (s, 1H), 7.264 (m, 1H), 7.420 (m, 2H), 7.618 (t, J=7.6 Hz, 1H), 7.722 (m, 2H), 7.975 (d, J=10.0 Hz, 1H). Mass spectrum (ESI): 541.5 (M+1).

EXAMPLE ABA17

7-(1-tert-Butylpiperidin-4-yl)-1-(2,6-dichlorophenyl)-5-[3-(trifluoromethyl)phenyl]quinolin-2(1H)-one

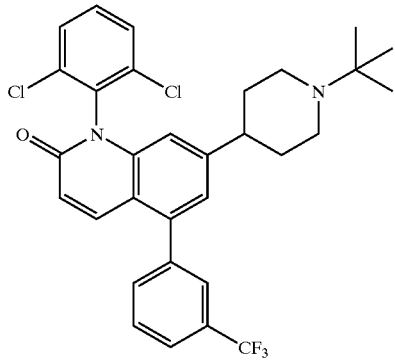

The title compound was prepared from 5-bromo-7-(1-tert-butyl-1,2,3,6-tetrahydropyridin-4-yl)-1-(2,6-dichlorophenyl)quinolin-2(1H)-one (INTERMEDIATE ABA5) and using 3-trifluoromethylphenylboronic acid as described in EXAMPLE ABA11. $^1$H NMR (CD$_3$OD, 500 MHz) TFA salt: δ 1.358 (s, 9H), 1.780 (q, J=10.5, 12.8 Hz, 2H), 2.062 (d, J=15.6 Hz, 2H), 2.702 (m, 1H), 3.004 (t, J=13.0 Hz, 2H), 3.612 (d, J=13.0 Hz, 2H), 6.460 (s, 1H), 6.682 (d, J=10.2 Hz, 1H), 7.204 (s, 1H), 7.565 (t, J=8.8 Hz, 1H) 7.672–7.742 (m, 5H), 7.778 (m, 1H), 7.844 (d, J=10.2 Hz, 1H). Mass spectrum (ESI): 573.5 (M+1).

EXAMPLE ABA18

7-(1-tert-Butylpiperidin-4-yl)-1-(2,6-dichlorophenyl)-5-(4-fluoro-2-methylphenyl)quinolin-2(1H)-one

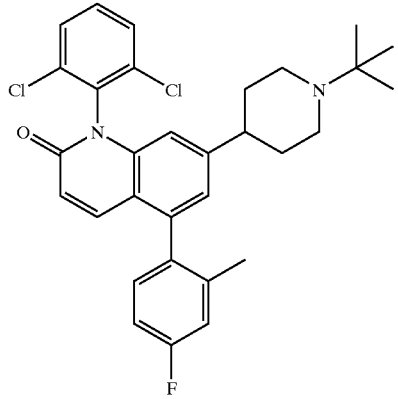

The title compound was prepared from 5-bromo-7-(1-tert-butyl-1,2,3,6-tetrahydropyridin-4-yl)-1-(2,6-dichlorophenyl)quinolin-2(1H)-one (INTERMEDIATE ABA5) and using 4-fluoro-2-methylphenylboronic acid as described in EXAMPLE ABA11. $^1$H NMR (CD$_3$OD, 500 MHz): δ 1.252 (s, 9H), 1.734 (bs, 2H), 1.955 (bs, 2H), 2.384 (s, 3H), 2.865 (bs, 4H), 3.497 (m, 2H), 6.451 (s, 1H), 6.685 (d, J=8.5 Hz, 1H), 7.190 (m, 2H), 7.265 (m, 1H), 7.332 (d, J=8.2 Hz, 1H), 7.618 (t, J=8.2H, 1H), 7.720 (m, 2H), 7.962 (d, J=10.7 Hz, 1H. Mass spectrum (ESI): 537.2 (M+1).

EXAMPLE ABA19

5-(3-Aminophenyl)-7-(1-tert-butylpiperidin-4-yl)-1-(2,6-dichlorophenyl)quinolin-2(1H)-one

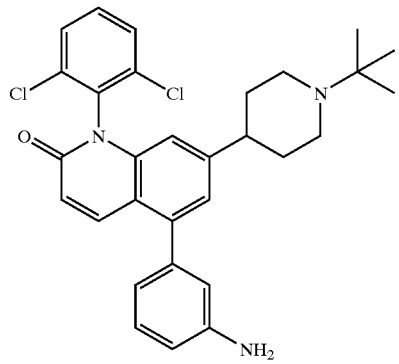

The title compound was prepared from 5-bromo-7-(1-tert-butyl-1,2,3,6-tetrahydropyridin-4-yl)-1-(2,6-dichlorophenyl)quinolin-2(1H)-one (INTERMEDIATE ABA5) and using 3-aminophenylboronic acid as described in EXAMPLE ABA11. $^1$H NMR (CD$_3$OD, 500 MHz): δ 1.112 (s, 9H), 1.582 (m, 2H), 1.814 (m, 2H), 2.266 (m, 2H), 2.549 (m, 1H), 3.139 (m, 2H), 6.408 (s, 1H), 6.639 (d, J=9.9 Hz, 1H), 6.720 (d, J=7.3 Hz, 1H), 6.783 (s, 1H), 6.813 (d, J=8.0 Hz, 1H), 7.181 (s, 1H), 7.231 (t, J=7.7 Hz, 1H), 7.607 (t, J=7.8 Hz, 1H), 7.718 (m, 2H), 8.059 (d, J=9.9 Hz, 1H). Mass spectrum (ESI): 520.4 (M+1).

COMPOUND HHH1

7-Bromo-5-(2-chlorophenyl)-1-(2,6-dichlorophenyl)-3,4-dihydro-1,6-naphthyridin-2(1H)-one

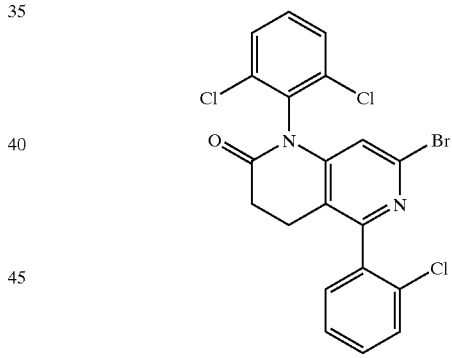

Step A: 4,6-Dibromo-3-(bromomethyl)-2-(2-chlorophenyl)pyridine

To a suspension of 6.3 g of 4,6-dibromo-2-(2-chlorophenyl)-3-methylpyridine (COMPOUND W-1) in 75 mL of CCl$_4$ was added 3.7 g of N-bromosuccinimide and 420 mg of benzoyl peroxide. The mixture was heated to reflux and stirred at this temperature for 6 h, then cooled and concentrated. The residue was dissolved in 150 mL of 1:1 hexanes-Et$_2$O and filtered through a pad of silica gel, then purified in two batches by flash chromatography on Biotage 40M columns, eluting with a gradient system of 99:1 to 97:3 hexanes-Et$_2$O, to yield the title compound as a white solid.

Step B: tert-Butyl 3-[6-bromo-2-(2-chlorophenyl)pyridin-3-yl]propanoate

To 25 mL of THF at −78° C. was added 26.6 mL of a 1.0M solution of lithium hexamethyldisilazane in THF. t-Butyl acetate (4.47 mL) was added dropwise to the cold solution, and the mixture was stirred for 10 min at −78° C. 4,6-Dibromo-3-(bromomethyl)-2-(2-chlorophenyl)pyridine (9.74 g) in 25 mL of THF was added dropwise over 15 min. The mixture was stirred 20 min at −78° C., then quenched by addition of 5 mL of saturated aqueous NaHCO₃. The mixture was warmed to rt, diluted with 200 mL of saturated aqueous NaHCO₃, and extracted with 3×100 mL of EtOAc. The combined organics were washed with 100 mL of brine, and dried over MgSO₄. The residue was purified by flash chromatography on a Biotage 65M column, eluting with a gradient system of 95:5 to 90:10 hexanes-Et₂O to yield the title compound as a white solid. Mass spectrum (ESI) 476 (M+1).

Step C: 3-[6-Bromo-2-(2-chlorophenyl)pyridin-3-yl]-N-(2, 6-dichlorophenyl)propanamide tert-Butyl 3-[6-bromo-2-(2-chlorophenyl)pyridin-3-yl] propanoate (6.82 g) in 3.6 mL of anisole was dissolved in 25 mL of trifluoroacetic acid and the mixture was stirred for 20 min at rt, then co-concentrated with 50 mL of toluene. The residue was dissolved in 100 mL of benzene and 10 mL of MeOH and 7.6 mL of a 2.0M solution of TMSCH₂N₂ was added dropwise. The mixture was stirred 30 min at rt; then 2 drops of trifluoroacetic acid were added and then mixture was concentrated. The residue was dissolved in 25 mL of CH₂Cl₂. To 2,6-dichloroaniline in 75 mL of CH₂Cl₂ was added a 2.0M solution of trimethyl aluminum dropwise. The mixture was stirred 15 min at rt; then the methyl ester solution ws added and the mixture was stirred overnight at rt. Water (50 mL) was added carefully, then 25 mL of Rochelle salt and 50 mL of CH₂Cl₂ and the mixture was stirred vigorously for 1 h. The mixture was filtered and the solids were dissolved in ca. 500 mL of CH₂Cl₂ and washed with 200 mL of brine, dried (Na₂SO₄) and concentrated. The filtrate was separated into organic and aqueous phases and the organic phase was washed with 25 mL of brine, dried (Na₂SO₄) and concentrated. The combined solids were recrystallized from EtOH to yield the title compound as a white solid. Mass spectrum (ESI) 565 (M+1).

Step D: 7-Bromo-5-(2-chlorophenyl)-1-(2,6-dichlorophenyl)-3,4-dihydro-1,6-naphthyridin-2(1H)-one To a suspension of 7.54 g of 3-[6-bromo-2-(2-chlorophenyl)pyridin-3-yl]-N-(2,6-dichlorophenyl) propanamide in 100 mL of DMF was added CuI (3.82 g) and powdered, dried K₂CO₃ (3.70 g). The mixture was heated to 155° C. for 30 min, then cooled and diluted with 250 mL of half-saturated NaHCO₃ and 100 mL of EtOAc. The phases were separated and the aqueous phase was extracted 2×50 mL of EtOAc. The combined organics were washed with brine, dried (Na₂SO₄), and concentrated. The reside was purified by flash chromatography on a Biotage 65M column, eluting with a gradient system of 99:1 CH₂Cl₂-acetone to 97:3 CH₂Cl₂-acetone to yield the title compound as an off-white solid. Mass spectrum (ESI) 483 (M+1). ¹H NMR (500 MHz, CDCl₃): δ 2.72–2.92 (m, 3H); 2.96–3.06 (m, 1H); 6.37 (s, 1H); 7.39–7.54 (m. 2H); 7.56–7.60 (m, 2H).

COMPOUND HHH2
7-Bromo-5-(2-chlorophenyl)-1-(2,6-dichlorophenyl)-1,6-naphthyridin-2(1H)-one

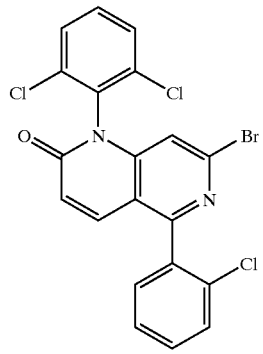

To a solution of 2.31 g of 7-bromo-5-(2-chlorophenyl)-1-(2,6-dichlorophenyl)-3,4-dihydro-1,6-naphthyridin-2 (1H)-one (COMPOUND HHH1) in 100 mL of CCl₄ was added 40 mg of 2,2'azobis(2-methylpropionitrile). The mixture was heated to 80° C.; then 940 mg of recrystallized N-bromosuccinimide was added and the mixture was stirred for 1 h at 80° C. DBU (0.72 mL) was added and the mixture was cooled to rt. The mixture was washed with 200 mL of half-saturated NaHCO₃ and the aqueous phase was back-extracted with 100 mL of CH₂Cl₂. The combined organics were washed with 100 mL of brine, dried (Na₂SO₄), and concentrated to yield the title compound. Mass spectrum (ESI) 481 (M+1). ¹H NMR (500 MHz, CDCl₃): δ 6.61 (s, 1H); 6.75 (d, J=10 Hz, 1H); 7.41–7.57 (m, 6H); 7.50–7.65 (m, 2H).

EXAMPLE HHH1
7-(1-tert-Butylpiperidin-4-yl)-5-(2-chlorophenyl)-1-(2,6-dichlorophenyl)-1,6-naphthyridin-2(1H)-one

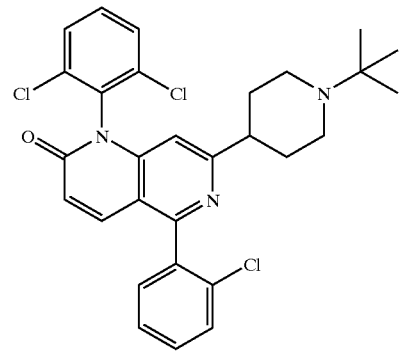

Step A: 7-(1-tert-Butyl-1,2,3,6-tetrahydropyridin-4-yl)-5-(2-chlorophenyl)-1-(2,6-dichlorophenyl)-1,6-naphthyridin-2(1H)-one A mixture of 100 mg of 7-bromo-5-(2-chlorophenyl)-1-(2,6-dichlorophenyl)-1,6-naphthyridin-2(1H)-one (COMPOUND HHH2) and 94 mg of 1-tert-butyl-4-(trimethylstannyl)-1,2,3,6-tetrahydropyridine (COMPOUND PPA-2) in 2 mL of dry dioxane was evacuated and purged three times with Ar. Pd(Ph₃P)₄ (23 mg) was added and the mixture was evacuated and purged again with Ar. The mixture was heated to reflux and stirred at this temperature overnight, then filtered through Celite and concentrated. The residue was purified by preparative thin-layer chromatography, eluting with 95:5 CH₂Cl₂-2M NH₃ in MeOH, to yield the title compound. The HCl salt was prepared by dissolving this compound in CH₂Cl₂, adding 1 eq 1M HCl in Et₂O, and concentrating. Mass spectrum (ESI) 540 (M+1).

Step B: 7-(1-tert-Butylpiperidin-4-yl)-5-(2-chlorophenyl)-1-(2,6-dichlorophenyl)-1,6-naphthyridin-2(1H)-one To a solution of 75 mg of 1-tert-butyl-4-[5-(2-chlorophenyl)-1-(2,6-dichlorophenyl)-2-oxo-1,2-dihydro-1,6-naphthyridin-7-yl]-1,2,3,6-tetrahydropyridinium chloride in 3 mL of MeOH and 1 mL of EtOAc was added 35 mg of PtO₂ (Adam's catalyst). The mixture was evacuated and purged with N₂, then evacuated and purged with H₂, then stirred under an H₂ balloon for 1 h. The mixture was filtered through Celite, washing with MeOH, and concentrated. The residue was purified by preparative thin-layer chromatography, eluting with 95:5 CH₂Cl₂-2M NH₃ in MeOH, followed by preparative HPLC (YMC C8 19×50 mm column; 10:90 to 90:10 v/v acetonitrile/water+0.05% TFA over 12 min; 20 mL/minute) to yield the title compound. Mass spectrum (ESI) 542 (M+1). ¹H NMR (500 MHz, CD₃OD): δ 1.40 (s, 9H); 2.04–2.20 (m, 4H); 3.00–3.12 (m, 3H); 3.68 (br d, J=12.5 Hz, 2H); □6.46 (s, 1H); 6.75 (d, J=10 Hz, 1H); 7.48–7.75 (m, 8H).

COMPOUND HHH3

7-[3-(tert-Butylamino)-1-ethylpropyl]-5-(2-chlorophenyl)-1-(2,6-dichlorophenyl)-1,6-naphthyridin-2(1H)-one

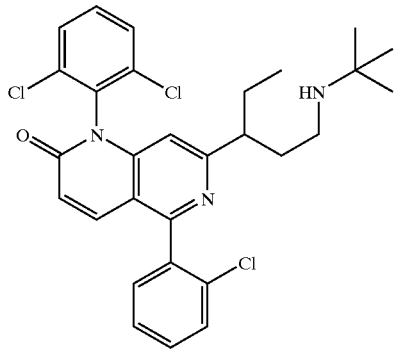

7-[3-(tert-Butylamino)-1-ethylpropyl]-5-(2-chlorophenyl)-1-(2,6-dichlorophenyl)-1,6-naphthyridin-2(1H)-one was isolated as a side product in the reduction of 7-(1-tert-butylpiperidin-4-yl)-5-(2-chlorophenyl)-1-(2,6-dichlorophenyl)-1,6-naphthyridin-2(1H)-one (EXAMPLE HHH1, Step B). Mass spectrum (ESI) 544 (M+1).

COMPOUND HHH4

5-(2-Cholorophenyl)-1-(2,6-dichlorophenyl)-7-[(2,2,6,6-tetramethylpiperidin-4-yl)amino]-1,6-naphthyridin-2(1H)-one

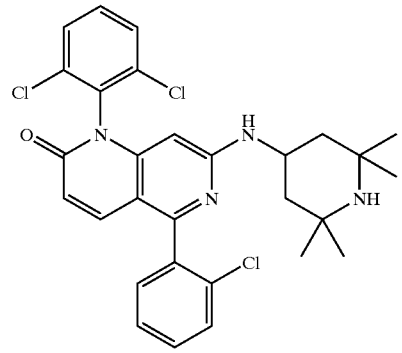

A mixture of 200 mg of 7-bromo-5-(2-chlorophenyl)-1-(2,6-dichlorophenyl)-1,6-naphthyridin-2(1H)-one (COMPOUND HHH2) and 1 mL of 4-amino-2,2,6,6-tetramethylpiperidine in 0.5 mL of DMSO was stirred at 130° C. for 3 h. The mixture was cooled, filtered, and purified by reverse-phase preparative HPLC (YMC C18 100×50 mm column; 10:90 to 90:10 v/v acetonitrile/water+0.1% TFA over 15 min; 20 mL/min) to yield the title compound. Mass spectrum (ESI) 557 (M+1). ¹H NMR (500 MHz, CD₃OD): selected peaks δ 1.32–1.58 (m, 14H), 2.05–2.24 (m, 2H), 4.40 (br s, 1H).

COMPOUND HHH5

5-(2-Chlorophenyl)-1-(2,6-dichlorophenyl)-1,6-naphthyridin-2(1H)-one

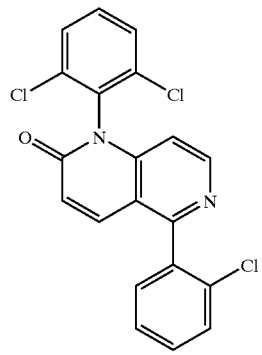

5-(2-Chlorophenyl)-1-(2,6-dichlorophenyl)-1,6-naphthyridin-2(1H)-one was isolated as a side product in the Stille coupling of 7-bromo-5-(2-chlorophenyl)-1-(2,6-dichlorophenyl)-1,6-naphthyridin-2(1H)-one (COMPOUND HHH2) and 94 mg of 1-tert-butyl-4-(trimethylstannyl)-1,2,3,6-tetrahydropyridine (EXAMPLE HHH1, Step A). Mass spectrum (ESI) 403 (M+1).

EXAMPLE HHH2

5-(2-Chlorophenyl)-1-(2,6-dichlorophenyl)-7-(1-isopropylpiperidin-4-yl)-1,6-naphthyridin-2(1H)-one

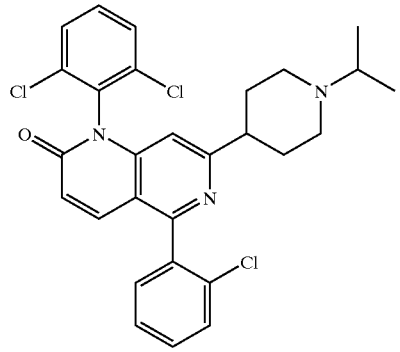

Step A: tert-Butyl 4-[5-(2-chlorophenyl)-1-(2,6-dichlorophenyl)-2-oxo-1,2-dihydro-1,6-naphthyridin-7-yl]-3,6-dihydropyridine-1(2H)-carboxylate The title compound was prepared from 7-bromo-5-(2-chlorophenyl)-1-(2,6-dichlorophenyl)-1,6-naphthyridin-2(1H)-one (COMPOUND HHH2) and tert-butyl 4-(trimethylstannyl)-3,6-dihydropyridine-1(2H)-carboxylate (INTERMEDIATE 69)by a procedure analogous to that described in EXAMPLE HHH1, Step A. Mass spectrum (ESI) 582 (M+1).

Step B: tert-Butyl 4-[5-(2-chlorophenyl)-1-(2,6-dichlorophenyl)-2-oxo-1,2-dihydro-1,6-naphthyridin-7-yl]piperidine-1-carboxylate The title compound was prepared from tert-butyl 4-[5-(2-chlorophenyl)-1-(2,6-dichlorophenyl)-2-oxo-1,2-dihydro-1,6-naphthyridin-7-yl]-3,6-dihydropyridine-1(2H)-carboxylate by a procedure analogous to that described in EXAMPLE HHH1, Step B. Mass spectrum (ESI) 586 (M+1).

Step C: 5-(2-Chlorophenyl)-1-(2,6-dichlorophenyl)-7-piperidin-4-yl-1,6-naphthyridin-2(1H)-one To a solution of 50 mg of tert-butyl 4-[5-(2-chlorophenyl)-1-(2,6-dichlorophenyl)-2-oxo-1,2-dihydro-1,6-naphthyridin-7-yl]piperidine-1-carboxylate in 5 mL of $CH_2Cl_2$ was added 2 mL of trifluoroacetic acid. The mixture was stirred at rt for 1 h, then concentrated. The residue was dissolved in 10 mL of $CH_2Cl_2$, washed with 5 mL $NaHCO_3$, dried ($Na_2SO_4$), and concentrated. The residue was purified by preparative thin-layer chromatography, eluting with 95:5 $CH_2Cl_2$-2M $NH_3$ in MeOH, followed by preparative HPLC (YMC C18 20×50 mm column; 10:90 to 100:0 v/v acetonitrile/water+0.1% TFA over 5 min; 20 mL/min) to yield the title compound.

Mass spectrum (ESI) 486 (M+1).

Step D: 5-(2-Chlorophenyl)-1-(2,6-dichlorophenyl)-7-(1-isopropylpiperidin-4-yl)-1,6-naphthyridin-2(1H)-one To a solution of 14 mg of 5-(2-chlorophenyl)-1-(2,6-dichlorophenyl)-7-piperidin-4-yl-1,6-naphthyridin-2(1H)-one in 1 mL of MeOH was added 0.1 mL of acetone, then 9 mg of sodium cyanoborohydride. The mixture was stirred 5 h at rt, then diluted with 1 mL of EtOAc and 10 mL $NaHCO_3$. The phases were separated and the aqueous phase was extracted with 2×10 mL of EtOAc. The combined organics were washed with 10 mL of brine, dried ($Na_2SO_4$), and concentrated. The residue was purified by preparative thin-layer chromatography, eluting with 95:5 $CH_2Cl_2$-2M $NH_3$ in MeOH to yield the title compound. Mass spectrum (ESI) 528 (M+1). $^1$H NMR (500 MHz, $CDCl_3$): selected peaks δ 1.07 (d, J=6.5 Hz, 6H), 1.71 (br s, 2H); 1.99 (br s, 2H); 2.26 (br s, 2H); 2.80 (br s, 2H); 3.02 (br s, 2H).

EXAMPLE HHH3

5-(2-Chlorophenyl)-1-(2,6-dichlorophenyl)-7-(8-methyl-8-azabicyclo[3.2.1]oct-3-yl)-1,6-naphthyridin-2(1H)-one

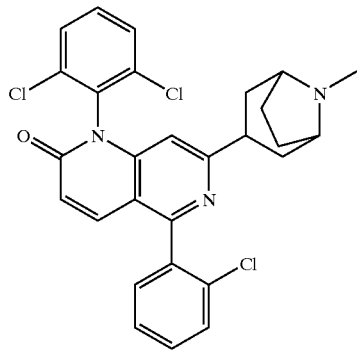

Step A: 5-(2-Chlorophenyl)-1-(2,6-dichlorophenyl)-7-(8-methyl-8-azabicyclo[3.2.1]oct-2-en-3-yl)-1,6-naphthyridin-2(1H)-one The title compound was prepared from 7-bromo-5-(2-chlorophenyl)-1-(2,6-dichlorophenyl)-1,6-naphthyridin-2(1H)-one (COMPOUND HHH2) and 8-methyl-3-(trimethylstannyl)-8-azabicyclo[3.2.1]oct-2-one (COMPOUND VV-2) by a procedure analogous to that described in EXAMPLE HHH1, Step A. Mass spectrum (ESI) 524 (M+1).

Step B: 5-(2-Chlorophenyl)-1-(2,6-dichlorophenyl)-7-(8-methyl-8-azabicyclo[3.2.1]oct-3-yl)-1,6-naphthyridin-2(1H)-one The title compound was prepared from 5-(2-chlorophenyl)-1-(2,6-dichlorophenyl)-7-(8-methyl-8-azabicyclo[3.2.1]oct-2-en-3-yl)-1,6-naphthyridin-2(1H)-one by a procedure analogous to that described in EXAMPLE HHH1, Step B.

Mass spectrum (ESI) 526 (M+1). $^1$H NMR (500 MHz, $CD_3OD$): selected peaks δ 1.19 (s, 6H); 1.26 (s, 6H); 2.17 (s, 2H); 6.62 (s, 1H).

EXAMPLE HHH4

7-[(1-tert-Butylpiperidin-4-yl)methyl]-5-(2-chlorophenyl)-1-(2,6-dichlorophenyl)-1,6-naphthyridin-2(1H)-one

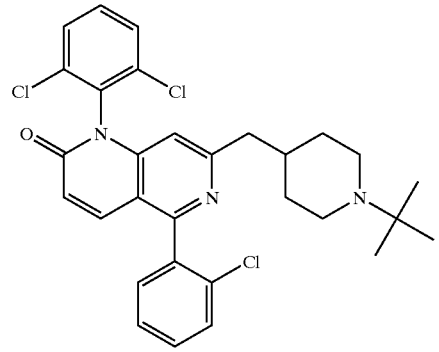

Step A: 7-[(1-tert-Butylpiperidin-4-ylidene)methyl]-5-(2-chlorophenyl)-1-(2,6-dichlorophenyl)-1,6-naphthyridin-2(1H)-one The title compound was prepared from 7-bromo-5-(2-chlorophenyl)-1-(2,6-dichlorophenyl)-1,6-naphthyridin-2(1H)-one (COMPOUND HHH2) and 1-tert-butyl-4-[(trimethylstannyl)methylene]piperidine (INTERMEDIATE ABA3) by a procedure analogous to that described in EXAMPLE HHH1, Step A. Mass spectrum (ESI) 554 (M+1).

Step B: 7-[(1-tert-Butylpiperidin-4-yl)methyl]-5-(2-chlorophenyl)-1-(2,6-dichlorophenyl)-1,6-naphthyridin-2(1H)-one The title compound was prepared from 7-[(1-tert-butylpiperidin-4-ylidene)methyl]-5-(2-chlorophenyl)-1-(2,6-dichlorophenyl)-1,6-naphthyridin-2(1H)-one by a procedure analogous to that described in EXAMPLE HHH1, Step B. Mass spectrum (ESI) 556 (M+1). $^1$H NMR (500 MHz, $CD_3OD$): selected peaks δ 1.38 (s, 9H); 1.45–1.60 (m, 2H); 1.88–2.10 (m, 2H); 2.78 (br d, J=7 Hz, 2H); 2.87–2.97 (m, 2H); 3.58 (br d, J=12 Hz, 2H).

EXAMPLE HHH5

5-(2-Chlorophenyl)-1-(2,6-dichlorophenyl)-7-(4-isopropylpiperazin-1-yl)-1,6-naphthyridin-2(1H)-one

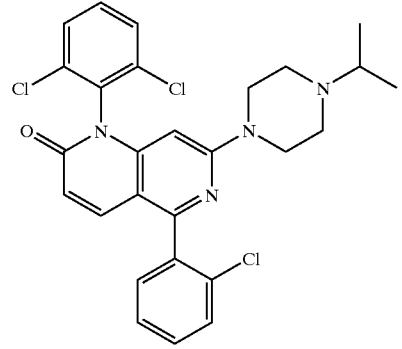

The title compound was prepared from 50 mg of 7-bromo-5-(2-chlorophenyl)-1-(2,6-dichlorophenyl)-1,6-naphthyridin-2(1H)-one (COMPOUND HHH2) and 1 mL of 1-isopropylpiperazine by a procedure analogous to that described in COMPOUND HHH4. Mass spectrum (ESI) 529 (M+1). $^1$H NMR (500 MHz, $CDCl_3$): selected peaks δ

1.04 (d, J=6.5 Hz, 6H); 2.55 (br s, 4H); 2.70 (m, 1H); 3.49 (br s, 4H).

EXAMPLE HHH6

5-(2-Chlorophenyl)-1-(2,6-dichlorophenyl)-7-{4-[2-(dimethylamino)ethyl]piperazin-1-yl}-1,6-naphthyridin-2(1H)-one

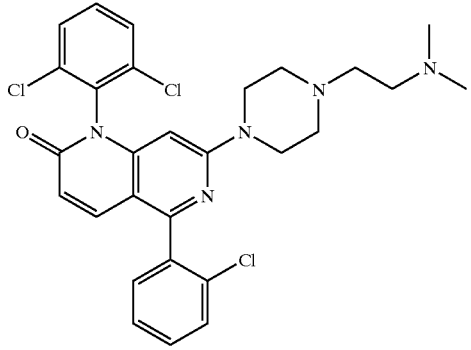

The title compound was prepared from 50 mg of 7-bromo-5-(2-chlorophenyl)-1-(2,6-dichlorophenyl)-1,6-naphthyridin-2(1H)-one (COMPOUND HHH2) and 1 mL of N,N-dimethyl-2-piperazin-1-ylethanamine by a procedure analogous to that described in COMPOUND HHH4. Mass spectrum (ESI) 558 (M+1). $^1$H NMR (500 MHz, CD$_3$OD): selected peaks δ 2.94 (s, 6H); 3.23 (m, 4H); 3.44 (t, J=7.5 Hz, 2H); 3.56 (t, J=6.5 Hz, 2H); 3.76 (m, 4H).

EXAMPLE HHH7

5-(2-Chlorophenyl)-1-(2,6-dichlorophenyl)-7-[3-(hydroxymethyl)piperazin-1-yl]-1,6-naphthyridin-2(1H)-one

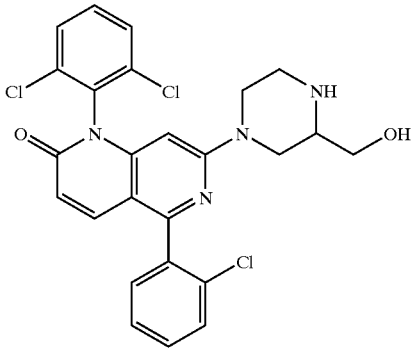

Step A: 7-[3-(tert-Butoxymethyl)piperazin-1-yl]-5-(2-chlorophenyl)-1-(2,6-dichlorophenyl)-1,6-naphthyridin-2(1H)-one The title compound was prepared from 25 mg of 7-bromo6-5-(2-chlorophenyl)-1-(2,6-chlorophenyl)-1,6-naphthyridin-2(1H)-one (COMPOUND HHH2), 46 mg of 2-(tert-butoxymethyl)piperazinediium diacetate, and 40 µL of diisopropyl ethylamine by a procedure analogous to that described in COMPOUND HHH4. Mass spectrum (ESI) 573 (M+1).

Step B: 5-(2-Chlorophenyl)-1-(2,6-dichlorophenyl)-7-[3-(hydroxymethyl)piperazin-1-yl]-1,6-naphthyridin-2(1H)-one To 25 mg of 7-[3-(tert-butoxymethyl)piperazin-1-yl]-5-(2-chlorophenyl)-1-(2,6-dichlorophenyl)-1,6-naphthyridin-2(1H)-one was added 1 mL of TFA. The mixture was stirred 2 h at rt, then concentrated. The residue was purified by preparative thin-layer chromatography, eluting with 9:1 CH$_2$Cl$_2$-2M NH$_3$ in MeOH.

Mass spectrum (ESI) 517 (M+1). $^1$H NMR (500 MHz, CDCl$_3$): selected peaks δ 2.78–3.02 (m, 4H); 3.09 (br d, J=12 Hz, 1H); 3.59 (m, 1H); 3.68 (dd, J=3.5, 10.5 Hz, 1H); 3.84 (br d, J=12 Hz, 1H); 4.05 (br d, J=13 Hz, 1H).

EXAMPLE HHH8

5-(2-Chlorophenyl)-1-(2,6-dichlorophenyl)-7-[(1-isopropylpiperidin-4-yl)amino]-1,6-naphthyridin-2(1H)-one

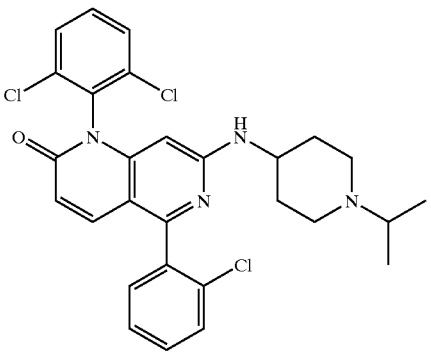

Step A: tert-Butyl 4-{[5-(2-chlorophenyl)-1-(2,6-dichlorophenyl)-2-oxo-1,2-dihydro-1,6-naphthyridin-7-yl]amino}piperidine-1-carboxylate The title compound was prepared from 50 mg of 7-bromo-5-(2-chlorophenyl)-1-(2,6-dichlorophenyl)-1,6-naphthyridin-2(1H)-one (COMPOUND HHH2) and 63 mg of tert-butyl 4-aminopiperidine-1-carboxylate by a procedure analogous to that described in COMPOUND HHH4. Mass spectrum (ESI) 599 (M+1).

Step B: 5-(2-Chlorophenyl)-1-(2,6-dichlorophenyl)-7-(piperidin-4-ylamino)-1,6-naphthyridin-2(1H)-one The title compound was prepared from tert-butyl 4-{[5-(2-chlorophenyl)-1-(2,6-dichlorophenyl)-2-oxo-1,2-dihydro-1,6-naphthyridin-7-yl]amino}piperidine-1-carboxylate by a procedure analogous to that described in EXAMPLE HHH2, Step C. Mass spectrum (ESI) 501 (M+1). Step C: 5-(2-Chlorophenyl)-1-(2,6-dichlorophenyl)-7-[(1-isopropylpiperidin-4-yl)amino]-1,6-naphthyridin-2(1H)-one The title compound was prepared from 5-(2-chlorophenyl)-1-(2,6-dichlorophenyl)-7-(piperidin-4-ylamino)-1,6-naphthyridin-2(1H)-one by a procedure analogous to that described in EXAMPLE HHH2, Step D. Mass spectrum (ESI) 543 (M+1). $^1$H NMR (500 MHz, CDCl$_3$): selected peaks δ 1.03 (d, J=6 Hz, 6H); 1.50 (m, 2H); 1.96 (m, 2H); 2.21 (m, 2H); 2.68–2.85 (m, 3H); 3.34 (br s, 1H).

COMPOUND HHH6

5-(2-Chlorophenyl)-1-(2,6-dichlorophenyl)-7-[(2,2,6,6-tetramethylpiperidin-4-yl)oxy]-1,6-naphthyridin-2(1H)-one

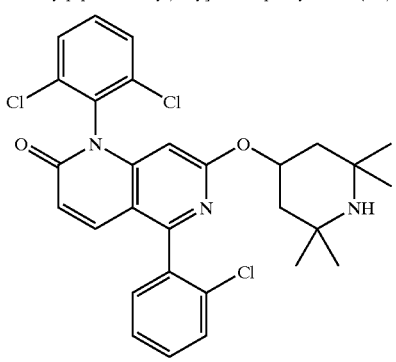

To a solution of 82 mg of 2,2,6,6-tetramethylpiperidin-4-ol in 1 mL of DMSO was added 13 mg of NaH. The mixture was stirred 15 min at rt; then 50 mg of 7-bromo-5-(2-chlorophenyl)-1-(2,6-dichlorophenyl)-1,6-naphthyridin-2(1H)-one (COMPOUND HHH2) was added and the mixture was stirred at 50° C. for 4h, then cooled and quenched by addition of 0.1 mL water plus one drop of TFA. The mixture was filtered and purified by reverse-phase preparative HPLC (YMC C18 20×100 mm column; 10:90 to 100:0 v/v acetonitrile/water+0.1% TFA over 15 min; 20 mL/min) to yield the title compound. Mass spectrum (ESI) 556 (M+1). $^1$H NMR (500 MHz, CDCl$_3$): δ 3H); 1.38 (s, 3H); 1.40 (s, 3H), 1.41 (s, 3H); 2.09 (m, 2H); 218 (m, 2H); 3.50 (s, 0.6H); 5.53 (m, 1H); 5.57 (s, 1H); 6.54 (d, J=10 Hz, 1H); 7 (m, 8H).

EXAMPLE HHH9
5-(2-Chlorophenyl)-1-(2,6-dichlorophenyl)-7-[(8-methyl-8-azabicyclo[3.2.1]oct-3-yl)oxy]-1,6-naphthyridin-2(1H)-one

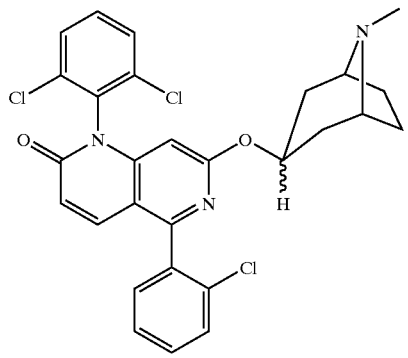

Step A: Tropine and Pseudotroine

To a 3.7 mL of a 1M solution of lithium aluminum hydride in 16 mL of THF was added a solution of tropinone in 5 mL of THF dropwise over ca. 10 min. The mixture was stirred 30 min at rt, then quenched by careful addition of 0.14 mL of water, 0.14 mL of 15% aqueous NaOH, and 0.52 mL of water. The mixture was stirred vigorously for 15 min, then filtered, washing liberally with CH$_2$Cl$_2$ and concentrated to yield a ca. 1.4:1 mixture of pseudotropine and tropine. Mass spectrum (ESI) 142 (M+1).

Step B: 5-(2-Chlorophenyl)-1-(2,6-dichlorophenyl)-7-[(8-methyl-8-azabicyclo[3.2.1]oct-3-yl)oxy]-1,6-naphthyridin-2(1H)-one The title compound was prepared from 100 mg of 7-bromo-5-(2-chlorophenyl)-1-(2,6-dichlorophenyl)-1,6-naphthyridin-2(1H)-one (COMPOUND HHH2), 147 mg of a ca. 1.4:1 mixture of pseudotropine and tropine (EXAMPLE HHH9, Step A), and 25 mg of NaH by a procedure analogous to that described in COMPOUND HHH6.

Diastereomer 1 (from pseudotropine): Mass spectrum (ESI) 542 (M+1). $^1$H NMR (500 MHz, CDCl$_3$): selected peaks δ (m, 2H); 1.83 (m, 2H); 2.00 (m, 4H); 2.36 (s, 3H); 3.24 (br s, 2H); 5.35 (m, 1H).

Diastereomer 2 (from tropine): Mass spectrum (ESI) 542 (M+1).). $^1$H NMR (500 MHz, CDCl$_3$): selected peaks δ 2.00–2.30 (m, 6H); 2.35–2.65 (m, 5H); 3.30 (br s, 2H); 5.39 (m, 1H).

COMPOUND HHH7
5-(2-Chlorophenyl)-1-(2,6-dichlorophenyl)-7-hydroxy-1,6-naphthyridin-2(1H)-one

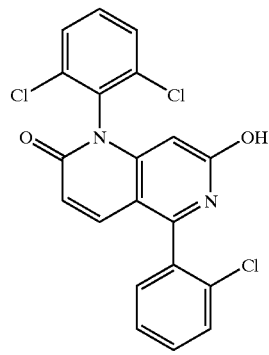

5-(2-Chlorophenyl)-1-(2,6-dichlorophenyl)-7-hydroxy-1,6-naphthyridin-2(1H)-one was isolated as a side product in the coupling of 7-bromo-5-(2-chlorophenyl)-1-(2,6-dichlorophenyl)-1,6-naphthyridin-2(1H1)-one (COMPOUND HHH2) and a mixture of pseudotropine and tropine (EXAMPLE HHH9, Step B).

Mass spectrum (ESI) 419 (M+1).

EXAMPLE HHH10
7-[(1-tert-Butylpiperidin-4-yl)oxy]-5-(2-chlorophenyl)-1-(2,6-dichlorophenyl)-1,6-naphthyridin-2(1H)-one

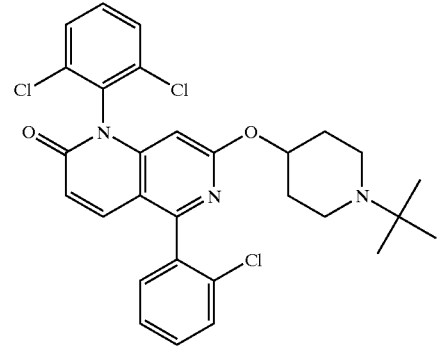

Step A: 1-tert-Butylpiperidin-4-ol

To a 0° C. solution of 1.0 g of 1-tert-butylpiperidin-4-one (COMPOUND PPA-1) in 2 mL of THF was added 6.4 mL of a 1M solution of lithium aluminum hydride in THF dropwise. The mixture was stirred 10 min at rt, then quenched by careful addition of 0.2 mL of water, 0.2 mL of 15% aqueous NaOH, and 0.6 mL of water. The mixture was stirred vigorously for 30 min, then filtered and concentrated to yield the title compound.

Step B: 7-[(1-tert-Butylpiperidin-4-yl)oxy]-5-(2-chlorophenyl)-1-(2,6-dichlorophenyl)-1,6-naphthyridin-2(1H)-one The title compound was prepared from 40 mg of 7-bromo-5-(2-chlorophenyl)-1-(2,6-dichlorophenyl)-1,6-naphthyridin-2(1H)-one (COMPOUND HHH2), 55 mg of 1-tert-butylpiperidin-4-ol, and 8 mg of NaH by a procedure analogous to that described in COMPOUND HHH6. Mass spectrum (ESI) 556 (M+1). $^1$H NMR (500 MHz, CDCl$_3$; doubling of peaks due to restricted rotation) δ 1.44 and 1.42 (2 s, 9H); 2.20–2.53 (m, 4H); 2.77 (m, 0.6H); 3.05 (br s, 1.6H); 3.50 (m, 1.5H); 3.70 (m, 0.8H); 4.60–5.40 (m, 2.9H); 5.39 (br s, 0.8H); 5.75 and 5.80 (2 s, 1H); 6.54 and 6.56 (2 d, J=8.5 Hz and J=10 Hz, 1H); 7.36–7.66 (m, 8H).

EXAMPLE HHH11
5-(2-Chlorophenyl)-1-(2,6-dichlorophenyl)-7-(1-isopropylpiperidin-4-yl)quinolin-2(1H)-one

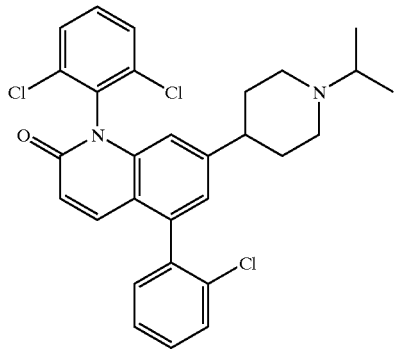

Step A: 5-(2-Chlorophenyl)-1-(2,6-dichlorophenyl)-2-oxo-1,2-dihydroquinolin-7-yl trifluoromethanesulfonate The title compound was prepared from 5-(2-chlorophenyl)-1-(2,6-dichlorophenyl)-7-hydroxyquinolin-2(1H)-one (INTERMEDIATE 7) by a procedure analogous to that described in EXAMPLE 1, Step A.

Step B: tert-Butyl 4-[5-(2-chlorophenyl)-1-(2,6-dichlorophenyl)-2-oxo-1,2-dihydroquinolin-7-yl]-3,6-dihydropyridine-1(2H)-carboxylate The title compound was prepared from 5-(2-chlorophenyl)-1-(2,6-dichlorophenyl)-2-oxo-1,2-dihydroquinolin-7-yl trifluoromethanesulfonate by a procedure analogous to that described in EXAMPLE 1, Step B. Mass spectrum (ESI) 583 (M+1).

Step C: tert-Butyl 4-[5-(2-chlorophenyl)-1-(2,6-dichlorophenyl)-2-oxo-1,2-dihydroquinolin-7-yl]piperidine-1-carboxylate The title compound was prepared from tert-butyl 4-[5-(2-chlorophenyl)-1-(2,6-dichlorophenyl)-2-oxo-1,2-dihydroquinolin-7-yl]-3,6-dihydropyridine-1(2H)-carboxylate by a procedure analogous to that described in EXAMPLE HHH2, Step B. Mass spectrum (ESI) 585 (M+1).

Step D: 5-(2-chlorophenyl)-1-(2,6-dichlorophenyl)-7-piperidin-4-ylquinolin-2(1H)-one The title compound was prepared from tert-butyl 4-[5-(2-chlorophenyl)-1-(2,6-dichlorophenyl)-2-oxo-1,2-dihydroquinolin-7-yl]-3,6-dihydropyridine-1(2H)-carboxylate by a procedure analogous to that described in EXAMPLE HHH2, Step C. Mass spectrum (ESI) 483 (M+1).

Step E: 5-(2-Chlorophenyl)-1-(2,6-dichlorophenyl)-7-(1-isopropylpiperidin-4-yl)quinolin-2(1H)-one The title compound was prepared from 5-(2-chlorophenyl)-1-(2,6-dichlorophenyl)-7-piperidin-4-ylquinolin-2(1H)-one by a procedure analogous to that described in EXAMPLE HHH2, Step D. Mass spectrum (ESI) 527 (M+1). $^1$H NMR (500 MHz, CDCl$_3$): δ 1.09 (br s, 6H); 1.42–1.96 (m, 4H); 2.10–3.20 (m, 6H); 6.38 (s, 1H); 6.65 (d, J=10 Hz, 1H); 7.34–7.62 (m, 7H).

EXAMPLE HHH12
5-(2-Chlorophenyl)-1-(2,6-dichlorophenyl)-7-(1-isopropyl-1,2,3,6-tetrahydropyridin-4-yl)quinolin-2(1H)-one

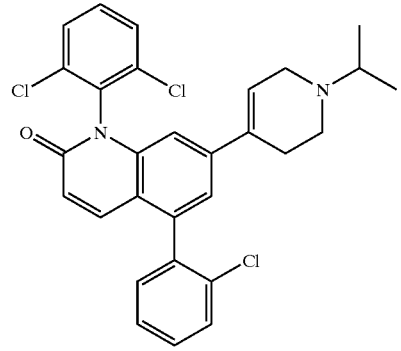

Step A: 5-(2-Chlorophenyl)-1-(2,6-dichlorophenyl)-7-(1,2,3,6-tetrahydropyridin-4-yl)quinolin-2(l1H)-one The title compound was prepared from tert-butyl 4-[5-(2-chlorophenyl)-1-(2,6-dichlorophenyl)-2-oxo-1,2-dihydroquinolin-7-yl]-3,6-dihydropyridine-1(2H)-carboxylate by a procedure analogous to that described in EXAMPLE HHH2, Step C. Mass spectrum (ESI) 482 (M+1).

Step B: 5-(2-Chlorophenyl)-1-(2,6-dichlorophenyl)-7-(1-isopropyl-1,2,3,6-tetrahydropyridin-4-yl)quinolin-2(1H)-one The title compound was prepared from 5-(2chlorophenyl)-1-(2,6-dichlorophenyl)-7-(1,2,3,6-tetrahydropyridin-4-yl)quinolin-2(1H)-one by a procedure analogous to that described in EXAMPLE HHH2, Step D. Mass spectrum (ESI) 525 (M+1). $^1$H NMR (500 MHz, CDCl$_3$): δ

COMPOUND HHH8
4-[5-(2-Chlorophenyl)-1-(2,6-dichlorophenyl)-2-oxo-1,2-dihydroquinolin-7-yl]-1-isopropylpyridinium

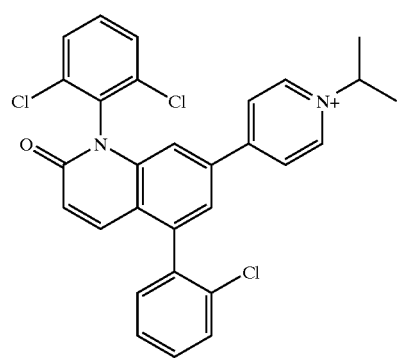

4-[5-(2-Chlorophenyl)-1-(2,6-dichlorophenyl)-2-oxo-1,2-dihydroquinolin-7-yl]-1-isopropylpyridinium was a minor product in the reductive amination of 5-(2-chlorophenyl)-1-

(2,6-dichlorophenyl)7-(1,2,3,6-tetrahydropyridin-4-yl) quinolin-2(1H)-one (EXAMPLE HHH12, Step B). Mass spectrum (ESI) 519 (M+).

EXAMPLE HHH13
5-(2-Chlorophenyl)-7-{[1-(1-cyclopropylethyl)piperidin-4-yl]oxy}-1-(2,6-dichlorophenyl)quinolin-2(1H)-one

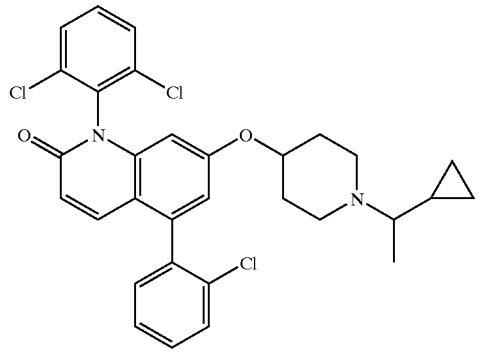

Step A: tert-Butyl 4-{[5-(2-chlorophenyl)-1-(2,6-dichlorophenyl)-2-oxo-1,2-dihydroquinolin-7-yl]oxy}piperidine-1-carboxylate The title compound was prepared from 55 mg 5-(2-chlorophenyl)-1-(2,6-dichlorophenyl)-7-hydroxyquinolin-2(1H)-one (INTERMEDIATE 9), 500 mg of polymer-bound Ph₃P, 128 mg of tert-butyl 4-hydroxypiperidine-1-carboxylate, and 122 mg of diethyl azodicarboxylate by a procedure analogous to that described in EXAMPLE 2. Mass spectrum (ESI) 599 (M+1).

Step B: 5-(2-Chlorophenyl)-1-(2,6-dichlorophenyl)-7-(piperidin-4-yloxy)quinolin-2(1H)-one The title compound was prepared from tert-butyl 4-{[5-(2-chlorophenyl)-1-(2,6-dichlorophenyl)-2-oxo-1,2-dihydroquinolin-7-yl]oxy}piperidine-1-carboxylate by a procedure analogous to that described in EXAMPLE HHH2, Step C. Mass spectrum (ESI) 99 (M+1).

Step C: 5-(2-Chlorophenyl)-7-{[1-(1-cyclopropylethyl)piperidin-4-yl]oxy}-1-(2,6-dichlorophenyl)quinolin-2(1H)-one To a solution of 8.8 mg of 5-(2-chlorophenyl)-1-(2,6-dichlorophenyl)-7-(piperidin-4-yloxy)quinolin-2(1H)-one in 0.9 mL of MeOH was added 0.1 mL of 1-cyclopropylethanone, then 6.5 mg of sodium cyanoborohydride. The mixture was stirred 4 d at rt. Another 0.5 mL of 1-cyclopropylethanone was added and the mixture was heated to reflux overnight, then concentrated and purified by preparative thin-layer chromatography, eluting with 95:5 CH₂Cl₂-2M NH₃ in MeOH to yield the title compound. Mass spectrum (ESI) 567 (M+1).

EXAMPLE HHH14
5-(2-Chlorophenyl)-1-(2,6-dichlorophenyl)-3-methyl-7-(2-piperidin-1-ylethyoxy)-3,4-dihydroquinolin-2(1H)-one

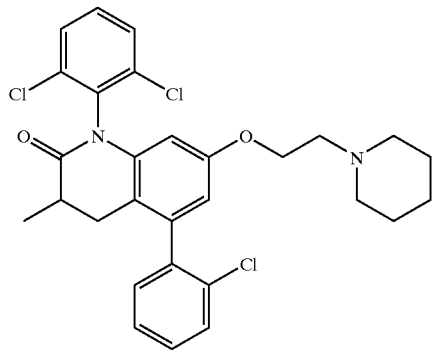

Step A: 5-(2-Chlorophenyl)-1-(2,6-dichlorophenyl)-7-methoxy-3-methyl-3,4-dihydroquinolin-2(1H)-one To 1 mL of THF at −78° C. was added 130 μL of a 1M solution of lithium bis(trimethylsilyl)amide in THF, then a solution of 50 mg of 5-(2-chlorophenyl)-1-(2,6-dichlorophenyl)-7-methoxyquinolin-2(1H)-one (INTERMEDIATE 6) in 2 mL of THF dropwise. The mixture was stirred for 30 min at −78° C.; then 57 mg of methyl iodide was added dropwise. The mixture was stirred 10 min at −78° C., then removed from the bath and allowed to warm to rt. The reaction was quenched by addition of 100 μL of MeOH, then poured into 10 mL of water and extracted with 2×10 mL of CH₂Cl₂. The combined organics were washed with 10 mL of brine, dried (MgSO₄), and concentrated. The residue was purified by preparative thin-layer chromatography, eluting with 95:5 CH₂Cl₂-acetone, to yield a 1:1.5 mixture of 5-(2-chlorophenyl)-1-(2,6-dichlorophenyl)-7-hydroxyquinolin-2(1H)-one and the title compound. Mass spectrum (ESI) 446 (M+1).

Step B: 5-(2-Chlorophenyl)-1-(2,6-dichlorophenyl)-7-hydroxy-3-methyl-3,4-dihydroquinolin-2(1H)-one The title compound was prepared from 43 mg of 5-(2-chlorophenyl)-1-(2,6-dichlorophenyl)-7-methoxy-3-methyl-3,4-dihydroquinolin-2(1H-one by a procedure analogous to that described in INTERMEDIATE 3.

Step C: 5-(2-Chlorophenyl)-1-(2,6-dichlorophenyl)-3-methyl-7-(2-piperidin-1-ylethoxy)-3,4-dihydroquinolin-2(1H)-one The title compound was prepared from 7 mg of 5-(2-chlorophenyl)-1-(2,6-dichlorophenyl)-7-hydroxy-3-methyl-3,4-dihydroquinolin-2(1H)-one, 40 mg of Ph₃P, 20 μL of 1-piperidine ethanol, and 20 μL of diethyl azodicarboxylate by a procedure analogous to that described in EXAMPLE 2. Mass spectrum (ESI) 545 (M+1).

EXMPLE RRR-1
5-(2-Chlorophenyl)-1-(2,6-dichlorophenyl)-7-[(1-methylpyrrolidin-3-yl)oxy]-3,4-dihydroquinolin-2(1H)-one

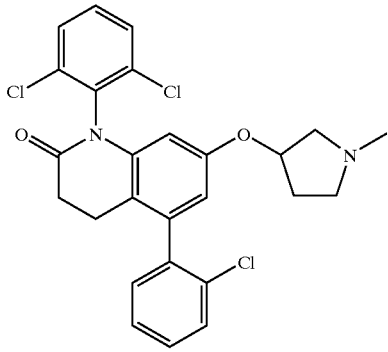

Step A: Benzyl 3-{[5-(2-chlorophenyl)-1-(2,6-dichlorophenyl)-2-oxo-1,2,3,4-tetrahydroquinolin 7-yl]oxy}pyrrolidine-1-carboxylate A solution of 0.046 g of 5-(2-chlorophenyl)-1-(2,6-dichlorophenyl)-7-hydroxy-3,4-dihydro-1-quinolin-2(1H)-one (INTERMEDIATE 6), triphenylphosphine (0.086 g), and (R)-3-hydroxy-N-Boc-pyrrolidine (0.062 g) in 8 mL of THF was heated to 65° C. DEAD (87 μL) was added dropwise over 2 min and the mixture was stirred at rt for 1 h. Purification was achieved by preparative thin layer chromatography eluting with 50% ethyl acetate/hexanes to give 0.051 g. Mass spectrum m/z (ESI) 587.2 (M+1).

Step B: 5-(2-Chlorophenyl)-1-(2,6-dichlorophenyl)-7-(pyrrolidin-3-yloxy)-3,4-dihydroquinolin-2(1H)-one To a solution of benzyl 3-([5-(2-chlorophenyl)-1-(2,6-dichlorophenyl)-2-oxo-1,2,3,4-tetrahydroquinolin-7-yl]oxy}pyrrolidine-1-carboxylate (0.051 g) in 6 mL of $CH_2Cl_2$ was added 1 mL of TFA and the mixture was stirred for 1 h at rt. The reaction mixture was purified by preparative thin layer chromatography eluting with 10% ethanol/dichloromethane to give the product. Mass spectrum m/z (ESI) 487.15 (M+1).

Step C: 5-(2-Chlorophenyl)-1-(2,6-dichlorophenyl)-7-[(1-methylpyrrolidin-3-yl)oxy]-3,4-dihydroquinolin-2(1H)-one To a solution of 5-(2-chlorophenyl)-1-(2,6-dichlorophenyl)-7-(pyrrolidin-3-yloxy)-3,4-dihydroquinolin-2(1H)-one (0.046 g) in 5 mL of methanol was added formaldehyde (50 μL) and sodium cyanoborohydride (0.012 g). The reaction mixture was stirred for 48 h, then washed with 1N HCl (5 mL), extracted with 5×5 mL of ethyl acetate, washed with brine (5 mL), dried with sodium sulfate, and concentrated. Purification was achieved by preparative thin layer chromatography eluting with 10% ethanol/dichloromethane to yield product. Mass spectrum (ESI) 501.1 (M+1). $^1$H NMR (500 MHz, $CDCl_3$): δ 7.50–7.48 (m, 3H), 7.36–7.30 (m, 4H) 6.38 (s, 1H), 5.85 (s, 1H), 4.66 (m, 1H), 2.87–2.65 (m, 8H), 2.36 (s, 3H), 2.18–2.15 m, 1H), 1.94–1.91 (m, 1H).

COMPOUND RRR-1
7-Bromo-1-(2,6-dichlorophenyl)-5-(2,4-difluorophenyl)-1,6-naphthyridin-2(1H)-one

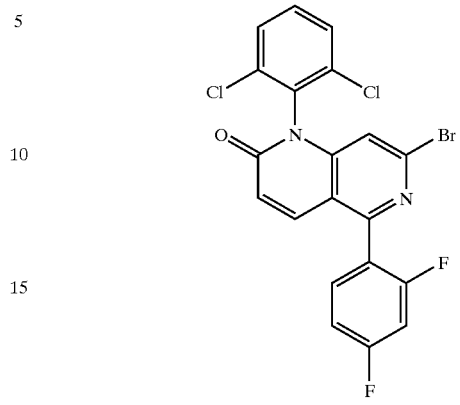

Step A: 2-(2,4-difluorophenyl)-3-methyl-5-nitropyridine

To a stirred solution of 2-chloro-3-methyl-5-nitropyridine (prepared according to the procedure of Hawkins and Roe, J. Am. Chem. Soc., page 330, 1948) (17.6 g, 102 mmol, 1 eq.) in DMF (220 mL) was added 2,4-difluorobenzeneboronic acid (16.16 g, 102 mmol, 1 eq.) followed by $Cs_2CO_3$ (41.1 g, 122.7 mmol, 1.2 eq). The mixture was degassed with argon. To the mixture was added tetrakis(triphenylphosphine)palladium(0) (2.5 g, 2 mmol, 0.02 eq). The mixture was degassed with argon and then heated to 100° C. under argon. After 18 h the mixture was cooled. The mixture was filtered and the filtrate concentrated under reduced pressure. The filtrate was partitioned between water and ethyl acetate. The aqueous layer was extracted several times with ethyl acetate. The organic extracts were combined, dried over anhydrous $Na_2SO_4$, filtered and concentrated. The material was purified by flash column chromatography eluting with 5:1 hekanes/acetone giving 7.5 g 2-(2,4-difluorophenyl)-3-methyl-5-nitropyridine. Mass spectrum (ESI) 251.3 (M+1). $^1$H NMR (500 MHz, $CDCl_3$) δ$CHCl_3$: 9.35 (1H, s); 8.42 (1H, s); 7.47 (1H,m); 7.07 (1H, m); 6.97 (1H, m); 2.41 (3H, s).

Step B: 6-(2,4-difluorophenyl)-5-methylpyridin-3-amine

To a stirred solution of 2-(2,4-difluorophenyl)-3-methyl-5-nitropyridine (7.5 g, 30 mmol, 1 eq) in methanol (100 mL) in a 500 mL round bottom flask was added 7 g of Raney Nickel slurry. The flask was evacuated and charged with hydrogen 4 times. The mixture was stirred under $H_2$. After 5 h the reaction flask was purged with nitrogen. The mixture was filtered and the methanol was removed under reduced pressure giving 6.4 g 6-(2,4-difluorophenyl)-5-methylpyridin-3-amine.

Mass spectrum (ESI) 221.3 (M+1).

Step C: 2,4-dibromo-6-(2,4-difluorophenyl)-5-methylpyridin-3-amine

To a stirred solution of (2,4-difluorophenyl)-5-methylpyridin-3-amine (6.4 g, 29.3 mmol, 1 eq) in THF (20 mL) was added 2N aqueous HCl (40 mL). The mixture was cooled to 0 C. and bromine (4.6 mL, 89.28 mmol, 3 eq) was added dropwise via syringe. There was noticeable warming of the reaction mixture. The cooling bath was removed and the mixture was stirred 6 h. The reaction was quenched by addition of aqueous $NaHSO_3$. Ethyl acetate was added to the mixture and aqueous. layer made basic to effect dissolution of the solids. The mixture was extracted 3× with ethyl acetate. The organic extracts were combined, dried over anhydrous $Na_2SO_4$, filtered and concentrated giving 2,4-dibromo-6-(2,4-difluorophenyl)-5-methylpyridin-3-amine. Mass spectrum (ESI) 377.2 (M+1); 379.2 (M+3); 381.2 (M+5). $^1$H NMR (500 MHz, CDCl$_3$) δCHCl$_3$: 7.39 (1H m); 6.98 (1H, m); 6.88 (1H, m); 4.69 (2H, br s); 2.25 (3H, s):

Step D: 4,6-dibromo-2-(2,4-difluorophenyl)-3-methylpyridine

To a stirred solution of 2,4-dibromo-6-(2,4-difluorophenyl)-5-methylpyridin-3-amine (10 g, 26.4 mmol, 1 eq) in THF (100 mL) was added tert-butylnitrite (4.7 mL, 39.6 mmol, 1.5 eq). The solution warmed and gas evolution was evident. After 2 h, the mixture was heated to and maintained at 60° C. for 45 min. The mixture was cooled and concentrated in vacuo. The product was purified by flash column chromatography eluting with 2% Et$_2$O in hexanes to give 4,6-dibromo-2-(2,4-difluorophenyl)-3-methylpyridine. Mass spectrum (ESI) 362.2 (M+1); 364.2 (M+3); 366.2 (M+5).

Step E: 4,6-dibromo-3-(bromomethyl)-2-(2,4-difluorophenyl)pyridine

To a stirred solution of 4,6-dibromo-2-(2,4-difluorophenyl)-3-methylpyridine (5.0 g, 13.77 mmol, 1 eq) in CCl$_4$ (125 mL) was added N-bromosuccinimide (2.95 g, 16.6 mmol 1.2 eq) and benzoyl peroxide (340 mg, 1.37 mmol, 0.1 eq). The mixture was brought to and maintained at reflux until all the starting material was consumed (approx 3.5 h). The reaction mixture was cooled to 0° C. and the succinimide was filtered off. The solvent was removed under reduced pressure and the product was purified by flash column chromatography on silica gel elufing with 2% Et$_2$O in hexanes giving 4,6-dibromo-3-(bromomethyl)-2-(2,4-difluorophenyl)pyridine. Mass spectrum (ESI) 440.1 (M+1); 442.1 (M+3); 444.1 (M+5); 446.1 (M+7). $^1$H NMR (500 MHz, CDCl$_3$) δCHCl$_3$: 7.84 (1H, s); 7.50 (1H, m); 7.05 (1H, m); 6.96 (1H, m); 4.44 (2H br s).

Step F: tert-Butyl 3-[4,6-dibromo-2-(2,4-difluorophenyl)pyridin-3-yl]propanoate

To a −78° C. solution of the lithium bis(trimethylsilylamide) (14 mL) in mL of THF was added t-butylacetate (2 mL). After stirring for 10 min, 4,6-dibromo-2-(2,4-difluorophenyl)-3-methylpyridine (1.0 g) dissolved in 3 mL THF was added dropwise. The mixture stirred at −78° C. for 1.5 h, then warmed to −50° C. The reaction mixture was then recooled to −78° C. and 3 mL of methanol was added. The solution stirred for 24 h at rt. The crude mixture was purified by flash chromatography, eluting with 50% ethyl acetate/hexanes. Mass spectrum m/z (ESI) 478.3 (M+1).

Step G: 3-[4,6-Dibromo-2-(2,4-difluorophenyl)pyridin-3-yl]-N-(2,6-dichlorophenyl)propanamide A solution of tert-butyl 3-[4,6-dibromo-2-(2,4-difluorophenyl)pyridin-3-yl]propanoate (3.56 g) in 20 mL of TEA was stirred for 45 min at rt, then co-concentrated with 40 mL of toluene. The resulting oil was dissolved in 50 mL of benzene and 5 mL of MeOH. Trimethylsilyldiazomethane (6 mL) was added dropwise and the mixture was stirred for 30 min, then quenched by addition of 1 mL of TFA, then concentrated to an off-white solid. To a solution of 2,6-dichloroaniline (2.42 g) in 40 mL of CH$_2$Cl$_2$ was added dropwise 7.5 mL of trimethylaluminum; this mixture was stirred for 15 min. The methyl ester was dissolved in 40 mL of CH$_2$Cl$_2$ and added to the 2,6-dichloroaniline mixture. After stirring for 24 h at rt, water was carefully added. A solution of 25 mL of Rochelle salt and 25 mL of CH$_2$Cl$_2$ was added and the mixture was stirred for 1 h at rt. A white solid precipitated and was filtered. The remaining solid was dissolved in CH$_2$Cl$_2$ and extracted with brine, dried with sodium sulfate and concentrated to yield the amide. Mass spectrum m/z (ESI) 562.8 (M+1).

Step H: 7-Bromo-1-(2,6-dichlorophenyl)-5-(2,4-difluorophenyl)-3,4-dihydro-1,6-naphthyridin-2(1H)-one To a solution of 3-[4,6-dibromo-2-(2,4-difluorophenyl)pyridin-3-yl]-N-(2,6-dichlorophenyl)propanamide (1 g) in 30 mL of DMF was added potassium carbonate (0.489 g) and copper iodide (0.5 g). The reaction mixture was stirred for 24 h at 155° C., then cooled and diluted with 10 mL of saturated sodium bicarbonate. This solution was extracted twice with 10 mL of ethyl acetate, washed with 10 mL of brine, dried with sodium sulfate, then concentrated. The residue was purified by flash chromatography with 1% acetone in CH$_2$Cl$_2$. Mass spectrum m/z (ESI) 485.3 (M+1).

Step I: 7-Bromo-1-(2,6-dichlorophenyl)-5-(2,4-difluorophenyl)-1,6-naphthyridin-2(1H)-one To a refluxing solution of 7-bromo-1-(2,6-dichlorophenyl)-5-(2,4-difluorophenyl)-3,4-dihydro-1,6-naphthyridin-2(1H)-one (0.747 g) and AIBN (0.03 g) in 30 mL of CCl$_4$ was added recrystallized N-bromosuccinimide (0.302 g). The reaction was stirred at reflux for 1 h, then removed from the heat. DBU (0.23 mL) was added and the mixture was stirred at rt for 15 min. The reaction mixture was washed with 100 mL of saturated sodium bicarbonate and back extracted with 50 mL of dichloromethane. The combined organics were washed with 100 mL of brine, dried with sodium sulfate, and concentrated to give the desired product. Mass spectrum m/z (ESI) 481.3 (M+1).

EXAMPLE RRR-2
7-(1-tert-Butyl-1,2,3,6-tetrahydropyridin-4-yl)-1-(2,6-dichlorophenyl)-5-(2,4-difluorophenyl)-1,6-naphthyridin-2(1H)-one

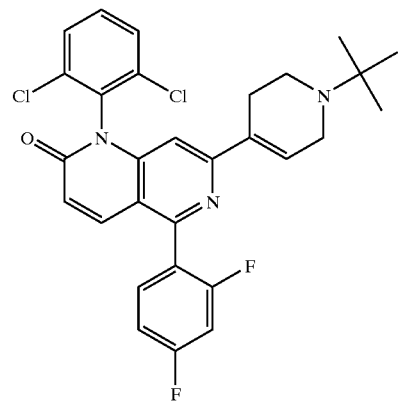

To a solution of 0.10 g of 7-bromo-5-(2,4-difluorophenyl)-1-(2,6-dichlorophenyl)-1,6-naphthyridin-2(1H)-one (COMPOUND RRR-1) in 5 mL of dioxane was added 0.083 g of 1-tert-butyl-1,2,3,6-tetrahydropyridin-4-trimethyltin (COMPOUND PPA-2) dissolved in 1 mL of dioxane. The solution was purged with argon; then tetra(triphenylphosphine)palladium ,(0.053 g) was added and the mixture was heated to 100° C. for 7 h. The product was purified by preparative thin layer chromatography eluting with 50% ethyl acetate/hexanes, then by high pressure liquid chromatography (flow rate=20 ml/min., gradient=10%–100% acetonitrile [0.05% TFA] in water [0.05% TFA] over 12 min, column=XTerra C8 19×50 mm). Mass spectrum (ESI) 540.5 (M+1). $^1$H NMR (500 MHz, CDCl$_3$): δ 7.66 (d, J=10 Hz 1H), 7.59 (m, 3H), 7.46 (t, J=4 Hz, 1H), 7.09 (t, J=4 Hz, 1H), 6.99 (t, J=4 Hz, 1H), 671 (d, J=10 Hz, 1H), 6.63 (s, 1H), 6.31 (s, 1H), 3.34 (s, 2H), 2.73 (s, 2H), 2.48 (s, 2H), 1.06 (s, 9H).

EXAMPLE RRR-3
7-(1-tert-Butylpiperidin-4-yl)-1-(2,6-dichlorophenyl)-5-(2,4-difluorophenyl)-1,6-naphthyridin-2(1H)-one

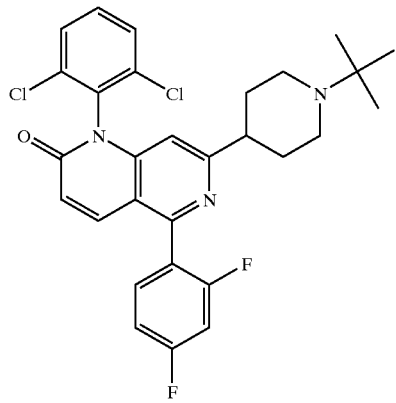

To a solution of 0.0237 g of 7-bromo-5-(2,4-difluorophenyl)-1-(2,6-dichlorophenyl)-1,6-naphthyridin-2(1H)-one (COMPOUND RRR-1) in 5 mL of 9:1 methanol-ethyl acetate was added platinum oxide (0.0115 g). The mixture was stirred under a hydrogen balloon for 30 min, then filtered and purified by high pressure liquid chromatography (flow rate=20 mL/min., gradient=10%–100% acetonitrile [0.05% TFA] in water [0.05% TFA] over 12 min, column=XTerra C8 19×50 mm), then by preparative thin layer chromatography. Mass spectrum (ESI) 542.4 (M+1). $^1$H NMR (500 MHz, CDCl$_3$): δ 7.66 (d, J=10 Hz, 1H), 7.59 (m, 3H), 7.46 (t, J=4 Hz, 1H), 7.09 (t, J=4 Hz, 1H), 6.99 (t, J=4 Hz,1H), 6.71 (d, J=10 Hz, 1H), 6.28 (s, 1H), 3.15 (br s, 2H), 2.74 (m, 1H), 2.20 (br s, 2H), 1.97 (br s, 2H), 1.64 (br s, 2H), 1.05 (s, 9H).

COMPOUND RRR-3
1-(2,6-Dichlorophenyl)-5-(2,4-difluorophenyl)-7-methyl-1,6-naphthyridin-2(1H)-one

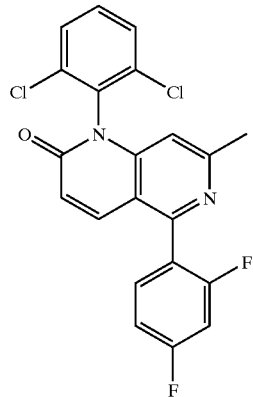

The title compound was a minor product in the coupling of 7-bromo-5-(2,4-difluorophenyl)-1-(2,6-dichlorophenyl)-1,6-naphthyridin-2(1H)-one) and 1-tert-butyl-1,2,3,6-tetrahydropyridin-4-trimethyltin (EXAMPLE RRR-2). Mass spectrum (ESI) 417.3 (M+1).

COMPOUND RRR-4
1-(2,6-Dichlorphenyl)-5-(2,4-difluorophenyl)-1,6-naphthyridin-2(1H)-one

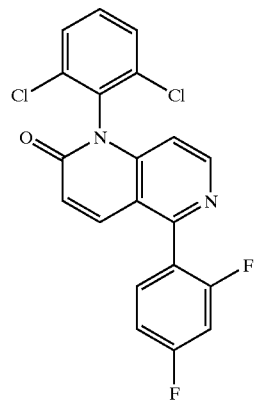

The title compound was a minor product in the coupling of 7-bromo-5-(2,4-difluorophenyl)-1-(2,6-dichlorophenyl)-1,6-naphthyridin-2(1H)-one) and 1-tert-butyl-1,2,3,6-tetrahydropyridin-4-trimethyltin (EXAMPLE RRR-2). Mass spectrum (ESI) 403.2 (M+1).

EXAMPLE RRR-4
7-[(tert-Butylazetidin-3-yl)oxy]-1-(2,6-dichlorphenyl)-5-(2,4-difluorophenyl)-1,6-naphthyridin-2((1H)-one

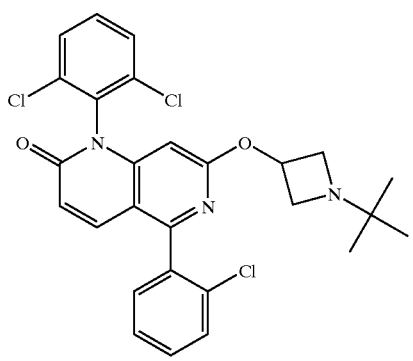

To a solution of N-tert-butylazetidin-4-ol (prepared as described by V. Gaertner, *Tetrahedron Lett.* 1966, 4691.)) in 5 mL of dioxane was added sodium hydride (0.005 g), The mixture wasp stirred at rt for 10 min; then 0.05 g of 7-bromo-5-(2chlorophenyl)-1-(2,6-chlorophenyl)-1,6-naphthyridin-2(1H)-one (COMPOUND HHH1) was added and the mixture, was heated to reflux and stirred at this temperature for 3 h. Purification of the product was achieved by preparative thin layer chromatography eluting with 10% methanol/dichloromethane. Mass spectrum (ESI) 528.04 (M+1). $^1$H NMR (500 MHz, CDCl$_3$): δ 7.41–7.62 (m, 3H), 7.51–7.39 (m, 5H), 6.54 (d, J=6 Hz, 1H), 5.79 (s, 1H), 5.28 (m, 1H), 3.89 (br s, 2H), 3.44 (br s, 2H), 1.09 (s, 9H).

COMPOUND RRR-5
8-(2,6-Dichlorophenyl)-4-(2,4-difluorophenyl)-2-(methylsulfonyl)pyrido(2,3-d]pyrimidin-7(8H)-one

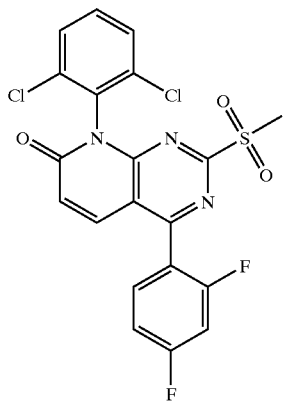

Step A: tert-Butyl 3-[4-chloro-6-(2,4-difluorophenyl)-2-(methylthio)pyrimidin-5-yl]propanoate To a −78° C. solution of LiHMDS (4.1 mL) in 3 mL of THF was added t-butylacetate (0.6 mL). After stirring for 10 min, 1.0 g of 5-(bromomethyl)-4-chloro-6-(2,4-difluorophenyl)-2-(methylthio)pyrimidine (COMPOUND VV-3) in 4 mL of THF was added dropwise. The mixture was stirred at −78° C. for 1.5 h, then warmed to −50° C. The reaction mixture was recooled to −78° C. and 3 mL of methanol was added. The solution stirred for 24 h at rt. The crude mixture was purified by flash chromatography, eluting with 2% diethyl ether/hexanes. Mass spectrum m/z (ESI) 401.5 (M+1).

Step B: 3-[4-Chloro-6-(2,4-difluorophenyl)-2-(methylthio)pyrimidin-5-yl]-N-(2,6-dichlorophenyl)propanamide A solution of tert-butyl 3-[4-chloro(2,4-difluorophenyl)-2-(methylthio)pyrimidin-5-yl]propanoate (1.0 g) in 5 mL of TFA was stirred for 45 min at rt, then co-concentrated with 10 mL of toluene. The resulting oil was dissolved in 15 mL of benzene and 2 mL of MeOH. Trimethylsilyldiazomethane (1.3 mL) was added dropwise and the mixture was stirred for 30 min; then 0.5 mL of TFA was added and the mixture was concentrated to an off-white solid. To a solution of 2,6-dichloroaniline (0.8 g) in 10 mL of $CH_2Cl_2$ was added dropwise 2.5 mL of trimethylaluminum, and the mixture was stirred 15 min. The methyl ester was dissolved in 10 mL of $CH_2Cl_2$ and added to the 2,6-dichloroaniline mixture. After stirring for 24 h at rt, water was carefully added. A solution of 5 mL of Rochelle salt and 10 mL $CH_2Cl_2$ was added and the mixture was stirred for 1 h at rt. A white solid precipitated and was filtered. The filtrate was extracted with brine, dried with sodium sulfate and concentrated to give the amide. Mass spectrum m/z (ESI) 488.3 (M+1).

Step C: 3-[4-Chloro-6-(2,4-difluorophenyl)-2-(methylthio)pyrimidin-5-yl]-N-(2,6-dichlorophenyl)propanamide To a solution of 3-[4-chloro-6-(2,4-difluorophenyl)-2-(methylthio)pyrimidin-5-yl]-N-(2,6-dichlorophenyl)propanamide (0.28 g) in 15 mL of dimethylformamide was added potassium carbonate (0.237 g) and copper iodide (0.218 g). The reaction mixture was stirred for 24 h at 150° C., then cooled and diluted with 5 mL of saturated sodium bicarbonate. This solution was extracted twice with 5 mL of ethyl acetate, washed with 5 mL of brine, dried with sodium sulfate, then concentrated. Purification was achieved by high pressure liquid chromatography (flow rate=20 mL/min, gradient=90%–10% water (0.01% TFA) in acetonitrile over 15 min, column=YMC C18 100×20 mm). Mass spectrum m/z (ESI) 452.4 (M+1).

Step D: 8-(2,6-Dichlorophenyl)-4-(2,4-difluorophenyl)-2-(methylthio)pyrido[2,3-d]pyrimidin-7(8H)-one To a refluxing solution of 3-[4-chloro-6-(2,4-difluorophenyl)-2-(methylthio)pyrimidin-5-yl]-N-(2,6-dichlorophenyl)propanamide (0.06 g) and AIBN (0.005 g) in 8 mL of $CCl_4$ was added recrystallized N-bromosuccinimide (0.026 g). The reaction was refluxed for 1 h, then removed from the heat. DBU (0.02 mL) was added and the solution was stirred at rt for 15 min. The reaction mixture was washed with 20 mL of saturated sodium bicarbonate and back extracted with 20 mL of $CH_2Cl_2$. The organic layer was washed with 20 mL of brine, dried with sodium sulfate, and concentrated to give the desired product. Mass spectrum m/z (ESI) 450.4 (M+1).

Step E: 8-(2,6-Dichlorophenyl)-4-(2,4-difluorophenyl)-2-[(trifluoromethyl)sulfonyl]pyrido[2,3-d]pyrimidin-7(8H)-one To a solution of 8-(2,6-dichlorophenyl)-4-(2,4-difluorophenyl)-2-(methylthio)pyrido[2,3-d]pyrimidin-7(8H)-one (0.022 g) in 1 mL of THF was added MMPP (0.048 g). The reaction mixture was stirred for 1 h at rt, then diluted with 5 mL of ethyl acetate and filtered through Celite. This filtrate was washed with saturated sodium bicarbonate and back extracted with $CH_2Cl_2$. The combined organics were washed with brine, dried with sodium sulfate, and concentrated. The product was obtained by preparative thin layer chromatography eluting with 5% acetone/dichloromethane. Mass spectrum m/z (ESI) 482.3 (M+1).

COMPOUND PS
4,6-dibromo-3-(bromomethyl)-2-(2-chloro-4-fluorophenyl)pyridine

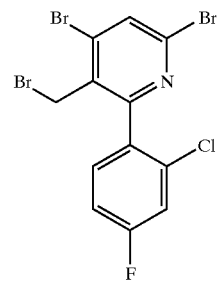

STEP A: 2-(2-chloro-4-fluorophenyl)-3-methyl-5-nitropyridine

To a stirred solution of 2-chloro-3-methyl-5-nitropyridine (prepared according to the procedure of Hawkins and Roe, J. Am. Chem. Soc., page 330, 1948) (5.3 g, 30.7 mmol, 1 eq.) in 1,2-dimethoxyethane (50 mL) and ethanol (25 mL) was added 2-chloro-4-fluorobenzeneboronic acid (5.9 g, 33.8 mmol, 1.1 eq.). The resulting mixture was degassed with argon. To the mixture was added a solution of $Na_2CO_3$ (11.4 g, 107.45 mmol, 3.5 eq) in water (50 mL). The mixture was degassed with argon, and tetrakis(triphenylphosphine)palladium(0) (1.1 g, 0.95 mmol, 0.03 eq) was added. The mixture was degassed with argon and heated to 90° C. under argon. After 4.5 h, the mixture was cooled. The solvent was removed under reduced pressure. The residue was diluted with water and extracted 3× with ethyl acetate. The aqueous layer was extracted several times with ethyl acetate. The organic extracts were combined, dried over anhydrous $Na_2SO_4$, filtered and concentrated. The product was purified by flash column chromatography on silica gel eluting with 5% $Et_2O$ in hexanes giving 2-(2-chloro-4-fluorophenyl)-3-methyl-5-nitropyridine. Mass spectrum (EST) 267 (M+1).

$^1$H NMR (500 MHz, $CDCl_3$) δ$CHCl_3$: 9.35 (1H, d, J=2.2 Hz); 8.42(1H, d, J=2.2 Hz); 7.3 (2H, m); 7.16 (1H, m); 2.32 (3H, s).

STEP B: 6-(2-chloro-4-fluorophenyl)-5-methylpyridin-3-amine

A 250 mL round bottom flask was charged with 2-(2-chloro-4-fluorophenyl)-3-methyl-5-nitropyridine (4 g) and methanol (50 mL). To the flask was added Raney nickel/methanol slurry (approx 4 g). The flask was evacuated and charged with hydrogen several times. The mixture was stirred under a balloon of hydrogen for 2.5 h. The flask was purged with nitrogen. The catalyst was filtered off and the filtrate was concentrated under reduced pressure giving 6-(2-chloro-4-fluorophenyl)-5-methylpyridin-3-amine as an off white solid. Mass spectrum (ESI) 237 (M+1).

STEP C: 2,4-dibromo-6-(2-chloro-4-fluorophenyl)-5-methylpyridin-3-amine

To a solution of 6-(2-chloro-4-fluorophenyl)-5-methylpyridin-3-amine (3.33 g, 14.11 mmol, 1 eq) in THF (10 mL) was added 2N aqueous HCl (20 mL). To this mixture was added bromine (2.17 g, 42.33 mmol, 3 eq) dropwise via syringe. The mixture was stirred 6 h and then quenched by addition of aqueous NaHSO$_3$. The mixture was made basic and then extracted 3× with isopropyl acetate. The organic extracts were combined, dried over anhydrous Na$_2$SO$_4$, filtered and concentrated to give 2,4-dibromo-6-(2-chloro-4-fluorophenyl)-5-methylpyridin-3-amine. Mass spectrum (ESI) 393 (M+1); 395 (M+3); 397 (M+5). $^1$H NMR (500 MHz, CDCl$_3$) δCHCl$_3$: 7.30 (1H, dd, J=6.2 Hz, J=8.5 Hz); 7.21 (1H, dd, J=8.5 Hz, J=2.5 Hz); 7.07 (1H, ddd, J=8.5 Hz, J=8.5 Hz, J=2.5 Hz); 4.7 (2H, br s); 2.18 (3H, s).

Step D: 4,6-dibromo-2-(2-chloro-4-fluorophenyl)-3-methylpyridine

To a stirred solution of 2,4-dibromo-6-(2-chloro-4-fluorophenyl)-5-methylpyridin-3-amine (4.8 g, 12.2 mmol, 1 eq) in THF (50 mL) was added tert-butylnitrite (2.2 mL, 18.25 mmol, 1.5 eq). The mixture was warmed to 60° C. and mild gas evolution was observed. After 1.75 h the heating bath was turned off and the mixture was allowed to stir overnight. Additional tert-butylnitrite (1 mL) was added and the mixture was again warmed to 60° C. After 2 h no starting material was left as assessed by HPLC analysis. The mixture was cooled and the solvent removed under reduced pressure. The product was purified by flash column chromatography on silica gel eluting with 2% Et$_2$O in hexanes to give 4,6-dibromo-2-(2-chloro-4-fluorophenyl)-3-methylpyridine. Mass spectrum (ESI) 378.0 (M+1); 380.0 (M+3); 382.0 (M+5).

Step E: 4,6-dibromo-3-(bromomethyl)-2-(2-chloro6-4-fluorophenyl)pyridine

To a solution of 4,6-dibromo-2-(2-chloro-4-fluorophenyl)-3-methylpyridine (3.55 g, 9.35 mmol, 1 eq) in 1,2-dichloroethane (90 mL) was added N-bromosuccinimide (2.0 g, 11.22 mmol, 1.2 eq) and benzoyl peroxide (226 mg, 0.9 mmol, 0.1 eq). The resulting mixture was degassed with argon then warmed to and maintained at reflux for 5.5 h. The mixture was cooled solvent was removed under reduced pressure, and the material was purified by flash column chromatography eluting with 2% Et2O in hexanes. The material was re-dissolved in CCl$_4$ and N-bromosuccinimide (667 mg) and benzoyl peroxide (75 mg) were added. The mixture was brought to and maintained at reflux for 6.5 h. The mixture was cooled to 0° C., filtered to remove the succinimide, and concentrated under reduced pressure. The product was purified by flash column chromatography on silica gel eluting with 2% Et2O in hexanes to give 4,6-dibromo-3-(bromomethyl)-2-(2-chloro-4-fluorophenyl)pyridine. Mass spectrum (ESI) 456.1 (M+1); 458.0 (M+3); 460.1 (M+5); 462.1 (M+7). $^1$H NMR (500 MHz, CDCl$_3$) δCHCl$_3$: 7.85 (1H, s); 7.46 (1H, dd, J=8.5 Hz, J=5.7 Hz); 7.27 (1H, dd, J=8.5 Hz, J=2.5 Hz); 7.16 (1H, ddd, J=8.5 Hz, J=8.3 Hz, J=2.5 Hz); 4.55 (1H, ½ ABq, J=10.8 Hz); 4.17 (1H, ½ ABq, J=10.8 Hz, COMPOUND CCC1
7-bromo-5-(2-chloro-4-fluorophenyl)-1-(2,6-dichlorophenyl)-1,6-naphthyridin-2(1H)-one

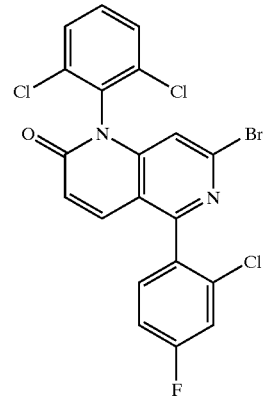

STEP A: tert-butyl 3-[4,6-dibromo-2-(2-chloro-4-fluorophenyl)pyridin-3-yl]propanoate To a 1M solution of lithium bis(trimethlsilyl)amide (10.5 mL) at −78° C. was added tert-butyl acetate (1.77 mL, 13.2 mmol) dropwise. To this mixture a solution of 4,6-dibromo-3-(bromomethyl)-2-(2-chloro-4-fluorophenyl)pyridine (4.02 g, 8.77 mmol) (COMPOUND PS) in 9.2 mL of THF was added dropwise over 20 min. After stirring for 30 min at −78° C., the reaction mixture was quenched by the dropwise addition of 3 mL of methanol, then warmed up to rt and partitioned between 30 mL each of saturated aqueous NaHCO$_3$ and ethyl acetate. The aqueous phase was extracted with 2×20 mL of ethyl acetate. The combined organic layers were washed with brine (20 mL), dried over Na$_2$SO$_4$, and concentrated under reduced pressure. The residue was triturated with warm Et$_2$O. The mother liquor was purified by flash chromatography on a Biotage 40M column eluting with 97:3 hexanes-ethyl acetate. The two batches were combined to give the tert-butyl 3-[4,6-dibromo-2-(2-chloro-4-fluorophenyl)pyridin-3-yl] propanoate. Mass spectrum (ESI) 492.4 (M+1).

STEP B: 3-[4,6-dibromo-2-(2-chloro-4-fluorophenyl)pyridin-3-yl]-N-(2,6-dichlorophenyl)propanamide tert-butyl 3-[-4,6-dibromo-2-(2-chloro-4-fluorophenyl)pyridin-3-yl]propanoate (3.42 g, 6.93 mmol) was dissolved in 12 mL of trifluoroacetic acid and stirred at rt for 0.75 h. 30 mL of toluene was added and the resulting mixture was concentrated under reduced pressure. The resulting solid was dissolved in 50 mL of benzene and 5 mL of methanol. A 2M solution of (trimethylsilyl)diazomethane in hexanes (4.16 mL, 8.32 mmol) was added dropwise and the reaction mixture was stirred for 30 min. 2 drops of trifluoroacetic acid were added and the solvent was removed under reduced pressure. The resulting methyl ester was dissolved in 12 mL of CH$_2$Cl$_2$. To 2,6-dichloroaniline (2.25 g, 13.9 mmol) in 36 mL of CH$_2$Cl$_2$ was added dropwise a 2M solution of trimethylaluminum in toluene (7.0 mL, 13.9 mmol) and the mixture was stirred for 15 min. Then the methyl ester solution in CH$_2$Cl$_2$ was added and the resulting mixture was stirred at rt overnight. 24 mL of water was added very carefully followed by 12 mL of an aqueous 1M solution of potassium sodium tartarate and 24 mL of CH$_2$Cl$_2$. The mixture was stirred vigorously for 1 h and then filtered. The filtered solids were dissolved with CH₂Cl₂, washed with brine, dried over Na₂SO₄, and concentrated under reduced pressure to give one pure crop. The filtrate was separated, washed with brine, dried over Na₂SO₄, and concentrated under reduced pressure. The residue was triturated with hot ethanol to give a second pure crop. The two crops were combined to give the 3-[4,6-dibromo-2-(2-chloro-4-fluorophenyl)pyridin-3-yl]-N-(2,6-dichlorophenyl) propanamide as a white solid.

Mass spectrum (ESI) 579.2 (M+1).

STEP C: 7-bromo-5-(2-chloro-4-fluorophenyl)-1-(2,6-dichlorophenyl)-3,4-dihydro-1,6-naphthyridin-2(1H)-one To 3-[4,6-dibromo-2-(2-chloro-4-fluorophenyl)pyridin-3-yl]-N-(2,6-dichlorophenyl)propanamide (3.14 g, 5.40 mmol) in DMF (50 mL) was added K₂CO₃ (1.49 g, 10.8 mmol) and CuI (1.54 g, 10.8 mmol). The resulting reaction mixture was evacuated and purged with argon 3 times, and then heated at 155° C. (oil bath) for 35 min. The reaction mixture was cooled to rt and diluted with 240 mL of half-saturated aqueous NaHCO₃ and 120 mL of ethyl acetate. The layers were separated and the aqueous layer was extracted with 2×180 mL of ethyl acetate. The combined organic layers were washed with 120 mL of brine, dried over Na₂SO₄, and concentrated under reduced pressure. The product was purified by flash chromatography on 2 Biotage 40M columns, eluting with 50:50 hexanes-CH₂Cl₂ to yield 7-bromo-5-(2-chloro-4-fluorophenyl)-1-(2,6-dichlorophenyl)-3,4-dihydro-1,6-naphthyridin-2(1H)-one. Mass spectrum (ESI) 499.2 (M+1).

STEP D: 7-bromo-5-(2-chloro-4-fluorophenyl)-1-(2,6-dichlorophenyl)-1,6-naphthyridin-2(1H)-one To 7-bromo-5-(2-chloro-4-fluorophenyl)-1-(2,6-dichlorophenyl)-3,4-dihydro-1,6-naphthyridin-2(1H)-one (2.33 g, 4.65 mmol) in 75 mL of CCl₄ was added recrystallized N-bromosuccinimide (993 mg, 5.58 mmol) and 2,2'azobis(2-methylpropionitrile) (76.4 mg, 0.465 mmol). The resulting reaction mixture was evacuated and flushed with argon 3 times, then heated and maintained at reflux for 2.5 h. 1,8-diazabicyclo[5.4.0]undec-7-ene (695 μL, 4.65 mmol) was added and the reaction mixture was cooled to rt, washed with 140 mL of half-saturated aqueous NaHCO₃, and the aqueous layer was back-extracted with 2×70 mL of ethyl acetate. The combined organic layers were washed with brine, dried over Na₂SO₄, and concentrated under reduced pressure. The product was purified by flash chromatography on Biotage 40M column, eluting with a gradient system of 90:10 hexanes-ethyl acetate to 80:20 hexanes-ethyl acetate to yield 7-bromo-5-(2-chloro-4-fluorophenyl)-1-(2,6-dichlorophenyl)-1,6-naphthyridin-2(1H)-one as an off white solid. Mass spectrum (ESI) 497 (M+1). ¹H NMR (500 MHz, CDCl₃): δ 6.64 (s, 1H); 6.79 (d, J=10.1 Hz, 1H); 7.21 (m, 1H), 7.31 (m, 1H); 7.54 (m, 3H); 7.65 (m, 2H), EXAMPLE CZC1
7-(1-tert-butyl-1,2,3,6-tetrahydropyridin-4-yl)-5-(2-chloro-4-fluorophenyl)-1-(2,6-dichlorophenyl)-1,6-naphthyridin-2(1H)-one

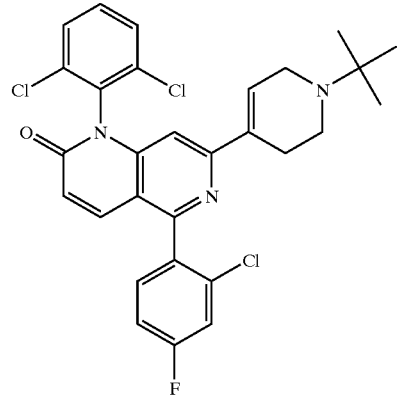

To 7-bromo-5-(2-chloro-4-fluorophenyl)-1-(2,6-dichlorophenyl)-1,6-naphthyridin-2(1H)-one (100 mg, 0.20 mmol) (COMPOUND CCC1) in anhydrous 1,4-dioxane (5 mL) was added 1-tert-butyl-4-(trimethylstannyl)-1,2,3,6-tetrahydropyridine (91 mg, 0.30 mmol) (COMPOUND PPA2). The reaction mixture was evacuated and purged three times with argon. Then tetrakis(triphenylphosphine)palladium(0) (35 mg, 0.03 mmol) was added and the mixture was evacuated and purged again with argon. The mixture was heated and maintained at reflux overnight. The mixture was cooled to rt, diluted with ethyl acetate, filtered through a pad of Celite, and concentrated under reduced pressure. The product was purified by preparative thin-layer chromatography, eluting with 95:5 CH₂Cl₂-2M NH₃ in methanol to yield the title compound. Mass spectrum (EST) 556.4 (M+1). ¹H NMR (400 MHz, CD₃OD): δ 1.13 (s, 9H); 2.46 (brs, 2H); 2.78 (t, J=5.2 Hz, 2H), 3.35 (brs, 2H); 6.45 (s, 1H); 6.72 (m, 2H); 7.31 (ddd, J=8.3 Hz, J=8.3 Hz, J=2.6 Hz, 1H); 7.46 (dd, J=8.8 Hz, J=2.5 Hz, 1H); 7.56 (dd, J=8.6 Hz, J=6 Hz, 1H); 7.65 (m, 2H); 7.75 (m, 2H).

EXAMPLE CCC1
7-(1-tert-butylpiperidin-4-yl)-5-(2-chloro-4-fluorophenyl)-1-(2,6-dichlorophenyl)-1,6-naphthyridin-2(1H)-one

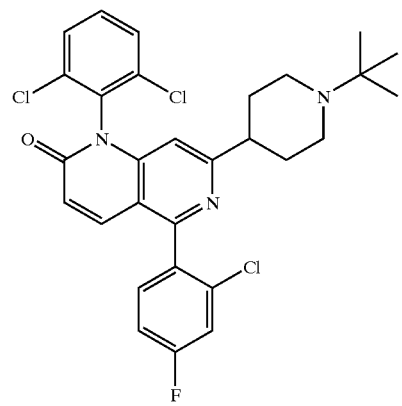

To 1-tert-butyl-4-[5-(2-chloro-4-fluorophenyl)-1-(2,6-dichlorophenyl)-2-oxo-1,2-dihydro-1,6-naphthyridin-7-yl]-1,2,3,6-tetrahydropyridinium chloride (682 mg, 1.15 mmol) (prepared by diluting 7-(1-tert-butyl-1,2,3,6-tetrahydropyridin-4-yl)-5-(2-chloro-4-fluorophenyl)-1-(2,6-dichlorophenyl)-1,6-naphthyridin-2(1H)-one (EXAMPLE CZC1) with CH₂Cl₂, adding 1 eq of a 2M solution of HCl in Et₂O, and concentrating under reduced pressure) in 24 mL of 9:1 methanol-ethyl acetate was added 341 mg of PtO₂ (Adam's catalyst) under nitrogen. The reaction flask was evacuated and charged with hydrogen several times and stirred for 0.75 h under hydrogen. The flask was purged with nitrogen and the reaction mixture was filtered through a pad of Celite washing with methanol and concentrated under reduced pressure. The product was purified by flash chromatography on a Biotage -40L column, eluting with a gradient of 100:0 CH$_2$Cl$_2$-methanol to 95:5 CH$_2$Cl$_2$-methanol, followed by reverse-phase preparative HPLC (Waters Xterra C8 19×50 column, 90:10 water (0.1% trifluoroacetic acid)-CH$_3$CN (0.1% trifluoroacetic acid) to 60:40 water (0.1% trifluoroacetic acid)CH$_3$CN (0.1% trifluoroacetic acid) over 27 min, at 20 mL per minute) to yield the title compound as the trifluoroacetate salt. Mass spectrum (ESI) 558.1 (M+1). $^1$H NMR (500 MHz, CD$_3$OD): δ 1.38 (s, 9H); 2.12 (m, 4H); 3.03 (brs, 3H); 3.65 (d, J=12.1, 2H); 6.47 (s, 1H); 6.76 (d, J=9.9 Hz, 1H); 7.32 (ddd, J=8.5 Hz, J=8.5 Hz, J=2.5 Hz, 1H); 7.48 (dd, J=8.7 Hz, J=2.5 Hz, 1H); 7.57 (dd, J=8.4 Hz, J=6.2 Hz, 1H); 7.66 (t, J=8.3 Hz, 1H); 7.70 (d, J=9.8 Hz, 1H); 7.75 (m, 2H).

EXAMPLE CCC1-A
7-(1-tert-butylpiperidin-4-yl)-5-(2-chloro-4-fluorophenyl)-1-(2,6-difluorophenyl)-1,6-naphthyridin-2(1H)-one

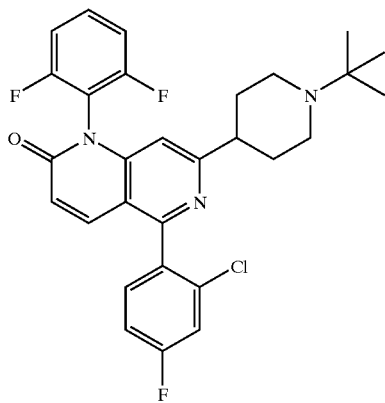

EXAMPLE CCC1-B
7-(1-tert-butylpiperidin-4-yl)-5-(2,4-difluorophenyl)-1-(2,6-difluorophenyl)-1,6-naphthyridin-2(1H)-one

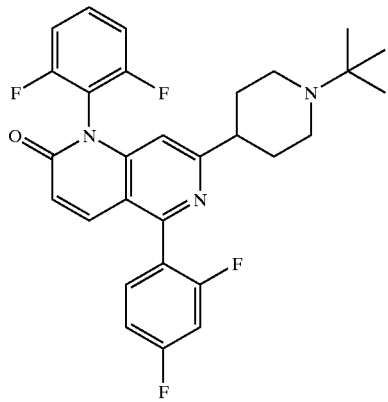

EXAMPLE CCC1-C
7-(1-tert-butylpiperidin-4-yl)-5-(2-chlorophenyl)-1-(2,6-difluorophenyl)-1,6-naphthyridin-2(1H)-one

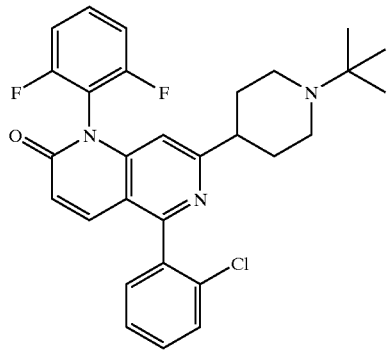

By procedures similar to that for EXAMPLE CCC1, EXAMPLE CCC1-A: 7-(1-tert-butylpiperidin-4-yl)-5-(2-chloro-4-fluorophenyl)-1-(2,6-difluorophenyl)-1,6-naphthyridin-2(1H)-one, EXAMPLE CCC1-B: 7-(1-tert-butylpiperidin-4-yl)-5-(2,4-difluorophenyl)-1-(2,6-difluorophenyl)-1,6-naphthyridin-2(1H)-one, and EXAMPLE CCC1-C: 7-(1-tert-butylpiperidin-4yl)-5-(2-chlorophenyl)-1-(2,6-difluorophenyl)-1,6-naphthyridin-2(1H)-one can be made.

EXAMPLE CCC2
7-(1-tert-butylpiperidin-4-yl)-1-(2,6-dichlorophenyl)-5-(4-fluorophenyl)-3,4-dihydro-1,6-naphthyridin-2(1H)-one

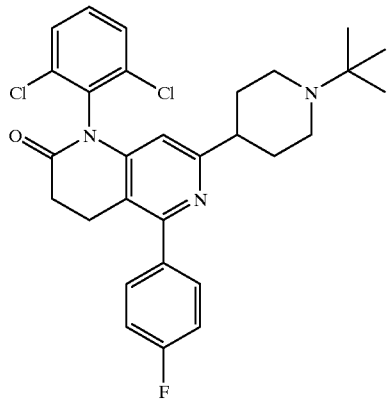

7-(1-tert-butylpiperidin-4-yl)-1-(2,6-dichlorophenyl)-5-(4-fluorophenyl)-3,4-dihydro-1,6-naphthyridin-2(1H)-one was isolated as a side product in the reduction of 1-tertbutyl-4-[5-(2-chloro-4-fluorophenyl)-1-(2,6-dichlorophenyl)-2-oxo-1,2-dihydro-1,6-naphthyridin-7-yl]-1,2,3,6-tetrahydropyridinium chloride (EXAMPLE CCC1). Mass spectrum (ESI) 526.2 (M+1). $^1$NMR (500 MHz, CD$_3$OD): δ 1.40 (s, 9H); 2.04 (m, 2H); 2.13 (d, J=13 Hz, 2H); 2.84 (t, J=6.9 Hz, 2H); 2.97 (m, 1H); 3.05 (m, 2H); 3.18 (t, J=7.1 Hz, 2H); 3.68 (d, J=12.3 Hz, 2H); 6.12 (s, 1H); 7.28 (t, J=8.7 Hz, 2H); 7.58 (t, J=7.5 Hz, 1H); 7.66 (m, 4H).

EXAMPLE CCC3
7-(1-tert-butylpiperidin-4-yl)-5-(2-chloro-4-fluorophenyl)-1-(2,6-dichlorophenyl)-3,4-dihydro-1,6-naphthyridin-2(1H)-one

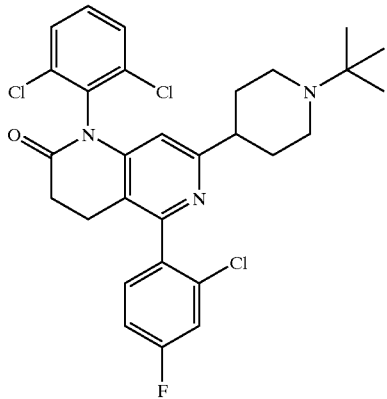

7-(1-tert-butylpiperidin-4-yl)-5-(2-chloro-4-fluorophenyl)-1-(2,6-dichlorophenyl)-3,4-dihydro-1,6-naphthyridin-2(1H)-one was isolated as a side product in the reduction of 1-tert-butyl-4-[5-(2-chloro-4-fluorophenyl)-1-(2,6-dichlorophenyl)-2-oxo-1,2-dihydro-1,6-naphthyridin-7-yl]-1,2,3,6-tetrahydropyridinium chloride (EXAMPLE CCC1). Mass spectrum (ESI) 560.1 (M+1). $^1$H NMR (500 MHz, CD$_3$OD): δ 1.11 (s, 9H); 1.61 (m, 2H); 1.87 (m, 2H); 2.30 (m, 2 H); 2.65 (m, 1H); 2.88 (m, 4H); 3.16 (d, J=10.5 Hz, 2H); 6.17(s, 1H); 7.26 (ddd, J=8.4 Hz, J=8.4 Hz, J=2.5 Hz, 1H); 7.42 (dd, J=8.7 Hz, J=2.6 Hz, 1H); 7.49 (dd, J=8.5 Hz, J=6.1 Hz, 1H); 7.58 (t, J=8 Hz, 1H); 7.68 (d, J=8.5 Hz, 1H).

EXAMPLE CCC4
5-(2-chloro-4-fluorophenyl)-1-(2,6-dichlorophenyl)-7-(8-isopropyl-8-azabicyclo[3.2.1]oct-3-yl)-1,6-naphthyridin-2(1H)-one

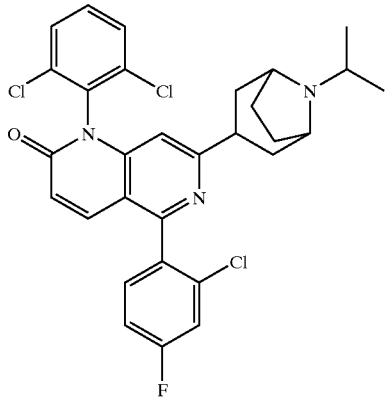

STEP A: tert-butyl 3-[5-(2-chloro-4-fluorophenyl)-1-(2,6-dichlorophenyl)-2-oxo-1,2-dihydro-1,6-naphthyridin-7-yl]-8-azabicyclo[3.2.1]oct-2-ene-8-carboxylate The tert-butyl 3-[5-(2-chloro-4-fluorophenyl)-1-(2,6-dichlorophenyl)-2-oxo-1,2-dihydro-1,6-naphthyridin-7-yl]-8-azabicyclo[3.2.1]oct-2-ene-8-carboxylate was prepared from 7-bromo-5-(2-chloro-4-fluorophenyl)-1-(2,6-dichlorophenyl)-1,6-naphthyridin-2(1H)-one (COMPOUND CCC1) and tert-butyl 3-(trimethylstannyl)-8-azabicyclo[3.2.1]oct-2-ene-8-carboxylate (COMPOUND PPA-3) by a procedure analogous to that described in EXAMPLE CZC1, except that the eluting solvents in the purification step were 20:80 acetone-hexanes. Mass spectrum (ESI) 626 (M+1).

STEP B: 7-(8-azabicyclo[3.2.1]oct-2-en-3-yl)-5-(2-chloro-4-fluorophenyl)-1-(2,6-dichlorophenyl)-1,6-naphthyridin-2(1H)-one tert-butyl 3-[5-(2-chloro-4-fluorophenyl)-1-(2,6-dichlorophenyl)2-oxo-1,2-dihydro-1,6-naphthyridin-7-yl]-8-azabicyclo[3.2.1]oct-2-ene-8-carboxylate (103 mg) was dissolved in 1 mL of trifluoroacetic acid and stirred under nitrogen at rt for 0.75 h. The resulting reaction mixture was concentrated under reduced pressure and purified by preparative thin-layer chromatography, eluting with 95:5 CH$_2$Cl$_2$-2M NH$_3$ in methanol to yield 7-(8-azabicyclo[3.2.1]oct-2-en-3-yl)-5-(2-chloro-4-fluorophenyl)-1-(2,6-dichlorophenyl)-1,6-naphthyridin-2(1H)-one. Mass spectrum (ESI) 526 (M+1).

STEP C: 7-(8-azabicyclo[3.2.1]oct-3-yl)-5-(2-chloro-4-fluorophenyl)-1-(2,6-dichlorophenyl)-1,6-naphthyridin-2(1H)-one 39 mg of PtO$_2$ (Adam's catalyst) was added to the mixture of 7-(8-azabicyclo[3.2.1]oct-2-en-3-yl)-5-(2chloro-4-fluorophenyl)-1-(2,6-dichlorophenyl)-1,6-naphthyridin-2(1H)-one (77 mg) in 2 mL ethyl acetate. The resulting reaction mixture was evacuated and purged with argon. Then hydrogen was bubbled through and the reaction mixture was stirred under hydrogen for 8 h. The reaction mixture was filtered, concentrated under reduced pressure, and purified by preparative thin-layer chromatography, eluting with 95:5 CH$_2$Cl$_2$-2M NH$_3$ in methanol to yield 7-(8-azabicyclo[3.2.1]oct-3-yl)-5-(2-chloro-4-fluorophenyl)-1-(2,6-dichlorophenyl)-1,6-naphthyridin-2(1H)-one. Mass spectrum (ESI) 528.6 (M+1).

STEP D: 5-(2-chloro-4-fluorophenyl)-1-(2,6-dichlorophenyl)-7-(8-isopropyl-8-azabicyclo[3.2.1]oct-3-yl)-1,6-naphthyridin-2(1H)-one To a mixture of 7-(8-azabicyclo[3.2.1]oct-3-yl)-5-(2-chloro-4-fluorophenyl)-1-(2,6-dichlorophenyl)-1,6-naphthyridin-2(1H)-one (36 mg, 0.068 mmol) in 1 mL of 1,2-dichloroethane was added 0.6 mL acetone and 4 drops of acetic acid. The resulting reaction mixture was stirred under nitrogen for 30 min and NaBH(OAc)$_3$ (145 mg, 0.68 mmol) was added. The reaction was stirred at rt for 14 days, then quenched with 2M aqueous NaOH and extracted 3 times with ethyl acetate. The combined organic layers were dried (Na$_2$SO$_4$) and concentrated under reduced pressure. The product was purified twice by preparative thin-layer chromatography, eluting with 95:5 CH$_2$Cl$_2$-2M NH$_3$ in methanol followed by reverse-phase preparative HPLC (Waters Xterra C8 19×50 column, 90:10 water (0.1% trifluoroacetic acid)-CH$_3$CN (0.1% trifluoroacetic acid) to 60:40 water (0.1% trifluoroacetic acid)-CH$_3$CN (0.1% trifluoroacetic acid) over 27 min, at 20 mL/min) to yield 5-(2-chloro-4-fluorophenyl)-1-(2,6-dichlorophenyl)-7-(8-isopropyl-8-azabicyclo[3.2.1]oct-3-yl)-1,6-naphthyridin-2(1H)-one as the trifluoroacetate salt.

Mass spectrum (ESI) 570 (M+1). $^1$H NMR (500 MHz, CD$_3$OD): selected peaks δ 1.31 (m, 6H); 6.61 (d, J=24.5 Hz, 1H); 6.77 (d, J=9.8 Hz, 1H); 7.33 (ddd, J=8.5 Hz, J=8.5 Hz, J=2.5 Hz, 1H); 7.50 (dd, J=8.7 Hz, J=2.6 Hz, 1H); 7.57 (m, 1H); 7.67 (m, 2H); 7.75 (d, J=8.0 Hz, 2H).

EXAMPLE CCC5
7-[(1-tert-butylpiperidin-4-yl)methyl]-5-(2-chloro-4-fluorophenyl)-1-(2,6-dichlorophenyl)-1,6-naphthyridin-2(1H)-one

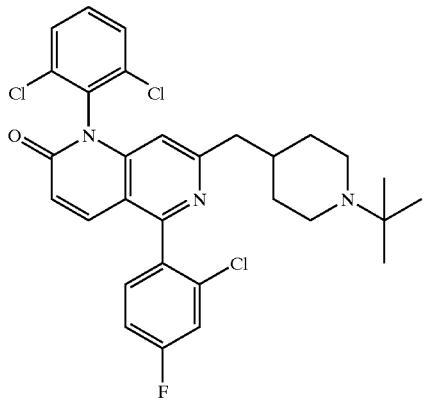

STEP A: 7-[(1-tert-butylpiperidin-4-ylidene)methyl]-5-(2-chloro-4-fluorophenyl)-1-(2,6-dichlorophenyl)-1,6-naphthyridin-2(1H)-one The 7-[(1-tert-butylpiperidin-4-ylidene)methyl]-5-(2-chloro-4-fluorophenyl)-1-(2,6-dichlorophenyl)-1,6-naphthyridin-2(1H)-one was prepared from 7-bromo-5-(2-chloro-4-fluorophenyl)-1-(2,6-dichlorophenyl)-1,6-naphthyridin-2(1H)-one (COMPOUND CCC1) and 1-tert-butyl-4-[(trimethylstannyl)methylene]piperidine (INTERMEDIATE ABA3) by a procedure analogous to that described in EXAMPLE CZC1. Mass spectrum (ESI) 570 (M+1).

STEP B: 7-[(1-tert-butylpiperidin-4-yl)methyl]-5-(2-chloro-4-fluorophenyl)-1-(2,6-dichlorophenyl)-1,6-naphthyridin-2(1H)-one The 7-[(1-tert-butylpiperidin-4-yl)methyl]-5-(2-chloro-4-fluorophenyl)-1-(2,6-dichlorophenyl)-1,6-naphthyridin-2(1H)-one was prepared from 7-[(1-tert-butylpiperidin-4-ylidene)methyl]-5-(2-chloro-4-fluorophenyl)-1-(2,6-dichlorophenyl)-1,6-naphthyridin-2(1H)-one by a procedure analogous to that described in EXAMPLE CCC4, STEP C, except that the purification was done by reverse-phase preparative HPLC (Waters Xterra C8 19×50 column, 90:10 water (0.1% trifluoroacetic acid)-CH$_3$CN (0.1% trifluoroacetic acid) to 60:40 water (0.1% trifluoroacetic acid)-CH$_3$CN (0.1% trifluoroacetic acid) over 25 min, at 20 Ml/min) to give the trifluoroacetate salt. Mass spectrum (ESI) 572.7 (M+1). $^1$H NMR (500 MHz, CD$_3$OD): selected peaks δ 1.38 (s, 9H); 1.51 (m, 2H); 1.93 (d, J=14.4 Hz, 2H); 2.05 (m, 1H); 2.78 (d, J=7.3 Hz, 2H); 2.92 (m, 2H); 3.58 (d, J=12.2 Hz, 2H).

EXMPLE CCC6
5-(2-chlorophenyl)-1-(2,6-dichlorophenyl)-7-(5-isopropyl-2,5-diazabicyclo[2.2.1]hept-2-yl)-1,6-naphthyridin-2(1H)-one

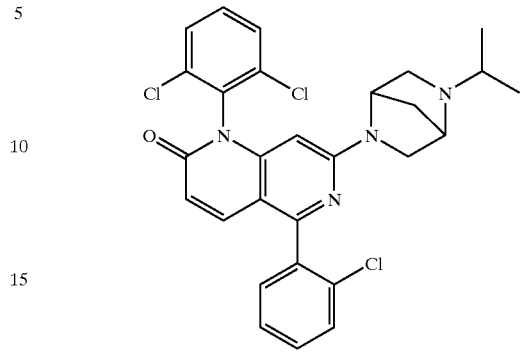

A mixture of 7-bromo-5-(2-chlorophenyl)-1-(2,6-dichlorophenyl)-1,6-naphthyridin-2(1H)one (26 mg, 0.054 mmol) (COMPOUND HHH2) and 2-isopropyl-2,5-diazabicyclo[2.2.1]heptane (INTERMEDIATE ABA2) (11 mg, 0.078 mmol) in 0.5 mL of DMSO was stirred under nitrogen at 130° C. for 25 h. The mixture was cooled to rt, filtered, and purified by reverse-phase preparative HPLC (Waters Xterra C8 19×50 column, 90:10 water (0.1% trifluoroacetic acid)-CH$_3$CN (0.1% trifluoroacetic acid) to 0:100 water (0.1% trifluoroacetic acid)-CH$_3$CN (0.1% trifluoroacetic acid) over 12 min, at 20 mL/min) followed by preparative thin-layer chromatography, eluting with 90:10 CH$_2$Cl$_2$-2M NH$_3$ in methanol to yield the title compound. Mass spectrum ESI) 539.2 (M+1). $^1$H NMR (500 MHz, CD$_3$OD): δ 1.05 (d, J=6.2 Hz, 6H); 1.87 (m, 2H); 2.53 (m, 2H); 3.01 (m, 1H); 3.18 (d, J=8.5 Hz, 1H); 3.3 (brs, 1H); 3.81 (s, 1H); 4.7 (brs, 1H); 5.25 (s, 1H); 6.30 (d, J=9.6 Hz, 1H); 7.42 (d, J=9.7 Hz, 1H); 7.49 (m, 3H); 7.59 (m, 2H); 7.71 (m, 2H).

EXAMPLE CCC7
5-(2-chlorophenyl)-7-(3,8-diazabicyclo[3.2.1]oct-3-yl)-1-(2,6-dichlorophenyl)-1,6-naphthyridin-2(1H)-one

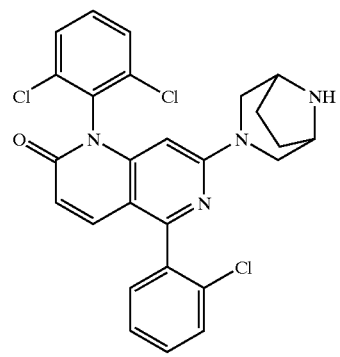

A mixture of 7-bromo-5-(2-chlorophenyl)-1-(2,6-dichlorophenyl)-1,6-naphthyridin-2(1H)-one (81 mg, 0.17 mmol) (COMPOUND HHH2), 3,8-diazabicyclo[3.2.1] octane dihydrochloride (62 mg, 0.34 mmol), and 1,8-diazabicyclo[5.4.0]undec-7-ene (65 mg, 0.43 mmol) in 0.5 mL of DMSO was stirred under nitrogen at 130° C. for 10.2 h. The mixture was cooled to rt, filtered, and purified by reverse-phase preparative HPLC (Waters Xterra C8 19×50 column, 90:10 water (0.1% trifluoroacetic acid)-CH$_3$CN (0.1% trifluoroacetic acid) to 0:100 water (0.1% trifluoroacetic acid)-CH$_3$CN (0.1% trifluoroacetic acid) over 12 min, at 20 mL/min) to yield the title compound as the trifluoroacetate salt. Mass spectrum (ESI) 511 (M+1).

$^1$H NMR (500 MHz, CD$_3$OD): selected peaks δ 2.02 (m, 4H); 3.17 (d, J=12.1 Hz, 2H); 4.13 (m, 4H).

EXAMPLE CCC8
7-(3-aminopyrrolidin-1-yl)-5-(2-chlorophenyl)-1-(2,6-dichlorophenyl)-1,6-naphthyridin-2(1H)-one

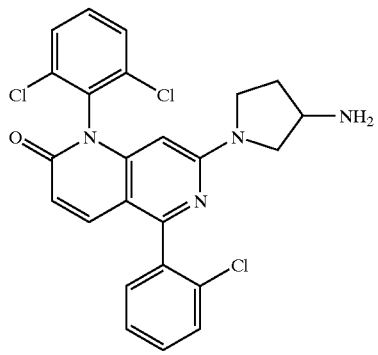

A mixture of 7-bromo-5-(2-chlorophenyl)-1-(2,6-dichlorophenyl)-1,6-naphthyridin-2(1H)-one (80 mg, 0.17 mmol) (COMPOUND HHH2), pyrrolidin-3-amine dihydrochloride (135 mg, 0.85 mmol), and 1,8-diazabicyclo[5.4.0]undec-7-ene (259 mg, 1.7 mmol) in 0.5 mL of DMSO was stirred under nitrogen at 130° C. for 7 h. The mixture was cooled to rt, filtered, and purified by reverse-phase preparative HPLC (Waters Xterra C8 19×50 column, 90:10 water (0.1% trifluoroacetic acid)-CH$_3$CN (0.1% trifluoroacetic acid) to 0:100 water (0.1% trifluoroacetic acid)-CH$_3$CN (0.1% trifluoroacetic acid) over 12 min, at 20 mL/min) followed by preparative thin-layer chromatography, eluting with 95:5 CH$_2$Cl$_2$-2M NH$_3$ in methanol to yield the title compound. Mass spectrum (ESI) 485 (M+1). $^1$H NMR (500 MHz, CDCl$_3$): selected peaks δ0 1.76 (m, 1H); 2.16 (m, 1H); 3.11 (brs, 1H); 3.40 (brs, 1H); 3.57 (brs, 2H); 3.68 (m, 1H).

EXAMPLE CCC9
5-(2-chlorophenyl)-1-(2,6-dichlorophenyl)-7-{4-[3-(dimethylamino)propyl]piperazin-1-yl}-1,6-naphthyridin-2(1H)-one

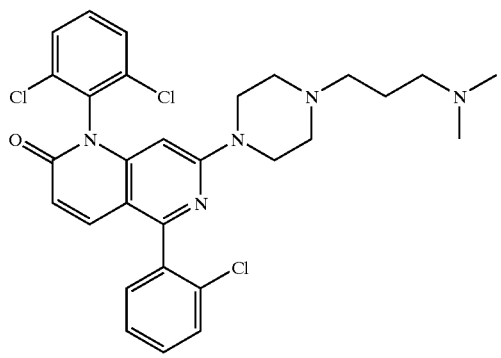

A mixture of 7-bromo-5-(2-chlorophenyl)-1-(2,6-dichlorophenyl)-1,6-naphthyridin-2(1H)-one (40 mg, 0.083 mmol) (COMPOUND HHH2) and N,N-dimethyl-3-piperazin-1-ylpropan-1-amine (72 mg, 0.42 mmol) in 0.5 mL of DMSO was stirred under nitrogen at 130° C. for 6.5 h. The mixture was cooled to rt, filtered, and purified by reverse-phase preparative HPLC (Waters Xterra C8 19×50 column, 90:10 water (0.1% trifluoroacetic acid)-CH$_3$CN (0.1% trifluoroacetic acid) to 0:100 water (0.1% trifluoroacetic acid )-CH$_3$CN (0.1% trifluoroacetic acid) over 12 min, at 20 mL/min) The trifluoroacetate salt was partitioned between 2M aqueous NaOH and ethyl acetate and the water layer extracted with ethyl acetate twice. The combined organic layers were dried (Na$_2$SO$_4$), and concentrated under reduced pressure to yield the title compound. Mass spectrum ESI) 570 (M+1). $^1$H NMR (500 CD$_3$OD): selected peaks δ 2.20 (m, 2H); 2.91 (s, 6H); 3.20 (m, 5H); 3.36 (brs, 4H); 3.81 (brs, 3H).

EXAMPLE CCC10
5-(2-chlorophenyl)-1-(2,6-dichlorophenyl)-7-[(8-methyl-8-azabicyclo[3.2.1]oct-3-yl)amino]-1,6-naphthyridin-2(1H)-one

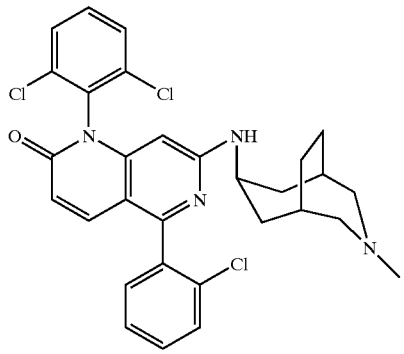

A mixture of 7-bromo-5-(2-chlorophenyl)-1-(2,6-dichlorophenyl)-1,6-naphthyridin-2(1H)-one (80 mg, 0.17 mmol) (COMPOUND HHH2) and 8-methyl-8-azabicyclo[3.2.1]octan-3-amine (279 mg, 1.99 mmol) in 0.5 mL of DMSO was stirred under nitrogen at 130° C. for 29 h. The mixture was cooled to rt, filtered, and purified twice by reverse-phase preparative HPLC (Waters Xterra C8 19×50 column, 90:10 water (0.1% trifluoroacetic acid)-CH$_3$CN (0.1% trifluoroacetic acid) to 0:100 water (0.1% trifluoroacetic acid)-CH$_3$CN (0.1% trifluoroacetic acid) over 12 min, at 20 mL/min) to yield the title compound as the trifluoroacetate salt. Mass spectrum (ESI) 539 (M+1). $^1$H NMR (500 MHz, CD$_3$OD): selected peaks δ 2.30 (m, 8H); 2.75 (s, 3H); 3.83 (brs, 2H); 4.08 (brs, 1H).

EXAMPLE CCC11
7-(1-azabicyclo[2.2.2.]oct-3-ylamino)-5-(2-chlorophenyl)-1-(2,6-dichlorophenyl)-1,6-naphthyridin-2(1H)-one

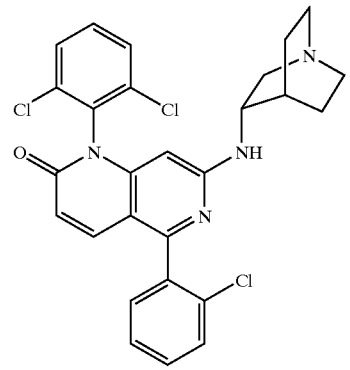

A mixture of 7-bromo-5-(2-chlorophenyl)I-(2,6-dichlorophenyl)-1,6-naphthyridin-2(1H)-one (40 mg, 0.083 mmol) (COMPOUND HHH2), quinuclidin-3-amine dihydrochloride (84 mg, 0.42 mmol), and 1,8-diazabicyclo[5.4.0]undec-7-ene (70 mg, 0.46 mmol) in 0.5 mL of DMSO was stirred under nitrogen at 130° C. for 6.5 hours. The mixture was cooled to rt, filtered, and purified by reverse-phase preparative HPLC (YMC C18 100×20 mm, 90:10 water (0.1% trifluoroacetic acid)-CH$_3$CN (0.1% trifluoroacetic acid) to 10:90 water (0.1% trifluoroacetic acid)-CH$_3$CN (0.1% trifluoroacetic acid) over 15 minutes, at 20 mL per minute) to yield 24 mg of the title compound as the trifluoroacetate salt. Mass spectrum (ESI) 525.1 (M+1). $^1$H NMR (500 MHz, CD$_3$OD): selected peaks δ 5.66 (m, 1H); 6.41 (d, J=9.6 Hz, 1H); 7.49 (m, 4H); 7.61 (m, 2H); 7.30 (d, J=8.4 Hz, 2H).

EXAMPLE CCC12

5-(2-chlorophenyl)-1-(2,6-dichlorophenyl)-7-[4-(2-pyrrolidin-1-ylethyl)piperazin-1-yl]-1,6-naphthyridin-2(1H)-one

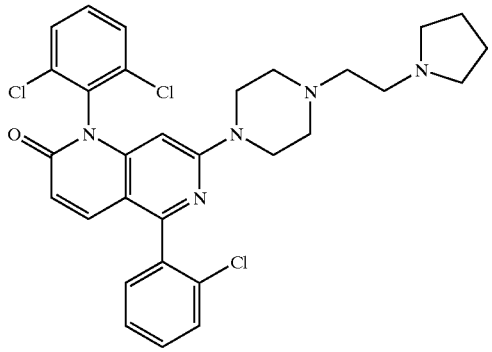

A mixture of 7-bromo-5-(2-chlorophenyl)-1-(2,6-dichlorophenyl)1,6-naphthyridin-2(1H)-one (40 mg, 0.083 mmol) (COMPOUND HHH2) and 1-(2-pyrrolidin-1-ylethyl)piperazine (77 μL) in 0.5 mL of DMSO was stirred under nitrogen at 130° C. for 6.5 h. The mixture was cooled tort, filtered, and purified by reverse-phase preparative HPLC (Waters Xterra C8 19×50 column, 90:10 water (0.1% trifluoroacetic acid)-CH$_3$CN (0.1% trifluoroacetic acid) to 0:100 water (0.1% trifluoroacetic acid)-CH$_3$CN (0.1% trifluoroacetic acid) over 12 min, at 20 mL/min) to yield the title compound as the trifluoroacetate salt. Mass spectrum (ESI) 582.2 (M+1). $^1$H NMR (500 MHz, CD$_3$OD): selected peaks δ 2.09 (m, 4H); 2.86 (brs, 4H); 3.02 (brs, 2H); 4.43 (m, 6H); 3.63 (brs, 4H).

EXAMPLE CCC13

5-(2-chlorophenyl)-1-(2,6-dichlorophenyl)-7-{[(1-morpholin-4-ylcyclopentyl)methyl]amino}-1,6-naphthyridin-2(1H)-one

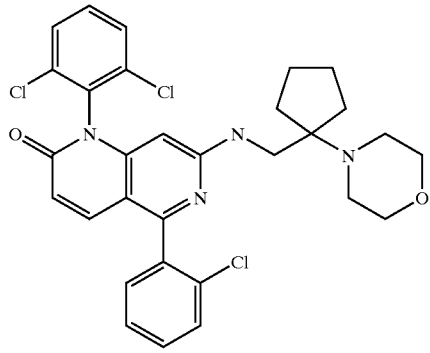

A mixture of 7-bromo-5-(2-chlorophenyl)-1-(2,6-dichlorophenyl)-1,6-naphthyridin-2(1H)-one (40 mg, 0.083 mmol) (COMPOUND HHH2) and 1-(1-morpholin-4-ylcyclopentyl)methanamine(77 μL) in 1 mL of DMSO was stirred under nitrogen at 130° C. for 12.35 h. The mixture was cooled to rt, filtered, and purified by reverse-phase preparative HPLC (YMC C18 100×20 mm, 90:10 water (0.1% trifluoroacetic acid)-CH$_3$CN (0.1% trifluoroacetic acid) to 10:90 water (0.1% trifluoroacetic acid)-CH$_3$CN (0.1% trifluoroacetic acid) over 15 min, at 20 mL/min) to yield the title compound as the trifluoroacetate salt. Mass spectrum (ESI) 583.2 (M+1). $^1$H NMR (500 MHz, CD$_3$OD): selected peaks δ 1.84 (m, 9H); 3.34 (m, 1H); 3.49 (m, 5H); 3.80 (m. 4H).

EXAMPLE CCC14

5-(2-chlorophenyl)-1-(2,6-dichlorophenyl)-7-[4-(pyridin-2-ylmethyl)piperazin-1-yl]-1,6-naphthyridin-2(1H)-one

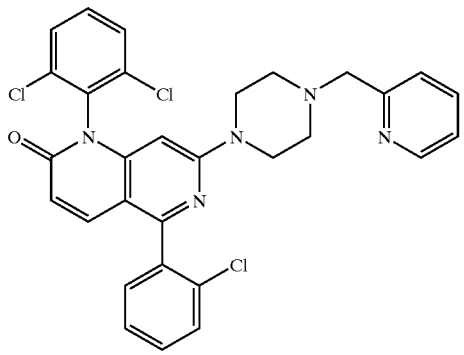

A mixture of 7-bromo-5-(2-chlorophenyl)-1-(2,6-dichlorophenyl)-1,6-naphthyridin-2(1H)-one (40 mg, 0.083 mmol) (COMPOUND HHH2), 1-(pyridin-2-ylmethyl)piperazine bis(trifluoroacetate) (170 mg, 0.42 mmol), and 1,8-diazabicyclo[5.4.0]undec-7-ene (141 μL, 0.75 mmol) in 1 mL of DMSO was stirred under nitrogen at 130° C. for 3.6 h. The mixture was cooled to rt, filtered, and purified by reverse-phase preparative HPLC (YMC C18 100×20 mm, 90:10 water (0.1% trifluoroacetic acid)-CH$_3$CN (0.1% trifluoroacetic acid) to 10:90 water (0.1% trifluoroacetic acid)-CH$_3$CN (0.1% trifluoroacetic acid) over 15 min, at 20 mL/min) to yield the title compound as the trifluoroacetate salt. Mass spectrum (ESI) 5761 (M+1). $^1$H NMR (500 MHz, CD$_3$OD): selected peaks δ 3.40 (t, J=5.1 Hz, 4H); 3.82 (brs, 4H); 4.50 (s, 2H).

EXAMPLE CCC15

5-(2-chlorophenyl)-1-(2,6-dichlorophenyl)-7-[3-(2-phenylethyl)piperidin-1-yl]-1,6-naphthyridin-2(1H)-one

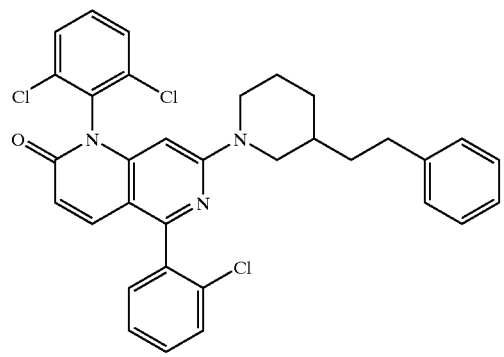

The title compound was prepared from 7-bromo-5-(2-chlorophenyl)-1-(2,6-dichlorophenyl)-1,6-naphthyridin-2(1H)-one (COMPOUND HHH2) and 3-(2-phenylethyl)

piperidine hydrochloride by a procedure analogous to that described in EXAMPLE CCC14. Mass spectrum (ESI) 588.1 (M+1). $^1$H NMR (500 MHz, CD$_3$OD): selected peaks δ 1.28 (m, 1H); 1.47 (m, 4H); 1.65 (m, 1H); 1.85 (d, J=11.5 Hz, 1H); 2.50 (m, 2H); 2.71 (m, 1H); 2.95 (m, 1H); 4.04 (m, 2H).

EXAMPLE CCC16

5-(2-chlorophenyl)-1-(2,6-dichlorophenyl)-7-[(tetrahydro-2H-pyran-3-ylmethyl)amino]-1,6-naphthyridin-2(1H)-one

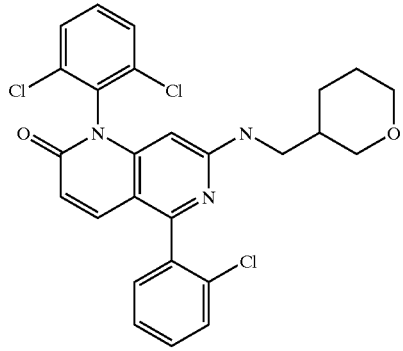

The title compound was prepared from 7-bromo-5-(2-chlorophenyl)-1-(2,6-dichlorophenyl)-1,6-naphthyridin-2 (H1)-one (COMPOUND HHH2) and 1-tetrahydro-2H-pyran-3-ylmethanamine hydrochloride by a procedure analogous to that described in EXAMPLE CCC14. Mass spectrum (ESI) 514 (M+1): $^1$H NMR (500 MHz, CD$_3$OD): selected peaks δ 1.25 (m, 1H); 1.52 (m, 4H); 1.81 (m, 1H); 3.23 (m, 1H); 3.37 (m, 2H); 3.46 (m, 3H); 3.86 (d, J=12.6 Hz, 1H).

EXAMPLE CCC17

5-(2-chlorophenyl)-1-(2,6-dichlorophenyl)-7-{4-[2-(diethylamino)ethyl]piperazin-1-yl}-1,6-naphthyridin-2(1H)-one

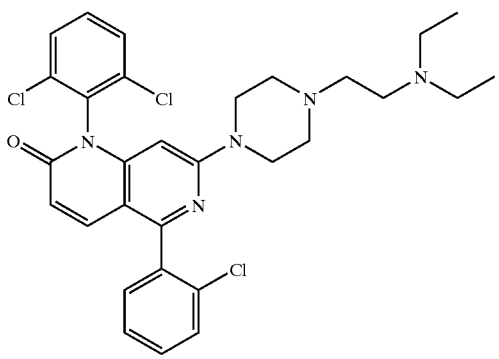

A mixture of 7-bromo-5-(2-chlorophenyl)-1-(2,6-dichlorophenyl)-1,6-naphthyridin-2(1H)-one (40 mg, 0.083 mmol) (COMPOUND HHH2) and N,N-diethyl-2-piperazin-1-ylethanamine (78 µL) in 1 mL of DMSO was stirred under nitrogen at 130° C. for 3.6 h and then stirred at rt for 2 days. The mixture was filtered and purified by reverse-phase preparative HPLC (YMC C18 100×20 mm, 90:10 water (0.1% trifluoroacetic acid)-CH$_3$CN (0.1% trifluoroacetic acid) to 10:90 water (0.1% trifluoroacetic acid)-CH$_3$CN (0.1% trifluoroacetic acid) over 15 min, at 20 mL/min) to yield the title compound as the trifluoroacetate salt. Mass spectrum (ESI) 584.1 M+1). $^1$H NMR (500 MHz, CD$_3$OD): selected peaks δ 1.32 (t, J=7.1 Hz, 6H); 2.76 (t, J=4.8 Hz, 4H); 2.92 (t, J=6.2 Hz, 2H); 3.27 (m, 4H); 3.35 (t, J=6.2 Hz, 2H); 3.56 (t, J=4.6 Hz, 4H).

COMPOUND CCC3

5-(2-chlorophenyl)-1-(2,6-dichlorophenyl)-7-nitro-3,4-dihydroquinazolin-2(1H)-one

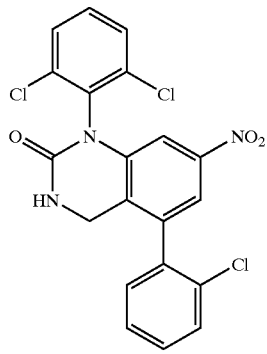

STEP A: 1,3-dibromo-2-(bromomethyl)-5-nitrobenzene

To a mixture of 2,6-dibromo-4-nitrotoluene (5.00 g, 16.95 mmol) in CCl$_4$ (131 mL) was added N-bromosuccinimide (4.22 g, 23.73 mmol) and dibenzoyl peroxide (411 mg, 1.70 mmol). The mixture was evacuated and flushed with argon three times, then heated using an oil bath. At reflux azo-bis-isobutyronitrile (278 mg, 1.695 mmol) was added. The reaction was stopped after 3.75 h, cooled to rt and filtered washing with CCl$_4$. The filtrate was concentrated under reduced pressure to give a yellow solid, which was purified using flash chromatography on Biotage 40M column, eluting with 90:10 hexanes-CH$_2$Cl$_2$ to yield 1,3-dibromo-2-(bromomethyl)-5-nitrobenzene. $^1$H NMR (500 MHz, CDCl$_3$): δ 4.8 (s, 2H), 8.4 (s, 2H).

STEP B: N-(2,6-dibromo-4-nitrobenzyl)-N-(4-methoxybenzyl)amine 4-methoxybenzylamine (2.15 g, 15.7 mmol) was added to a solution of 1,3-dibromo-2-(bromomethyl)-5-nitrobenzene (4.91 g, 13.1 mmol) in DMF (100 mL) under nitrogen at rt. K$_2$CO$_3$ (1.99 g, 14.4 mmol) was then added and the reaction mixture was stirred at rt overnight. The reaction mixture was quenched with 500 mL of water, and extracted with ethyl acetate (3×150 mL). The combined organic layers were dried over MgSO$_4$, filtered and concentrated under reduced pressure. The product was purified by flash chromatography on Biotage 40M columns, eluting with 90:10 hexanes-ethyl acetate to provide N-(2,6-dibromo-4-nitrobenzyl)-N-(4-methoxybenzyl)amine as a red viscous liquid. $^1$H NMR (500 MHz, CDCl$_3$): δ 3.81 (d, J=3.6 Hz, 4H); 4.20 (s, 3H); 6.88 (d, J=8.4 Hz, 2H); 7.27 (d, J=5.9 Hz, 2H); 8.40 (s, 2H).

STEP C: N-(2,6-dibromo-4-nitrobenzyl)-N'-(2,6-dichlorophenyl)-N-(4-methoxybenzyl)urea 2,6-dichlorophenylisocyanate (1.54 g, 8.18 mmol) was added under nitrogen to a solution of N-(2,6-dibromo-4-nitrobenzyl)-N-(-4-methoxybenzyl)amine (3.35 g, 7.79 mmol) in CH$_2$Cl$_2$ (95 mL). The resulting mixture was stirred at rt for ca. 3 h. The reaction mixture was then concentrated under reduced pressure to yield N-(2,6-dibromo-4-nitrobenzyl)-N'-(2,6-dichlorophenyl)-N-(4-methoxybenzyl) urea as a yellow solid. Mass spectrum (ESI) 616 (M+1).

STEP D: 5-bromo-1-(2,6-dichlorophenyl)-3-(4-methoxybenzyl)-7-nitro-3,4-dihydroquinolin-2(1H)-one Diisopropylethylamine (1.78 g, 13.8 mmol) and CuI (2.63 g, 13.8 mmol) was added to N-(2,6-dibromo-4-nitrobenzyl)-N'-(2,6-dichlorophenyl)-N-(4-ethoxybenzyl)urea (4.25 g, 6.88 mmol) in DMF (150 mL). After evacuating and flushing three times with argon, the reaction mixture was heated to 130° C. for 3 h, cooled to rt, and filtered. The filtrate was concentrated under reduced pressure and purified by flash chromatography on Biotage 40M columns, eluting with 80:20 hexanes-acetone to yield 5-bromo-1-(2,6-dichlorophenyl)-3-(4-methoxybenzyl)-7-nitro-3,4-dihydroquinazolin-2(1H)-one. Mass spectrum (ESI) 536.0 (M+1).

STEP E: 5-(2-chlorophenyl)-1-(2,6-dichlorophenyl)-3-(4-methoxybenzyl)-7-nitro-3,4-dihydroquinazolin-2(1H)-one 1.07 g of 5-bromo-1-(2,6-dichlorophenyl)-3-(4-methoxybenzyl)-7-nitro-3,4-dihydroquinazolin-2(1H)-one (1.99 mmol) were dissolved in 26 mL of toluene. $Na_2CO_3$ (1.26 g, 11.9 mmol), 2-chlorophenylboronic acid (934 mg, 5.97 mmol), and ethanol/water (6.4 mL:6.4 mL) were added under argon followed by $Pd(Ph_3P)_4$ (115 mg, 0.0995 mmol). The resulting reaction mixture stirred at 100° C. for ca.4 h, cooled to rt, diluted with 150 mL of ethyl acetate, washed with 2×100 mL of saturated aqueous $NaHCO_3$ and 100 mL of brine, dried over $Na_2SO_4$, and concentrated under reduced pressure. The product was purified by flash chromatography on Biotage 40M column, eluting with 80:20 hexanes-acetone to yield 5-(2-chlorophenyl)-1-(2,6-dichlorophenyl)-3-(4-methoxybenzyl)-7-nitro-3,4-dihydroquinazolin-2(1H)-one. Mass spectrum (ESI) 568.1 (M+1).

STEP F: 5-(2-chlorophenyl)-1-(2,6-dichlorophenyl)-7-nitro-3,4-dihydroquinazolin-2(1H)-one A solution of 5-(2-chlorophenyl)-1-(2,6-dichlorophenyl)-3-(4-methoxybenzyl)-7-nitro-3,4-dihydroquinazolin-2(1H)-one (32 mg, 0.56 mmol) in 1 mL trifluoroacetic acid was stirred at 95° C. for 1.25 h. The solvent was removed under reduced pressure and the product was purified by preparative thin-layer chromatography, eluting with 93:7 $CH_2Cl_2$-methanol to yield 5-(2-chlorophenyl)-1-(2,6-dichlorophenyl)-7-nitro-3,4-dihydroquinazolin-2(1H)-one. Mass spectrum (ESI) 448 (M+1). $^1H$ NMR (500 MHz, $CDCl_3$): δ 3.35 (½ ABq, J=15.5 Hz, 1H); 3.52 (½ ABq, J=15.5 Hz. 1H); 7.00 (s, 1H); 7.32 (d, J=2.1 Hz, 1H); 7.46 (m, 3H); 7.58 (m, 3H); 7.81 (s, 1H).

COMPOUND CCC4
7-amino-5-(2-chlorophenyl)-1-(2,6-dichlorophenyl)-3,4-dihydroquinazolin-2(1H)-one

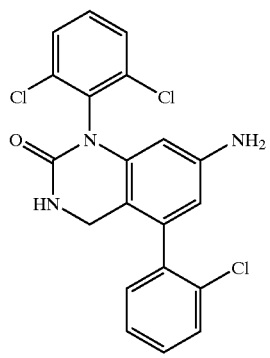

STEP A: 7-amino-5-(2-chlorophenyl)-1-(2,6-dichlorophenyl)-3-(4-methoxybenzyl)-3,4-dihydroquinazolin-2(1H)-one To a solution of 5-(2-chlorophenyl)-1-(2,6-dichlorophenyl)-3-(4-methoxybenzyl)-7-nitro-3,4-dihydroquinazolin-2(1H)-one (20.0 mg, 0.035 mmol) in ethyl acetate (2 mL) was added 10% Pd/C (14.5 mg) under argon. Hydrogen was bubbled through and the reaction mixture was stirred under hydrogen for 1.5 h. The reaction flask was purged with argon. The catalyst was filtered off washing with methanol. The filtrate was concentrated under reduced pressure to yield 7-amino-5-(2-chlorophenyl)-1-(2, 6-dichlorophenyl)-3-(4-methoxybenzyl)-3,4-dihydroquinazolin-2(1H)-one. Mass spectrum (ESI) 538.2 (M+1).

STEP B: 7-amino-5-(2-chlorophenyl)-1-(2.6-dichlorophenyl)-3,4-dihydroquinazolin-2(1H)-one The 7-amino-5-(2-chlorophenyl)-1-(2,6-dichlorophenyl)-3,4-dihydroquinazolin-2(1H)-one was prepared from 7-amino-5-(2-chlorophenyl)-1-(2,6-dichlorophenyl)-3-(4-methoxybenzyl)-3,4dihydroquinazolin-2(1H)-one by a procedure analogous to that on COMPOUND CCC3, STEP F. Mass spectrum (ESI) 418.0 (M+1). $^1H$ NMR (500 MHz, $CD_3OD$): δ 4.07 (½ ABq, J=14.2 Hz, 1H); 4.18 (½ ABq, J=14.2 Hz, 1H); 5.54 (d, J=2 Hz, 1H); 6.24 (d, J=2.1 Hz, 1H); 7.29 (m, 1H, 7.40 (m, 2H); 7.47 (m, 2H); 7.58 (m, 2H).

EXAMPLE CCC18
5-(2-chlorophenyl)-1-(2,6-dichlorophenyl)-7-(piperidin-4-ylamino)-3,4-dihydroquinazolin-2(1H)-one

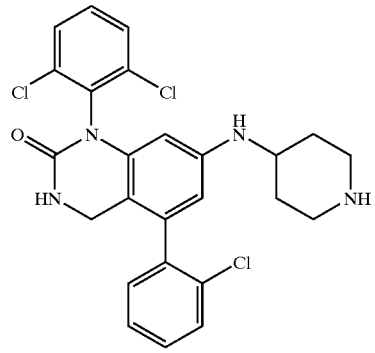

STEP A: tert-butyl 4-{[5-(2-chlorophenyl)-1-(2,6-dichlorophenyl)-3-(4-methoxybenzyl)-2-oxo-1,2,3,4-tetrahydroquinazolin-7-yl]amino}piperidine-1-carboxylate tert-butyl 4-oxopiperidine-1-carboxylate (37.9 mg, 0.19 mmol) was added to a mixture of 7-amino-5-(2-chlorophenyl)-1-(2,6-dichlorophenyl)-3-(4-methoxybenzyl)-3,4-dihydroquinazolin-2(1H)-one (78 mg, 0.15 mmol) in 1 mL of 1,2-dichloroethane. $NaBH(OAc)_3$ (58 mg, 0.27 mmol) was added after 45 min. The reaction mixture was stirred at rt overnight. The reaction mixture was quenched with ca 5 mL of 2.5M aqueous NaOH, extracted with (3×20 mL) of ethyl acetate, washed with brine, dried over $Na_2SO_4$ and concentrated under reduced pressure. The product was purified by preparative thin-layer chromatography, eluting with 90:10 hexanes-ethyl acetate to yield tert-butyl 4-{[5-(2-chlorophenyl)-1-(2,6-dichlorophenyl)-3-(4-methoxybenzyl)-2-oxo-1,2,3,4-tetrahydroquinazolin-7-yl]amino}piperidine-1-carboxylate. Mass spectrum (ESI) 721.2 (M+1).

STEP B: 5-(2-chlorophenyl)-1-(2,6-dichlorophenyl)-7-(piperidin-4-ylamino)-3,4-dihydroquinazolin-2(1H)-one The solution of tert-butyl 4-{([5-(2-chlorophenyl)-1-(2,6-dichlorophenyl)-3-(4-methoxybenzyl)-2-oxo-1,2,3,4-tetrahydroquinazolin-7-yl]amino}piperidine-1-carboxylate (50 mg, 0.069 mmol) in 1 mL of trifluoroacetic acid was heated at 95° C. for 0.5 h and then concentrated under reduced pressure. The product was purified by reverse-phase preparative HPLC (YMC C18 100×20 mm, 90:10 water (0.1% trifluoroacetic acid)-CH₃CN (0.1% trifluoroacetic acid) to 10:90 water (0.1% trifluoroacetic acid)-CH₃CN (0.1% trifluoroacetic acid) over 15 min, at 20 Ml/min) to yield 5-(2-chlorophenyl)-1-(2,6-dichlorophenyl)-7-(piperidin-4-ylamino)-3,4-dihydroquinazolin-2(1H)-one as the trifluoroacetate salt, which was diluted with ethyl acetate, washed with saturated aqueous NaHCO₃, dried over Na₂SO₄, and concentrated under reduced pressure to give the free base. Mass spectrum (ESI) 501 (M+1). ¹H NMR (500 MHz, CDCl₃): δ 1.23 (m, 2H); 1.95 (m, 2H); 2.58 (m, 2H); 3.04 (d, J=12.3 Hz, 2H); 3.12 (m, 1H); 3.48 (brs, 1H); 4.12 (dd, J=13.5 Hz, J=2.18 Hz, 1H); 4.30 (dd, J=13.5 Hz, J=2.14 Hz, 1H); 4.98 (s, 1H); 5.34 (d, J=2.3 Hz, 1H); 6.12 (d, J=2.3 Hz, 1H); 7.31 (m, 4H); 7.49 (m, 3H).

EXAMPLE CCC19

5-(2-chlorophenyl)-1-(2,6-dichlorophenyl)-7-[(1-isopropylpiperidin-4-yl)amino]-3,4-dihydroquinazolin-2(1H)-one

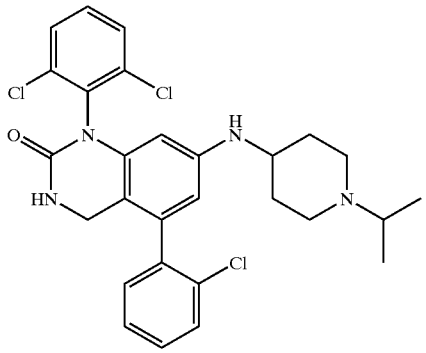

Acetone (98 mg, 1.69 mmol) was added to a mixture of 5-(2-chlorophenyl)-1-(2,6-dichlorophenyl)-7-(piperidin-4-ylamino)-3,4-hydroquinazolin-2(1H)-one (85 mg, 0.17 mmol) in 2 mL of 1,2-dichloroethane. 3 drops of acetic acid and NaBH(OAc)₃ (76 mg, 0.34 mmol) was then added. The reaction mixture was stirred under argon at rt over the weekend. The reaction mixture was quenched with 6 mL of 2M aqueous NaOH and extracted with (3×10 mL) of ethyl acetate. The combined organic layers were dried over Na₂SO₄ and concentrated under reduced pressure. The product was purified by reverse-phase preparative HPLC (YMC C18 100×20 mm, 90:10 water (0.1% trifluoroacetic acid)-CH₃CN (0.1% trifluoroacetic acid) to 10:90 water (0.1% trifluoroacetic acid)-CH₃CN (0.1% trifluoroacetic acid) over 15 min, at 20 mL/min.) The isolated trifluoroacetate salt was diluted with ethyl acetate and washed with saturated aqueous NaHCO₃, dried over Na₂SO₄, and concentrated under reduced pressure to yield the title compound. Mass spectrum (ESI) 543.2 (M+1). ¹H N (500 MHz, CDCl₃): δ 1.03 (d, J=6.4 Hz, 6H); 1.40 (m, 2H); 1.97 (m, 2H); 2.18 (m, 2H); 2.72 (m, 1H); 2.82 (d, J=10.7 Hz, 2H); 3.06 (m, 1H); 3.49 (m, 1H); 4.15 (dd, J=13.5 Hz, J=1.6 Hz, 1H); 4.31 (dd, J=13.8 Hz, J=1.4 Hz, 1H); 5.01 (s; 1H); 5.36 (d, J=2 Hz, 1H); 6.13 (d, J=2.3 Hz, 1H); 7.35 (m, 4H); 7.50 (m, 3H).

EXAMPLE CCC20

7-[(1-tert-butylpiperidin-4-yl)amino]-5-(2-chlorophenyl)-1-(2,6-dichlorophenyl)-3,4-dihydroquinazolin-2(1H)-one

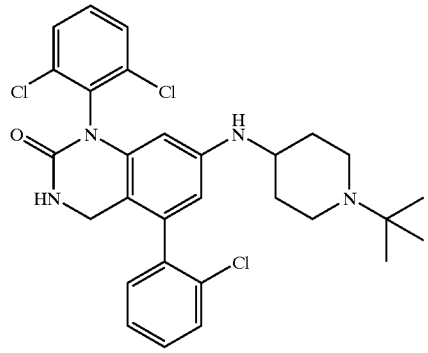

STEP A: 7-[(1-tert-butylpiperidin-4-yl)amino]-5-(2-chlorophenyl)-1-(2,6-dichlorophenyl)-3-(4-methoxybenzyl)-3,4-dihydroquinazolin-2(1H)-one The 7-[(1-tert-butylpiperidin-4-yl)amino]-5-(2-chlorophenyl)-1-(2,6-dichlorophenyl)-3-(4-methoxybenzyl)-3,4-dihydroquinazolin-2(1H)-one was prepared from 7-amino-5-(2-chlorophenyl)-1-(2,6-dichlorophenyl)-3-(4-methoxybenzyl)-3,4-dihydroquinazolin-2(1H)-one (COMPOUND CCC4, STEP A) and the 1-tert-butylpiperidin-4-one (COMPOUND PPA-1) by a procedure analogous to that described in EXAMPLE CCC18, STEP A. Mass spectrum (ESI) 677.2 (M+1).

STEP B: 7-[(1-tert-butylpiperidin-4-yl)amino]-5-(2-chlorophenyl)-1-(2,6-dichlorophenyl)-3,4-dihydroquinazolin-2(1H)-one The 7-[(1-tert-butylpiperidin-4-yl)amino]-5-(2-chlorophenyl)-1-(2,6-dichlorophenyl)-3,4-dihydroquinazolin-2(1H)-one was prepared from 7-[(1-tert-butylpiperidin-4-yl)amino]-5-(2-chlorophenyl)-1-(2,6-dichlorophenyl)-3-(4-methoxybenzyl)-3,4-dihydroquinazolin-2(1H)-one by a procedure analogous to that described in COMPOUND CCC3, STEP F. Mass spectrum (ESI) 557 (M+1). Trifluoroacetate salt ¹H NMR (500 MHz, CDCl₃): selected peaks δ 1.08 (s, 9H); 1.41 (m, 2H); 1.98 (d, J=4.6 Hz, 2H); 2.17 (brs, 2H); 2.96 (d, J=8.7 Hz, 2H); 3.05 (brs, 1H); 4.13 (dd, J=1.8 Hz, J=13.7 Hz, 1H); 4.31 (dd, J=1.1 Hz, J=13.7 Hz, 1H); 5.17 (s, 1H).

EXAMPLE CCC21

5-(2-chlorophenyl)-1-(2,6-dichlorophenyl)-7-[(8-methyl-8-azabicyclo[3.2.1]oct-3-yl)amino]-3,4-dihydroquinazolin-2(1H)-one

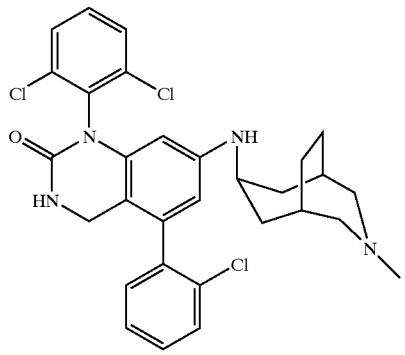

STEP A: 5-(2-chlorophenyl)-1-(2,6-dichlorophenyl)-3-(4-methoxybenzyl)-7-[(8-methyl-8-azabicyclo[3.2.1]oct-3-yl)amino]-3,4-dihydroquinolin-2(1H)-one The 5-(2-chlorophenyl)-1-(2,6-dichlorophenyl)-3-(4-methoxybenzyl)-7-[(8-methyl-8-azabicyclo[3.2.1]oct-3-yl)amino]-3,4-dihydroquinazolin-2(1H)-one was prepared from 7-amino-5-(2-chlorophenyl)-1-(2,6-dichlorophenyl)-3-(4-methoxybenzyl)-3,4-dihydroquinazolin-2(1H)-one (COMPOUND CCC4, STEP A) and 8-methyl-8-azabicyclo[3.2.1]octan-3-one by a procedure analogous to that described in EXAMPLE CCC18, STEP A. Mass spectrum (ESI) 661 (M+1).

STEP B: 5-(2-chlorophenyl)-1-(2,6-dichlorophenyl)-7-[(8-methyl-8-azabicyclo[3.2.1]oct-3-yl)amino]-3,4-dihydroquinazolin-2(1H)-one The 5-(2-chlorophenyl)-1-(2,6-dichlorophenyl)-7-[(8-methyl-8-azabicyclo[3.2.1]oct-3-yl)amino]-3,4-dihydroquinazolin-2(1H)-one was prepared from 5(2-chlorophenyl)-1-(2,6-dichlorophenyl)-3-(4-methoxybenzyl)-7-[(8-methyl-8-azabicyclo[3.2.1]oct-3-yl)amino]-3,4-dihydroquinazolin-2(1H)-one by a procedure analogous to that described in COMPOUND CCC3, STEP F. Mass spectrum (ESI) 541 (M+1). $^1$H NMR (500 MHz, CD$_3$OD): selected peaks δ 1.64 (d, J=14.5 Hz, 2H); 1.83 (d, J=12.1 Hz, 2H); 2.07 (m, 4H); 2.29 (s, 3H); 3.14 (brs, 2H); 3.36 (m, 1H 3.81 (d, J=4.1 Hz, 1H); 4.14 (½ ABq, J=13.7 Hz, 1H); 4.32 (½ ABq, J=13.7 Hz, 1H).

COMPOUND CCC5

N-[5-(2-chlorophenyl)-1-(2,6-dichlorophenyl)-2-oxo-1,2,3,4-tetrahydroquinazolin-7-yl]-1-methyl-1H-imidazole-4-sulfonamide

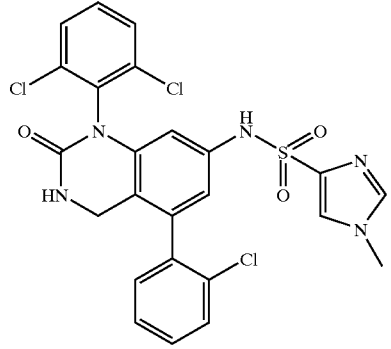

STEP A: N-[5-(2-chlorophenyl)-1-(2,6-dichlorophenyl)-3-(4-methoxybenzyl)-2-oxo-1,2,3,4-tetrahydroquinazolin-7-yl]-1-methyl-1H-imidazole-4-sulfonamide To a solution of 7-amino-5-(2-chlorophenyl)-1-(2,6-dichlorophenyl)-3-(4-methoxybenzyl)-3,4-dihydroquinazolin-2(1H)-one (150 mg, 0.278 mmol) (COMPOUND CCC4, STEP A) in 4 mL of THF cooled to 0° C. was added 1-methyl-1H-imidazole-4-sulfonyl chloride (100 mg, 0.556 mmol). A few crystals of 4-(dimethylamino) pyridine and diisopropylethylamine (53.9 mg, 0.417 mmol) were added. The resulting reaction mixture was stirred at 0° C. for 20 min, then heated to 70° C. for ca. 7.5 h. The reaction mixture was cooled to rt and partitioned between ethyl acetate and 1M aqueous HCl (added brine to improve the layer separation). The organic layer was concentrated under reduced pressure and triturated sequentially with Et$_2$O, methanol, and CH$_2$Cl$_2$ to yield the N-[5-(2-chlorophenyl)-1-(2,6-dichlorophenyl)-3-(4-methoxybenzyl)-2-oxo-1,2,3,4-tetrahydroquinazolin-7-yl]-1-methyl-1H-imidazole-4-sulfonamide. Mass spectrum (ESI) 682.0 (M+1).

STEP B: N-[5-(2-chlorophenyl)-1-(2,6-dichlorophenyl)-2-oxo-1,2,3,4-tetrahydroquinazolin-7-yl]-1-methyl-1H-imidazole-4-sulfonamide A solution of N-[5-(2-chlorophenyl)-1-(2,6-dichlorophenyl)-3-(4-methoxybenzyl)-2-oxo-1,2,3,4-tetrahydroquinazolin-7-yl]-1-methyl-1H-imidazole-4-sulfonamide (114 mg, 0.17 mmol) in 1.5 mL of trifluoroacetic acid was stirred at rt overnight. The resulting reaction mixture was concentrated under reduced pressure, diluted with CH$_2$Cl$_2$ and washed with saturated aqueous NaHCO$_3$ followed by brine. The organic layer was dried with Na$_2$SO$_4$ and concentrated under reduced pressure. The crude solid was purified by preparatory thin-layer chromatography, eluting with 90:10 CH$_2$Cl$_2$-2M NH$_3$ in methanol to yield N-[5-(2-chlorophenyl)-1-(2,6-dichlorophenyl)-2-oxo-1,2,3,4-tetrahydroquinazolin-7-yl]-1-methyl-1H-imidazole-4-sulfonamide. Mass spectrum (ESI) 562 (M+1). $^1$H NMR (500 MHz, DMSO-d$_6$): δ 3.67 (s, 3H); 3.93 (½ ABq, J=14.9 Hz, 1H); 3.99 (½ ABq, J=14.9 Hz, 1H); 4.02 (s, 1H); 5.95 (d, J=2.1 Hz, 1H); 6.55 (d, J=1.9 Hz, 1H); 7.30 (m, 2H); 7.35 (s, 1H); 7.43 (m, 2H); 7.58 (m, 2H); 7.69 (s, 1H); 7.72 (d, J=8.2 Hz, 2H).

EXAMPLE CCC22

N-[5-(2-chlorophenyl)-1-(2,6-dichlorophenyl)-2-oxo-1,2,3,4-tetrahydroquinazolin-7-yl]-3-morpholin-4-ylpropane-1-sulfonamide

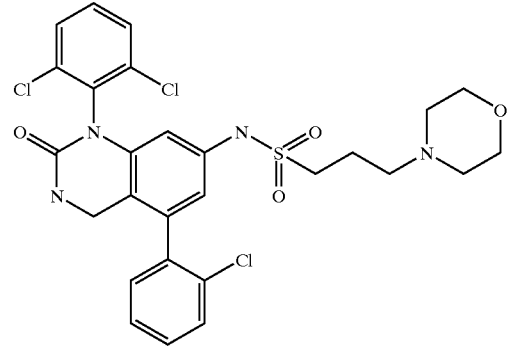

STEP A: 3-chloro-N-[5-(2-chlorophenyl)-1-(2,6-dichlorophenyl)-3-(4-methoxybenzyl)-2-oxo-1,2,3,4-tetrahydroquinazolin-7-yl]propane-1-sulfonamide The 3-chloro-N-[5-(2-chlorophenyl)-1-(2,6-dichlorophenyl)-3-(4-methoxybenzyl)-2-oxo-1,2,3,4-tetrahydroquinazolin-7-yl]propane-1-sulfonamide was prepared from 7-amino-5-(2chlorophenyl)-1-(2,6-dichlorophenyl)-3-(4-methoxybenzyl)-3,4-dihydroquinazolin-2(1H)-one (COMPOUND CCC4, STEP A) and 3-chloropropane-1-sulfonyl chloride by a procedure analogous to that described in COMPOUND CCC5, STEP A: Mass spectrum (ESI) 678.1 (M+1).

STEP B: N-[5-(2-chlorophenyl)-1-(2,6-dichlorophenyl)-3-(4-methoxybenzyl)-2-oxo-1,2,3,4-tetrahydroquinazolin-7-yl]-3-morpholin-4ylpropane-11-sulfonamide 3chloro-N-[5-(2-chlorophenyl)-1-(2,6-dichlorophenyl)-3-(4-methoxybenzyl)-2-oxo-1,2,3,4-tetrahydroquinazolin-7-yl]propane-1-sulfonamide (93 mg, 0.14 mmol) in morpholine (0.25 mL) was heated at 130° C. for 45 min. The reaction mixture was cooled to rt, diluted with ethyl acetate, washed with water, dried (Na$_2$SO$_4$), and concentrated under reduced pressure. The product was purified by flash chromatography on a Biotage 40S column, eluting with 60:40 hexanes-acetone to yield N-[5-(2-chlorophenyl)-1-(2,6-dichlorophenyl)-3-(4-methoxybenzyl)-2-oxo-1,2,3,4-tetrahydroquinazolin-7-yl]-3-morpholin-4-ylpropane-1-sulfonamide. Mass spectrum (ESI) 729 (M+1).

STEP C: N-[5-(2-chlorophenyl)-1-(2,6-dichlorophenyl)-2-oxo-1,2,3,4-tetrahydroquinazolin-7-yl]-3-morpholin-4-ylpropane-1-sulfonamide The N-[5-(2-chlorophenyl)-1-(2,6-dichlorophenyl)-2-oxo-1,2,3,4-tetrahydroquinazolin-7-yl]-3-morpholin-4-ylpropane-1-sulfonamide was prepared from N-[5-(2-chlorophenyl)-1-(2,6-dichlorophenyl)-3-(4-methoxybenzyl)-2-oxo-1,2,3,4-tetrahydroquinazolin-7-yl]-3-morpholin-4-ylpropane-1-sulfonamide by a procedure analogous to that described in COMPOUND CCC3, STEP F. Mass spectrum (ESI) 609 (M+1). $^1$H NMR (500 MHz, CDCl$_3$): selected peaks δ 1.97 (m, 2H); 2.38 (m, 6H); 3.16 (t, J=6.9 Hz, 2H); 3.61 (t, J=4.6 Hz, 4H); 4.26 (dd, J=14.4 Hz, J=1.6 Hz, 1H); 4.38 (dd, J=14.4 Hz, J=1.6 Hz, 1H).

COMPOUND CCC6

5-(2-chlorophenyl)-1-(2,6-dichlorophenyl)-7-iodo-3-(4-methoxybenzyl)-3,4-dihydroquinazolin-2(1H)-one

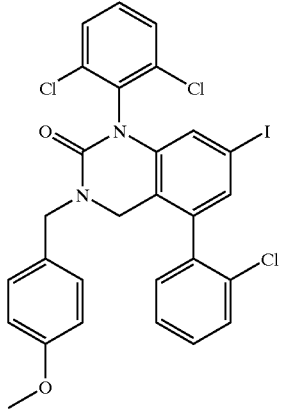

To a mixture of 7-amino-5-(2-chlorophenyl)-1-(2,6-dichlorophenyl)-3-(4-methoxybenzyl)-3,4-dihydroquinazolin-2(1H)-one (180.5 mg, 0.335 mmol) (COMPOUND CCC4, STEP A) in 2 mL of CH$_2$I$_2$ was added tert-butylnitrite (57.7 mg, 0.503 mmol). The reaction mixture was heated at 90° C. for ca. 45 min, cooled to rt, and purified by flash chromatography on a Biotage 40M column, eluting with hexanes followed by 2:1 hexanes-acetone to yield the title compound. Mass spectrum (ESI) 649.0 (M+1). $^1$H NMR (500 MHz, CDCl$_3$): δ 3.79 (s, 3H); 3.99 (½ ABq, J=15.1 Hz, 1H); 4.14 (½ ABq, J=14.8 Hz, 1H); 4.39 (½ ABq, J=14.9 Hz, 1H); 4.63 (½ ABq, J=14.8 Hz, 1H); 6.43 (d, J=1.4 Hz, 1H); 6.80 (m, 2H); 7.10 (dd, J=7.6 Hz, J=1.6 Hz, 1H); 7.15 (d, J=8.6 Hz, 2H); 7.19 (d, J=1.6 Hz, 1H); 7.26 (m, 1H); 7.33 (m, 1H); 7.37 (t, J=8.2 Hz, 1H); 7.43 (m, 1H); 7.53 (m, 2H).

COMPOUND CCC7

7-azido-5-(2-chlorophenyl)-1-(2,6-dichlorophenyl)-3-(4-methoxybenzyl)-3,4-dihydroquinazolin-2(1H)-one

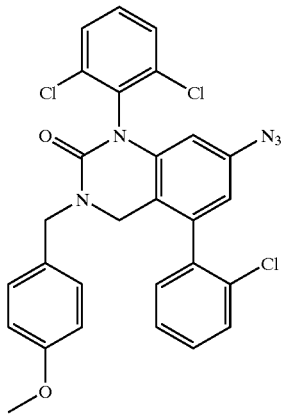

To a mixture of 7-amino-5-(2-chlorophenyl)-1-(2,6-dichlorophenyl)-3-(4-methoxybenzyl)-3,4-dihydroquinazolin-2(1H)-one (20 mg, 0.037 mmol) (COMPOUND CCC4, STEP A) in 0.9 mL of acetic acid at 0° C. was added NaNO$_2$ (2.6 mg dissolved in 79 μL of water). The reaction mixture was stirred at this temperature for 1 h. NaN$_3$ (3.6 mg dissolved in 79 μL of water) was then added and the reaction mixture was stirred at 0° C. for another 0.25 h. The reaction mixture was diluted with ca.5 mL of ethyl acetate, washed with 1 M aqueous NaOH, dried (Na$_2$SO$_4$), and concentrated under reduced pressure to yield the title compound. Mass spectrum (ESI) 564.1 (M+1).

COMPOUND CCC8

5-(2-chlorophenyl)-1-(2,6-dichlorophenyl)-3-(4-methoxybenzyl)-2-oxo-1,2,3,4-tetrahydroquinazoline-7-sulfonyl chloride

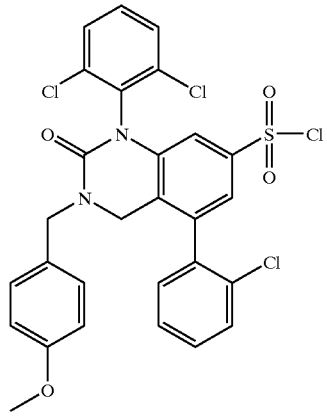

A mixture of 7-amino-5-(2-chlorophenyl)-1-(2,6-dichlorophenyl)-3-(4-methoxybenzyl)-3,4-dihydroquinazolin-2(1H)-one (300 mg, 0. 557 mmol) (COMPOUND CCC4, STEP A), concentrated HCl (2.2 mL), and acetic acid (0.6 mL) was cooled to ca. −10° C. A solution of NaNO$_2$ (57.7 mg, 0.836 mmol) in 0.9 mL of water was added and the reaction mixture was stirred at −10° C. for 0.5 h. To the reaction mixture was added a slurry of CuCl$_2$ (57.9 mg, 0.418 mmol) in acetic acid (1.3 mL) (through which SO$_2$ had been bubbled for 0.25 h), and the temperature of the reaction mixture was kept at ca. −10° C. for 1 h after the addition, while SO$_2$ was bubbled through the reaction mixture for 0.5 h after the addition. The reaction mixture was then stirred at rt overnight. Added the mixture to 25 mL of ice/water and extracted 3 times with ethyl acetate. The combined organic layers were washed with brine, dried (Na$_2$SO$_4$), and concentrated under reduced pressure. The product was purified by preparative thin-layer chromatography, eluting with 50:50 hexanes-acetone to yield the titled compound.

EXAMPLE CCC23
5-(2-chlorophenyl)-1-(2,6-dichlorophenyl)-7-[(5-isopropyl-2,5-diazabicyclo[2.2.1]hept-2-yl)sulfonyl]-3,4-dihydroquinazolin-2(1H)-one

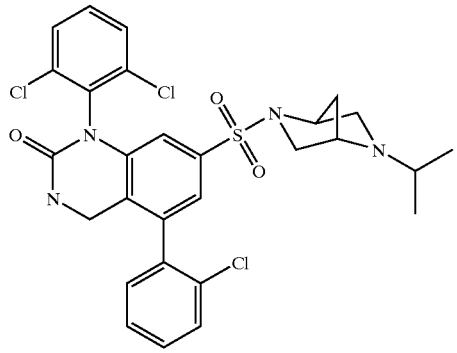

STEP A: 5-(2-chlorophenyl)-1-(2-dichlorophenyl)-7-[(5-isopropyl-2,5-diazabicyclo[2.2.1]hept-2-yl)sulfonyl]-3-(4-methoxybenzyl)-34-dihydroquinazolin-2(1H)-one 2-isopropyl-2,5-diazabicyclo[2.2.1]heptane (INTERMEDIATE ABA2) (35 µL, ca. 0.249 mmol) and diisopropylethylamine (32 mg, 0.249 mmol) were added to a mixture of 5-(2-chlorophenyl)-1-(2,6-dichlorophenyl)-3-(4-methoxybenzyl)-2-oxo-1,2,3,4-tetrahydroquinazoline-7-sulfonyl chloride (103 mg, 0.166 mmol) (COMPOUND CCC8) in 2 mL THF at 0° C. The mixture was warmed to rt, stirred at this temperature for 0.5 h, and concentrated under reduced pressure. The residue was diluted with ethyl acetate and added to 6 mL of 1M aqueous HCl The phases were separated and the aqueous was extracted with 3×15 mL of ethyl acetate. The combined organic layers were washed with brine, dried (Na$_2$SO$_4$), and concentrated under reduced pressure. The product was purified by preparative thin-layer chromatography, eluting with 93:7 CH$_2$Cl$_2$-methanol to yield the 5-(2-chlorophenyl)-1-(2,6-dichlorophenyl)-7-[(5-isopropyl-2,5-diazabicyclo[2.2.1]hept-2-yl)sulfonyl]-3-(4-methoxybenzyl)-3,4-dihydroquinazolin-2(1H)-one. Mass spectrum (ESI) 725 (M+1).

STEP B: 5-(2-chlorophenyl)-1-(2,6-dichlorophenyl)-7-[(5-isopropyl-2,5-diazabicyclo[2.2.1]hept-2-yl)sulfonyl]-3,4-dihydroquinazolin-2(1 H)-one The 5-(2-chlorophenyl)-1-(2,6-dichlorophenyl)-7-[(5-isopropyl-2,5-diazabicyclo[2.2.1]hept-2-yl)sulfonyl]-3,4-dihydroquinazolin-2(1H)-one was prepared from 5-(2-chlorophenyl)-1-(2,6-dichlorophenyl)-7-[(5-isopropyl-2,5-diazabicyclo[2.2.1]hept-2-yl)sulfonyl]-3-(4-methoxybenzyl)-3,4-dihydroquinazolin-2(1H)-one by a procedure analogous to that described in COMPOUND CCC3, STEP F. Mass spectrum (ESI) 605 (M+1). $^1$H NMR (500 MHz, CDCl$_3$):selected peaks δ 1.01 (d, J=5.9 Hz, 6H); 1.12 (m, 1H); 1.69 (d, J=9.8 Hz, 1H); 2.51 (t, 1=8.9 Hz, 1H); 2.56 (m, 1H), 2.93 (m, 1H); 3.02 (d, J=9.6 Hz, 1H); 3.49 (d, J=9.9 Hz, 1H); 3.62 (s, 1H); 4.09 (d, J=39.1, 1H); 4.37 (½ ABq, J=15.4 Hz, 1H); 4.45 (½ ABq, J=15.4 Hz, 1H).

EXAMPLE CCC24
5-(2-chlorophenyl)-1-(2,6-dichlorophenyl)-7-[(4-isopropylpiperazin-1-yl)sulfonyl]-3,4-dihydroquinazolin-2(1H)-one

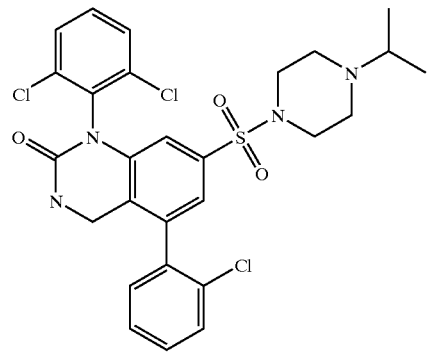

STEP A: 5-(2-chlorophenyl)-1-(2,6-dichlorophenyl)-7-[(4-isopropylpiperazin-1-yl)sulfonyl]-3-(4-methoxybenzyl)-3,4-dihydroquinolin-2(1H)-one The 5-(2-chlorophenyl)-1-(2,6-dichlorophenyl)7-[(4-isopropylpiperazin-1-yl)sulfonyl]-3-(4-methoxybenzyl)-3,4-dihydroquinazolin-2(1H)-one 2-oxo-1,2,3,4-tetrahydroquinazoline-7-sulfonyl chloride (COMPOUND CCC8) and 1-isopropylpiperazine by a procedure analogous to that described in EXAMPLE CCC23, STEP A. Mass spectrum (ESI) 713 (M+1).

STEP B: 5-(2-chlorophenyl)-1-(2,6-dichlorophenyl)-7-[(4-isopropylpiperazin-1-yl)sulfonyl]-3,4-dihydroquinazolin-2 (1H)-one The 5-(2-chlorophenyl)-1-(2,6-dichlorophenyl)-7-[(4-isopropylpiperazin-1-yl)sulfonyl]-3,4-dihydroquinazolin-2 (1H)-one was prepared from 5-(2-chlorophenyl)-1-(2,6-dichlorophenyl)-7-[(4-isopropylpiperazin-1-yl)sulfonyl]-3-(4-methoxybenzyl)-3,4-dihydroquinazolin-2(1H)-one by a procedure analogous to that described in COMPOUND CCC3, STEP F. Mass spectrum (ESI) 593 (M+1). $^1$H NMR (500 MHz, CDCl$_3$):selected peaks δ 1.03 (d, J=6.6 Hz, 6H); 2.57 (t, J=5 Hz, 4H); 2.69 (m, 1H); 3.00 (brs, 4H); 4.34 (dd, J=15.3 Hz, J=1.6 Hz, 1H); 4.46 (dd, J=15.3 Hz, J=1.6 Hz, 1H).

EXAMPLE CCC25
5-(2-chlorophenyl)-1-(2,6-dichlorophenyl)-7-{[4-(2-pyrrolidin-1-ylethyl)piperazin-1-yl]sulfonyl}-3,4-dihydroquinazolin-2(1H)-one

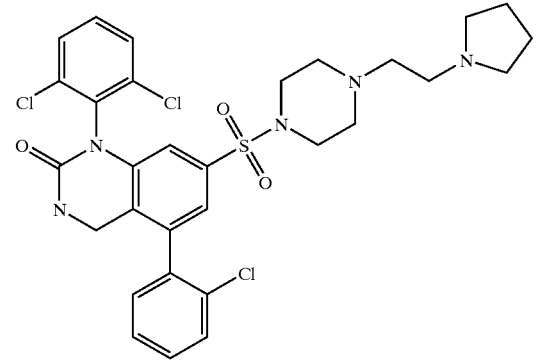

STEP A: 5-(2-chlorophenyl)-1-(2,6-dichlorophenyl)-2-oxo-1,2,3,4-tetrahydroquinazoline-7-sulfonyl chloride The 5-(2chlorophenyl)-1-(2,6-dichlorophenyl)-2-oxo-1,2,3,4-tetrahydroquinazoline-7-sulfonyl chloride was prepared from 7-amino-5-(2-chlorophenyl)-1-(2,6-dichlorophenyl)-3,4-dihydroquinazolin-2(1H)-one (COMPOUND CCC4) by a procedure analogous to that described in COMPOUND CCC8. $^1$H NMR (500 MHz, CDCl$_3$): δ 4.31 (½ ABq, J=16.0 Hz, 1H); 4.47 (½ ABq, J=16.0 Hz, 1H); 6.70 (d, J=1.8 Hz, 1H); 7.30 (dd, J=7.1 Hz, J=2.0 Hz, 2H); 7.41 (m, 3H); 7.54 (m, 3H).

STEP B: 5-(2-chlorophenyl)-1-(2,6-dichlorophenyl)-7-{[4-(2-pyrrolidin-1-ylethyl)piperazin-1-yl]sulfonyl}-3,4-dihydroquinazolin-2(1H)-one The 5-(2-chlorophenyl)-1-(2,6-dichlorophenyl)-7-{[4-(2-pyrrolidin-1-ylethyl)piperazin-1-yl]sulfonyl}-3,4-dihydroquinazolin-2(1H)-one was prepared from 5-(2-chlorophenyl)-1-(2,6-dichlorophenyl)-2-oxo-1,2,3,4-tetrahydroquinazoline-7-sulfonyl chloride and 1-(2-pyrrolidin-1-ylethyl)piperazine by a procedure analogous to that described in EXAMPLE CCC23, STEP A, except that no diisopropylethylamine was used. Mass spectrum (ESI) 648 (M+1). $^1$H NMR (500 MHz, CDCl$_3$): selected peaks δ 1.81 (brs, 4H); 2.58 (m, 12H); 3.00 (brs, 4H); 4.35 (dd, J=15.4 Hz, J=1.6 Hz, 1 H); 4.46 (dd, J=15.4 Hz, J=1.6 Hz, 1H).

EXAMPLE CCC26
5-(2-chlorophenyl)-1-(2,6-dichlorophenyl)-7-({4-[3-(dimethylamino)propyl]piperazin-1-yl}sulfonyl)-3,4-dihydroquinazolin-2(1H)-one

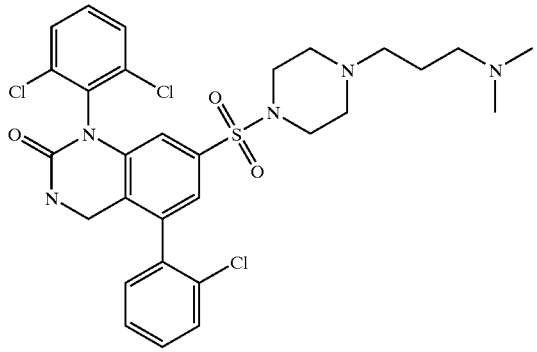

The title compound was prepared from 5-(2-chlorophenyl)-1-(2,6-dichlorophenyl)-2-oxo-1,2,3,4-tetrahydroquinazoline-7-sulfonyl chloride (EXAMPLE CCC25, STEP A) N,N-dimethyl-3-piperazin-1-ylpropan-1-amine by a procedure analogous to that described in EXAMPLE CCC25, STEP B. Mass spectrum (ESI) 636 (M+1). $^1$H NMR (500 MHz, CDCl$_3$): selected peaks δ 2.22 (s, 6H); 2.27 (t, J=7.3 Hz, 2H); 2.37 (t, J=7.3 Hz, 2H); 2.49 (brs, 4H); 3.00 (brs, 4H); 4.36 (½ ABq, J=15.3 Hz, 1H); 4.46 (½ ABq, J=15.3 Hz, 1H).

EXAMPLE CCC27
5-(2-chlorophenyl)-1-(2,6-dichlorophenyl)-7-[(2-methylpiperazin-1-yl)sulfonyl]-3,4-dihydroquinazolin-2(1H)-one

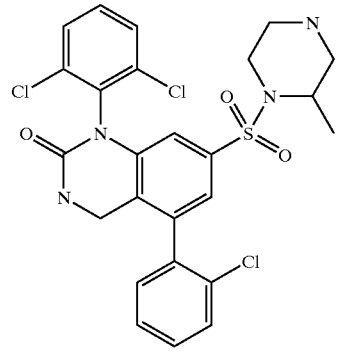

STEP A: 5-(2-chlorophenyl)-1-(2,6-dichlorophenyl)-3-(4-methoxybenzyl)-7-[(2-methylpiperazin-1-yl)sulfonyl]-3,4-dihydroquinazolin-2(1H)-one The 5-(2-chlorophenyl)-1-(2,6-dichlorophenyl)-3-(4-methoxybenzyl)-7-[(2-methylpiperazin-1-yl)sulfonyl]-3,4-dihydroquinazolin-2(1H)-one was prepared from 5-(2-chlorophenyl)-1-(2,6-dichlorophenyl)-3-(4-methoxybenzyl)-2-oxo-1,2,3,4-tetrahydroquinazoline-7-sulfonyl chloride (COMPOUND CCC8) and tert-butyl 3-methylpiperazine-1-carboxylate by a procedure analogous to that described in EXAMPLE CCC25, STEP B. Mass spectrum (ESI) 729 (M-t-Bu+1).

STEP B: 5-(2-chlorophenyl)-1-(2,6-dichlorophenyl)-7-[(2-methylpiperazin-1-yl)sulfonyl]-3,4-dihydroquinazolin-2(1H)-one The 5-(2-chlorophenyl)-1-(2,6-dichlorophenyl)-7-[(2-methylpiperazin-1-yl)sulfonyl]-3,4-dihydroquinazolin-2(1H)-one was prepared from 5-(2-chlorophenyl)-1-(2,6-dichlorophenyl)-3-(4-methoxybenzyl)-7-[(2-methylpiperazin-1-yl)sulfonyl]-3,4-dihydroquinazolin-2(1H)-one by a procedure analogous to that described in COMPOUND CCC3, STEP F. Mass spectrum (ESI) 565 (M+1). $^1$H NMR (500 MHz, CDCl$_3$): selected peaks δ 1.11 (m, 3H); 2.64 (m, 2H); 2.83 (m, 2H); 3.07 (m, 1H); 3.43 (m, 1H); 3.91 (m, 1H); 4.35 (½ ABq, J=15.3 Hz, 1H); 4.45 (½ ABq, J=15.3 Hz, 1H).

EXAMPLE CCC28
5-(2-chlorophenyl)-1-(2,6-dichlorophenyl)-7-({4-[2-(dimethylamino)ethyl]piperazin-1-yl}sulfonyl)-3,4-dihydroquinazolin-2(1H)-one

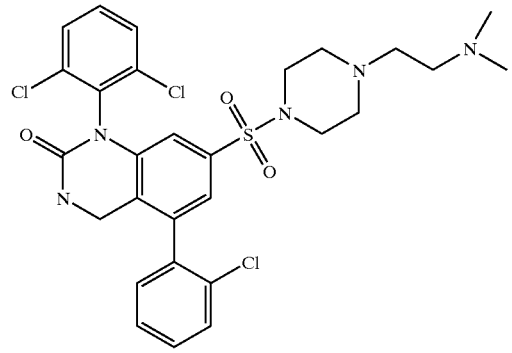

STEP A: 5-(2-chlorophenyl)-1-(2,6-dichlorophenyl)-7-({4-[2-(dimethylamino)ethyl]piperazin-1-yl}sulfonyl)-3-(4-methoxybenzyl)-3,4-dihydroquinazolin-2(1H)-one The 5-(2-chlorophenyl)-1-(2,6-dichlorophenyl)-7-({4-[2-(dimethylamino)ethyl]piperazin-1yl}sulfonyl)-3-(4-methoxybenzyl)-3,4-dihydroquinazolin-2(1H)-one was prepared from 5-(2-chlorophenyl)-1-(2,6-dichlorophenyl)-3-(4-methoxybenzyl)-2-oxo-1,2,3,4-tetrahydroquinazoline-7-sulfonyl chloride (COMPOUND CCC8) and N,N-dimethyl-2-piperazin-1-ylethanamine by a procedure analogous to that described in EXAMPLE CCC25, STEP B. Mass spectrum (ESI) 742 (M+1).

STEP B: 5-(2-chlorophenyl)-1-(2,6-dichlorophenyl)-7-({4-[2-(dimethylamino)ethyl]piperazin-1-yl}sulfonyl)-3,4-dihydroquinazolin-2(1H)-one The 5-(2-chlorophenyl)-1-(2,6-dichlorophenyl)-7-({4-[2-(dimethylamino)ethyl]piperazin-1-yl}sulfonyl)-3-(4-methoxybenzyl)-3,4-dihydroquinazolin-2(1H)-one was prepared from 5-(2-chlorophenyl)-1-(2,6-dichlorophenyl)-7-({4-[2-(dimethylamino)ethyl]piperazin-1-yl}sulfonyl)-3-(4-methoxybenzyl)-3,4-dihydroquinazolin-2(1H)-one by a procedure analogous to that described in COMPOUND CCC3, STEP F. Mass spectrum (ESI) 622 (M+1). $^1$H NMR (500 MHz, CDCl$_3$): selected peaks δ 2.23 (s, 6H); 2.39 (t, J=6.4 Hz, 2H); 2.50 (t, J=6.6 Hz, 2H); 2.53 (m, 4H); 3.01 (brs, 4H); 4.34 (½ ABq, J=15.3 Hz, 1H); 4.46 (½ ABq; J=15.3 Hz, 1H).

EXAMPLE CCC29

5-(2-chlorophenyl)-1-(2,6-dichlorophenyl)-7-({4-[2-(diethylamino)ethyl]piperazin-1-yl}sulfonyl)-3,4-dihydroquinazolin-2(1H)-one

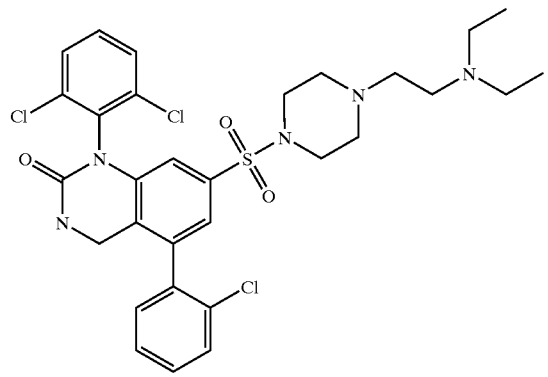

The title compound was prepared from 5-(2-chlorophenyl)-1-(2,6-dichlorophenyl)-2-oxo-1,2,3,4-tetrahydroquinazoline-7-sulfonyl chloride (EXAMPLE CCC25, STEP A) and N,N-diethyl-2-piperazin-1-ylethanamine by a procedure analogous to that described in EXAMPLE CCC25, STEP B. Mass spectrum (ESI) 650 (M+1). $^1$H NMR (500 MHz, CDCl$_3$): selected peaks δ 1.03 (t, J=7.1 Hz, 6H); 2.51 (m, 12H); 3.00 (brs, 4H); 4.35 (dd, J=15.4 Hz, J=1.6 Hz, 1H); 4.46 (½ ABq, J=15.4 Hz, J=1.6 Hz, 1H).

COMPOUND CCC9

5-(2-chlorophenyl)-1-(2,6-dichlorophenyl)-2-oxo-N-pyridin-3-yl-1,2,3,4-tetrahydroquinazoline-7-sulfonamide

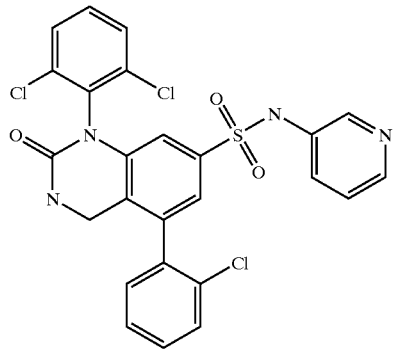

Pyridin-3-amine (9.4 mg, 0.10 mmol) and pyridine (6 μL, 0.075 mmol) were added to a mixture of 5-(2-chlorophenyl)-1-(2,6-dichlorophenyl)-2-oxo-1,2,3,4-tetrahydroquinazoline-7-sulfonyl chloride (25 mg, 0.050 mmol) (EXAMPLE CCC25, STEP A) in 0.5 mL THF. The mixture was stirred at rt overnight, and concentrated under reduced pressure. The residue was purified by preparative thin-layer chromatography, eluting with 95:5 CH$_2$Cl$_2$—NH$_3$ in methanol to yield the title compound. Mass spectrum (ESI) 559 (M+1).

COMPOUND CCC10

5-(2-chlorophenyl)-1-(2,6-dichlorophenyl)-2-oxo-N-pyridin-2-yl-1,2,3,4-tetrahydroquinazoline-7-sulfonamide

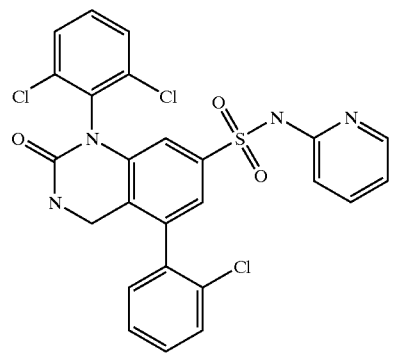

Pyridin-2-amine (14 mg, 0.15 mmol) and pyridine (12 μL, 0.15 mmol) were added to a mixture of 5-(2-chlorophenyl)-1-(2,6-dichlorophenyl)-2-oxo-1,2,3,4-tetrahydroquinazoline-7-sulfonyl chloride (25 mg, 0.050 mmol) (EXAMPLE CCC25, STEP A) in 0.5 mL THF. The mixture was stirred at rt overnight, then heated for 3 h at 70° C., and concentrated. The residue was purified by preparative thin-layer chromatography, eluting with 95:5 CH$_2$Cl$_2$—NH$_3$ in methanol to yield the title compound. Mass spectrum (ESI) 559.0 (M+1).

COMPOUND CCC11

5-(2-chlorophenyl)-1-(2,6-dichlorophenyl)-2-oxo-N-pyridin-4-yl-1,2,3,4-tetrahydroquinazonline-7-sulfonamide

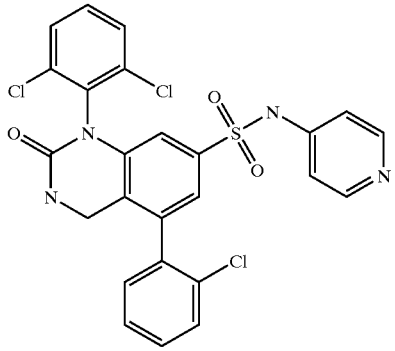

The title compound was prepared from 5-(2-chlorophenyl)-1-(2,6-dichlorophenyl)-2-oxo-1,2,3,4-tetrahydroquinazoline-7-sulfonyl chloride (EXAMPLE CCC25, STEP A) and pyridin-4-amine by a procedure analogous to that described in COMPOUND CCC10, STEP A. Mass spectrum (ESI) 559 (M+1).

$^1$H NMR (500 MHz, CD$_3$OD): δ 4.30 (ABq, J=23.3 Hz, J=6.0 Hz, 2H); 6.57 (d, J=1.6 Hz, 1H); 7.29 (brs, 2H); 7.40 (m, 1H); 7.48 (m, 3H); 7.57 (m, 2H); 7.65 (d, J=8.1 Hz,

EXAMPLE CCC30

5-(2-chlorophenyl)-1-(2,6-dichlorophenyl)-7-[3-methylpiperazin-1-yl)sulfonyl]-3,4-dihydroquinazolin-2(1H)-one

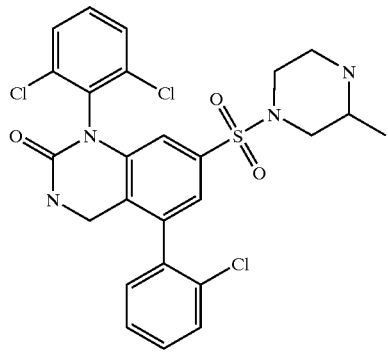

STEP A: benzyl 4-{[5-(2-chlorophenyl)-1-(2,6-dichlorophenyl)-3-(4-methoxybenzyl)-2-oxo-1,2,3,4-tetrahydroquinazolin-7-yl]sulfonyl}-2-methylpiperazine-1-carboxylate Benzyl 2-methylpiperazine-1-carboxylate (34 mg, 0.144 mmol) and diisopropylethylamine (19 mg, 0.144 mmol) were added to a mixture of 5-(2-chlorophenyl)-1-(2,6-dichlorophenyl)-3-(4-methoxybenzyl)-2-oxo-1,2,3,4-tetrahydroquinazoline-7-sulfonyl chloride (60 mg, 0.096 mmol) (COMPOUND CCC8) in 1 mL THF. The mixture was heated to 80° C. and stirred at this temperature for ca. 1 h. The reaction mixture was cooled to rt and concentrated. The residue was purified by preparative thin-layer chromatography, eluting with 50:50 hexanes-acetone to yield benzyl 4-{[5-(2-chlorophenyl)-1-(2,6-dichlorophenyl)-3-(4-methoxybenzyl)-2-oxo-1,2,3,4-tetrahydroquinazolin-7-yl]sulfonyl}-2-methylpiperazine-1-carboxylate. Mass spectrum (ESI) 819.1 (M+1).

STEP B: 5-(2-chlorophenyl)-1-(2,6-dichlorophenyl)-3-(4-methoxybenzyl)-7-[(3-methylpiperazin-1-yl)sulfonyl]-3,4-dihydroquinazolin-2(1H)-one The 5-(2-chlorophenyl)-1-(2,6-dichlorophenyl)-3-(4-methoxybenzyl)-7-[(3-methylpiperazin-1-yl)sulfonyl]-3,4-dihydroquinazolin-2(1H)-one was prepared from benzyl 4-{[5-(2-chlorophenyl)-1-(2,6-dichlorophenyl)-3-(4-methoxybenzyl)-2-oxo-1,2,3,4-tetrahydroquinazolin-7-yl]sulfonyl}-2-methylpiperazine-1-carboxylate by a procedure analogous to that described in COMPOUND CCC4, STEP A.

STEP C: 5-(2-chlorophenyl)-1-(2,6-dichlorophenyl)-7-[(3-methylpiperazin-1-yl)sulfonyl]-3,4-dihydroquinazolin-2(1H)-one The 5-(2-chlorophenyl)-1-(2,6-dichlorophenyl)-7-[(3-methylpiperazin-1-yl)sulfonyl]-3,4-dihydroquinazolin-2(1H)-one was prepared from 5-(2-chlorophenyl)-1-(2,6-dichlorophenyl)-3-(4-methoxybenzyl)-7-[(3-methylpiperazin-1-yl)sulfonyl]-3,4-dihydroquinazolin-2(1H)-one by a procedure analogous to that described in EXAMPLE CCC18, STEP B. Mass spectrum (ESI) 565 (M+1). $^1$H NMR (500 MHz, CD$_3$OD): selected peaks δ 1.29 (m, 3H); 2.43 (t, J=10.9, 1H); 2.65 (m, 1H); 3.19 (m, 1H); 3.43 (m, 2H); 3.72 (m, 2H); 4.32 (dd, J=16.0 Hz, J=7.1 Hz, 1H); 4.40 (dd, J=16.0 Hz, J=7.1 Hz, 1H).

COMPOUND CCA1

Methyl 5-(2-chlorophenyl)-1-(2,6-dichlorophenyl)-2-oxo-1,2-dihydroquinoline-7-carboxylate

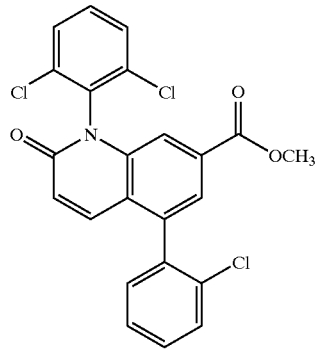

STEP A: Methyl 3,5-dibromo-4-formylbenzoate

Methyl 3,5-dibromo-4-(bromomethyl)benzoate (INTERMEDIATE 24) (3.9 g) was dissolved in acetonitrile (100 mL) and to this was added 4 Å molecular sieves and N-methylmorpholine N-oxide (1.18 g) and the reaction heated to 50° C. for 12 h. The reaction mixture was poured into brine and extracted into ethyl acetate, dried over MgSO$_4$ and concentrated. The residue was purified by silica gel chromatography eluting with 90% hexane:10% ethyl acetate to give the title compound. $^1$H NMR (500 MHz, CDCl$_3$): δ 10.27 (s, 1H); 8.29 (s, 2H); 3.99 (s, 3H).

STEP B: tert-Butyl (diphenoxyphosphoryl)acetate

To a solution of diphenylphosphite (2.25 mL) in dichloromethane at 0° C. was added t-butylbromoacetate (1.48 mL) followed by triethylamine (1.95 mL). The mixture was stirred at 0° C. for 15 min and then at rt for 1 h before being quenched with water and extracted into ethyl acetate, dried over MgSO$_4$ and concentrated. The residue was purified by silica gel chromatography eluting with hexane/ethyl acetate to give the title compound. $^1$H NMR (500 MHz, CDCl$_3$): δ 7.40–7.18 (m, 10H); 3.22 (s, 1H); 3.18 (s, 1H); 1.50 (s, 9H).

STEP C: Methyl 3,5-dibromo-4-[(1Z)-3-tert-butoxy-3-oxoprop-1-enyl]benzoate

To a solution of tert-butyl (diphenoxyphosphoryl)acetate (267 mg) in THF (7.5 mL) at 0° C. under nitrogen was added sodium hydride and the mixture stirred for 15 min until gas evolution ceased. This anion mixture was then cooled to −78° C. and a solution of methyl 3,5-dibromo-4-formylbenzoate (262 mg) in THF (7.5 mL) was added dropwise. The reaction mixture was stirred at −78° C. for an additional 40 min before being quenched with saturated ammonium chloride solution, extracted into ethyl acetate, dried over MgSO$_4$ and concentrated. The residue was purified by column chromatography on silica gel eluting with 90% hexane:10% ethyl acetate to give the title compound which also contained 20% of the E double-bond isomer. No attempt was made to separate these isomers at this stage. $^1$H NMR (500 MHz, CDCl$_3$): 88.23 (s, 1H, E isomer); 8.21 (s, 1H, Z isomer); 7.57 (d, J=16.3 Hz, 1H, E isomer); 6.76 (d, J=11.9 Hz, 1H, Z isomer); 6.38 (d, J=16.3 Hz, 1H E isomer); 6.12 (d, J=11.9 Hz, 1H Z isomer); 3.954 (s, 3H, E isomer); 3.948 (s, 3H, Z isomer); 1.28 (s, 9H, both isomers). Mass spectrum: m/z 365 (M+H-t-Bu).

STEP D: (2Z)-3-[2,6-Dibromo-4-(methoxycarbonyl)phenyl]pro-2-enoic acid

To a solution of the methyl 3,5-dibromo-4-[(1Z)-3-tert-butoxy-3-oxoprop-1-enyl]benzoate (340 mg) (contaminated with 20% of the E isomer from the previous step) in dichloromethane (1 mL) was added trifluoroacetic acid (10 mL) and the reaction stirred at ambient temperature for 45 min. After this time the reaction mixture was concentrated, toluene (100 mL) added and then concentrated again. The crude product was concentrated from toluene several more times to ensure the removal of all of the trifluoroacetic acid ultimately yielding the title compound (contaminated with 20% of the E isomer) which required no further purification. $^1$H NMR (500 MHz, CDCl$_3$): δ 10.19 (br.s. 1H, both isomers); 8.24 (s, 1H, E isomer); 8.20 (s, 1H, Z isomer); 7.74 (d, J=16.3 Hz, 1H, E isomer); 6.98 (d, J=11.9 Hz, 1H, Z isomer); 6.45 (d, J=16.3 Hz, 1H, E isomer); 6.24 (d, J=11.9 Hz, 1H Z isomer); 3.95 (s, 3H, both isomers). Mass spectrum: m/z 365 (M+H-t-Bu).

STEP E: Methyl 3,5-dibromo-4-{(1Z)-3-[(2,6-dichlorophenyl)amino]-3-oxoprop-1-enyl}benzoate To a solution of (2Z)-3-[2,6-dibromo-4-(methoxycarbonyl)phenyl]prop-2-enoic acid (1.24 g) (contaminated with 20% of the E isomer) in dichloromethane (34 mL) at 0° C. under nitrogen atmosphere was added oxalyl bromide (2 mL of a 2M solution in dichloromethane) followed by dimethylformamide (170 µL). The mixture was then warmed to rt and stirred until all gas evolution had ceased. The reaction was cooled again to 0° C. where diisopropylethylamine (83 µL) and 2,6-dichloroaniline (607 mg) were added and the reaction warmed to rt and stirred for 16 h. The reaction mixture was then poured into brine and extracted into ethyl acetate. A small amount of unreacted starting acid was removed by washing the organic layer with saturated sodium bicarbonate solution, before drying over MgSO$_4$ and concentrating. The residue was purified by column chromatography on silica gel to give the title compound still contaminated with 20% of the E isomer. $^1$H NMR (500 MHz, CDCl$_3$): δ 8.99 (br.s, 1H, Z isomer); 8.26 (br.s, 1H, E isomer); 8.20 (s, 1H, Z isomer); 7.80–6.40 (m, 6H); 3.96 (s, 3H, E isomer); 3.92 (s, 3H, Z isomer). Mass spectrum: m/z 507 (M+H).

STEP F: Methyl 5-bromo-1-(2,6-dichlorophenyl)-2-oxo-1,2-dihydroquinoline-7-carboxylate Methyl 3,5-dibromo-4-{(1Z)-3-[(2,6-dichlorophenyl)amino]-3-oxoprop-1-enyl}benzoate (1.25 g)(contaminated with 20% of the E isomer) was dissolved in dimethylformamide(36 mL) and the solution degassed with argon. Copper (I) iodide (340 mg) and dry potassium carbonate (468 mg) were added and the mixture heated to 80° C. for 30 min. The reaction mixture was poured into 5% ammonium hydroxide solution and extracted into ethyl acetate, dried over MgSO$_4$ and concentrated. The residue was purified by silica gel chromatography eluting with 80% hexane: 20% ethyl acetate to give the title compound.

$^1$H NMR (500 MHz, CDCl$_3$): δ 8.31 (d, J=9.8 Hz, 1H); 8.15 (s, 1H); 7.60 (d, J=8.0 Hz,1H); 7.50 (t, J=8 Hz, 2H); 7.12 (s, 1H); 6.98 (d, J=10.1 Hz, 1H); 3.90 (s, 3H).

Mass spectrum: m/z 428 (M+H).

STEP G: Methyl 5-(2-chlorophenyl)-1-(2,6-dichlorophenyl)-2-oxo-1,2-dihydroquinoline-7-carboxylate Methyl 5-bromo-1-(2,6-dichlorophenyl)-2-oxo-1,2-dihydroquinoline-7-carboxylate (80 mg), 2-chlorophenylboronic acid (58 mg), palladium tetrakis (triphenylphosphine) (22 mg) and 1M aqueous sodium carbonate (450 µL) were mixed in ethylene glycol dimethyl ether (2 mL), degassed with argon and then heated to reflux for 90 min. The cooled reaction mixture was diluted with ether, filtered through celite and concentrated. The residue was purified by silica gel chromatography eluting with 70% hexane:30% ethyl acetate to give the title compound. $^1$H NMR (500 MHz, CDCl$_3$): δ 7.82 (d, J=1.4 Hz, 1H); 7.65–7.39 (m, 8H); 7.23 (s, 1H); 6.82 (d, J=9.9 Hz, 1H), 3.90 (s, 3H). Mass spectrum: m/z 458 (M+H).

COMPOUND CCA2
5-(2-Chlorophenyl)-1-(2,6-dichlorophenyl)-2-oxo-1,2-dihydroquinoline-7-carboxamide

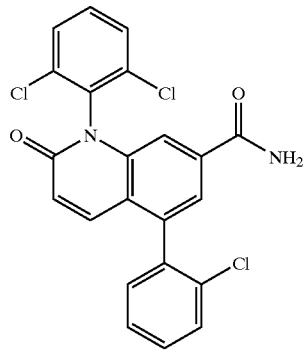

A solution of methyl 5-(2-chlorophenyl)-1-(2,6-dichlorophenyl)-2-oxo-1,2-dihydroquinoline-7-carboxylate (1.28 g) in methanol (100 mL) was treated with 1M potassium hydroxide (40 mL) and the reaction stirred at rt for 3 h. The reaction mixture was then acidified with 1N hydrochloric acid (100 mL) and extracted into dichloromethane. The organic phase was dried over MgSO$_4$, concentrated and the residue was dissolved in THF (16 mL). 1-(3-dimethylaminopropyl)-3-ethylcarbodiimide hydrochloride (314 mg) and 1-hydroxybenzotriazole hydrate (251 mg) were then added and this mixture was stirred at rt for 45 min before the addition of concentrated ammonium hydroxide (111 µL). The reaction was then stirred at rt for a further 24 h before being concentrated and purified by silica gel chromatography eluting with hexane/acetone to give the title compound. $^1$H NMR (500 MHz, CDCl$_3$): δ 7.65–7.39 (m, 9H); 7.08 (s, 1H); 6.80 (d, J=9.9 Hz, 1H); 6.02 (br.s, 1H); 5.70 (br.s, 1H). Mass spectrum: m/z 443 (M+H).

COMPOUND CCA3
7-Amino-5-(2-chlorophenyl)-1-(2,6-dichlorophenyl)quinolin-2(1H)-one

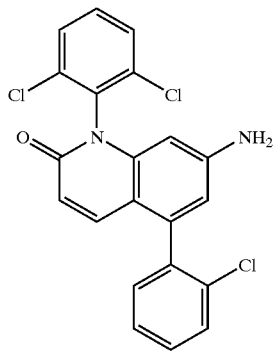

To 5-(2-chlorophenyl)-1-(2,6-dichlorophenyl)-2-oxo-1,2-dihydroquinoline-7-carboxamide (920 mg) in dioxane (330 mL) was added 5N NaOH (10 mL) and water (41 mL) followed by sodium hypochlorite (19.3 mL of a 10–13% aqueous solution) and the reaction mixture heated to 60° C. for 2 h. The cooled reaction mixture was then poured into brine and extracted into ethyl acetate, dried over MgSO$_4$ and concentrated. The residue was purified by silica gel chromatography eluting with hexane/ethyl acetate to give the title compound. $^1$H NMR (500 MHz, CDCl$_3$): δ 7.61–7.32 (m, 8H); 6.48 (d, J=2.1 Hz, 1H); 6.45 (d, J=9.7 Hz, 1H); 5.73 (d, J=2.1 Hz, 1H; 4.00 (br.s, 2H). Mass spectrum: m/z 415 (M+H).

COMPOUND CCA4
5-(2-Chlorophenyl)-1-(2,6-dichlorophenyl)-7-iodoquinolin-2(1H)-one

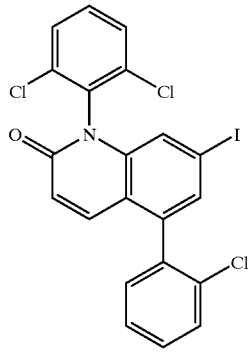

7-Amino-5-(2-chlorophenyl)-1-(2,6-dichlorophenyl) quinolin-2(1H)-one (560 mg), diiodomethane (3.5 mL) and t-butylnitrite (238 μl of a 90% solution) were heated to 90° C. for 15 min. The reaction mixture was directly loaded onto a silica gel column, with no work-up, and eluted with hexane/ethyl acetate to give the title compound. $^1$H NMR (500 MHz, CDCl$_3$): δ 7.65–7.37 (m, 9H); 6.89 (s, 1H); 6.74 (d, J=10.0 Hz, 1H). Mass spectrum: m/z 528 (M+H).

EXAMPLE CCA1
5-(2-Chlorophenyl)-1-(2,6-dichlorophenyl)-7-{4-[2-(dimethylamino) ethyl]piperazin-1-yl}quinolin-2(1H)-one

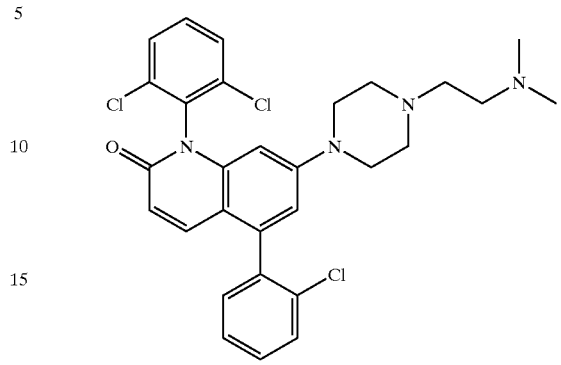

To the 5-(2-chlorophenyl)-1-(2,6-dichlorophenyl)-7-iodoquinolin-2(1H)-one (48 mg) in an oven-dried flask was added 18-crown-6 (34 mg), sodium t-butoxide (13 mg), tris(dibenzylideneacetone)dipalladium (0) (8.3 mg) and rac-2,2'-bis(diphenylphosphino)-1,1'-binaphthyl (17 mg) and the flask carefully filled with argon. The N,N-dimethyl-N-(2-piperazin-1-ylethyl)amine (17 mg) and THF (2 mL) were then added and the reaction stirred at rt for 16 h. The reaction mixture was then filtered and concentrated and the residue purified by reverse phase HPLC to yield the title compound. $^1$H NMR (500 Hz, CDCl$_3$): δ 7.62–7.35 (m, 8H); 6.74 (d, J=2.3 Hz, 1H); 6.49 (d, J=9.8 Hz, 1H); 5.86 (d, J=2.1 Hz, 1H); 3.16 (t, J=4.8 Hz, 4H); 2.57 (t, J=5.1 Hz, 4H); 2.53–2.46 (m, 4H), 2.28 (s, 6H). Mass spectrum: m/z 557 (M+H).

COMPOUND DDD-1
Methyl 5-(2-chlorophenyl)-1-(2,6-dichlorophenyl)-2-oxo-1,4-dihydro-2H-3,1-benzoxazine-7-carboxylate

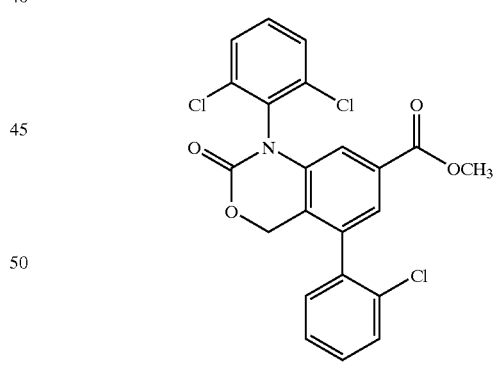

Step A: methyl 3,5-dibromo-4-(hydroxymethyl)benzoate

To a stirred solution of methyl 3,5-dibromo-4-(bromomethyl)benzoate (INTERMEDIATE 24) (12.53 g, 32.4 mmol, 1 eq) in dioxane (100 mL) and water (100 mL) was added CaCO3 (8.1 g, 81 mmol, 2.5 eq). The mixture was warmed to and stirred at 100° C. until reaction was complete by HPLC analysis. The mixture was cooled and the solvent removed under reduced pressure. The residue was diluted with water and extracted 3× with CH$_2$Cl$_2$. The organic extracts were combined, dried over anhydrous Na$_2$SO$_4$, filtered and concentrated giving methyl 3,5- dibromo-4-(hydroxymethyl)benzoate. The material was taken immediately to the next step.

Step B: methyl 3,5-dibromo-4-[({[(2,6-dichlorophenyl)amino]carbonyl}oxy)methyl]benzoate To a stirred solution of methyl 3,5-dibromo-4-(hydroxymethyl)benzoate (11 g, 34 mmol, 1 eq) in CH$_2$Cl$_2$ (50 mL) was added 2,6-dichlorophenylisocyanate (7 g, 37.2 mmol, 1.1 eq) and 4-N,N-dimethylaminopyridine (few crystals). Stirred at rt. After 15 min, the flask was thick with precipitate. Added 50 L CH$_2$Cl$_2$ to facilitate stirring and let stir overnight. Removed the CH$_2$Cl$_2$ under reduced pressure. Triturated the residue with Et$_2$O and collected the solids giving methyl 3,5-dibromo-4-[({[(2,6-dichlorophenyl)amino]carbonyl}oxy)methyl]benzoate.

$^1$H NMR (500 MHz, CDCl$_3$): δCHCl$_3$ 8.23 (sH, s); 7.38 (2H, d, J=8 Hz); 7.19 (1H, t, J=8 Hz); 6.39 (1H br s); 5.58 (2H, s); 3.96 (3H, s).

Step C: methyl 5-bromo-1-(2,6-dichlorophenyl)-2-oxo-1,4-dihydro-2H-3,1-benzoxazine-7-carboxylate To a solution of methyl 3,5-dibromo-4-[({[(2,6-dichlorophenyl)amino]carbonyl}oxy)methyl]benzoate (1 g, 1.96 mmol, 1 eq) in DMF (20 mL) was added CuI (411 mg, 2.16 mmol, 1.1 eq) and diisopropylethylamine (0.51 mL, 2.95 mmol, 1.5 eq). Degassed the reaction flask with argon and placed in a 140° C. oil bath. After 2.5 h the reaction was cooled. The mixture was filtered to remove inorganics. The solvent was removed under reduced pressure. The residue was dissolved in CH$_2$Cl$_2$, and washed with water. The aqueous layer was back-extracted 2× with CH$_2$Cl$_2$. The organic extracts were combined, dried over anhydrous Na$_2$SO$_4$, filtered and concentrated. The residue was triturated with Et$_2$O leaving 283 mg of solid methyl 5-bromo-1-(2,6-dichlorophenyl)-2-oxo-1,4-dihydro-2H-3,1-benzoxazine-7-carboxylate. The supernatant was further purified by flash column chromatography on silica gel eluting with 2:1 CH$_2$Cl$_2$/hexanes giving an additional 309 mg of not quite pure product. Mass spectrum (ESI) 430.0 (M+1); 432.0 (M+3); 434.0 (M+5).

Step D: methyl 5-(2-chlorophenyl)-1-(2,6-dichlorophenyl)-2-oxo-1,4-dihydro-2H-3,1-benzoxazine-7-carboxylate A stirred solution of methyl 5-bromo-1-(2,6-dichlorophenyl)-2-oxo-1,4-dihydro-2H-3,1-benzoxazine-7-carboxylate (280 mg, 0.65 mmol, 1 eq) in toluene (9 mL) was degassed with argon. To this solution was added 2-chlorophenylboronic acid (305 mg, 1.95 mmol, 3 eq) and Na$_2$CO$_3$ (427 mg, 4.03 mmol, 6.2 eq). The mixture was again degassed with argon. To the stirred mixture was then added water (2 mL) and ethanol (2 mL). The mixture was degassed with argon. To the mixture was added tetrakis(triphenylphosphine)palladium(0) (37 mg, 0.032 mmol, 0.05 eq). The reaction vessel was placed in a 100° C. oil bath and stirred under argon. After 1.5 h HPLC analysis indicated partial conversion of starting material. Added small amount tetrakis(triphenylphosphine)palladium(0) and continued to stir. After additional 1 h at 100° C. HPLC analysis showed little change. The mixture was cooled, diluted with ethyl acetate, washed 2× with saturated aqueous NaHCO3, and 1× with brine, The organic layer was dried over anhydrous Na$_2$SO$_4$, filtered and concentrated under reduced pressure. The product was purified by flash column chromatography eluting with 6:1 hexanes/ethyl acetate giving 193 mg methyl 5-(2-chlorophenyl)-1-(2,6-dichlorophenyl)-2-oxo-1,4-dihydro-2H-3,1-benzoxazine-7-carboxylate.

Mass spectrum (ESI) 462 (M+1); 464 (M+3).

EXAMPLE DDD1

5-(2-chlorophenyl)-1-(2,6-dichlorophenyl)-7-[(4-isopropylpiperazin-1-yl)carbonyl]-1,4-dihydro-2H-3,1-benzoxazin-2-one

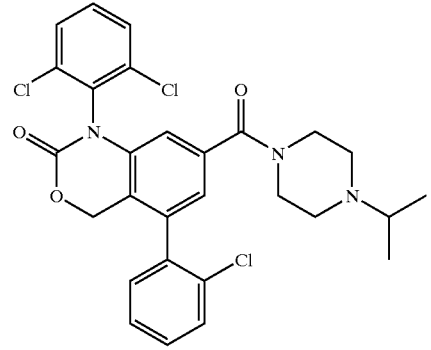

To a dry flask charged with anhydrous CH$_2$Cl$_2$ (1 mL) was added 1-isopropylpiperazine (0.057 mL, 0.434 mmol, 2 eq). The mixture was cooled to 0° C. under nitrogen. To this cooled mixture was added Al(CH$_3$)$_3$ (0.217 mL of a 2M toluene solution, 0.434 mmol, 2 eq). After 15 min, methyl 5-(2-chlorophenyl)-1-(2,6-dichlorophenyl)-2-oxo-1,4-dihydro-2H-3,1-benzoxazine-7-carboxylate (100 mg, 0.217 mmol, 1 eq) was dissolved in CH$_2$Cl$_2$ (1 mL) and added to the aluminum reagent at 0° C. under nitrogen. After 2 min the cooling bath was removed. Let stir at rt for 5d. The reaction was diluted with CH$_2$Cl$_2$, and washed with water. The aqueous layer was back extracted 2× with CH$_2$Cl$_2$. The organic extracts were combined, dried over anhydrous Na$_2$SO$_4$, filtered and concentrated. The product was purified by flash column chromatography on silica gel eluting with 2:1 hexanes/acetone giving 5-(2-chlorophenyl)-1-(2,6-dichlorophenyl)-7-[(4-isopropylpiperazin-1-yl)carbonyl]-1,4-dihydro-2H-3,1-benzoxazin-2-one. Mass spectrum (ESI) 458.0 (M+1); 460 (M+3).

EXAMPLE DDD2

5-(2-chlorophenyl)-1-(2,6-dichlorophenyl)-7-[(4-isopropylpiperazin-1-yl) methyl]-1,4-dihydro-2H-3,1-benzoxazin-2-one

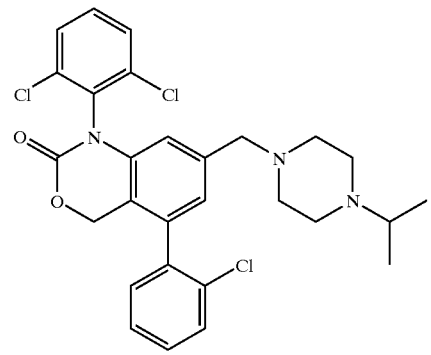

To a stirred solution of 5-(2-chlorophenyl)-1-(2,6-dichlorophenyl)-7-[(4-isopropylpiperazin-1-yl)carbonyl]-1,4-dihydro-2H-3,1-benzoxazin-2-one (31 mg, 0.055 mmol, 1 eq) in THF (0.1 mL) at 0° C. under nitrogen was added a solution of borane in THF (0.1 mL of a 1M solution, 0.1 mmol, 1.8 eq). The mixture was stirred 5 min at 0° C. and then the cooling bath was removed. The mixture was brought to and maintained at reflux for 2 h (twice added 0.1 mL of THF due to solvent loss). The mixture was cooled. To the reaction was added 6N aqueous HCl (0.1 mL) and the mixture was heated in a 70° C. oil bath for 15 min. The mixture was cooled and diluted with $CH_2Cl_2$ and aqueous NaHCO3. Aqueous 2N NaOH was added to increase basicity. Mixed and separated the layers. The aqueous layer was back extracted 2× with $CH_2Cl_2$. The organic extracts were combined, dried over anhydrous $Na_2SO_4$, filtered and concentrated. The product was purified by flash column chromatography on silica gel giving 5-(2-chlorophenyl)-1-(2,6-dichlorophenyl)-7-[(4-isopropylpiperazin-1-yl)methyl]-1,4-dihydro-2H-3,1-benzoxazin-2-one. Mass spectrum ESI) 544.2 (M+1); 546.2 (M+3).

COMPOUND DDD-2
5-(2-chlorophenyl)-(2,6-dichlorophenyl)-7-(1-hydroxy-1-methylethyl)-3,4-dihydroquinazolin-2(1H)-one

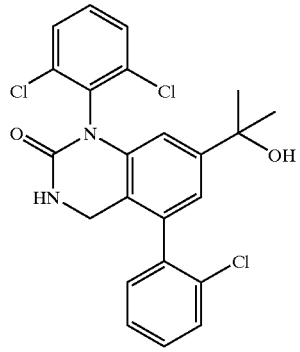

To a stirred solution of methyl 5-(2-chlorophenyl)-1-(2,6-dichlorophenyl)-2-oxo-1,2,3,4-tetrahydroquinazoline-7-carboxylate (1 g, 2.17 mmol, 1 eq) in THF (20 mL) under nitrogen at 0° C. was added a solution of methylmagnesium bromide (4.66 mL of a 1.4M solution in toluene, 6.52 mmol, 3 eq). The cooling bath was removed and the mixture allowed to stir 2 h and then the reaction was brought to and maintained at reflux for 1 h. The mixture was cooled and additional methylmagnesium bromide (2 mL of 1.4M solution in toluene) was added. A large amount of precipitate formed. Let stir 1 h. HPLC analysis showed some starting material still present. Added methylmagnesium bromide (2 mL of 1.4M solution in toluene) and let stir overnight. Poured the reaction into a separatory funnel containing water. Made acidic by addition of 2N aqueous HCl. Extracted 3× with $CH_2Cl_2$. Combined the organic extracts, dried over anhydrous $Na_2SO_4$, filtered and concentrated giving 5-(2-chlorophenyl)-1-(2,6-dichlorophenyl)-7-(-hydroxy-1-methylethyl)-3,4-dihydroquinazolin-2(1H)-one.
$^1$H NMR (500 MHz, CDCl$_3$): δCHCl$_3$ 7.54–7.50 (3H, m); 7.40–7.31 (4H, m); 6.98 (1H, d, J=1.6 hz); 6.35 (1H, d, J=1.6 Hz); 5.21 (1H, br s); 4.43 (1H, dd, J=14.4 Hz, J=1.6 Hz); 4.26 (1H, dd, J=114.4 Hz, J=1.8 Hz); 1.47 (3H s); 1.46 (3H, s).

COMPOUND DDD-3
2-bromo-N-{1-[5-(2-chlorophenyl)-1-(2,6-dichlorophenyl)-2-oxo-1,2,3,4-tetrahydroquinazolin-7-yl]-1-methylethyl}acetamide

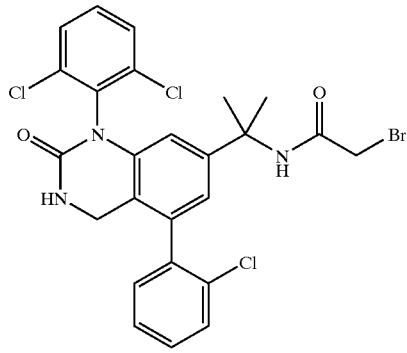

To a stirred suspension of 5-(2-chlorophenyl)-1-(2,6-dichlorophenyl)-7-(1-hydroxy-1-methylethyl)-3,4-dihydroquinazolin-2(1H)-one (460 mg) in acetic acid (0.4 mL) was added bromoacetonitrile (0.1 mL). To this mixture was added concentrated sulfuric acid (0.2 mL) and the resulting solution was allowed to stir overnight. The reaction was quenched by dropwise addition of the mixture to a rapidly stirred mixture of 2N aqueous NaOH and $CH_2Cl_2$. Transferred to a separatory funnel, diluted with water and extracted 3× with $CH_2Cl_2$. The organic extracts were combined, dried over anhydrous $Na_2SO_4$, filtered and concentrated. The product was purified by flash column chromatography on silica gel eluting with 2:1 hexanes/acetone giving 2-bromo-N-{1-[5-(2-chlorophenyl)-1-(2,6-dichlorophenyl)-2-oxo-1,2,3,4-tetrahydroquinazolin-7-yl]-1-methylethyl}acetamide.

Mass spectrum ESI) 580 (M+1); 582 M+3); 584 (M+5).
$^1$H NMR (500 MHz, CDCl$_3$): δCHCl$_3$ 7.55–7.50 (3H, m); 7.40–7.34 (4H, m); 6.91 (1H, d, J=1.9 Hz); 6.55 (1H, br s); 6.16 (1H, d, J=1.9 Hz); 5.17 (1H, br s); 4.41 (1H, ½ dd, J=14.4 Hz, J=1.6 Hz); 4.27 (1H, dd, J=14.4, Hz, J=1.6 Hz); 3.73 (1H, ½ ABq, J=13.6 Hz); 3.68 (1H, ½ ABq, J=13.6); 1.64 (3H, s); 1.57 (3H, s).

EXAMPLE DDD3
N-{1-[5-(2-chlorophenyl)-1-(2,6-dichlorophenyl)-2-oxo-1,2,3,4-tetrahydroquinazolin-7-yl]-1-methylethyl}-2-morpholin-4-ylacetamide

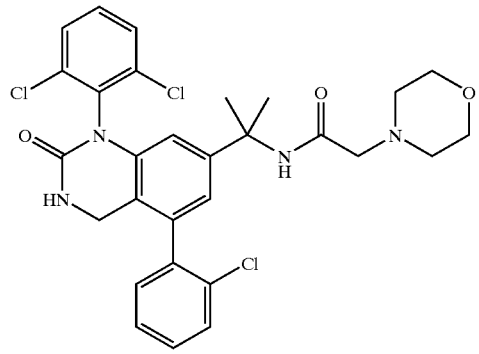

To a stirred solution of 2-bromo-N-{1-[5-(2-chlorophenyl)-1-(2,6-dichlorophenyl)-2-oxo-1,2,3,4-tetrahydroquinazolin-7-yl]-1-methylethyl}acetamide (30 mg, 0.05 mmol, 1 eq) in DMF (0.5 mL) was added morpholine (0.01 mL) and diisopropylethylamine (0.02 mL).

The mixture was warmed to and maintained at 80° C. for 1.5 h at which time HPLC analysis indicated complete reaction. The mixture was diluted with ethyl acetate and washed 3× with dilute NaOH. The organic extract was dried over anhydrous $Na_2SO_4$, filtered and concentrated giving N-{1-[5-(2-chlorophenyl)-(2,6-dichlorophenyl)-2-oxo-1,2,3,4-tetrahydroquinazolin-7-yl]-1-methylethyl}-2-morpholin-4-ylacetamide. Mass spectrum 587.2 (M+1); 589.2 (M+3).

EXAMPLE DDD4
N-{1-[5-(2-chlorophenyl)-1-(2,6-dichlorophenyl)-2-oxo-1,2,3,4-tetrahydroquinazolin-7-yl]-1-methylethyl}-2-(4-isopropylpiperazin-1-yl) acetamide

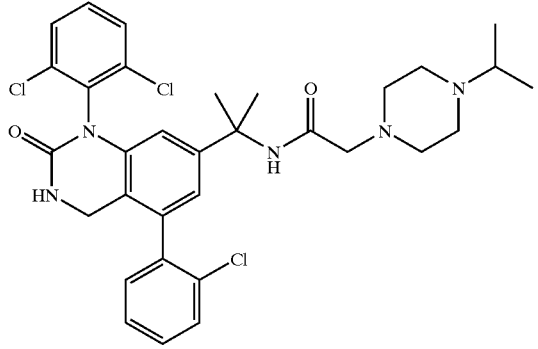

The title compound was made according to the procedure outlined in EXAMPLE DDD3 using isopropylpiperazine. The product was purified by preparative reverse phase HPLC [Waters Xterra C8 ms 19×100 mm column using a gradient elution of 90% water (+0.1% TFA)/10% $CH_3CN$ (+0.1% TFA) to 100% $CH_3CN$ (+0.1% TFA) over 12 min at 20 mL/min] giving N-{1-[5-(2-chlorophenyl)-1-(2,6-dichlorophenyl)-2-oxo-1,2,3,4-tetrahydroquinazolin-7-yl]-1-methylethyl}-2-(4-isopropylpiperazin-1-yl)acetamide as the TFA salt. $^1$H NMR (500 MHz, $CDCl_3$): δCHCl$_3$ 7.53–7.49 (3H, m); 7.39–7.34 (4H, m); 6.90 (1H, d, J=1.2 Hz); 6.15 (1H, d, J=1.2 Hz); 5.18 (1H, br s); 4.408 (1H, dd, J=14.4 Hz, J=1.2 Hz); 4.26 (1H, dd, J=14.4 Hz, J=1.4 Hz); 2.84 (1H, ½ ABq, J=16.3 Hz); 2.79 (1H, ½ ABq, J=16.3 Hz); 2.65 (1H, m); 2.47 (8H, br s); 1.61 (3H, s); 1.56 (3H, s); 1.06 (6H, m).

COMPOUND DDD-4
$N^1$-{1-[5-(2-chlorophenyl)-1-(2,6-dichlorophenyl)-2-oxo-1,2,3,4-tetrahydroquinazolin-7-yl]-1-methylethyl}-$N^2$-isopropylglycinamide

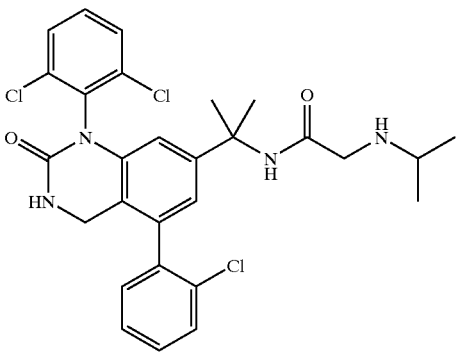

The title compound was made according to the procedure outlined in EXAMPLE DDD3 using isopropylamine. The product was purified by preparative reverse phase HPLC [Waters Xterra C8 ms 19×50 mm column using a gradient elution of 90% water (+0.1% TFA)/10% $CH_3CN$ (+0.1% TFA) to 100% $CH_3CN$ (+0.1% TFA) over 12 min at 20 mL/min] giving $N^1$-{1-[5-(2-chlorophenyl)-1-(2,6-dichlorophenyl)-2-oxo-1,2,3,4-tetrahydroquinazolin-7-yl]-1-methylethyl}-$N^2$-isopropylglycinamide as the TFA salt. Mass spectrum (ESI) 559.1 (M+1); 561.1 (M+3).

COMPOUND DDD-5
N-{1-[5-(2-chlorophenyl)-1-(2,6-dichlorophenyl)-2-oxo-1,2,3,4-tetrahydroquinazolin-7-yl]-1-methylethyl}acetamide

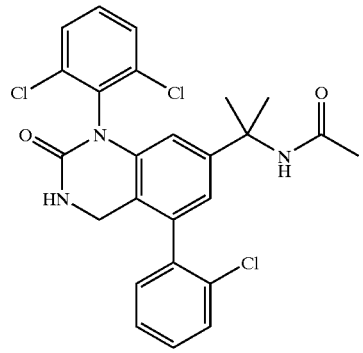

The title compound was prepared according to the procedure outlined in COMPOUND DDD-3 using acetonitrile instead of bromoacetonitrile. The product was purified by flash column chromatography on silica gel eluting with 2:1 hexanes/acetone and then by preparative thin layer chromatography eluting 3× with 3.5% MeOH in $CH_2Cl_2$ to give N-{1-[5-(2-chlorophenyl)-1-(2,6-dichlorophenyl)-2-oxo-1,2,3,4-tetrahydroquinazolin-7-yl]-1-methylethyl}acetamide. Mass spectrum (ESI) 502 (M+1); 504 (M+3).

COMPOUND DDD-6
5-(2-chloropenyl)-1-(2,6-dichlorophenyl)-7-(1-{[2-(isopropylamino)ethyl]amino}-1-methylethyl)-3,4-dihydroquinazolin-2(1H)-one

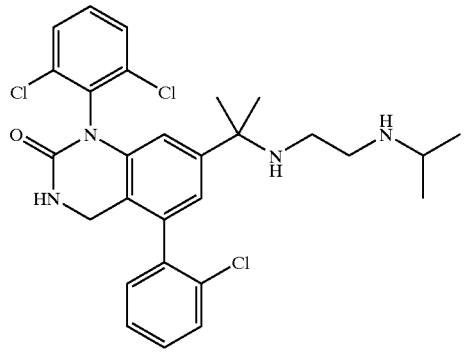

Dissolved $N^1$-{1-[5-(2-chlorophenyl)-1-(2,6-dichlorophenyl)-2-oxo-1,2,3,4-tetrahydroquinazolin-7-yl]-1-methylethyl}-$N^2$-isopropylglycinamide (COMPOUND DDD-4) (53 mg) borane-THF solution (3 mL of a 1M solution). The mixture was brought to and maintained at reflux for 4 h. The mixture was cooled. Aqueous 6N HCl (6 mL) was added and the mixture was heated to 80° C. for 30 min. The reaction was cooled and diluted with ethyl acetate. The aqueous layer was made basic by addition of 2N NaOH. The layers were mixed and then separated. The ethyl acetate layer was washed with aqueous 2N NaOH. The organic layer was dried over anhydrous $Na_2SO_4$, filtered and concentrated under reduced pressure. The product was purified by preparative reverse phase HPLC [Waters Xterra C8 ms 19×50 mm column using a gradient elution of 90% water (+0.1% TFA)/10% $CH_3CN$ (+0.1% TFA) to 100% $CH_3CN$ (+0.1% TFA) over 12 min at 20 mL/min] giving 5-(2-chlorophenyl)-1-(2,6-dichlorophenyl)-7-(1-{[2-(isopropylamino)ethyl]amino}-1-methylethyl)-3,4-dihydroquinazolin-2(1H)-one. Mass spectrum (ESI) 545 (M+1); 547 (M+3).

COMPOUND NAN-1

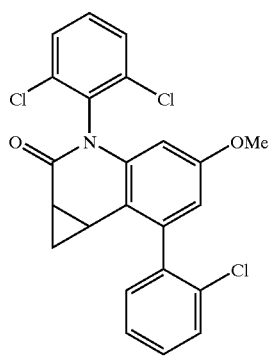

Oil free sodium hydride (36 mg) suspended in dry DMSO (5 mL) was added trimethylsulfoxonium chloride (193 mg) at room temperature. After bubbling subsided, the INTERMEDIATE 8 (300 mg) in DMSO (5 mL) was added to reaction mixture. The solution was stirred at rt for 1 h and at 60° C. for 18 h. The mixture was partitioned between ethyl acetate and water. The two layers were separated and the organic phase was washed with water (3x), brine, dried over MgSO$_4$, filtered and concentrated. The residue was purified by silica gel (hexanes/ethyl acetate=2/1) to give COMPOUND NAN-1. $^1$H NMR(CDCl$_3$, 500 MHz, diastereomers): 7.53 (m, 3H), 7.39 (m, 4H), 6.53 (d, 1H, one diastereomer), 6.48 (d, 1H, one diastereomer), 5.70(d, 1H, diastereomers mixture), 3.68 (s, 3H, one diastereomer), 3.51 (s, 3H, one diastereomer), 2.20 (m, 2H), 1.65 (m, 1H), 1.07 (m, 1H, one diastereomer), 0.97 (m, 1H, one diastereomer). MS(ES) 444 (M+M).

COMPOUND NAN-2

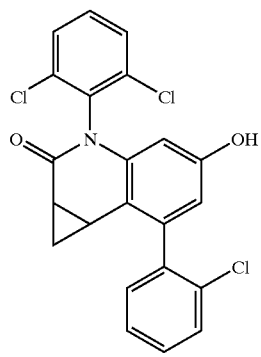

The title compound was prepared as described above in INTERMEDIATE 3. MS(ES) 430 (M+H).

EXAMPLE NAN1

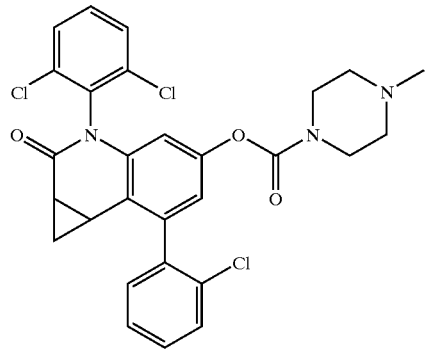

To a solution of COMPOUND NAN-2 (43 mg) in dichloromethane was added diisopropylethylamine (0.17 mL) and phosgen (0.5 mL, 1.9 M in toluene)at −20° C. The mixture was warmed up to rt and stirred for 16 h. The solution was concentrated to dry to give crude mixture. To a solution of this crude mixture in dichloromethane was added 1-methylpiperazine and diisopropylethylamine at rt and stirred for 16 h. Removal of the solvent and subsequent purification by preparative thin layer chromatography (hexanes/ethyl acetate=1/1) provided the title product. $^1$H NMR(CDCl$_3$, 500 MHz, diastereomers): 7.52 (m, 3H), 7.40 (m, 4H), 6.79 (d, 1H, one diastereomer), 6.76 (d, 1H, one diastereomer), 5.70 (d, 1H, one diastereomer), 5.88 (d, 1H, one diastereomer), 3.63 (m, 4H), 2.47 (m, 4H), 1.71 (m, 1H, one diastereomer), 1.57 (m, 1H, one diastereomer), 1.10 (m, 1H, one diastereomer), 1.02 (m, 1H, one diastereomer). MS(ES) 556 (M+H).

EXAMPLE MMM1A and EXAMPLE MMM1B
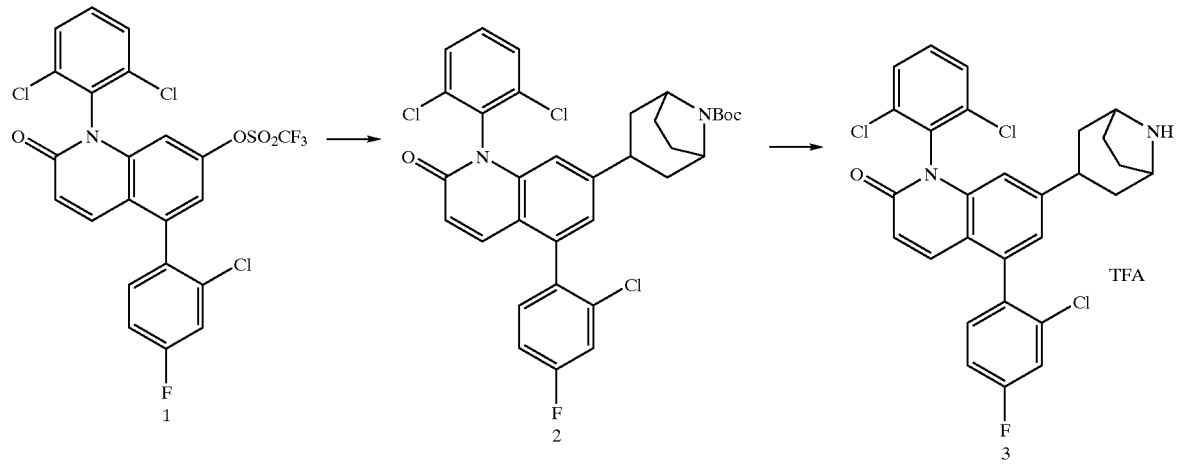
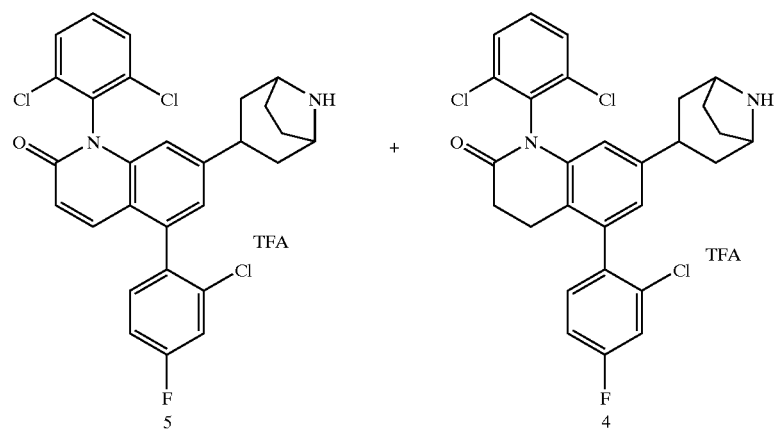
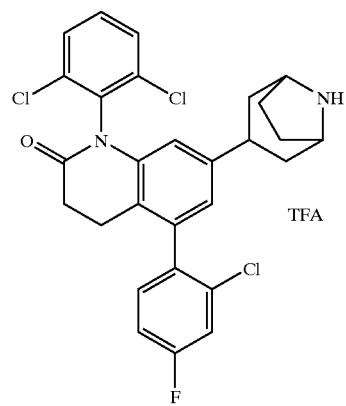
EXAMPLE MMM1A
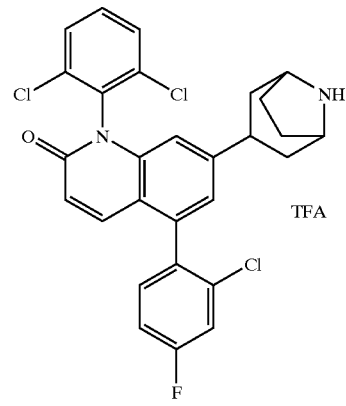
EXAMPLE MMM1B Step A: A mixture of 1 (232 mg, 0.409 mmol), LiCl (69 mg, 1.64 mmol), Pd(PPh$_3$)$_4$ (47 mg, 0.041 mmol) and tin reagent (228 mg, 0.61 mmol) in 5 mL of dioxane was heated under N$_2$ at 110° C. for 19 h. Solvent was removed and the residue was purified by flash chromatography EtOAc/Hexane=1:4 to give 2.

Step B: Compound 2 (0.2379 g, 0.38 mmol) was stirred in 5 mL of trifluoroacetic acid for 30 min. Then, volatiles were removed by vacuum to give 3 as TFA salt. Mass spectrum (ESI) 527 (M+1).

Step C: A solution of 3 (217.5 mg, 0.34 mmol) and PtO$_2$ (100 mg) in 10 mL of acetic acid was shaken under 40 PSI of H$_2$ for 6.5 h. Solvent was removed by vacuum and the residue was taken in CH$_2$Cl$_2$ and filtered through a plug of Celite. The crude was purified by reverse phase HPLC to give 5 (EXAMPLE MMM1A) and 4 (EXAMPLE MMM1B). Mass spectrum (ESI) for 5, 529 (M+1). Mass spectrum (ESI) for 4, 531 (M+1).

EXAMPLE MMM2

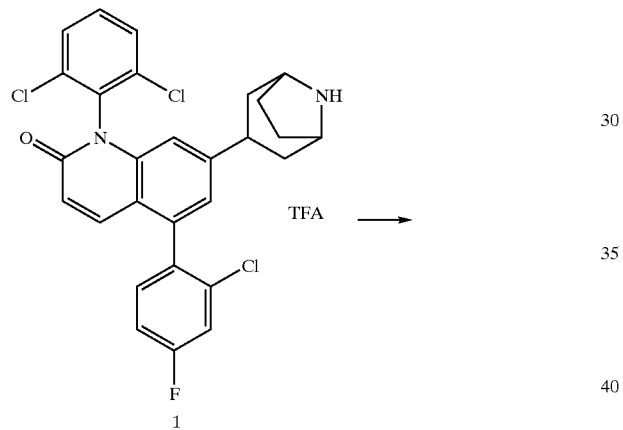

A mixture of 1 (23.3 mg, 0.036 mmol), HOAc (0.016 mL, 0.29 mmol) and HCHO (0.024 mL, 0.29 mmol) in 2 mL of THF was added CH$_3$CN (2 mL) and NaB(OAc)$_3$H (91 mg, 0.43 mmol). After stirring at rt for 4 h, it was removed of volatiles and was purified by HPLC to give 2 (EXAMPLE MMM2). Mass spectrum (ESI) for 2, 543 (M+1).

EXAMPLE MMM3

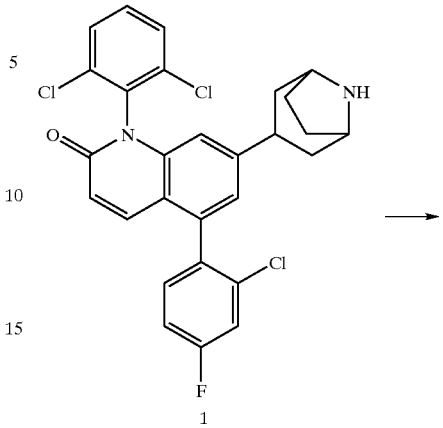

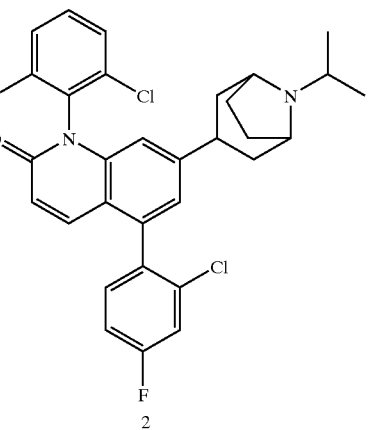

A solution of 1 (23.3 mg, 0.036 mmol), acetone (0.026 mL, 0.36 mmol) in CH$_2$Cl$_2$ was added Et$_3$N (0.020 mL, 0.144 mmol) and Na(OAc)$_3$H (15.2 mg, 0.072 mmol) and the mixture was stirred at rt for 24 h. Volatiles were removed and the residue was purified by HPLC to give 2 (EXAMPLE MMM3). Mass spectrum (ESI) for 2, 571 (M+1).

EXAMPLE MMM4

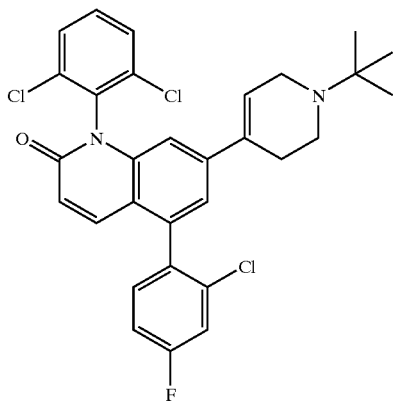

The title compound was prepared as EXAMPLE MMM1A, Step A.
Mass spectrum (ESI), 557 (M+1).

EXAMPLE MMM5A and EXAMPLE MMM5B

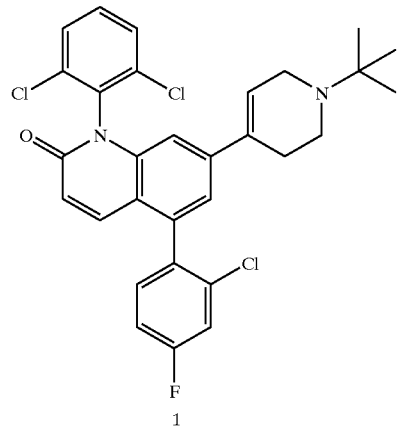

1

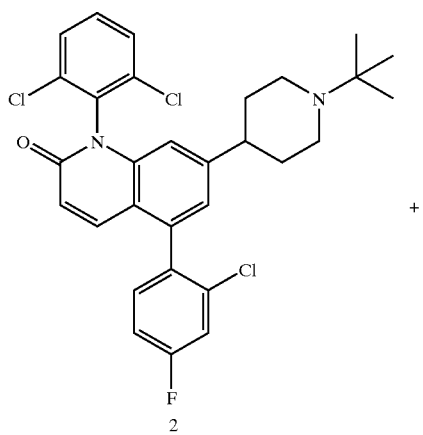

2

+

3

This reaction was carried out similarly as EXAMPLE 1A and MMM1B, Step C. Mass spectrum (ESI) for 2 (EXAMPLE MMM5A), 559 (M+1). Mass spectrum (ESI) for 3 (EXAMPLE MMM5B), 561 (M+1).

EXAMPLE MMM6

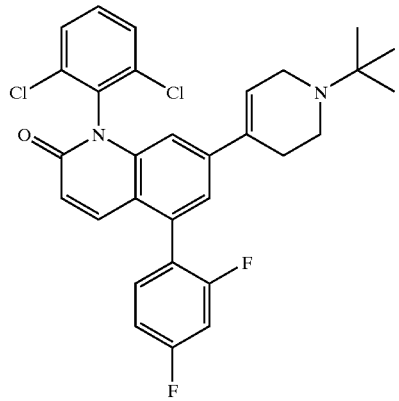

This reaction was carried out similarly as EXAMPLE MMM1A, Step A. Mass spectrum (ESI) for the title compound, 539 (M+1).

EXAMPLE MMM7

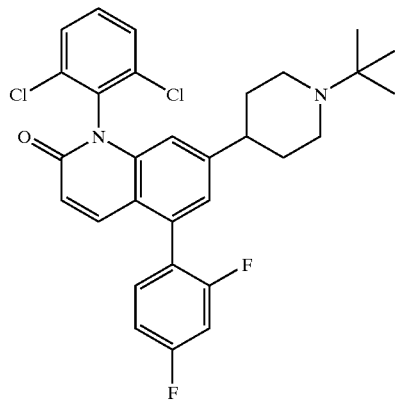

This reaction was carried out as EXAMPLE MMM1A, Step C except that the reaction was carried out with the H$_2$ pressure of 19 PSI for 15 min in a mixture of EOAc and methanol (9:1). Mass spectrum (ESI) for the title compound, 541 (M+1).

EXAMPLE MMM8

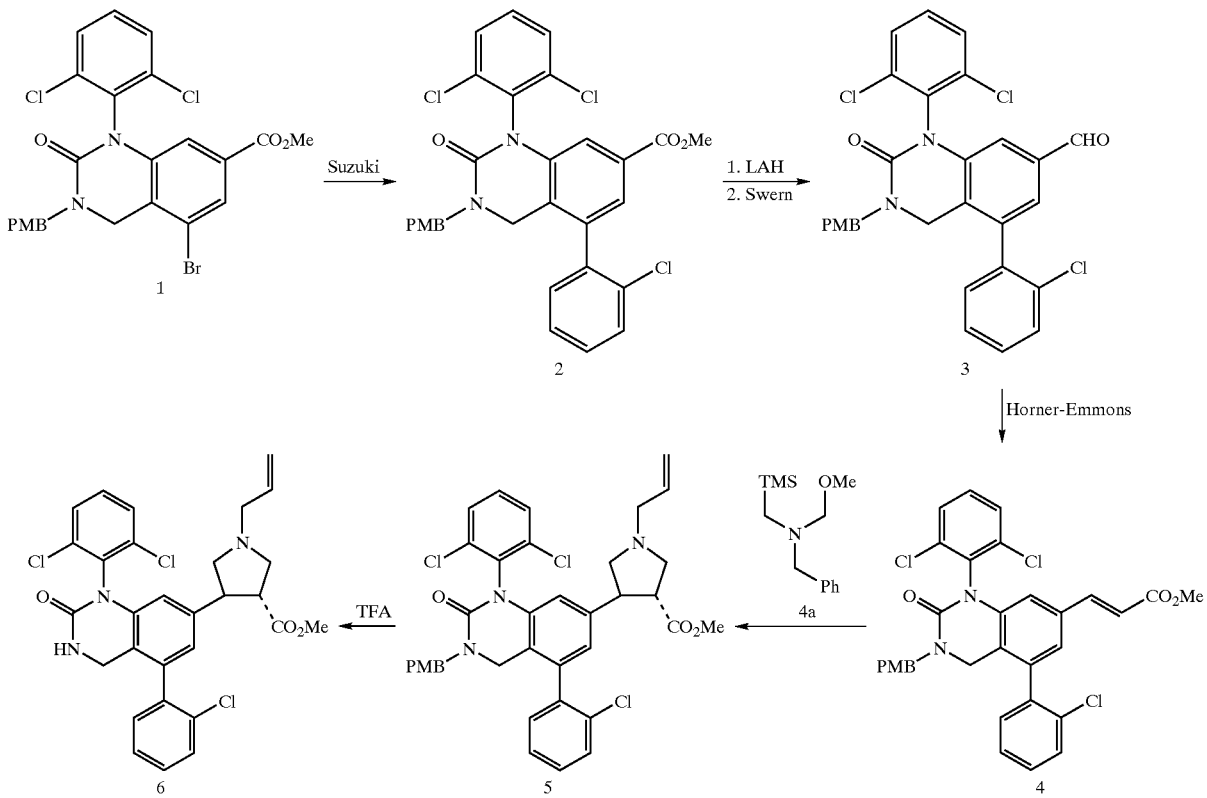

Step A: A mixture of 1 (1.516 g, 2.76 mmol), Pd(OAc)$_2$ (0.0186 g, 0.083 mmol) and PPh$_3$ in 15 mL of DME was purged with N$_2$ for 5 min. After the solution was stirred rt for 10 min, Na$_2$CO$_3$ (8.3 mmol, as 2M solution) was added and the solution was degassed again and stirred at rt for 1 h. Then 2-chlorophenylboronic (0.646 g, 4.13 mmol) was added and the solution was degassed again. The resulting solution was heated at 104° C. for 4 h and was then poured into CH$_2$Cl$_2$. The solution was washed once with water, dried with Na$_2$SO$_4$ and filtered. The crude was purified by flash chromatography with EtOAc/hex=1:4 to 3:7 to give 2. Mass spectrum (ESI) for 2, 581 (M+1).

Step B: A solution of 2 (0.89 g, 1.53 mmol) in 30 mL of THF was added LAH (1.42 mL, 1.42 mmol) at 0° C. and the solution was allowed to stirred for 1.5 h. The reaction was quenched by adding Na$_2$SO$_4$.10H$_2$O until no more gas was formed. The solution was filtered through Celite and evaporated to give alcohol.

Step C: A solution of oxalyl chloride (0.27 mL, 3.06 mmol) in CH$_2$Cl$_2$ was added DMSO (0.43 mL, 6.12 mmol) at −78° C. After 5 min, the above alcohol (0.85 g, 1.53 mmol) in 5 mL of CH$_2$Cl$_2$ was added and was followed by Et$_3$N (1.07 mL, 7,65 mmol). The mixture was allowed to warm up to rt for 30 min and was then poured into ether. The solution was washed with brine, dried with Na$_2$SO$_4$ and filtered to afford 3.

Step D: A solution of trimethyl phosphate (0.22 mL, 1.84 mmol) in 20 mL1 was added LHMDS (1.84 mL as 1M solution) at 0° C. After 40 min, the solution was cooled to −78° C. and the aldehyde 3 (0.85 g, 1.54 mmol) in 10 mL of THF was added. The solution was allowed to warmed slowly to rt overnight and was poured into ether. The solution was washed with NaHCO$_3$ (1×) and brine (1×), dried with Na$_2$SO$_4$. The crude was purified with EtOAc/hexane=3:7 to give 4. Mass spectrum (ESI) for 4, 609 (M+1).

Step E: A solution of 4 in 15 mL of CH$_2$Cl$_2$ was added trifluoroacetic acid (0.014 mL, 0.18 mmol) at 0° C. and solution was allowed to warmed to rt slowly overnight. The mixture was poured into CH$_2$Cl$_2$ and was washed with NaHCO$_3$, dried with Na$_2$SO$_4$. Mass spectrum (ESI) for 5, 692 (M+1). The crude was dissolved in 4 mL of TFA and stirred for 2.5 h. Solvent was removed and was dissolved in CH$_2$Cl$_2$. The solution was washed once with 2N NaOH, dried with Na$_2$SO$_4$ and was purified with flash chromatography with acetone/hexane=1:4 to give 6 (EXAMPLE MMM8). Mass spectrum (ESI) for 6, 572 (M+1).

EXAMPLE MMM9

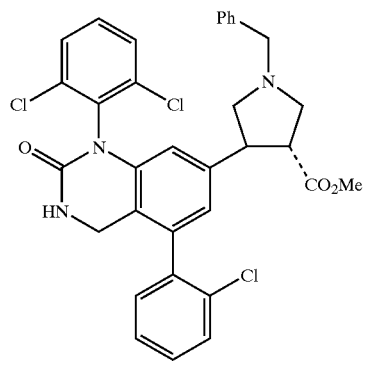

This compound was prepared similarly as EXAMPLE MMM8. Mass spectrum (ESI, 622 (M+1).

EXAMPLE MMM10

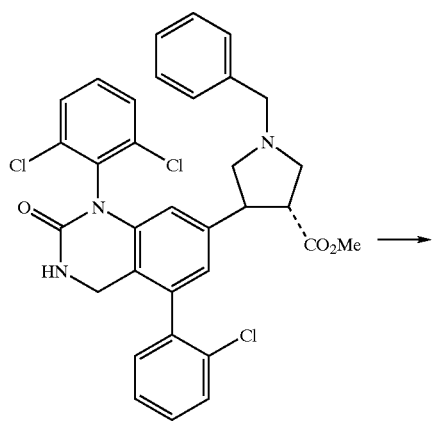

Ester 1 (26 mg, 0.042 mmol) and LiOH.H$_2$O (17.6 mg, 0.42 mmol) in 1.5 mL of methanol was added 0.5 mL of H$_2$O and the resulting solution was stirred at rt for 3 h. Upon removal of volatiles, the crude was purified by HPLC to give the title compound. Mass spectrum (ESI), 608 (M+1).

EXAMPLE MMM11

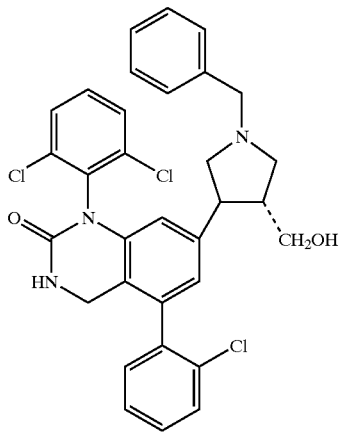

The title compound was prepared similarly as EXAMPLE MMM8, Step B. Mass spectrum (ESI), 592 (M+1).

EXAMPLE MMM12

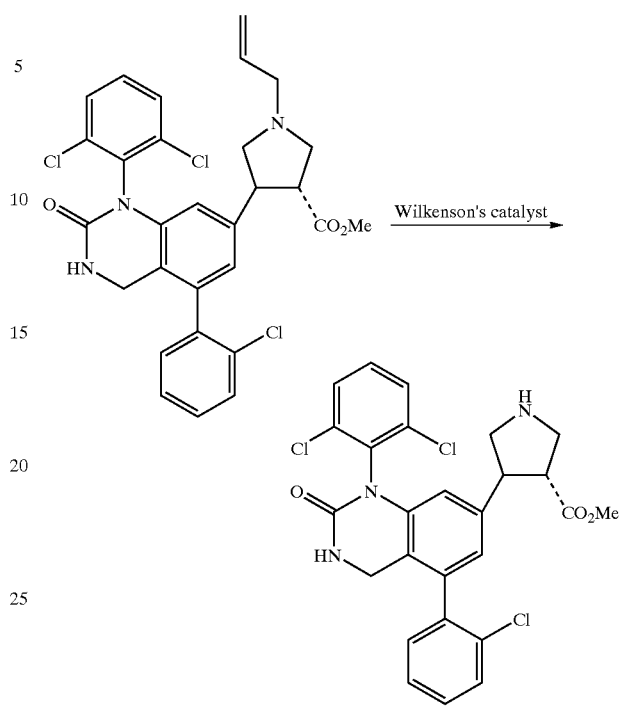

Compound 1 (1.18 g, 2.10 mmol) in 13.6 mL of CH$_3$CN was added (Ph$_3$P)$_3$RhCl (95 mg, 0.10 mmol) and H$_2$O (2.4 mL) and the solution was degassed with N$_2$ for 5 min. The mixture was then heated at reflux for 3 h with a Dean-Stark trap. After removal of solvents, the crude was purified by purified with flash chromatography with CH$_2$Cl$_2$/MeOH/ NH$_3$.H$_2$O=100:4:0.8 to give the title compound. Mass spectrum (ESI), 530 (M+1).

EXAMPLE MMM13

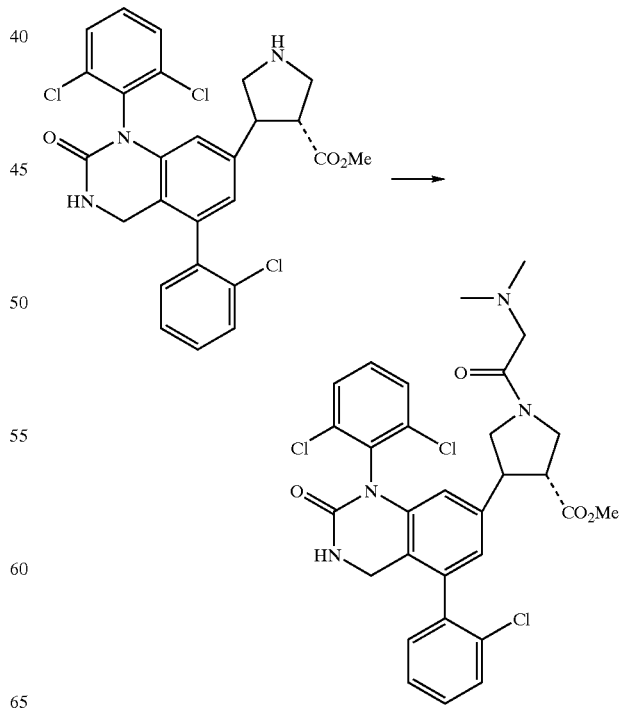

A solution of 1 (40 mg, 0.075 mmol), N,N-dimethylglycine (10.9 mg, 0.105 mmol), EDC (23.1 mg, 0.12 mmol) and DMAP (18.3 mg, 0.15 mmol) in 3 mL of CH$_2$Cl$_2$ was stirred at rt for 16 h. After removal of solvent, the crude was purified by HPLC to give the title compound, Mass spectrum (ESI), 615 (M+1).

EXAMPLE MMM14

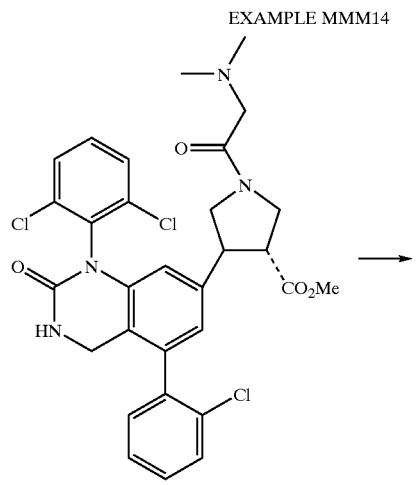

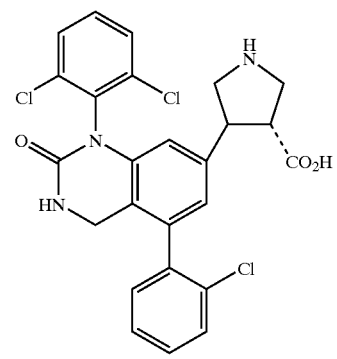

The title compound was prepared similarly as EXAMPLE MMM10, from the ester. Mass spectrum (ESI), 518 (M+1).

EXAMPLE MMM16

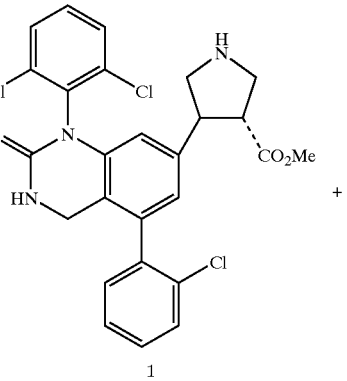

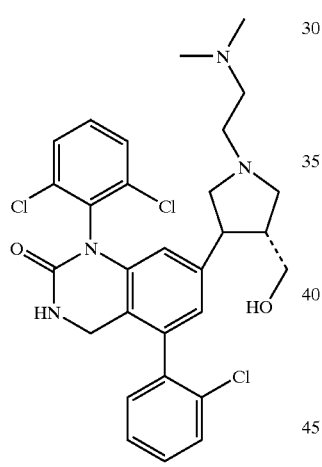

The title compound was prepared similarly as EXAMPLE MMM8, Step B. Mass spectrum (ESI), 575 (M+1).

EXAMPLE MMM15

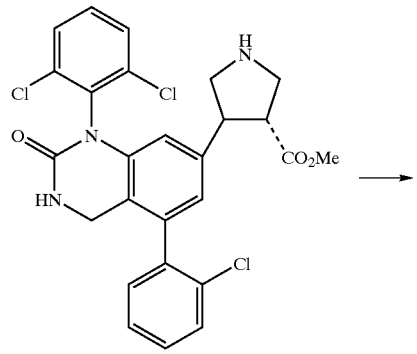

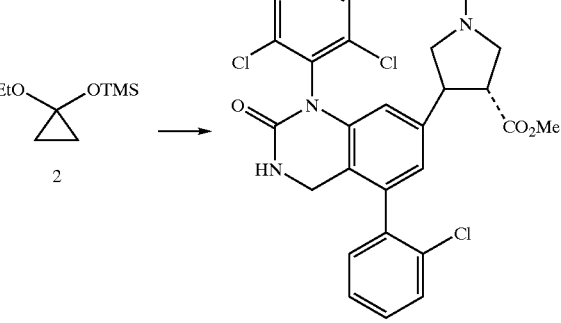

A solution of 1 (29.1 mg, 0.055 mmol), 2 (0.066 mL, 0.33 mmol) in 3 mL of MeOH was added NaBH$_3$CN (15.6 mg, 0.25 mmol) and HOAc (0.031 mL, 0.55 mmol) and the solution was heated at 100° C. for 3 h. It was poured into CH$_2$Cl$_2$ and was washed with 2N NaOH once, dried over Na$_2$SO$_4$ and purified by HPLC to give the title compound. Mass spectrum (ESI), 572 (M+1).

EXAMPLE MMM17

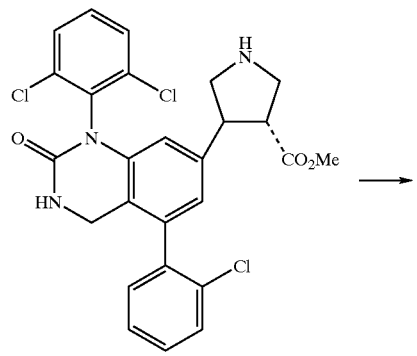

EXAMPLE MMM19

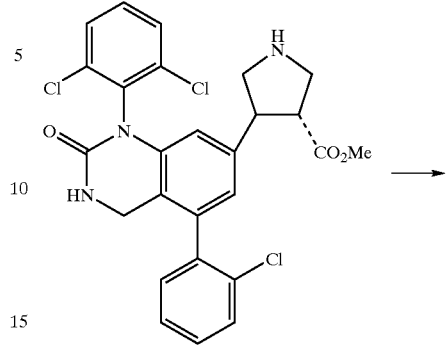

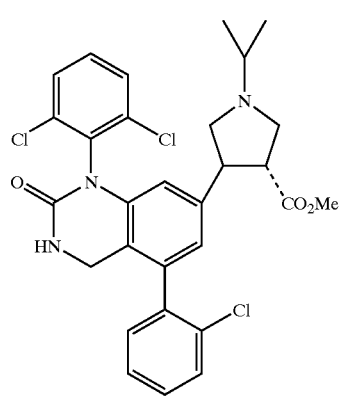

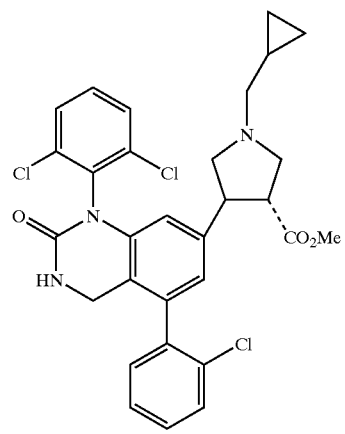

A solution of 1 (53.9 mg, 0.10 mmol), acetone (0.0298 mL, 0.41 mmol) in 3 mL of $CH_2Cl_2$ was added $NaBH_3CN$ (25.6 mg, 0.41 mmol) was stirred at rt overnight and was poured into $CH_2Cl_2$. The solution was washed with 2N NaOH, dried with $Na_2SO_4$ and purified by HPLC to give the title compound, Mass spectrum (ESI), 574 (M+1).

A solution of 1 (50.3 mg, 0.095 mmol), (bromomethyl) cyclopropane (0.055 mL, 0.57 mmol) in 2 mL of EtOH was added triethylamine (0.132 ml, 0.95 mmol) and the solution was heated at 70° C. for 14 h. After removal of volatiles, it was purified by HPLC to give the title compound. Mass spectrum (ESI), 586 (M+1).

EXAMPLE MMM18

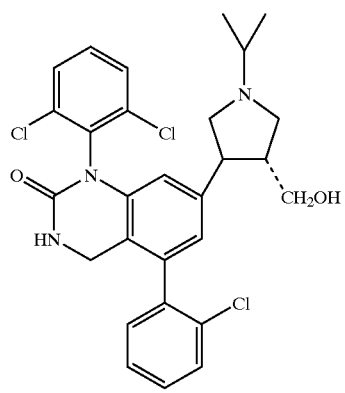

The title compound was prepared similarly as EXAMPLE MMM8, Step B. Mass spectrum (ESI), 544 (M+1).

EXAMPLE MMM20

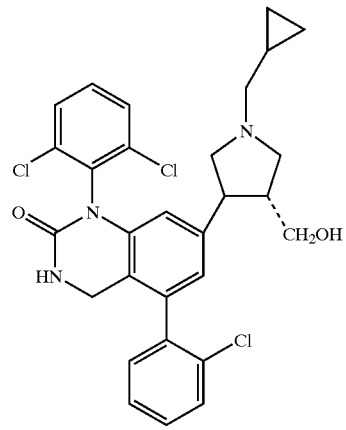

The title compound was prepared similarly as EXAMPLE MMM8.

Mass spectrum (ESI), 556 (M+1).

EXAMPLE MMM21

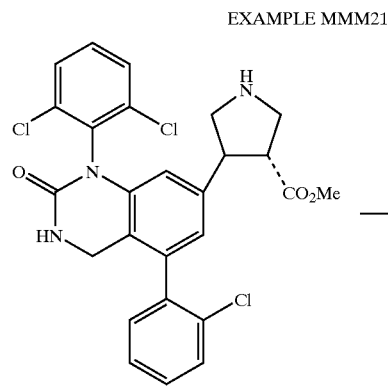

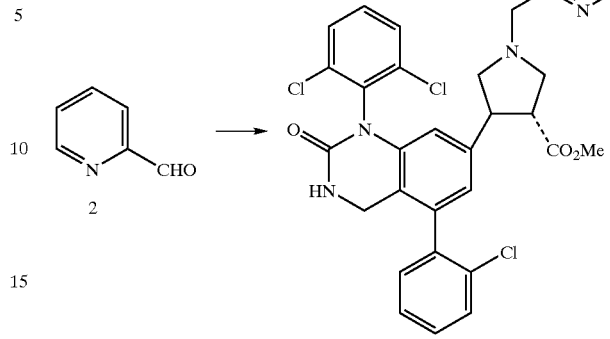

A solution of 1 (61.6 mg, 0.12 mmol), 2 (0.016 mL, 0.41 mmol) in 4 mL of $CH_2Cl_2$ was added $NaB(OAc)_3H$ (49.2 mg, 0.23 mmol) was stirred at rt overnight and the crude was purified by preparative TLC to give the title compound, Mass spectrum (ESI), 623 (M+1).

EXAMPLE MMM23

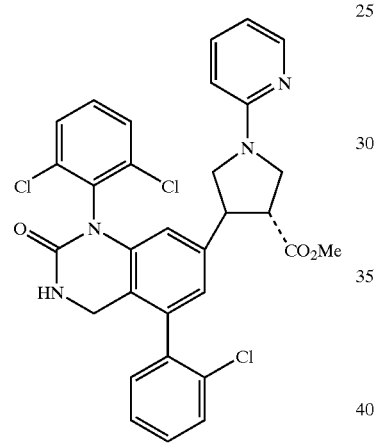

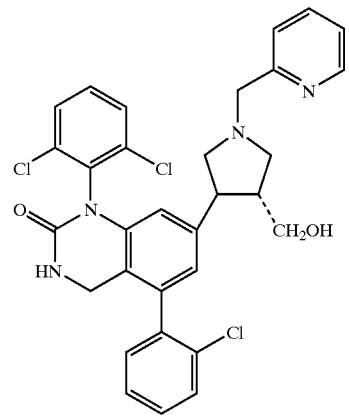

A solution of 1 (50.3 mg, 0.095 mmol), 2-fluoropyridine (0.016 mL, 0.19 mmol) and $K_2CO_3$ (39.4 mg, 0.285 mmol) in 4 ml of DMF was heated at 120° C. for 16 h. After removal of volatiles, it was purified by HPLC to give the title compound. Mass spectrum (ESI), 609 (M+1).

The title compound was prepared similarly as EXAMPLE MMM8, Step B. Mass spectrum (ESI), 593 (M+1).

EXAMPLE MMM24

EXAMPLE MMM22

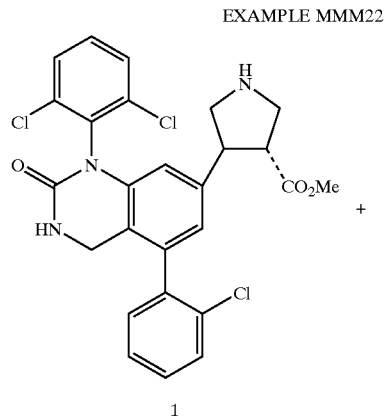

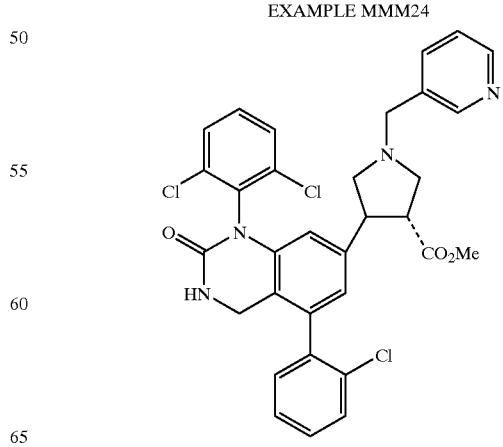

The title compound was prepared similarly as EXAMPLE MMM17.
Mass spectrum (ESI), 623 (M+1).

EXAMPLE MMM25

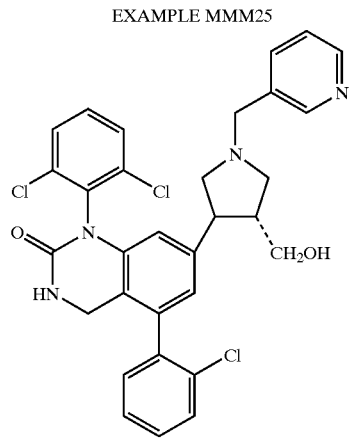

The title compound was prepared similarly as EXAMPLE MMM8, Step B. Mass spectrum (ESI), 593 (M+1).

EXAMPLE MMM26

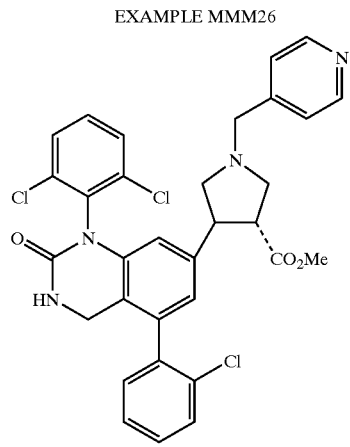

The title compound was prepared similarly as EXAMPLE MMM17.
Mass spectrum (ESI), 623 (M+1).

EXAMPLE MMM27

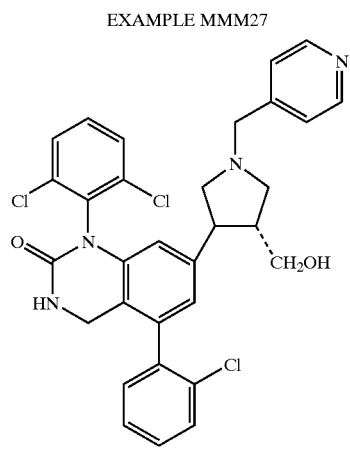

The title compound was prepared similarly as EXAMPLE MMM8, Step B. Mass spectrum (ESI), 593 (M+1).

EXAMPLE MMM28

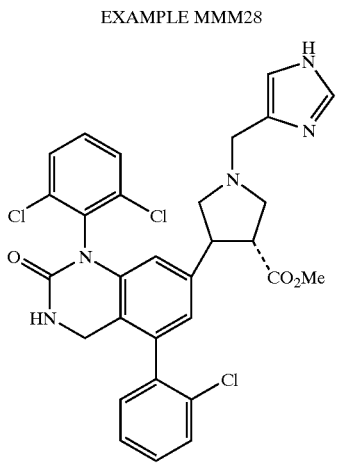

The title compound was prepared similarly as EXAMPLE MMM17.

Mass spectrum (ESI), 612 (M+1).

EXAMPLE MMM29

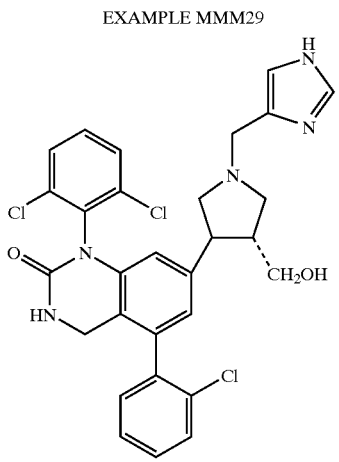

The title compound was prepared similarly as EXAMPLE MMM8, Step B. Mass spectrum (ESI), 582 (M+1).

EXAMPLE MMM30

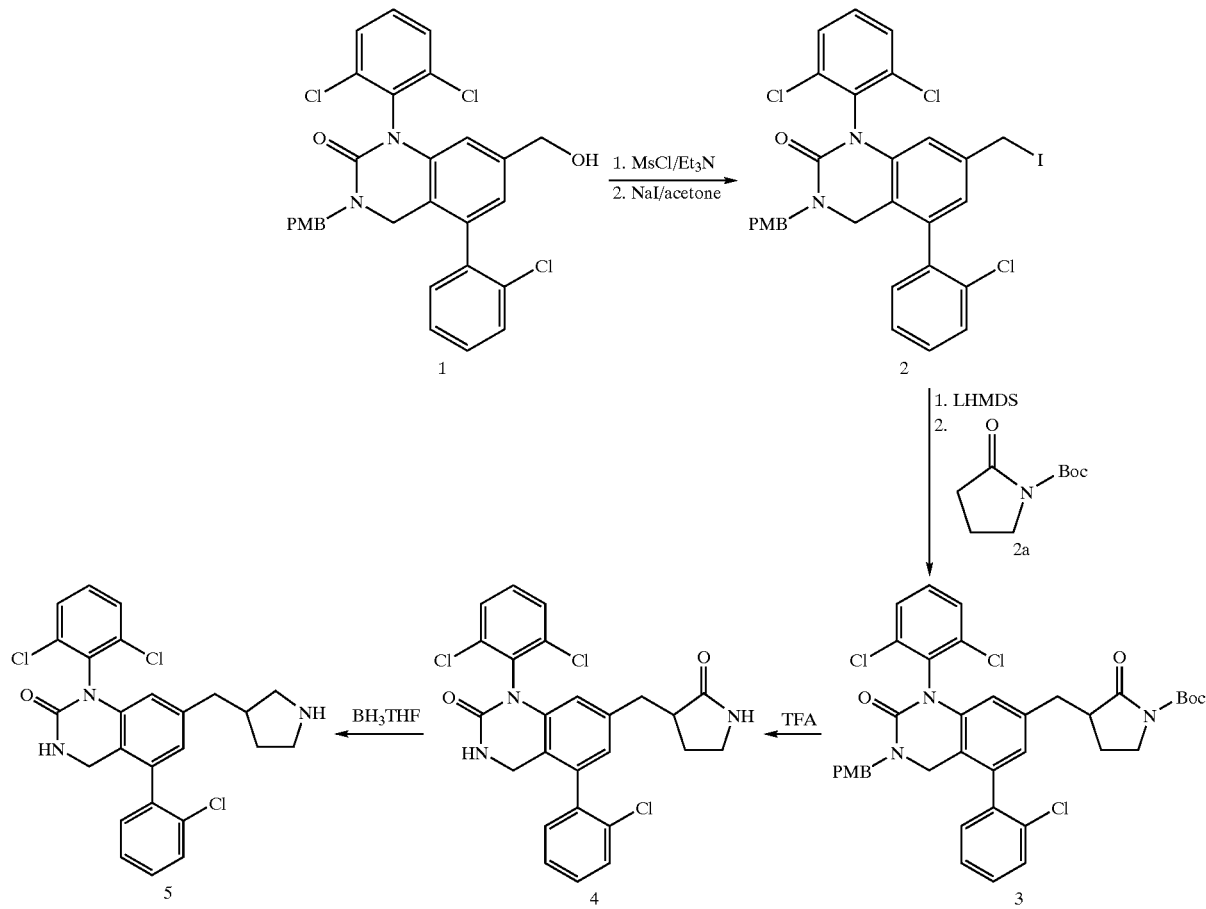

Step A: A solution of 1 (1.01 g, 1.83 mmol) in 20 mL of CH$_2$Cl$_2$ was added Et$_3$N (0.51 mL, 3.65 mmol) and MsCl (0.21 mL, 2.4 mmol) at 0° C. and was stirred for 1 h. It was poured into ether and was washed with NaHCO$_3$ and brine. The organic phase was dried with Na$_2$SO$_4$, filtered and evaporated. The residue was dissolved in 30 mL of acetone and the solution was added NaI (1.097 g, 7.32 mmol). After it was heated at reflux for 6 h, acetone was removed. The residue was dissolved in ether and was washed with NaHCO$_3$, dried with Na$_2$SO$_4$ and purified with flash chromatography EtOAc/hexane=3:7 to give 2. Mass spectrum (ESI), 665 (M+1).

Step B: A solution of 2a (0.030 mL, 0.18 mmol) in 2 mL of THF was added LHMDS (0.21 mL as 1M solution in THF) at −78° C. After 20 min, 2 (117 mg, 0.18 mmol) was added at −78° C. and the solution was allowed to warmed to rt slowly overnight. It was poured into CH$_2$Cl$_2$, washed with NaHCO$_3$ and dried with Na$_2$SO$_4$. It was purified by preparative TLC with acetone/hexane=1:2 to give 3.

Step C: A solution of 3 in TFA was heated at 90° C. for 3.5 h and THF was removed. The crude was purified by HPLC to give 4. Mass spectrum (ESI), 502 (M+1).

Step D: A solution of 4 (21.6 mg, 0.043 mmol) in 3 mL of THF was added BH$_3$.THF (0.173 mL as 1M solution) and the mixture was heated at reflux for 3 h. The crude was purified by HPLC to give 5 (EXAMPLE MMM30). Mass spectrum (ESI), 488 (M+1).

EXAMPLE MMM31

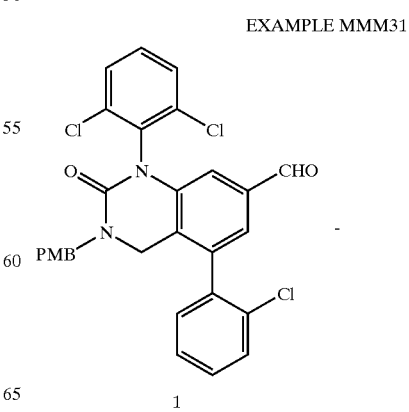

-continued

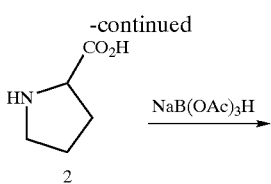
2

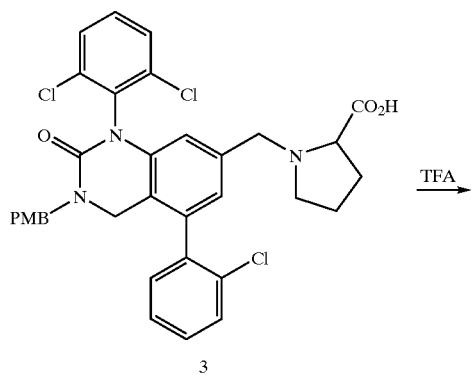
3

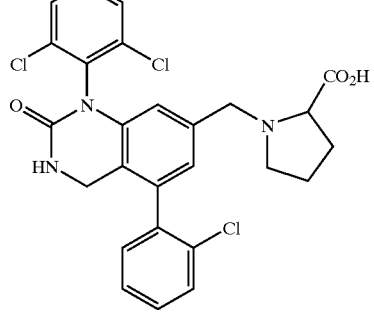

Step A: Compound 3 was prepared similarly as EXAMPLE MMM17, Mass spectrum (ESI), 652 (M+1).
Step B: EXAMPLE MMM31 was prepared from 3 similarly as EXAMPLE MMM8, Step E. Mass spectrum ESI), 532 (M+1).

EXAMPLE MMM32

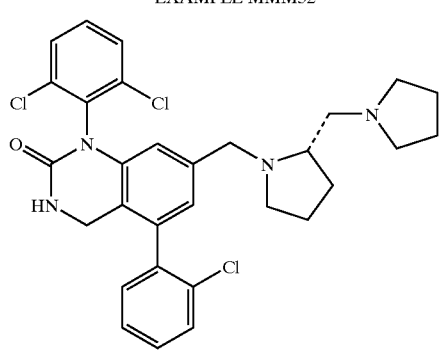

The title compound was prepared similarly as EXAMPLE MMM22.
Mass spectrum (ESI), 571 (M+1).

EXAMPLE MMM33

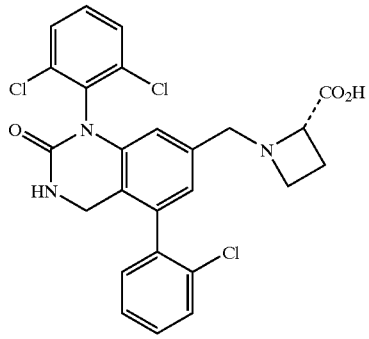

The title compound was prepared similarly as EXAMPLE MMM22.
Mass spectrum (ESI), 518 (M+1).

EXAMPLE MMM34

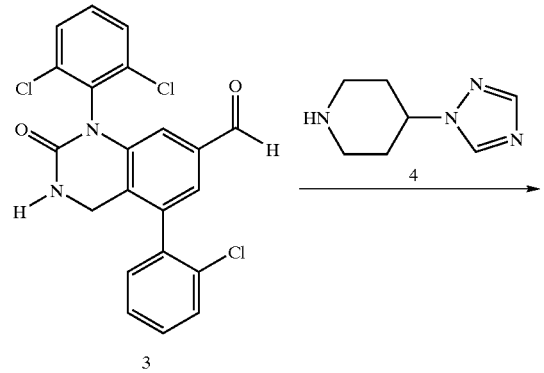

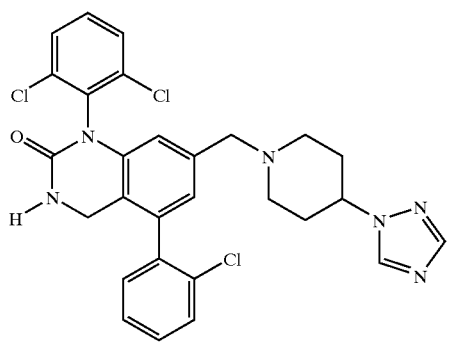
5

Mass spectrum (ESI) for 5, 568 (M+1).

EXAMPLE MMM35

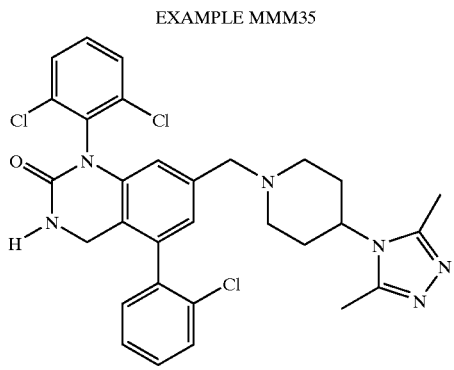

The title compound was prepared similarly as EXAMPLE MMM34.

Mass spectrum (ESI), 432 (M+1).

EXAMPLE MMM36

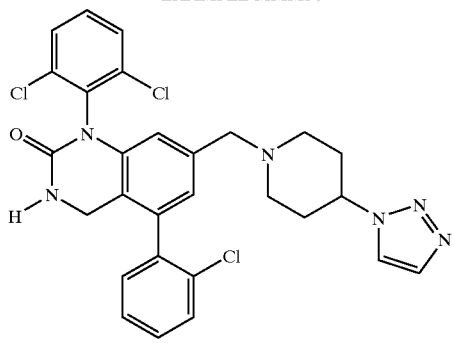

The title compound was prepared similarly as EXAMPLE MMM34.

Mass spectrum (ESI), 568 (M+1).

EXAMPLE MMM37

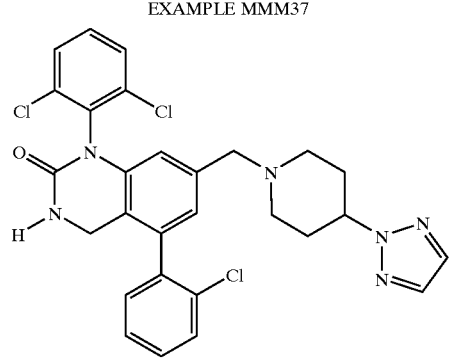

The title compound was prepared similarly as EXAMPLE MMM34.

Mass spectrum (ESI), 568 (M+1).

EXAMPLE MMM38

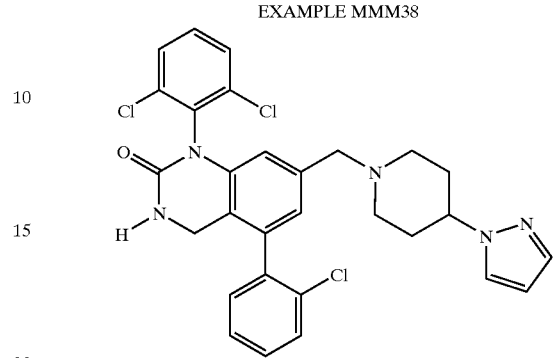

The title compound was prepared similarly as EXAMPLE MM34.

Mass spectrum (ESI), 567 (M+1).

EXAMPLE MMM39

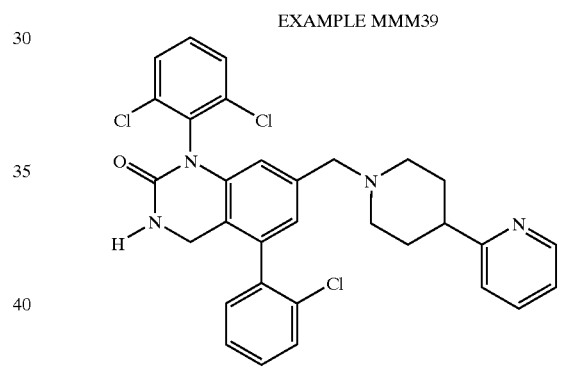

The title compound was prepared similarly as EXAMPLE MMM34.

Mass spectrum (ESI), 578 (M+1).

EXAMPLE MMM40

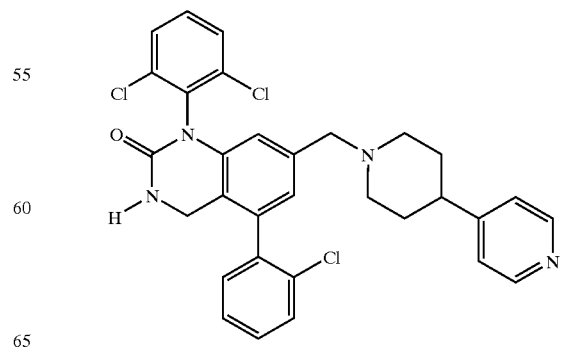

The title compound was prepared similarly as EXAMPLE MMM34.

Mass spectrum (ESI), 578 (M+1).

EXAMPLE MMM41

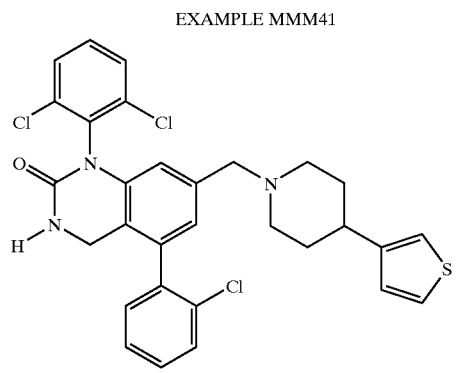

The title compound was prepared similarly as EXAMPLE MMM34.

Mass spectrum (ESI), 583 (M+1).

EXAMPLE MMM42

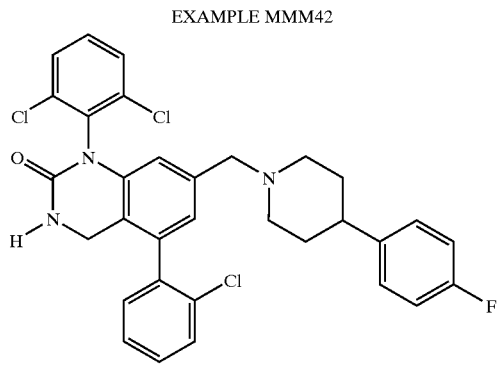

The title compound was prepared similarly as EXAMPLE MMM34.

Mass spectrum (ESI) for 3, 595 (M+1).

EXAMPLE MMM43

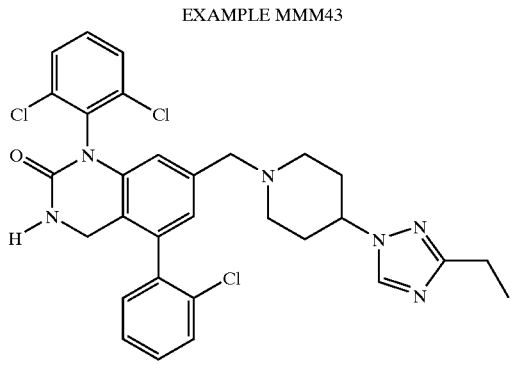

The title compound was prepared similarly as EXAMPLE MMM34.
Mass spectrum (ESI), 596 (M+1).

EXAMPLE MMM44

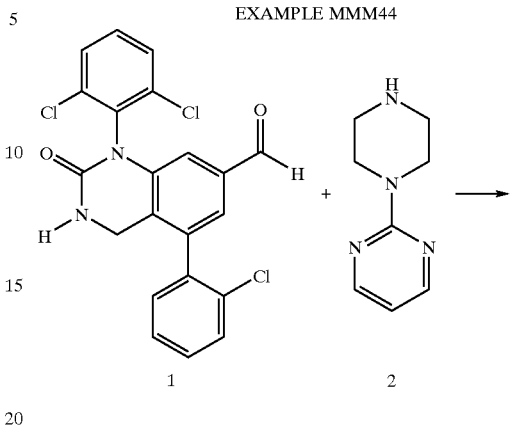

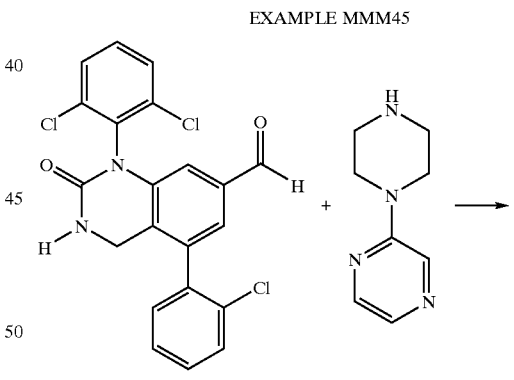

The title compound was prepared similarly as EXAMPLE MMM34.
Mass spectrum (ESI), 580'(M+1).

EXAMPLE MMM45

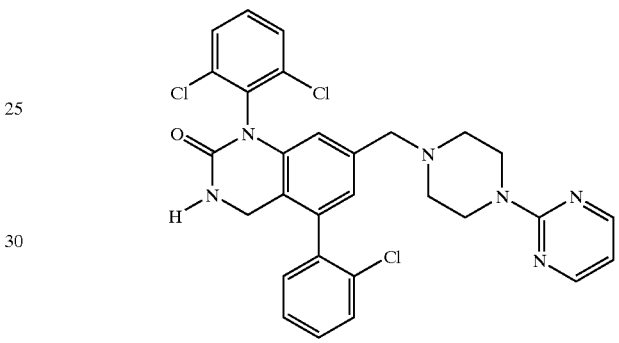

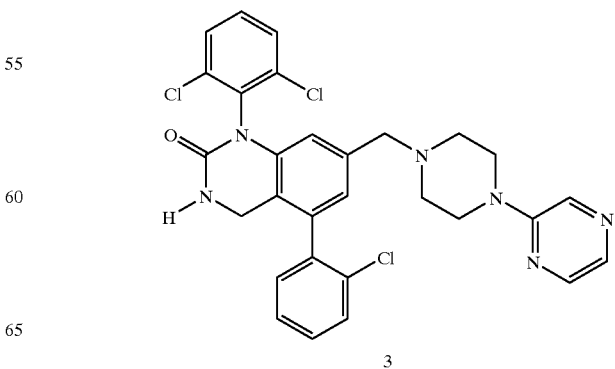

The title compound was prepared similarly as EXAMPLE MMM34.
Mass spectrum (ESI) for 3, 580 (M+1).
EXAMPLE MMM46
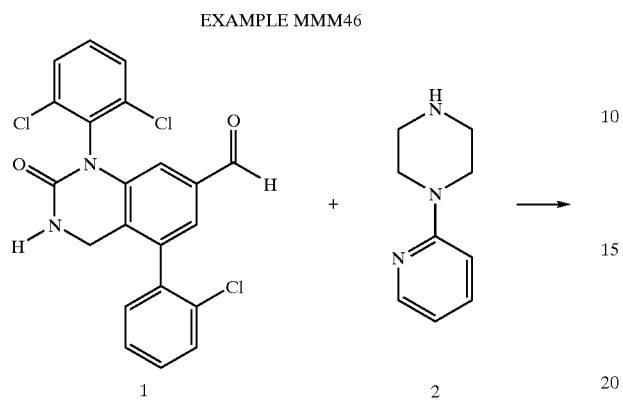
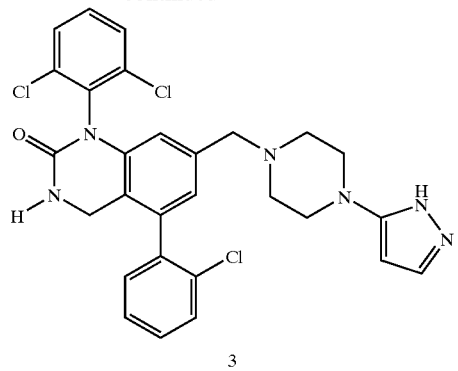
The title compound was prepared similarly as EXAMPLE MMM34.
Mass spectrum (ESI) for 3, 567 (M+1).
EXAMPLE MMM48
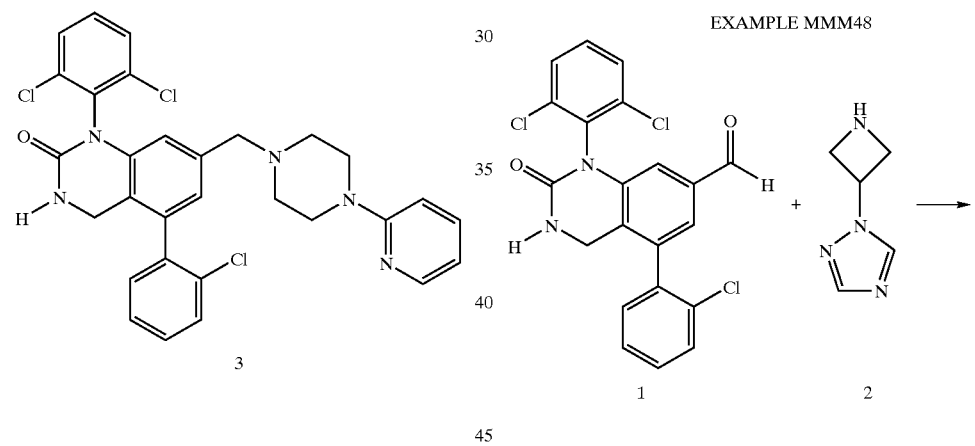
The title compound was prepared similarly as EXAMPLE MMM34.
Mass spectrum (ESI) for 3, 579 (M+1).
EXAMPLE MMM47
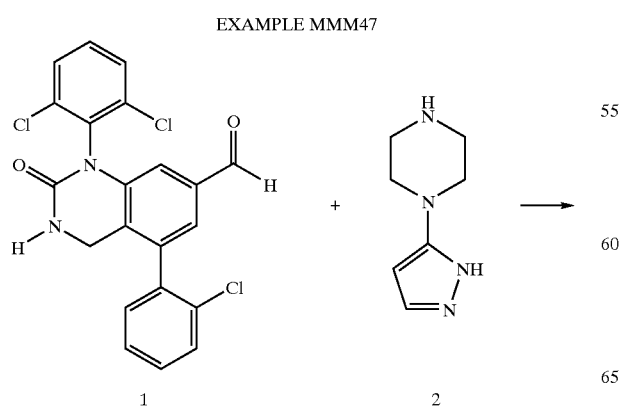
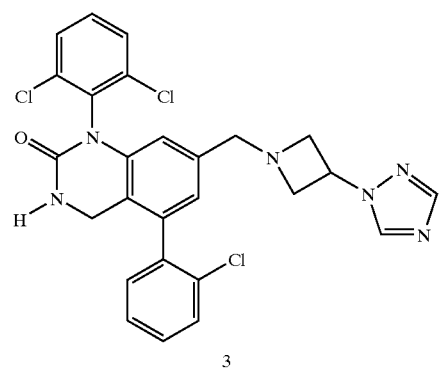

EXAMPLE MMM49

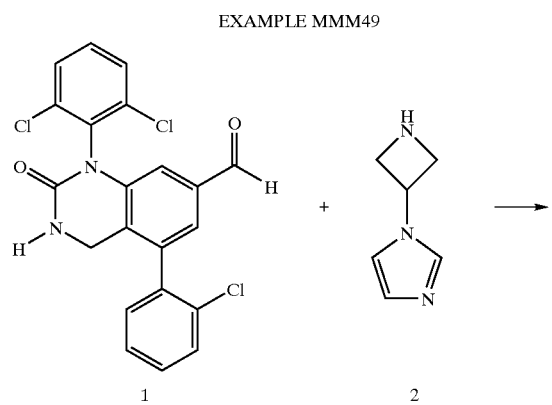

The title compound was prepared similarly as EXAMPLE MMM34.
Mass spectrum (ESI) for 3, 568 (M+1).

EXAMPLE MMM50

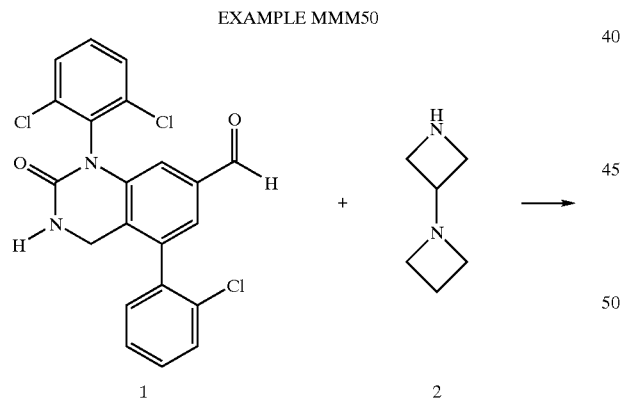

The title compound was prepared similarly as EXAMPLE MMM34.
Mass spectrum (ESI) for 3, 541 (M+1).

EXAMPLE MMM51

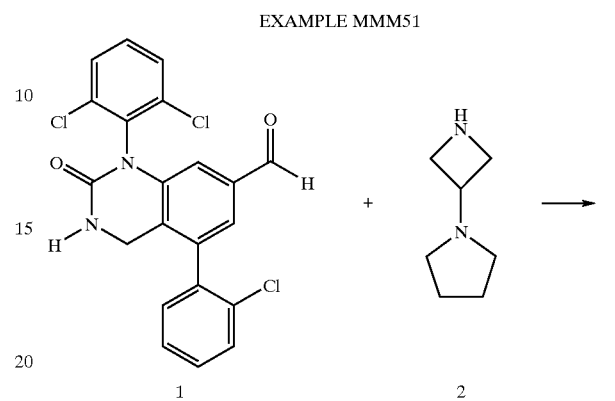

The title compound was prepared similarly as EXAMPLE MMM34.
Mass spectrum (ESI) for 3, 528 (M+1).

EXAMPLE MMM52

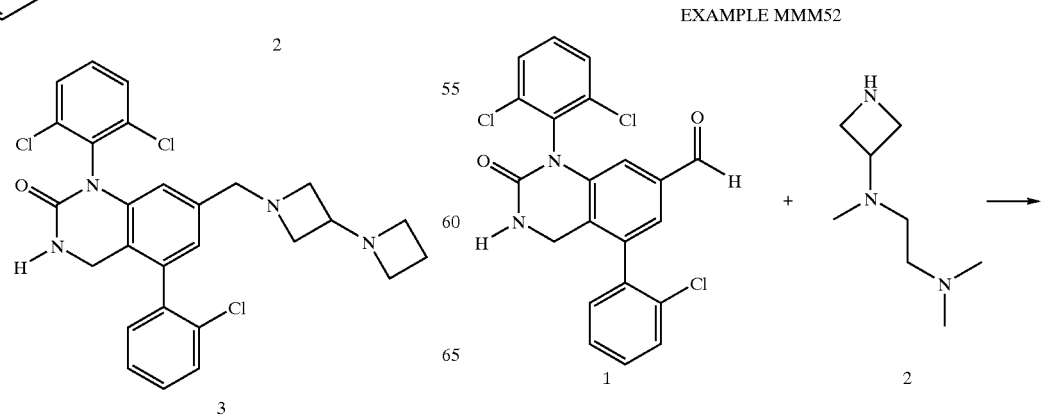

The title compound was prepared similarly as EXAMPLE MMM34.
Mass spectrum (ESI) for 3, 532 (M+1).

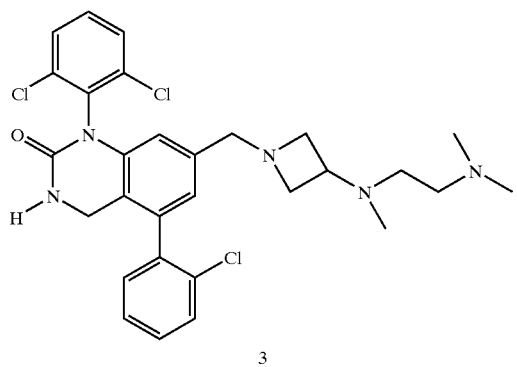
3
The title compound was prepared similarly as EXAMPLE MMM34.
Mass spectrum (ESI) for 3, 573 (M+1).
EXAMPLE MMM53
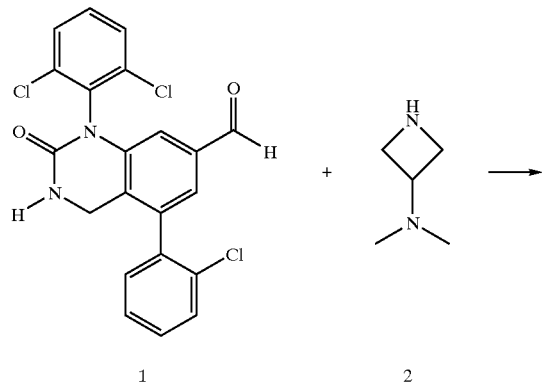
Mass spectrum (ESI) for 3,515 (M + 1).
EXAMPLE MMM54
[reaction scheme: 1 + 2 →]
[product 3]
Mass spectrum (ESI) for 3,544 (M + 1).
EXAMPLE MMM55
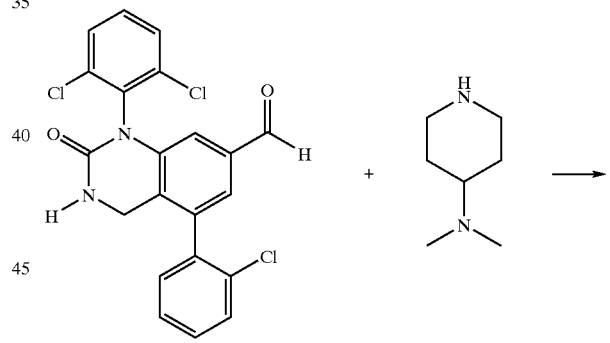
Mass spectrum (ESI) for 3,544 (M + 1).

EXAMPLE MMM56
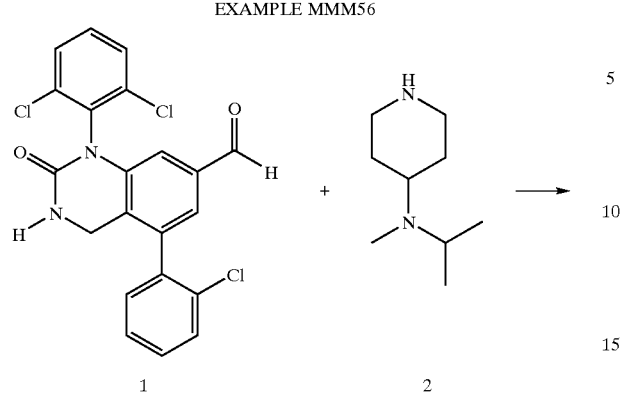
Mass spectrum (ESI) for 3,572 (M + 1).
EXAMPLE MMM57
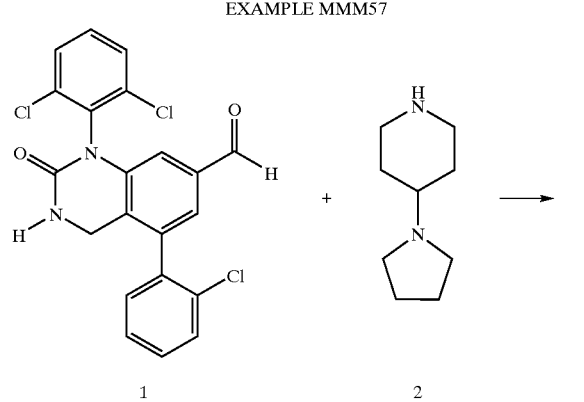
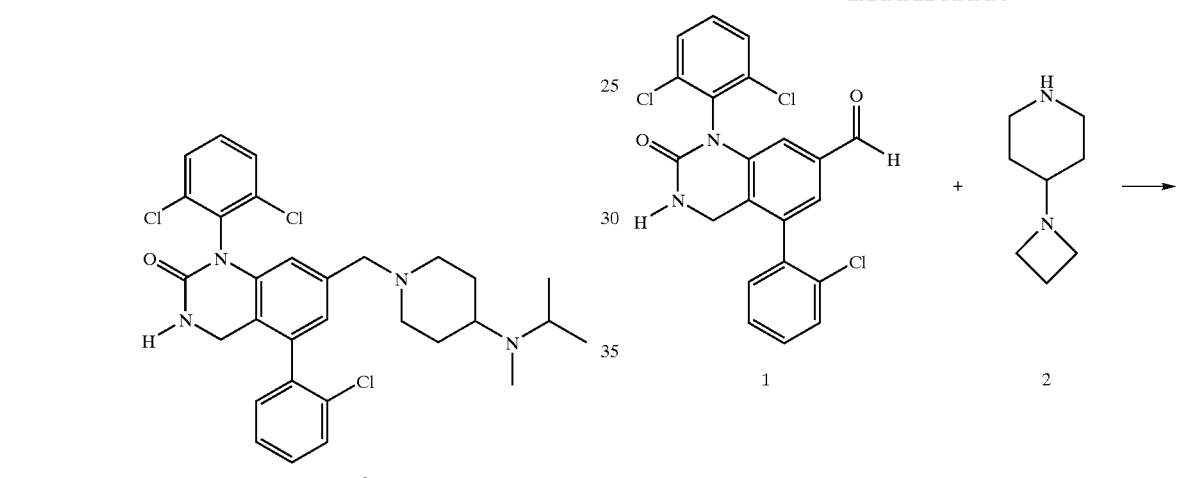
Mass spectrum (ESI) for 3,570 (M + 1).
EXAMPLE MMM58
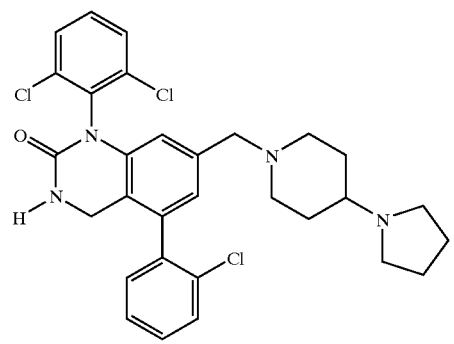
Mass spectrum (ESI) for 3,556 (M + 1).

EXAMPLE MMM59
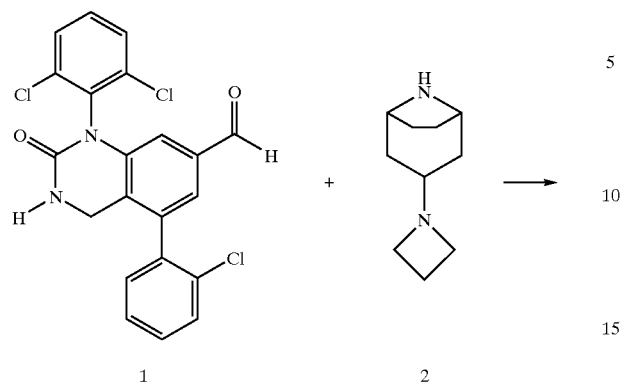
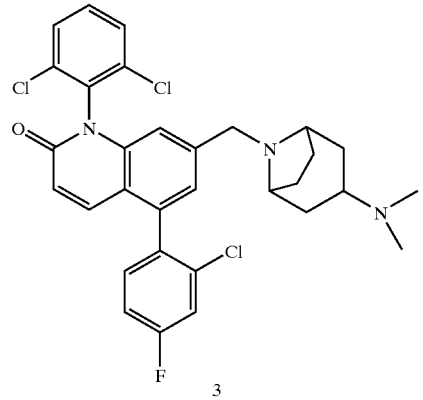
Mass spectrum (ESI) for 3,586 (M + 1).
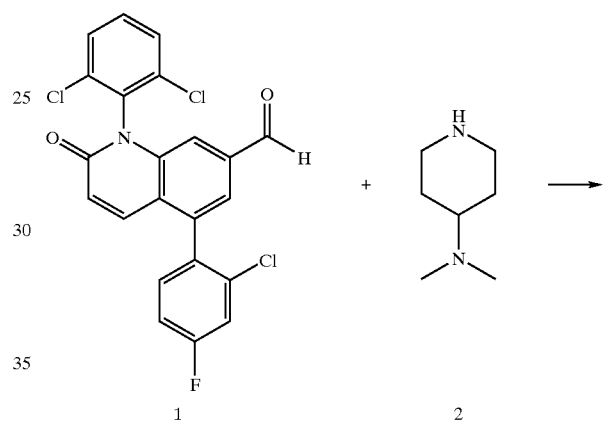
Mass spectrum (ESI) for 3,582 (M + 1).
EXAMPLE MMM61
EXAMPLE MMM60
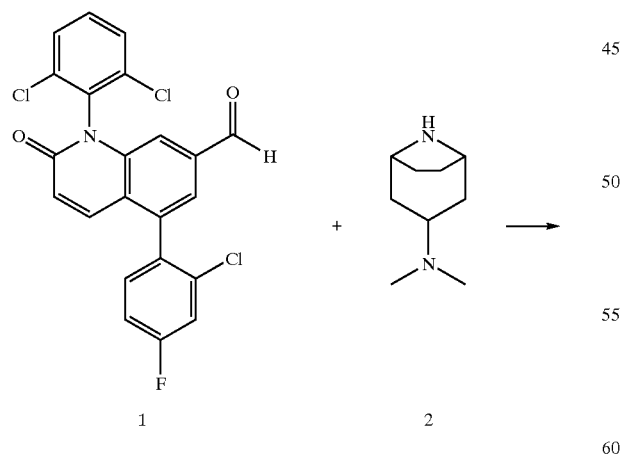
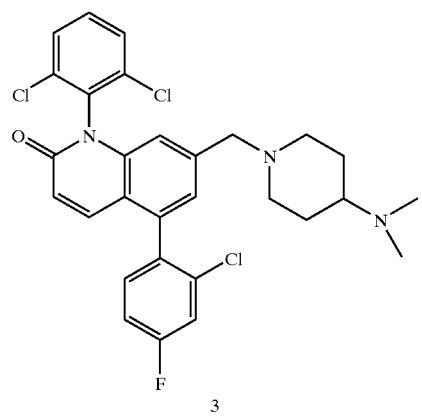
Mass spectrum (ESI) for 3,560 (M + 1).

EXAMPLE MMM62
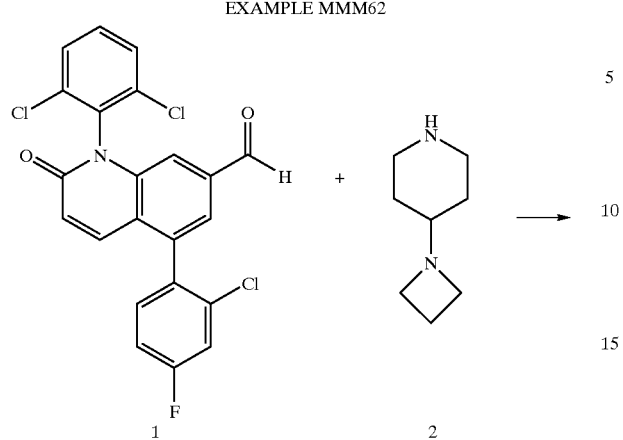
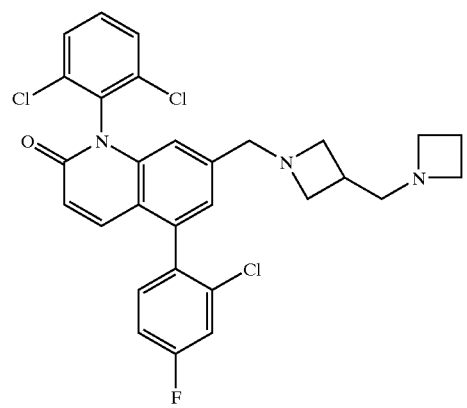
Mass spectrum (ESI) for 3, 557 (M + 1).
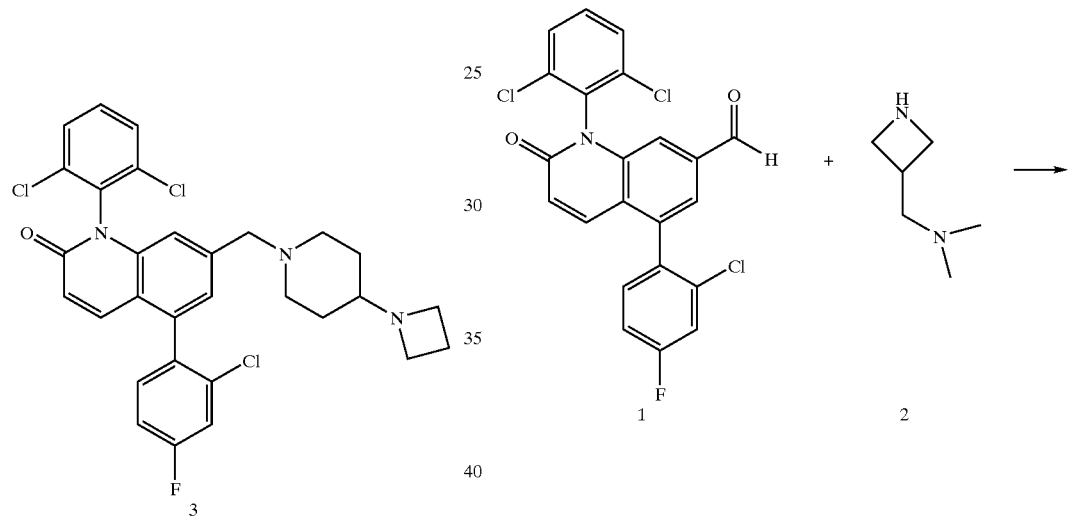
Mass spectrum (ESI) for 3, 571 (M + 1).
EXAMPLE MMM63
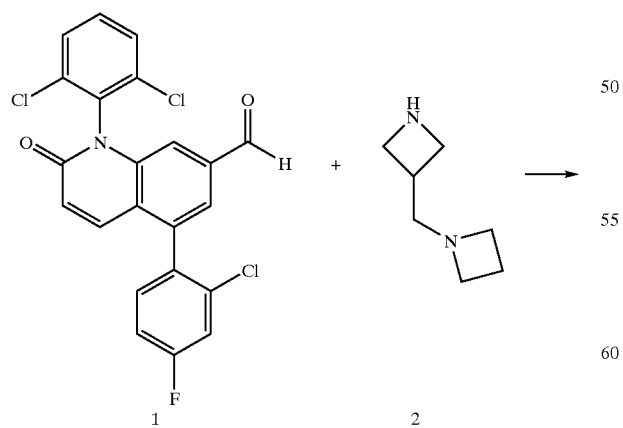
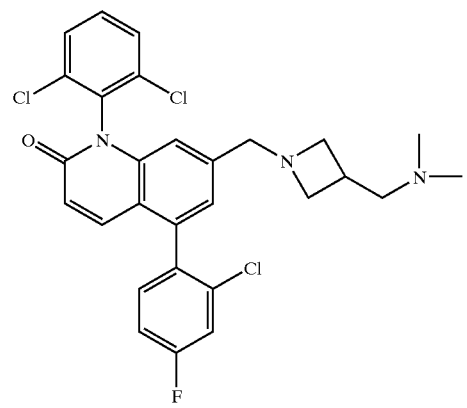
Mass spectrum (ESI) for 3, 545 (M + 1).

EXAMPLE MMM65
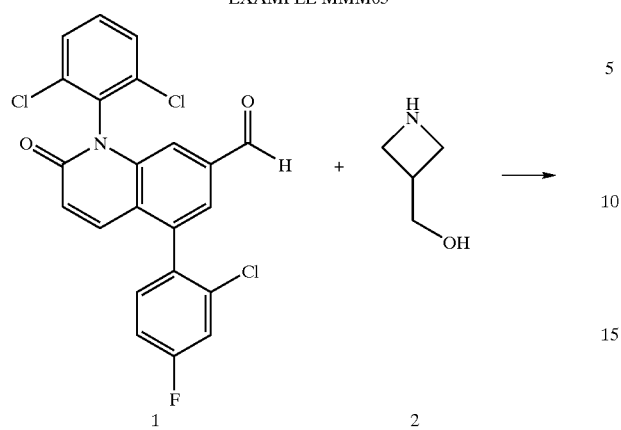
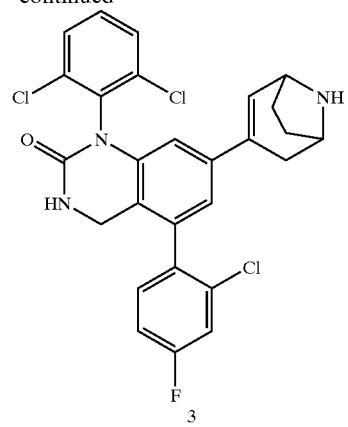
Mass spectrum (ESI) for 3,529 (M + 1).
EXAMPLE MMM67
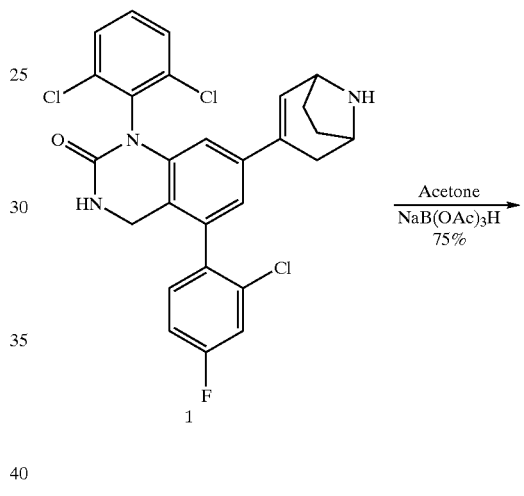
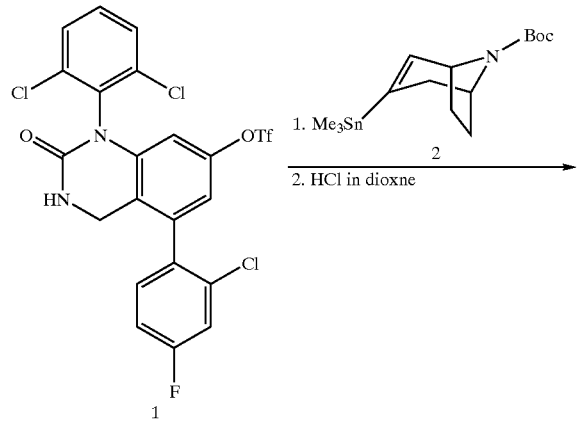
Mass spectrum (ESI) for 3,518 (M + 1).
EXAMPLE MMM66
Mass spectrum (ESI) for 2,571 (M + 1).

EXAMPLE MMM68
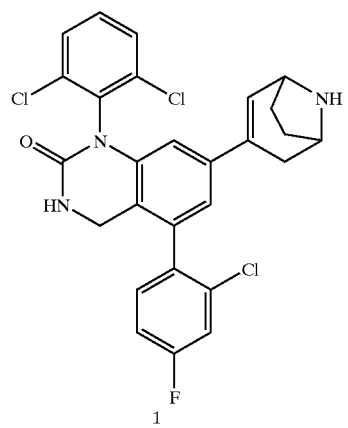
Pt₂O, H₂ →
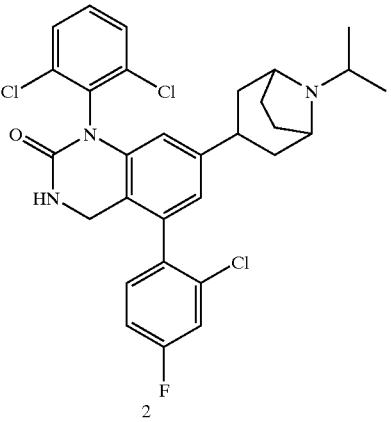
Mass spectrum (ESI) for 2, 573 (M + 1).
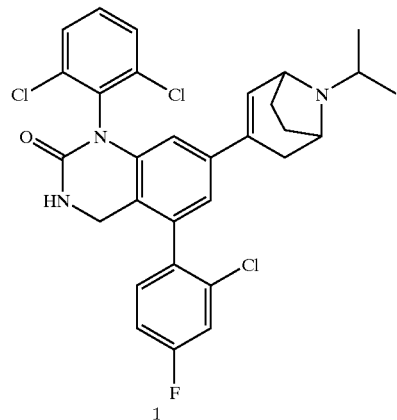
Mass spectrum (ESI) for 2, 531 (M + 1).
EXAMPLE MMM69
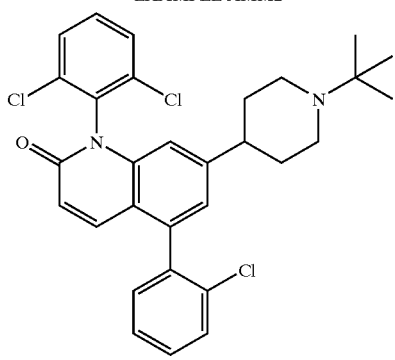
Pt₂O, H₂ →
EXAMPLE AMM1
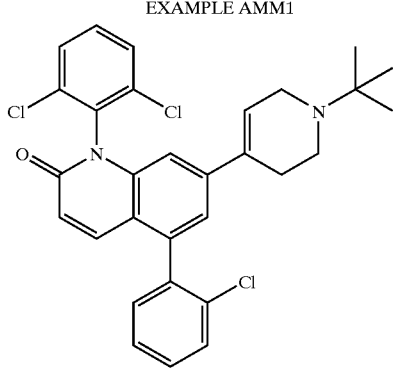
The title compound was prepared as for EXAMPLE PPP1. Mass spectrum (ESI), 539 (M+1).
EXAMPLE AMM2
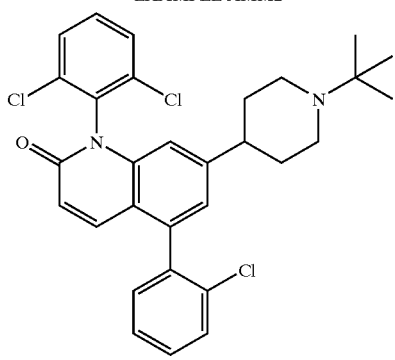
The title compound was prepared as for EXAMPLE PPP1. Mass spectrum (ESI), 541(M+1).

EXAMPLE BMM1

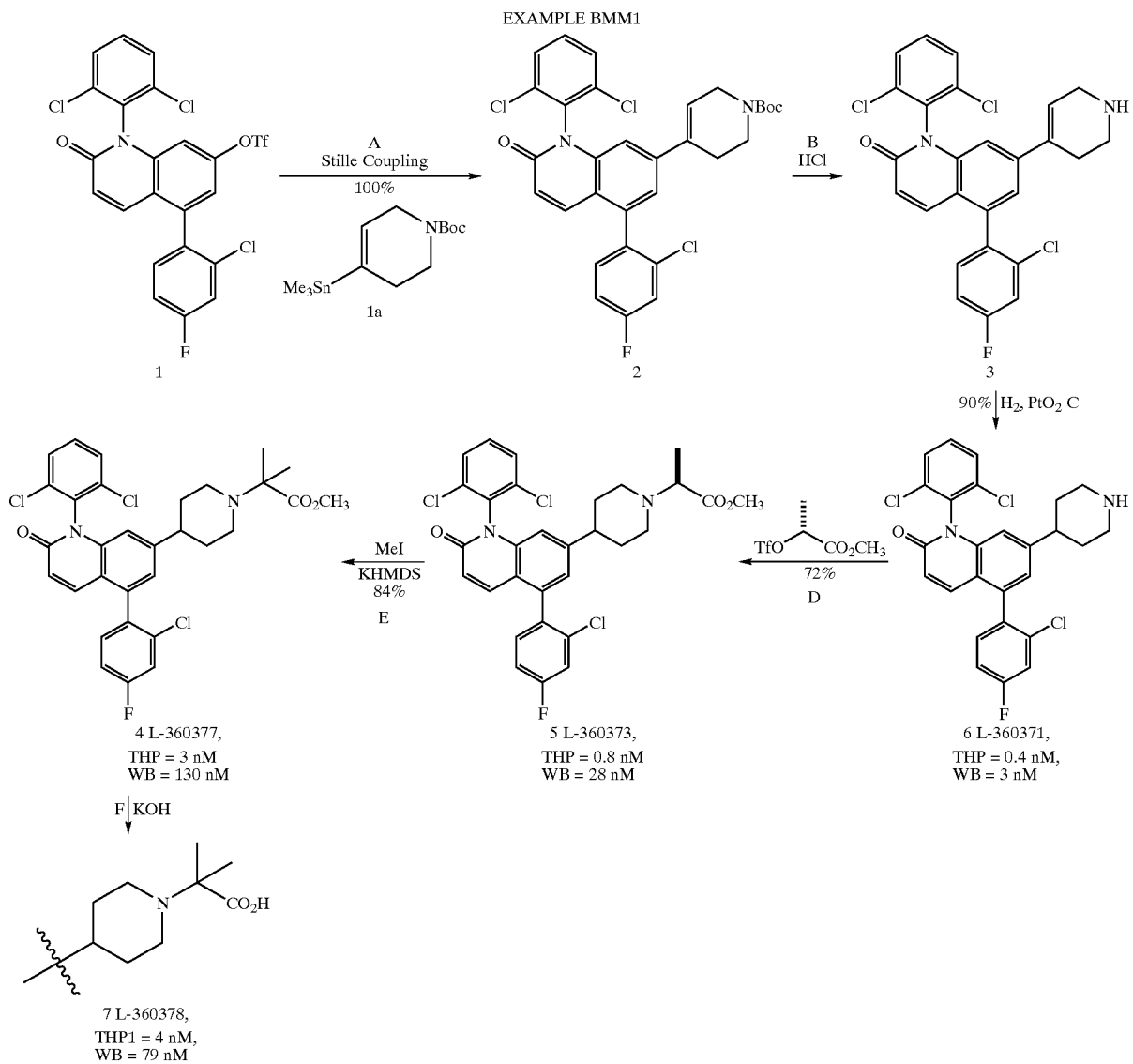

Step A: Compound 1 (0.95 g, 1.68 mmol), 1a (0.76 g, 2.19 mmol), Pd(PPh₃)₄ (0.19 g, 0.17 mmol) and LiCl (0.28 g, 6.72 mmol) in 30 mL of dioxane were purged with nitrogen for 3 times and the solution was heated at 108° C. for 20 h. Solvent was removed by vacuum and the residue was dissolved in EtOAc. The organic layer was washed with aqueous NaHCO₃, dried with Na₂SO₄ and was purified by flash chromatography EtOAc/hexane=1:3 to give compound 2. Step B: Compound 2 (1.00 g, 1.68 mmol) in 10 mL of CH₂Cl₂ was added solution of HCl in dioxane (6.7 mL as 4M solution) and the resulting solution was stirred at rt for 24 h. Volatiles were removed by vacuum to give compound 6 as HCl salt. Mass spectrum (ESI), 499 (M+1).

Step C: A solution of the salt 3 (1.68 mmol) from the last step in 20 mL of EtOAc was added 2.5 mL of MeOH and PtO₂ (360 mg, 1.59 mmol) was shaken on Parr hydrogenator at 3 psi for 20 min. The solution was filtered through celite. Upon removal of volatiles, the crude was purified by flash chromatography with CH₂Cl₂/MeOH/NH₄OH=100:10:1 to give compound 6. Mass spectrum (ESI), 501 (M+1).

Step D: A solution of R-(+)-methyl lactate (0.043 mL, 0.4 mmol) in 4 mL of CH₂Cl₂ was added 2,6-lutidine (0.064 mL, 0.55 mmol) and Tf₂O (0.081 mL, 0.48 mmol) at 0° C. After 0.5 h, to the solution was added diisopropylethylamine (0.11 mL, 0.64 mmol) and compound 6 (0.228 g, 0.45 mmol) in 4 mL of CH₂Cl₂. The solution was then allowed to stirred at rt for 14 h. Volatiles were removed by vacuum and the residue was purified by flash chromatography with Hexanes/EtOAc/2N NH₃ in MeOH=100:20:4 to give compound 5. Mass spectrum (ESI), 587 (M+1).

Step E: A solution of 5 (0.104 g, 0.177 mmol) in 2.5 mL of THF was added KHMDS (0.71 mL, 0.35 mmol as 0.5M in toluene) at −78° C. After 15 min, MeI (0.044 ml, 0.71 mmol) was added and the solution was stirred for 1 h. The reaction was quenched with NaHCO₃ and warmed to rt. Mixture was poured into CH₂Cl₂ and was washed once with brine. The organic phase was dried with Na₂SO₄ and filtered through Celite. Upon removal of volatiles, the residue was purified by preparative TLC plate with Hexanes/EtOAc/2N NH₃ in MeOH=100:30:6 to give compound 4. Mass spectrum (ESI), 601 (M+1).

Step F: A solution of 4 (22.4 mg, 0.037 mmol) in 1.5 mL of MeOH was added KOH (20.9 mg, 0.37 mmol) and 0.5 mL of water. The solution was heated at 80° C. for 24 h. Upon removal of volatiles, the residue was purified by reversed phase HPLC to give compound 7 (EXAMPLE BMM1).

Mass spectrum (ESI), 587 (M+1).

COMPOUND BMM-1

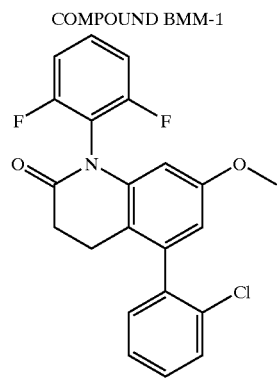

The title compound was prepared similarly as EXAMPLE PPP1.

Mass spectrum (ESI), 400 (M+1).

COMPOUND BMM-2

The title compound was was prepared similarly as EXAMPLE PPP1.

Mass spectrum (ESI), 402 (M+1).

COMPOUND BMM-3

The title compound was was prepared similarly as EXAMPLE PPP1.

Mass spectrum (ESI), 398 (M+1).

COMPOUND BMM-4

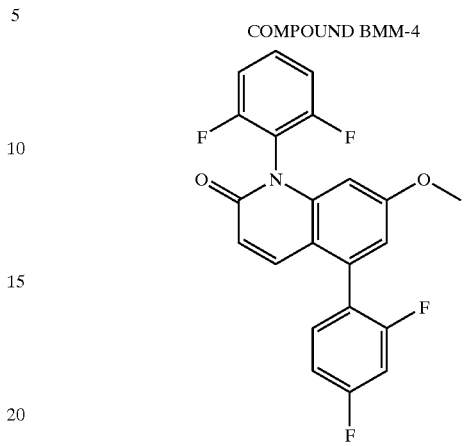

The title compound was prepared similarly as EXAMPLE PPP1.

Mass spectrum (ESI), 400 (M+1).

COMPOUND BMM-5

The title compound was prepared similarly as EXAMPLE PPP1.

Mass spectrum (ESI), 384 (M+1).

COMPOUND BMM-6

The title compound was prepared similarly as EXAMPLE PPP1.

Mass spectrum (ESI), 386 (M+1).

COMPOUND CMM-1

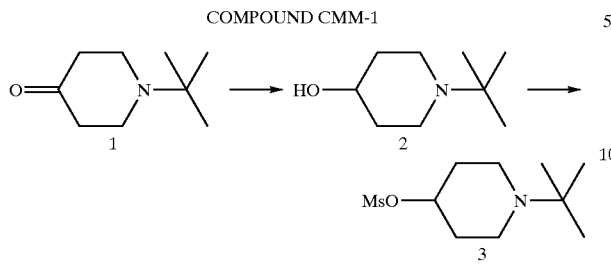

To a solution of compound 1 (2.06 g, 13.3 mmol) in 15 mL THF was added LAH (1 m in THF) (15 mL, 15 mmol), and the solution was stirred for 0.5 h at 0° C. To it was added slowly 1 mL of 1M NaOH and filtered through a plug Celite. After removal of solvent, it was afford compound 2(white solid). Mass spectrum (ESI) for 2, 158 (M+1). The reaction mixture of compound 2 (1.75 g, 11.13 mmoL), triethylamine (2.5 mL, 17.81 mmol) and methanesulfonyl chloride (1.53 g, 13.36 mmoL) were stirred at 0° C. for 1 h. Then it was poured into 100 mL of ether and 20 mL of aq NaHCO$_3$ and extracted with ether (30 mL×3). The combined organic layer was dried over Na$_2$CO$_3$ and concentrated to afford white solid. Mass spectrum (ESI) for 3, 236 (M+1).

EXAMPLE CMM1

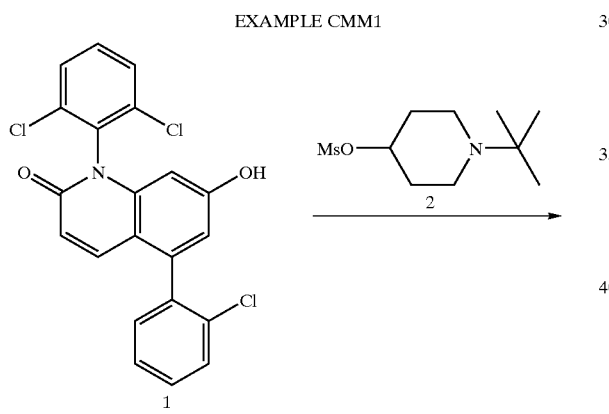

The mixture of compound 1 (126 mg, 0.3 mmol) and sodium hydride (60%) (12 mg, 0.3 mmol) in 6 mL of DMF was stirred for 1 h at rt. Then the compound 2 (78 mg, 0.33 mmol) was added and stirred for 12 h at 135° C. Potassium carbonate (83 mg, 0.6 mmol) and compound 2 (78 mg, 0.33 mmol) was again added to the reaction mixture and stirred for another 24 h at 135° C. After removal of solvent, it was poured in to 30 mL of ethyl acetate and 10 mL of aq Na$_2$CO$_3$, and it was extracted with ethyl acetate (15 mL×3). The combined organic layer was dried over Na$_2$CO$_3$ and concentrated. After removal of solvent, the residue was purified by TLC with hexane/ethyl acetate/2N NH$_3$ in MeOH to afford compound 3 (white solid). Mass spectrum (ESI) for 3, 555 (M+1) and 557 (M+3).

EXAMPLE CMM2

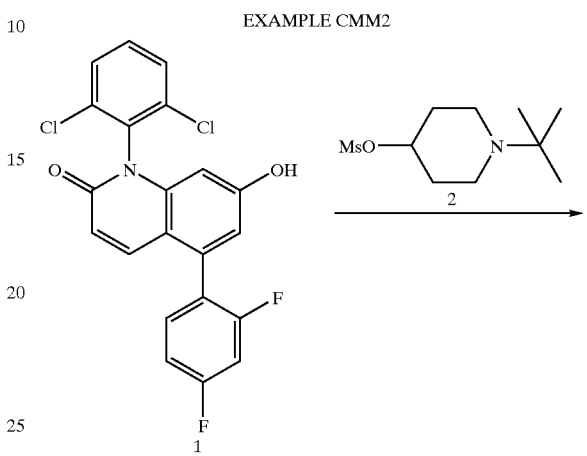

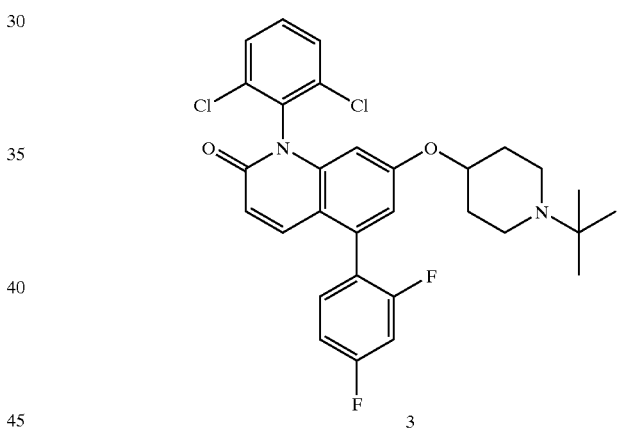

Mass spectrum (ESI) for 3,557 (M + 1) and 559 (M + 3).

EXAMPLE CMM3

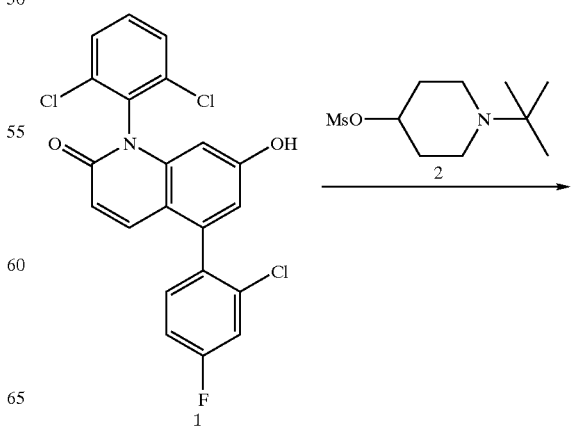

-continued
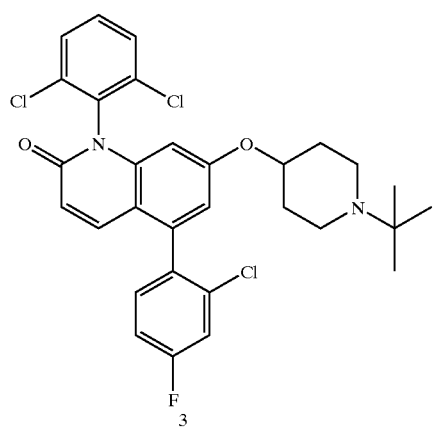
Mass spectrum (ESI) for 3, 573 (M + 1) and 575 (M + 3).
EXAMPLE CMM-2
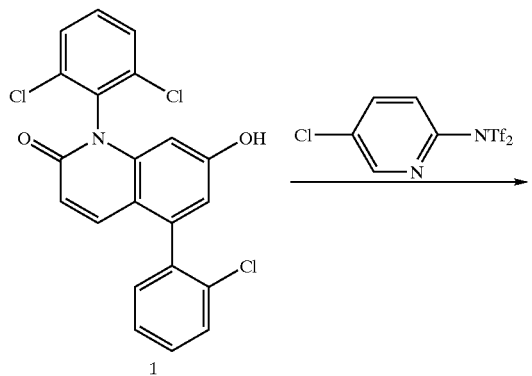
Mass spectrum (ESI) for 2, 548 (M + 1) and 550 (M + 3).
EXAMPLE CMM4
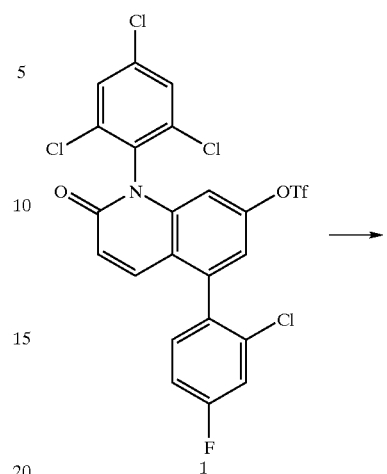
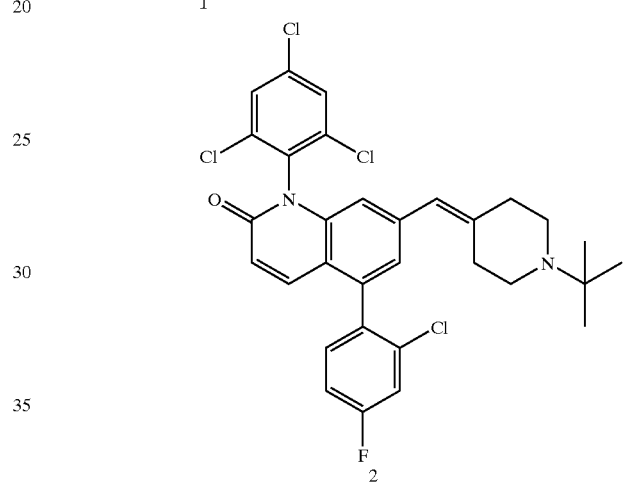
Mass spectrum (ESI) for 2, 604 (M + 1) and 606 (M + 3).
EXAMPLE CMM5 and EXAMPLE CMM6
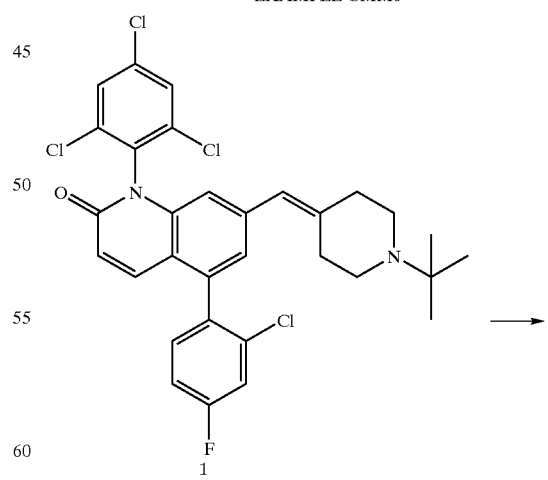

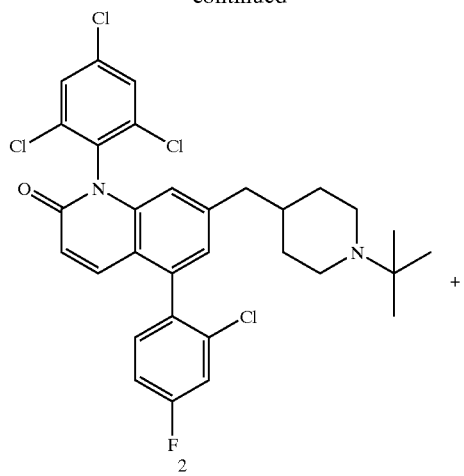
+
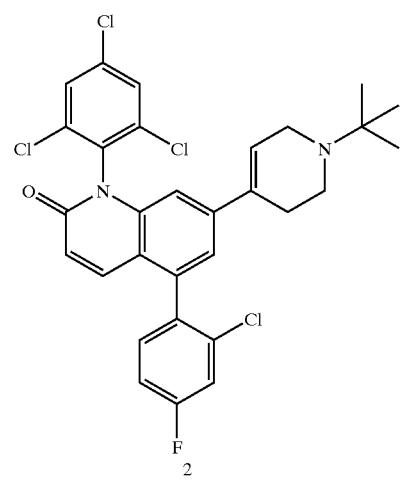
Mass spectrum (ESI) for 2, 590 (M + 1) and 592 (M + 3).
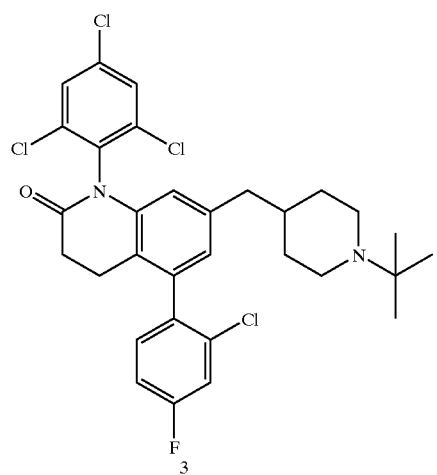
Mass spectrum (ESI) for 2 (EXAMPLE CMM5, 606 (M+1) and 608 (M+3). Mass spectrum (ESI) for 3 (EXAMPLE CMM6), 608 (M+) and 610 (M+3).
EXAMPLE CMM7
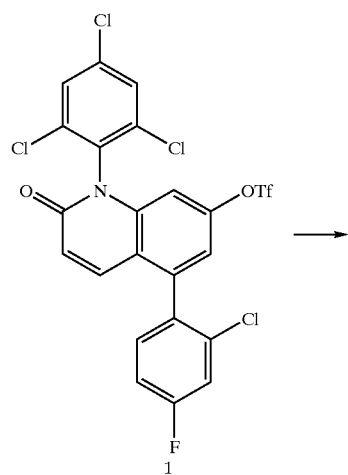
→
EXAMPLE CMM8 and EXAMPLE CMM 9
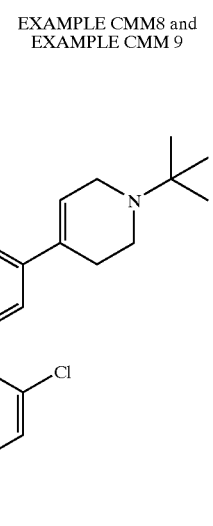
→
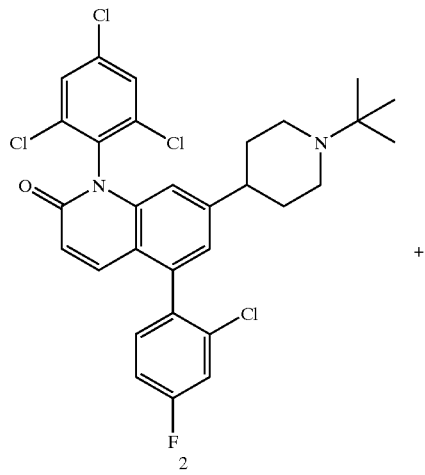
+

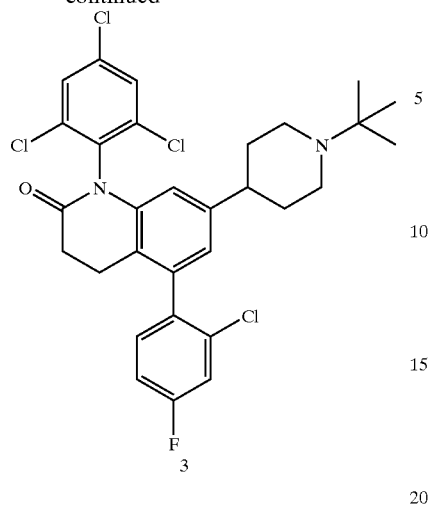
3
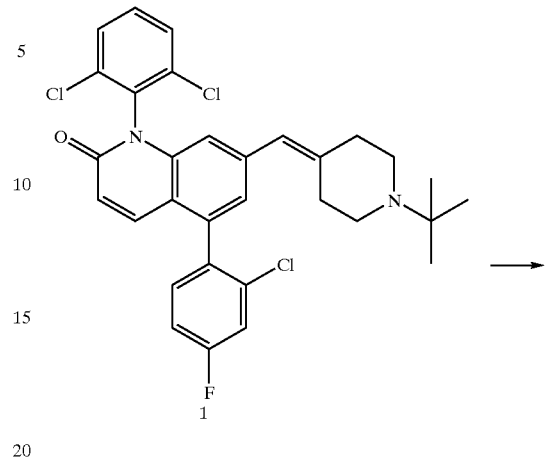
EXAMPLE CMM13 and EXAMPLE CMM11
1
Mass spectrum (ESI) for 2 (EXAMPLE CMM8), 592 (M+1) and 594(M+3). Mass spectrum (ESI) for 3 (EXAMPLE CMM9), 594 (M+1) and 596 (M+3).
EXAMPLE CMM10
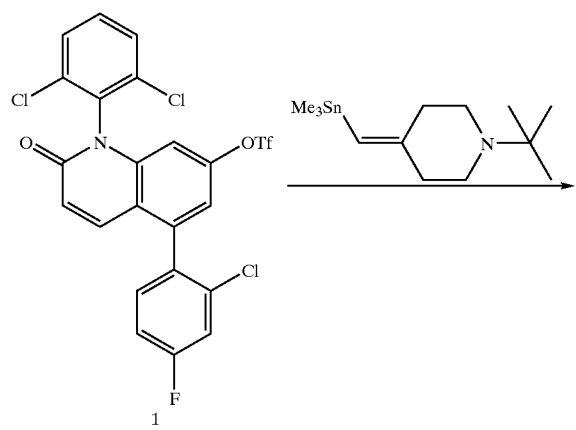
1
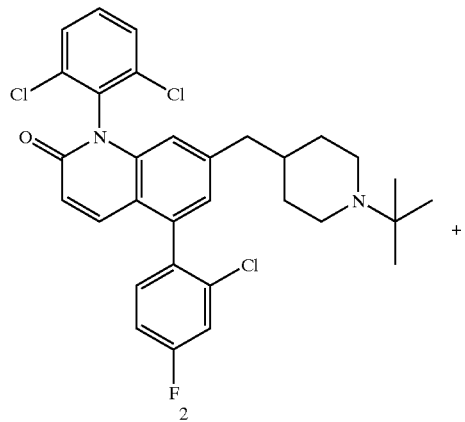
2
+
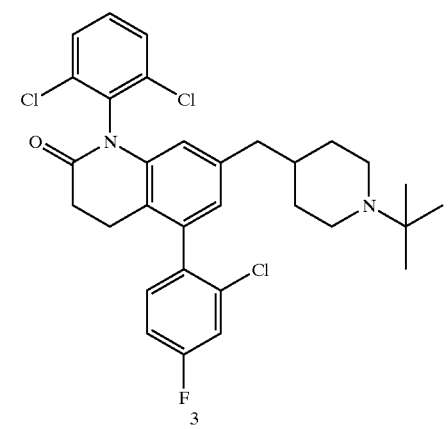
3
2
Mass spectrum (ESI) for 2,569 (M + 1) and 571 (M + 3).
Mass spectrum (ESI) for 2 (EXAMPLE CMM13), 571 (M+1) and 573 (M+3). Mass spectrum (ESI) for 3(EXAMPLE CMM11), 573 (M+1) and 575 (M+3).

COMPOUND CMM-A9
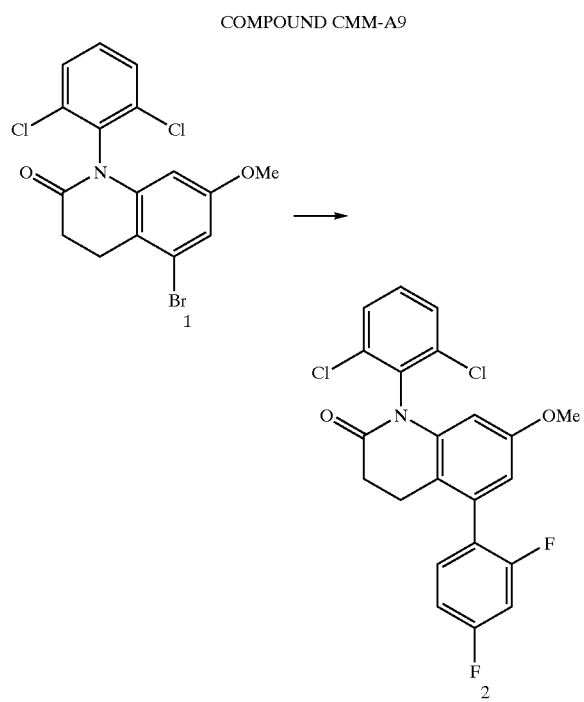
Mass spectrum (ESI) for 2,434 (M + 1) and 436 (M + 3).
COMPOUND CMM-9
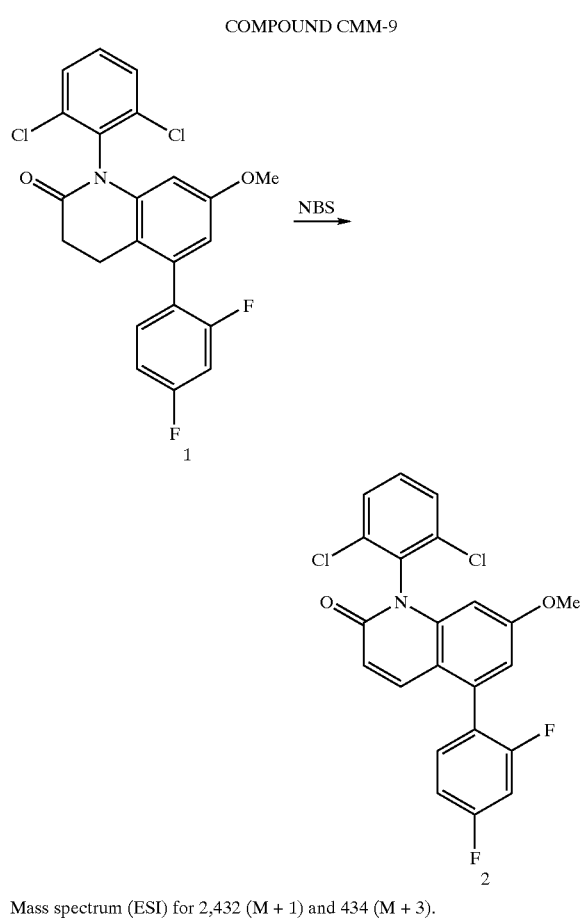
Mass spectrum (ESI) for 2,432 (M + 1) and 434 (M + 3).
COMPOUND CMM-10
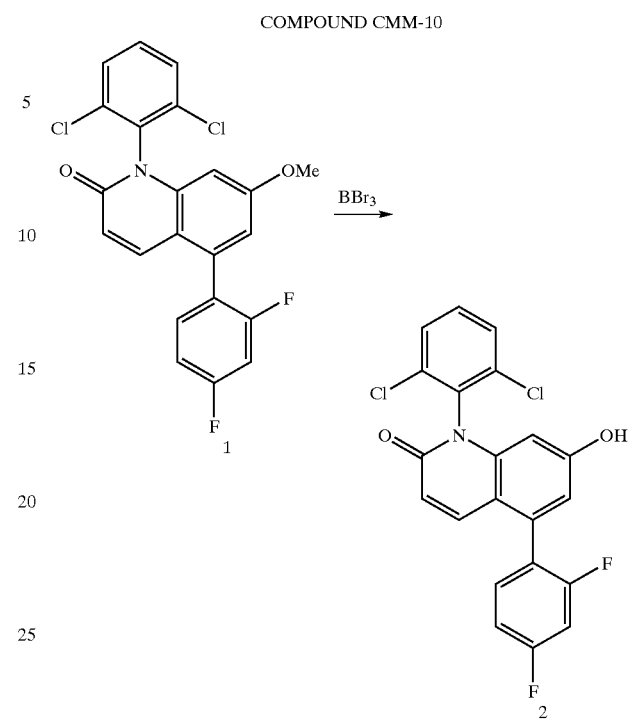
Mass spectrum (ESI) for 2,418 (M + 1) and 420 (M + 3).
COMPOUND CMM-11
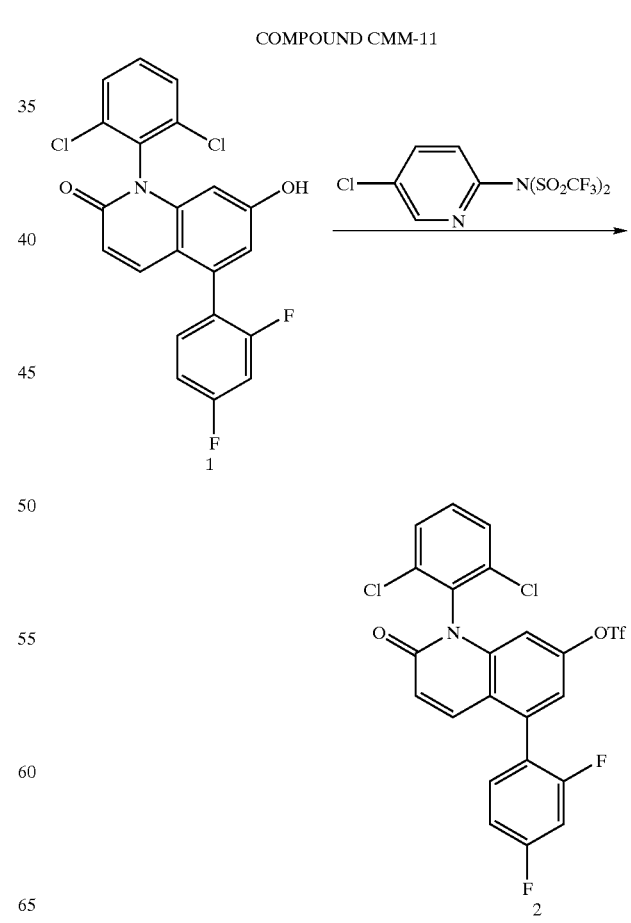
Mass spectrum (ESI) for 2,549 (M + 1) and 551 (M + 3).

EXAMPLE CMM17 and EXAMPLE CMM18

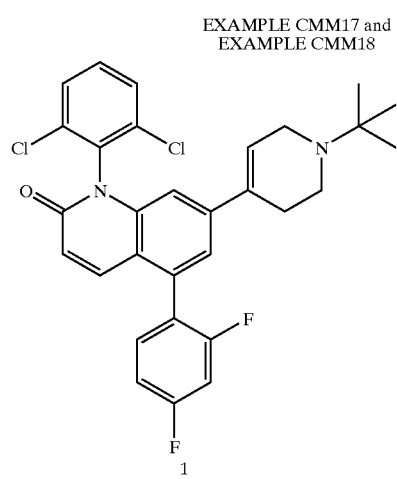

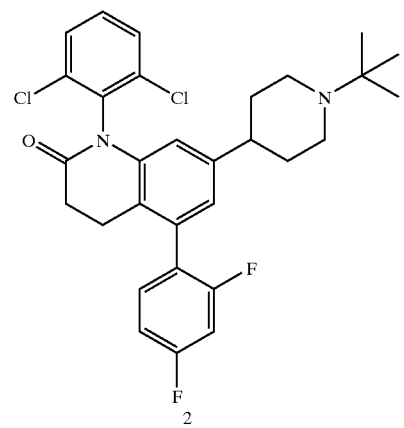

Mass spectrum (ESI) for 2 (EXAMPLE CMM17), 541 (M+1) and 543 (M+3). Mass spectrum (ESI) for 3 (EXAMPLE CMM18), 543 (M+1) and 545 (M+3).

COMPOUND DMM-1

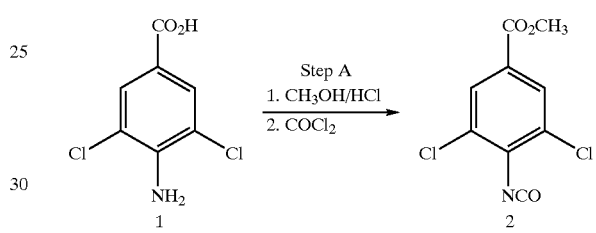

Step A: To a solution of 1 (8.06 g, 39.1 mmol) in 150 mL of methanol was added 20 mL of HCl in dioxane (C=4M) and the mixture wash heated at reflux for 5 h. Volatiles were removed, dissolved in $CH_2Cl_2$, washed once with $NaHCO_3$, dried with $Na_2SO_4$ and filtered through a plug of silica gel to yield a solid. It was dissolved in 100 mL of THF and was added 100 mL of $(COCl)_2$ in toluene (20% weight). The solution was heated to reflux for 3 h. All volatiles were removed to give a yellow solid, which was used in next step directly.

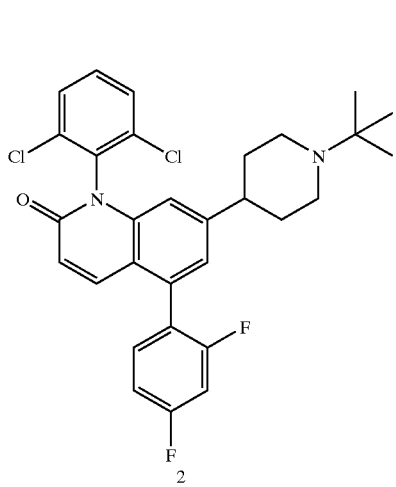

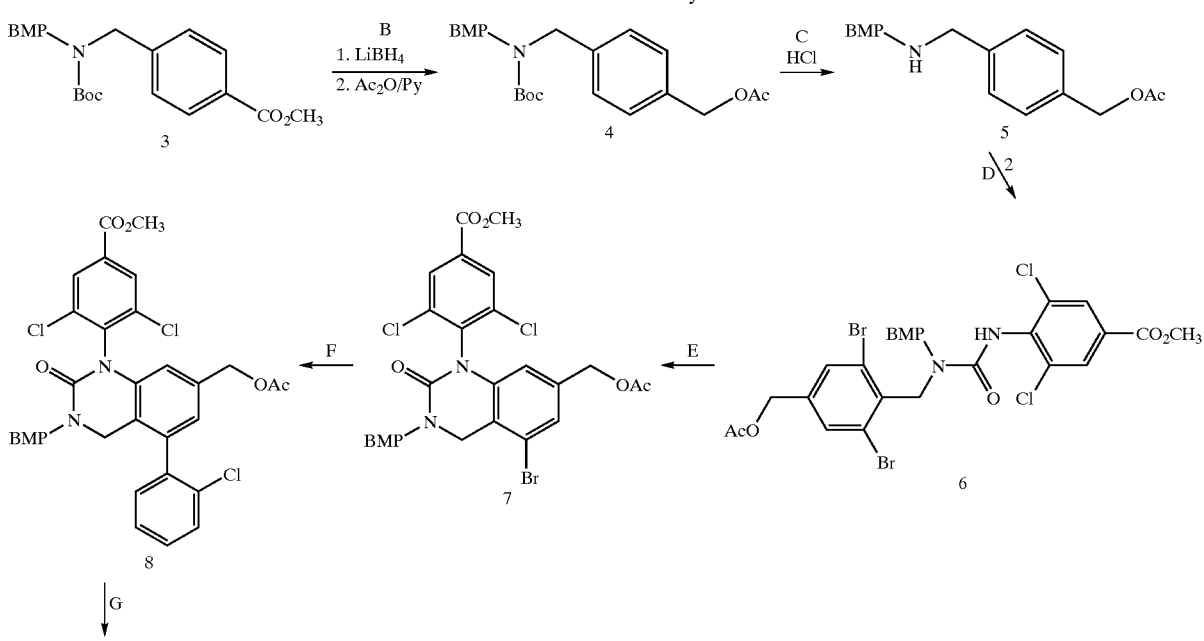

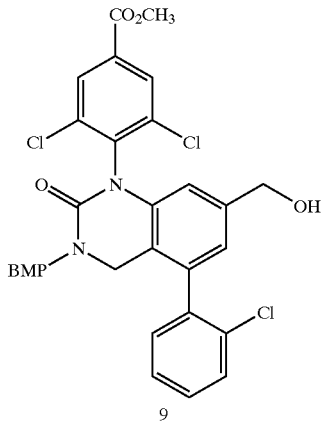

Step B: A solution of 3 (13.96 g, 25.70 mmol) in 60 mL of THF was added LiBH4 (37.7 mL, as 2M solution in THF) and the solution was stirred at rt for 45 h. The reaction was quenched with 20 mL of water and was removed of THF by vacuum. The residue was dissolved in $CH_2Cl_2$, washed with $NaHCO_3$, dried with $Na_2SO_4$. Upon removal of solvent, the residue was dissolved in 30 mL of pyridine and was added acetic an hydride (4.83 mL, 51.2 mmol). After 3 h at rt, volatiles were removed by vacuum, the residue was dissolved in ether and was washed by $NaHCO_3$ and brine, dried by $Na_2SO_4$ and filtered to give 4.

Step C: A solution of 4 (14.44 g, 25.6 mmol) in 100 mL of $CH_2Cl_2$ was added to 25.6 mL of HCl in dioxane (C=4M). After 18 h, it was removed of volatiles and was dissolved in $CH_2Cl_2$, washed with NaOH and taken to next step.

Step D: A solution of 5 in 100 mL of $CH_2Cl_2$ was added $Et_3N$ (4.28 mL, 30.72 mmol) and 2 (26.88 mmol) in 27 mL of $CH_2Cl_2$. After 16 h at rt, it was loaded on silica gel and eluted with EtOAc:hexane=1:3 give 6 (16.62 g). Mass spectrum (ESI) for 6, 703 (M+1).

Step E: This reaction was carried out similarly to procedures described above to give 7. Mass spectrum (ESI) for 7, 622 (M+1).

Step F: This Suzuki reaction was carried out with standard conditions. Mass spectrum (ESI) for 8, 654 (M+1).

Step G: A solution of 8 in 10 mL of $CH_2Cl_2$ (1.2235 g) was added $K_2CO_3$ (50 mg) and 40 mL of MeOH and the solution was heated at 45° C. for 4 h. Volatiles were removed and the residue was purified by flash chromatography EtOAc/hexane=3:7 to give 9. Mass spectrum (ESI) for 9, 613 (M+1).

EXAMPLE DMM1

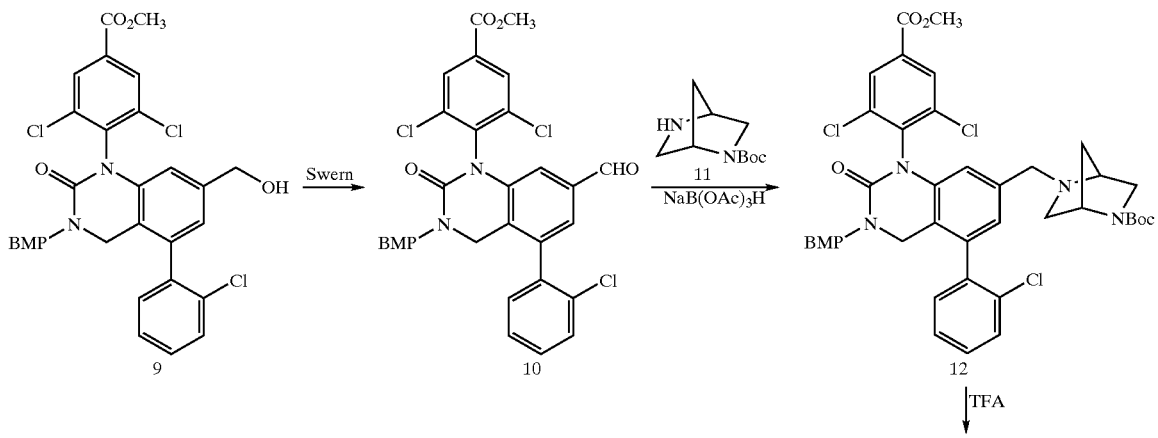

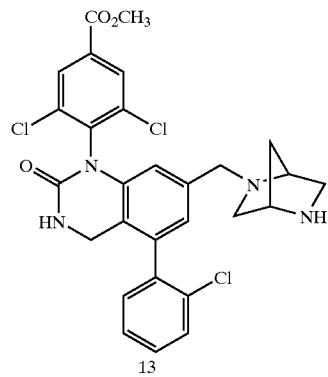

13

Compound 9 (COMPOUND DMM-1) was converted to aldehyde 10 via standard Swern reaction. Aldehyde 10 was coupled with amine 11 via NaB(OAc)$_3$H to afford 12. Treatment of 12 with TFA afford 13 (EXAMPLE DMM1). Mass spectrum (ESI) for 13, 573 (M+1).

EXAMPLE DMM2

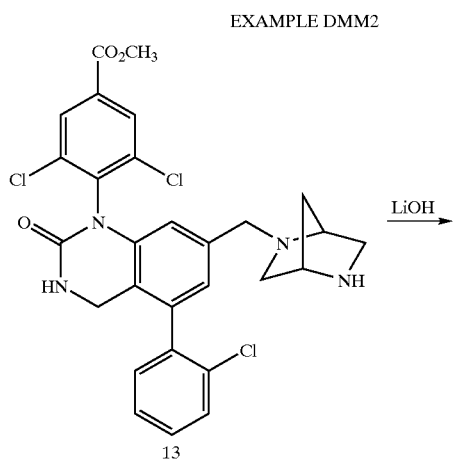

13

A solution of 13 (EXAMPLE DMM1) (31.1 mg, 0.054 mmol) in 1.5 mL of MeOH was added 0.5mL of water and LiOH.H$_2$O (11.4 mg, 0.27 mmol). The solution was stirred at rt for 2 h and was purified by reversed phase HPLC to give 14. Mass spectrum (ESI) for 14 (EXAMPLE DMM2), 559 (M+1).

EXAMPLE DMM3

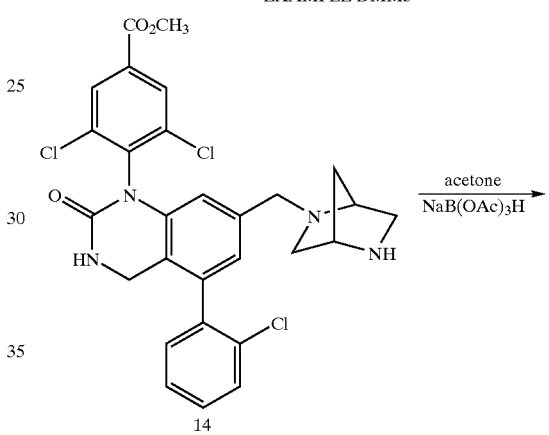

14

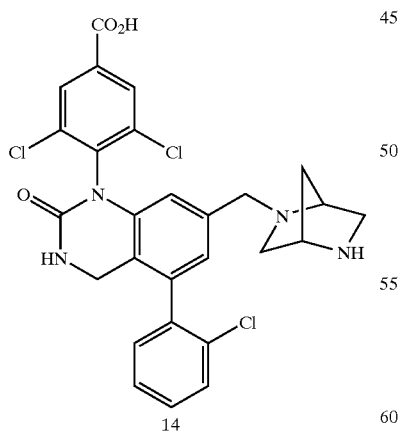

14

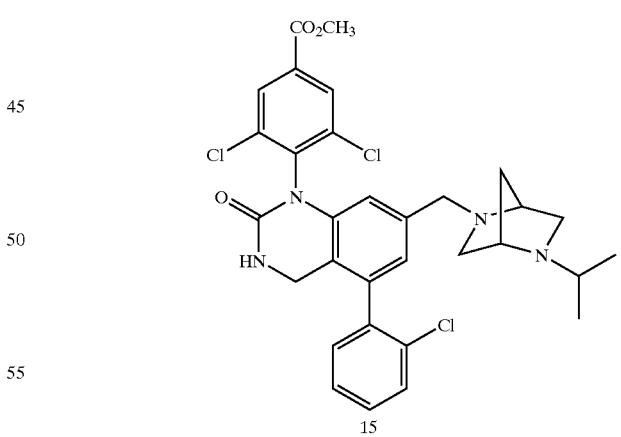

15

A solution of 14 (EXAMPLE DMM2) (0.27 g, 0.47 mmol) and NaB(OAc)$_3$H (0.20 g, 0.94 mmol) in CH$_2$Cl$_2$ was added acetone (0.34 mL, 4.7 mmol) and the mixture was stirred for 16 h at rt. It was diluted with CH$_2$Cl$_2$, washed with NaHCO$_3$, dried with Na$_2$SO$_4$ and filtered through Celite. Removal of solvent give 15 (EXAMPLE DMM3). Mass spectrum (ESI) for 15, 615 (M+1).

EXAMPLE DMM4

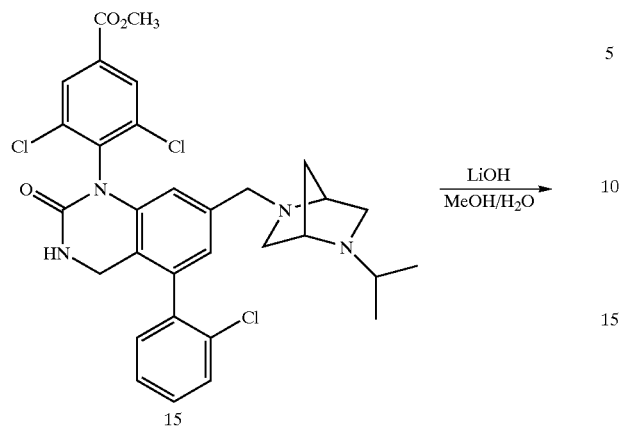

15

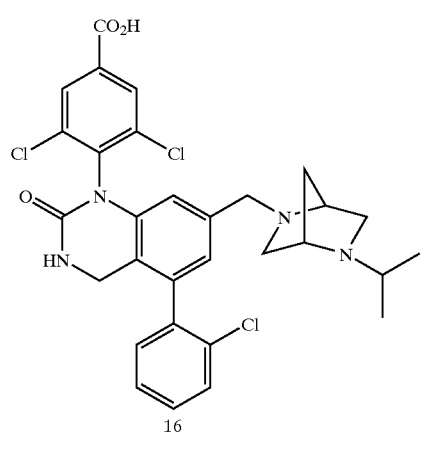

16

This reaction was carried out as EXAMPLE DMM3 to give 16 (EXAMPLE DMM4) as TFA salt. Mass spectrum (ESI) for 16, 601 (M+1).

EXAMPLE DMM5

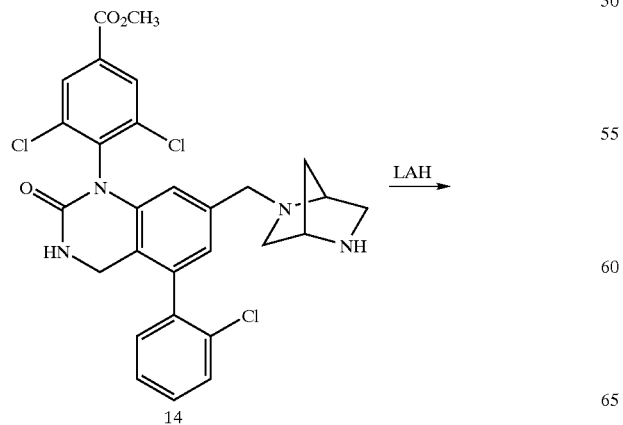

14

-continued

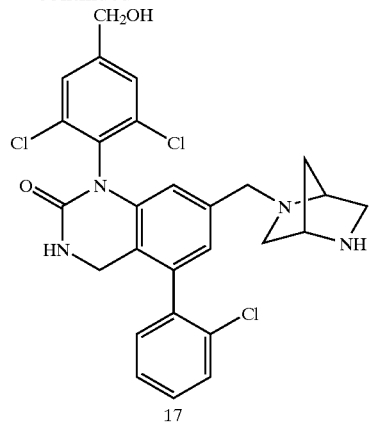

17

A solution of 14 (EXAMPLE DMM2) (30.8 mg, 0.050 mmol) in 2.5 mL of THF was added LAH (0.090 mL as 1M THF solution) at 0° C. After 30 min, it was quenched with 2 drops of water. After 5 min, $Na_2SO_4$ was added to remove excess water and filtered through Celite. The residue was purified by reversed phase HPLC to give 17 (EXAMPLE DMM5) as TFA salt. Mass spectrum (ESI) for 17, 543 (M+1).

EXAMPLE DMM6

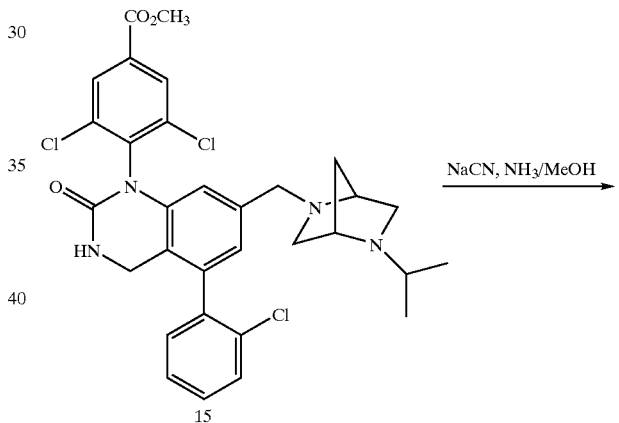

15

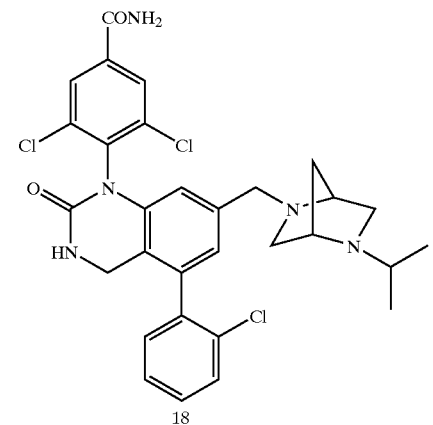

18

A solution of 15 (EXAMPLE DMM3) (0.17 g, 0.28 mmol) in 5 mL of 2M NH₃ in MeOH was added NaCN (10 mg, 0.20 mmol) and was heated at 50° C. for 5 h. Volatiles were removed and the residue was purified by reversed phase HPLC to give 18 (EXAMPLE DMM6). Mass spectrum (ESI) for 18, 598 (M+1).

EXAMPLE DMM7

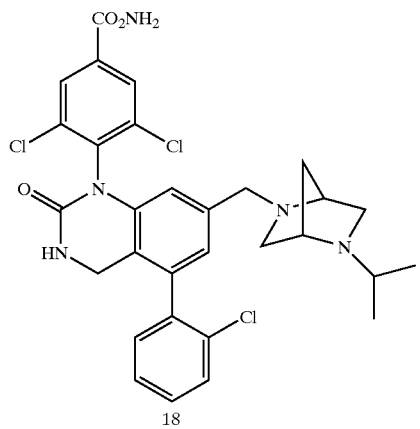

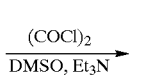

18

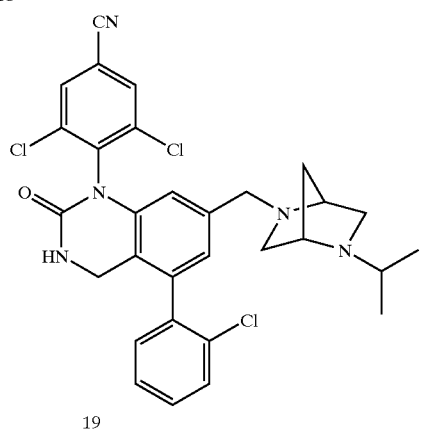

19

This reaction was carried out under standard Swern reaction conditions. The crude was purified by HPLC to give 19 (EXAMPLE DMM7) as TFA salt. Mass spectrum (ESI) for 19, 580 (M+1).

EXAMPLE DMM8

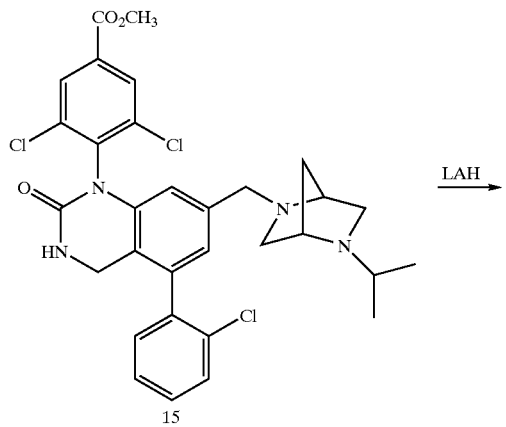

15

-continued

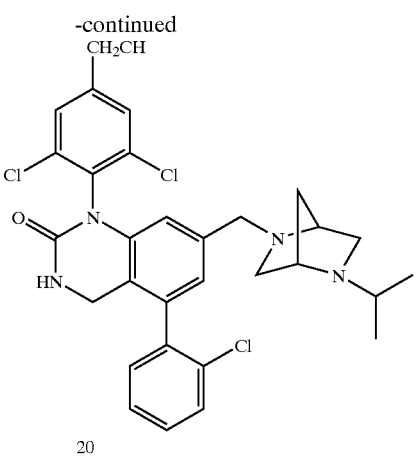

20

This reaction was carried out as EXAMPLE DMM5 to give 20 (EXAMPLE DMM8). Mass spectrum (ESI) for 20, 585 (M+1).

EXAMPLE DMM9

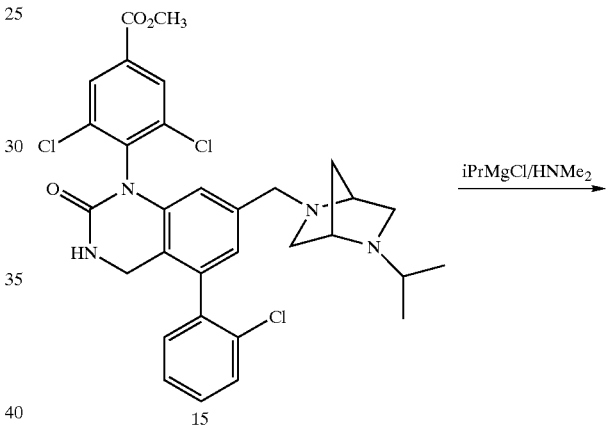

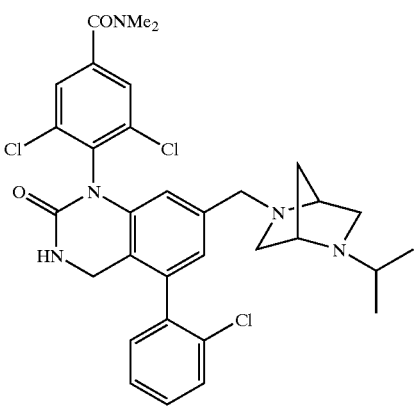

21

A solution of 15 (EXAMPLE DMM3) (32.6 mg, 0.053 mmol) and dimethylamine (0.053 mL, 0.106 mmol) in 2 mL of THF was added iPrMgCl (0.080 mL, 0.159 mmol) at −20° C. The solution was warmed up to −10° C. over 40 min and was quenched with 2 drops of water. It was diluted with 10 mL of CH₂Cl₂ and filtered through celite. The crude was purified by HPLC to give 21 (EXAMPLE DMM9) as TFA salt. Mass spectrum (ESI) for 21; 626 (M+1).

EXAMPLE DMM10
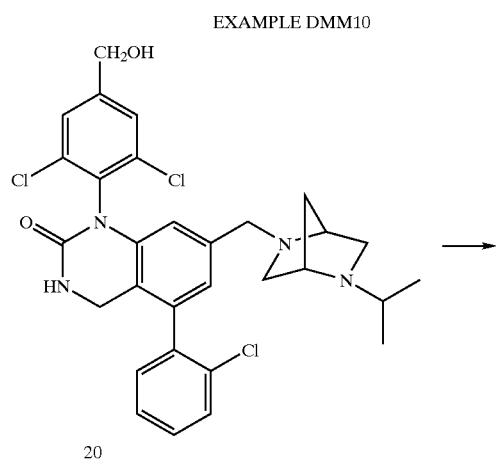
Step A: 22 was obtained via standard Swern reaction conditions.
Step B: The reaction was carried out as EXAMPLE DMM3. Mass spectrum (ESI) for 23 (EXAMPLE DMM10), 598 (M+1).
EXAMPLE DMM11
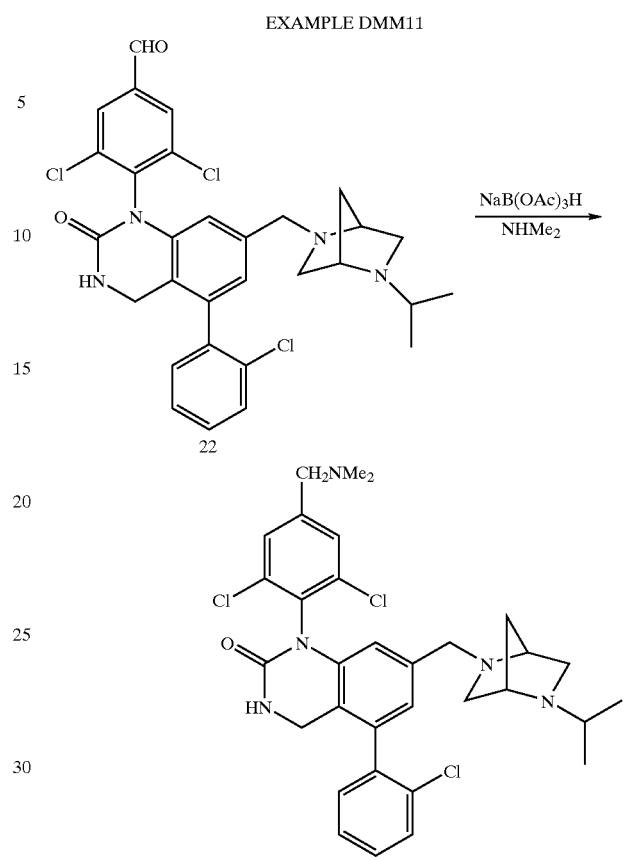
The reaction was carried out as EXAMPLE DMM3. Mass spectrum (ESI) for 24 (EXAMPLE DMM11), 612 (M+1).
COMPOUND DMM-2
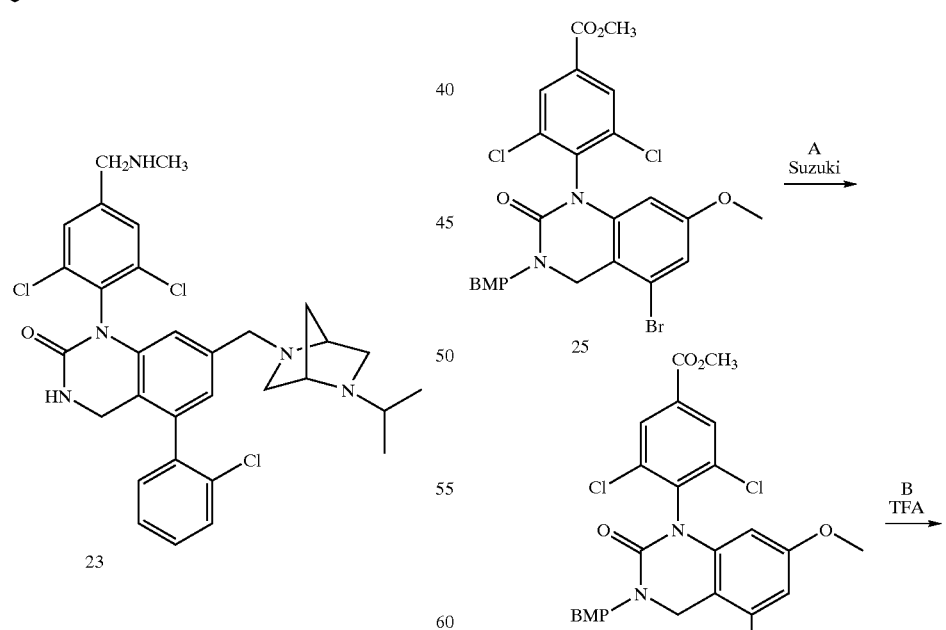

-continued
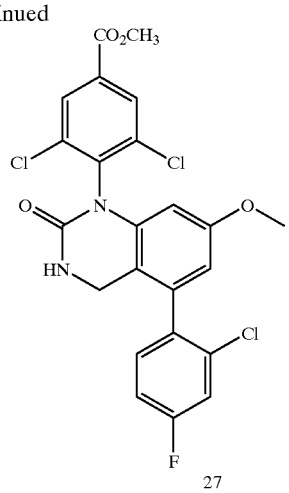
27
Step A: This reaction was carried via give 26.
Step B: The PMB group of 26 was removed via treatment of TFA. The crude was purified by flash chromatography (EtOAc: hexane=3:7) to give 27 (COMPOUND DMM-2). Mass spectrum (ESI) for 27, 509 (M+1).
COMPOUND DMM-3
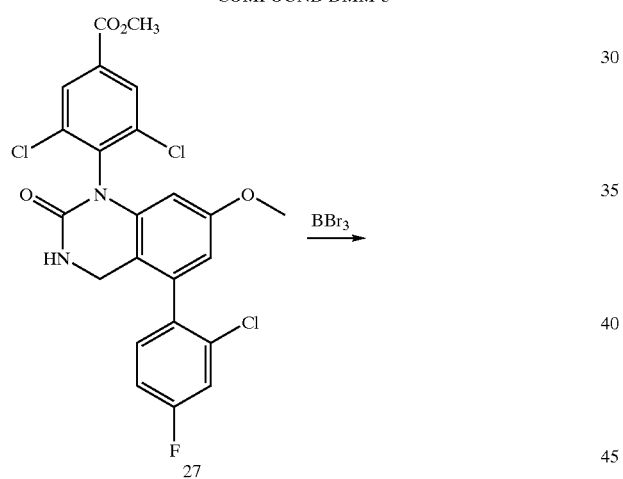
This reaction was carried out similarly to procedures described above.
Mass spectrum (ESI) for 28 (COMPOUND DMM-3), 495 (M+1).
EXAMPLE DMM12
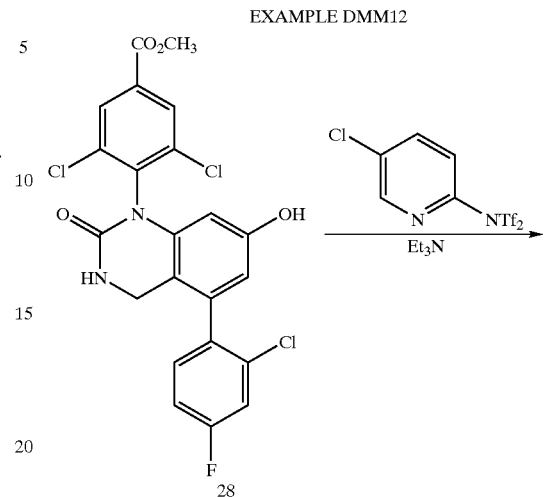
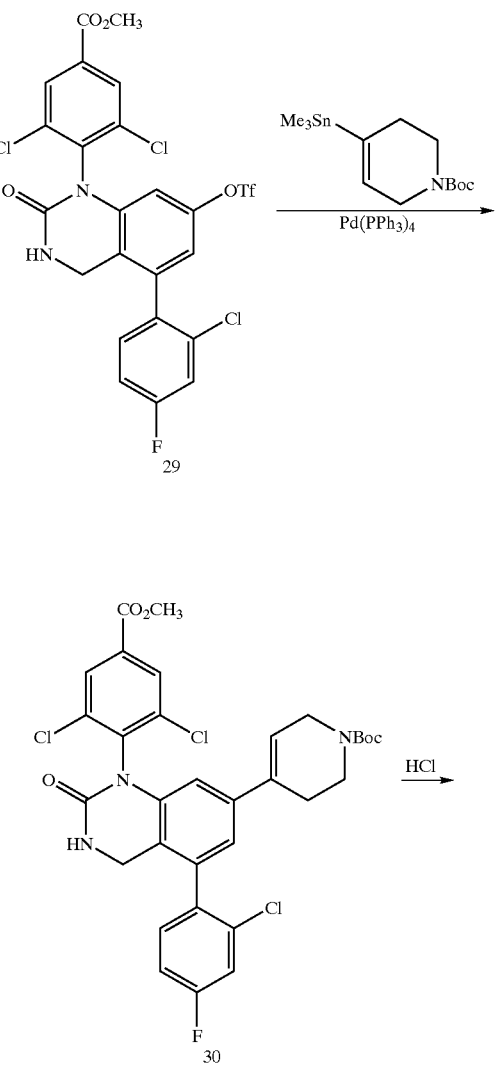

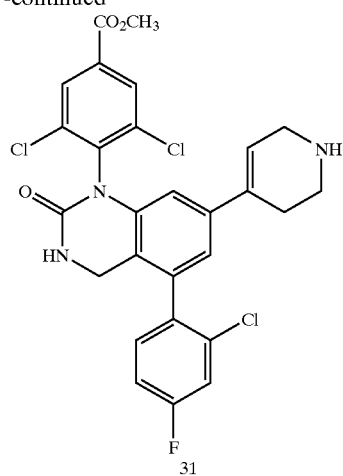
31
Compound 31 (EXAMPLE DMM12) was prepared from 28 (COMPOUND DMM-3) through the standard steps in the scheme. Mass spectrum (ESI) for 31, 560 (M+1).
EXAMPLE DMM13
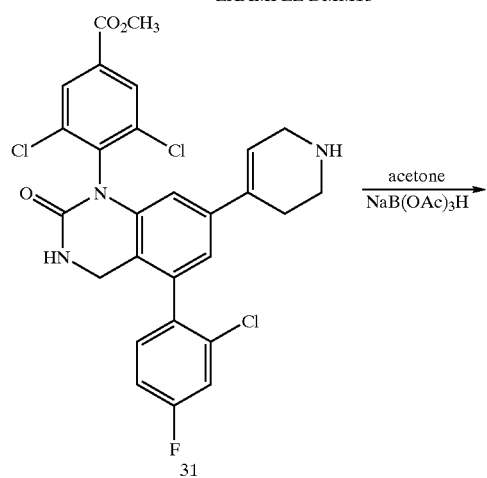
This reaction was carried out as EXAMPLE DMM3. Mass spectrum (ESI) for 32 (EXAMPLE DMM13), 602 (M+1).
EXAMPLE DMM14
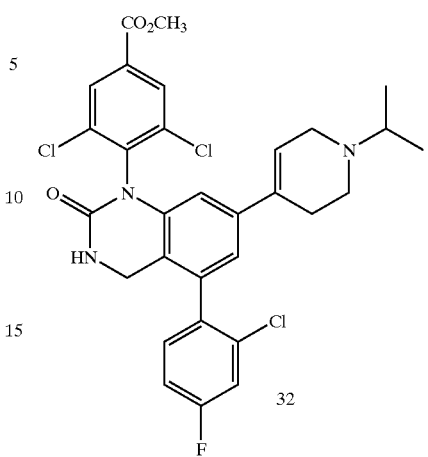
32
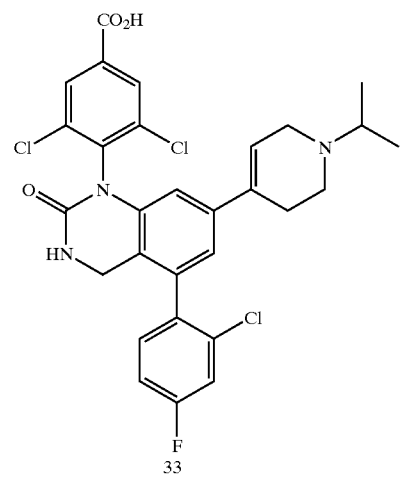
33
This reaction was carried out similarly to that described for EXAMPLE DMM4. Mass spectrum (ESI) for 33 (EXAMPLE DMM14), 588 (M+1).
EXAMPLE DMM15
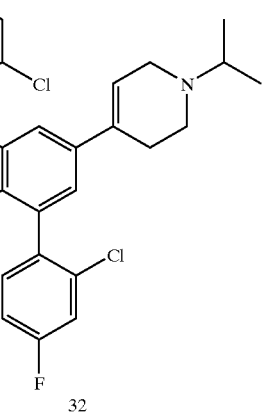
32

-continued

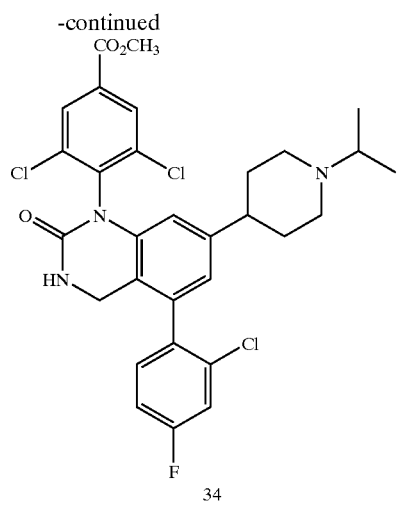

34

This reaction was carried out with 32 psi of $H_2$ for 16 h in EtOAc. Mass spectrum (ESI) for 34 (EXAMPLE DMM15), 604 (M+1).

EXAMPLE DMM16

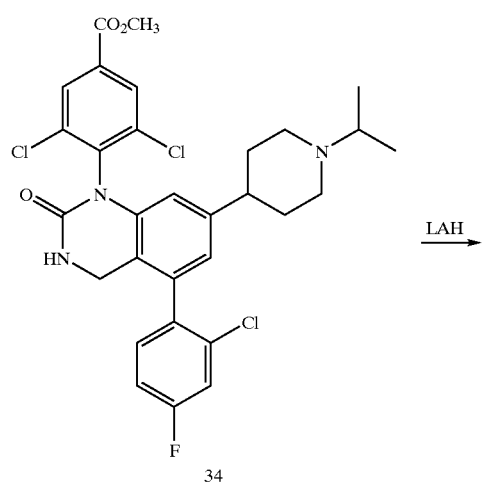

34

→ LAH

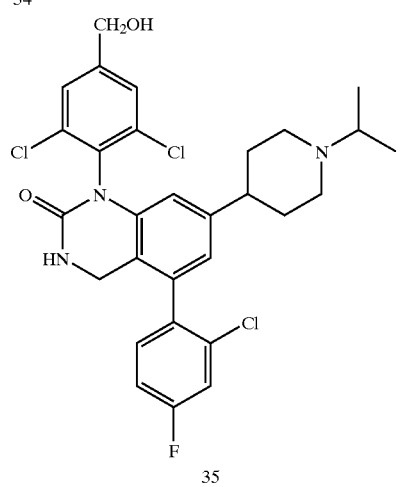

35

This reaction was carried out similarly to procedures described above.

Mass spectrum (ESI) for 35 (EXAMPLE DMM16), 576 (M+1).

EXAMPLE DMM17

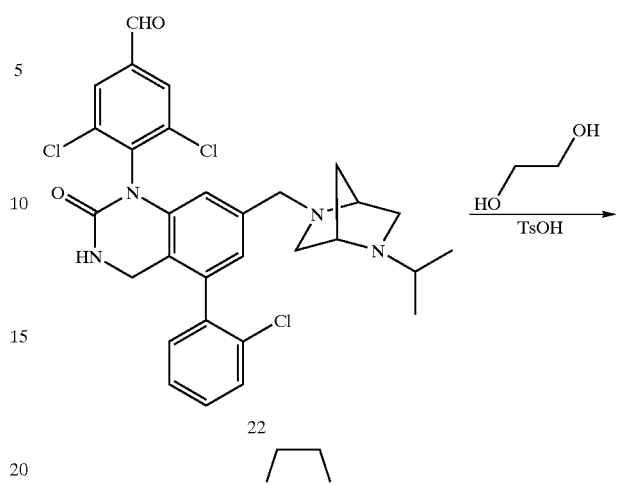

22

36

A solution of 22 from EXAMPLE DMM10 (33.2 mg, 0.057 mmol) and ethylene glycol (0.032 mL, 0.57 mmol) in 2.5 mL of benzene was added $TsOH \cdot H_2O$ (26 mg, 0.14 mmol) and was heated at reflux for 1 h. Volatiles were removed and the crude was purified by HPLC to give 36 (EXAMPLE DMM17) as a TFA salt. Mass spectrum (ESI) for 36, 627 (M+1).

EXAMPLE DMM18

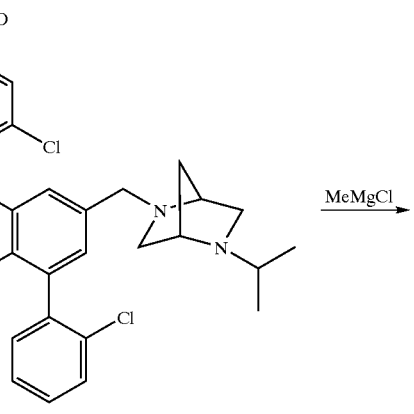

22

→ MeMgCl

-continued

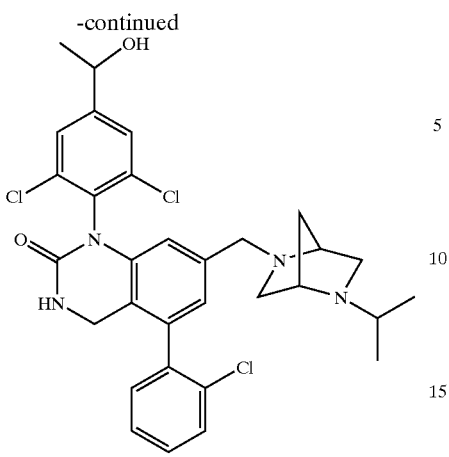

A solution of 22 from EXAMPLE7DMM10 (95.2 mg, 0.163 mmol) in 4 mL of THF was added MeMgCl (0.16 mL, 3M solution in THF) at rt. After 1.5 h, it was quenched with 3 drops of water and was filtered through celite. The crude was purified by HPLC to give 37 (EXAMPLE DMM18) as a TFA salt. Mass spectrum (ESI) for 37, 599 (M+1).

COMPOUND DMM-4

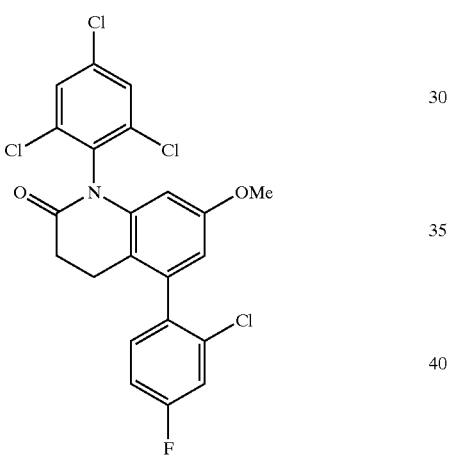

Mass spectrum (ESI) for 38, 484 (M + 1).

COMPOUND DMM-5

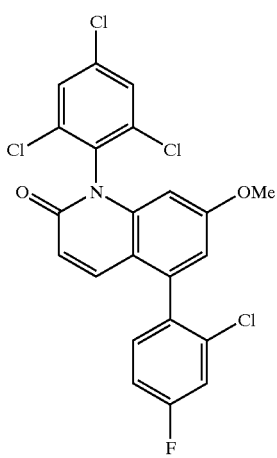

Mass spectrum (ESI) for 39, 482 (M + 1).

COMPOUND DMM-6

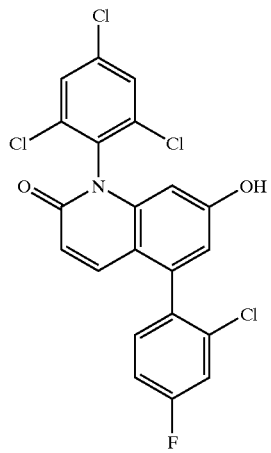

Mass spectrum (ESI) for 40, 468 (M + 1).

Compound CN-1

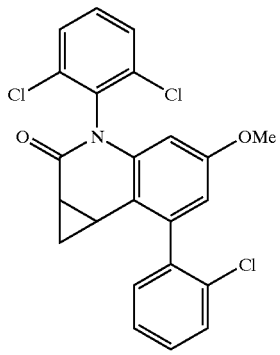

Oil free sodium hydride (36 mg) suspended in dry DMSO (5 mL) was added trimethylsulfoxonium chloride (193 mg) at rt. After bubbling subsided, the INTERMEDIATE 8 (300 mg) in DMSO (5 mL) was added to reaction mixture. The solution was stirred at rt for 1 h and at 60° C. for 18 h. The mixture was partitioned between ethyl acetate and water. The two layers were separated and the organic phase was washed with water (3×), brine, dried over MgSO$_4$, filtered and concentrated. The residue was purified by silica gel (hexanes/ethyl acetate=2/1) to give title compound. $^1$H NMR(CDCl$_3$, 500 MHz, diastereomers): 7.53 (m, 3H), 7.39 (m, 4H), 6.53 (d, 1H, one diastereomer), 6.48 (d, 1H, one diastereomer), 5.70(d, 1H, diastereomers mixture), 3.68 (s, 3H, one diastereomer), 3.51 (s, 3H, one diastereomer), 2.20 (m, 2H), 1.65 (m, 1H), 1.07 (m, 1H, one diastereomer), 0.97 (m, 1H, one diastereomer). MS(ES) 444 (M+H).

Compound CN-2

The title compound was prepared as described in INTERMEDIATE 3. MS(ES) 430 (M+H).

EXAMPLE CN-1

To a solution of Compound CN-2 (43 mg) in dichloromethane was added diisopropylethylamine (0.17 mL) and phosgen (0.5 mL, 1.9M in toluene)at −20C. The mixture was warmed up to rt and stirred for 16 h. The solution was concentrated to dry to give crude mixture. To a solution of this crude mixture in dichloromethane was added t-butyl-2, 5-diazabicyclo[2.2.1]heptane-2-carboxylate and diisopropylethylamine at rt and stirred for 16 h. Removal of the solvent and subsequent purification by preparative thin layer chromatography (hexanes/ethyl acetate=2/1) provided the coupling product. The coupling product in ethyl acetate at 0C was bubbled though hydrogen chloride gas until saturation occurred. The reaction was stirred for 15 min, until thin layer chromatography analysis indicated that the reaction was complete. The solution was concentrated to remove the ethyl acetate. The residue was the redissolved in dichloromethane and hexanes was added followed by evaporation in vacuo to afford the title product as a solid. $^1$H NMR(CD$_3$OD, 500 MHz, mixture of diastereomers ): 7.64–7.42 (m, 7H), 6.81 (m, 1H), 5.94 (m, 1H), 4.45 (s, 1H), 3.67 (s, 1H), 3.52 (m, 1H), 3.42 (m, 1H), 2.38–2.15 (m, 4H), 1.78–162 (m, 1M), 1.37 (m, 2H), 0.95 (m, 1H). MS(ES) 556 (M+H).

What is claimed is:
1. A compound represented by (I):

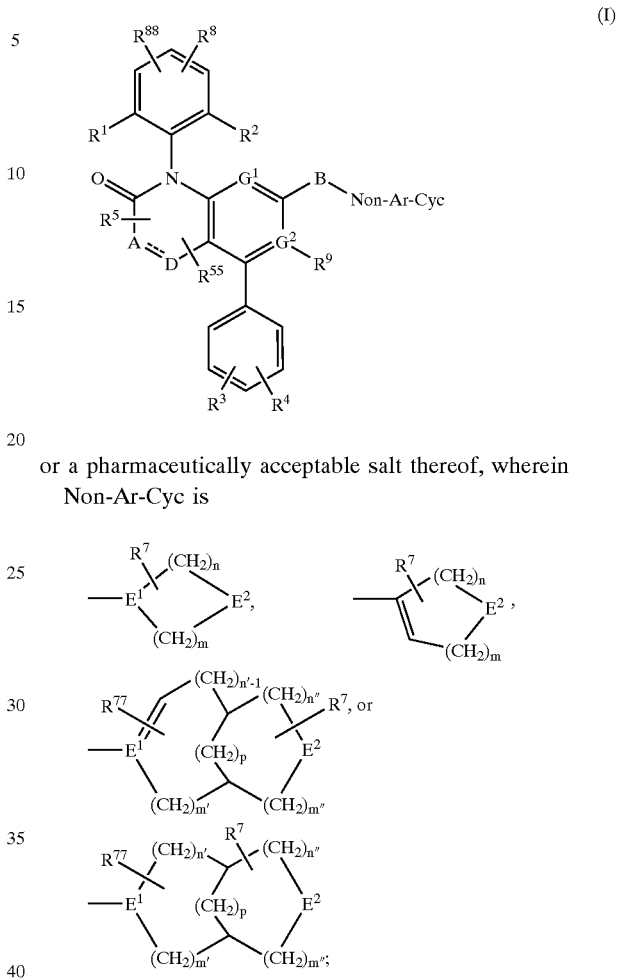

or a pharmaceutically acceptable salt thereof, wherein
Non-Ar-Cyc is

A is, O, CH$_2$, or CH;
B is —C$_{1-6}$alkyl-, —C$_{0-3}$alkyl-O—C$_{0-3}$alkyl-, —C$_{0-3}$alkyl-NH—C$_{0-3}$alkyl-, —C$_{0-3}$alkyl-NH—C$_{3-7}$cycloalkyl-, —C$_{0-3}$alkyl-N(C$_{0-3}$alkyl)-C(O)—C$_{0-3}$alkyl-, —C$_{0-3}$alkyl-NH—SO$_2$—C$_{0-3}$alkyl-, —C$_{0-3}$alkyl-, —C$_{0-3}$alkyl-S—C$_{0-3}$alkyl-, C$_{0-3}$alkyl-SO$_2$—C$_{0-3}$alkyl-, —C$_{0-3}$alkyl-PH—C$_{0-3}$alkyl-, —C$_{0-3}$alkyl-C(O)—C$_{0-3}$alkyl, or a direct bond;
D is CH, CH$_2$, N, or NH; optionally A and D are bridged by —C$_{1-4}$alkyl- to form a fused bicyclo ring with A and D at the bicyclo cusps;
E$^1$ is CH, N, or CR$^6$; or B and E$^1$ form —CH=C<;
E$^2$ is CH$_2$, CHR, C(OH)R NH, NR, O, S, —S(O)—, or —S(O)$_2$—;
G$^1$ is N, CH, or C(C$_{1-3}$alkyl);
G$^2$ is N, CH, or C(C$_{1-3}$alkyl)
R, R$^7$ and R$^{77}$ each independently is hydrogen, C$_{1-6}$alkyl-group, C$_{2-6}$alkenyl-group, C$_{4-6}$cycloalkyl-C$_{0-6}$alkyl-group, N(C$_{0-4}$alkyl)(C$_{0-4}$alkyl)-C$_{1-4}$alkyl-N(C$_{0-4}$alkyl)-group, —N(C$_{0-4}$alkyl)(C$_{0-4}$alkyl) group, C$_{1-3}$alkyl-CO—C$_{0-4}$alkyl-group, C$_{0-6}$alkyl-O—C(O)—C$_{0-4}$alkyl-group, C$_{0-6}$alkyl-C(O)—O—C$_{0-4}$alkyl-group, N(C$_{0-4}$alkyl)(C$_{0-4}$alkyl)-(C$_{0-4}$alkyl)C(O)(C$_{0-4}$alkyl)-group, phenyl-C$_{0-4}$alkyl-group, pyridyl-C$_{0-4}$ alkyl-group, pyrimidinyl-C$_{0-4}$alkyl-group, pyrazinyl-$C_{0-4}$alkyl-group, thiophenyl-$C_{0-4}$alkyl-group, pyrazolyl-$C_{0-4}$alkyl-group, imidazolyl-$C_{0-4}$alkyl-group, triazolyl-$C_{0-4}$alkyl-group, azetidinyl-$C_{0-4}$alkyl-group, pyrrolidinyl-$C_{0-4}$alkyl-group, isoquinolinyl-$C_{0-4}$alkyl-group, indanyl-$C_{0-4}$alkyl-group, benzothiazolyl-$C_{0-4}$alkyl-group, any of the groups optionally substituted with 1–6 substituents, each substituent independently being —OH, —N($C_{0-4}$alkyl)($C_{0-4}$alkyl), $C_{1-4}$alkyl, $C_{1-6}$alkoxyl, $C_{1-6}$alkyl-CO—$C_{0-4}$alkyl-, pyrrolidinyl-$C_{0-4}$alkyl-, or halogen;

or $R^7$ together with a bond from an absent ring hydrogen is =O;

n'+n"=n;

m'+m"=m;

n is 1, 2, 3, or 4;

m is 0, 1, 2, 3, or 4;

n+m is 2, 3, 4, 5, or 6;

p is 0, 1, 2, or 3;

$R^1$, $R^2$, $R^3$, $R^4$, and $R^6$ are each independently halogen, $C_{0-4}$alkyl, —C(O)—O($C_{0-4}$alkyl), or —C(O)—N($C_{0-4}$alkyl)($C_{0-4}$alkyl), $R^5$ and $R^{55}$ independently is H, $CH_3$, $CH_2CH_3$, or absent;

$R^{88}$ and $R^8$ each is independently —CN, —$C_{0-4}$alkyl, —C(O)—N($C_{0-4}$alkyl)($C_{0-4}$alkyl), —C(O)—O—$C_{0-4}$alkyl or 1,3dioxolan-2-yl-$C_{0-4}$alkyl-;

$R^9$ is —$C_{0-4}$alkyl, or absent; and any alkyl optionally substituted with 1–6 independent halogen or —OH.

2. The compound according to claim 1, or a pharmaceutically acceptable salt thereof, wherein D is $CH_2$.

3. The compound according to claim 2, or a pharmaceutically acceptable salt thereof, wherein B is a direct bond.

4. The compound according to claim 2, or a pharmaceutically acceptable salt thereof, wherein B is $C_{0-3}$alkyl-O—$C_{0-3}$alkyl.

5. The compound according to claim 2, or a pharmaceutically acceptable salt thereof, wherein B is $C_{0-3}$alkyl-C(O)—$C_{0-3}$alkyl.

6. The compound according to claim 2, or a pharmaceutically acceptable salt thereof, wherein B is $C_{1-6}$alkyl.

7. The compound according to claim 2, or a pharmaceutically acceptable salt thereof, wherein B is $C_{0-3}$alkyl-NH—$C_{0-3}$alkyl.

8. The compound according to claim 2, or a pharmaceutically acceptable salt thereof, wherein $G^2$ is N.

9. A compound represented by

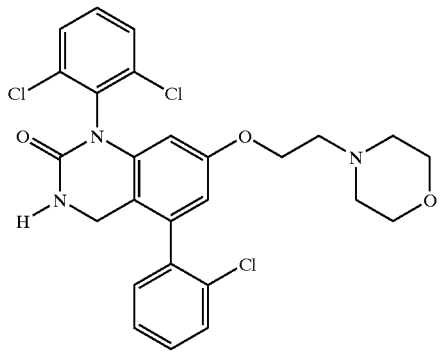

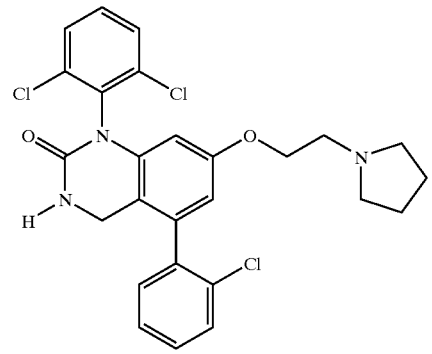

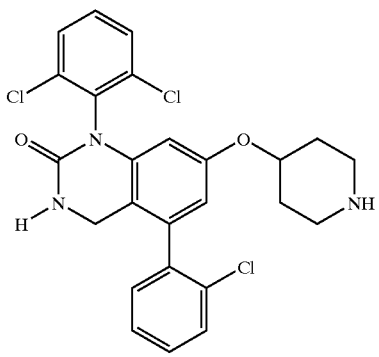

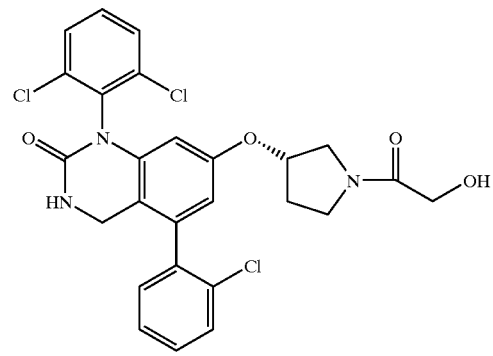

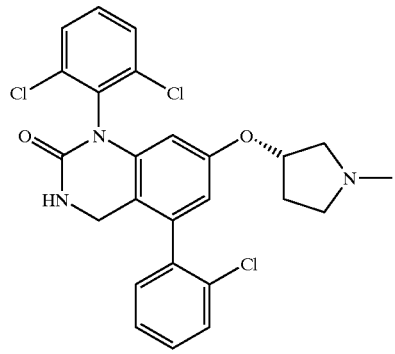
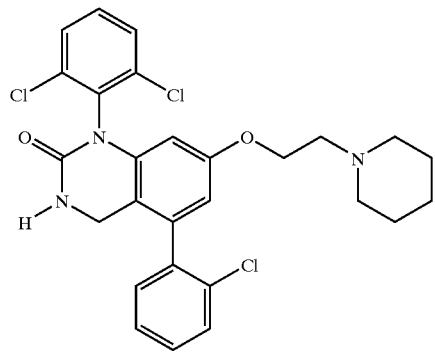
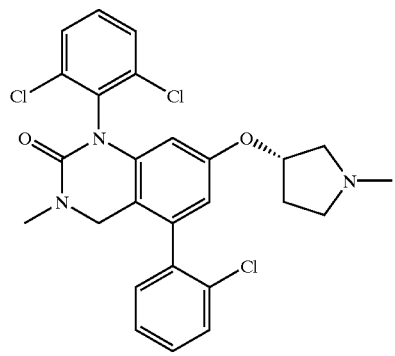
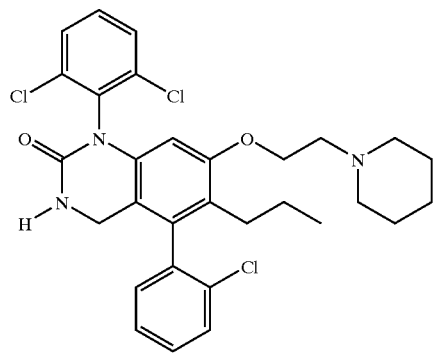
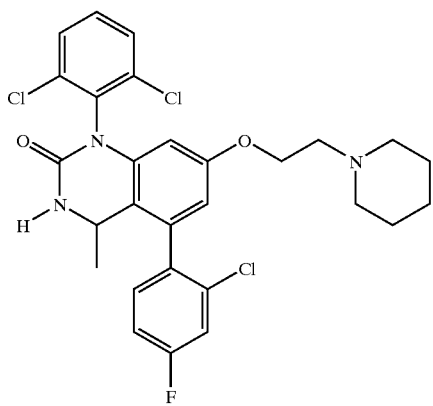
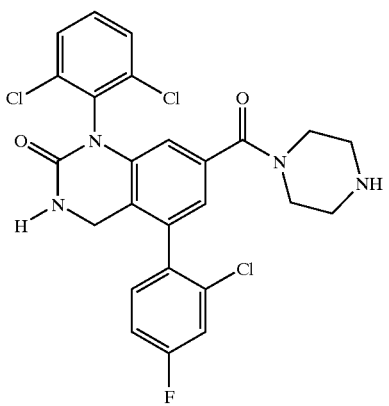
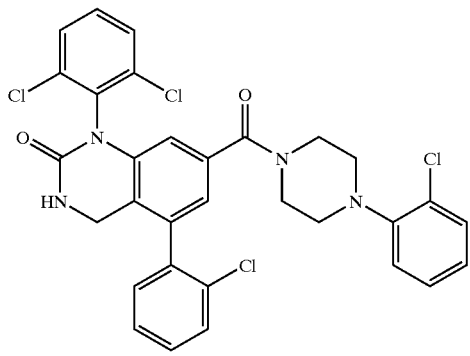
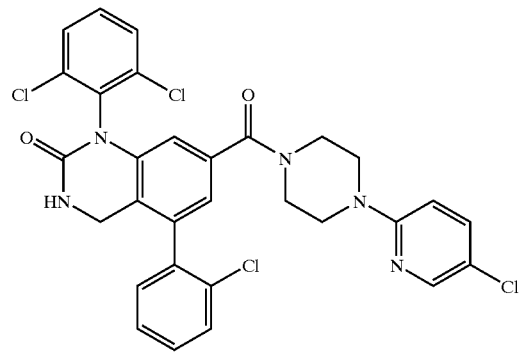

-continued
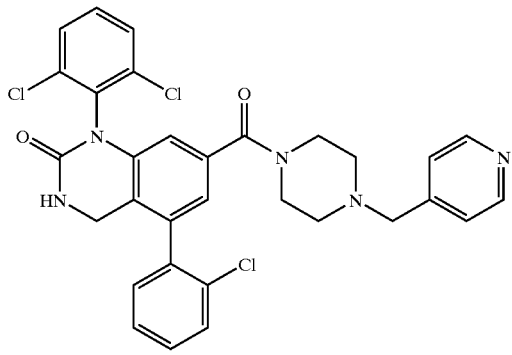
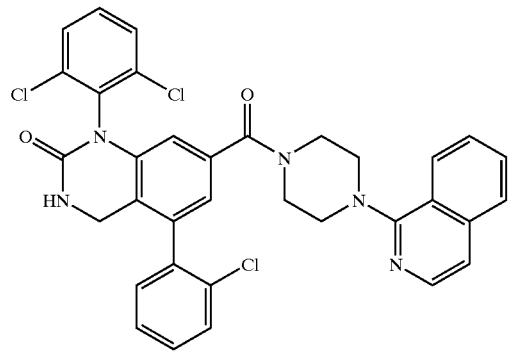
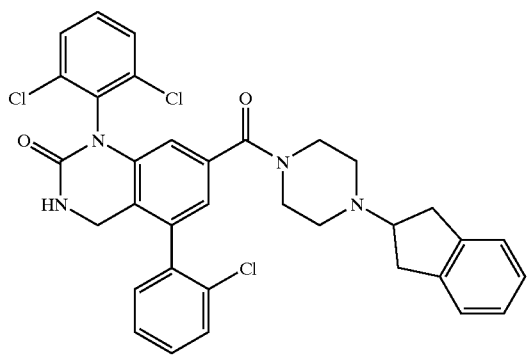
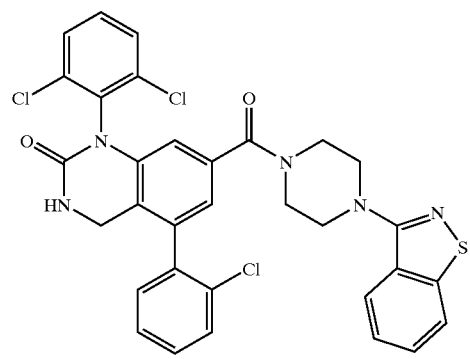
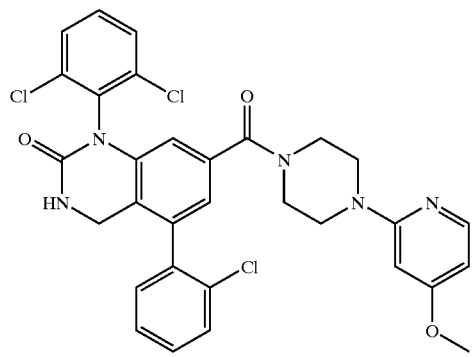
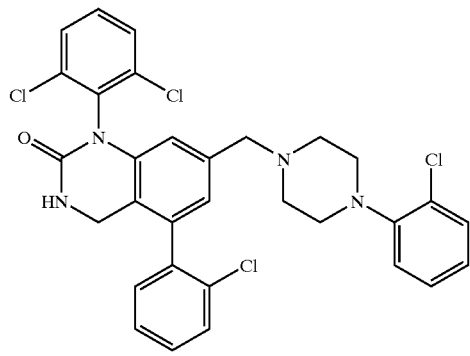
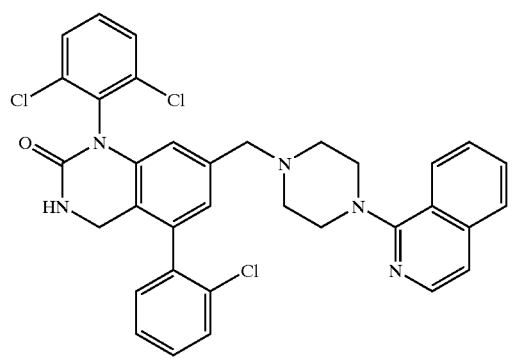
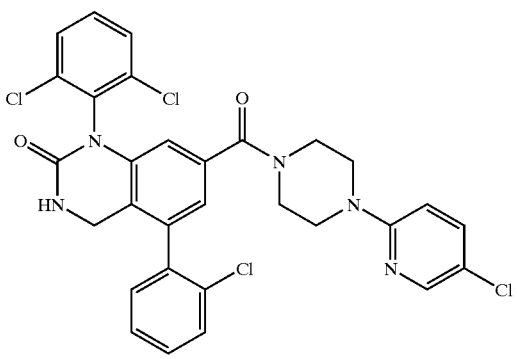

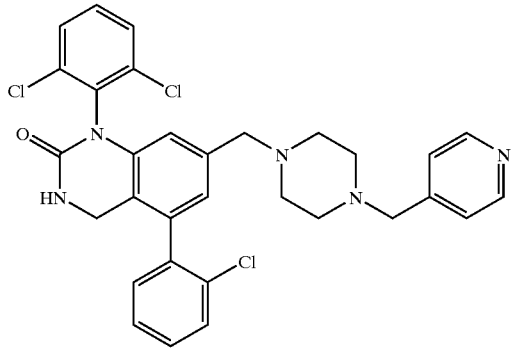
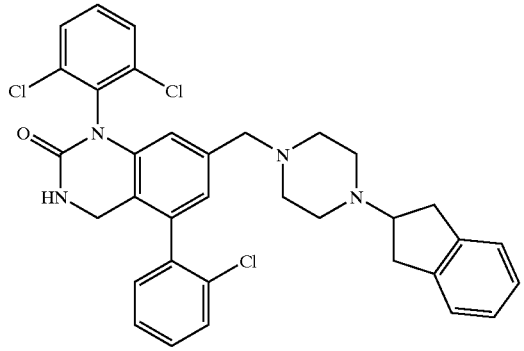
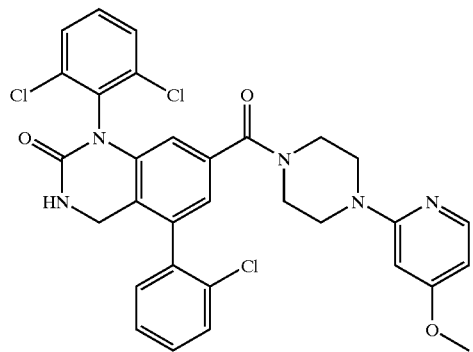
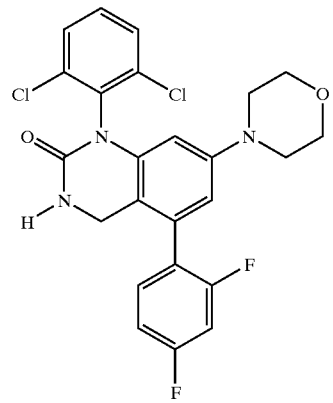
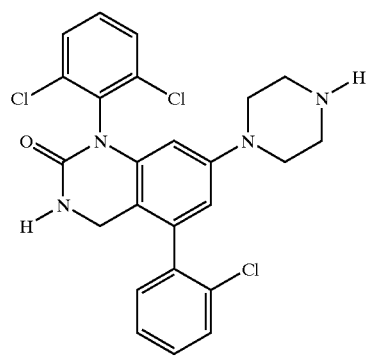
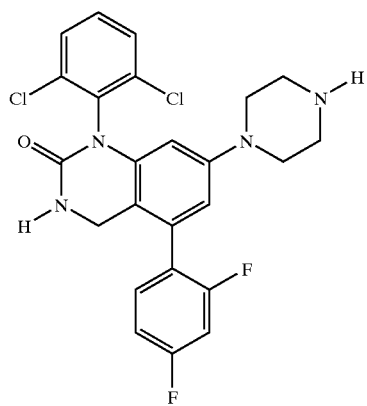
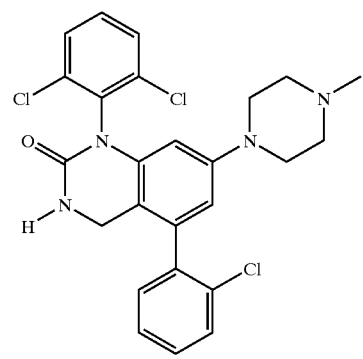
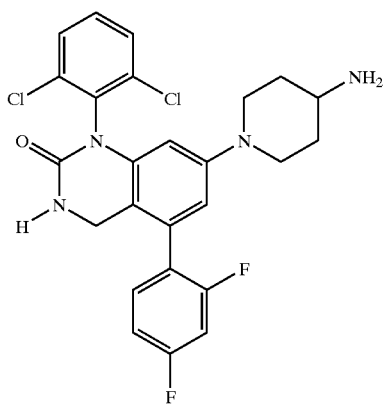

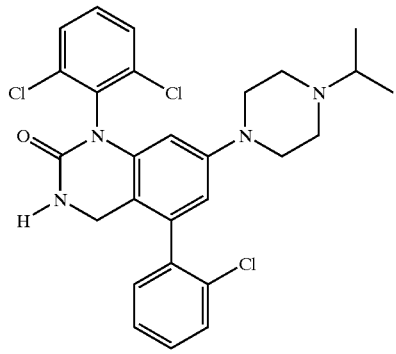
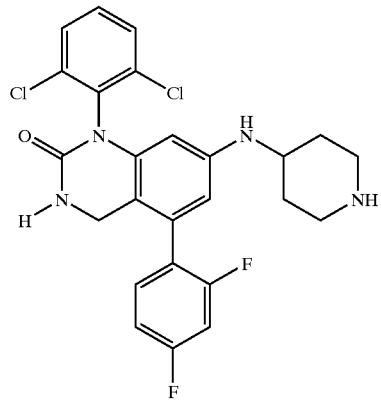
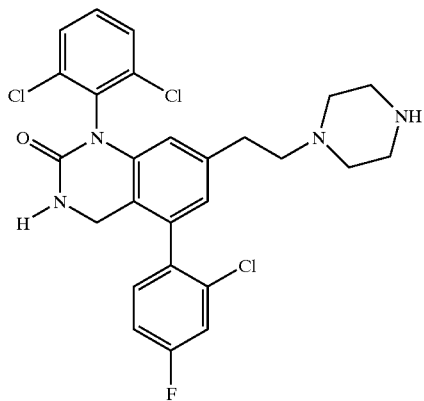
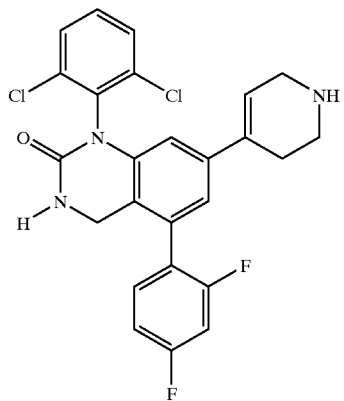
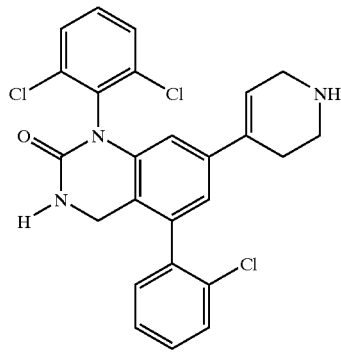
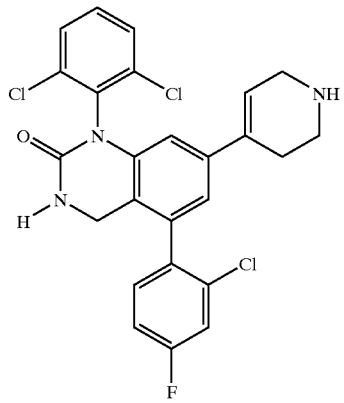
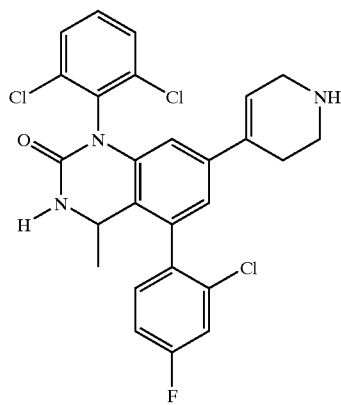
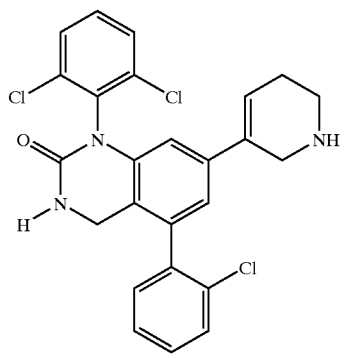

-continued
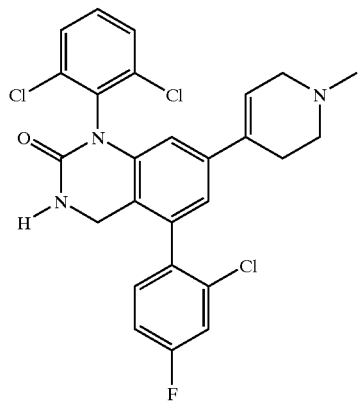
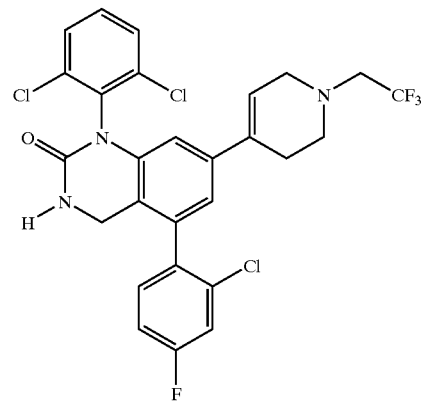
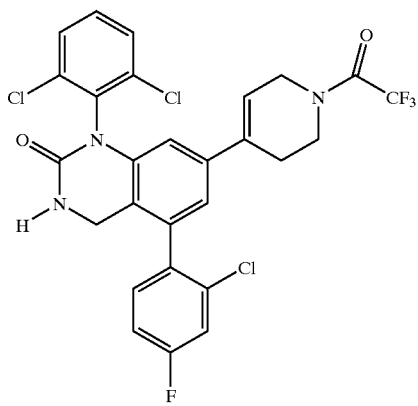
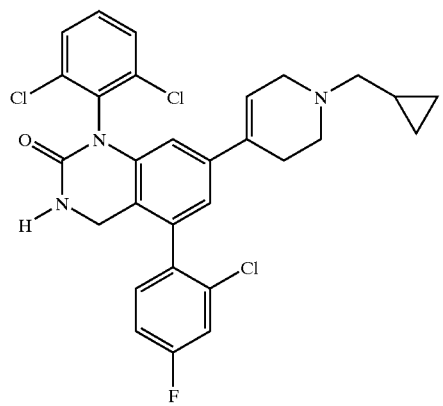
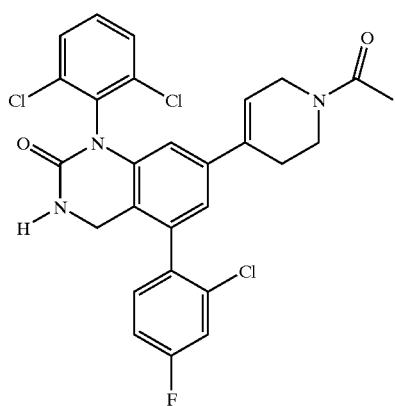
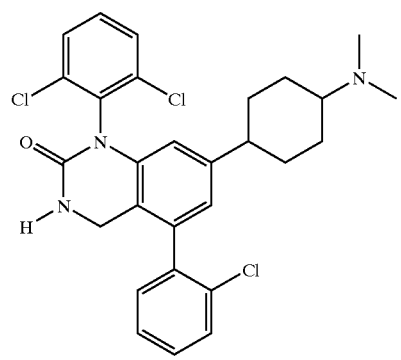

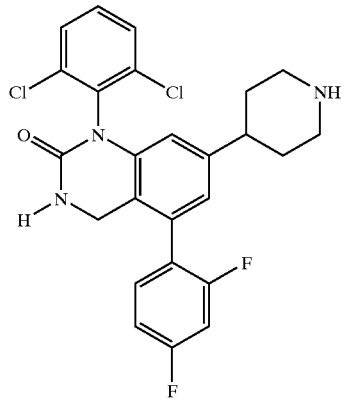
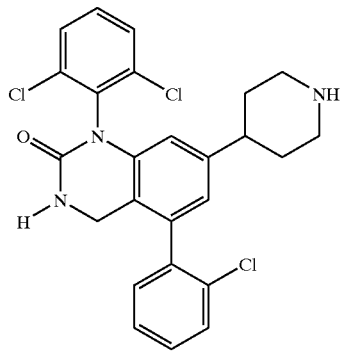
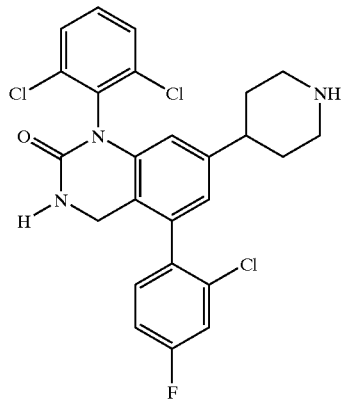
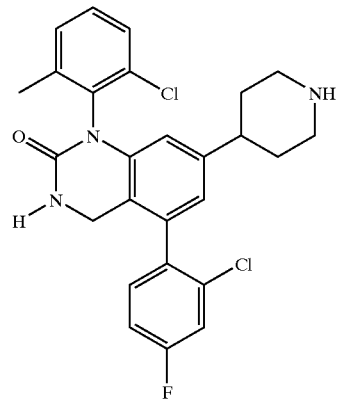
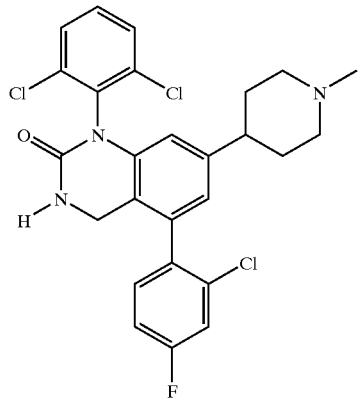
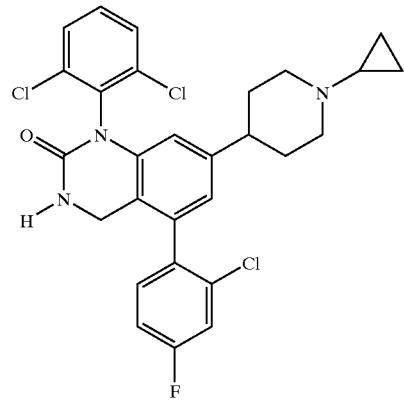
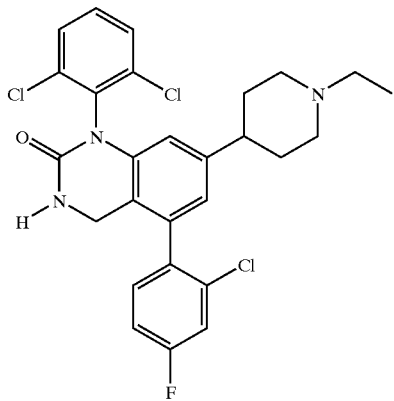
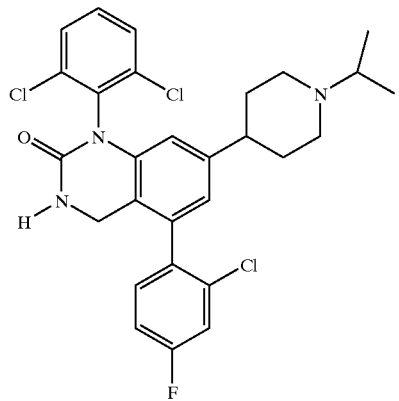

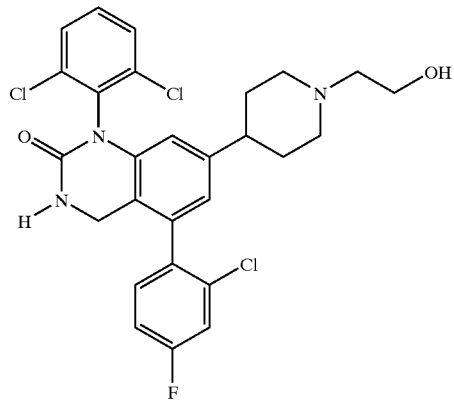
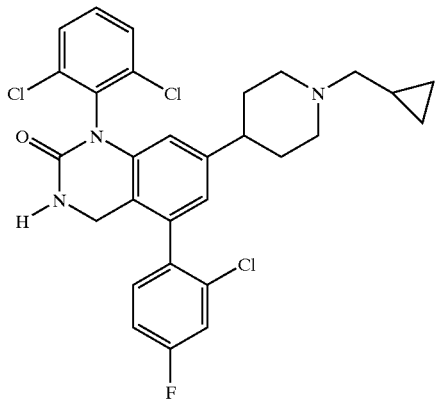
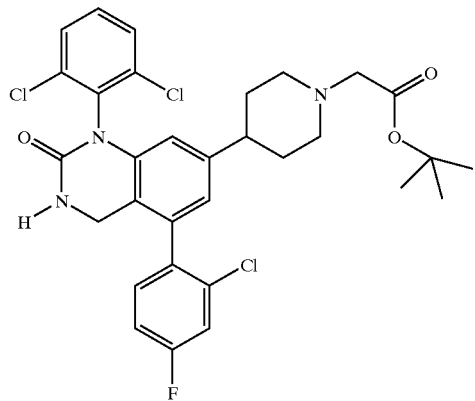
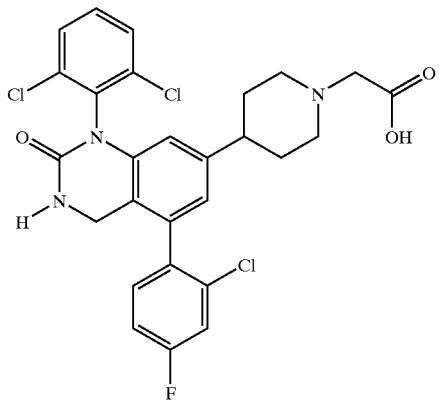
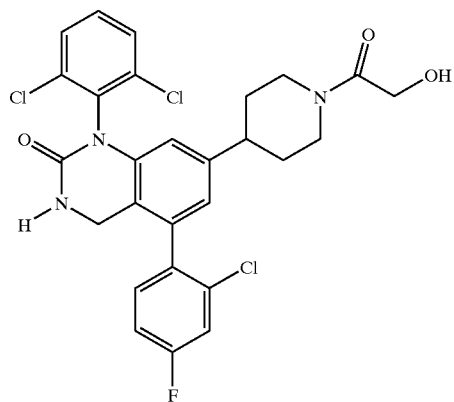
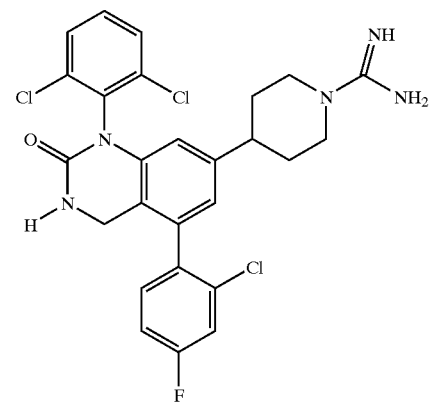
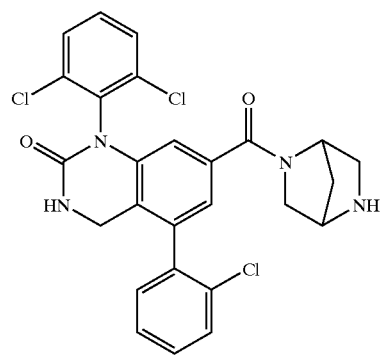
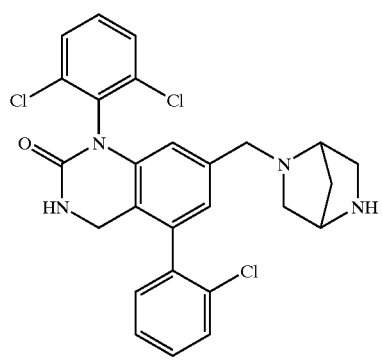

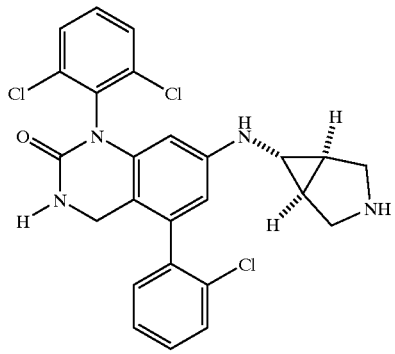
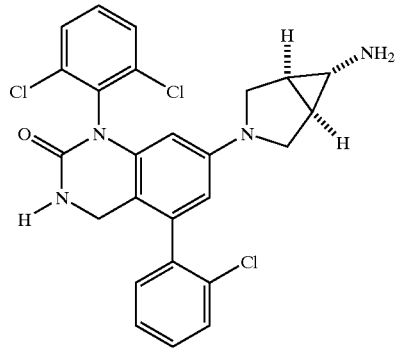
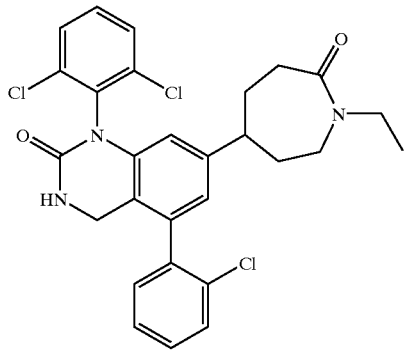
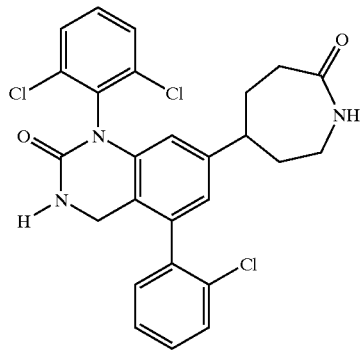
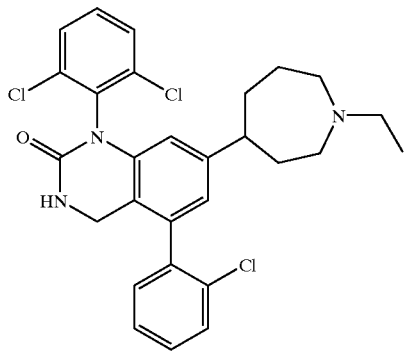
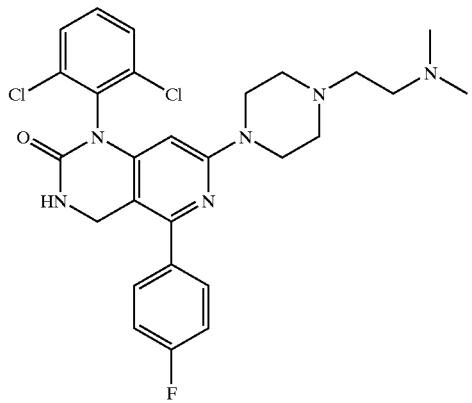
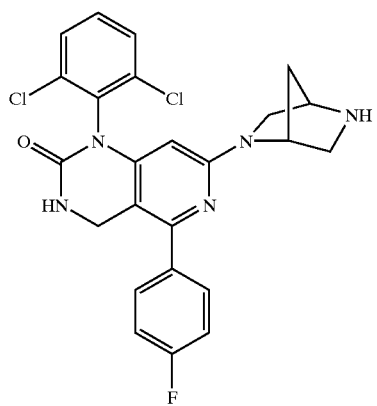
or a pharmaceutically acceptable salt thereof.

10. The compound according to claim 1, or a pharmaceutically acceptable salt thereof, wherein D is CH.

11. A compound described by the chemical formula (IIIA):

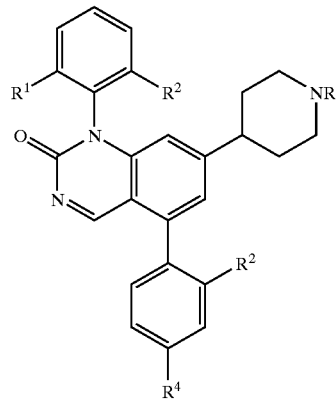

(IIIA)

or a pharmaceutically acceptable salt thereof.

12. The compound according to claim 1, or a pharmaceutically acceptable salt thereof, wherein A is O;

D is $CH_2$.

13. The compound according to claim 12 described by the chemical formula (IVA):

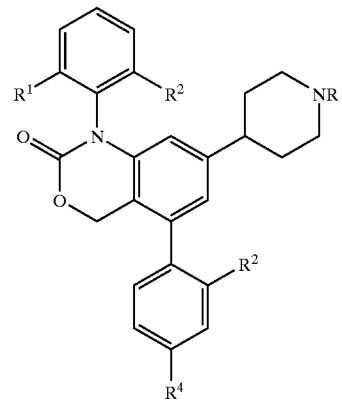

(IVA)

or a pharmaceutically acceptable salt thereof.

14. The compound according to claim 1, or a pharmaceutically acceptable salt thereof, wherein A is $CH_2$;

D is $CH_2$.

15. The compound according to claim 14, or a pharmaceutically acceptable salt thereof, wherein B is a direct bond.

16. The compound according to claim 14, or a pharmaceutically acceptable salt thereof, wherein B is $C_{0-3}$alkyl-O—$C_{0-3}$alkyl.

17. The compound according to claim 14 represented by

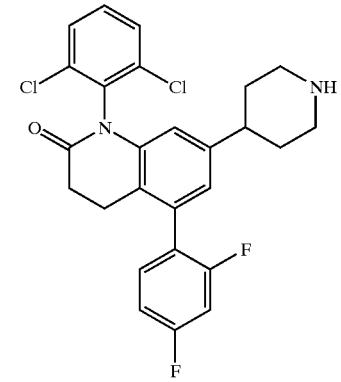
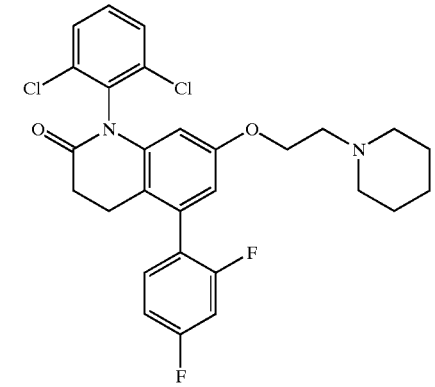
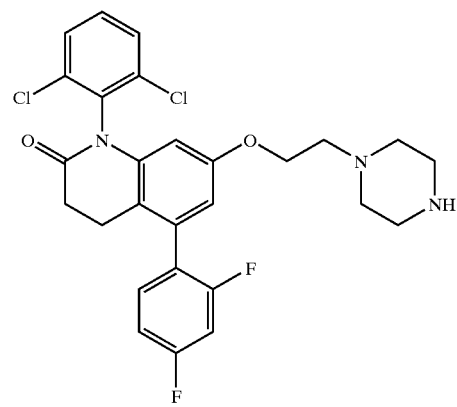
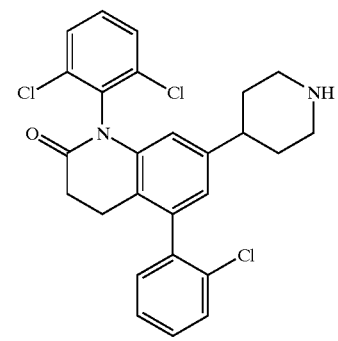

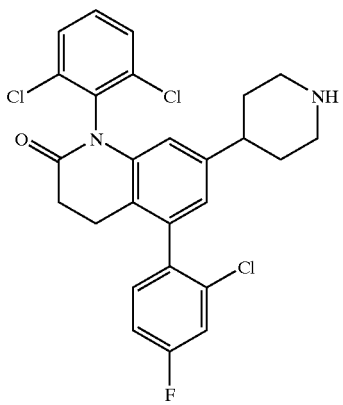
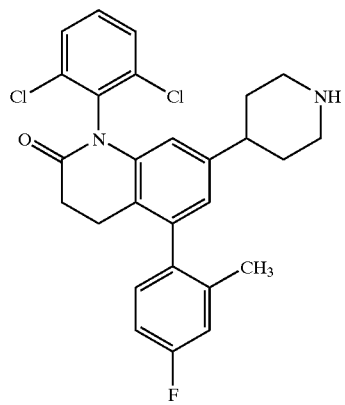
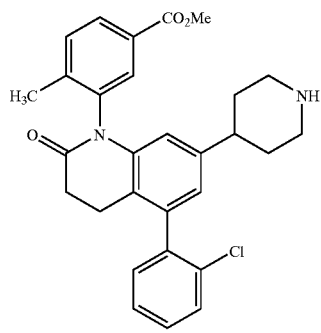

or a pharmaceutically acceptable salt thereof.

18. The compound according to claim 1, or a pharmaceutically acceptable salt thereof, wherein A is CH;
D is CH.

19. The compound according to claim 18, or a pharmaceutically acceptable salt thereof, wherein
B is a direct bond.

20. The compound according to claim 18, or a pharmaceutically acceptable salt thereof, wherein
B is $C_{0-3}$alkyl-O—$C_{0-3}$alkyl.

21. The compound according to claim 18 comprising

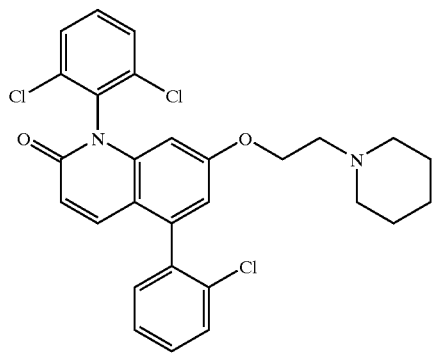
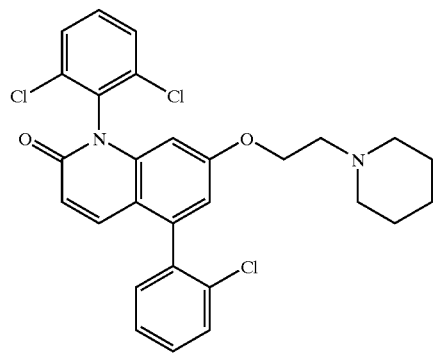

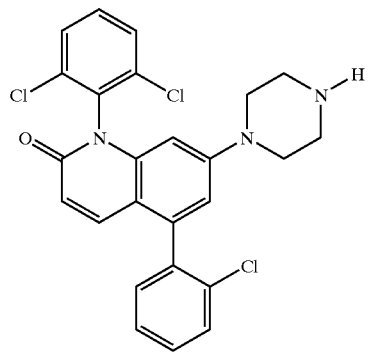
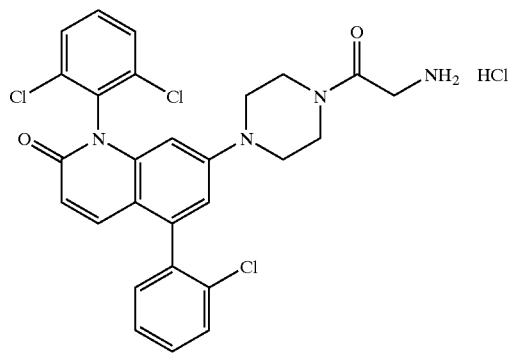
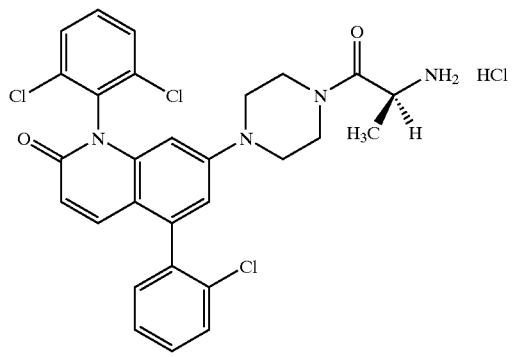
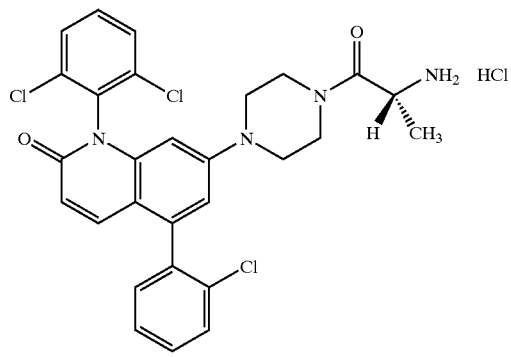
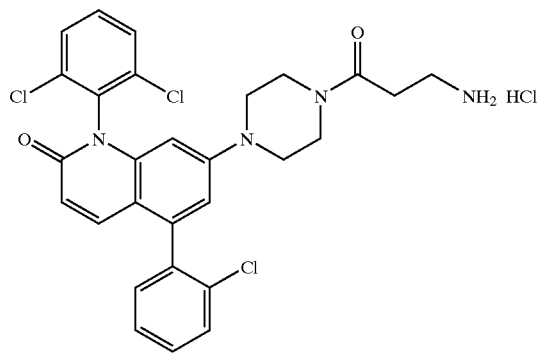
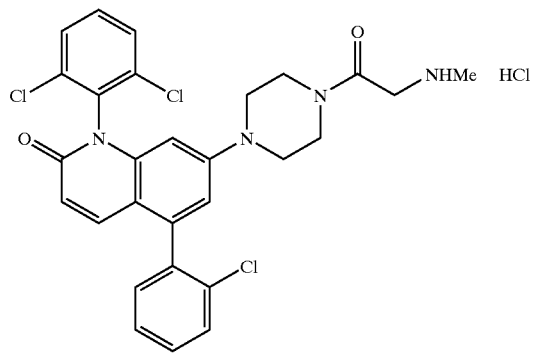
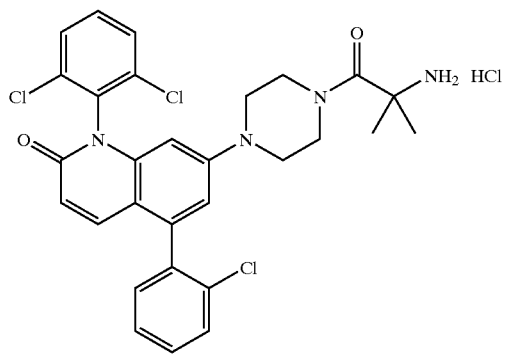

or a pharmaceutically acceptable salt thereof.
22. A compound represented by
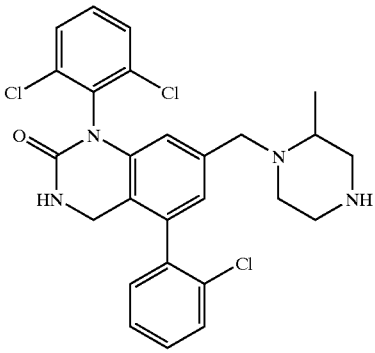
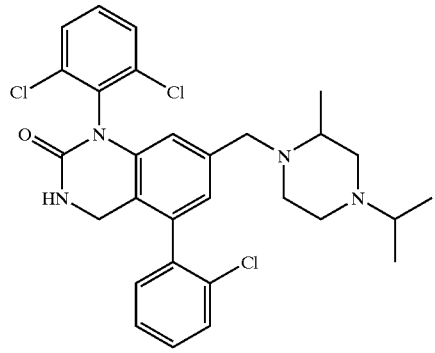
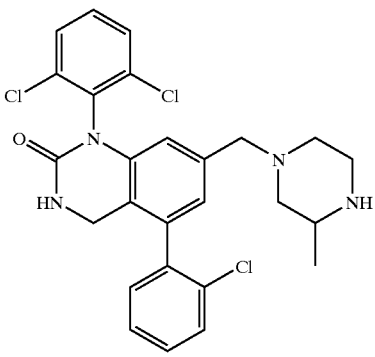
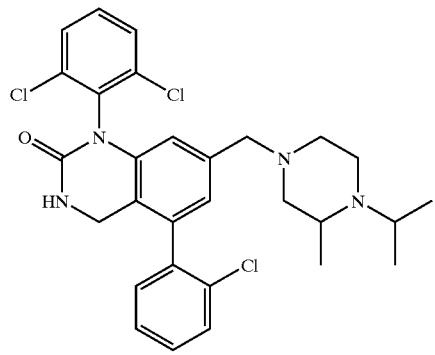
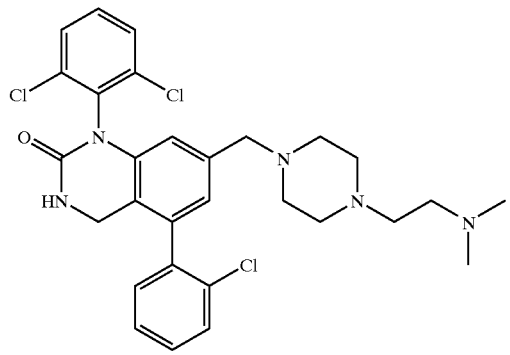
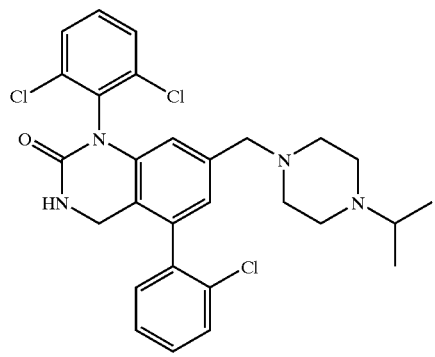
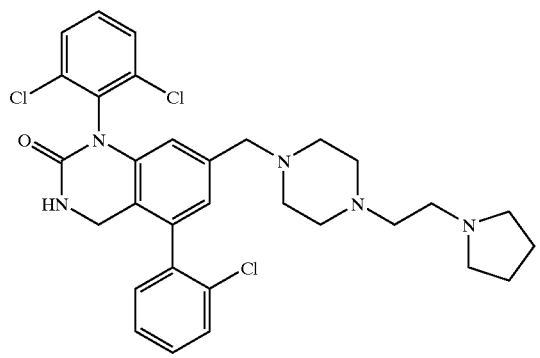
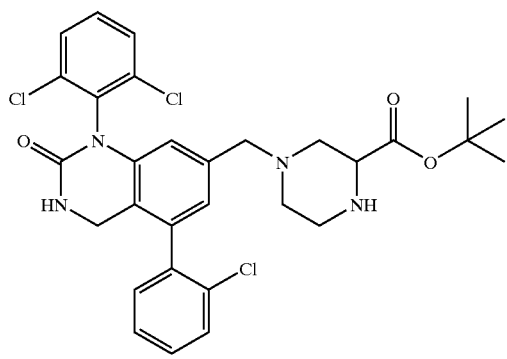

-continued
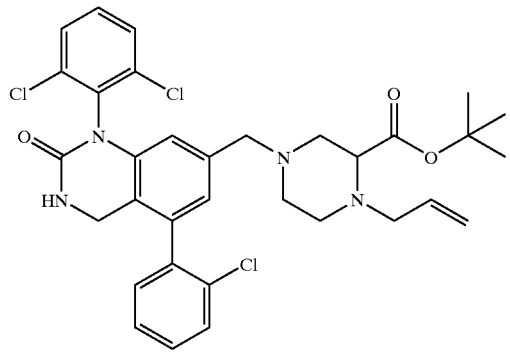
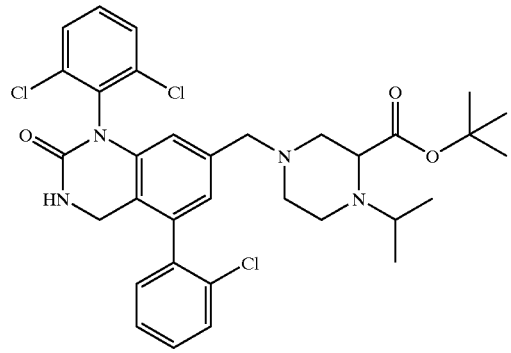
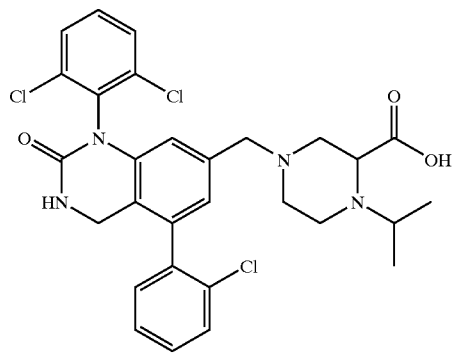
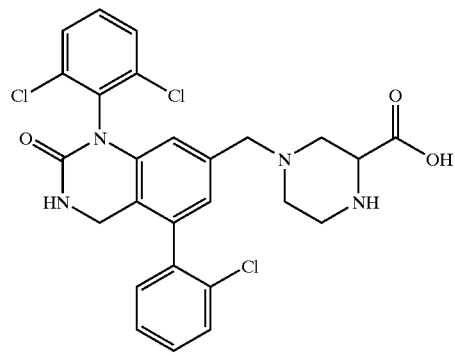
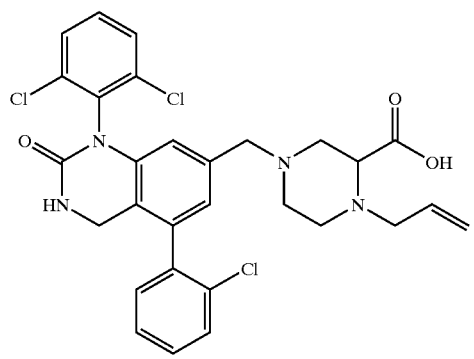
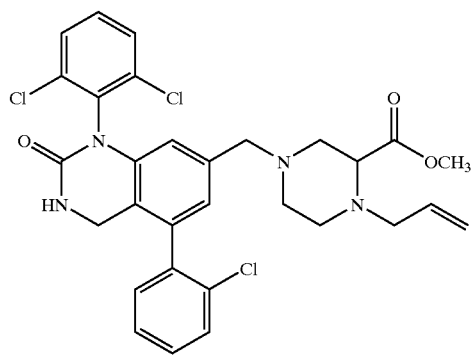
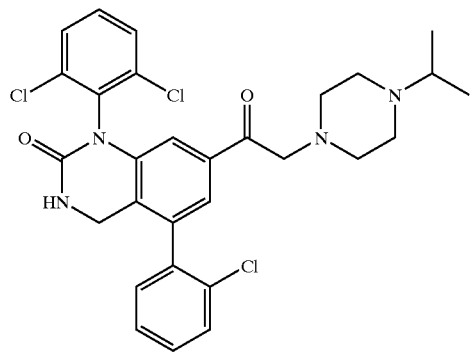
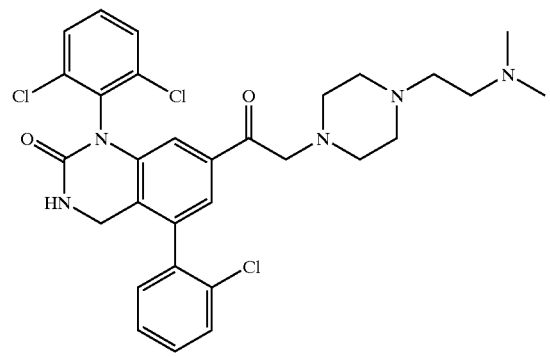

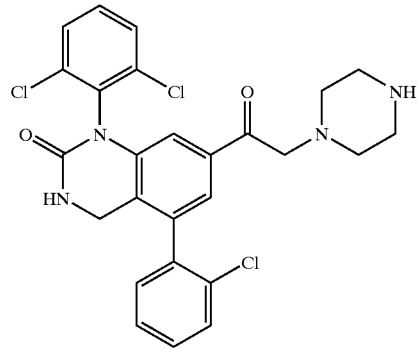
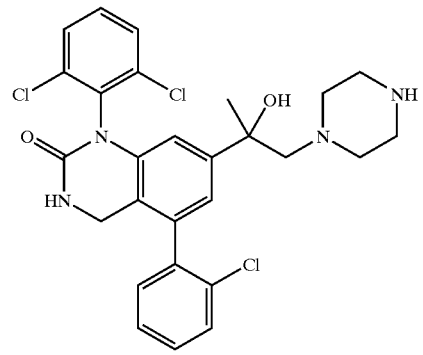
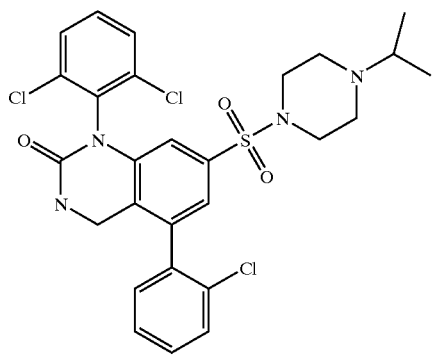
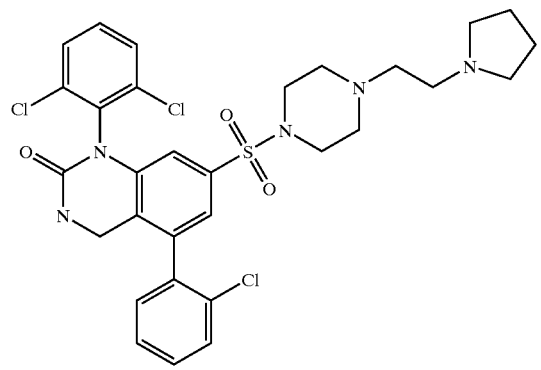
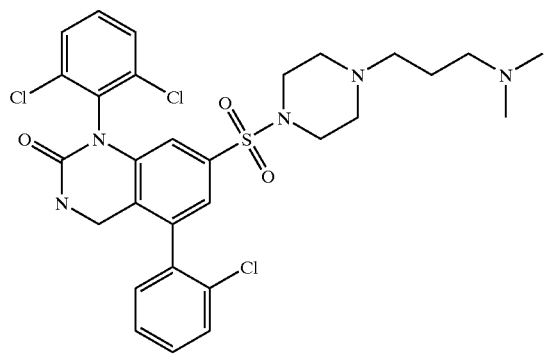
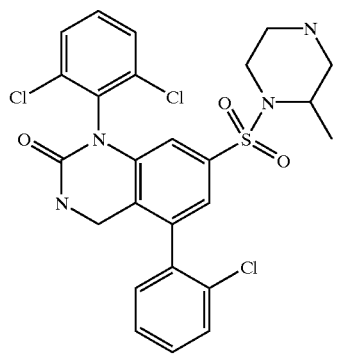
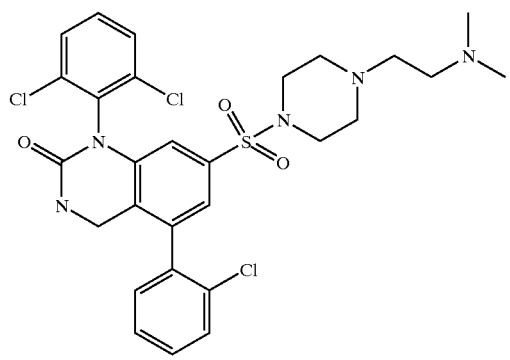
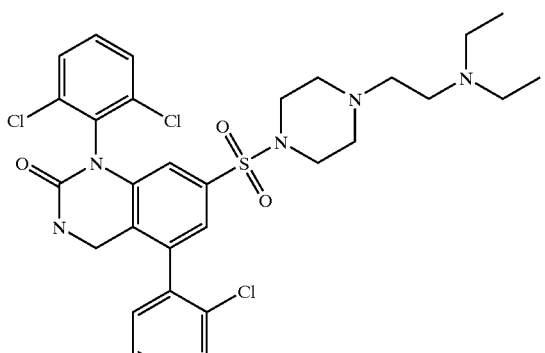

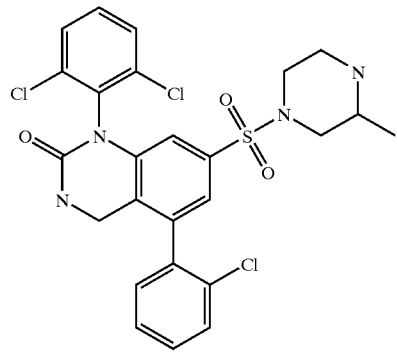
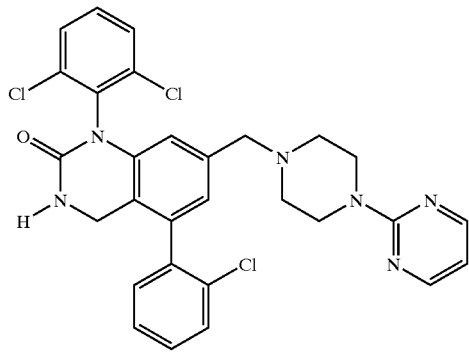
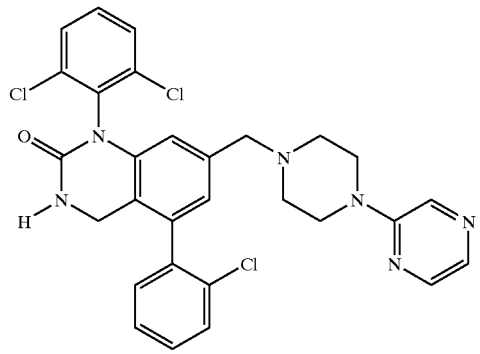
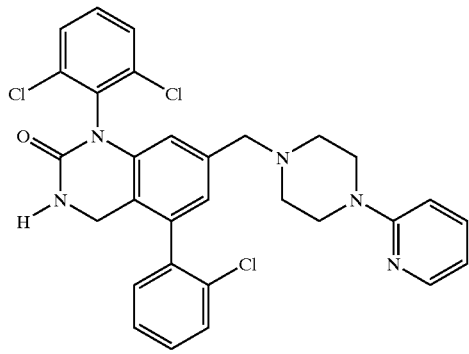
or a pharmaceutically acceptable salt thereof.
23. A compound represented by
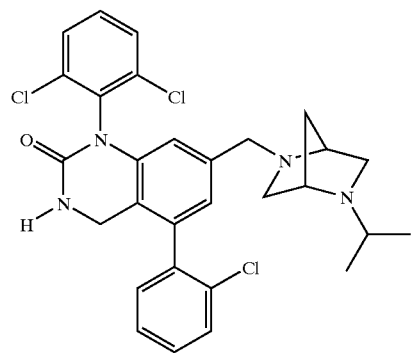
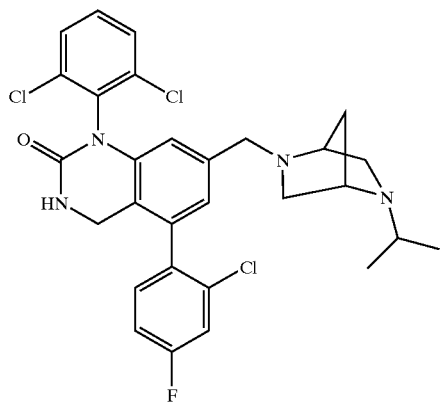

-continued
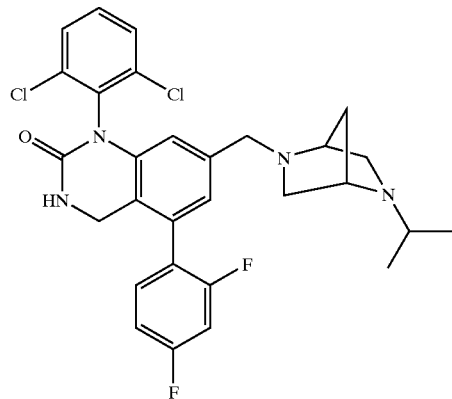
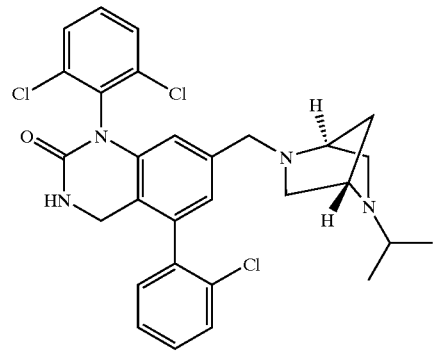
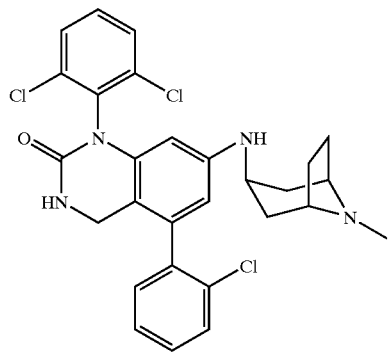
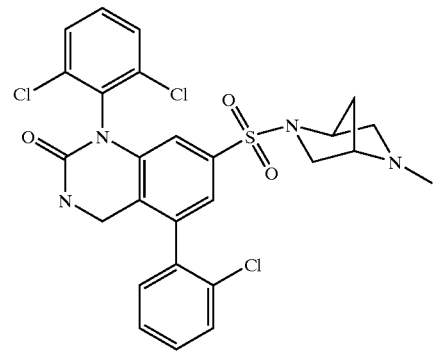
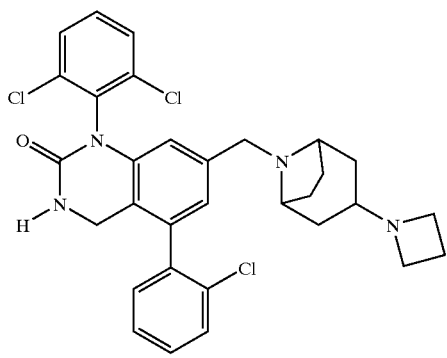
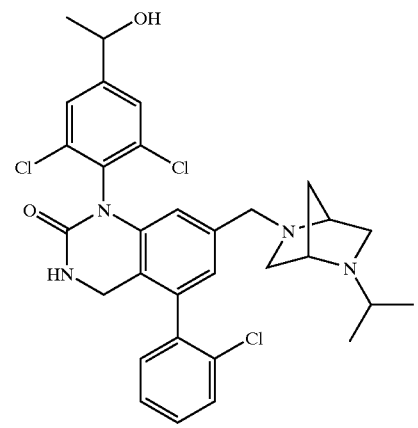
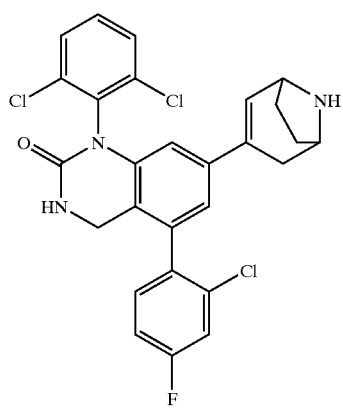
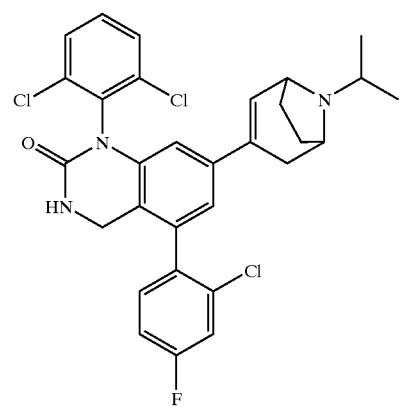

| 397 | 398 |
|---|---|
| 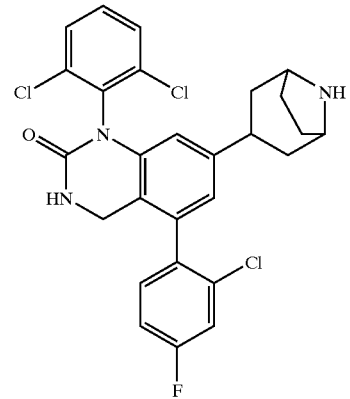 | 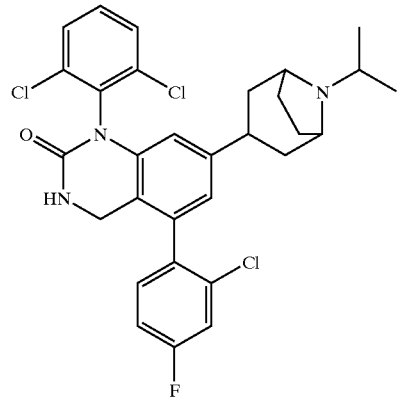 |
| 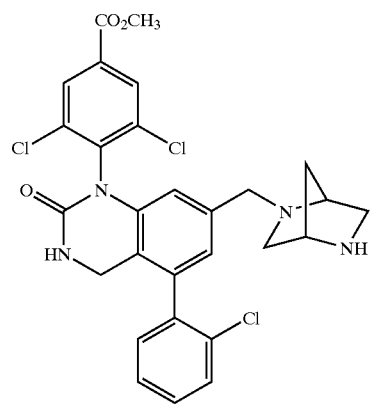 | 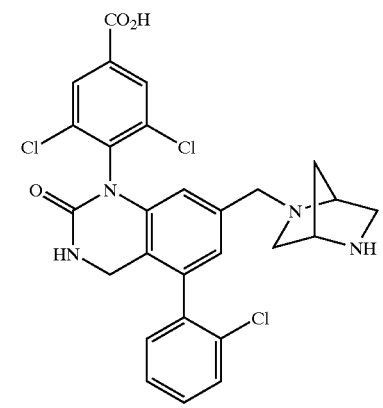 |
| 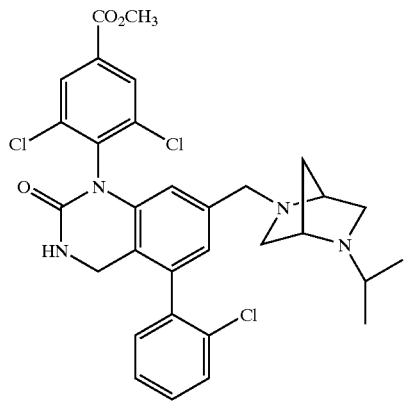 | 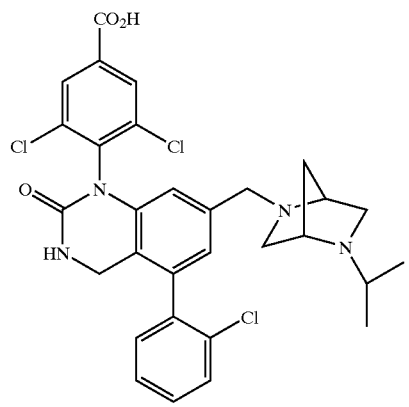 |
| 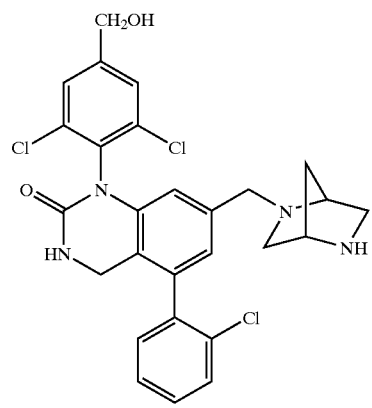 | 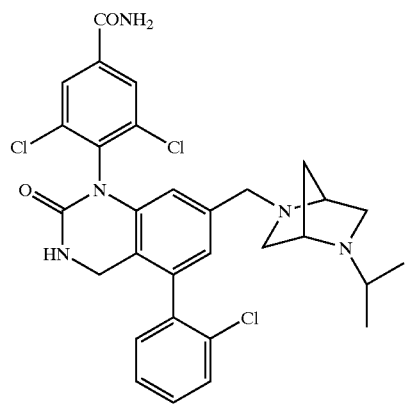 |

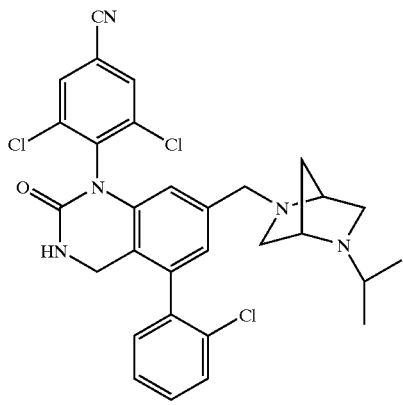
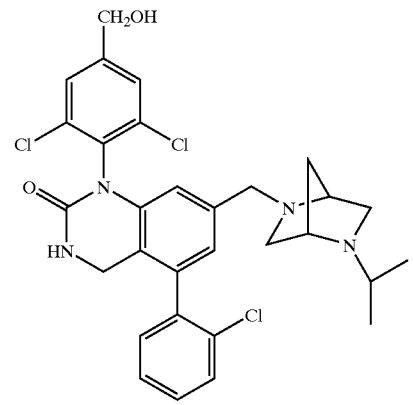
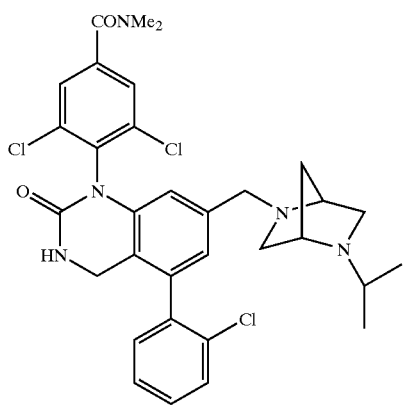
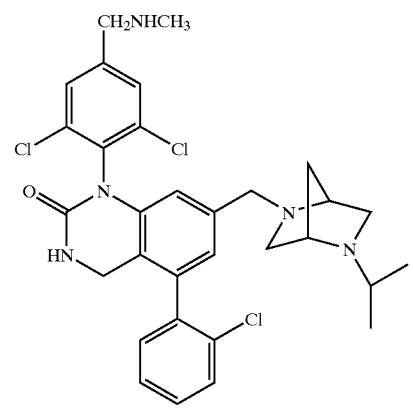
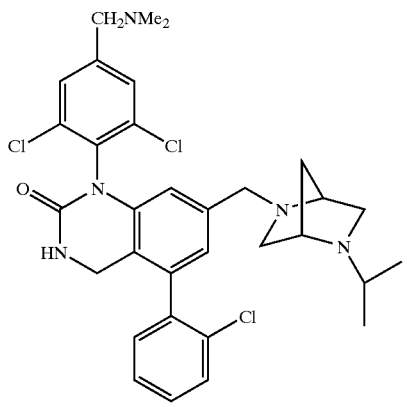
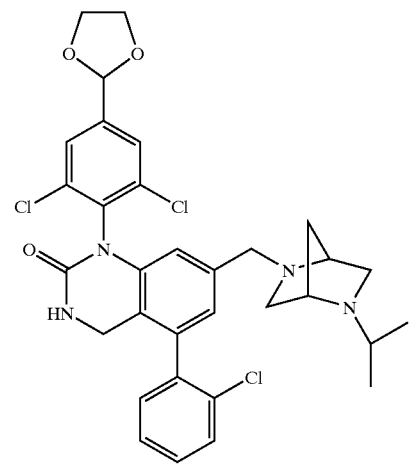

401
or a pharmaceutically acceptable salt thereof.
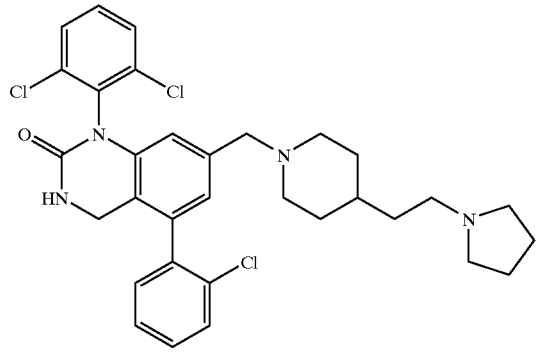
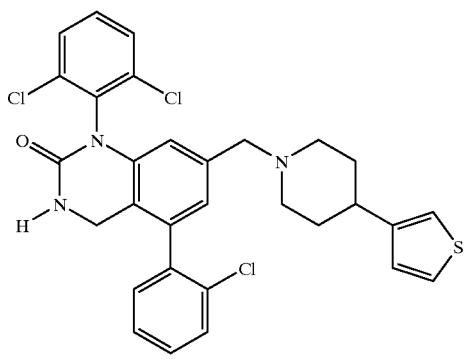
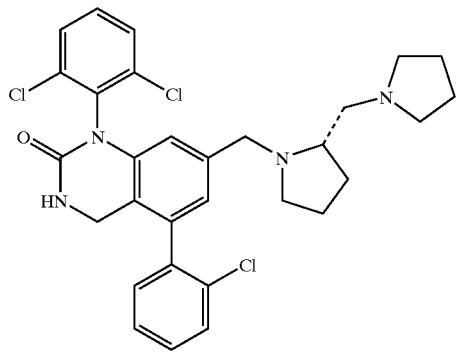
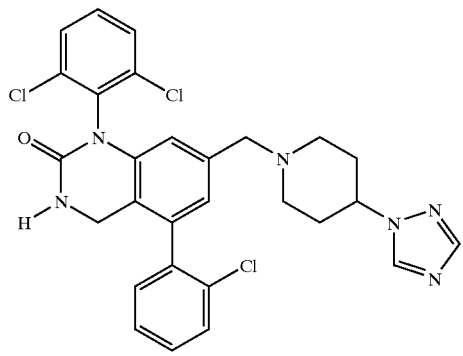
402
24. A compound represented by
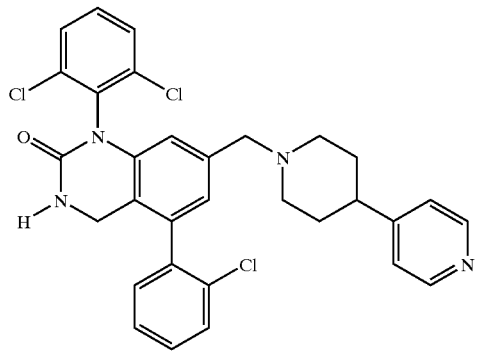
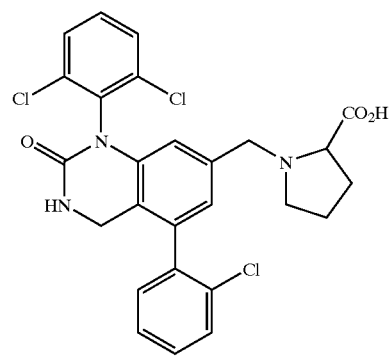
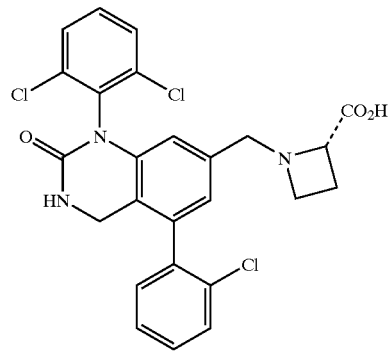
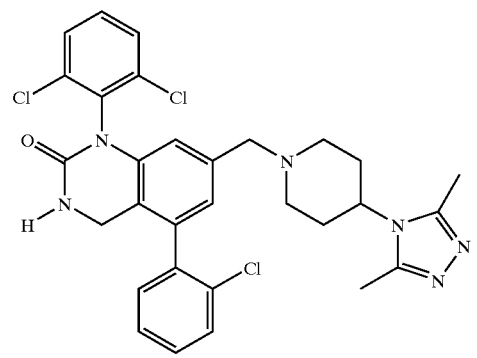

-continued
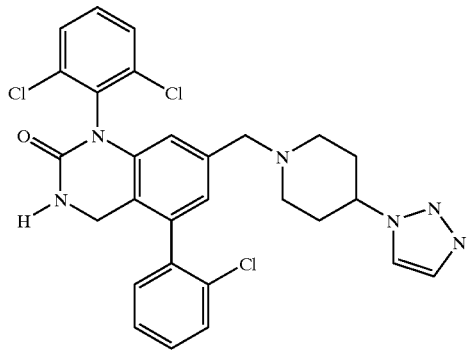
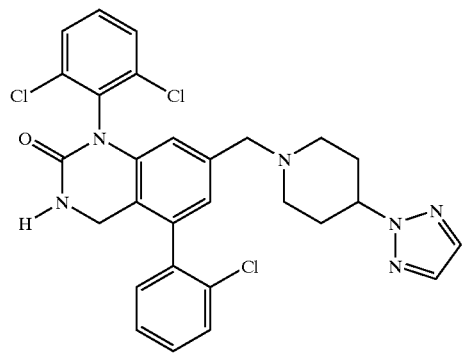
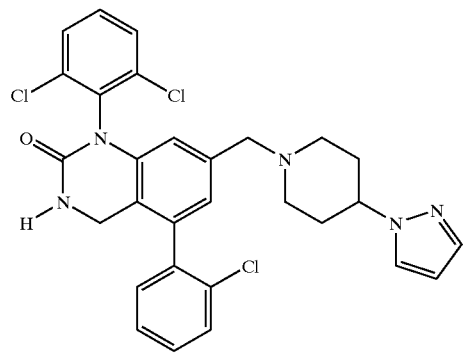
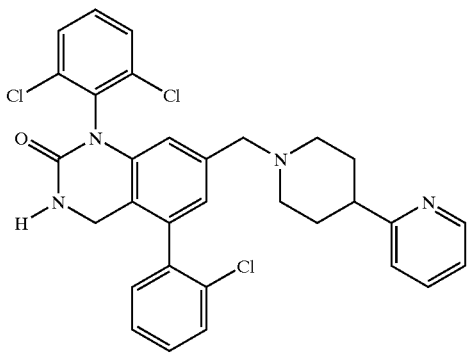
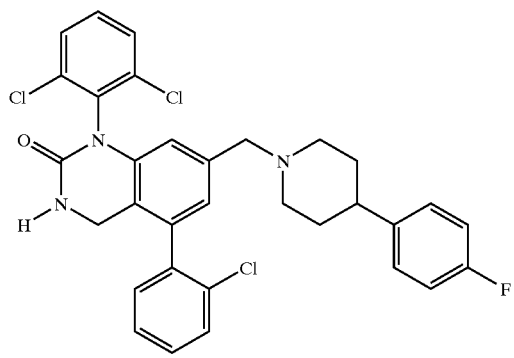
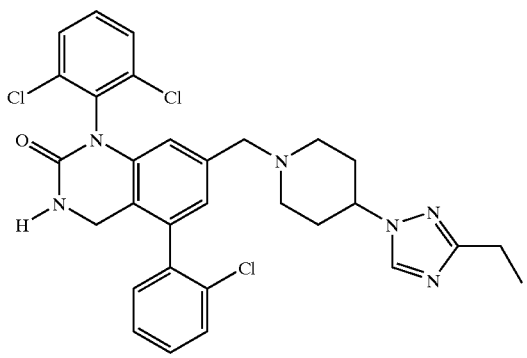
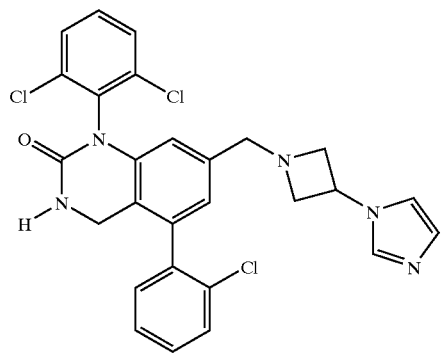
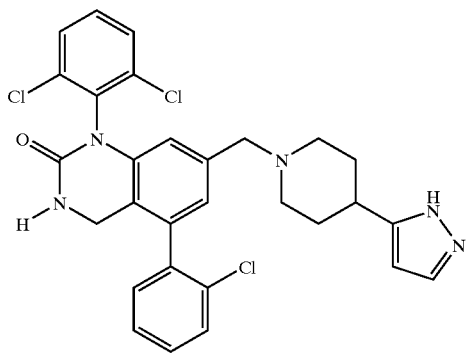

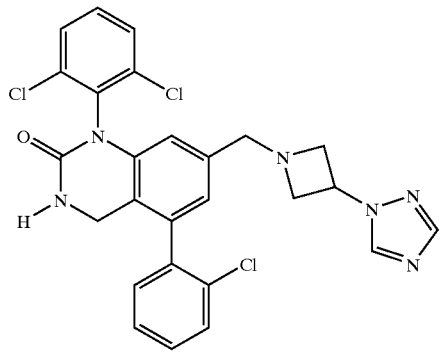
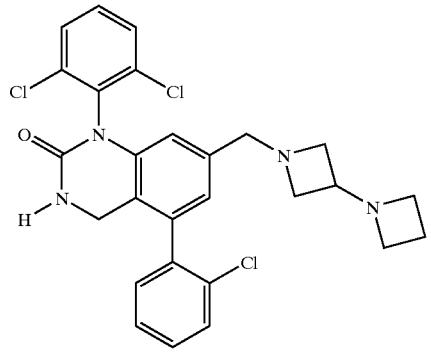
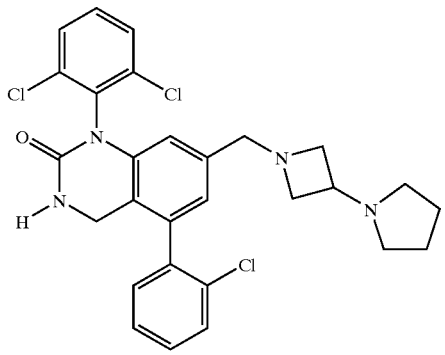
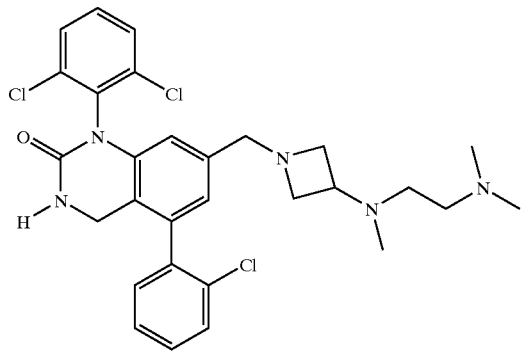
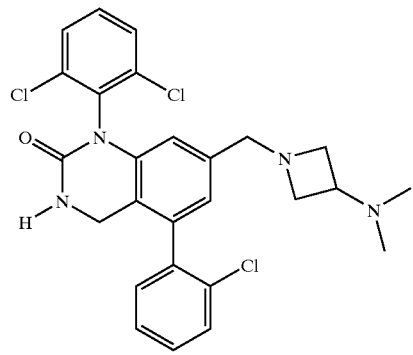
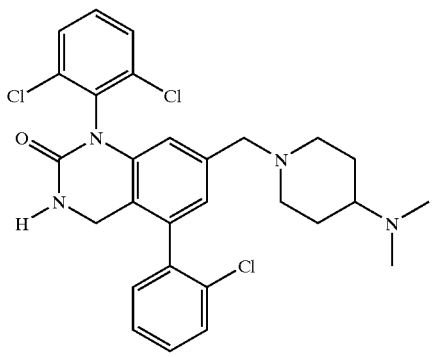
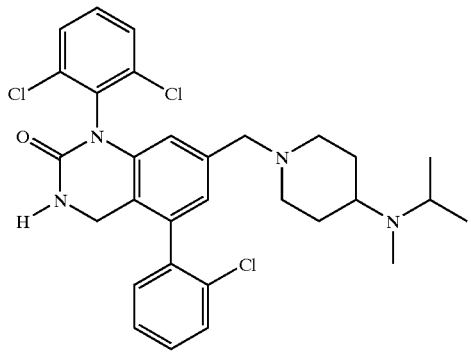
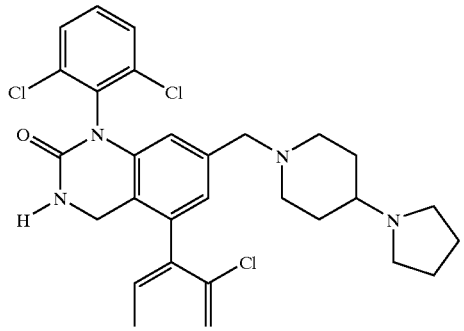

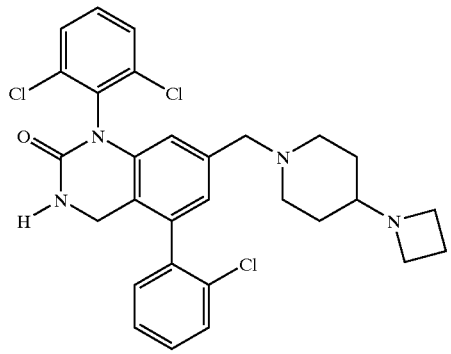
or a pharmaceutically acceptable salt thereof.
25. A compound represented by
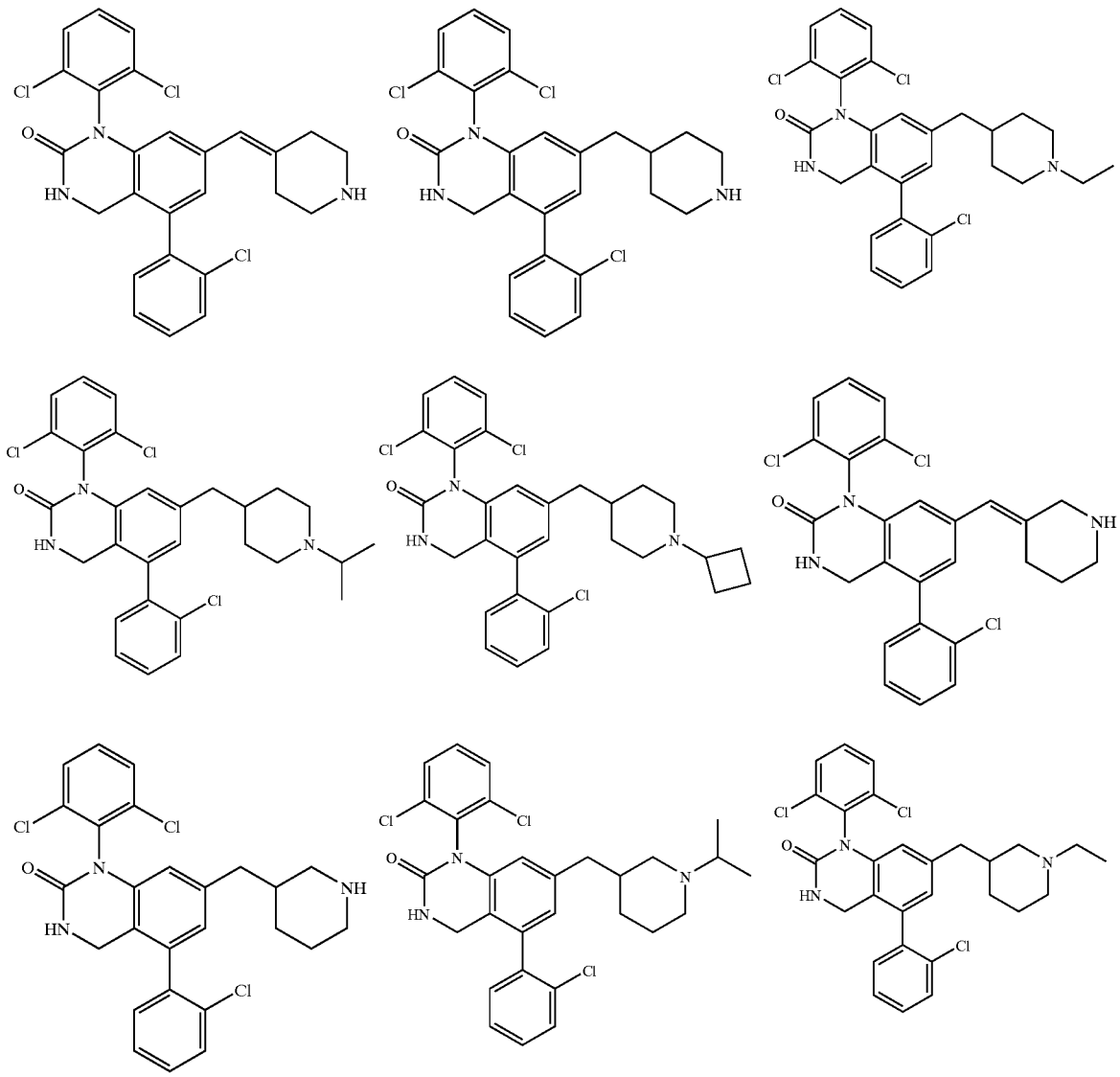

-continued
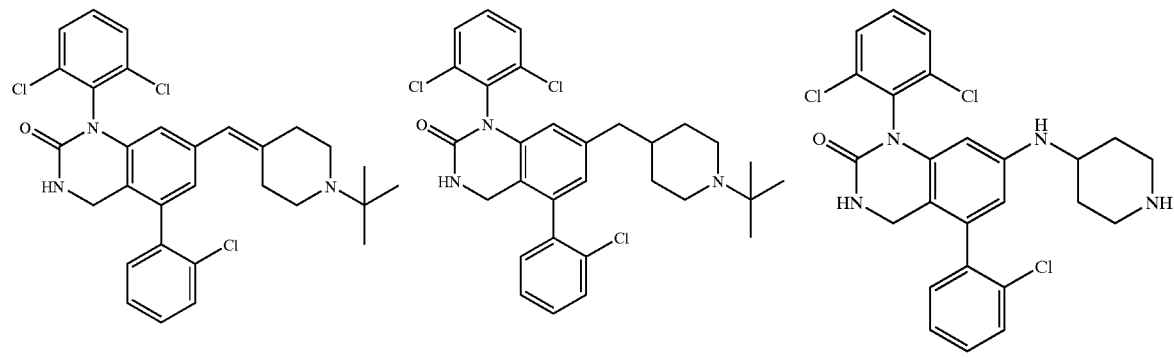
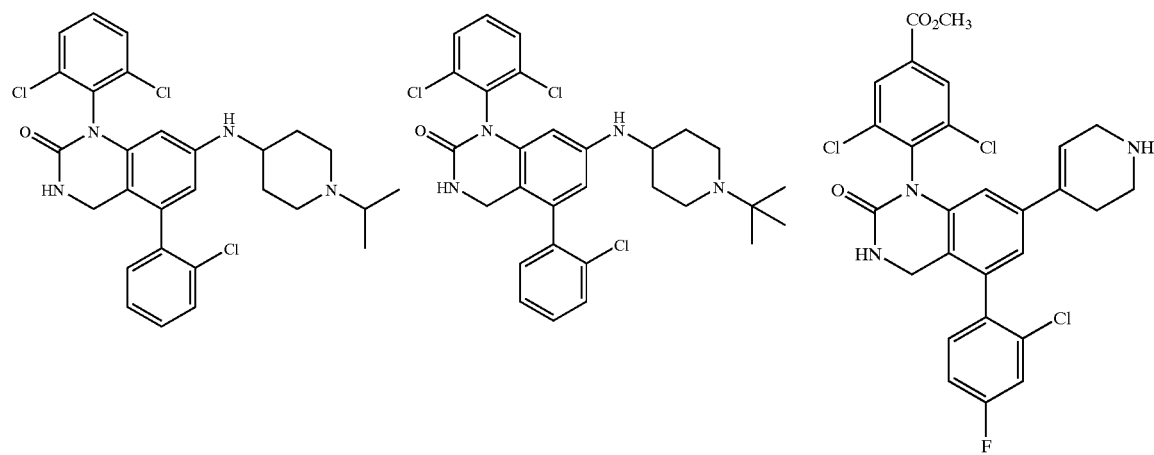
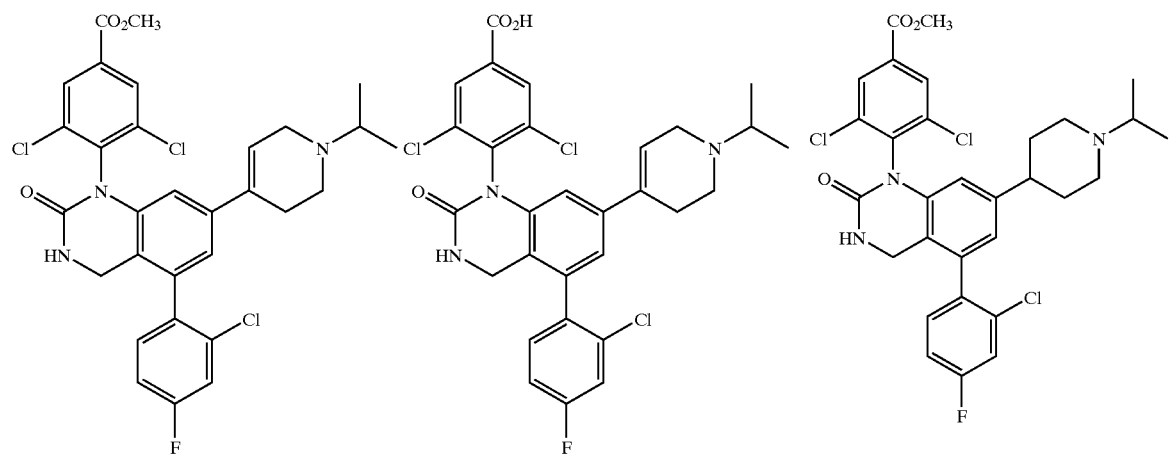

411
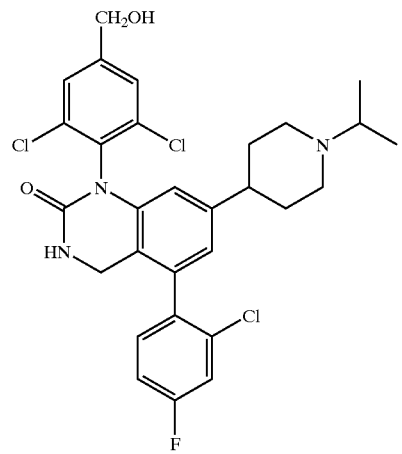
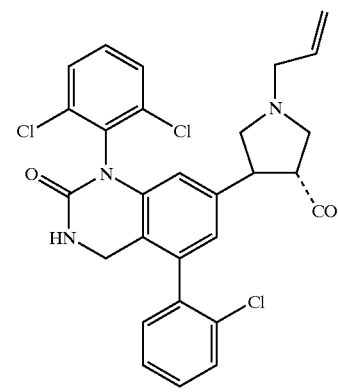
412
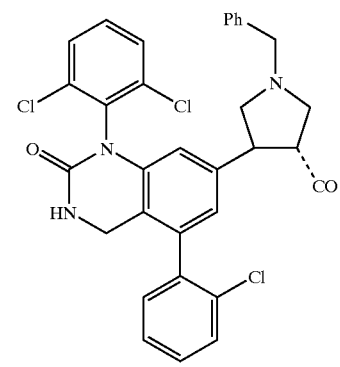
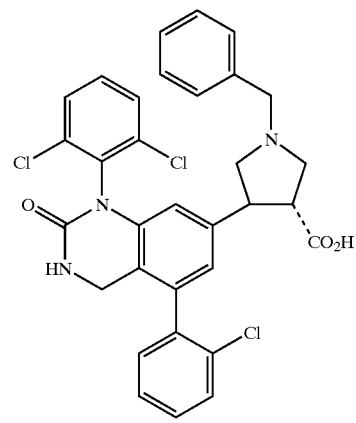
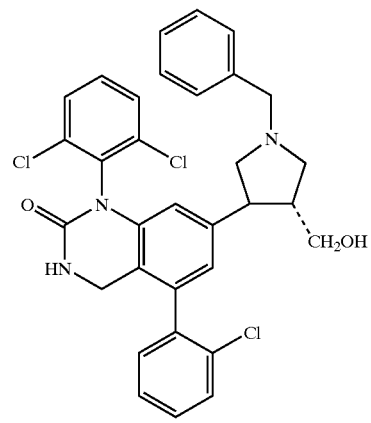
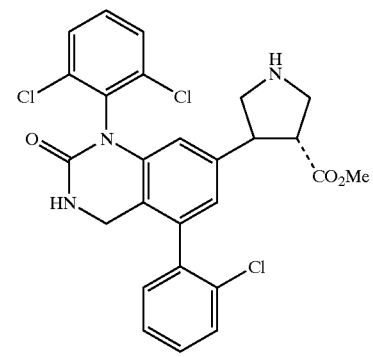
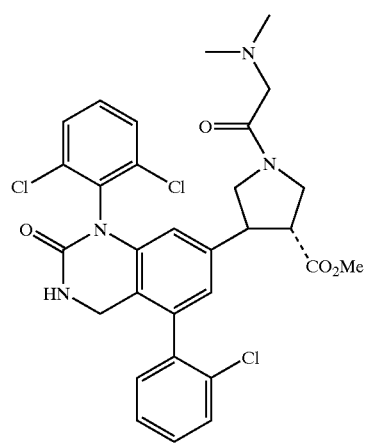
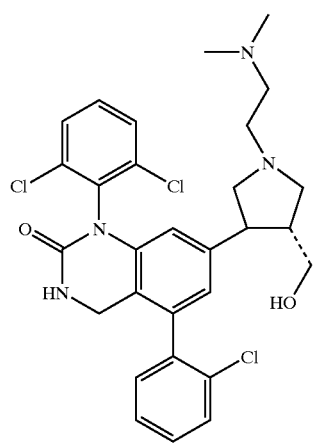
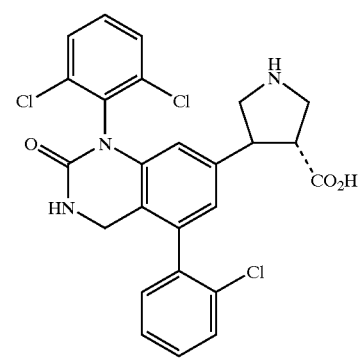

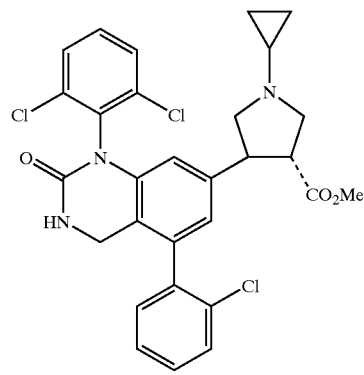
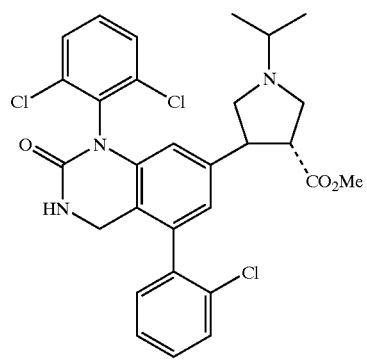
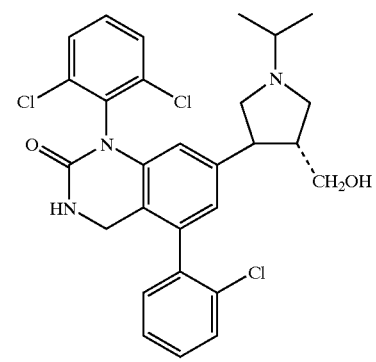
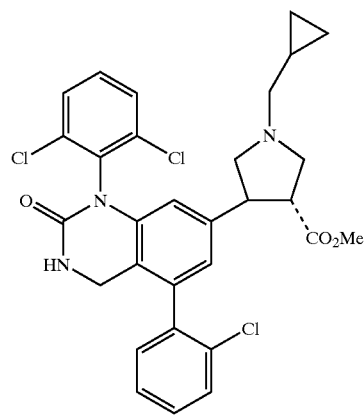
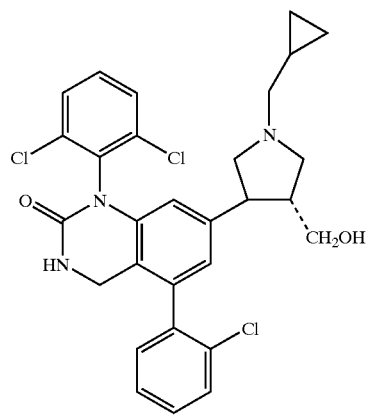
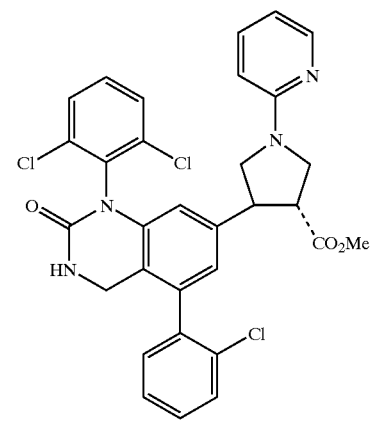
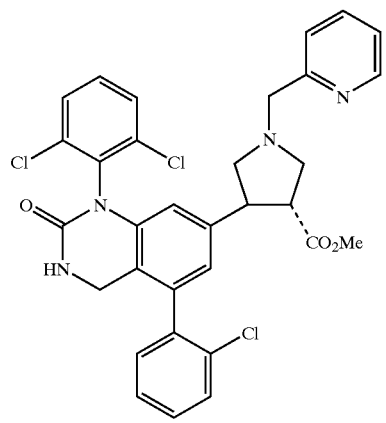
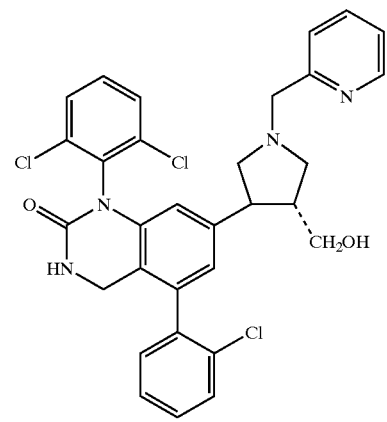
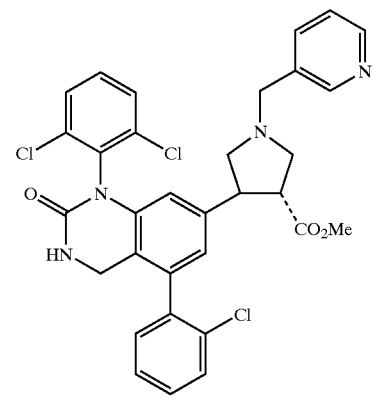

-continued
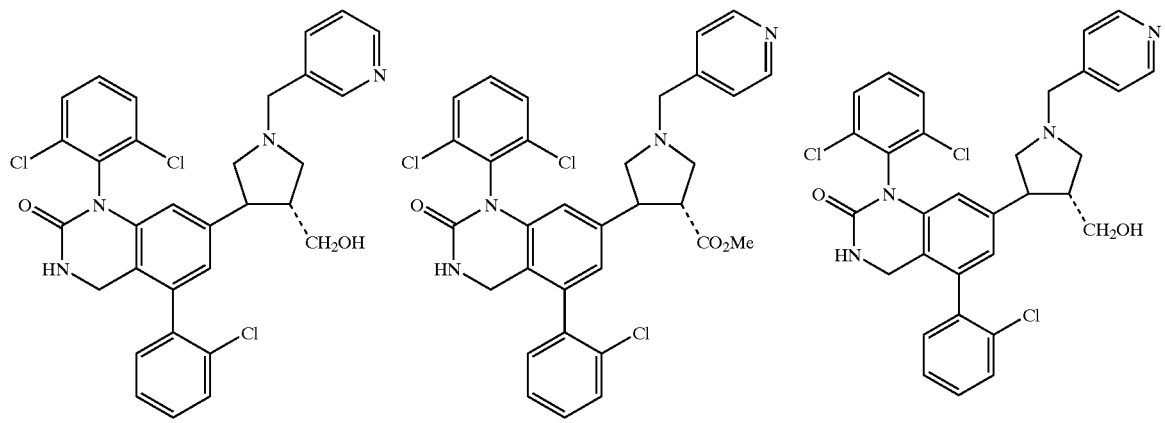
or a pharmaceutically acceptable salt thereof.
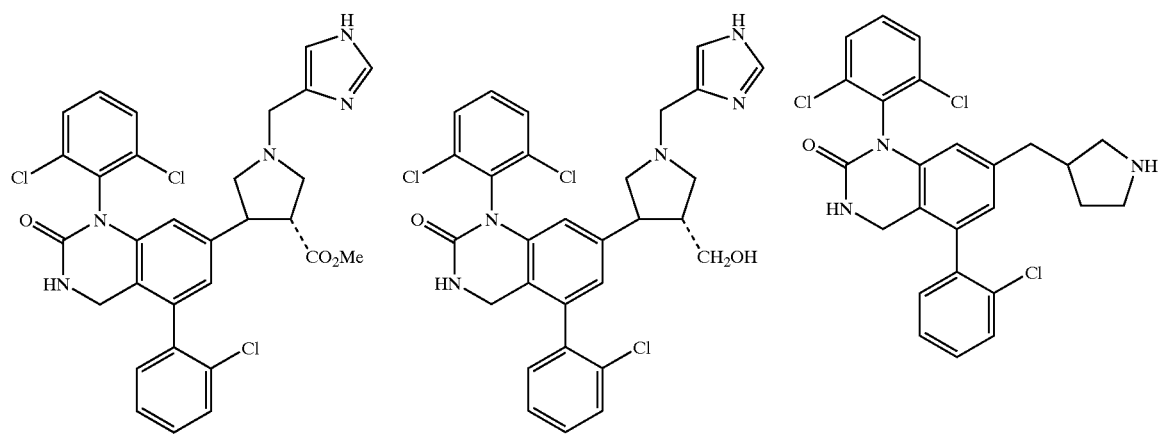
26. A compound represented by
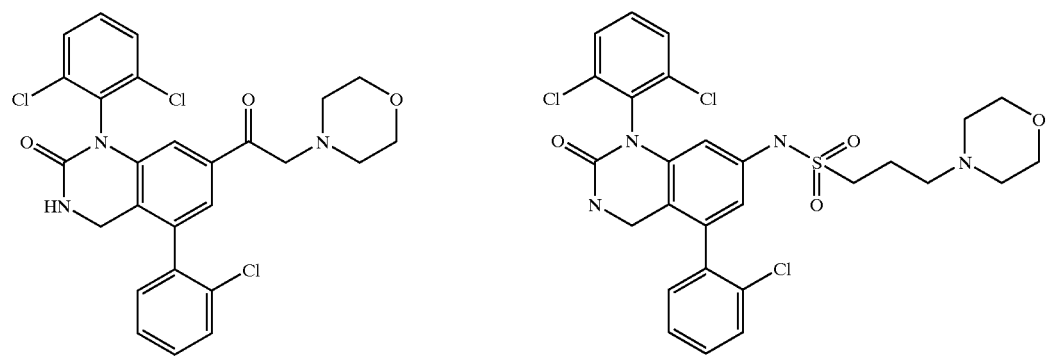

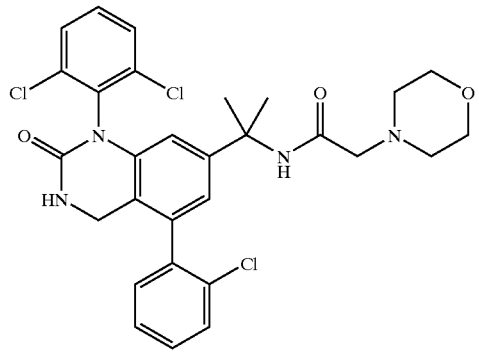
or a pharmaceutically acceptable salt thereof.
27. A compound represented by
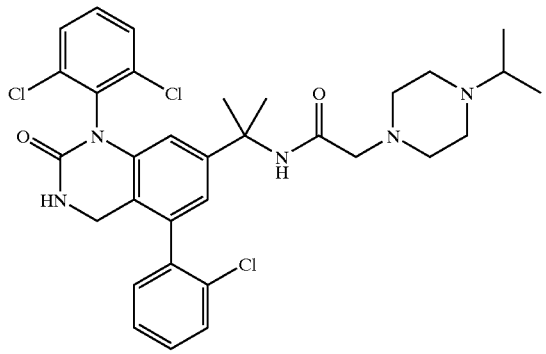
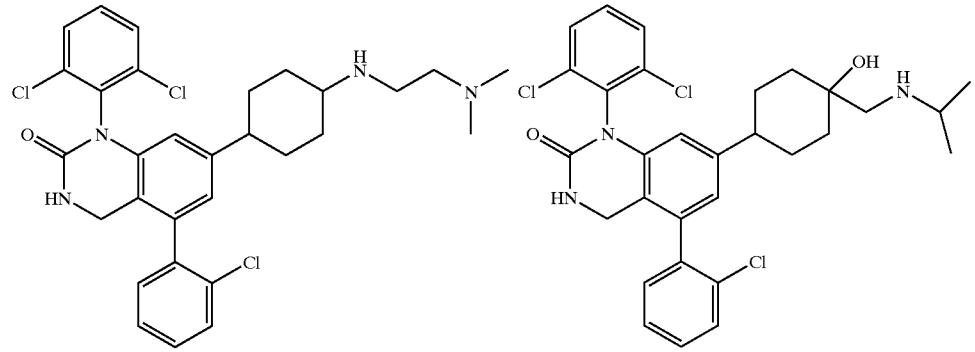
or a pharmaceutically acceptable salt thereof.
28. The compound according to claim 14 represented by
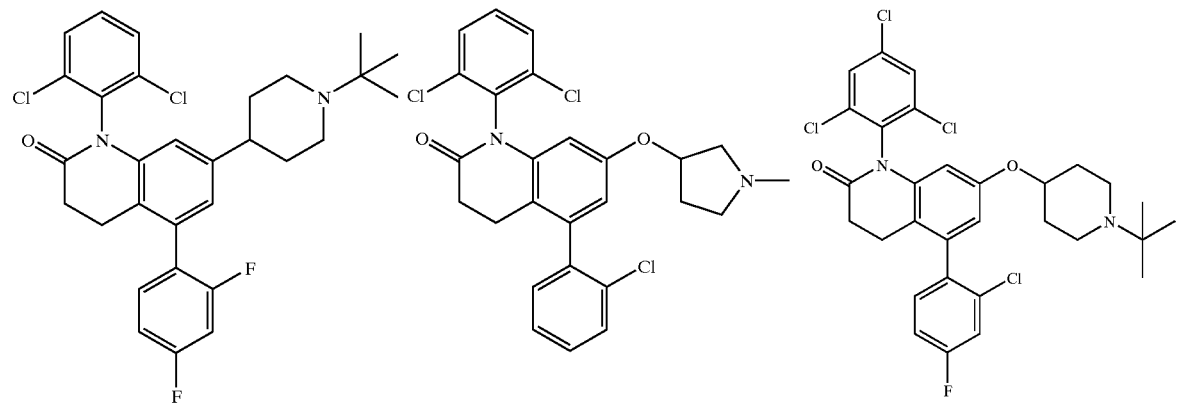

-continued
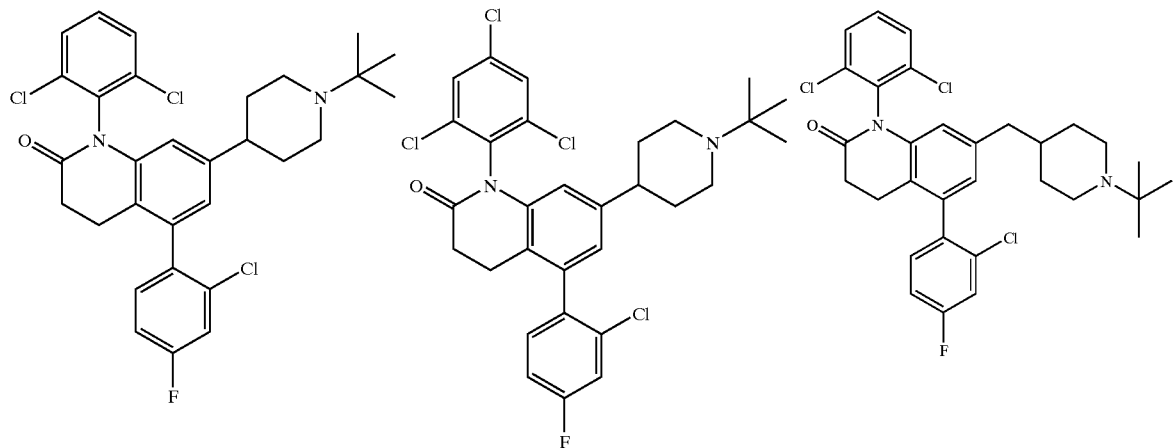
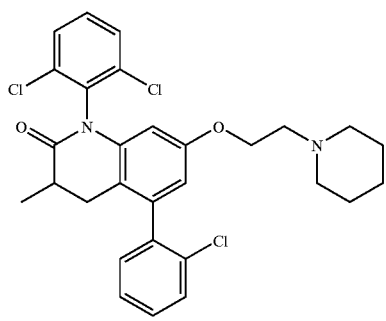
or a pharmaceutically acceptable salt thereof.
29. The compound according to claim 18 represented by
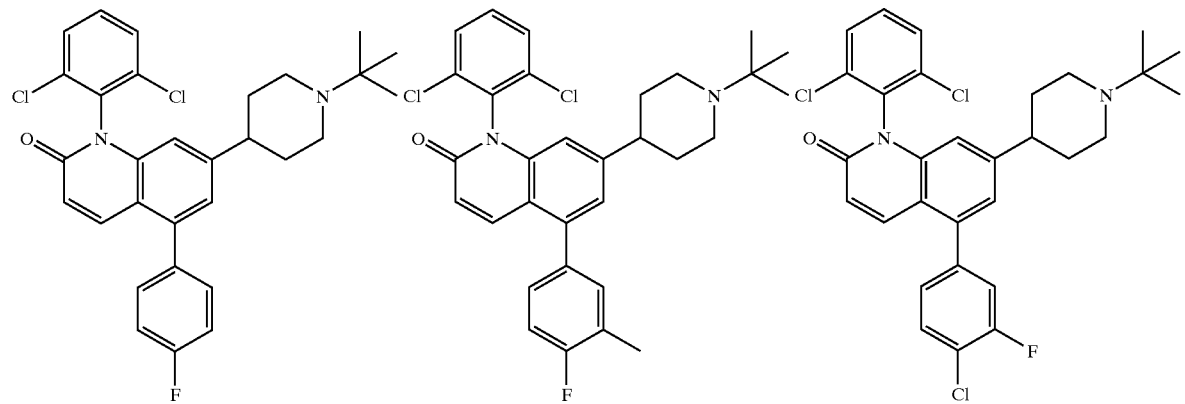

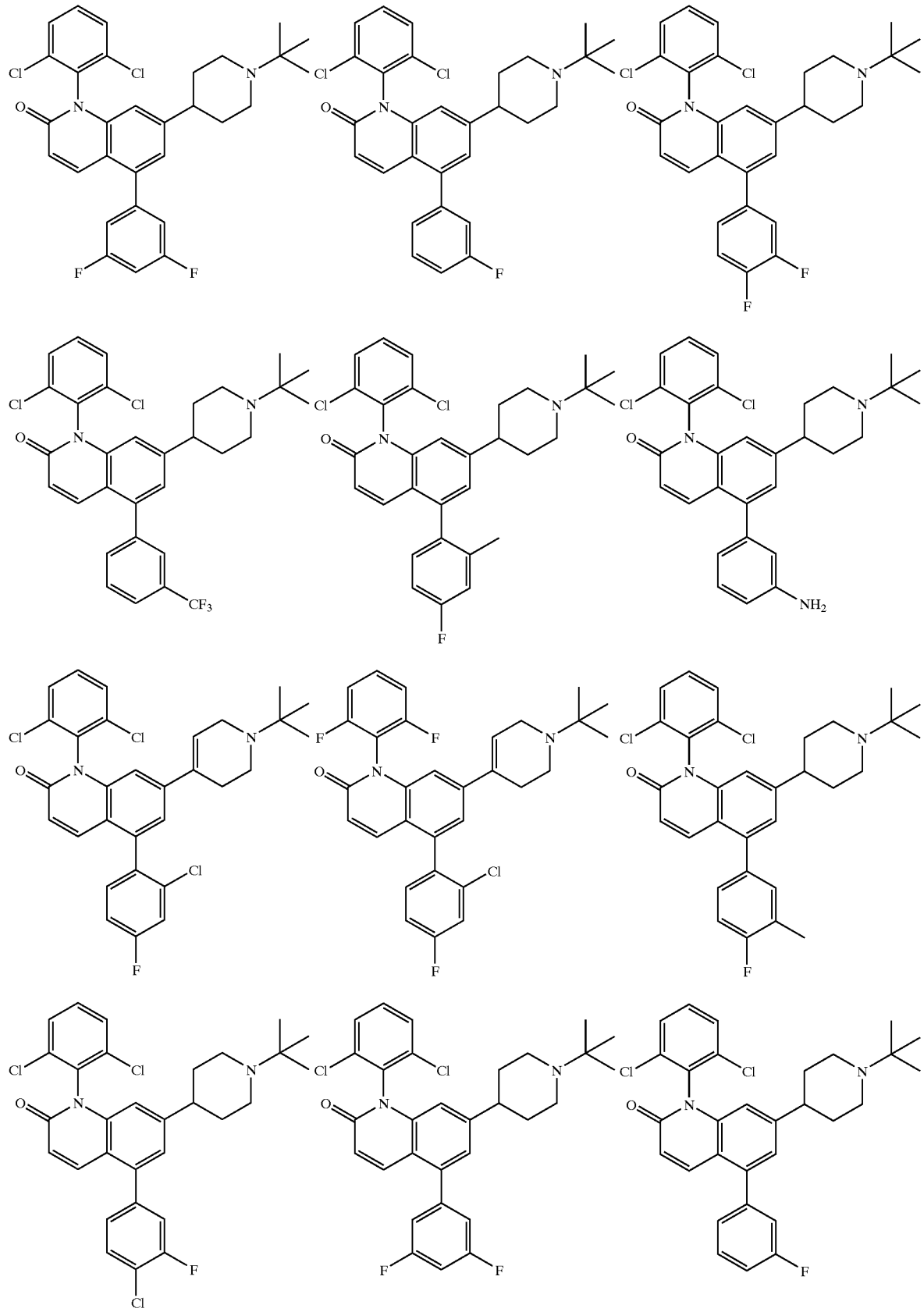

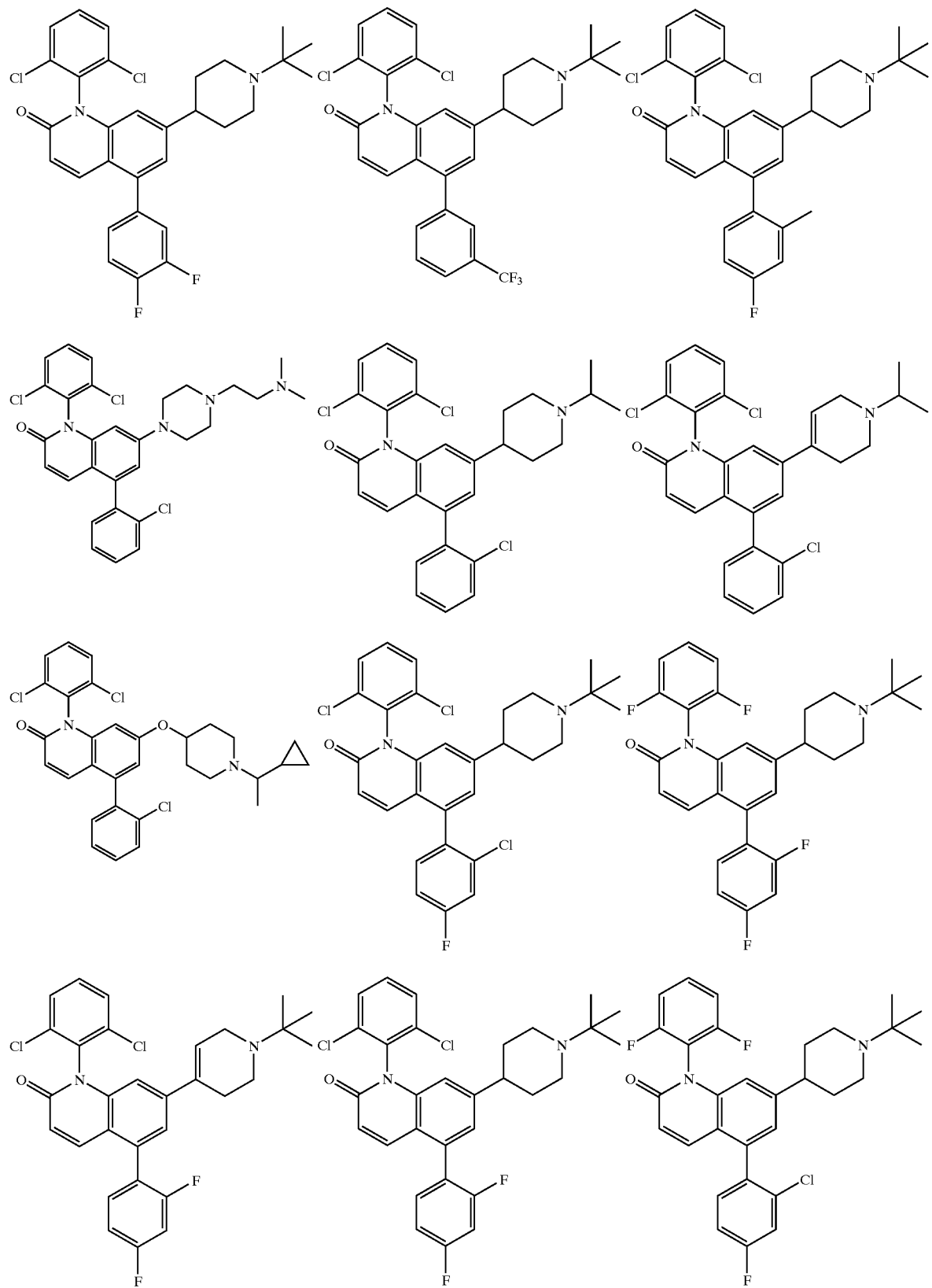

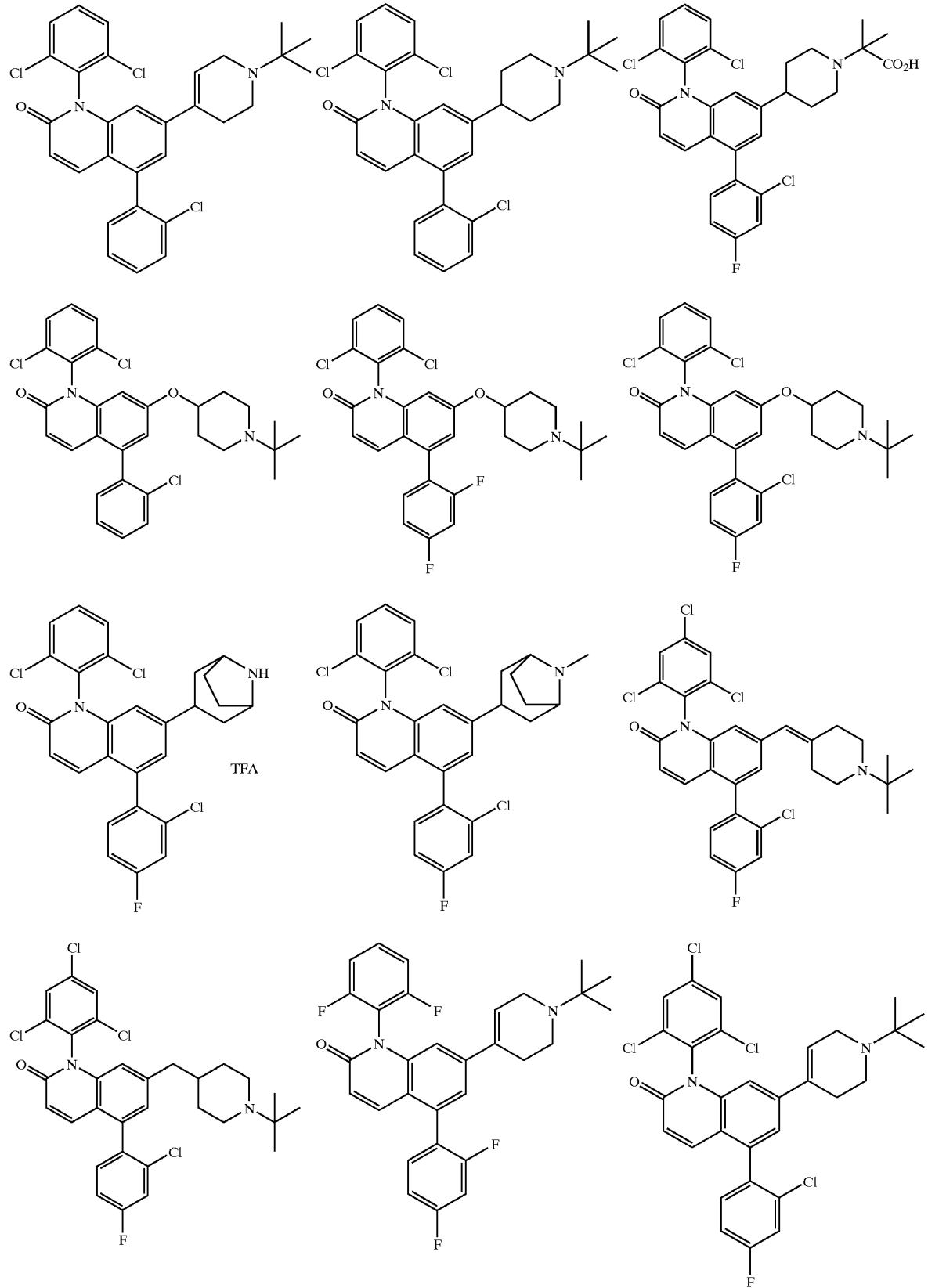

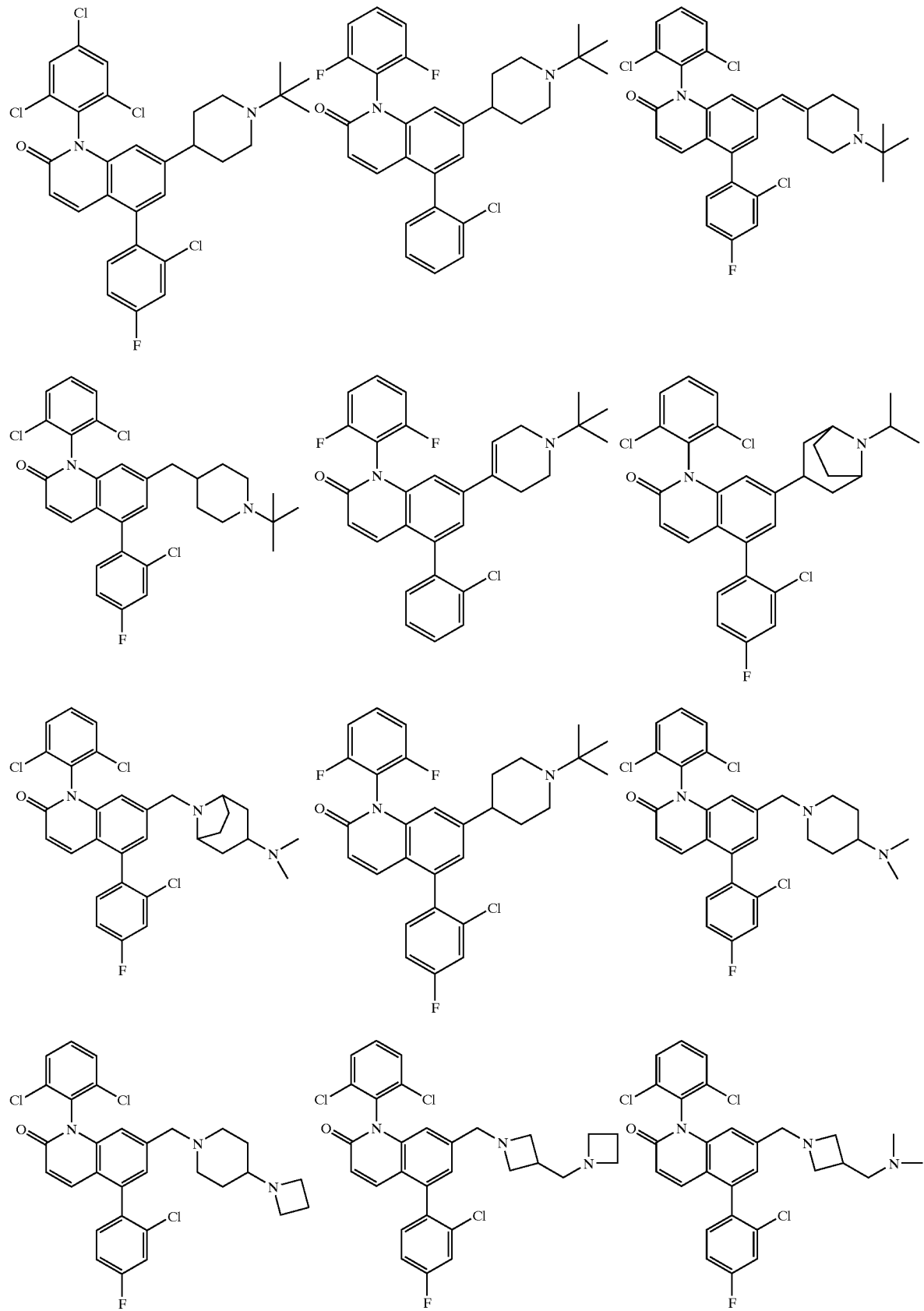

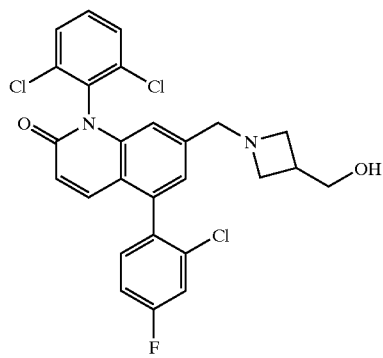
or a pharmaceutically acceptable salt thereof.
30. The compound according to claim 1, wherein
A is CH;
D is CH; and
G¹ is N.
31. The compound according to claim 30 represented by
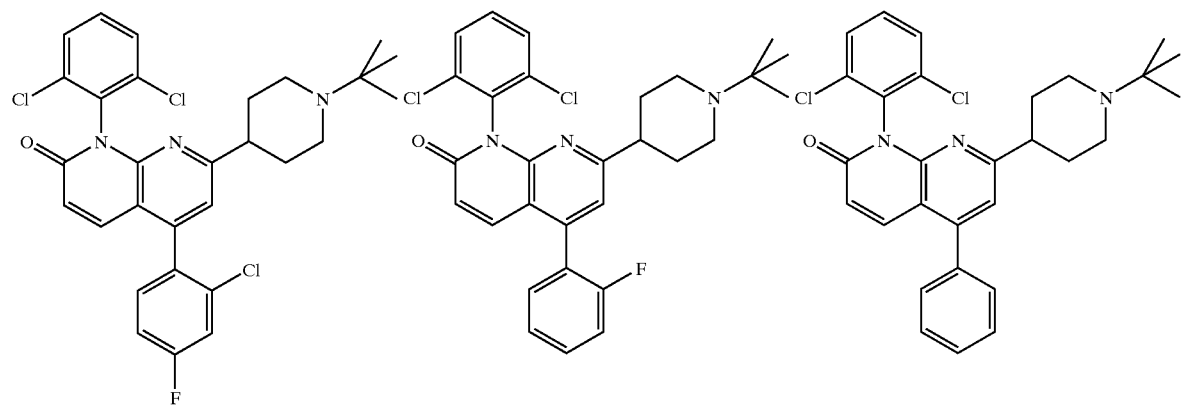
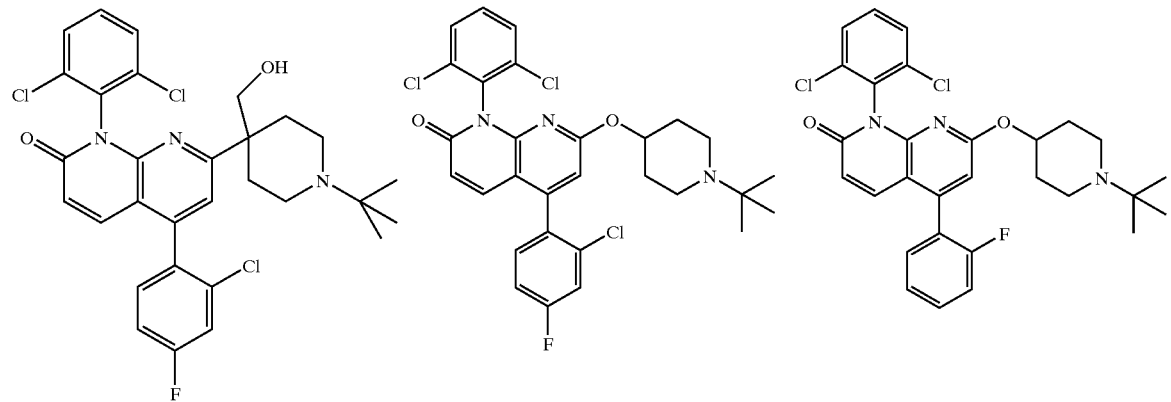

431 432
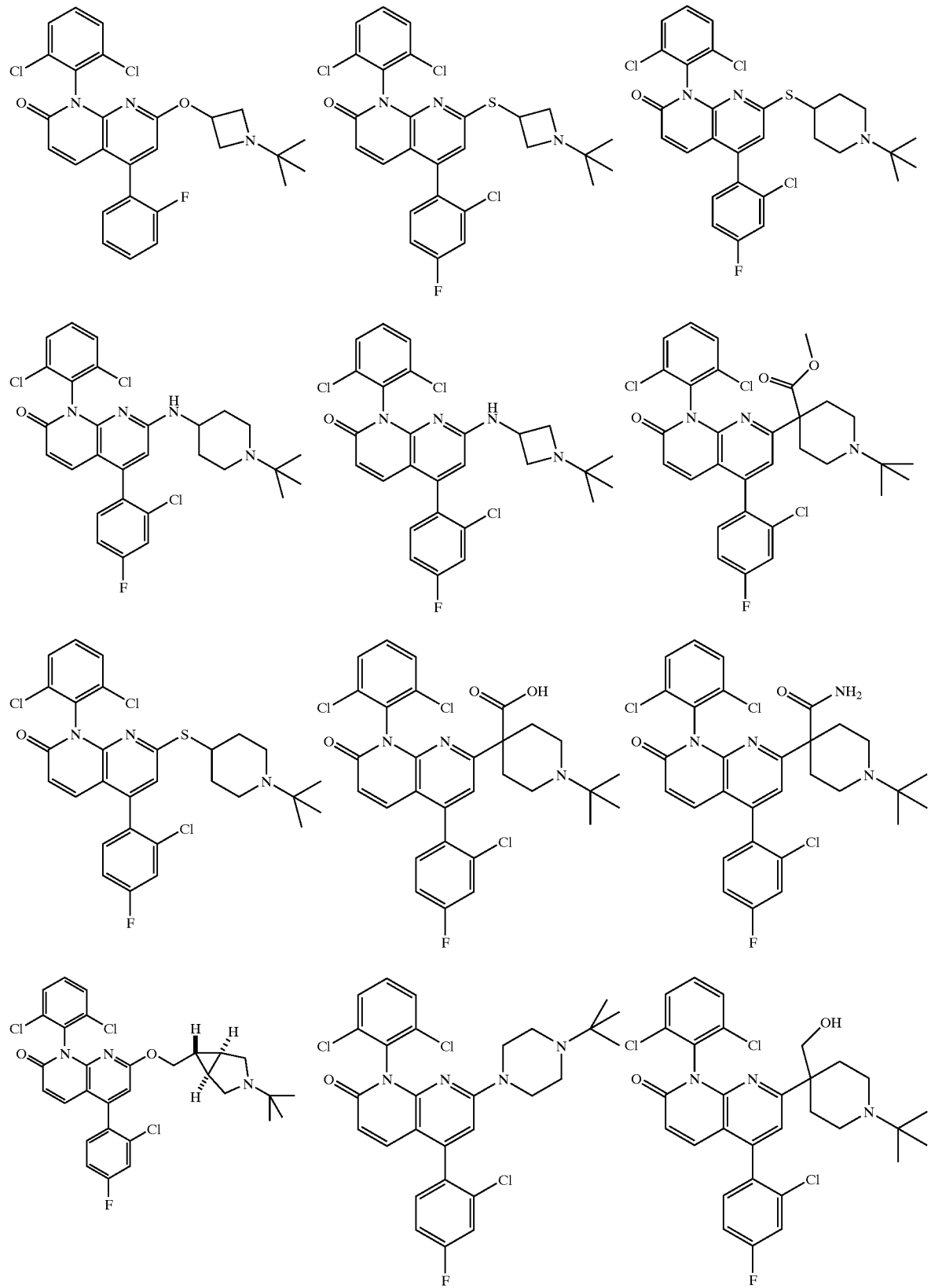

or a pharmaceutically acceptable salt thereof.
32. The compound according to claim 1 wherein
A is CH;
D is CH; and
$G^2$ is N.
33. The compound according to claim 32 represented by
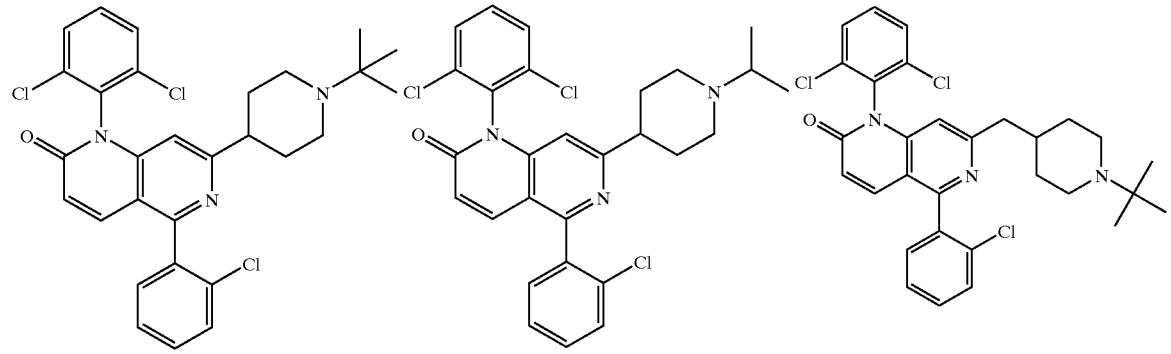
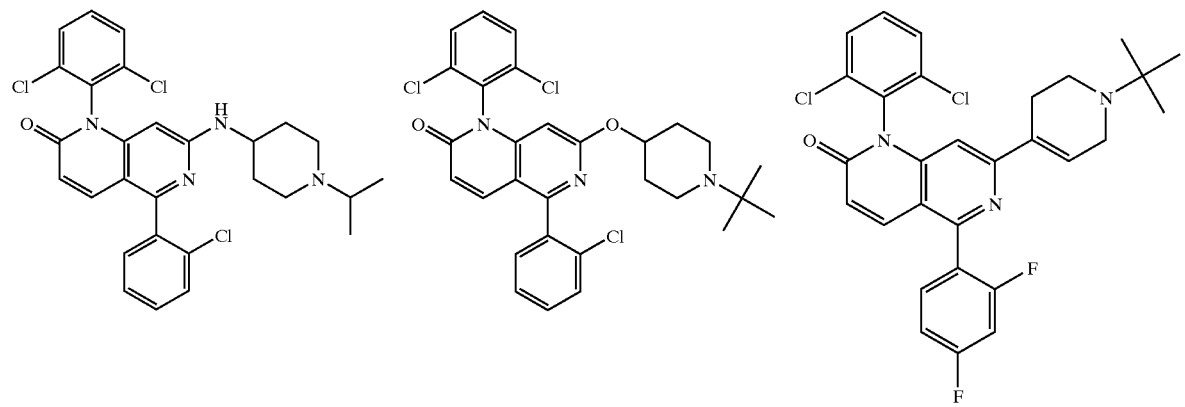
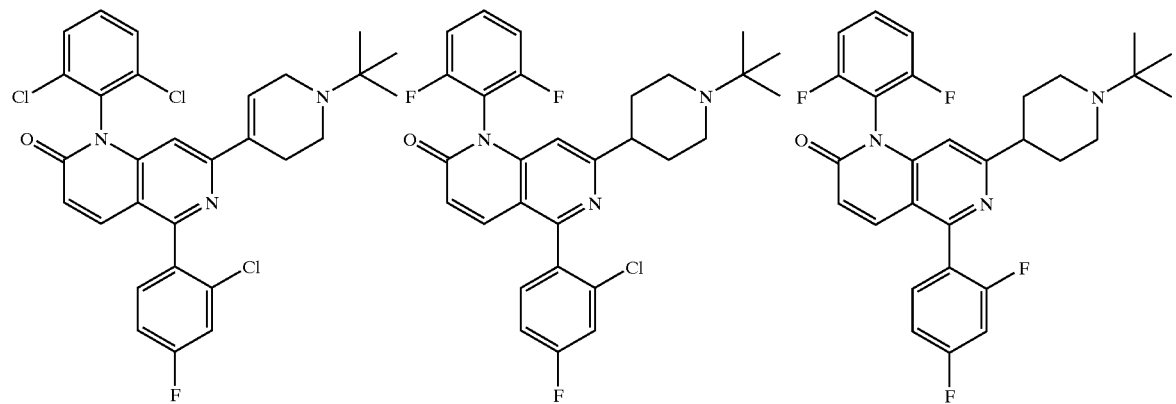

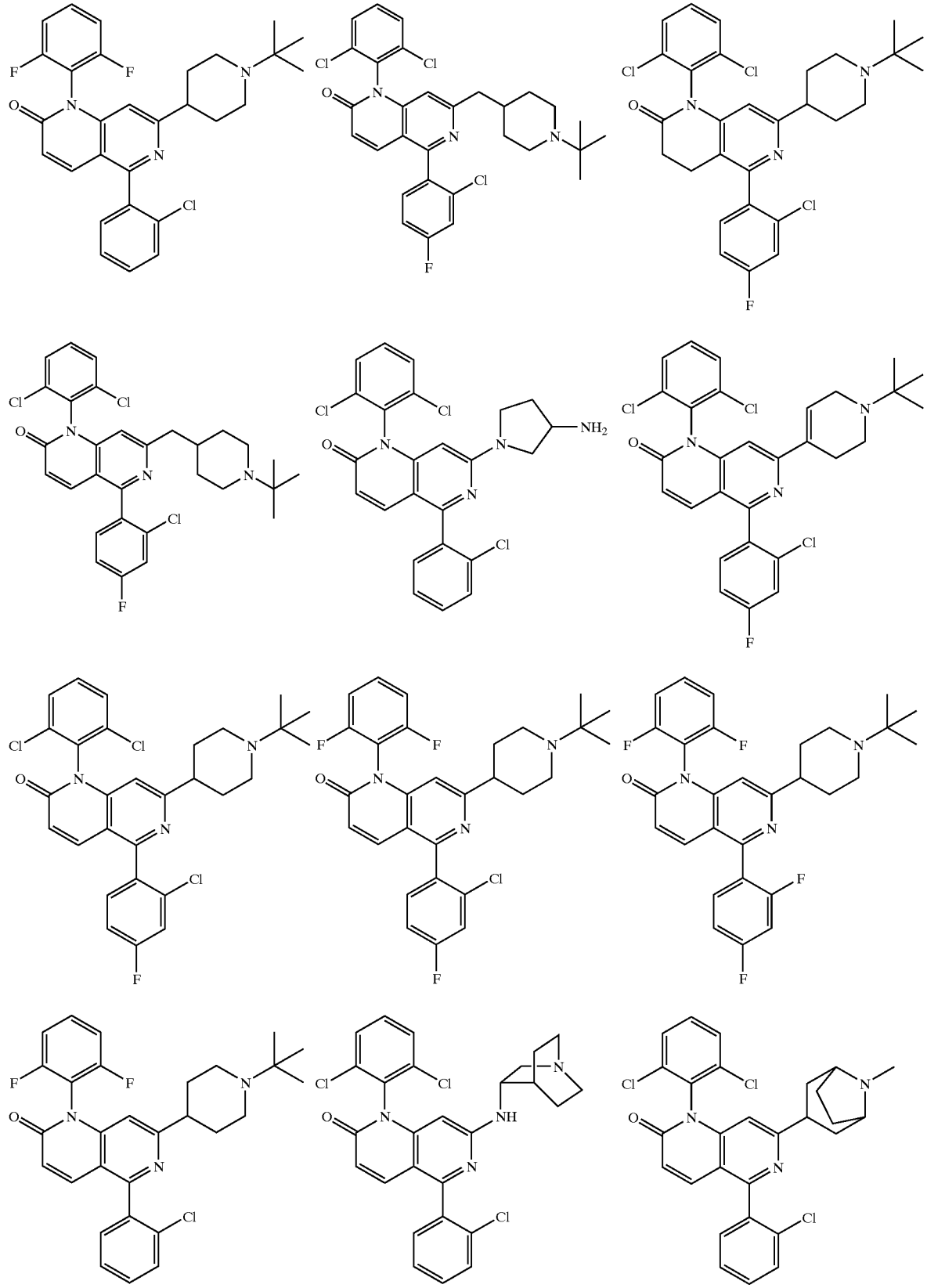

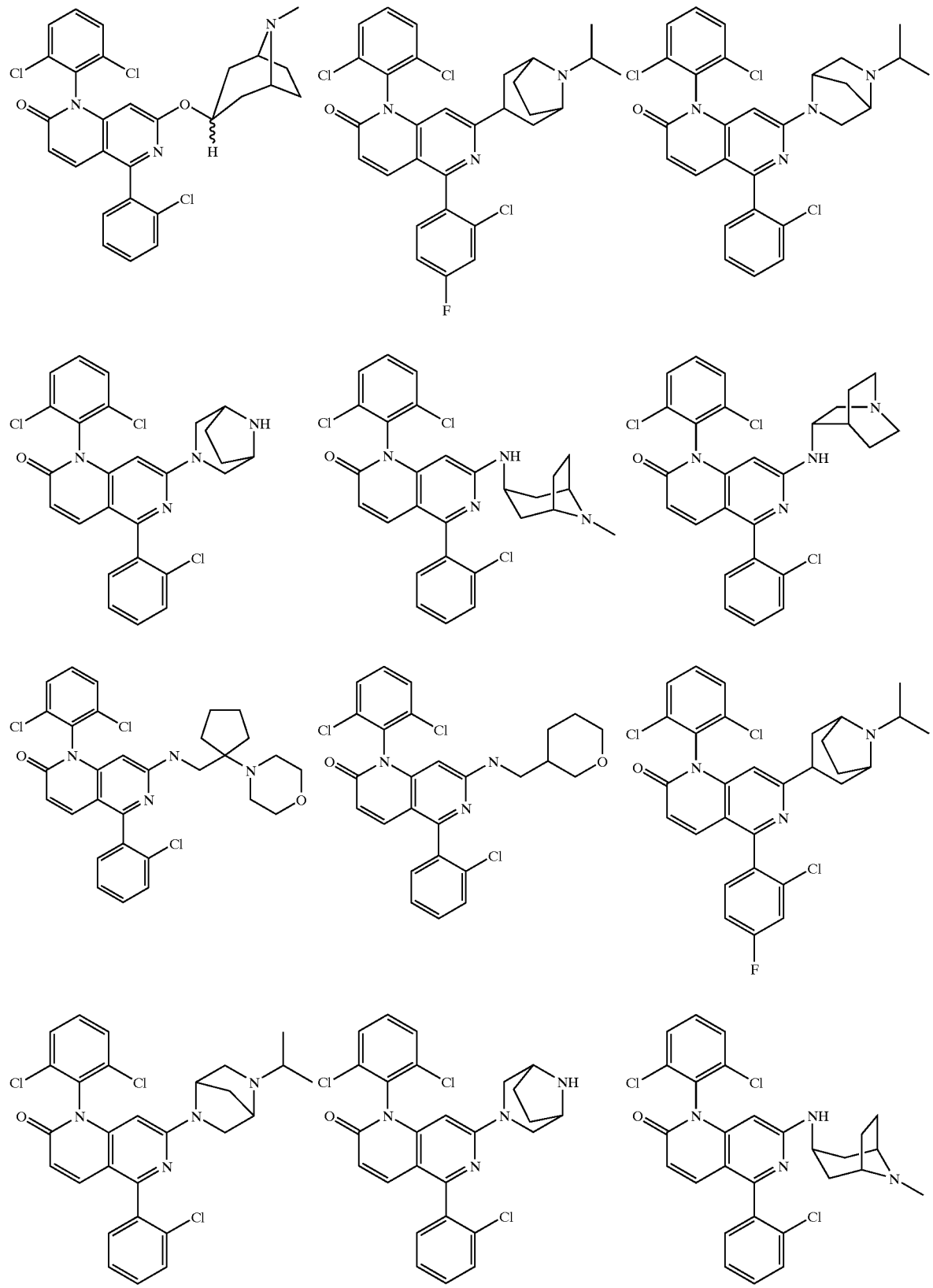

-continued
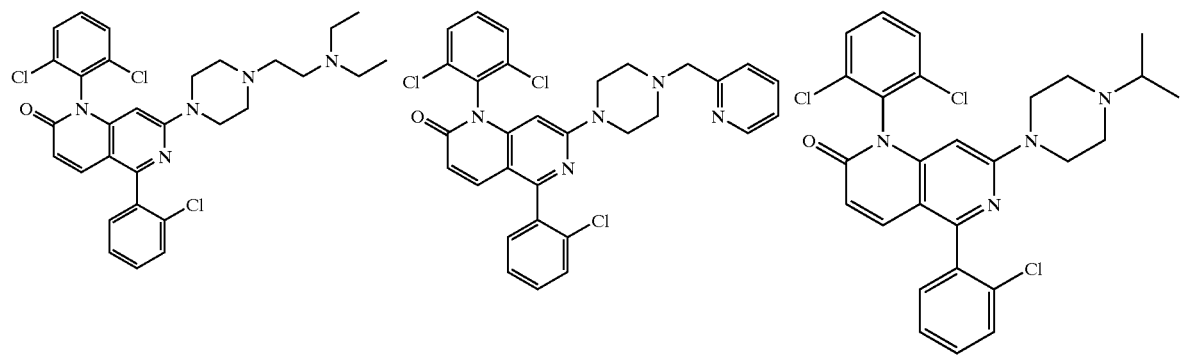
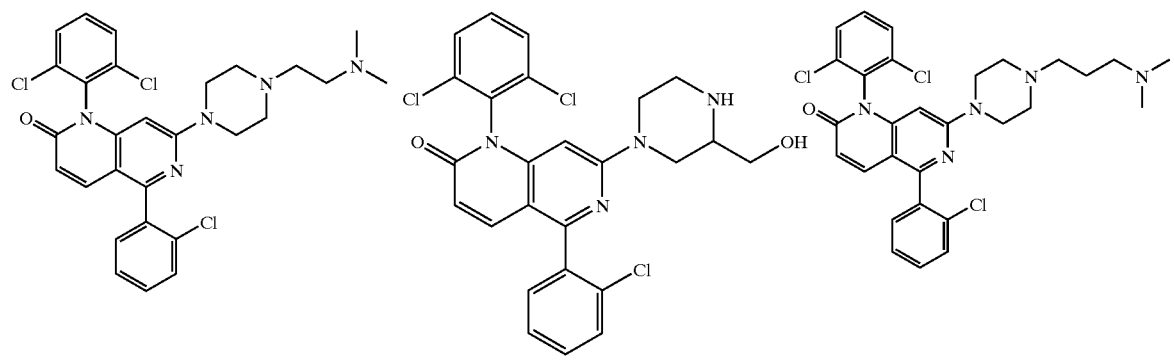
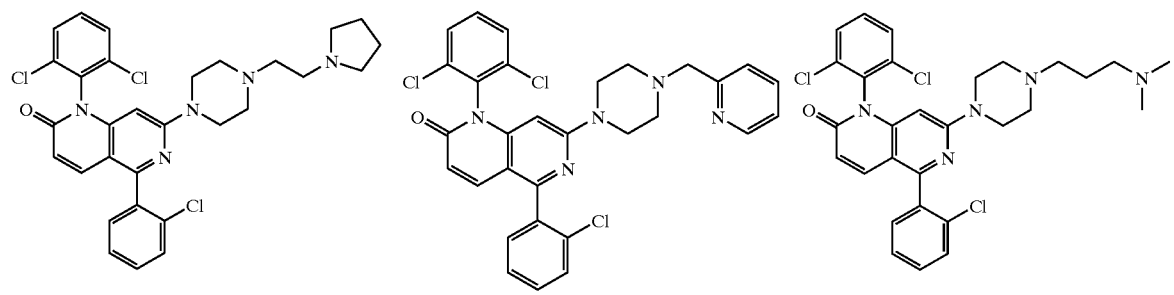
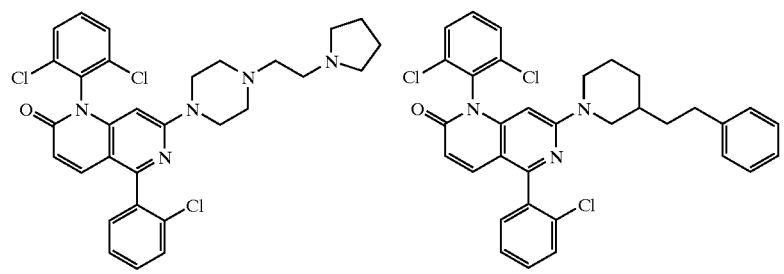

or a pharmaceutically acceptable salt thereof.

34. The compound according to claim 1 wherein

A is $CH_2$;

D is $CH_2$; and $G^2$ is N.

35. The compound according to claim 34 represented by or a pharmaceutical acceptable salt thereof.

36. The compound according to claim 1 wherein

A is CH;

D is CH; and

A and D are bridged by —$C_{1-4}$alkyl- to form a fused bicyclo ring with A and D at the bicyclo cusps.

37. The compound according to claim 36 represented by or a pharmaceutically acceptable thereof.

38. The compound according to claim 12 represented by or a pharmaceutically acceptable thereof.

39. A compound represented by or a pharmaceutically acceptable salt thereof.

40. A compound represented by
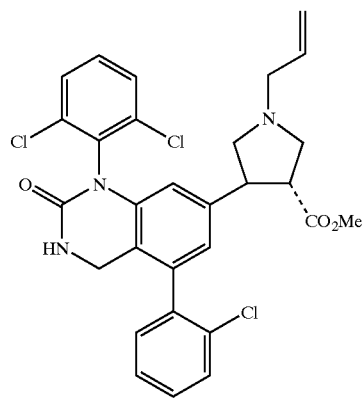
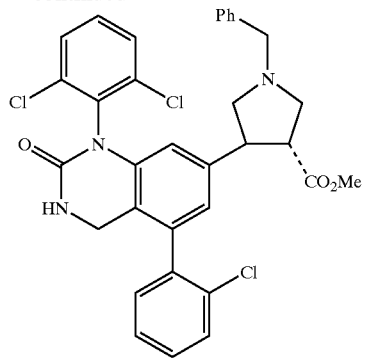
or a pharmaceutically acceptable salt thereof.
* * * * *